US012043643B2

(12) United States Patent
Parameswarappa et al.

(10) Patent No.: US 12,043,643 B2
(45) Date of Patent: *Jul. 23, 2024

(54) VACCINE AGAINST KLEBSIELLA PNEUMONIAE

(71) Applicant: IDORSIA PHARMACEUTICALS LTD, Allschwil (CH)

(72) Inventors: Sharavathi Guddehalli Parameswarappa, Berlin (DE); Marilda P. Lisboa, Berlin (DE); Sylvia Oestreich, Berlin (DE); Jessica Przygodda, Berlin (DE); Bopanna Monnanda, Berlin (DE); Arne Von Bonin, Basel (CH); Claney Lebev Pereira, Berlin (DE)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/818,931

(22) Filed: Aug. 10, 2022

(65) Prior Publication Data

US 2023/0122752 A1  Apr. 20, 2023

Related U.S. Application Data

(63) Continuation of application No. 16/768,301, filed as application No. PCT/EP2018/083246 on Nov. 30, 2018, now Pat. No. 11,479,574.

(30) Foreign Application Priority Data

Nov. 30, 2017 (EP) .................................... 17204817

(51) Int. Cl.
    C07H 15/26    (2006.01)
    A61K 39/108   (2006.01)
    A61K 47/61    (2017.01)
    G01N 33/569   (2006.01)

(52) U.S. Cl.
    CPC ......... *C07H 15/26* (2013.01); *A61K 39/0266* (2013.01); *A61K 47/61* (2017.08); *G01N 33/56916* (2013.01); *G01N 2333/26* (2013.01)

(58) Field of Classification Search
    None
    See application file for complete search history.

(56) References Cited

U.S. PATENT DOCUMENTS

| 11,479,574 B2 | 10/2022 | Parameswarappa et al. |
| 2021/0386845 A1 | 12/2021 | Naini et al. |

FOREIGN PATENT DOCUMENTS

| WO | WO 2014/080251 | 5/2014 |
| WO | WO 2015/052344 | 4/2015 |
| WO | WO 2016/044773 | 3/2016 |
| WO | WO 2016/156338 | 10/2016 |

OTHER PUBLICATIONS

U.S. Appl. No. 16/768,301, filed May 29, 2020, Parameswarappa et al.
Adamo, R., "Advancing Homogeneous Antimicrobial Glycoconjugate Vaccines," Acc Chem Res (2017) 50:1270-1279.
Alonso Develasco et al., "*Streptococcus pneumoniae*: Virulence Factors, Pathogenesis, and Vaccines," Microbiological Reviews (1995) 59(4):591-603.
Anish et al., "Chemical Biology Approaches to Designing Defined Carbohydrate Vaccines," Chemistry and Biology (2014) 21(1):38-50.
Anraku et al., "The design and synthesis of an α-Gal trisaccharide epitope that provides a highly specific anti-Gal immune response," Organic & Biomolecular Chemistry (2017) DOI: 10.1039/c7ob00448f, 14 pages.
Arcuri et al., "The influence of conjugation variables on the design and immunogenicity of a glycoconjugate vaccine against *Salmonella* Typhi," PLoS One (2017) 12(12):e0189100, 19 pages.
Baek et al., "Directing effect by remote electron-withdrawing protecting groups at O-3 or O-4 position of donors in glucosylations and galactosylations," Tetrahedron (2015) 71(33):5315-5320.
Bai et al., "2,3-Anhydrosugars in Glycoside Bond Synthesis. Application to α-D-Galactofuranosides," J. Org. Chem. (2006) 71:9658-9671.
Berti et al., "Antimicrobial glycoconjugate vaccines: an overview of classic and modern approaches for protein modification," Chem. Soc. Rev. (2018) 47:9015-9025.
Boeckler et al., "Immunogenicity of new heterobifunctional cross-linking reagents used in the conjugation of synthetic peptides to liposomes," J. Immun. Meth. (1996) 191:1-10.
Crich et al., "Synthesis of the Antigenic Tetrasaccharide Side Chain from the Major Glycoprotein of *Bacillus anthracis* Exosporium," J. Org. Chem. (2007) 72(17):6513-6520.
Cryz et al., "Safety and immunogenicity of a polyvalent *Klebsiella* capsular polysaccharide vaccine in humans," Vaccine (1986) 4(1):15-20.
Ferriéres et al., "A new approach to a disaccharidic hapten containing a galactofuranosyl entity," J. Carb. Chem. (2001) 20(9):855-865.
Grandjean et al., "On the Preparation of Carbohydrate-Protein Conjugates Using the Traceless Staudinger Ligation," J. Org. Chem. (2005) 70:7123-7132.

(Continued)

*Primary Examiner* — Layla D Berry
(74) *Attorney, Agent, or Firm* — Hoxie & Associates LLC

(57) ABSTRACT

The present invention relates to a synthetic saccharide of general formula (I) that is related to *Klebsiella pneumoniae* serotype O1, O2, O2ac, and O8 O-polysaccharide and carbapenem-resistant *Klebsiella pneumoniae* ST258 O-polysaccharide and conjugate thereof. Said synthetic saccharide, said conjugate and pharmaceutical composition containing said synthetic saccharide or said conjugate are useful for prevention and/or treatment of diseases associated with *Klebsiella pneumoniae*. Furthermore, the synthetic saccharide of general formula (I) is useful as marker in immunological assays for detection of antibodies against *Klebsiella pneumoniae* bacteria.

23 Claims, 12 Drawing Sheets

(56) References Cited

OTHER PUBLICATIONS

Hsieh et al., "D-galactan II is an immunodominant antigen in O1 lipopoylsaccharide and affects virulence in *Klebsiella pneumoniae*: implication in vaccine design," Frontiers in Microbiology (2014) 5:Art. 608, 14 pages.
Huang et al., "PEG as a spacer arm markedly increases the immunogenicity of meningococcal group Y polysaccharide conjugate vaccine," Journal of Controlled Release (2013) 172:382-389.
International Preliminary Report on Patentability completed Feb. 10, 2020, for PCT Application No. PCT/EP2018/083246, filed Nov. 30, 2018.
International Search Report and Written Opinion dated Jan. 3, 2019, for PCT Application No. PCT/EP2018/083246, filed Nov. 30, 2018.
Kawano et al., "Natural killer-like nonspecific tumor cell lysis mediated by specific ligand-activated Vα14 NKT cells," Proc. Natl Acad. Sci. USA (1998) 95(10):5690-5693.
Kelly et al., "Structures of the O-antigens of *Klebsiella* serotypes O2 (2a,2e), O2 (2a,2e,2h), and O2 (2a,2f,2g), members of a family of related D-galactan O-antigens in *Klebsiella* spp.," J. Endotoxin Res. (1995) 2:131-140.
Kelly et al., "Clonally Diverse rfb Gene Clusters Are Involved in Expression of a Family of Related D-Galactan O Antigens in *Klebsiella* Species," Journal of Bacteriology (1996) 178(17):5205-5214.
Khatun et al., "An Overview of Structural Features of Antibacterial Glycoconjugate Vaccines That Influence Their Immunogenicity," Chem. Eur. J. (2017) 23:4233-4254.
Knirel, Y., "Structure of O-Antigens," Bacterial Lipopolysaccharides (2011) 41, 54-56, DOI: 10.1007/978-3-7091-0733-1_3.
Nakashima et al., "A First Total Synthesis of a Hybrid-Type Ganglioside Associated with Amyotrophic Lateral Sclerosis-Like Disorder," Chem. Eur. J. (2011) 17:588-597.
Ovodov, Y., "Bacterial Capsular Antigens. Structural Patterns of Capsular Antigens," Biochemistry (Moscow) (2006) 71(9):937-954.
Peeters et al., Preparation of Polysaccharide-Conjugate Vaccines. In: Robinson A., Hudson M.J., Cranage M.P. (eds) Vaccine Protocols. Methods in Molecular Medicine ™ (2003) vol. 87. Humana Press. https://doi.org/10.1385/1-59259-399-2:153.
Remington's Pharmaceutical Sciences, Mack Publishing Co., Easton PA (1975) (Cover and Table of Contents Only).
Sarkar et al., "Chemical synthesis of the hexasaccharide related to the repeating unit of the capsular polysaccharide from carbapenem resistant *Klebsiella pneumoniae* 2796 and 3264," RSC Adv. (2016) 6:40147.
Seeberger, P., "Automated carbohydrate synthesis as platform to address fundamental aspects of glycobiology-current status and future challenges," Carbohydrate Research (2008) 343(12):1889-1896.
Seeberger, et al., "A Semi-Synthetic Glycoconjugate Vaccine Candidate for Carbapenem-Resistant *Klebsiella pneumoniae*," Angew. Chem. Intl. Ed. (2017) 56(45): 13973-13978.
Smoot et al., "Development of an Arming Participating Group for Stereoselective Glycosylation and Chemoselective Oligosaccharide Synthesis," Angew. Chem. Intl. Ed. (2005) 44:7123-7126.
Stojkovic et al., "Identification of D-Galactain-III as Part of the Lipopolysaccharide of *Klebsiella pneumoniae* Serotype O1," Frontiers in Microbiology (2017) 8:Art. 684, 8 pages.
Szijártó et al., "Both clades of the epidemic KPC-producing Klebsiella pneumoniae clone ST258 share a modified galactan O-antigen type," Int J Med Microbiol (2016) 306:89-98.
Verkhnyatskaya et al., "Pyranoside-into-Furanoside Rearrangement of 4-Pentenyl Glycosides in the Synthesis of a Tetrasaccharide-Related to Galactan I of *Klebsiella pneumonia*," Eur. J. Org. Chem. (2017) 3:710-718.
Vinogradov et al., "Structural analysis of the core region of the lipopolysaccharides from eight serotypes of *Klesbiella pneumonia*," Carbohydrate Research (2001) 335:291-296.
Vinogradov et al., "Structures of Lipopolysaccharides from *Klebsiella pneumonia*," Journal of Biological Chemistry (2002) 277(28):25070-25081.
Wang et al., "First Synthesis of β-D-Galf-(1->3)- D-Galp—the repeating unit of the backbone structure of the O-antigenic polysaccharide present in the lipopolysaccharide (LPS) of the genus *Klebsiella*," Carbohydrate Research (2003) 338:1033-1037.
Wang et al., "Influence of Silyl Protections on the Anomeric Reactivity of Galactofuranosyl Thioglycosides and Application of the Silylated Thiogalactofuranosides to One-Pot Synthesis of Diverse β-D-Oligogalactofuranosides," J. Org. Chem. (2014) 79:10203-10217.
Whitfield et al., "Expression of Two Structurally Distinct D-Galactan O Antigens in Lipopolysaccharide of *Klebsiella pneumoniae* Serotype O1," J Bacteriol. (1991) 173(4):1420-1431.
Yeh et al., "Surface antigens contribute differently to the pathophysiological features in serotype K1 and K2 *Klebsiella pneumoniae* strain isolated from liver abscesses," Gut Pathog (2016) 8(4) DOI: 10.1186/s13099-016-0085-5, 9 pages.
Zhu et al., "Synthesis of tetra- and hexasaccharide fragments corresponding to the O-antigenic polysaccharide of *Klebsiella penumonie*," Tetrahedron (2012) 68:3795-3802.
U.S. Appl. No. 16/768,350, filed May 29, 2020, Naini et al.
Fang, J. et al., "Synthesis of α-Gal epitope derivatives with a galactosyltransferase-epimerase fusion enzyme," Carbohydrate Research (2000) 329:873-878.
Fenn, L. et al., "Structural resolution of carbohydrate positional and structural isomers based on gas-phase ion mobility-mass spectrometry," Physical Chemistry Chemical Physics (2011) 13:2196-2205.
Knels, U. et al., "Comparative structural analysis of snail galactans by a radioimmunoassay to elucidate species-specific determinants," J Comp Physiol B (1989) 159:629-639.

Figure 1

Serotype

D　　　　C　　　　B'　　　A　　　B　　　A"
[-3)-β-Galp-(1-3)-α-Galp-(1-]ₘ-β-Galf-(1-[3)-α-Galp-(1-3)-β-Galf-(1-]ₙ-3)-α-Galp-CP　　　O1

B'　　　A　　　B　　　A"
β-Galf-(1-[3)-α-Galp-(1-3)-β-Galf-(1-]ₙ-3)-α-Galp-CP　　　O1, O2a, O2a,c

D(D')　　　C　　　**B'(B*)　　　A　　　B　　　A"**
[-5)-β-Galf-(1-3)-β-GlcNAc-(1-]ₘ-β-Galf-(1-[3)-α-Galp-(1-3)-β-Galf-(1-]ₙ-3)-α-Galp-CP　　　O2a,c

E　　　D　　　C　　　B　　　A　　　N　　　Q
T-[2)-α-Man-(1-2)-α-Man-(1-2)-α-Man-(1-3)-α-Man-(1-3)-α-Man-(1-]ₙ-3)-α-Man-(1-3)-α-Man-CP　　　O3

F　　　　L　　　　M
-3)-β-GlcNAc-(1-5)-α-Kdo-(2-6)-anhMan　　　　CP (common part)
　　　　　　P-(1-4)┘ a, P = H
b, P = α-Hep

Figure 2
a)
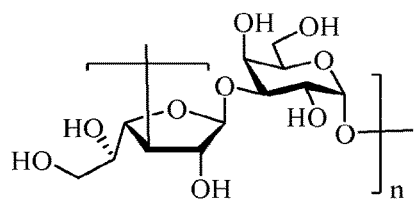
Galactan-I
O1, O2a, O2ac
b)
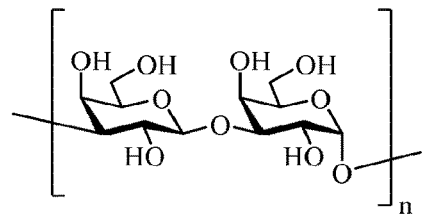
Galactan-II
c)
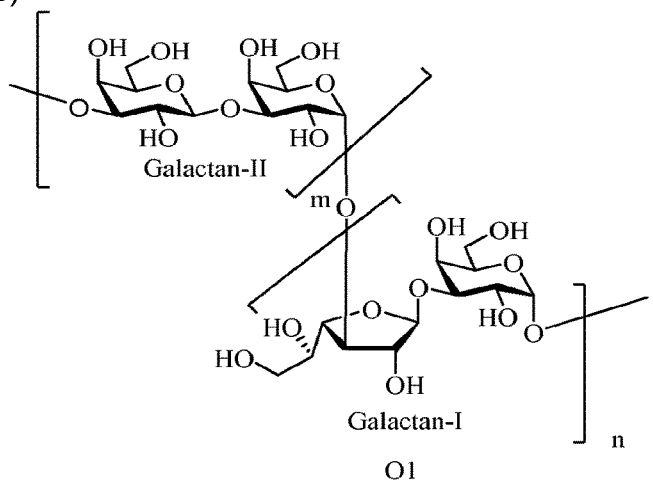
d)
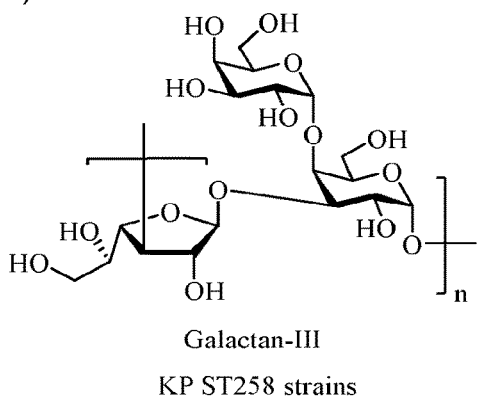
Galactan-III
KP ST258 strains
f)
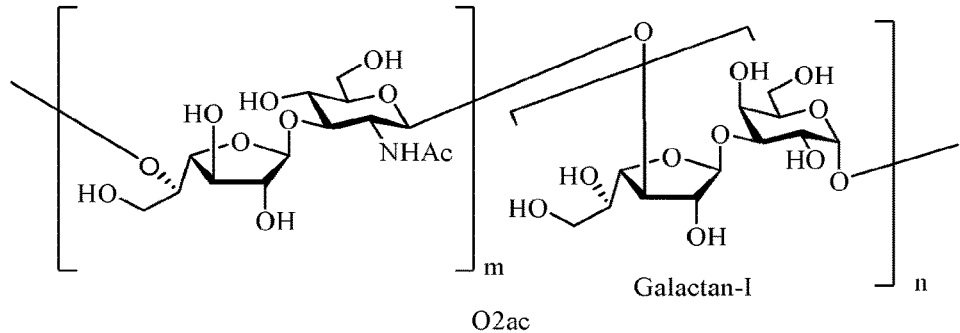

Figure 3

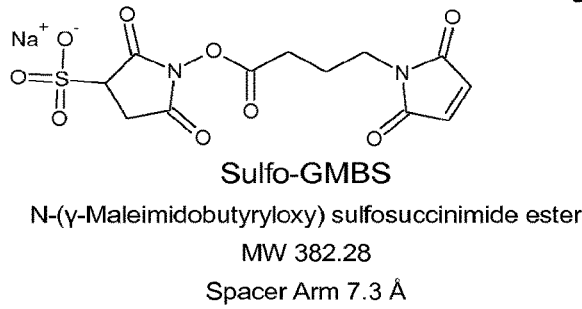

Sulfo-GMBS
N-(γ-Maleimidobutyryloxy) sulfosuccinimide ester
MW 382.28
Spacer Arm 7.3 Å

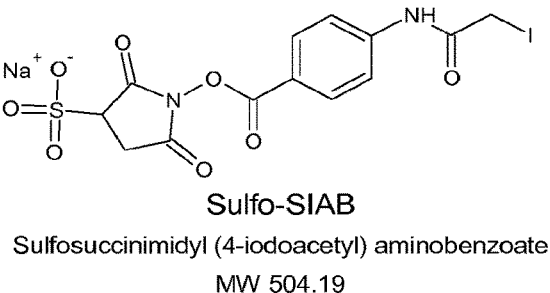

Sulfo-SIAB
Sulfosuccinimidyl (4-iodoacetyl) aminobenzoate
MW 504.19
Spacer Arm 10.6 Å

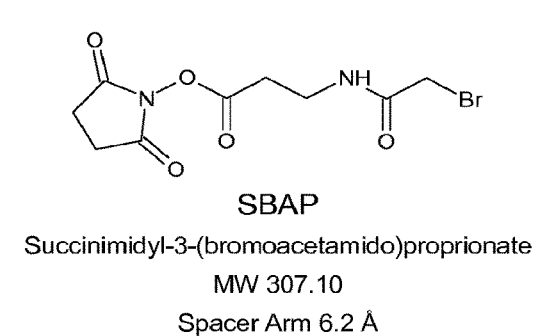

SBAP
Succinimidyl-3-(bromoacetamido)proprionate
MW 307.10
Spacer Arm 6.2 Å

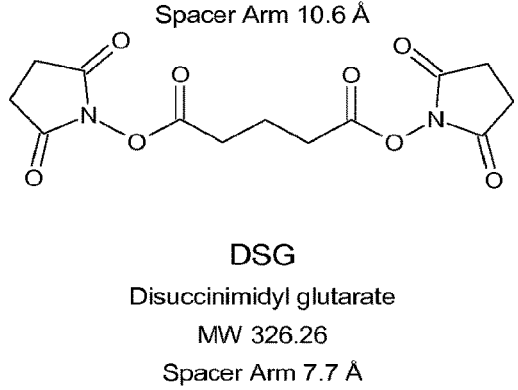

DSG
Disuccinimidyl glutarate
MW 326.26
Spacer Arm 7.7 Å

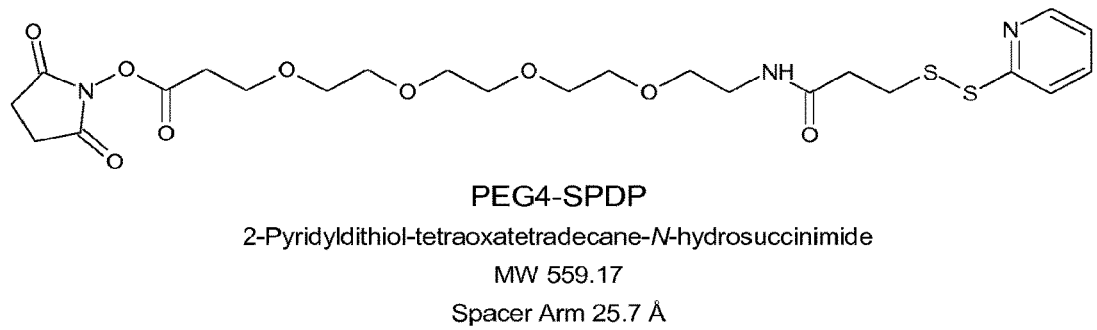

PEG4-SPDP
2-Pyridyldithiol-tetraoxatetradecane-N-hydrosuccinimide
MW 559.17
Spacer Arm 25.7 Å

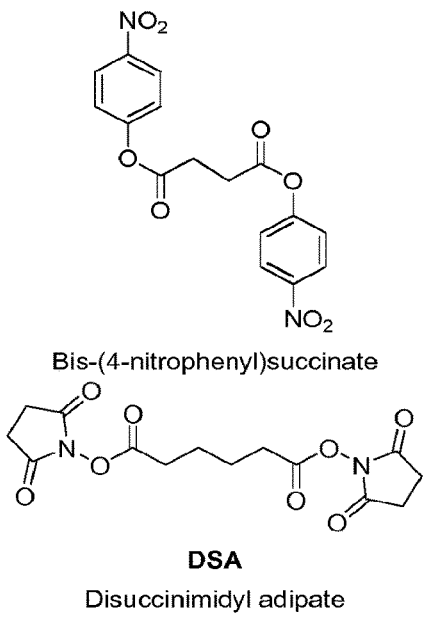

Bis-(4-nitrophenyl)succinate

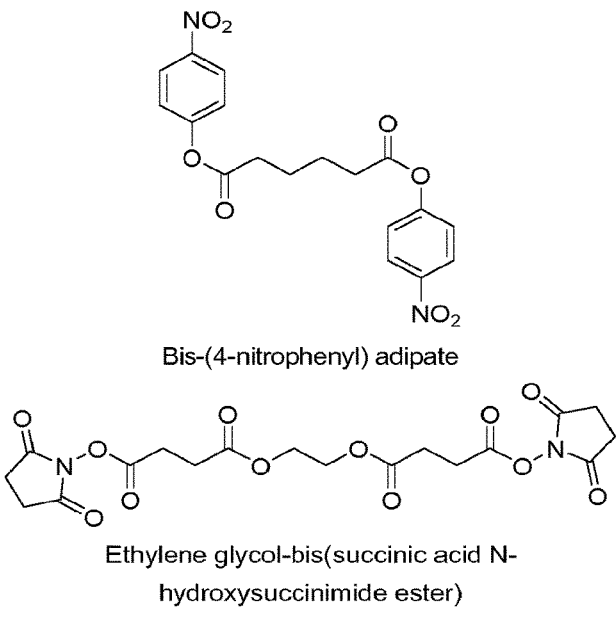

Bis-(4-nitrophenyl) adipate

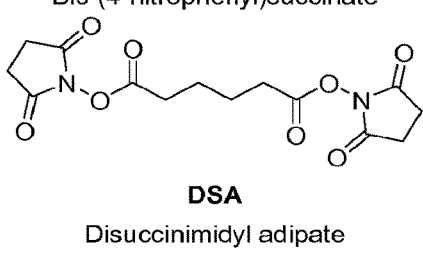

DSA
Disuccinimidyl adipate

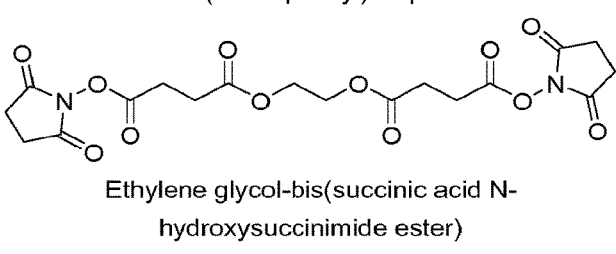

Ethylene glycol-bis(succinic acid N-hydroxysuccinimide ester)

Fig. 4B
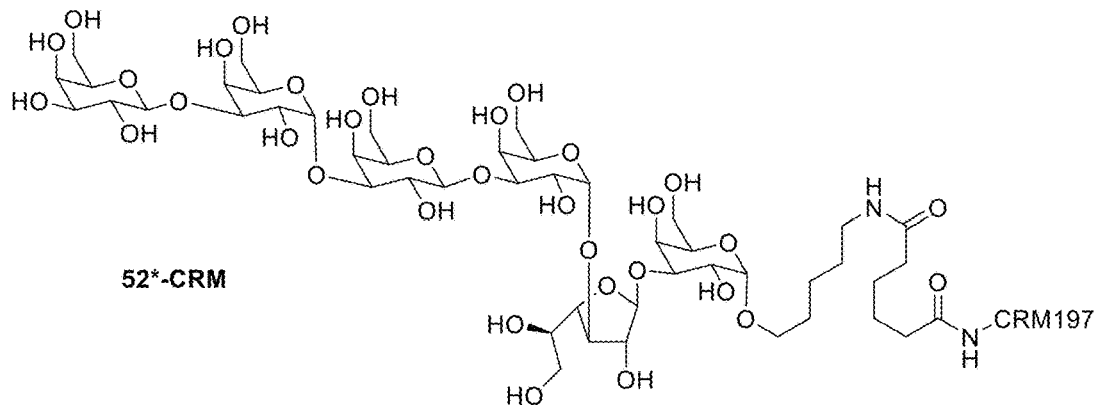
52*-CRM
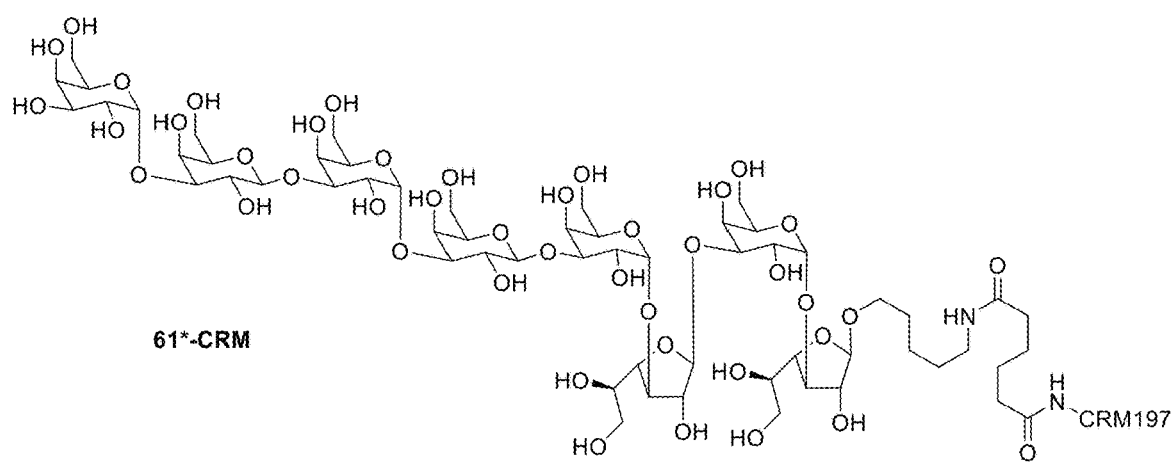
61*-CRM
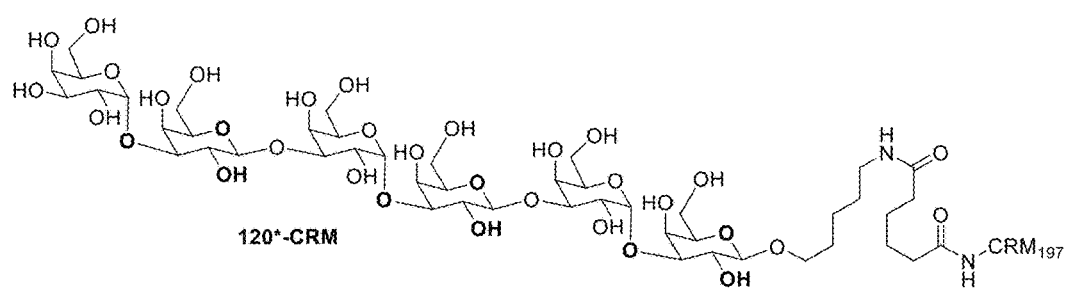
120*-CRM
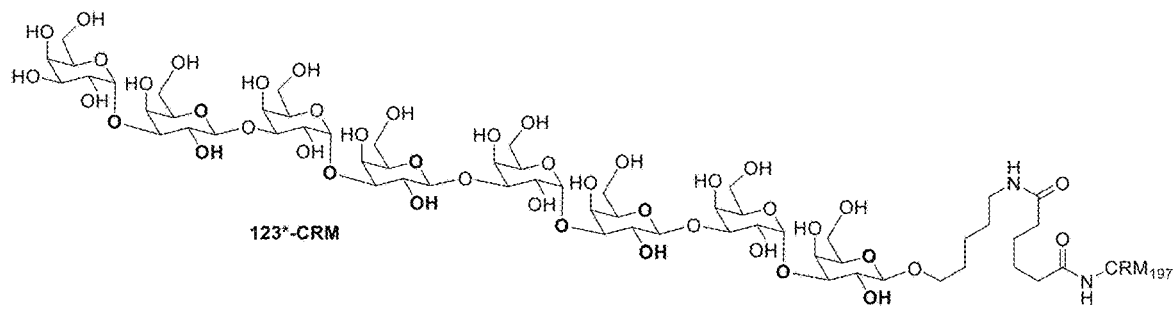
123*-CRM

Fig. 4C
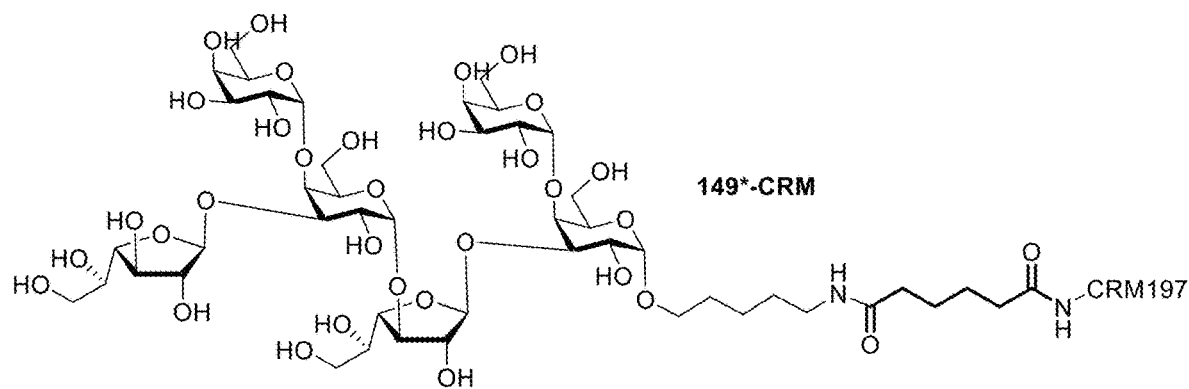
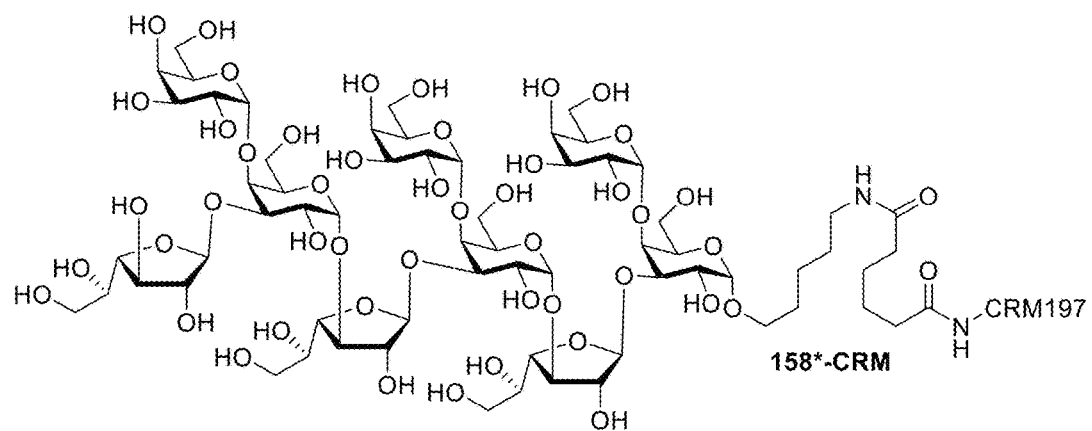
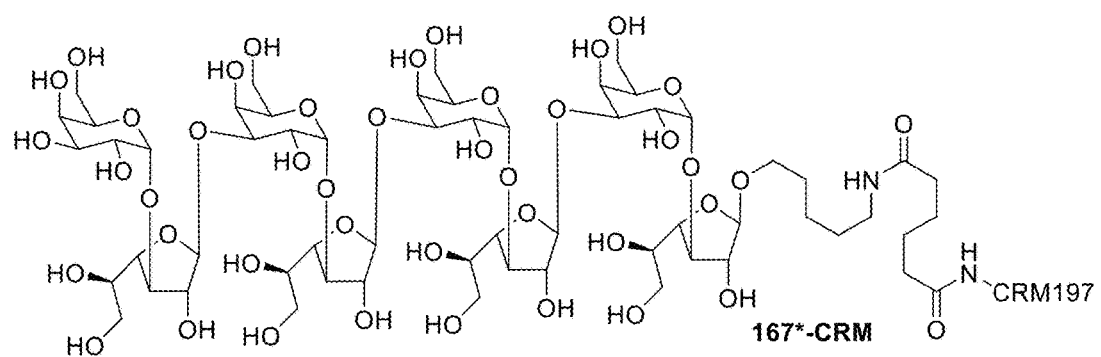

Figure 11

VACCINE AGAINST KLEBSIELLA PNEUMONIAE

CROSS REFERENCE TO RELATED APPLICATIONS

This application is a continuation of U.S. patent application Ser. No. 16/768,301, filed May 29, 2020, now issued as U.S. Pat. No. 11,479,574, which is a U.S. National Phase Application of PCT International Application No. PCT/EP2018/083246, filed Nov. 30, 2018, designating the United States of America and published in the English language, which claims priority to EP Application No. 17204817.5, filed Nov. 30, 2017. The disclosures of the above-referenced applications are hereby incorporated by reference in their entireties.

FIELD OF THE INVENTION

The present invention relates to a synthetic saccharide of general formula (I) that is related to *Klebsiella pneumoniae* serotype O1, O2, O2ac, and O8 O-polysaccharide and carbapanem-resistant *Klebsiella pneumoniae* ST258 O-polysaccharide and conjugate thereof. Said synthetic saccharide, said conjugate and pharmaceutical composition containing said synthetic saccharide or said conjugate are useful for prevention and/or treatment of diseases associated with *Klebsiella pneumoniae*. Furthermore, the synthetic saccharide of general formula (I) is useful as marker in immunological assays for detection of antibodies against *Klebsiella pneumoniae* bacteria.

BACKGROUND OF THE INVENTION

*Klebsiella pneumoniae* is a gram-negative, facultative anaerobic, rod-shaped bacterium colonizing mostly of the respiratory and urinary tracts and causing *K. pneumoniae* infections (KPIs). KPI is the main cause of nosocomial infections, primarily affecting immunocompromised patients. In the last ten years, infections caused by *K. pneumoniae* are becoming an important challenge in healthcare settings due to the emergence of strains resistant to almost all available antimicrobial agents and their worldwide dissemination. Infections caused by *Klebsiella pneumoniae* are responsible of high rates of morbidity and mortality. Thus, prevention of infections caused by *K. pneumoniae* is highly desirable, and vaccination of risk groups is the most cost-efficient and the most powerful means.

Like most bacteria, *K. pneumoniae* usually develop capsules composed of complex polysaccharides on the bacterial surface, which are highly immunogenic and nontoxic. In comparison with proteins, carbohydrates are evolutionarily more stable and have been exploited in a series of commonly employed vaccines. When covalently connected to a carrier protein, oligosaccharide antigens can elicit long lasting, T-cell-dependent protection. *K. pneumoniae* typically expresses both, lipopolysaccharide (LPS) and capsular polysaccharide (CPS, K-antigen), which contribute to the virulence of this species. LPS is a main surface antigen built of the O-specific polysaccharide (O-PS) containing different number of oligosaccharide repeating units (RU), core oligosaccharide and lipid A. O-PS structures (O-antigens) define O-serotypes of *Klebsiella* strains. Variability of *K. pneumoniae* O-antigens is currently limited to 9 major O-serotypes: O1, O2, O2ac, O3 (including O3a and O3b), O4, O5, O7, O8, O12 and a few subtypes within these serogroups such as subtypes O2a, O2ab, O2ae, O2aeh, and O2afg of serotype O2. *Klebsiella pneumoniae* has also been classified serologically into numerous capsular (K) types. Therefore, various *K. pneumoniae* strains having different K antigens belong to a specific O-antigen serotype. For example, numerous K-serotypes of *Klebsiella pneumoniae* strains belonging to O1 serotype have been identified (Infection and Immunity, 1983, p. 56-61). Most popular K-serotypes of *Klebsiella pneumoniae* strains belonging to O1 serotype are O1:K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70.

Recently, carbapenem resistant *Klebsiella pneumoniae* (CRKP) has emerged and spread globally. Carbapenem resistant *K. pneumoniae* (CRKP) is a major health concern due to the very limited treatment options. Such CRKP has usually carbapenemases that are able to cleave most beta-lactam type antibiotics. A specific lineage termed sequence type (ST) 258 has been shown to be responsible for the majority of KPC-producing *Klebsiella* infections. It is also known that CRKP ST258 strains have different capsular polysaccharide (CPS).

Lipopolysaccharide (LPS) and capsular polysaccharide (CPS), two surface components of *Klebsiella pneumoniae* are mainly discussed as candidates for an anti-*Klebsiella* vaccine. CPS has been proven to be highly immunogenic. However, the serious disadvantage of *Klebsiella* CPS vaccine is the great number of K-types (more 80 different antigens). In the utilization of LPS antigens in *Klebsiella* vaccines, the adverse toxic reactions caused mainly by the lipid A of LPS present a great drawback of active immunization with LPS-containing vaccines. In comparison with proteins, carbohydrates are evolutionarily more stable. When covalently connected to a carrier protein, polysaccharide or oligosaccharides can elicit long lasting, T-cell-dependent protection (*Microbiol Rev* 1995, 591). For a review on current development of carbohydrate vaccines see *Chem. & Biol.* 2014, 21, 38-50. For a review on automated carbohydrate synthesis and its application in the development of carbohydrate-based vaccines see *Carbohydr. Res.* 2008, 343, 1889-1896. WO 2016/156338 A1 discloses synthetic carbapenem-resistant *Klebsiella pneumoniae* saccharides and conjugates thereof for the treatment of diseases caused by *Klebsiella pneumoniae* bacteria. Later, the same group showed by glycan microarray studies that substructures of the prepared hexasaccharide are not recognized by monoclonal antibody 1C8 that cross-reacts with natural CR-*K. pneumoniae* CPS (*Angew. Chem. Int. Ed.* 2017, 56, 13973-13978).

The article Vaccine 1986, 4, 15 reports on a hexavalent *Klebsiella* vaccine composed of the capsular polysaccharide derived from K2, K3, K10, K21, K30 and K55 serotypes. The tested vaccine was found to be highly protective against fatal experimental *Klebsiella* K2 burn wound sepsis, thus indicating that functional antibody is elicited following vaccination.

Since O-antigens are far less variable than CPS, *Klebsiella pneumoniae* LPS O-antigens without the core oligosaccharides and lipid A can be potential target antigens for immunotherapy both prophylactic and therapeutic.

The repeating units of the O-antigens, i.e. O-polysaccharides of *K. pneumoniae* were elucidated (Journal of Bacteriology, 1996, p. 5205-5214; The *Journal of Biological Chemistry*, 2002, 277 (28), pp. 25070-25081) (see FIGS. 1 and 2).

The common structure of the O-polysaccharide (OPS) of *K. pneumoniae* serotype O1, O2a, O2ac consists of a disaccharide repeating unit:

→3)-β-D-Galf-(1→3)-α-D-Galp-(1→(galactan I).

The common structure of the O-polysaccharide (OPS) of *K. pneumoniae* serotypes O1, and O8 consists of a disaccharide repeating unit:

→3)-β-D-Galp-(1→3)-α-D-Galp-(1→(galactan II)

The repeating unit of the O-polysaccharide of *K. pneumoniae* serotype O1 consists of:

[→3)-β-D-Galp-(1→3)-α-D-Galp-(1→]$_m$-[→3)-β-D-Galf-(1→3)-α-D-Galp-(1→]$_n$.

The repeating unit of the O-polysaccharide of *K. pneumoniae* serotype O2a consists of:

→3)-β-D-Galf-(1→3)-α-D-Galp-(1→.

The repeating unit of the O-polysaccharide of *K. pneumoniae* serotype O2ac consists of:

[→5)-β-D-Galf-(1→3)-β-D-GlcNAc-(1→]$_m$-[→3)-β-D-Galf-(1→3)-α-D-Galp-(1→]$_n$.

The repeating unit of the O-polysaccharide of *K. pneumoniae* serotypes O2ae and O2aeh consists of:

→3)-β-D-Galf-(1→3)-α-D-Galp-(1→
                               2
                               ↑
                               1
                          α-D-Galp The repeating unit of the O-polysaccharide of *K. pneumoniae* serotype O2afg, and carbapenem resistant *K. pneumoniae* (CRKP) ST258 strains consists of:

→3-β-D-Galf-(1→3)-α-D-Galp-(1→.
                              4
                              ↑
                              1
                         α-D-Galp The repeating unit of the O-polysaccharide of *K. pneumoniae* serotype O8 consists of a pentasaccharide:

[→3)-β-D-Galf-(1→3)-α-D-Galp-(1→]$_m$-[→3)-α-D-Galp-(1→3)-α-D-Galp-(1→]$_n$
                 2 or 6
                   ↑
                O-acetyl It is the objective of the present invention to provide a well-defined synthetic saccharide of general formula (I) that is related *Klebsiella pneumoniae* O-polysaccharide and contains a protective immunogenic O-antigen epitope i.e. an O-antigen epitope that elicits antibodies which protect against diseases caused by *Klebsiella pneumoniae*. Said saccharide can be conjugated to an immunogenic carrier to provide a conjugate and pharmaceutical composition thereof that are useful for prevention and/or treatment of diseases associated with *Klebsiella pneumoniae*. Furthermore, the synthetic saccharide of general formula (I) is useful as marker in immunological assays for detection of antibodies against *Klebsiella pneumoniae* bacteria.

The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of a saccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. By keeping a certain distance between the saccharide and the immunogenic carrier the shielding of immunogenic saccharide epitopes by the structure of the immunogenic carrier (e.g. secondary structure of a carrier protein) is avoided. In addition, the linker provides greater efficiency of coupling with saccharides by reducing steric hindrance of reactive groups (Methods in Molecular Medicine 2003, 87, 153-174). More specifically, one extremity of the linker is connected to the exocyclic oxygen atom at the anomeric center of the reducing-end monosaccharide and the other extremity is connected via the nitrogen atom with the interconnecting molecule, or directly with the immunogenic carrier or the solid support.

Any linker for saccharide conjugates (e.g. saccharide-carrier protein conjugate, antibody-drug conjugate) known in the art can be used within the present invention. From the large number of publications directed to saccharide carrier protein conjugates the person skilled in the art can readily envision suitable linkers for the herein disclosed saccharides and conjugates (see "Antimicrobial glycoconjugate vaccines: an overview of classic and modern approaches for protein modification" in Chem Soc Rev. 2018, Advance Article, DOI: 10.1039/C8CS00495A; Acc Chem Res 2017, 50, 1270-1279) since the used linker, i.e. its length and linkage type, does not significantly influence the immunogenicity of a saccharide conjugate (see PLoS ONE 2017, 12(12): e0189100, J. Immun. Meth. 1996, 191, 1-10). Such suitable linkers are harmless (i.e. non-toxic) and non-immunogenic (i.e. do not lead to the formation of nonprotective antibodies on immunization with a conjugate) and include but are not restricted to commercially available bifunctional polyethylene glycol (Journal of Controlled Release 2013, 172, 382-389, J. Immun. Meth. 1996, 191, 1-10), glutaric acid derivatives (J. Org. Chem. 2005, 70(18), 7123-7132), adipic acid derivatives, squarate derivatives, alkynes, N-hydroxysuccinimides, such as the commercially available MFCO-NHS (monofluoro-substituted cyclooctyne N-hydroxysuccinimide ester), maleimides (as disclosed in Acc Chem Res 2017, 50, 1270-1279), or hydrophilic alkyl phosphinates and sulfonyls (as described in WO2014080251A1).

As used herein, the term "interconnecting molecule" refers to a bifunctional molecule containing functional group X and functional group Y, wherein functional group X is capable of reacting with the terminal amino group on the linker L and the functional group Y is capable of reacting with a functionality present on an immunogenic carrier or on a solid support. FIG. 3 displays examples of commercially available interconnecting molecules, but does not restrict the interconnecting molecules that can be used according to the present invention to the examples displayed herein.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:

mineral-containing compositions, including calcium salts and aluminium salts (or mixtures thereof). Calcium salts include calcium phosphate. Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminium hydroxide and aluminium phosphate may be also used. The invention can use any of the "hydroxide" or "phosphate" adjuvants that are in general used as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i. e. aluminium hydroxyphosphate sulfate). They may be obtained by precipitation, and the reaction conditions and concentrations during precipitation influence the degree of substitution of phosphate for hydroxyl in the salt. Mixtures of both an aluminium hydroxide and an aluminium phosphate can be employed in the formulation according to the present invention;

saponins, which are a heterologous group of sterol glycosides and triterpenoid glycosides that are found in the bark, leaves, stems, roots and even flowers of a wide range of plant species. Saponins from the bark of the *Quillaia saponaria*, Molina tree have been widely studied as adjuvants. Saponins can also be commercially obtained from *Smilax ornata* (sarsaprilla), *Gypsophilla paniculata* (brides veil), and *Saponaria oficianalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS 7, QS 17, QS 18, QS2 1, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 pm in diameter, more preferably 200 nm to 30 pm in diameter, or 500 nm to 10 pm in diameter) formed from materials that are biodegradable and non-toxic. Such non-toxic and biodegradable materials include, but are not restricted to poly($\alpha$-hydroxy acid), polyhydroxybutyric acid, polyorthoester, polyanhydride, polycaprolactone;

CD1d ligands, such as an $\alpha$-glycosylceramide, phytosphingosine-containing $\alpha$-glycosylceramides, OCH, KRN7000 [(2S,3S,4R)-1-O-($\alpha$-D-galactopyranosyl)-2-(N-hexacosanoylamino)-1,3,4-octadecanetriol], CRONY-101, 3"-sulfo-galactosyl-ceramide, 7DW8-5 (Funakoshi Co., Ltd.)

immunostimulatory oligonucleotides, such CpG motif containing ones (a dinucleotide sequence containing an unmethylated cytosine residue linked by a phosphate bond to a guanosine residue), or CpI motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as the TLR4 antagonist E5564;

oil emulsions (e.g. Freund's adjuvant);

Zwitterionic polysaccharides (ZPSs), comprising both positive and negative charges on adjacent monosaccharide units;

Outer membrane vesicles (OMVs).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can:

direct and optimize immune responses that are appropriate or desirable for the vaccine;

enable mucosal delivery of vaccines, i.e. administration that results in contact of the vaccine with a mucosal surface such as buccal or gastric or lung epithelium and the associated lymphoid tissue;

promote cell-mediated immune responses;

enhance the immunogenicity of weaker immunogens, such as highly purified or recombinant antigens;

reduce the amount of antigen or the frequency of immunization required to provide protective immunity; and improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:

increasing the biological or immunologic half-life of antigens;

improving antigen delivery to antigen-presenting cells (APCs), as well as antigen processing and presentation by the APCs e.g., by enabling antigen to cross endosomal membranes into the cytosol after ingestion of antigen-adjuvant complexes by APC;

mimicking danger inducing signals from stressed or damaged cells, which serve to initiate an immune response;

inducing the production of immunomodulatory cytokines;

biasing the immune response towards a specific subset of the immune system; and—blocking the rapid dispersal of the antigen challenge.

Saccharides are known by the person skilled in the art as TI-2 (T cell independent-2) antigens and poor immunogens, if they are not zwitterionic. Therefore, to produce a saccharide-based vaccine, said saccharides are conjugated to an immunogenic carrier to provide a conjugate, which presents an increased immunogenicity in comparison with the saccharide. In this context the term "immunogenic carrier" is defined as a structure, which is conjugated to the saccharide to form a conjugate that presents an increased immunity in comparison with the saccharide per se. Thus, the conjugation of the saccharides to the immunogenic carrier, preferably protein carrier, has as effect the stimulation of the immune response against said saccharide, without inducing an immune response against the said immunogenic carrier.

Hence, the present invention is directed to a saccharide of general formula (I)

(I)

wherein $U_1$ represents

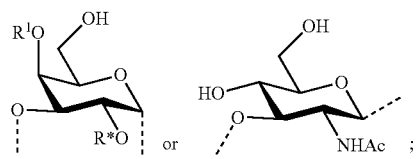
;

$U_2$ represents

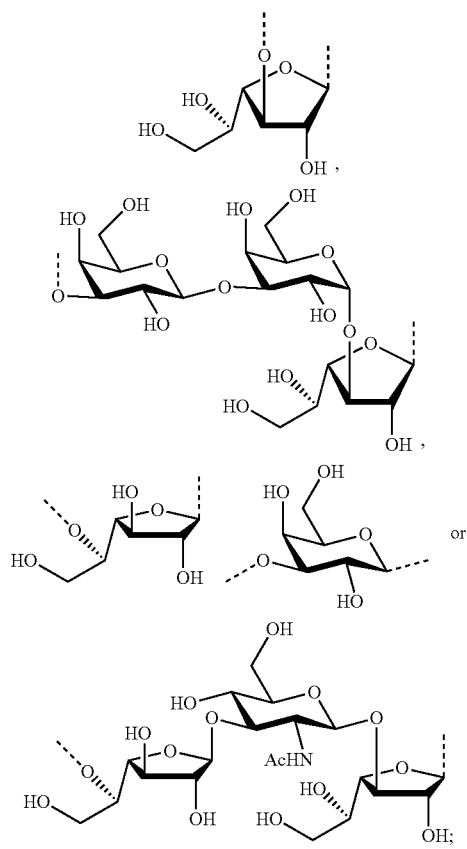

$U_3$ represents

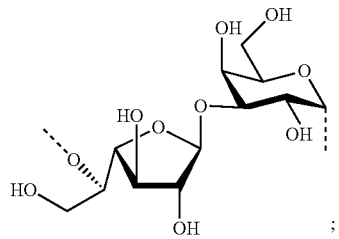
;

$U_4$ represents

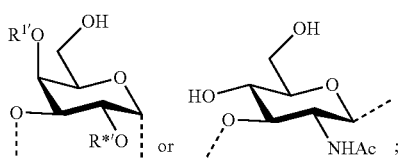
;

$U_5$ represents a covalent bond or

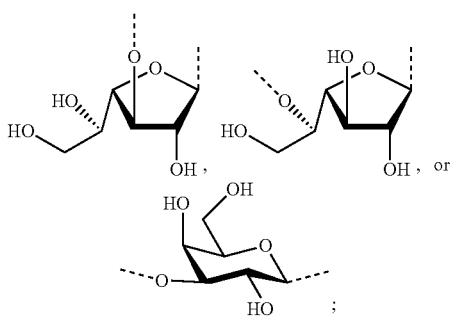
;

$U_6$ represents

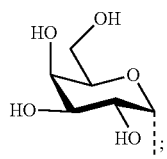
;

$R^1$, $R^{1'}$, $R^*$ and $R^{*'}$ represent independently from each other —H or $U_6$, wherein $R^1$ and $R^*$ cannot be simultaneously —$U_6$ and $R^{1'}$ and $R^{*'}$ cannot be simultaneously —$U_6$, L represents a linker;

E  represents  —$NH_2$, —$N_3$, —CN, —O—$NH_2$, —CH=$CH_2$, —C≡CH, —Br, —Cl, —I, —$CO_2R'$, —CO-(3-sulfo-N-hydroxysuccinimidyl), —CO-(dibenzocyclooctyne-sulfo-N-hydroxysuccinimidyl), —CONH—$NH_2$, —OH, —SH, or —SAc;

R' represents —H, -Me, -Et,

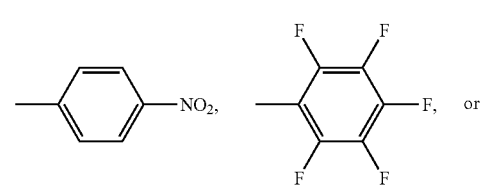

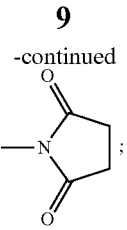

n is an integer from 1 to 20;
m is an integer from 0 to 20;
k is an integer selected from 0 to 20;
x and y are independently of each other the integer 0 or 1; and
when $U_1$ and $U_2$ are monosaccharides and n is 1, m, x, and y are not 0 at the same time;
or anomers, hydrates, or pharmaceutically acceptable salts thereof.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen atom (i.e. the oxygen of —O-L-NH$_2$) and the NH$_2$-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the NH$_2$-group) consists of 2 to 6 atoms, these are preferably carbon atoms. In case the shortest chain consists of 4 to 8 atoms, the chain may contain 1 or 2 heteroatoms selected from O, N and S. In case the shortest chain consists of 9 to 14 atoms, the chain may contain 1, 2, 3, or 4 heteroatoms selected from O, N and S.

It is also preferred that the linker -L-, or the shortest chain is fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L- may also contain amide (—NH—CO—, —CO—NH—) and/or urea (—NH—CO—NH—) residues and preferably only one amide or urea residue. The linker may also contain substituents and preferably two substituents such as $R^{10}$ and $R^{11}$ or four substituents such as $R^{10}$, $R^{11}$, $R^{15}$ and $R^{14}$, which have the meanings as defined herein and which are preferably selected from: —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$, and —N(C$_2$H$_5$)$_2$.

In case the linker -L- is fluorinated, more than two substituents —F are preferred.

Preferably the linker -L- is selected from: —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$O—CH$_2$—, —CH$_2$—O—(CH$_2$)$_2$—, —(CH$_2$)$_2$O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$-;

wherein

-L$^a$- is selected from: —(CH$_2$)$_o$—, —(CF$_2$)$_o$—, —(CH$_2$—CH$_2$—O)$_o$—C$_2$H$_4$—, —(CH$_2$—CH$_2$—O)$_o$C—H$_2$—, —(CR$^{10}$R$^{11}$)$_o$—,

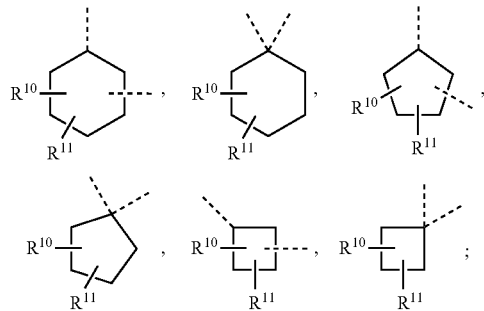

-L$^b$- and -L$^c$- are independently of each other selected from: —O—, —NH—C(O)—NH—, —NH—C(S)—NH—, —NH—C(O)—, —C(O)—NH—, —NH—C(O)—O—, —NR$^9$—, —NR$^{18}$—, —SO$_2$—, —NH—CO—CH$_2$—NH—,

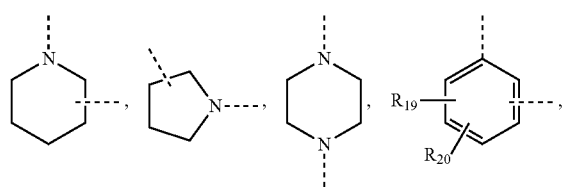

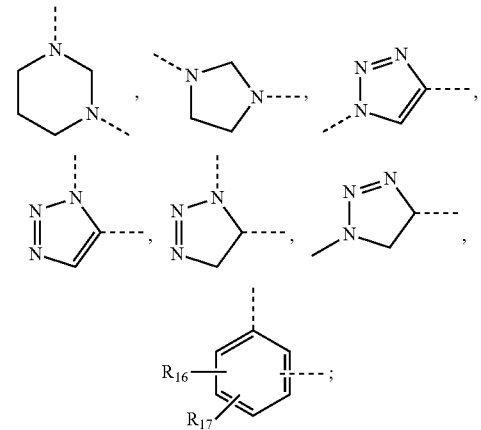

-L$^d$- represents —(CH$_2$)$_q$—, —(CF$_2$)$_q$—, —(CR$^{12}$R$^{13}$)$_g$—, —(CH$_2$—CH$_2$—O)$_q$C$_2$H$_4$—, —(CH$_2$—CH$_2$—O)$_q$—CH$_2$—,

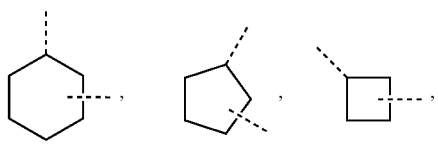

-continued

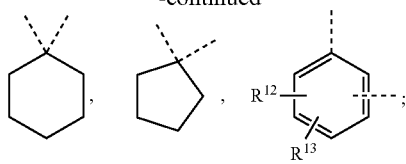

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—,

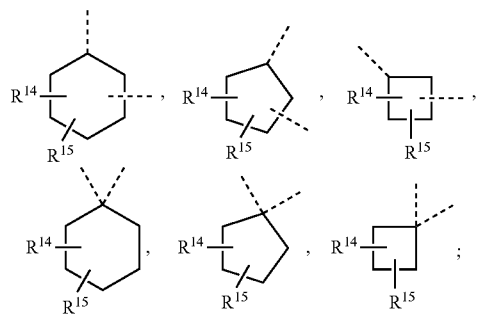

R$^9$ and R$^{18}$ are independently of each other selected from: —CH$_3$, —C$_2$H$_5$, —C$_3$H$_7$ and —C(O)CH$_3$;
R$^{10}$, R$^{11}$, R$^{12}$, R$^{13}$, R$^{14}$, R$^{15}$, R$^{16}$, R$^{17}$, R$^{19}$, R$^{20}$, R$^{21}$ and R$^{22}$ are independently of each other selected from: —H, —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$ and —N(C$_2$H$_5$)$_2$;
o, q, p1 and p2 are independently of each other an integer selected from 1, 2, 3, 4, 5, 6, 7, 8, 9, and 10.
More preferred, -L- represents -L$^a$-, -L$^a$-L$^e$-, -L$^a$-L$^b$-L$^e$-, or -L$^a$-L$^d$-L$^e$-;
-L$^a$- represents —(CH$_2$)$_o$—, —(CH$_2$—CH$_2$—O)$_o$—C$_2$H$_4$—, or —(CH$_2$—CH$_2$—O)$_o$—CH$_2$;
-L$^b$- represents —O—, —NH—CO—NH—, —NH—CO—CH$_2$—NH—, —NH—CO—; -L$^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;
-L$^e$- represents —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and
o, q, p1 and p2 are independently of each other an integer selected from 1, 2, 3, 4, 5, and 6, with the proviso that L is not —C$_3$H$_6$— if -E is —NH$_2$.
Still more preferably, -L-E represents -L$^a$-E, -L$^a$-L$^e$-E, -L$^a$-L$^b$-L$^e$-E, or -L$^a$-L$^d$-L$^e$-E;
-L$^a$- represents —(CH$_2$)$_o$—, —(CH$_2$—CH$_2$—O)$_o$—C$_2$H$_4$—, or —(CH$_2$—CH$_2$—O)$_o$—CH$_2$;
-L$^b$- represents —O—, —NH—CO—NH—, —NH—CO—CH$_2$—NH—, —NH—CO—; -L$^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;
-L$^e$- represents —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and
-E represents —NH$_2$, —N$_3$, —O—NH$_2$, —CH=CH$_2$, —C≡CH, —Br, —Cl, —I, —COOH, —COOCH$_3$, —COOC$_2$H$_5$, —CO$_2$R', —CO-(3-sulfo-N-hydroxysuccinimidyl), —CO-(dibenzocyclooctyne-sulfo-N-hydroxysuccinimidyl), —CONH—NH$_2$, —O, or —SH;

R' represents

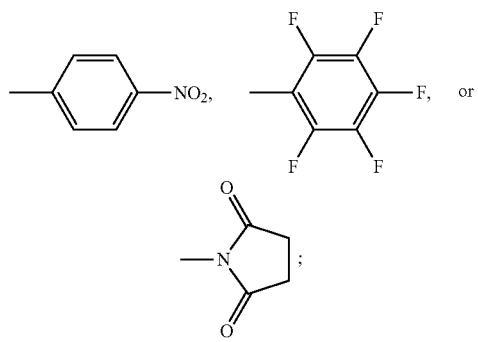

o, q, p1 and p2 are independently of each other an integer selected from 1, 2, 3, 4, 5, and 6, with the proviso that -L-E is not —C$_3$H$_6$—NH$_2$.

Still most preferred, the saccharide of the formula (I) has the residue —O-L-E selected from the group consisting of:

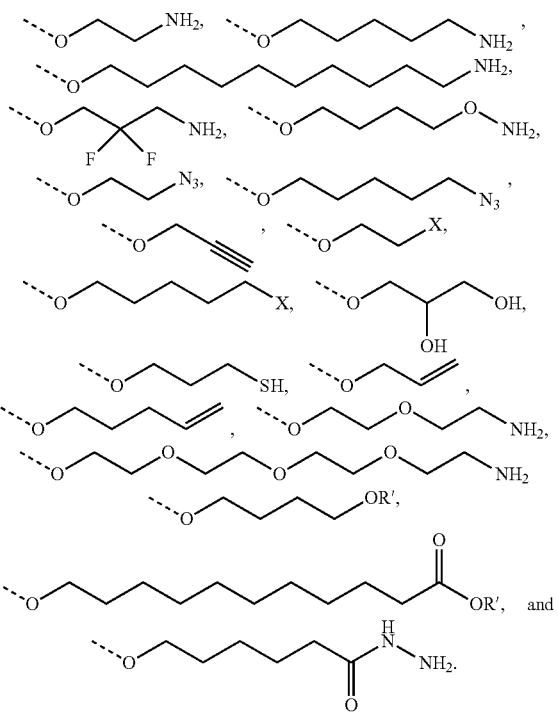

wherein R' represents —H, -Me, -Et,

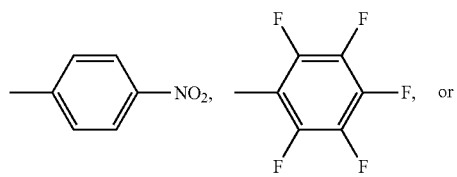

-continued

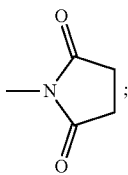

X represents —Br, —Cl, —I, —CO$_2$H, or —SAc.

In a more preferred embodiment, —O-L-E is selected from the group consisting of:

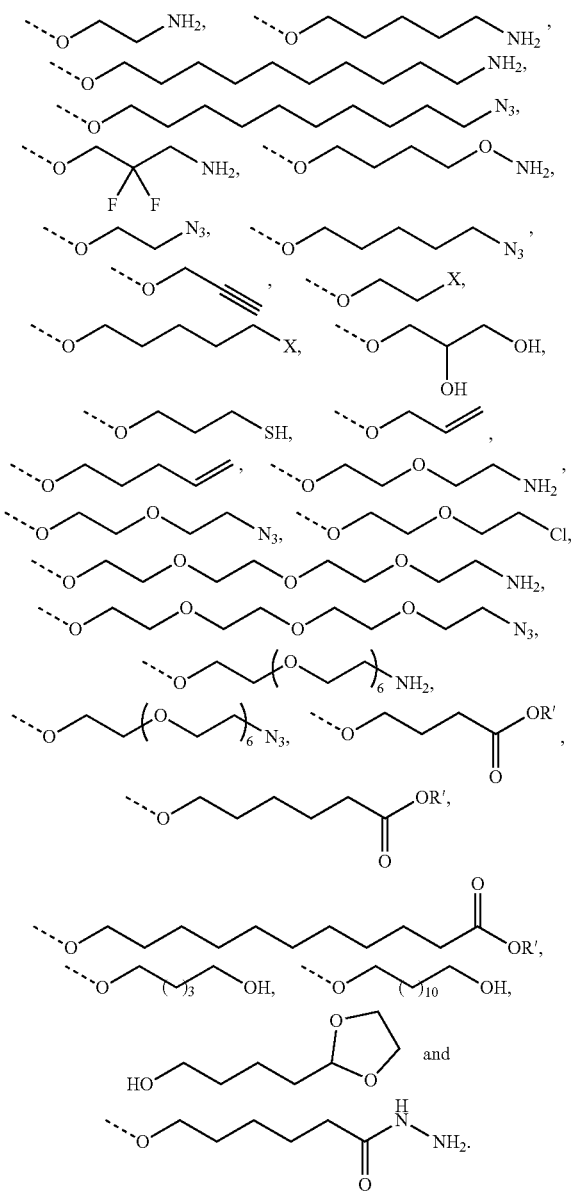

wherein R' represents —H, -Me, -Et, 4-nitrophenyl, pentafluorophenyl, or —N-hydroxysuccinimidyl, -(3-sulfo-N-hydroxysuccinimidyl), or -(dibenzocyclooctyne-sulfo-N-hydroxysuccinimidyl);

X represents —Br, —Cl, —I, —CO$_2$H, or —SAc.

Particularly preferred, —O-L-E is selected from the group consisting of:

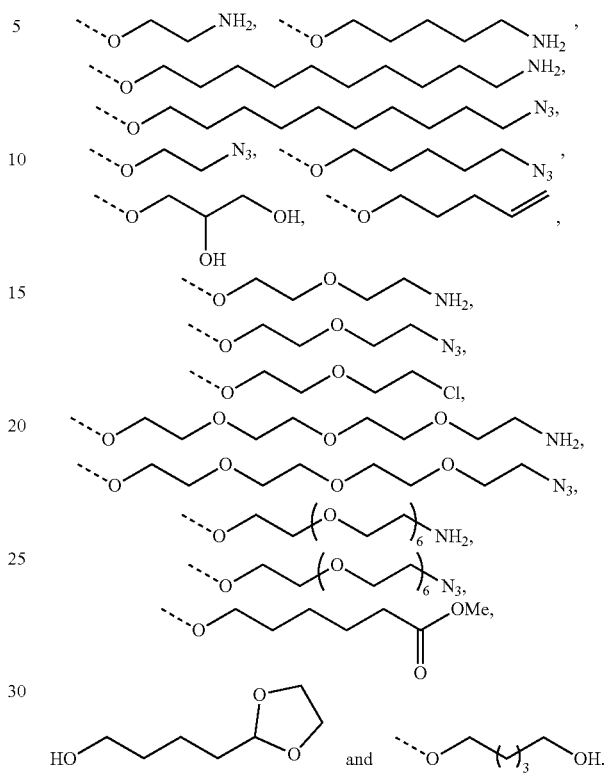

The anomers of saccharides of the present invention mean the α/β-anomers at C-1-position to which the group —O-L-E is bounded. It is clear for the skilled person in the art of carbohydrate chemistry that the stereochemistry of the glycosidic bond is defined by the stereochemistry indicated for the anomeric center of the sugar fragment $U_1$, and $U_2$ in the general formula (I).

The saccharides of the present invention are hygroscopic and thus can build various hydrates thereof. Preferred, molar ratio of water molecule to the saccharide is in the range of 1 to 20, more preferred, 1 to 10, most preferred, 5-10.

The saccharides of the present invention bear basic and/or acidic substituents and they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

Surprisingly, it was found that a saccharide of general formula (I) contains an immunogenic protective epitope and is able to induce a protective immune response against *K. pneumoniae* bacteria or serotypes O1, O2, O2ac, O8 and carbapanem-resistant *Klebsiella pneumoniae* ST258 in a human and/or animal host. The saccharide of general formula (I) elicits antibodies that are cross-reacting with the *K. pneumoniae* serotype O1, O2, O2ac, O8 O-polysaccharide as well as carbapanem-resistant *Klebsiella pneumoniae* ST258 O-polysaccharide, and also opsonize them for killing by phagocytes.

The saccharides of the present invention overcome all the problems associated with the saccharides produced from bacterial sources and conjugates thereof in terms of purity and easiness of production. Even though it is an established and accepted method, there are several drawbacks to this approach. First, it requires culturing large volumes of a pathogenic species of interest for the generation of the native carbohydrate, followed by harvesting and purification of the carbohydrate. Depending on the biosafety level of the species of interest, as well as the ease of culturing, this step can present a major hurdle regarding the expansion of the technique to novel pathogenic species. Further, it is well known that the isolation and purification of pure saccharides of defined length and structure from capsular polysaccharides of pathogenic bacteria is a tedious and sometimes not feasible process. Firstly, the production of capsular polysaccharides requires optimization of the growth conditions. Secondly, depolymerization conditions under which the structural integrity of the constituting monosaccharides is maintained need to be found. Finally, purification conditions enabling the isolation of the pure saccharide of defined length and structure need to be determined. Besides usual contaminants, such as cellular polysaccharides, nucleic acids and proteins, also the undesired saccharides obtained through the depolymerization process, must be excluded. Thus, the production of pure saccharides of defined structure and length from bacterial sources is a tedious, almost impossible process.

Preferred, are synthetic saccharides of general formula (I),

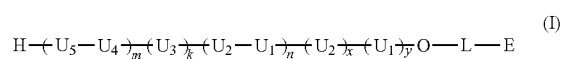

(I)

wherein $U_1$ represents

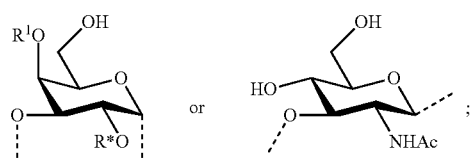

$U_2$ represents

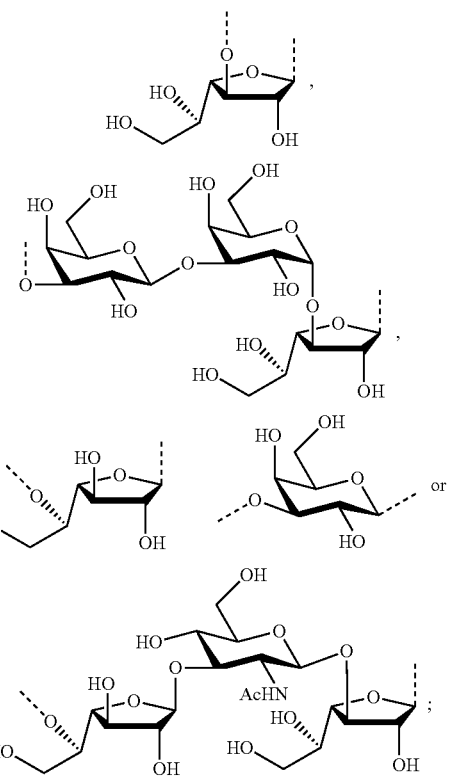

$U_3$ represents

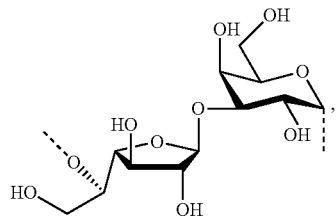

$U_4$ represents

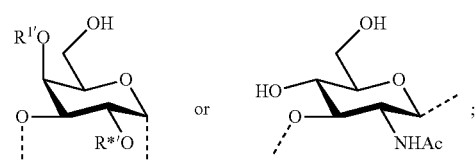

$U_5$ represents a covalent bond or

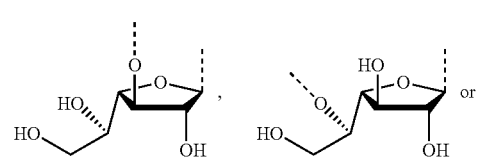

-continued

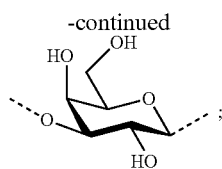

$U_6$ represents O

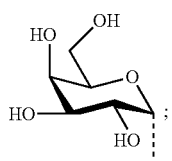

$R^1$, $R^{1'}$ $R^*$ and $R^{*'}$ represent independently from each other —H or $U_6$, wherein $R^1$ and $R^*$ cannot be simultaneously —$U_6$ and $R^{1'}$ and $R^{*'}$ cannot be simultaneously —$U_6$, L represents a linker;

E represents —$NH_2$, —$N_3$, —CN, —O—$NH_2$, —CH=$CH_2$, —C≡CH, —Br, —Cl, —I, —$CO_2R^1$, —CO-(3-sulfo-N-hydroxysuccinimidyl), —CO-(dibenzocyclooctyne-sulfo-N-hydroxysuccinimidyl), —CONH—$NH_2$, —OH, —SH, or —SAc;

R' represents —H, -Me, -Et,

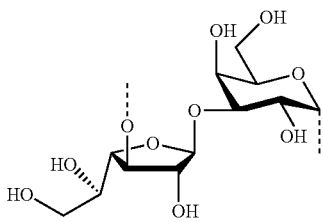

n is an integer from 1 to 20;
m is an integer from 0 to 20;
k is an integer selected from 0 to 10;
x and y are independently of each other the integer 0 or 1;
and
when $U_2$—$U_1$ represents

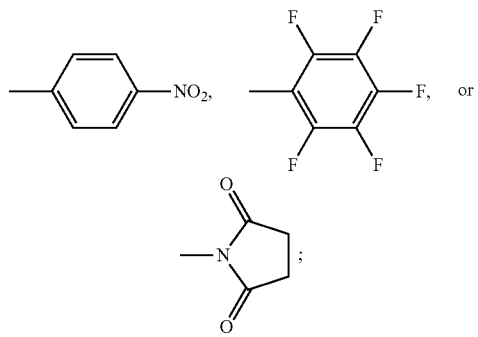

m cannot be 0 and
$U_5$—$U_4$ cannot be $U_2$—$U_1$;
when $U_1$ and $U_2$ are monosaccharides and n is 1, m, x, and y are not 0 at the same time;

or anomers, hydrates, or pharmaceutically acceptable salts thereof.

Preferred, are synthetic saccharides of general formula (I),

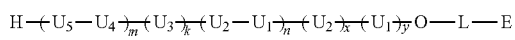

(I)

wherein
$U_1$ represents

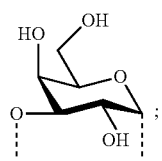

$U_2$ represents

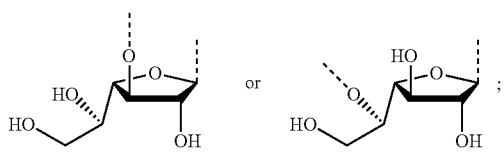

$U_4$ represents

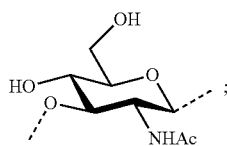

$U_5$ represents

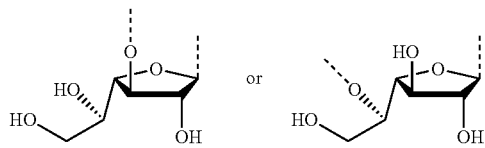

m represents an integer selected from 1 to 10;
k is 0;
n represents an integer selected from 1 to 10; and
x, y, L and E have the meanings as defined herein.

Preferred, are synthetic saccharides of general formula (I),

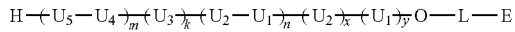

(I)

wherein $U_1$ represents

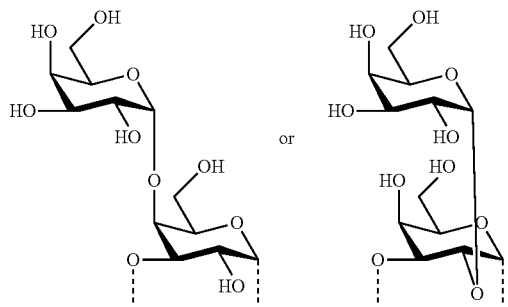

or $U_2$ represents

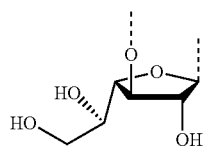

$U_3$ represents

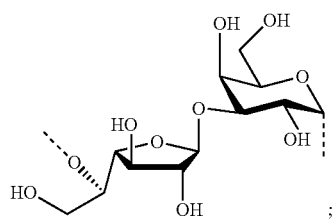

$U_5$ represents a covalent bond m, n, k, x, y, L and E have the meanings as defined herein.

Preferred, are synthetic saccharides of general formula (I), wherein $U_1$ represents

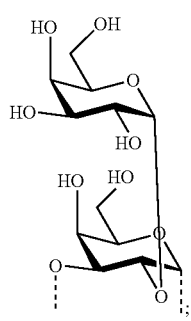

$U_2$ represents

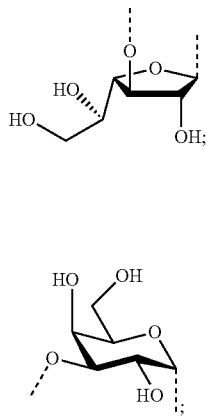

$U_4$ represents

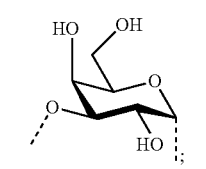

$U_5$ represents a covalent bond, or

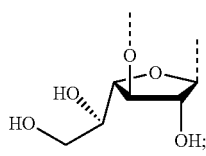

m is an integer selected from 0 and 1;
k is 0,
n, $U_3$, x, y, L and E have the meanings as defined herein.

Preferred, are synthetic saccharides of general formula (I), wherein $U_1$ represents O

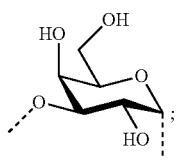

$U_2$ represents

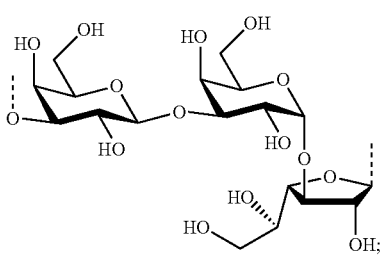

$U_4$ represents

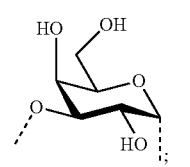

$U_5$ represents a covalent bond,

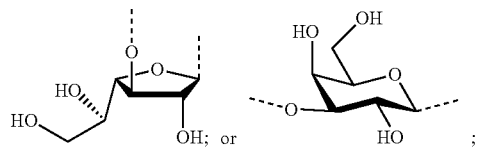

m is an integer selected from 0 and 1,
k is 0,
n, $U_3$, x, y, L and E have the meanings as defined herein.
Preferred, are synthetic saccharides of general formula (I), wherein
$U_2$ represents

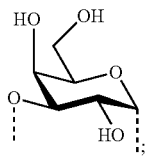

$U_2$ represents

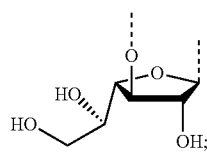

$U_4$ represents

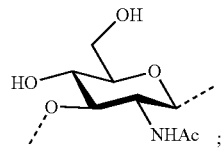

$U_5$ represents a covalent bond, or

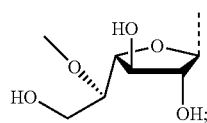

m is an integer from 1 to 10,
k is 0,
n, $U_3$, x, y, L and E have the meanings as defined in claim 1.
Preferred are synthetic saccharides of general formula (I-A), $$H\!-\!(U_5\!-\!U_4)_m\!-\!(U_2\!-\!U_1)_n\!-\!(U_2)_x\!-\!(U_1)_y\!-\!O\!-\!L\!-\!E \qquad (I\text{-}A)$$

wherein
$U_1$ represents

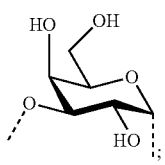

$U_2$ represents

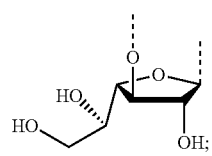

$U_4$ represents

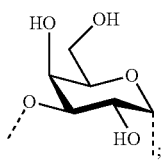

$U_5$ represents a covalent bond or

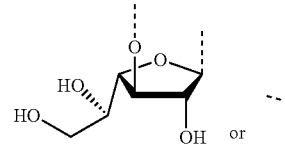

L, E, m, n, x, and y have the same meanings as defined herein, or anomers, hydrates, or pharmaceutically acceptable salt of these saccharides.

As defined above, $U_1$ and $U_2$ are monosaccharides and thus when n is 1, m, x, and y are not 0 at the same time;

Preferred, are synthetic saccharides of general formula (I-A),
wherein
$U_1$ represents

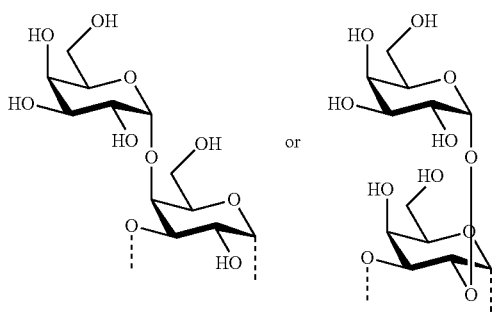

U₂ represents

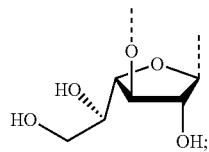

m is 0;

L, E, n, x, and y have the meanings as defined herein.

Preferred, are synthetic saccharides of general formula (I-A), wherein

U₁ represents

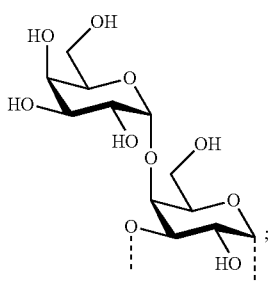

U₂ represents

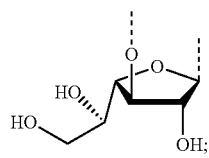

m is 0;

L, E, n, x, and y have the meanings as defined herein.

Preferred, are synthetic saccharides of general formula (I-A), wherein

U₁ represents

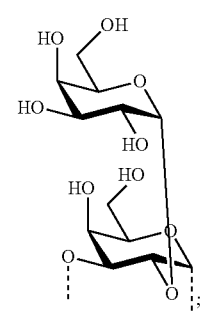

U₂ represents

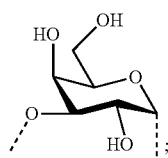

U₄ represents

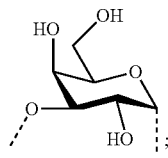

U₅ represents a covalent bond,

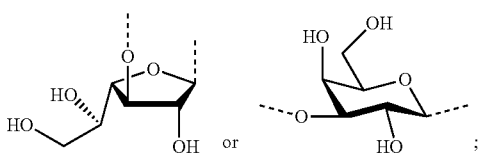

m is an integer selected from 0 and 1;

L, E, n, x, and y have the meanings as defined herein.

Preferred, are synthetic saccharides of general formula (I-A), wherein

U₁ represents

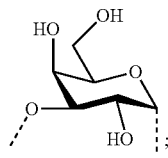

U₂ represents

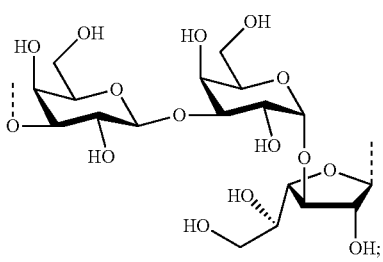

$U_4$ represents

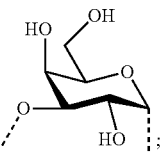

$U_5$ represents a covalent bond, or

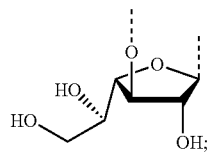

m is an integer selected from 0 and 1;
L, E, n, x, and y have the meanings as defined herein.
Preferred, are synthetic saccharides of general formula (I-A), wherein
$U_1$ represents

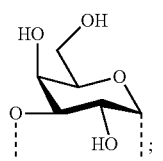

$U_2$ represents

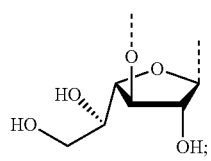

$U_4$ represents

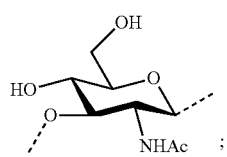

$U_5$ represents a covalent bond, or

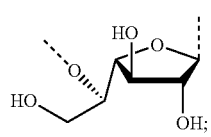

m is an integer from 1 to 10;
L, E, n, x, and y have the same meanings as defined herein.

Preferred, are synthetic saccharides of general formula (I-A), wherein
$U_1$ represents

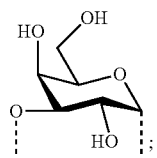

$U_2$ represents

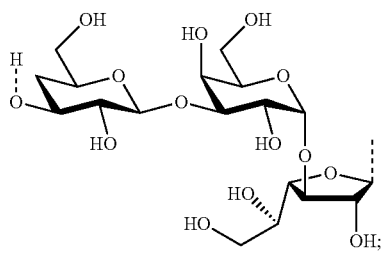

m, x, and y are 0;
L, E, and n have the same meanings as defined herein.
Preferred, are synthetic saccharides of general formula (I-A), wherein
$U_1$ represents

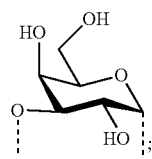

$U_2$ represents

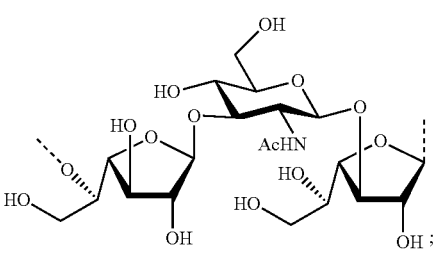

m, x, and y are 0;
L, E, and n have the same meanings as defined herein.
Preferred, are synthetic saccharides of general formula (I-A), wherein
$U_1$ and $U_4$ represent

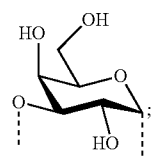

$U_2$ and $U_5$ represent

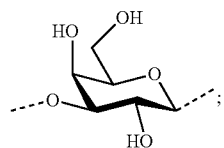

m is an integer from 1 to 10.

L, E, n, x, and y have the same meanings as defined herein.

As defined above, $U_1$ and $U_2$ are monosaccharides and thus when n is 1, m, x, and y are not 0 at the same time;

More preferred, the saccharide of general formula (I-A), wherein n is an integer from 1 to 10.

Preferred, are also synthetic saccharides of general formula (I-B),

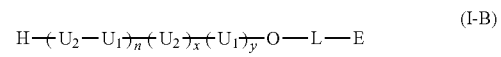

(I-B)

wherein $U_1$ represents

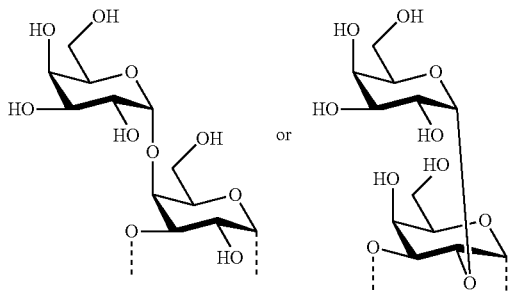

$U_2$ represents

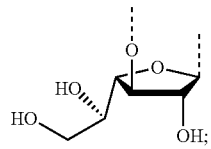

n is an integer selected from 1, 2, 3, 4, 5, 6, 7, 8 and 9, x and y are 1, and

L and E have the meanings as defined herein.

Hence, within the scope of the present invention falls also a synthetic saccharide of any one of formulae (II-1)-(II-17):

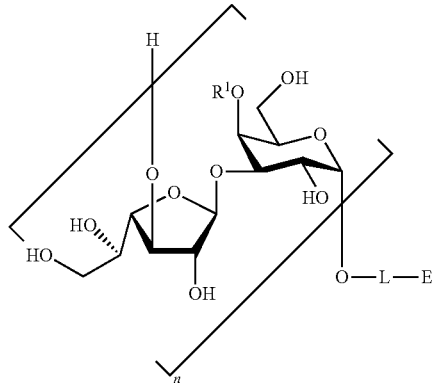

(II-1)

wherein n, $R^1$, m, L and E have the same meanings as defined above when $R^1$ is —H, n is an integer from 2 to 20, preferably, n is an integer from 2 to 12;

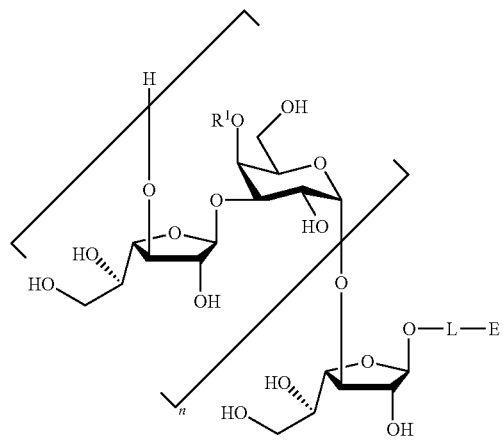

(II-2)

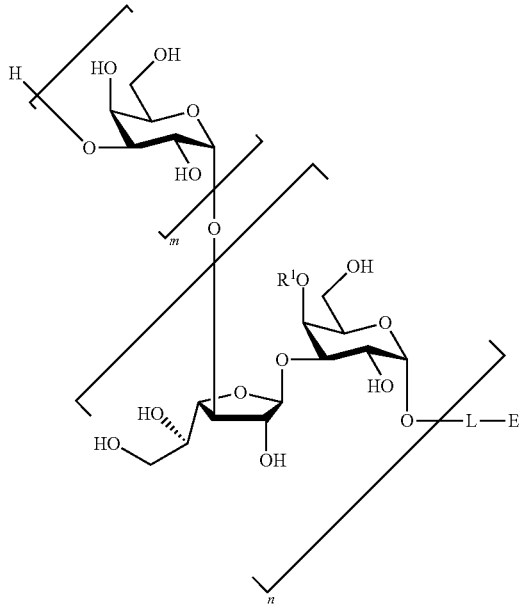

(II-3)

-continued
(II-4)
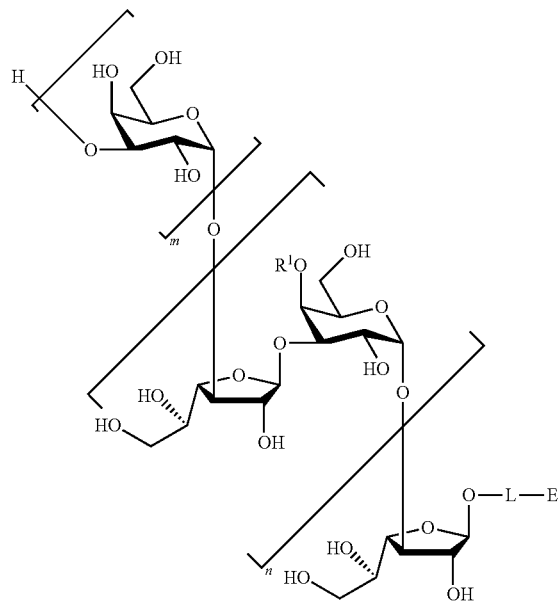
(II-5)
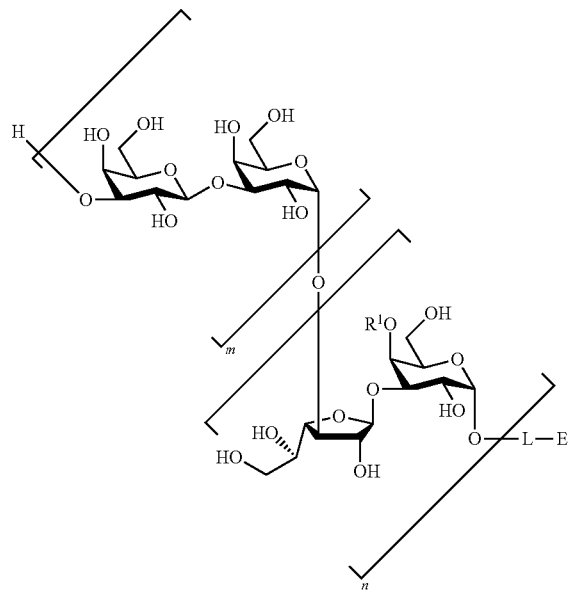
(II-6)
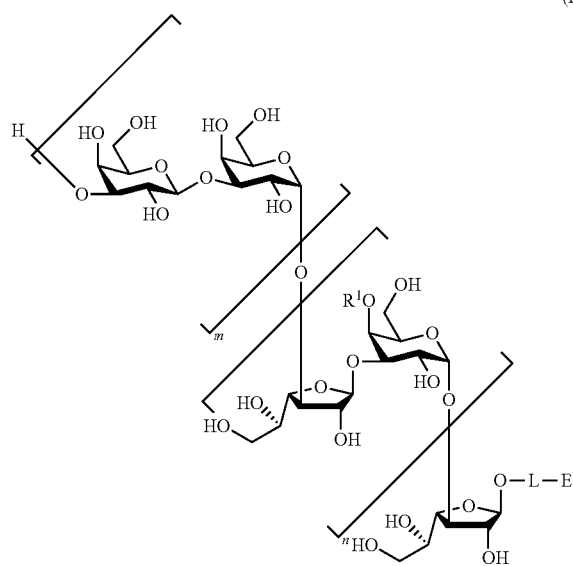
(II-7)

-continued
(II-8)
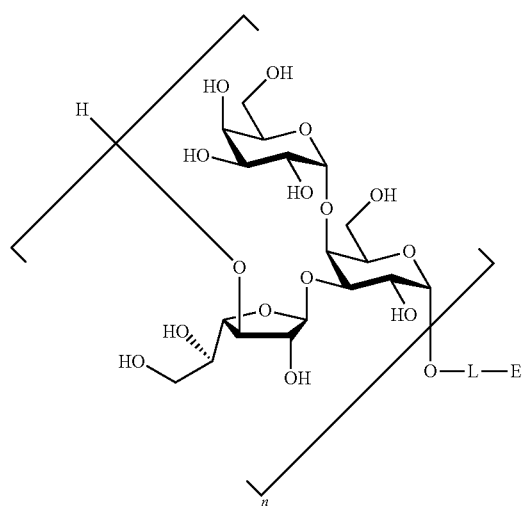
(II-9)
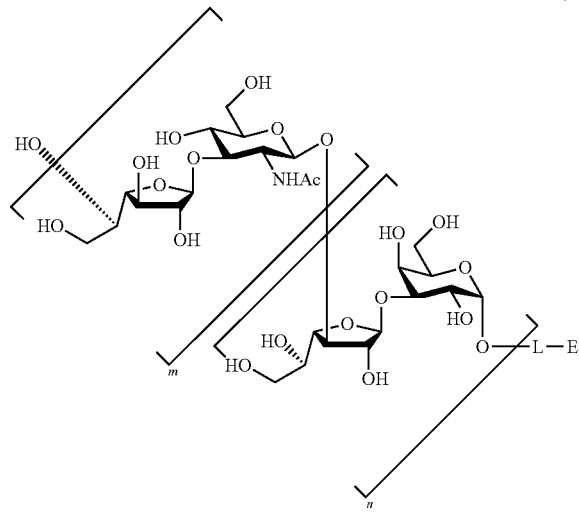
(II-10)
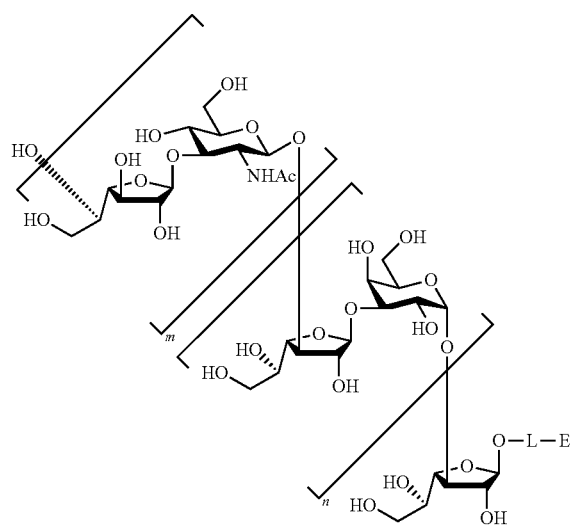
(II-11)
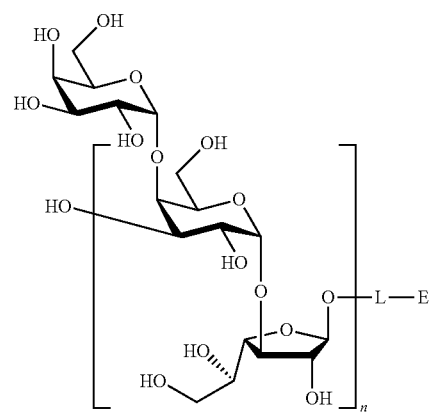
(II-12)
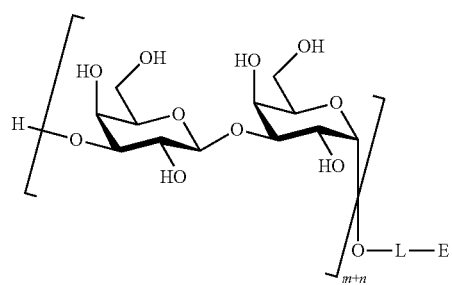
(II-13)
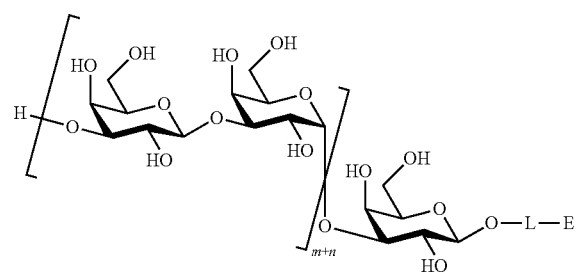

-continued
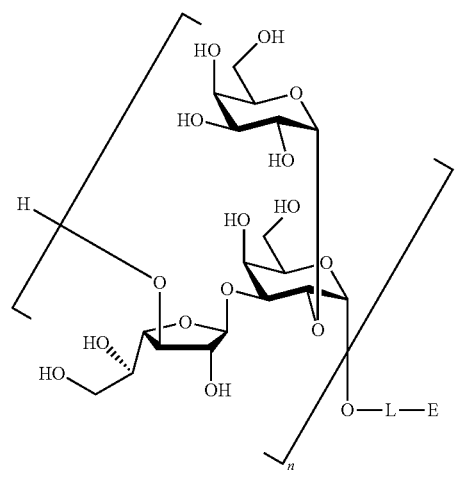
(II-14)
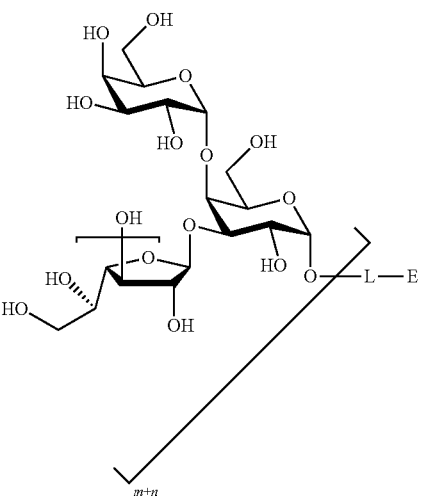
(II-15)
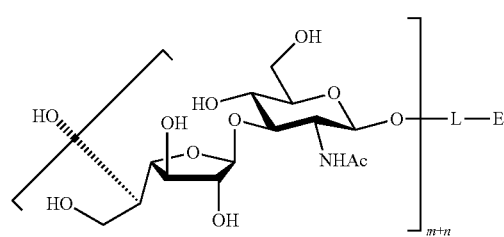
(II-16)
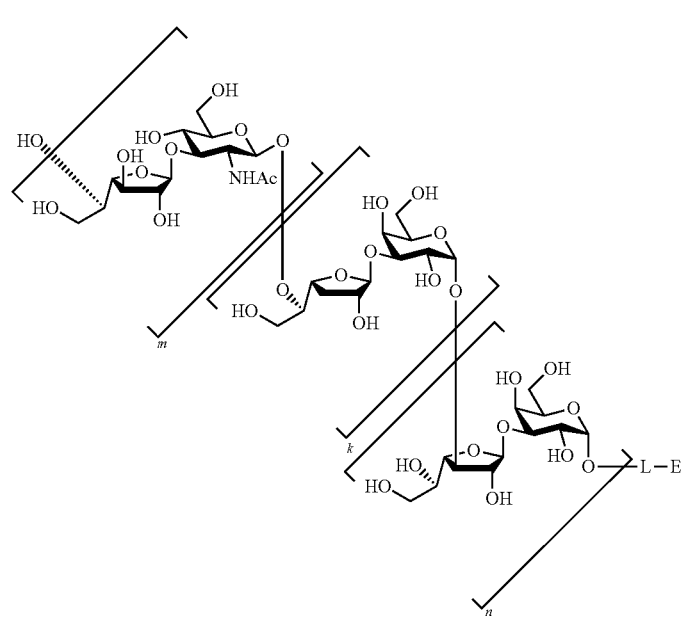
(II-17)

wherein $R^1$, m, n, k, L and E have the same meanings as defined above, n and m are integers independently selected between 1 to 20, preferably 1 to 10 and k is an integer from 0 to 20, preferably from 0 to 10.

Preferably, the linker -L- represents in the general formulae (I), (I-A), (I-B) and (II-1)-(II-17)

-$L^a$-, -$L^a$-$L^e$-, -$L^a$-$L^b$-$L^e$-, or -$L^a$-$L^d$-$L^e$-; wherein

-$L^a$- represents —$(CH_2)_o$—, —$(CH_2—CH_2—O)_o$ $C_2H_4$—, or —$(CH_2—CH_2—O)_o$—$CH_2$—;

-$L^b$- represents —O—, —NH—CO—NH—, —NH—CO—$CH_2$—NH—, —NH—CO—; -$L^d$- represents —$(CH_2)_q$—, —$(CH(OH))_q$, —$(CF_2)_q$—, —$CH_2$—$CH_2$—$O)_q$$C_2H_4$—, or —$(CH_2—CH_2—O)_q$G-$CH_2$—;

-$L^e$- represents —$(CH_2)_{p1}$—, —$(CF_2)_{p1}$—, —$C_2H_4$ $(O—CH_2—CH_2)_{p1}$—, —$CH_2$—$(O—CH_2—CH_2)_{p1}$— or —$(CH_2)_{p1}$—O—$(CH_2)_{p2}$—; and o, q, p1 and p2 are independently of each other an integer selected from 1, 2, 3, 4, 5, and 6, with the proviso that L is not —$C_3H_6$— if -E is —$NH_2$.

Still more preferably, -L-E represents in the general formulae (I), (I-A), (I-B) and (II-1)-(II-17)

-$L^a$-E, -$L^a$-$L^e$-E, -$L^a$-$L^b$-$L^e$-E, or -$L^a$-$L^d$-$L^e$-E; wherein -$L^a$- represents —$(CH_2)_o$—, —$(CH_2—CH_2—O)_o$ $C_2H_4$—, or —$(CH_2—CH_2—O)_oC$—$H_2$;

-$L^b$- represents —O—, —NH—CO—NH—, —NH—CO—$CH_2$—NH—, —NH—CO—; -$L^d$- represents —$(CH_2)_q$—, —$(CH(OH))_q$, —$(CF_2)_q$—, —$CH_2$—$CH_2$—$O)_q$—$C_2H_4$—, or —$(CH_2—CH_2—O)_q$— $CH_2$—;

-$L^e$- represents —$(CH_2)_{p1}$—, —$(CF_2)_{p1}$—, —$C_2H_4$ $(O—CH_2—CH_2)_{p1}$—, —$CH_2$—$(O—CH_2—CH_2)_{p1}$— or —$(CH_2)_{p1}$—O—$(CH_2)_{p2}$—; and -E represents —$NH_2$, —$N_3$, —O—$NH_2$, —CH=$CH_2$, —C≡CH, —Br, —Cl, —I, —COOH, —$COOCH_3$, —$COOC_2H_5$, —$CO_2R^1$, —CO-(3-sulfo-N-hydroxysuccinimidyl), —CO-(dibenzocyclooctyne-sulfo-N-hydroxysuccinimidyl), —CONH—$NH_2$, —OH, or —SH;

R' represents

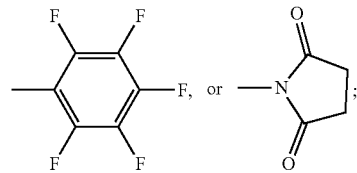

o, q, p1 and p2 are independently of each other an integer selected from 1, 2, 3, 4, 5, and 6, with the proviso that -L-E is not —$C_3H_6$—$NH_2$.

Still most preferred, the saccharide of the formula (I), (I-A), (I-B) and (II-1)-(II-17) has the residue —O-L-E selected from the group consisting of:

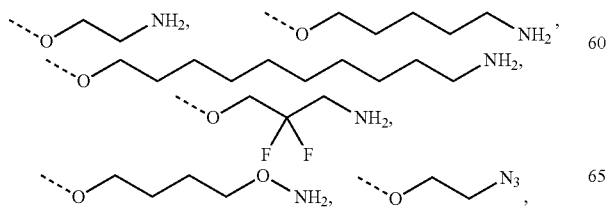

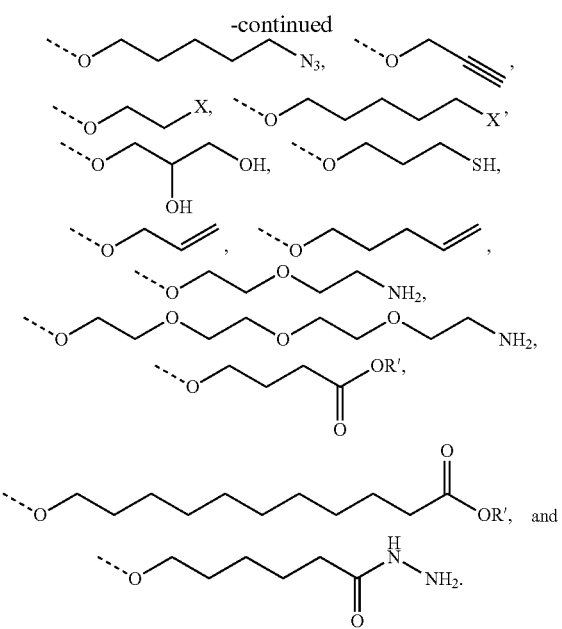

wherein R' represents —H, -Me, -Et,

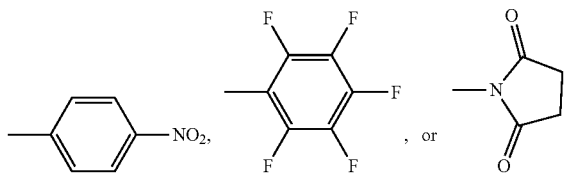

X represents —Br, —Cl, —I, —$CO_2H$, or —SAc;

Most preferred, the saccharide of the formula (I), (I-A), (I-B) or (II-1)-(II-17) has the residue —O-L-E selected from the group consisting of:

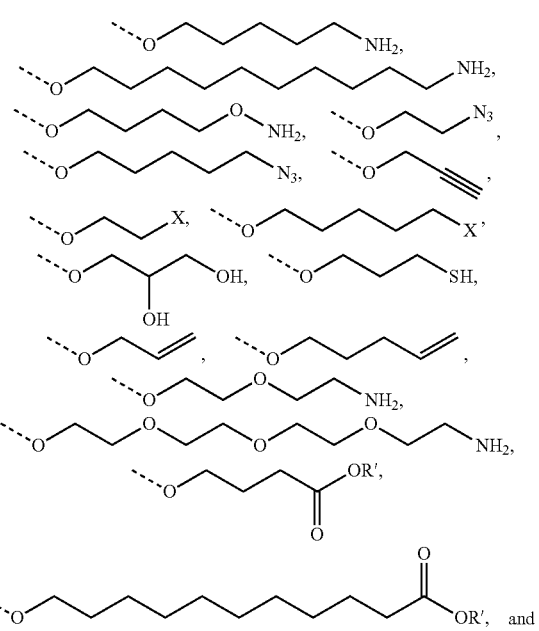

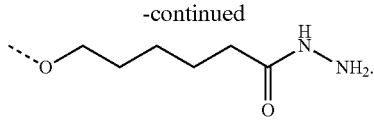

wherein R' represents —H, -Me, -Et,

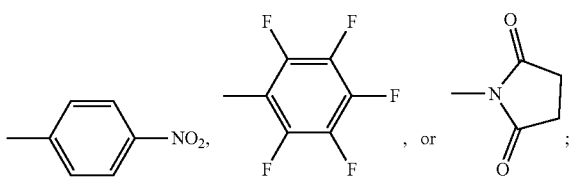

X represents —Br, —Cl, —I, —CO₂H, or —SAc.

In the most preferred embodiment, -L- represents —(CH₂)$_o$— and o is an integer selected from 4, 5 and 6. Hence, an especially preferred synthetic saccharide is a saccharide of any one of general formulae (I), (I-A), (I-B) and (II-1)-(II-17), wherein -L- represents —(CH₂)$_o$— and o is an integer selected from 4, 5 and 6.

In yet another preferred embodiment, the saccharide according to the present invention is selected from the group consisting of: compounds A-01-A-140, B-01-B-140, C-01-C-70, D-01-D-70, E-01-E-70, F-01-F-530, G-01-G-350, H-01-H-350, J-01-J-350, K-01-K-350, M-01-M-70, N-01-N-70, O-01-O-70, P-01-P-70 and Q-1-Q-700.

Most preferred, the saccharide according to the present invention is selected from the group consisting of: compounds A-01-A-O7, A-11-A17, A-21-A-27, A-31-A-37, A-41-A-47, A-51-A-57, A-61-A-67, A-71-A-77, A-81-A-87, A-91-A-97, A-101-A-107, A-111-A-117, A-121-A-127, A-131-A-137, F-01, F-19, F-27, F-31, F-36, F-54, F-62, F-66, F-71, F-89, F-97, F-101, F-106, F-124, F-132, F-136, F-141, F-159, F-167, F-171, F-176, F-194, F-202, F-206, F-211, F-229, F-237, F-241, F-246, F-264, F-299, F-281, F-272, F-276, F-307, F-311, F-316, F-334, F-342, F-346, F-351, F-414, F-417, F-421, F-426, F-444, F-452, F-456, F-461, F-479, F-487, F-491, F-496, F-514, F-522, F-526, K-O1, K-O6, K-11, K-26, K-31, K-36, K-51, K-56, K-61, K-76, K-81, K-86, K-101, K-106, K-111, K-126, K-131, K-136, K-151, K-156, K-161, K-176, K-181, K-186, K-201, K-206, K-211, K-226, K-231, K-236, K-251, K-256, K-261, K-276, K-281, K-286, K-301, K-306, K-311, K-326, K-331, K-336, O-01, O-02, O-03, O-06, O-07, O-08, O-11, O-12, O-13, O-16, O-17, O-18, O-21, O-22, O-23, O-26, O-27, O-28, 0-31, O-32, O-33, O-36, O-37, O-38, O-41, O-42, O-43, O-46, O-47, O-48, O-51, O-52, 0-53, O-56, O-57, O-58, O-61, O-62, O-63, O-66, O-67, O-88, P-01-P-03, P-06-P-08, P-11-P-13, P-16-P-18, P-21-P-23, P-26-P-28, P-31-P-33, P-36-P-38, P-41-P-43, P-46-P-48, P-51-P-53, P-56-P-58, P-61-P-63, P-66-P-68, Q-1, Q-26, Q-101, Q-151, Q-251, Q-301, Q-351, Q-376, Q-451, Q-501, Q-551, Q-601 and Q-651.

TABLE 1

(II-A)

[Structure with —O—L—E group, n1]

| —O—L—E | n1 | Compound No. |
|---|---|---|
| ⋯O—(CH₂)₅—NH₂ | 2 | A-01 |
| | 3 | A-02 |
| | 4 | A-03 |
| | 5 | A-04 |
| | 6 | A-05 |
| | 5 | A-06 |
| | 8 | A-07 |
| | 9 | A-08 |
| | 10 | A-09 |
| | 11 | A-10 |
| ⋯O—(CH₂)₁₀—NH₂ | 2 | A-11 |
| | 3 | A-12 |
| | 4 | A-13 |
| | 5 | A-14 |
| | 6 | A-15 |
| | 7 | A-16 |
| | 8 | A-17 |
| | 9 | A-18 |
| | 10 | A-19 |
| | 11 | A-20 |
| ⋯O—(CH₂)₅—N₃ | 2 | A-21 |
| | 3 | A-22 |
| | 4 | A-23 |
| | 5 | A-24 |
| | 6 | A-25 |
| | 7 | A-26 |
| | 8 | A-27 |
| | 9 | A-28 |
| | 10 | A-29 |
| | 11 | A-30 |
| ⋯O—(CH₂)₄—O—NH₂ | 2 | A-31 |
| | 3 | A-32 |
| | 4 | A-33 |
| | 5 | A-34 |
| | 6 | A-35 |
| | 7 | A-36 |
| | 8 | A-37 |
| | 9 | A-38 |
| | 10 | A-39 |
| | 11 | A-40 |
| ⋯O—(CH₂)₃—C(O)OH | 2 | A-41 |
| | 3 | A-42 |
| | 4 | A-43 |
| | 5 | A-44 |
| | 6 | A-45 |
| | 7 | A-46 |
| | 8 | A-47 |
| | 9 | A-48 |
| | 10 | A-49 |
| | 11 | A-50 |

TABLE 1-continued
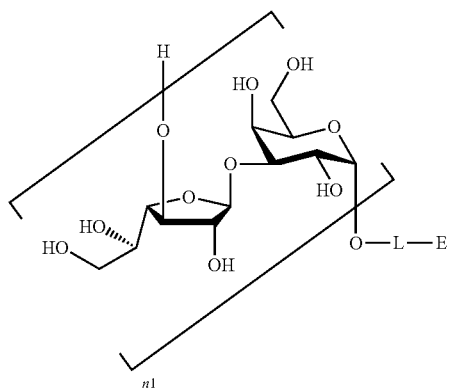
(II-A)
| —O—L—E | n1 | Compound No. |
|---|---|---|
| (CH2)10COOH ether | 2 | A-51 |
|  | 3 | A-52 |
|  | 4 | A-53 |
|  | 5 | A-54 |
|  | 6 | A-55 |
|  | 7 | A-56 |
|  | 8 | A-57 |
|  | 9 | A-58 |
|  | 10 | A-59 |
|  | 11 | A-60 |
| (CH2)5C(O)NHNH2 ether | 2 | A-61 |
|  | 3 | A-62 |
|  | 4 | A-63 |
|  | 5 | A-64 |
|  | 6 | A-65 |
|  | 7 | A-66 |
|  | 8 | A-67 |
|  | 9 | A-68 |
|  | 10 | A-69 |
|  | 11 | A-70 |
| (CH2)3SH ether | 2 | A-71 |
|  | 3 | A-82 |
|  | 4 | A-73 |
|  | 5 | A-74 |
|  | 6 | A-75 |
|  | 7 | A-76 |
|  | 8 | A-77 |
|  | 9 | A-78 |
|  | 10 | A-79 |
|  | 11 | A-80 |
| allyl (CH2)3 ether | 2 | A-81 |
|  | 3 | A-82 |
|  | 4 | A-83 |
|  | 5 | A-84 |
|  | 6 | A-85 |
|  | 7 | A-86 |
|  | 8 | A-87 |
|  | 9 | A-88 |
|  | 10 | A-89 |
|  | 11 | A-90 |
| propargyl ether | 2 | A-91 |
|  | 3 | A-92 |
|  | 4 | A-93 |
|  | 5 | A-94 |
|  | 6 | A-95 |
|  | 7 | A-96 |
|  | 8 | A-97 |
|  | 9 | A-98 |
|  | 10 | A-99 |
|  | 11 | A-100 |
TABLE 1-continued
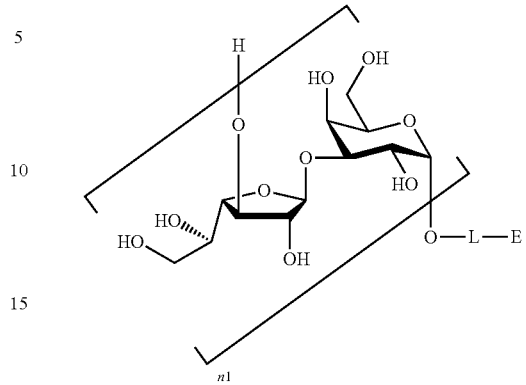
(II-A)
| —O—L—E | n1 | Compound No. |
|---|---|---|
| O(CH2)5Br | 2 | A-101 |
|  | 3 | A-102 |
|  | 4 | A-103 |
|  | 5 | A-104 |
|  | 6 | A-105 |
|  | 7 | A-106 |
|  | 8 | A-107 |
|  | 9 | A-108 |
|  | 10 | A-109 |
|  | 11 | A-110 |
| OCH2CH2OCH2CH2NH2 | 2 | A-111 |
|  | 3 | A-112 |
|  | 4 | A-113 |
|  | 5 | A-114 |
|  | 6 | A-115 |
|  | 7 | A-116 |
|  | 8 | A-117 |
|  | 9 | A-118 |
|  | 10 | A-119 |
|  | 11 | A-120 |
| O(CH2CH2O)3CH2CH2NH2 | 2 | A-121 |
|  | 3 | A-122 |
|  | 4 | A-123 |
|  | 5 | A-124 |
|  | 6 | A-125 |
|  | 7 | A-126 |
|  | 8 | A-127 |
|  | 9 | A-128 |
|  | 10 | A-129 |
|  | 11 | A-130 |
| OCH2CH(OH)CH2OH | 2 | A-131 |
|  | 3 | A-132 |
|  | 4 | A-133 |
|  | 5 | A-134 |
|  | 6 | A-135 |
|  | 7 | A-136 |
|  | 8 | A-137 |
|  | 9 | A-138 |
|  | 10 | A-139 |
|  | 11 | A-140 |

TABLE 2
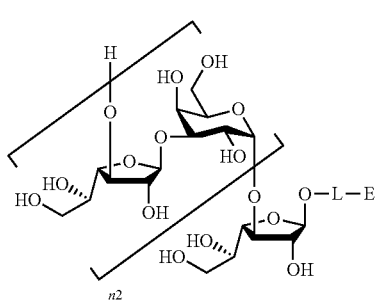
(II-B)
| —O—L—E | n2 | Compound No. |
|---|---|---|
| ~O~(~)₅~NH₂ | 1 | B-01 |
| | 2 | B-02 |
| | 3 | B-03 |
| | 4 | B-04 |
| | 5 | B-05 |
| | 6 | B-06 |
| | 7 | B-07 |
| | 8 | B-08 |
| | 9 | B-09 |
| | 10 | B-10 |
| ~O~(~)₁₀~NH₂ | 1 | B-11 |
| | 2 | B-12 |
| | 3 | B-13 |
| | 4 | B-14 |
| | 5 | B-15 |
| | 6 | B-16 |
| | 7 | B-17 |
| | 8 | B-18 |
| | 9 | B-19 |
| | 10 | B-20 |
| ~O~(~)₅~N₃ | 1 | B-21 |
| | 2 | B-22 |
| | 3 | B-23 |
| | 4 | B-24 |
| | 5 | B-25 |
| | 6 | B-26 |
| | 7 | B-27 |
| | 8 | B-28 |
| | 9 | B-29 |
| | 10 | B-30 |
| ~O~(~)₄~O~NH₂ | 1 | B-31 |
| | 2 | B-32 |
| | 3 | B-33 |
| | 4 | B-34 |
| | 5 | B-35 |
| | 6 | B-36 |
| | 7 | B-37 |
| | 8 | B-38 |
| | 9 | B-39 |
| | 10 | B-40 |
| ~O~(~)₃~C(O)OH | 1 | B-41 |
| | 2 | B-42 |
| | 3 | B-43 |
| | 4 | B-44 |
| | 5 | B-45 |
| | 6 | B-46 |
| | 7 | B-47 |
| | 8 | B-48 |
| | 9 | B-49 |
| | 10 | B-50 |
| ~O~(~)₁₀~C(O)OH | 1 | B-51 |
| | 2 | B-52 |
| | 3 | B-53 |
| | 4 | B-54 |
| | 5 | B-55 |
| | 6 | B-56 |
TABLE 2-continued
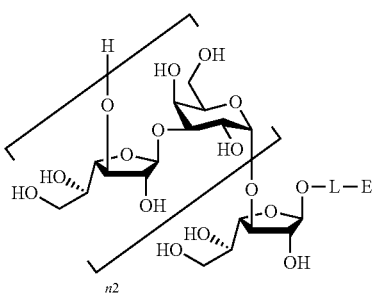
(II-B)
| —O—L—E | n2 | Compound No. |
|---|---|---|
| | 7 | B-57 |
| | 8 | B-58 |
| | 9 | B-59 |
| | 10 | B-60 |
| ~O~(~)₅~C(O)NHNH₂ | 1 | B-61 |
| | 2 | B-62 |
| | 3 | B-63 |
| | 4 | B-64 |
| | 5 | B-65 |
| | 6 | B-66 |
| | 7 | B-67 |
| | 8 | B-68 |
| | 9 | B-69 |
| | 10 | B-70 |
| ~O~(~)₃~SH | 1 | B-71 |
| | 2 | B-82 |
| | 3 | B-73 |
| | 4 | B-74 |
| | 5 | B-75 |
| | 6 | B-76 |
| | 7 | B-77 |
| | 8 | B-78 |
| | 9 | B-79 |
| | 10 | B-80 |
| ~O~(~)₃~CH=CH₂ | 1 | B-81 |
| | 2 | B-82 |
| | 3 | B-83 |
| | 4 | B-84 |
| | 5 | B-85 |
| | 6 | B-86 |
| | 7 | B-87 |
| | 8 | B-88 |
| | 9 | B-89 |
| | 10 | B-90 |
| ~O~CH₂C≡CH | 1 | B-91 |
| | 2 | B-92 |
| | 3 | B-93 |
| | 4 | B-94 |
| | 5 | B-95 |
| | 6 | B-96 |
| | 7 | B-97 |
| | 8 | B-98 |
| | 9 | B-99 |
| | 10 | B-100 |

TABLE 2-continued
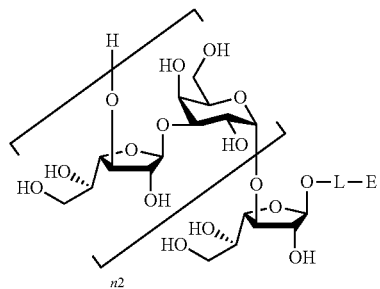
(II-B)
| —O—L—E | n2 | Compound No. |
|---|---|---|
| ⋯O-(CH₂)₅-Br | 1 | B-101 |
| | 2 | B-102 |
| | 3 | B-103 |
| | 4 | B-104 |
| | 5 | B-105 |
| | 6 | B-106 |
| | 7 | B-107 |
| | 8 | B-108 |
| | 9 | B-109 |
| | 10 | B-110 |
| ⋯O-CH₂CH₂-O-CH₂CH₂-NH₂ | 1 | B-111 |
| | 2 | B-112 |
| | 3 | B-113 |
| | 4 | B-114 |
| | 5 | B-115 |
| | 6 | B-116 |
| | 7 | B-117 |
| | 8 | B-118 |
| | 9 | B-119 |
| | 10 | B-120 |
| ⋯O-CH₂CH₂-(O-CH₂CH₂)₃-NH₂ | 1 | B-121 |
| | 2 | B-122 |
| | 3 | B-123 |
| | 4 | B-124 |
| | 5 | B-125 |
| | 6 | B-126 |
| | 7 | B-127 |
| | 8 | B-128 |
| | 9 | B-129 |
| | 10 | B-130 |
| ⋯O-CH₂-CH(OH)-CH₂-OH | 1 | B-131 |
| | 2 | B-132 |
| | 3 | B-133 |
| | 4 | B-134 |
| | 5 | B-135 |
| | 6 | B-136 |
| | 7 | B-137 |
| | 8 | B-138 |
| | 9 | B-139 |
| | 10 | B-140 |
TABLE 3
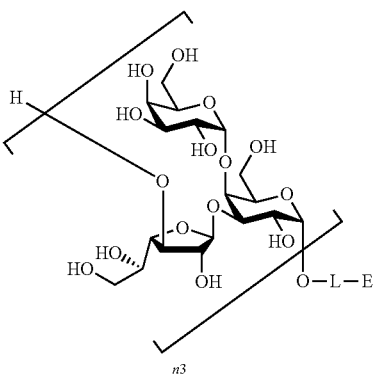
(II-C)
| —O—L—E | n3 | Compound No. |
|---|---|---|
| ⋯O-(CH₂)₅-NH₂ | 5 | C-01 |
| | 6 | C-02 |
| | 7 | C-03 |
| | 8 | C-04 |
| | 9 | C-05 |
| ⋯O-(CH₂)₁₀-NH₂ | 5 | C-06 |
| | 6 | C-07 |
| | 7 | C-08 |
| | 8 | C-09 |
| | 9 | C-10 |
| ⋯O-(CH₂)₅-N₃ | 5 | C-11 |
| | 6 | C-12 |
| | 7 | C-13 |
| | 8 | C-14 |
| | 9 | C-15 |
| ⋯O-(CH₂)₄-O-NH₂ | 5 | C-16 |
| | 6 | C-17 |
| | 7 | C-18 |
| | 8 | C-19 |
| | 9 | C-20 |
| ⋯O-(CH₂)₃-C(O)-OH | 5 | C-21 |
| | 6 | C-22 |
| | 7 | C-23 |
| | 8 | C-24 |
| | 9 | C-25 |
| ⋯O-(CH₂)₁₀-C(O)-OH | 5 | C-26 |
| | 6 | C-27 |
| | 7 | C-28 |
| | 8 | C-29 |
| | 9 | C-30 |
| ⋯O-(CH₂)₅-C(O)-NH-NH₂ | 5 | C-31 |
| | 6 | C-32 |
| | 7 | C-33 |
| | 8 | C-34 |
| | 9 | C-35 |
| ⋯O-(CH₂)₃-SH | 5 | C-36 |
| | 6 | C-37 |
| | 7 | C-38 |
| | 8 | C-39 |
| | 9 | C-40 |
| ⋯O-CH₂-CH=CH₂ | 5 | C-41 |
| | 6 | C-42 |
| | 7 | C-43 |
| | 8 | C-44 |
| | 9 | C-45 |
| ⋯O-CH₂-C≡CH | 5 | C-46 |
| | 6 | C-47 |
| | 7 | C-48 |

TABLE 3-continued
(II-C)
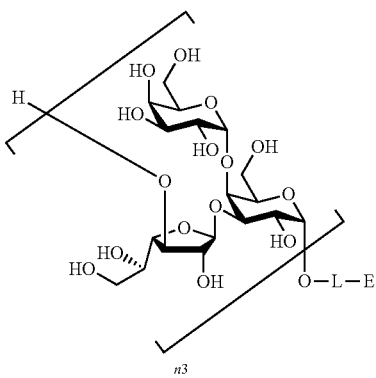
| —O—L—E | n3 | Compound No. |
|---|---|---|
| | 8 | C-49 |
| | 9 | C-50 |
| ⋯O⟨⟩₅Br | 5 | C-51 |
| | 6 | C-52 |
| | 7 | C-53 |
| | 8 | C-54 |
| | 9 | C-55 |
| ⋯O∼O∼NH₂ | 5 | C-56 |
| | 6 | C-57 |
| | 7 | C-58 |
| | 8 | C-59 |
| | 9 | C-60 |
| ⋯O∼(O)₃∼NH₂ | 5 | C-61 |
| | 6 | C-62 |
| | 7 | C-63 |
| | 8 | C-64 |
| | 9 | C-65 |
| ⋯O∼OH, OH | 5 | C-66 |
| | 6 | C-67 |
| | 7 | C-68 |
| | 8 | C-69 |
| | 9 | C-70 |
TABLE 4
(II-D)
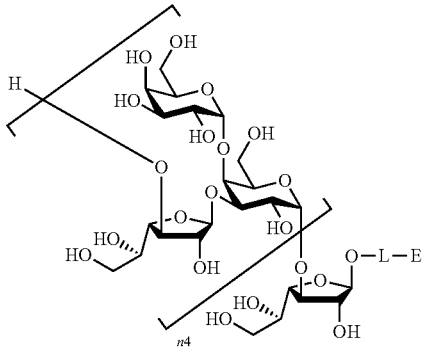
| —O—L—E | n4 | Compound No. |
|---|---|---|
| ⋯O⟨⟩₅NH₂ | 1 | D-01 |
| | 2 | D-02 |
| | 3 | D-03 |
TABLE 4-continued
(II-D)
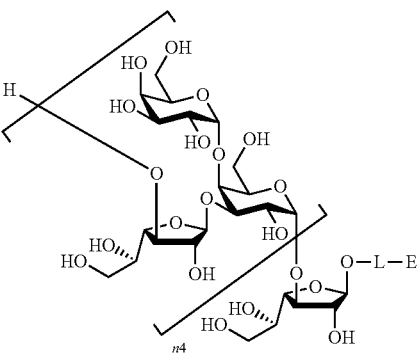
| —O—L—E | n4 | Compound No. |
|---|---|---|
| | 4 | D-04 |
| | 5 | D-05 |
| ⋯O⟨⟩₁₀NH₂ | 1 | D-06 |
| | 2 | D-07 |
| | 3 | D-08 |
| | 4 | D-09 |
| | 5 | D-10 |
| ⋯O⟨⟩₅N₃ | 1 | D-11 |
| | 2 | D-12 |
| | 3 | D-13 |
| | 4 | D-14 |
| | 5 | D-15 |
| ⋯O⟨⟩₄O∼NH₂ | 1 | D-16 |
| | 2 | D-17 |
| | 3 | D-18 |
| | 4 | D-19 |
| | 5 | D-20 |
| ⋯O⟨⟩₃COOH | 1 | D-21 |
| | 2 | D-22 |
| | 3 | D-23 |
| | 4 | D-24 |
| | 5 | D-25 |
| ⋯O⟨⟩₁₀COOH | 1 | D-26 |
| | 2 | D-27 |
| | 3 | D-28 |
| | 4 | D-29 |
| | 5 | D-30 |
| ⋯O⟨⟩₅C(O)NHNH₂ | 1 | D-31 |
| | 2 | D-32 |
| | 3 | D-33 |
| | 4 | D-34 |
| | 5 | D-35 |
| ⋯O⟨⟩₃SH | 1 | D-36 |
| | 2 | D-37 |
| | 3 | D-38 |
| | 4 | D-39 |
| | 5 | D-40 |
| ⋯O⟨⟩₃CH=CH₂ | 1 | D-41 |
| | 2 | D-42 |
| | 3 | D-43 |
| | 4 | D-44 |
| | 5 | D-45 |
| ⋯O∼C≡CH | 1 | D-46 |
| | 2 | D-47 |
| | 3 | D-48 |
| | 4 | D-49 |
| | 5 | D-50 |

TABLE 4-continued
(II-D)
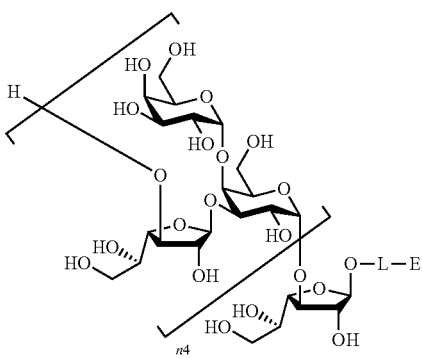
| —O—L—E | n4 | Compound No. |
|---|---|---|
| 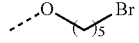 | 1 | D-51 |
| | 2 | D-52 |
| | 3 | D-53 |
| | 4 | D-54 |
| | 5 | D-55 |
| 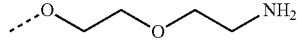 | 1 | D-56 |
| | 2 | D-57 |
| | 3 | D-58 |
| | 4 | D-59 |
| | 5 | D-60 |
| 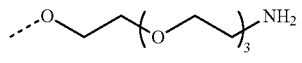 | 1 | D-61 |
| | 2 | D-62 |
| | 3 | D-63 |
| | 4 | D-64 |
| | 5 | D-65 |
| 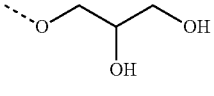 | 1 | D-66 |
| | 2 | D-67 |
| | 3 | D-68 |
| | 4 | D-69 |
| | 5 | D-70 |
TABLE 5
(II-E)
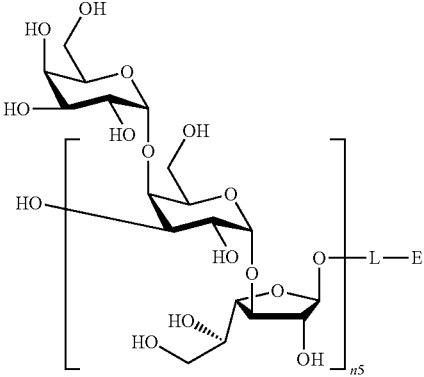
| —O—L—E | n5 | Compound No. |
|---|---|---|
|  | 1 | E-01 |
| | 2 | E-02 |
| | 3 | E-03 |
| | 4 | E-04 |
| | 5 | E-05 |
TABLE 5-continued
(II-E)
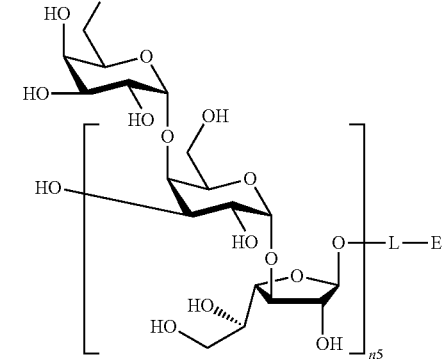
| —O—L—E | n5 | Compound No. |
|---|---|---|
|  | 1 | E-06 |
| | 2 | E-07 |
| | 3 | E-08 |
| | 4 | E-09 |
| | 5 | E-10 |
| 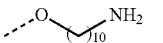 | 1 | E-11 |
| | 2 | E-12 |
| | 3 | E-13 |
| | 4 | E-14 |
| | 5 | E-15 |
| 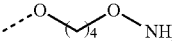 | 1 | E-16 |
| | 2 | E-17 |
| | 3 | E-18 |
| | 4 | E-19 |
| | 5 | E-20 |
|  | 1 | E-21 |
| | 2 | E-22 |
| | 3 | E-23 |
| | 4 | E-24 |
| | 5 | E-25 |
|  | 1 | E-26 |
| | 2 | E-27 |
| | 3 | E-28 |
| | 4 | E-29 |
| | 5 | E-30 |
|  | 1 | E-31 |
| | 2 | E-32 |
| | 3 | E-33 |
| | 4 | E-34 |
| | 5 | E-35 |
| 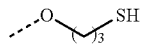 | 1 | E-36 |
| | 2 | E-37 |
| | 3 | E-38 |
| | 4 | E-39 |
| | 5 | E-40 |
| 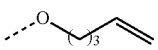 | 1 | E-41 |
| | 2 | E-42 |
| | 3 | E-43 |
| | 4 | E-44 |
| | 5 | E-45 |
|  | 1 | E-46 |
| | 2 | E-47 |
| | 3 | E-48 |
| | 4 | E-49 |
| | 5 | E-50 |
|  | 1 | E-51 |
| | 2 | E-52 |
| | 3 | E-53 |

TABLE 5-continued (II-E)

| —O—L—E | n5 | Compound No. |
|---|---|---|
| | 4 | E-54 |
| | 5 | E-55 |
| ⋯O⌒O⌒NH₂ | 1 | E-56 |
| | 2 | E-57 |
| | 3 | E-58 |
| | 4 | E-59 |
| | 5 | E-60 |
| ⋯O⌒(O⌒)₃NH₂ | 1 | E-61 |
| | 2 | E-62 |
| | 3 | E-63 |
| | 4 | E-64 |
| | 5 | E-65 |
| ⋯O⌒(OH)OH | 1 | E-66 |
| | 2 | E-67 |
| | 3 | E-68 |
| | 4 | E-69 |
| | 5 | E-70 |

TABLE 6

(II-F)

| —O—L—E | m6 | n6 | Compound No. |
|---|---|---|---|
| ⋯O(⌒)₅NH₂ | 1 | 1 | F-01 |
| | | 2 | F-02 |
| | | 3 | F-03 |
| | | 4 | F-04 |
| | | 5 | F-05 |
| ⋯O(⌒)₅NH₂ | 2 | 1 | F-06 |
| | | 2 | F-07 |
| | | 3 | F-08 |
| | | 4 | F-09 |
| | | 5 | F-10 |
| ⋯O(⌒)₅NH₂ | 3 | 1 | F-11 |
| | | 2 | F-12 |
| | | 3 | F-13 |
| | | 4 | F-14 |
| | | 5 | F-15 |
| ⋯O(⌒)₅NH₂ | 4 | 1 | F-16 |
| | | 2 | F-17 |
| | | 3 | F-18 |
| | | 4 | F-19 |
| | | 5 | F-20 |
| ⋯O(⌒)₅NH₂ | 5 | 1 | F-21 |
| | | 2 | F-22 |
| | | 3 | F-23 |
| | | 4 | F-24 |
| | | 5 | F-25 |
| ⋯O(⌒)₅NH₂ | 6 | 1 | F-26 |
| | | 2 | F-27 |
| | | 3 | F-28 |
| | | 4 | F-29 |
| | | 5 | F-30 |
| ⋯O(⌒)₅NH₂ | 7 | 1 | F-31 |
| | | 2 | F-32 |
| | | 3 | F-33 |
| | | 4 | F-34 |
| | | 5 | F-35 |
| ⋯O(⌒)₁₀NH₂ | 1 | 1 | F-36 |
| | | 2 | F-37 |
| | | 3 | F-38 |
| | | 4 | F-39 |
| | | 5 | F-40 |
| ⋯O(⌒)₁₀NH₂ | 2 | 1 | F-41 |
| | | 2 | F-42 |
| | | 3 | F-43 |
| | | 4 | F-44 |
| | | 5 | F-45 |
| ⋯O(⌒)₁₀NH₂ | 3 | 1 | F-46 |
| | | 2 | F-47 |
| | | 3 | F-48 |
| | | 4 | F-49 |
| | | 5 | F-50 |

TABLE 6-continued (II-F)

| —O—L—E | m6 | n6 | Compound No. |
|---|---|---|---|
| ⋯O-(CH₂)₁₀-NH₂ | 4 | 1 | F-51 |
| | | 2 | F-52 |
| | | 3 | F-53 |
| | | 4 | F-54 |
| | | 5 | F-55 |
| ⋯O-(CH₂)₁₀-NH₂ | 5 | 1 | F-56 |
| | | 2 | F-57 |
| | | 3 | F-58 |
| | | 4 | F-59 |
| | | 5 | F-60 |
| ⋯O-(CH₂)₁₀-NH₂ | 6 | 1 | F-61 |
| | | 2 | F-62 |
| | | 3 | F-63 |
| | | 4 | F-64 |
| | | 5 | F-65 |
| ⋯O-(CH₂)₁₀-NH₂ | 7 | 1 | F-66 |
| | | 2 | F-67 |
| | | 3 | F-68 |
| | | 4 | F-69 |
| | | 5 | F-70 |
| ⋯O-(CH₂)₅-N₃ | 1 | 1 | F-71 |
| | | 2 | F-72 |
| | | 3 | F-73 |
| | | 4 | F-74 |
| | | 5 | F-75 |
| ⋯O-(CH₂)₅-N₃ | 2 | 1 | F-76 |
| | | 2 | F-77 |
| | | 3 | F-78 |
| | | 4 | F-79 |
| | | 5 | F-80 |
| ⋯O-(CH₂)₅-N₃ | 3 | 1 | F-81 |
| | | 2 | F-82 |
| | | 3 | F-83 |
| | | 4 | F-84 |
| | | 5 | F-85 |
| ⋯O-(CH₂)₅-N₃ | 4 | 1 | F-86 |
| | | 2 | F-87 |
| | | 3 | F-88 |
| | | 4 | F-89 |
| | | 5 | F-90 |
| ⋯O-(CH₂)₅-N₃ | 5 | 1 | F-91 |
| | | 2 | F-92 |
| | | 3 | F-93 |
| | | 4 | F-94 |
| | | 5 | F-95 |
| ⋯O-(CH₂)₅-N₃ | 6 | 1 | F-96 |
| | | 2 | F-97 |
| | | 3 | F-98 |
| | | 4 | F-99 |
| | | 5 | F-100 |
| ⋯O-(CH₂)₅-N₃ | 7 | 1 | F-101 |
| | | 2 | F-102 |
| | | 3 | F-103 |
| | | 4 | F-104 |
| | | 5 | F-105 |
| ⋯O-(CH₂)₄-O-NH₂ | 1 | 1 | F-106 |
| | | 2 | F-107 |
| | | 3 | F-108 |
| | | 4 | F-109 |
| | | 5 | F-110 |
| ⋯O-(CH₂)₄-O-NH₂ | 2 | 1 | F-111 |
| | | 2 | F-112 |
| | | 3 | F-113 |
| | | 4 | F-114 |
| | | 5 | F-115 |
| ⋯O-(CH₂)₄-O-NH₂ | 3 | 1 | F-116 |
| | | 2 | F-117 |
| | | 3 | F-118 |
| | | 4 | F-119 |
| | | 5 | F-120 |
| ⋯O-(CH₂)₄-O-NH₂ | 4 | 1 | F-121 |
| | | 2 | F-122 |
| | | 3 | F-123 |
| | | 4 | F-124 |
| | | 5 | F-125 |
| ⋯O-(CH₂)₄-O-NH₂ | 5 | 1 | F-126 |
| | | 2 | F-127 |
| | | 3 | F-128 |
| | | 4 | F-129 |
| | | 5 | F-130 |
| ⋯O-(CH₂)₄-O-NH₂ | 6 | 1 | F-131 |
| | | 2 | F-132 |
| | | 3 | F-133 |
| | | 4 | F-134 |
| | | 5 | F-135 |
| ⋯O-(CH₂)₄-O-NH₂ | 7 | 1 | F-136 |
| | | 2 | F-137 |
| | | 3 | F-138 |
| | | 4 | F-139 |
| | | 5 | F-140 |

TABLE 6-continued (II-F)

| —O—L—E | m6 | n6 | Compound No. |
|---|---|---|---|
| ⟨structure: –O–(CH₂)₃–C(O)OH⟩ | 1 | 1 | F-141 |
| | | 2 | F-142 |
| | | 3 | F-143 |
| | | 4 | F-144 |
| | | 5 | F-145 |
| ⟨structure: –O–(CH₂)₃–C(O)OH⟩ | 2 | 1 | F-146 |
| | | 2 | F-147 |
| | | 3 | F-148 |
| | | 4 | F-149 |
| | | 5 | F-150 |
| ⟨structure: –O–(CH₂)₃–C(O)OH⟩ | 3 | 1 | F-151 |
| | | 2 | F-152 |
| | | 3 | F-153 |
| | | 4 | F-154 |
| | | 5 | F-155 |
| ⟨structure: –O–(CH₂)₃–C(O)OH⟩ | 4 | 1 | F-156 |
| | | 2 | F-157 |
| | | 3 | F-158 |
| | | 4 | F-159 |
| | | 5 | F-160 |
| ⟨structure: –O–(CH₂)₃–C(O)OH⟩ | 5 | 1 | F-161 |
| | | 2 | F-162 |
| | | 3 | F-163 |
| | | 4 | F-164 |
| | | 5 | F-165 |
| ⟨structure: –O–(CH₂)₃–C(O)OH⟩ | 6 | 1 | F-166 |
| | | 2 | F-167 |
| | | 3 | F-168 |
| | | 4 | F-169 |
| | | 5 | F-170 |
| ⟨structure: –O–(CH₂)₃–C(O)OH⟩ | 7 | 1 | F-171 |
| | | 2 | F-172 |
| | | 3 | F-173 |
| | | 4 | F-174 |
| | | 5 | F-175 |
| ⟨structure: –O–(CH₂)₁₀–C(O)OH⟩ | 1 | 1 | F-176 |
| | | 2 | F-177 |
| | | 3 | F-178 |
| | | 4 | F-179 |
| | | 5 | F-180 |
| ⟨structure: –O–(CH₂)₁₀–C(O)OH⟩ | 2 | 1 | F-181 |
| | | 2 | F-182 |
| | | 3 | F-183 |
| | | 4 | F-184 |
| | | 5 | F-185 |
| ⟨structure: –O–(CH₂)₁₀–C(O)OH⟩ | 3 | 1 | F-186 |
| | | 2 | F-187 |
| | | 3 | F-188 |
| | | 4 | F-189 |
| | | 5 | F-190 |
| ⟨structure: –O–(CH₂)₁₀–C(O)OH⟩ | 4 | 1 | F-191 |
| | | 2 | F-192 |
| | | 3 | F-193 |
| | | 4 | F-194 |
| | | 5 | F-195 |
| ⟨structure: –O–(CH₂)₁₀–C(O)OH⟩ | 5 | 1 | F-196 |
| | | 2 | F-197 |
| | | 3 | F-198 |
| | | 4 | F-199 |
| | | 5 | F-200 |
| ⟨structure: –O–(CH₂)₁₀–C(O)OH⟩ | 6 | 1 | F-201 |
| | | 2 | F-202 |
| | | 3 | F-203 |
| | | 4 | F-204 |
| | | 5 | F-205 |
| ⟨structure: –O–(CH₂)₁₀–C(O)OH⟩ | 7 | 1 | F-206 |
| | | 2 | F-207 |
| | | 3 | F-208 |
| | | 4 | F-209 |
| | | 5 | F-210 |
| ⟨structure: –O–(CH₂)₅–C(O)NHNH₂⟩ | 1 | 1 | F-211 |
| | | 2 | F-212 |
| | | 3 | F-213 |
| | | 4 | F-214 |
| | | 5 | F-215 |
| ⟨structure: –O–(CH₂)₅–C(O)NHNH₂⟩ | 2 | 1 | F-216 |
| | | 2 | F-217 |
| | | 3 | F-218 |
| | | 4 | F-219 |
| | | 5 | F-220 |
| ⟨structure: –O–(CH₂)₅–C(O)NHNH₂⟩ | 3 | 1 | F-221 |
| | | 2 | F-222 |
| | | 3 | F-223 |
| | | 4 | F-224 |
| | | 5 | F-225 |
| ⟨structure: –O–(CH₂)₅–C(O)NHNH₂⟩ | 4 | 1 | F-226 |
| | | 2 | F-227 |
| | | 3 | F-228 |
| | | 4 | F-229 |
| | | 5 | F-230 |

TABLE 6-continued
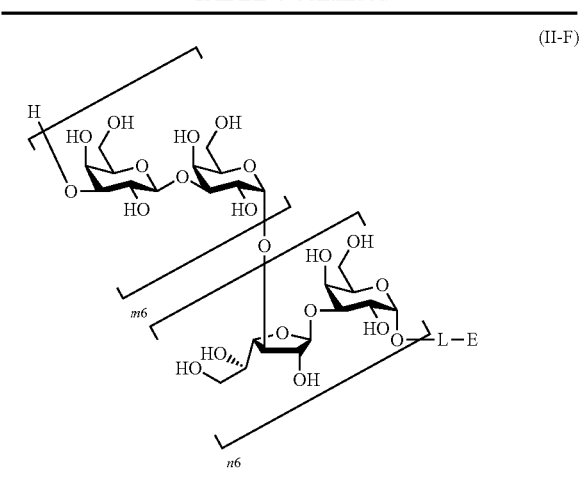
(II-F)
| —O—L—E | m6 | n6 | Compound No. |
|---|---|---|---|
| 5-C(=O)-NH-NH2) | 5 | 1 | F-231 |
| | | 2 | F-232 |
| | | 3 | F-233 |
| | | 4 | F-234 |
| | | 5 | F-235 |
| ![hydrazide] | 6 | 1 | F-236 |
| | | 2 | F-237 |
| | | 3 | F-238 |
| | | 4 | F-239 |
| | | 5 | F-240 |
| ![hydrazide] | 7 | 1 | F-241 |
| | | 2 | F-242 |
| | | 3 | F-243 |
| | | 4 | F-244 |
| | | 5 | F-245 |
| 3-SH) | 1 | 1 | F-246 |
| | | 2 | F-247 |
| | | 3 | F-248 |
| | | 4 | F-249 |
| | | 5 | F-250 |
| ![thiol] | 2 | 1 | F-251 |
| | | 2 | F-252 |
| | | 3 | F-253 |
| | | 4 | F-254 |
| | | 5 | F-255 |
| ![thiol] | 3 | 1 | F-256 |
| | | 2 | F-257 |
| | | 3 | F-258 |
| | | 4 | F-259 |
| | | 5 | F-260 |
| ![thiol] | 4 | 1 | F-261 |
| | | 2 | F-262 |
| | | 3 | F-263 |
| | | 4 | F-264 |
| | | 5 | F-265 |
| ![thiol] | 5 | 1 | F-266 |
| | | 2 | F-267 |
| | | 3 | F-268 |
| | | 4 | F-269 |
| | | 5 | F-270 |
| ![thiol] | 6 | 1 | F-271 |
| | | 2 | F-272 |
| | | 3 | F-273 |
| | | 4 | F-274 |
| | | 5 | F-275 |
TABLE 6-continued
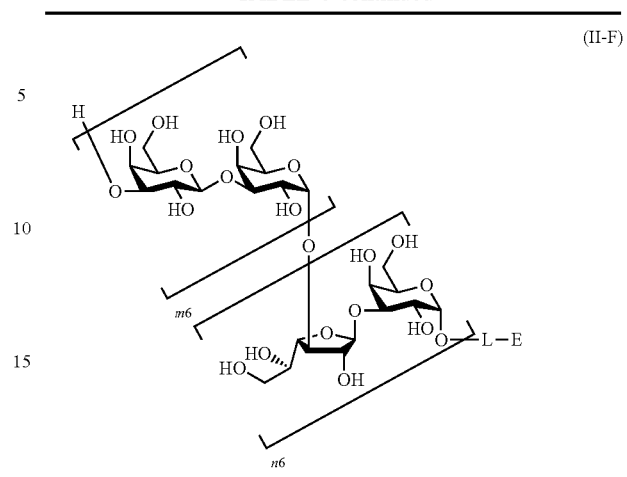
(II-F)
| —O—L—E | m6 | n6 | Compound No. |
|---|---|---|---|
| 3-SH) | 7 | 1 | F-276 |
| | | 2 | F-277 |
| | | 3 | F-278 |
| | | 4 | F-279 |
| | | 5 | F-280 |
| 3-CH=CH2) | 1 | 1 | F-281 |
| | | 2 | F-282 |
| | | 3 | F-283 |
| | | 4 | F-284 |
| | | 5 | F-285 |
| ![allyl] | 2 | 1 | F-286 |
| | | 2 | F-287 |
| | | 3 | F-288 |
| | | 4 | F-289 |
| | | 5 | F-290 |
| ![allyl] | 3 | 1 | F-291 |
| | | 2 | F-292 |
| | | 3 | F-293 |
| | | 4 | F-294 |
| | | 5 | F-295 |
| ![allyl] | 4 | 1 | F-296 |
| | | 2 | F-297 |
| | | 3 | F-298 |
| | | 4 | F-299 |
| | | 5 | F-300 |
| ![allyl] | 5 | 1 | F-301 |
| | | 2 | F-302 |
| | | 3 | F-303 |
| | | 4 | F-304 |
| | | 5 | F-305 |
| ![allyl] | 6 | 1 | F-306 |
| | | 2 | F-307 |
| | | 3 | F-308 |
| | | 4 | F-309 |
| | | 5 | F-310 |
| ![allyl] | 7 | 1 | F-311 |
| | | 2 | F-312 |
| | | 3 | F-313 |
| | | 4 | F-314 |
| | | 5 | F-315 |
| | 1 | 1 | F-316 |
| | | 2 | F-317 |
| | | 3 | F-318 |
| | | 4 | F-319 |
| | | 5 | F-320 |

TABLE 6-continued

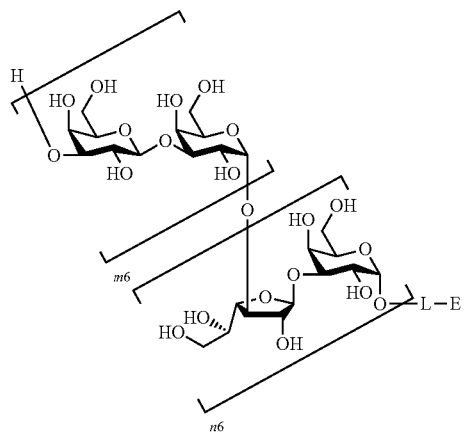

(II-F)

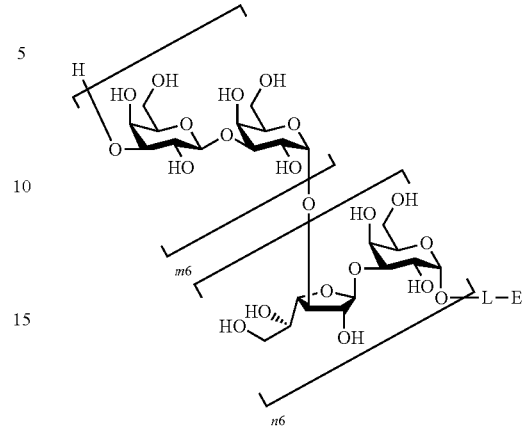

(II-F)

| —O—L—E | m6 | n6 | Compound No. | —O—L—E | m6 | n6 | Compound No. |
|---|---|---|---|---|---|---|---|
| propargyl ether | 2 | 1 | F-321 | —O—(CH₂)₅—Br | 4 | 1 | F-406 |
|  |  | 2 | F-322 |  |  | 2 | F-407 |
|  |  | 3 | F-323 |  |  | 3 | F-408 |
|  |  | 4 | F-324 |  |  | 4 | F-409 |
|  |  | 5 | F-325 |  |  | 5 | F-410 |
| propargyl ether | 3 | 1 | F-326 | —O—(CH₂)₅—Br | 5 | 1 | F-411 |
|  |  | 2 | F-327 |  |  | 2 | F-412 |
|  |  | 3 | F-328 |  |  | 3 | F-413 |
|  |  | 4 | F-329 |  |  | 4 | F-414 |
|  |  | 5 | F-330 |  |  | 5 | F-415 |
| propargyl ether | 4 | 1 | F-331 | —O—(CH₂)₅—Br | 6 | 1 | F-416 |
|  |  | 2 | F-332 |  |  | 2 | F-417 |
|  |  | 3 | F-333 |  |  | 3 | F-418 |
|  |  | 4 | F-334 |  |  | 4 | F-419 |
|  |  | 5 | F-335 |  |  | 5 | F-420 |
| propargyl ether | 5 | 1 | F-336 | —O—(CH₂)₅—Br | 7 | 1 | F-421 |
|  |  | 2 | F-337 |  |  | 2 | F-422 |
|  |  | 3 | F-338 |  |  | 3 | F-423 |
|  |  | 4 | F-339 |  |  | 4 | F-424 |
|  |  | 5 | F-340 |  |  | 5 | F-425 |
| propargyl ether | 6 | 1 | F-341 | —O—CH₂CH₂—O—CH₂CH₂—NH₂ | 1 | 1 | F-426 |
|  |  | 2 | F-342 |  |  | 2 | F-427 |
|  |  | 3 | F-343 |  |  | 3 | F-428 |
|  |  | 4 | F-344 |  |  | 4 | F-429 |
|  |  | 5 | F-345 |  |  | 5 | F-430 |
| propargyl ether | 7 | 1 | F-346 | —O—CH₂CH₂—O—CH₂CH₂—NH₂ | 2 | 1 | F-431 |
|  |  | 2 | F-347 |  |  | 2 | F-432 |
|  |  | 3 | F-348 |  |  | 3 | F-433 |
|  |  | 4 | F-349 |  |  | 4 | F-434 |
|  |  | 5 | F-350 |  |  | 5 | F-435 |
| —O—(CH₂)₅—Br | 1 | 1 | F-351 | —O—CH₂CH₂—O—CH₂CH₂—NH₂ | 3 | 1 | F-436 |
|  |  | 2 | F-352 |  |  | 2 | F-437 |
|  |  | 3 | F-353 |  |  | 3 | F-438 |
|  |  | 4 | F-354 |  |  | 4 | F-439 |
|  |  | 5 | F-355 |  |  | 5 | F-440 |
| —O—(CH₂)₅—Br | 2 | 1 | F-356 | —O—CH₂CH₂—O—CH₂CH₂—NH₂ | 4 | 1 | F-441 |
|  |  | 2 | F-357 |  |  | 2 | F-442 |
|  |  | 3 | F-358 |  |  | 3 | F-443 |
|  |  | 4 | F-359 |  |  | 4 | F-444 |
|  |  | 5 | F-400 |  |  | 5 | F-445 |
| —O—(CH₂)₅—Br | 3 | 1 | F-401 | —O—CH₂CH₂—O—CH₂CH₂—NH₂ | 5 | 1 | F-446 |
|  |  | 2 | F-402 |  |  | 2 | F-447 |
|  |  | 3 | F-403 |  |  | 3 | F-448 |
|  |  | 4 | F-404 |  |  | 4 | F-449 |
|  |  | 5 | F-405 |  |  | 5 | F-450 |

TABLE 6-continued
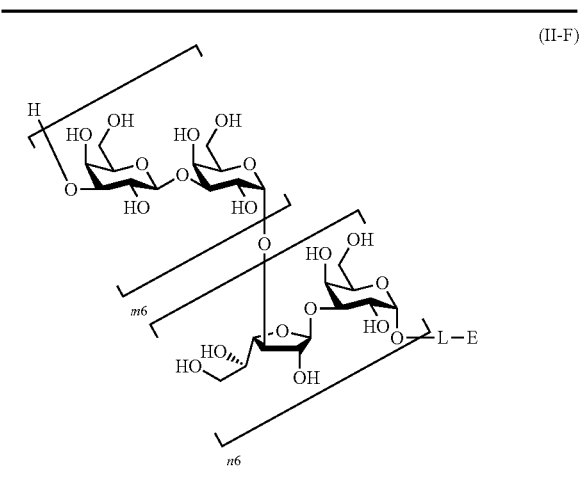
(II-F)
| —O—L—E | m6 | n6 | Compound No. |
|---|---|---|---|
| ⋯O〜O〜NH₂ | 6 | 1 | F-451 |
|  |  | 2 | F-452 |
|  |  | 3 | F-453 |
|  |  | 4 | F-454 |
|  |  | 5 | F-455 |
| ⋯O〜O〜NH₂ | 7 | 1 | F-456 |
|  |  | 2 | F-457 |
|  |  | 3 | F-458 |
|  |  | 4 | F-459 |
|  |  | 5 | F-460 |
| ⋯O〜(O〜)₃NH₂ | 1 | 1 | F-461 |
|  |  | 2 | F-462 |
|  |  | 3 | F-463 |
|  |  | 4 | F-464 |
|  |  | 5 | F-465 |
| ⋯O〜(O〜)₃NH₂ | 2 | 1 | F-466 |
|  |  | 2 | F-467 |
|  |  | 3 | F-468 |
|  |  | 4 | F-469 |
|  |  | 5 | F-470 |
| ⋯O〜(O〜)₃NH₂ | 3 | 1 | F-471 |
|  |  | 2 | F-472 |
|  |  | 3 | F-473 |
|  |  | 4 | F-474 |
|  |  | 5 | F-475 |
| ⋯O〜(O〜)₃NH₂ | 4 | 1 | F-476 |
|  |  | 2 | F-477 |
|  |  | 3 | F-478 |
|  |  | 4 | F-479 |
|  |  | 5 | F-480 |
| ⋯O〜(O〜)₃NH₂ | 5 | 1 | F-481 |
|  |  | 2 | F-482 |
|  |  | 3 | F-483 |
|  |  | 4 | F-484 |
|  |  | 5 | F-485 |
| ⋯O〜(O〜)₃NH₂ | 6 | 1 | F-486 |
|  |  | 2 | F-487 |
|  |  | 3 | F-488 |
|  |  | 4 | F-489 |
|  |  | 5 | F-490 |
| ⋯O〜(O〜)₃NH₂ | 7 | 1 | F-491 |
|  |  | 2 | F-492 |
|  |  | 3 | F-493 |
|  |  | 4 | F-494 |
|  |  | 5 | F-495 |
TABLE 6-continued
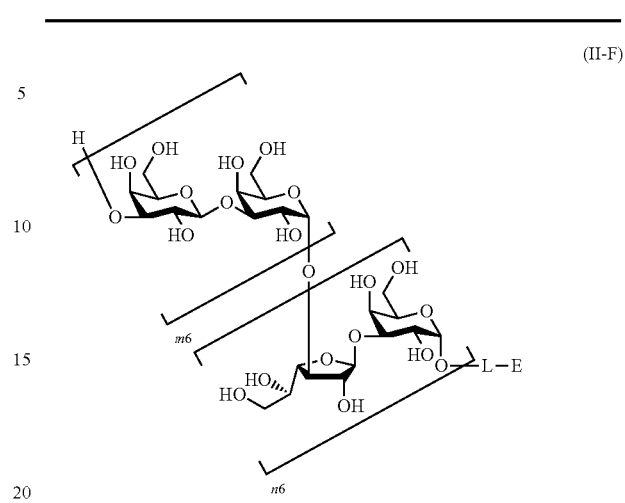
(II-F)
| —O—L—E | m6 | n6 | Compound No. |
|---|---|---|---|
| ⋯O〜OH (OH) | 1 | 1 | F-496 |
|  |  | 2 | F-497 |
|  |  | 3 | F-498 |
|  |  | 4 | F-499 |
|  |  | 5 | F-500 |
| ⋯O〜OH (OH) | 2 | 1 | F-501 |
|  |  | 2 | F-502 |
|  |  | 3 | F-503 |
|  |  | 4 | F-504 |
|  |  | 5 | F-505 |
| ⋯O〜OH (OH) | 3 | 1 | F-506 |
|  |  | 2 | F-507 |
|  |  | 3 | F-508 |
|  |  | 4 | F-509 |
|  |  | 5 | F-510 |
| ⋯O〜OH (OH) | 4 | 1 | F-511 |
|  |  | 2 | F-512 |
|  |  | 3 | F-513 |
|  |  | 4 | F-514 |
|  |  | 5 | F-515 |
| ⋯O〜OH (OH) | 5 | 1 | F-516 |
|  |  | 2 | F-517 |
|  |  | 3 | F-518 |
|  |  | 4 | F-519 |
|  |  | 5 | F-520 |
| ⋯O〜OH (OH) | 6 | 1 | F-521 |
|  |  | 2 | F-522 |
|  |  | 3 | F-523 |
|  |  | 4 | F-524 |
|  |  | 5 | F-525 |
| ⋯O〜OH (OH) | 7 | 1 | F-526 |
|  |  | 2 | F-527 |
|  |  | 3 | F-528 |
|  |  | 4 | F-529 |
|  |  | 5 | F-530 |

TABLE 7
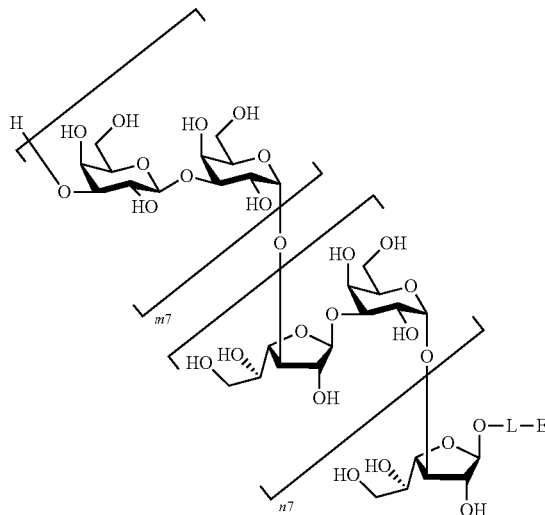
(II-G)
| —O—L—E | m7 | n7 | Compound No. |
|---|---|---|---|
| ⋯O∼∼NH₂ (5) | 1 | 1 | G-01 |
| | | 2 | G-02 |
| | | 3 | G-03 |
| | | 4 | G-04 |
| | | 5 | G-05 |
| ⋯O∼∼NH₂ (5) | 2 | 1 | G-06 |
| | | 2 | G-07 |
| | | 3 | G-08 |
| | | 4 | G-09 |
| | | 5 | G-10 |
| ⋯O∼∼NH₂ (5) | 3 | 1 | G-11 |
| | | 2 | G-12 |
| | | 3 | G-13 |
| | | 4 | G-14 |
| | | 5 | G-15 |
| ⋯O∼∼NH₂ (5) | 4 | 1 | G-16 |
| | | 2 | G-17 |
| | | 3 | G-18 |
| | | 4 | G-19 |
| | | 5 | G-20 |
| ⋯O∼∼NH₂ (5) | 5 | 1 | G-21 |
| | | 2 | G-22 |
| | | 3 | G-23 |
| | | 4 | G-24 |
| | | 5 | G-25 |
| ⋯O∼∼NH₂ (10) | 1 | 1 | G-26 |
| | | 2 | G-27 |
| | | 3 | G-28 |
| | | 4 | G-29 |
| | | 5 | G-30 |
| ⋯O∼∼NH₂ (10) | 2 | 1 | G-31 |
| | | 2 | G-32 |
| | | 3 | G-33 |
| | | 4 | G-34 |
| | | 5 | G-35 |
| ⋯O∼∼NH₂ (10) | 3 | 1 | G-36 |
| | | 2 | G-37 |
| | | 3 | G-38 |
| | | 4 | G-39 |
| | | 5 | G-40 |
| ⋯O∼∼NH₂ (10) | 4 | 1 | G-41 |
| | | 2 | G-42 |
| | | 3 | G-43 |
| | | 4 | G-44 |
| | | 5 | G-45 |

TABLE 7-continued
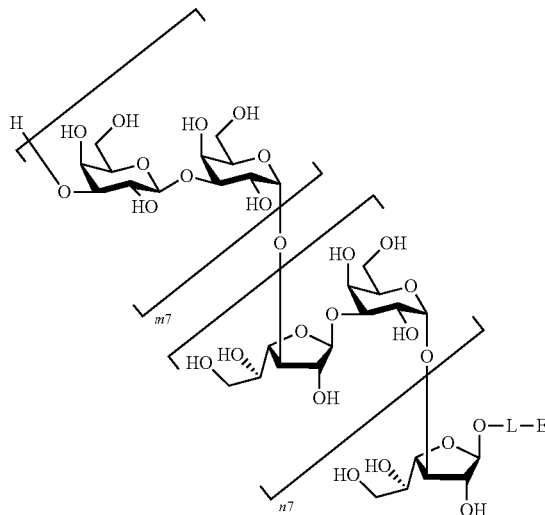
(II-G)
| —O—L—E | m7 | n7 | Compound No. |
|---|---|---|---|
| ...O~(CH2)10~NH2 | 5 | 1 | G-46 |
| | | 2 | G-47 |
| | | 3 | G-48 |
| | | 4 | G-49 |
| | | 5 | G-50 |
| ...O~(CH2)5~N3 | 1 | 1 | G-51 |
| | | 2 | G-52 |
| | | 3 | G-53 |
| | | 4 | G-54 |
| | | 5 | G-55 |
| ...O~(CH2)5~N3 | 2 | 1 | G-56 |
| | | 2 | G-57 |
| | | 3 | G-58 |
| | | 4 | G-59 |
| | | 5 | G-60 |
| ...O~(CH2)5~N3 | 3 | 1 | G-61 |
| | | 2 | G-62 |
| | | 3 | G-63 |
| | | 4 | G-64 |
| | | 5 | G-65 |
| ...O~(CH2)5~N3 | 4 | 1 | G-66 |
| | | 2 | G-67 |
| | | 3 | G-68 |
| | | 4 | G-69 |
| | | 5 | G-70 |
| ...O~(CH2)5~N3 | 5 | 1 | G-71 |
| | | 2 | G-72 |
| | | 3 | G-73 |
| | | 4 | G-74 |
| | | 5 | G-75 |
| ...O~(CH2)4~O~NH2 | 1 | 1 | G-76 |
| | | 2 | G-77 |
| | | 3 | G-78 |
| | | 4 | G-79 |
| | | 5 | G-80 |
| ...O~(CH2)4~O~NH2 | 2 | 1 | G-81 |
| | | 2 | G-82 |
| | | 3 | G-83 |
| | | 4 | G-84 |
| | | 5 | G-85 |
| ...O~(CH2)4~O~NH2 | 3 | 1 | G-86 |
| | | 2 | G-87 |
| | | 3 | G-88 |
| | | 4 | G-89 |

TABLE 7-continued
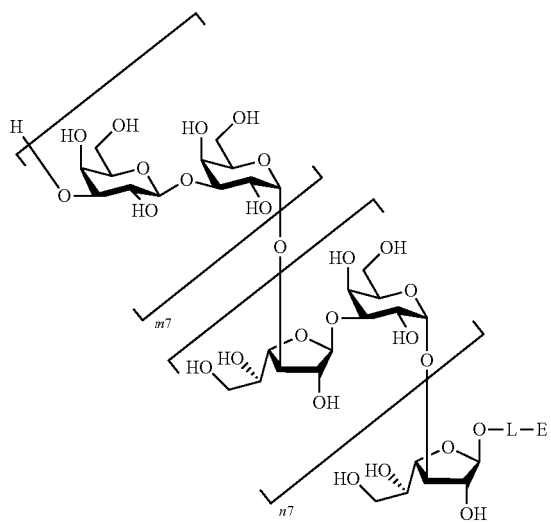
(II-G)
| —O—L—E | m7 | n7 | Compound No. |
|---|---|---|---|
| | | 5 | G-90 |
| ⋯O\(CH₂)₄O\NH₂ | 4 | 1 | G-91 |
| | | 2 | G-92 |
| | | 3 | G-93 |
| | | 4 | G-94 |
| | | 5 | G-95 |
| ⋯O\(CH₂)₄O\NH₂ | 5 | 1 | G-96 |
| | | 2 | G-97 |
| | | 3 | G-98 |
| | | 4 | G-99 |
| | | 5 | G-100 |
| ⋯O(CH₂)₃C(O)OH | 1 | 1 | G-101 |
| | | 2 | G-102 |
| | | 3 | G-103 |
| | | 4 | G-104 |
| | | 5 | G-105 |
| ⋯O(CH₂)₃C(O)OH | 2 | 1 | G-106 |
| | | 2 | G-107 |
| | | 3 | G-108 |
| | | 4 | G-109 |
| | | 5 | G-110 |
| ⋯O(CH₂)₃C(O)OH | 3 | 1 | G-111 |
| | | 2 | G-112 |
| | | 3 | G-113 |
| | | 4 | G-114 |
| | | 5 | G-115 |
| ⋯O(CH₂)₃C(O)OH | 4 | 1 | G-116 |
| | | 2 | G-117 |
| | | 3 | G-118 |
| | | 4 | G-119 |
| | | 5 | G-120 |
| ⋯O(CH₂)₃C(O)OH | 5 | 1 | G-121 |
| | | 2 | G-122 |
| | | 3 | G-123 |
| | | 4 | G-124 |
| | | 5 | G-125 |
| ⋯O(CH₂)₁₀C(O)OH | 1 | 1 | G-126 |
| | | 2 | G-127 |
| | | 3 | G-128 |
| | | 4 | G-129 |
| | | 5 | G-130 |

TABLE 7-continued
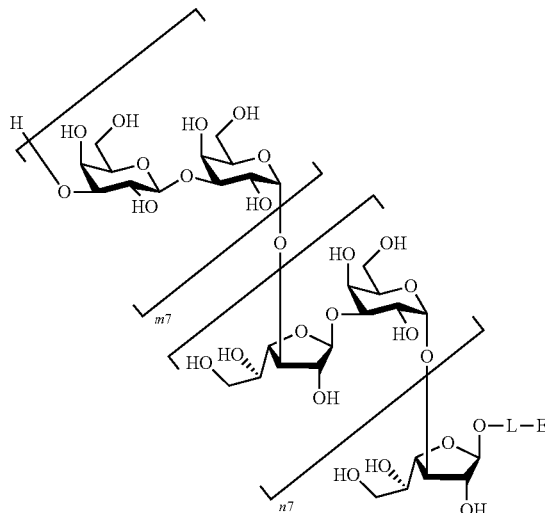
(II-G)
| —O—L—E | m7 | n7 | Compound No. |
|---|---|---|---|
| ![structure: ---O-(CH2)10-COOH] | 2 | 1 | G-131 |
|  |  | 2 | G-132 |
|  |  | 3 | G-133 |
|  |  | 4 | G-134 |
|  |  | 5 | G-135 |
| ![structure: ---O-(CH2)10-COOH] | 3 | 1 | G-136 |
|  |  | 2 | G-137 |
|  |  | 3 | G-138 |
|  |  | 4 | G-139 |
|  |  | 5 | G-140 |
| ![structure: ---O-(CH2)10-COOH] | 4 | 1 | G-141 |
|  |  | 2 | G-142 |
|  |  | 3 | G-143 |
|  |  | 4 | G-144 |
|  |  | 5 | G-145 |
| ![structure: ---O-(CH2)10-COOH] | 5 | 1 | G-146 |
|  |  | 2 | G-147 |
|  |  | 3 | G-148 |
|  |  | 4 | G-149 |
|  |  | 5 | G-150 |
| ![structure: ---O-(CH2)5-C(O)-NH-NH2] | 1 | 1 | G-151 |
|  |  | 2 | G-152 |
|  |  | 3 | G-153 |
|  |  | 4 | G-154 |
|  |  | 5 | G-155 |
| ![structure: ---O-(CH2)5-C(O)-NH-NH2] | 2 | 1 | G-156 |
|  |  | 2 | G-157 |
|  |  | 3 | G-158 |
|  |  | 4 | G-159 |
|  |  | 5 | G-160 |
| ![structure: ---O-(CH2)5-C(O)-NH-NH2] | 3 | 1 | G-161 |
|  |  | 2 | G-162 |
|  |  | 3 | G-163 |
|  |  | 4 | G-164 |
|  |  | 5 | G-165 |
| ![structure: ---O-(CH2)5-C(O)-NH-NH2] | 4 | 1 | G-166 |
|  |  | 2 | G-167 |
|  |  | 3 | G-168 |
|  |  | 4 | G-169 |
|  |  | 5 | G-170 |
| ![structure: ---O-(CH2)5-C(O)-NH-NH2] | 5 | 1 | G-171 |
|  |  | 2 | G-172 |
|  |  | 3 | G-173 |
|  |  | 4 | G-174 |
|  |  | 5 | G-175 |

TABLE 7-continued
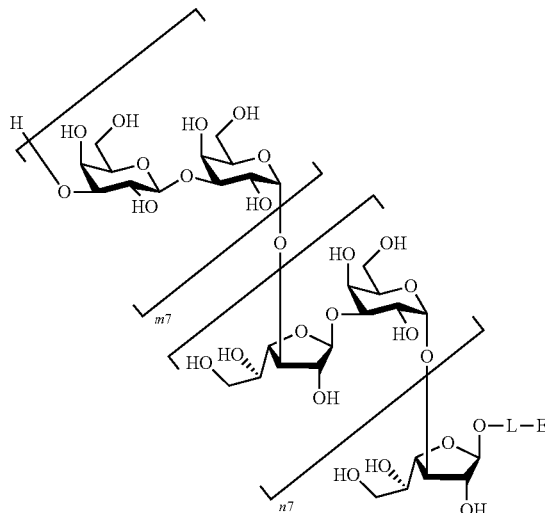
(II-G)
| —O—L—E | m7 | n7 | Compound No. |
|---|---|---|---|
| ~O~SH (3) | 1 | 1 | G-176 |
|  |  | 2 | G-177 |
|  |  | 3 | G-178 |
|  |  | 4 | G-179 |
|  |  | 5 | G-180 |
| ~O~SH (3) | 2 | 1 | G-181 |
|  |  | 2 | G-182 |
|  |  | 3 | G-183 |
|  |  | 4 | G-184 |
|  |  | 5 | G-185 |
| ~O~SH (3) | 3 | 1 | G-186 |
|  |  | 2 | G-187 |
|  |  | 3 | G-188 |
|  |  | 4 | G-189 |
|  |  | 5 | G-190 |
| ~O~SH (3) | 4 | 1 | G-191 |
|  |  | 2 | G-192 |
|  |  | 3 | G-193 |
|  |  | 4 | G-194 |
|  |  | 5 | G-195 |
| ~O~SH (3) | 5 | 1 | G-196 |
|  |  | 2 | G-197 |
|  |  | 3 | G-198 |
|  |  | 4 | G-199 |
|  |  | 5 | G-200 |
| ~O~=CH₂ (3) | 1 | 1 | G-201 |
|  |  | 2 | G-202 |
|  |  | 3 | G-203 |
|  |  | 4 | G-204 |
|  |  | 5 | G-205 |
| ~O~=CH₂ (3) | 2 | 1 | G-206 |
|  |  | 2 | G-207 |
|  |  | 3 | G-208 |
|  |  | 4 | G-209 |
|  |  | 5 | G-210 |
| ~O~=CH₂ (3) | 3 | 1 | G-211 |
|  |  | 2 | G-212 |
|  |  | 3 | G-213 |
|  |  | 4 | G-214 |
|  |  | 5 | G-215 |
| ~O~=CH₂ (3) | 4 | 1 | G-216 |
|  |  | 2 | G-217 |
|  |  | 3 | G-218 |
|  |  | 4 | G-219 |

TABLE 7-continued
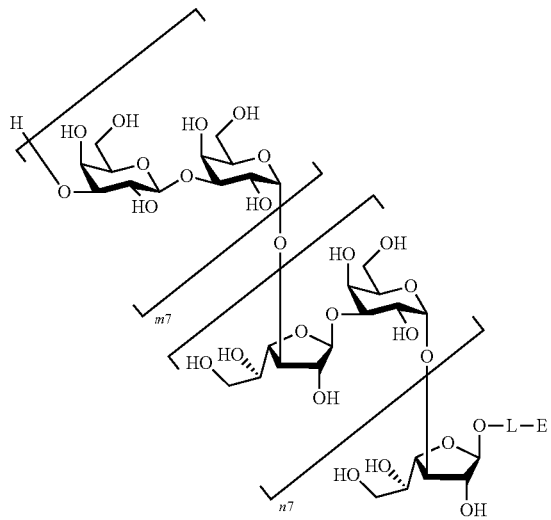
(II-G)
| —O—L—E | m7 | n7 | Compound No. |
|---|---|---|---|
|  |  | 5 | G-220 |
| ⋯O⟍⟋⟍₍₎₃ | 5 | 1 | G-221 |
|  |  | 2 | G-222 |
|  |  | 3 | G-223 |
|  |  | 4 | G-224 |
|  |  | 5 | G-225 |
| ⋯O⟍⟋≡ | 1 | 1 | G-226 |
|  |  | 2 | G-227 |
|  |  | 3 | G-228 |
|  |  | 4 | G-229 |
|  |  | 5 | G-230 |
| ⋯O⟍⟋≡ | 2 | 1 | G-231 |
|  |  | 2 | G-232 |
|  |  | 3 | G-233 |
|  |  | 4 | G-234 |
|  |  | 5 | G-235 |
| ⋯O⟍⟋≡ | 3 | 1 | G-236 |
|  |  | 2 | G-237 |
|  |  | 3 | G-238 |
|  |  | 4 | G-239 |
|  |  | 5 | G-240 |
| ⋯O⟍⟋≡ | 4 | 1 | G-241 |
|  |  | 2 | G-242 |
|  |  | 3 | G-243 |
|  |  | 4 | G-244 |
|  |  | 5 | G-245 |
| ⋯O⟍⟋≡ | 5 | 1 | G-246 |
|  |  | 2 | G-247 |
|  |  | 3 | G-248 |
|  |  | 4 | G-249 |
|  |  | 5 | G-250 |
| ⋯O⟍⟋⟍₍₎₅Br | 1 | 1 | G-251 |
|  |  | 2 | G-252 |
|  |  | 3 | G-253 |
|  |  | 4 | G-254 |
|  |  | 5 | G-255 |
| ⋯O⟍⟋⟍₍₎₅Br | 2 | 1 | G-256 |
|  |  | 2 | G-257 |
|  |  | 3 | G-258 |
|  |  | 4 | G-259 |
|  |  | 5 | G-260 |
| ⋯O⟍⟋⟍₍₎₅Br | 3 | 1 | G-261 |
|  |  | 2 | G-262 |
|  |  | 3 | G-263 |

TABLE 7-continued
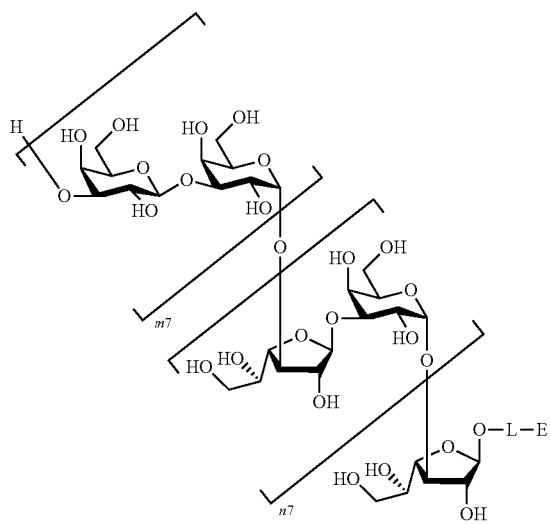
(II-G)
| —O—L—E | m7 | n7 | Compound No. |
|---|---|---|---|
|  |  | 4 | G-264 |
|  |  | 5 | G-265 |
| ⸺O⸺(CH₂)₅Br | 4 | 1 | G-266 |
|  |  | 2 | G-267 |
|  |  | 3 | G-268 |
|  |  | 4 | G-269 |
|  |  | 5 | G-270 |
| ⸺O⸺(CH₂)₅Br | 5 | 1 | G-271 |
|  |  | 2 | G-272 |
|  |  | 3 | G-273 |
|  |  | 4 | G-274 |
|  |  | 5 | G-275 |
| ⸺O⸺⸺O⸺⸺NH₂ | 1 | 1 | G-276 |
|  |  | 2 | G-277 |
|  |  | 3 | G-278 |
|  |  | 4 | G-279 |
|  |  | 5 | G-280 |
| ⸺O⸺⸺O⸺⸺NH₂ | 2 | 1 | G-281 |
|  |  | 2 | G-282 |
|  |  | 3 | G-283 |
|  |  | 4 | G-284 |
|  |  | 5 | G-285 |
| ⸺O⸺⸺O⸺⸺NH₂ | 3 | 1 | G-286 |
|  |  | 2 | G-287 |
|  |  | 3 | G-288 |
|  |  | 4 | G-289 |
|  |  | 5 | G-290 |
| ⸺O⸺⸺O⸺⸺NH₂ | 4 | 1 | G-291 |
|  |  | 2 | G-292 |
|  |  | 3 | G-293 |
|  |  | 4 | G-294 |
|  |  | 5 | G-295 |
| ⸺O⸺⸺O⸺⸺NH₂ | 5 | 1 | G-296 |
|  |  | 2 | G-297 |
|  |  | 3 | G-298 |
|  |  | 4 | G-299 |
|  |  | 5 | G-300 |
| ⸺O⸺(CH₂CH₂O)₃⸺NH₂ | 1 | 1 | G-301 |
|  |  | 2 | G-302 |
|  |  | 3 | G-303 |
|  |  | 4 | G-304 |
|  |  | 5 | G-305 |

TABLE 7-continued
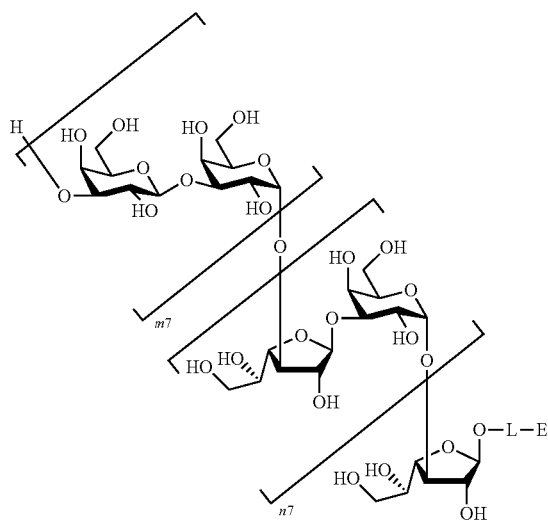
(II-G)
| —O—L—E | m7 | n7 | Compound No. |
|---|---|---|---|
| ⋯O~~O~~₃NH₂ | 2 | 1 | G-306 |
|  |  | 2 | G-307 |
|  |  | 3 | G-308 |
|  |  | 4 | G-309 |
|  |  | 5 | G-310 |
| ⋯O~~O~~₃NH₂ | 3 | 1 | G-311 |
|  |  | 2 | G-312 |
|  |  | 3 | G-313 |
|  |  | 4 | G-314 |
|  |  | 5 | G-315 |
| ⋯O~~O~~₃NH₂ | 4 | 1 | G-316 |
|  |  | 2 | G-317 |
|  |  | 3 | G-318 |
|  |  | 4 | G-319 |
|  |  | 5 | G-320 |
| ⋯O~~O~~₃NH₂ | 5 | 1 | G-321 |
|  |  | 2 | G-322 |
|  |  | 3 | G-323 |
|  |  | 4 | G-324 |
|  |  | 5 | G-325 |
| ⋯O-CH₂-CH(OH)-CH₂-OH | 1 | 1 | G-326 |
|  |  | 2 | G-327 |
|  |  | 3 | G-328 |
|  |  | 4 | G-329 |
|  |  | 5 | G-330 |
| ⋯O-CH₂-CH(OH)-CH₂-OH | 2 | 1 | G-331 |
|  |  | 2 | G-332 |
|  |  | 3 | G-333 |
|  |  | 4 | G-334 |
|  |  | 5 | G-335 |
| ⋯O-CH₂-CH(OH)-CH₂-OH | 3 | 1 | G-336 |
|  |  | 2 | G-337 |
|  |  | 3 | G-338 |
|  |  | 4 | G-339 |
|  |  | 5 | G-340 |
| ⋯O-CH₂-CH(OH)-CH₂-OH | 4 | 1 | G-341 |
|  |  | 2 | G-342 |
|  |  | 3 | G-343 |
|  |  | 4 | G-344 |
|  |  | 5 | G-345 |

TABLE 7-continued
(II-G)
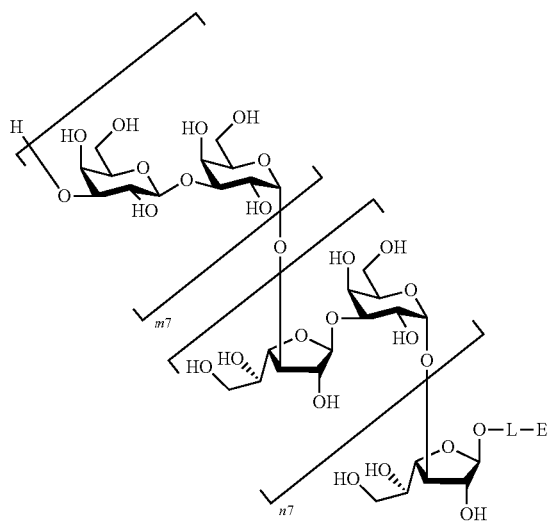
| —O—L—E | m7 | n7 | Compound No. |
|---|---|---|---|
|  | 5 | 1 | G-346 |
| | | 2 | G-347 |
| | | 3 | G-348 |
| | | 4 | G-349 |
| | | 5 | G-350 |
TABLE 8
(II-H)
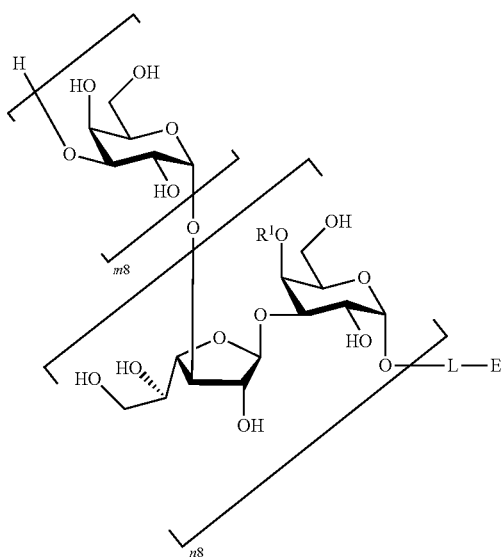
| —O—L—E | m8 | n8 | Compound No. |
|---|---|---|---|
| $\cdots O\!\!\left(\!\!\rule{0pt}{1.2em}\right)_{\!\!5}\!NH_2$ | 1 | 1 | H-01 |
| | | 2 | H-02 |
| | | 3 | H-03 |
| | | 4 | H-04 |
| | | 5 | H-05 |
| $\cdots O\!\!\left(\!\!\rule{0pt}{1.2em}\right)_{\!\!5}\!NH_2$ | 2 | 1 | H-06 |
| | | 2 | H-07 |
| | | 3 | H-08 |
| | | 4 | H-09 |
| | | 5 | H-10 |

TABLE 8-continued
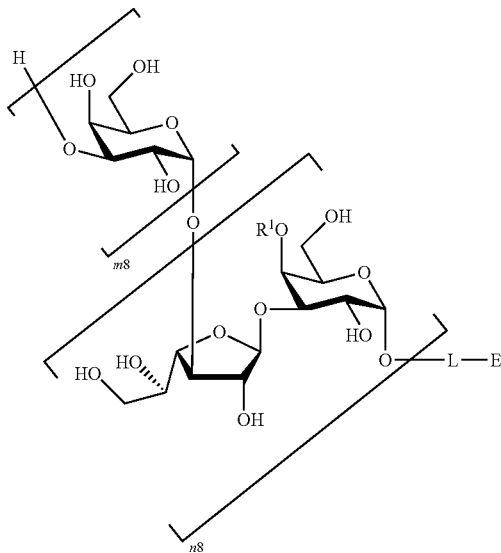
(II-H)
| —O—L—E | m8 | n8 | Compound No. |
|---|---|---|---|
|  | 3 | 1 | H-11 |
|  |  | 2 | H-12 |
|  |  | 3 | H-13 |
|  |  | 4 | H-14 |
|  |  | 5 | H-15 |
|  | 4 | 1 | H-16 |
|  |  | 2 | H-17 |
|  |  | 3 | H-18 |
|  |  | 4 | H-19 |
|  |  | 5 | H-20 |
|  | 5 | 1 | H-21 |
|  |  | 2 | H-22 |
|  |  | 3 | H-23 |
|  |  | 4 | H-24 |
|  |  | 5 | H-25 |
|  | 1 | 1 | H-26 |
|  |  | 2 | H-27 |
|  |  | 3 | H-28 |
|  |  | 4 | H-29 |
|  |  | 5 | H-30 |
|  | 2 | 1 | H-31 |
|  |  | 2 | H-32 |
|  |  | 3 | H-33 |
|  |  | 4 | H-34 |
|  |  | 5 | H-35 |
|  | 3 | 1 | H-36 |
|  |  | 2 | H-37 |
|  |  | 3 | H-38 |
|  |  | 4 | H-39 |
|  |  | 5 | H-40 |
|  | 4 | 1 | H-41 |
|  |  | 2 | H-42 |
|  |  | 3 | H-43 |
|  |  | 4 | H-44 |
|  |  | 5 | H-45 |
|  | 5 | 1 | H-46 |
|  |  | 2 | H-47 |
|  |  | 3 | H-48 |
|  |  | 4 | H-49 |
|  |  | 5 | H-50 |

TABLE 8-continued
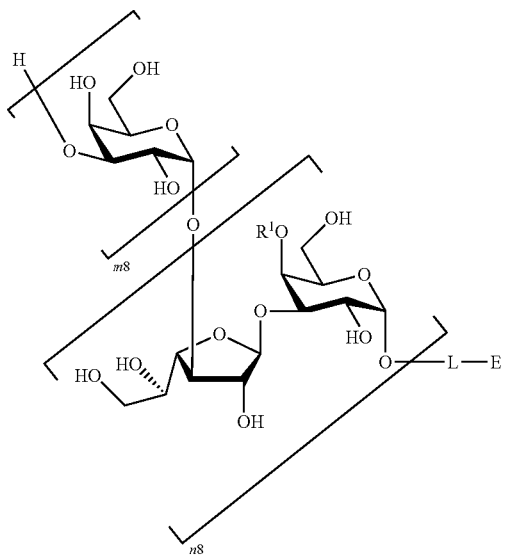
(II-H)
| —O—L—E | m8 | n8 | Compound No. |
|---|---|---|---|
| ⋯O(CH₂)₅N₃ | 1 | 1 | H-51 |
| | | 2 | H-52 |
| | | 3 | H-53 |
| | | 4 | H-54 |
| | | 5 | H-55 |
| ⋯O(CH₂)₅N₃ | 2 | 1 | H-56 |
| | | 2 | H-57 |
| | | 3 | H-58 |
| | | 4 | H-59 |
| | | 5 | H-60 |
| ⋯O(CH₂)₅N₃ | 3 | 1 | H-61 |
| | | 2 | H-62 |
| | | 3 | H-63 |
| | | 4 | H-64 |
| | | 5 | H-65 |
| ⋯O(CH₂)₅N₃ | 4 | 1 | H-66 |
| | | 2 | H-67 |
| | | 3 | H-68 |
| | | 4 | H-69 |
| | | 5 | H-70 |
| ⋯O(CH₂)₅N₃ | 5 | 1 | H-71 |
| | | 2 | H-72 |
| | | 3 | H-73 |
| | | 4 | H-74 |
| | | 5 | H-75 |
| ⋯O(CH₂)₄ONH₂ | 1 | 1 | H-76 |
| | | 2 | H-77 |
| | | 3 | H-78 |
| | | 4 | H-79 |
| | | 5 | H-80 |
| ⋯O(CH₂)₄ONH₂ | 2 | 1 | H-81 |
| | | 2 | H-82 |
| | | 3 | H-83 |
| | | 4 | H-84 |
| | | 5 | H-85 |
| ⋯O(CH₂)₄ONH₂ | 3 | 1 | H-86 |
| | | 2 | H-87 |
| | | 3 | H-88 |
| | | 4 | H-89 |
| | | 5 | H-90 |
| ⋯O(CH₂)₄ONH₂ | 4 | 1 | H-91 |
| | | 2 | H-92 |
| | | 3 | H-93 |

TABLE 8-continued
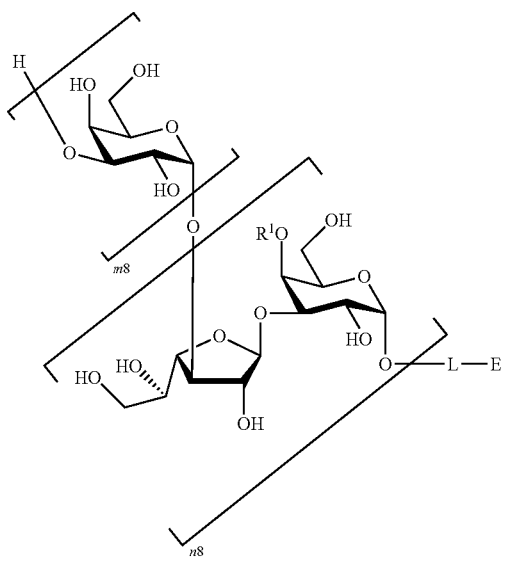
(II-H)
| —O—L—E | m8 | n8 | Compound No. |
|---|---|---|---|
| | | 4 | H-94 |
| | | 5 | H-95 |
| ⋯O∼(  )₄∼O–NH₂ | 5 | 1 | H-96 |
| | | 2 | H-97 |
| | | 3 | H-98 |
| | | 4 | H-99 |
| | | 5 | H-100 |
| ⋯O∼(  )₃–C(O)OH | 1 | 1 | H-101 |
| | | 2 | H-102 |
| | | 3 | H-103 |
| | | 4 | H-104 |
| | | 5 | H-105 |
| ⋯O∼(  )₃–C(O)OH | 2 | 1 | H-106 |
| | | 2 | H-107 |
| | | 3 | H-108 |
| | | 4 | H-109 |
| | | 5 | H-110 |
| ⋯O∼(  )₃–C(O)OH | 3 | 1 | H-111 |
| | | 2 | H-112 |
| | | 3 | H-113 |
| | | 4 | H-114 |
| | | 5 | H-115 |
| ⋯O∼(  )₃–C(O)OH | 4 | 1 | H-116 |
| | | 2 | H-117 |
| | | 3 | H-118 |
| | | 4 | H-119 |
| | | 5 | H-120 |
| ⋯O∼(  )₃–C(O)OH | 5 | 1 | H-121 |
| | | 2 | H-122 |
| | | 3 | H-123 |
| | | 4 | H-124 |
| | | 5 | H-125 |
| ⋯O∼(  )₁₀–C(O)OH | 1 | 1 | H-126 |
| | | 2 | H-127 |
| | | 3 | H-128 |
| | | 4 | H-129 |
| | | 5 | H-130 |
| ⋯O∼(  )₁₀–C(O)OH | 2 | 1 | H-131 |
| | | 2 | H-132 |
| | | 3 | H-133 |
| | | 4 | H-134 |
| | | 5 | H-135 |

TABLE 8-continued
(II-H)
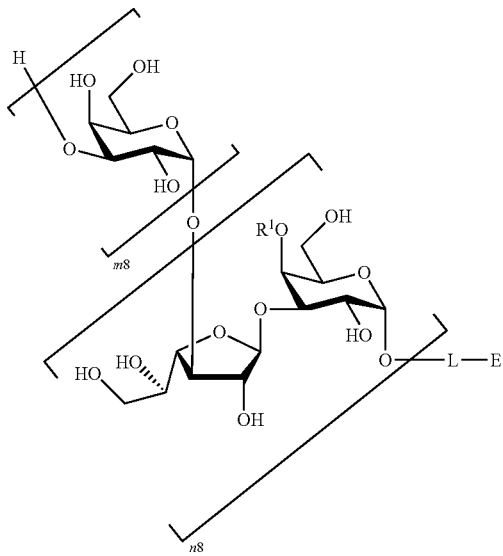
| —O—L—E | m8 | n8 | Compound No. |
|---|---|---|---|
| 10-COOH) | 3 | 1 | H-136 |
|  |  | 2 | H-137 |
|  |  | 3 | H-138 |
|  |  | 4 | H-139 |
|  |  | 5 | H-140 |
| 10-COOH) | 4 | 1 | H-141 |
|  |  | 2 | H-142 |
|  |  | 3 | H-143 |
|  |  | 4 | H-144 |
|  |  | 5 | H-145 |
| 10-COOH) | 5 | 1 | H-146 |
|  |  | 2 | H-147 |
|  |  | 3 | H-148 |
|  |  | 4 | H-149 |
|  |  | 5 | H-150 |
| 5-C(O)NHNH2) | 1 | 1 | H-151 |
|  |  | 2 | H-152 |
|  |  | 3 | H-153 |
|  |  | 4 | H-154 |
|  |  | 5 | H-155 |
| 5-C(O)NHNH2) | 2 | 1 | H-156 |
|  |  | 2 | H-157 |
|  |  | 3 | H-158 |
|  |  | 4 | H-159 |
|  |  | 5 | H-160 |
| 5-C(O)NHNH2) | 3 | 1 | H-161 |
|  |  | 2 | H-162 |
|  |  | 3 | H-163 |
|  |  | 4 | H-164 |
|  |  | 5 | H-165 |
| 5-C(O)NHNH2) | 4 | 1 | H-166 |
|  |  | 2 | H-167 |
|  |  | 3 | H-168 |
|  |  | 4 | H-169 |
|  |  | 5 | H-170 |
| 5-C(O)NHNH2) | 5 | 1 | H-171 |
|  |  | 2 | H-172 |
|  |  | 3 | H-173 |
|  |  | 4 | H-174 |
|  |  | 5 | H-175 |
| 3-SH) | 1 | 1 | H-176 |
|  |  | 2 | H-177 |
|  |  | 3 | H-178 |

TABLE 8-continued
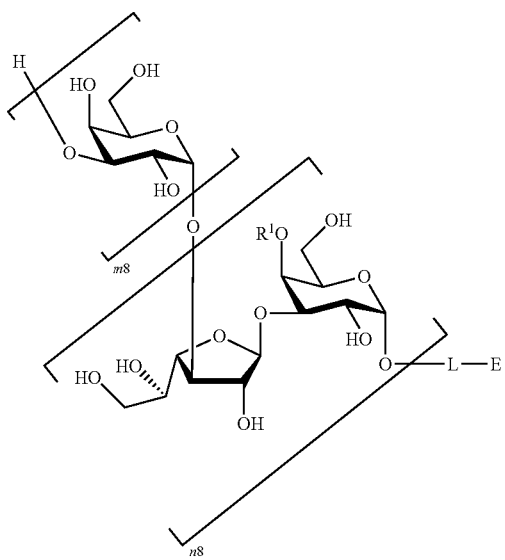
(II-H)
| —O—L—E | m8 | n8 | Compound No. |
|---|---|---|---|
|  |  | 4 | H-179 |
|  |  | 5 | H-180 |
| ⋯O(⟋)₃SH | 2 | 1 | H-181 |
|  |  | 2 | H-182 |
|  |  | 3 | H-183 |
|  |  | 4 | H-184 |
|  |  | 5 | H-185 |
| ⋯O(⟋)₃SH | 3 | 1 | H-186 |
|  |  | 2 | H-187 |
|  |  | 3 | H-188 |
|  |  | 4 | H-189 |
|  |  | 5 | H-190 |
| ⋯O(⟋)₃SH | 4 | 1 | H-191 |
|  |  | 2 | H-192 |
|  |  | 3 | H-193 |
|  |  | 4 | H-194 |
|  |  | 5 | H-195 |
| ⋯O(⟋)₃SH | 5 | 1 | H-196 |
|  |  | 2 | H-197 |
|  |  | 3 | H-198 |
|  |  | 4 | H-199 |
|  |  | 5 | H-200 |
| ⋯O(⟋)₃⟍ | 1 | 1 | H-201 |
|  |  | 2 | H-202 |
|  |  | 3 | H-203 |
|  |  | 4 | H-204 |
|  |  | 5 | H-205 |
| ⋯O(⟋)₃⟍ | 2 | 1 | H-206 |
|  |  | 2 | H-207 |
|  |  | 3 | H-208 |
|  |  | 4 | H-209 |
|  |  | 5 | H-210 |
| ⋯O(⟋)₃⟍ | 3 | 1 | H-211 |
|  |  | 2 | H-212 |
|  |  | 3 | H-213 |
|  |  | 4 | H-214 |
|  |  | 5 | H-215 |
| ⋯O(⟋)₃⟍ | 4 | 1 | H-216 |
|  |  | 2 | H-217 |
|  |  | 3 | H-218 |
|  |  | 4 | H-219 |
|  |  | 5 | H-220 |

TABLE 8-continued
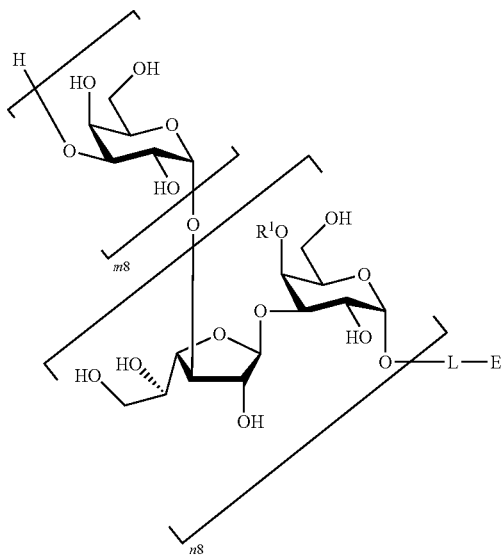
(II-H)
| —O—L—E | m8 | n8 | Compound No. |
|---|---|---|---|
| ⋯O–(CH₂)₃–CH=CH₂ | 5 | 1 | H-221 |
|  |  | 2 | H-222 |
|  |  | 3 | H-223 |
|  |  | 4 | H-224 |
|  |  | 5 | H-225 |
| ⋯O–CH₂–C≡CH | 1 | 1 | H-226 |
|  |  | 2 | H-227 |
|  |  | 3 | H-228 |
|  |  | 4 | H-229 |
|  |  | 5 | H-230 |
| ⋯O–CH₂–C≡CH | 2 | 1 | H-231 |
|  |  | 2 | H-232 |
|  |  | 3 | H-233 |
|  |  | 4 | H-234 |
|  |  | 5 | H-235 |
| ⋯O–CH₂–C≡CH | 3 | 1 | H-236 |
|  |  | 2 | H-237 |
|  |  | 3 | H-238 |
|  |  | 4 | H-239 |
|  |  | 5 | H-240 |
| ⋯O–CH₂–C≡CH | 4 | 1 | H-241 |
|  |  | 2 | H-242 |
|  |  | 3 | H-243 |
|  |  | 4 | H-244 |
|  |  | 5 | H-245 |
| ⋯O–CH₂–C≡CH | 5 | 1 | H-246 |
|  |  | 2 | H-247 |
|  |  | 3 | H-248 |
|  |  | 4 | H-249 |
|  |  | 5 | H-250 |
| ⋯O–(CH₂)₅–Br | 1 | 1 | H-251 |
|  |  | 2 | H-252 |
|  |  | 3 | H-253 |
|  |  | 4 | H-254 |
|  |  | 5 | H-255 |
| ⋯O–(CH₂)₅–Br | 2 | 1 | H-256 |
|  |  | 2 | H-257 |
|  |  | 3 | H-258 |
|  |  | 4 | H-259 |
|  |  | 5 | H-260 |
| ⋯O–(CH₂)₅–Br | 3 | 1 | H-261 |
|  |  | 2 | H-262 |
|  |  | 3 | H-263 |

TABLE 8-continued
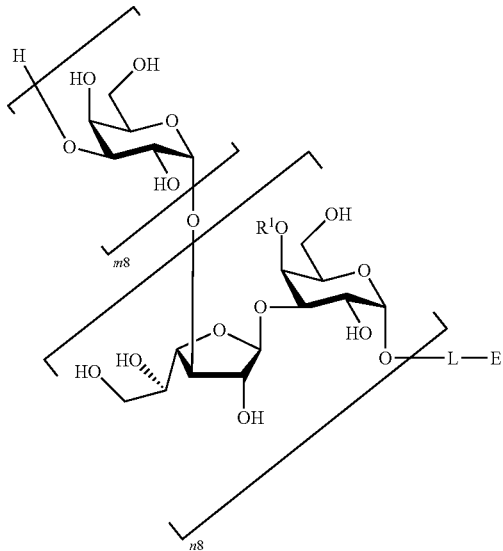
(II-H)
| —O—L—E | m8 | n8 | Compound No. |
|---|---|---|---|
| | | 4 | H-264 |
| | | 5 | H-265 |
| ⋯O(CH₂)₅Br | 4 | 1 | H-266 |
| | | 2 | H-267 |
| | | 3 | H-268 |
| | | 4 | H-269 |
| | | 5 | H-270 |
| ⋯O(CH₂)₅Br | 5 | 1 | H-271 |
| | | 2 | H-272 |
| | | 3 | H-273 |
| | | 4 | H-274 |
| | | 5 | H-275 |
| ⋯O-CH₂CH₂-O-CH₂CH₂-NH₂ | 1 | 1 | H-276 |
| | | 2 | H-277 |
| | | 3 | H-278 |
| | | 4 | H-279 |
| | | 5 | H-280 |
| ⋯O-CH₂CH₂-O-CH₂CH₂-NH₂ | 2 | 1 | H-281 |
| | | 2 | H-282 |
| | | 3 | H-283 |
| | | 4 | H-284 |
| | | 5 | H-285 |
| ⋯O-CH₂CH₂-O-CH₂CH₂-NH₂ | 3 | 1 | H-286 |
| | | 2 | H-287 |
| | | 3 | H-288 |
| | | 4 | H-289 |
| | | 5 | H-290 |
| ⋯O-CH₂CH₂-O-CH₂CH₂-NH₂ | 4 | 1 | H-291 |
| | | 2 | H-292 |
| | | 3 | H-293 |
| | | 4 | H-294 |
| | | 5 | H-295 |
| ⋯O-CH₂CH₂-O-CH₂CH₂-NH₂ | 5 | 1 | H-296 |
| | | 2 | H-297 |
| | | 3 | H-298 |
| | | 4 | H-299 |
| | | 5 | H-300 |
| ⋯O-CH₂CH₂-(O-CH₂CH₂)₃-NH₂ | 1 | 1 | H-301 |
| | | 2 | H-302 |
| | | 3 | H-303 |
| | | 4 | H-304 |
| | | 5 | H-305 |

TABLE 8-continued
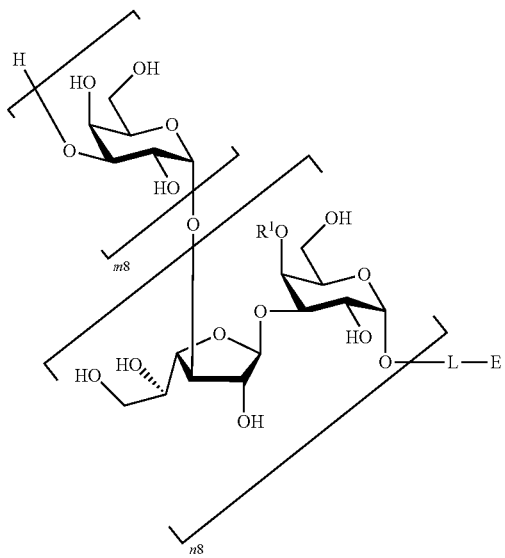
(II-H)
| —O—L—E | m8 | n8 | Compound No. |
|---|---|---|---|
| ⋯O(CH₂CH₂O)₃NH₂ | 2 | 1 | H-306 |
|  |  | 2 | H-307 |
|  |  | 3 | H-308 |
|  |  | 4 | H-309 |
|  |  | 5 | H-310 |
| ⋯O(CH₂CH₂O)₃NH₂ | 3 | 1 | H-311 |
|  |  | 2 | H-312 |
|  |  | 3 | H-313 |
|  |  | 4 | H-314 |
|  |  | 5 | H-315 |
| ⋯O(CH₂CH₂O)₃NH₂ | 4 | 1 | H-316 |
|  |  | 2 | H-317 |
|  |  | 3 | H-318 |
|  |  | 4 | H-319 |
|  |  | 5 | H-320 |
| ⋯O(CH₂CH₂O)₃NH₂ | 5 | 1 | H-321 |
|  |  | 2 | H-322 |
|  |  | 3 | H-323 |
|  |  | 4 | H-324 |
|  |  | 5 | H-325 |
| ⋯O-CH₂CH(OH)CH₂OH | 1 | 1 | H-326 |
|  |  | 2 | H-327 |
|  |  | 3 | H-328 |
|  |  | 4 | H-329 |
|  |  | 5 | H-330 |
| ⋯O-CH₂CH(OH)CH₂OH | 2 | 1 | H-331 |
|  |  | 2 | H-332 |
|  |  | 3 | H-333 |
|  |  | 4 | H-334 |
|  |  | 5 | H-335 |
| ⋯O-CH₂CH(OH)CH₂OH | 3 | 1 | H-336 |
|  |  | 2 | H-337 |
|  |  | 3 | H-338 |
|  |  | 4 | H-339 |
|  |  | 5 | H-340 |
| ⋯O-CH₂CH(OH)CH₂OH | 4 | 1 | H-341 |
|  |  | 2 | H-342 |
|  |  | 3 | H-343 |
|  |  | 4 | H-344 |
|  |  | 5 | H-345 |

TABLE 8-continued
(II-H)
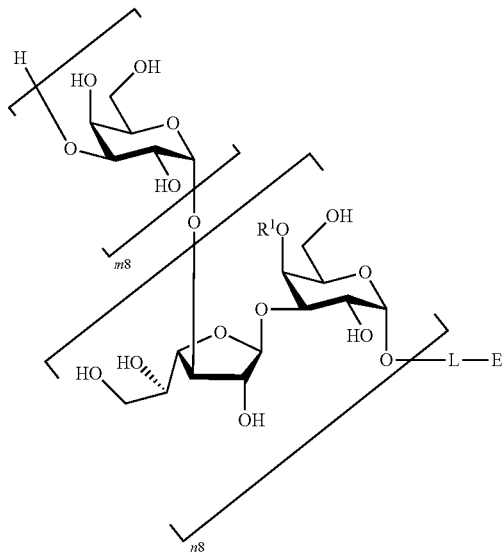
| —O—L—E | m8 | n8 | Compound No. |
|---|---|---|---|
| (structure: O-CH2-CH(OH)-CH2-OH with OH) | 5 | 1 | H-346 |
| | | 2 | H-347 |
| | | 3 | H-348 |
| | | 4 | H-349 |
| | | 5 | H-350 |
TABLE 9
(II-I)
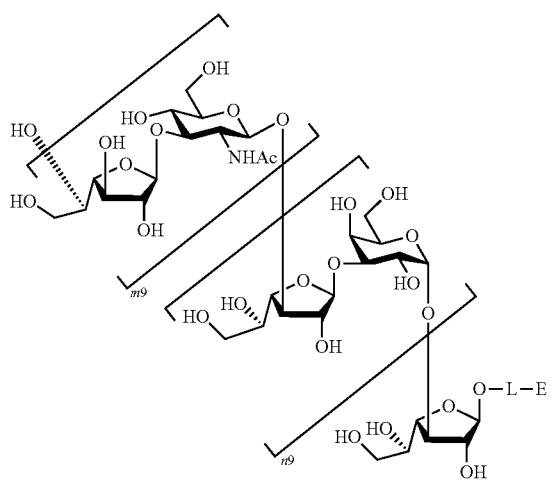
| —O—L—E | m9 | n9 | Compound No. |
|---|---|---|---|
| $\cdots O{\sim}_5 NH_2$ | 1 | 1 | J-01 |
| | | 2 | J-02 |
| | | 3 | J-03 |
| | | 4 | J-04 |
| | | 5 | J-05 |
| $\cdots O{\sim}_5 NH_2$ | 2 | 1 | J-06 |
| | | 2 | J-07 |
| | | 3 | J-08 |
| | | 4 | J-09 |
| | | 5 | J-10 |

TABLE 9-continued
(II-I)
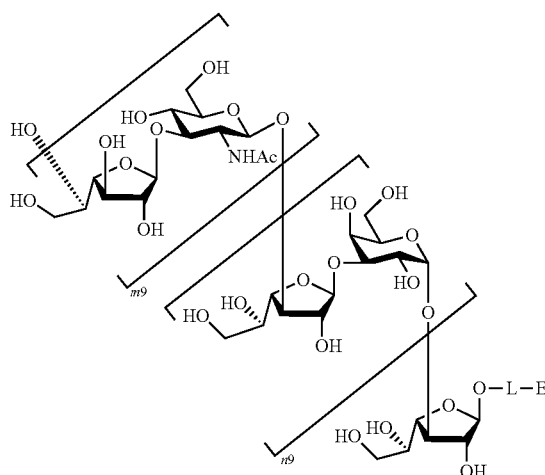
| —O—L—E | m9 | n9 | Compound No. |
|---|---|---|---|
| ⋯O(⋯)₅NH₂ | 3 | 1 | J-11 |
| | | 2 | J-12 |
| | | 3 | J-13 |
| | | 4 | J-14 |
| | | 5 | J-15 |
| ⋯O(⋯)₅NH₂ | 4 | 1 | J-16 |
| | | 2 | J-17 |
| | | 3 | J-18 |
| | | 4 | J-19 |
| | | 5 | J-20 |
| ⋯O(⋯)₅NH₂ | 5 | 1 | J-21 |
| | | 2 | J-22 |
| | | 3 | J-23 |
| | | 4 | J-24 |
| | | 5 | J-25 |
| ⋯O(⋯)₁₀NH₂ | 1 | 1 | J-26 |
| | | 2 | J-27 |
| | | 3 | J-28 |
| | | 4 | J-29 |
| | | 5 | J-30 |
| ⋯O(⋯)₁₀NH₂ | 2 | 1 | J-31 |
| | | 2 | J-32 |
| | | 3 | J-33 |
| | | 4 | J-34 |
| | | 5 | J-35 |
| ⋯O(⋯)₁₀NH₂ | 3 | 1 | J-36 |
| | | 2 | J-37 |
| | | 3 | J-38 |
| | | 4 | J-39 |
| | | 5 | J-40 |
| ⋯O(⋯)₁₀NH₂ | 4 | 1 | J-41 |
| | | 2 | J-42 |
| | | 3 | J-43 |
| | | 4 | J-44 |
| | | 5 | J-45 |
| ⋯O(⋯)₁₀NH₂ | 5 | 1 | J-46 |
| | | 2 | J-47 |
| | | 3 | J-48 |
| | | 4 | J-49 |
| | | 5 | J-50 |
| ⋯O(⋯)₅N₃ | 1 | 1 | J-51 |
| | | 2 | J-52 |
| | | 3 | J-53 |
| | | 4 | J-54 |
| | | 5 | J-55 |

TABLE 9-continued
(II-I)
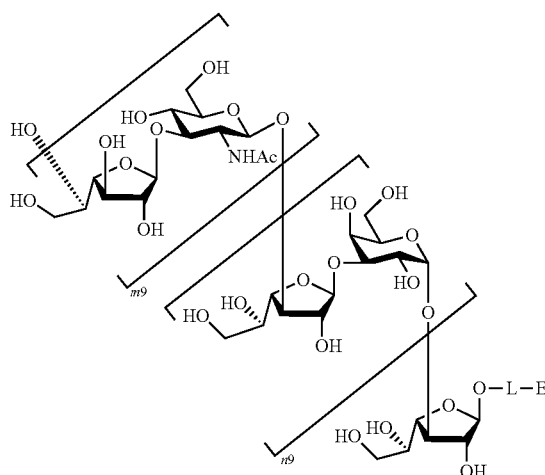
| —O—L—E | m9 | n9 | Compound No. |
|---|---|---|---|
| ⸺O⟋₅N₃ | 2 | 1 | J-56 |
|  |  | 2 | J-57 |
|  |  | 3 | J-58 |
|  |  | 4 | J-59 |
|  |  | 5 | J-60 |
| ⸺O⟋₅N₃ | 3 | 1 | J-61 |
|  |  | 2 | J-62 |
|  |  | 3 | J-63 |
|  |  | 4 | J-64 |
|  |  | 5 | J-65 |
| ⸺O⟋₅N₃ | 4 | 1 | J-66 |
|  |  | 2 | J-67 |
|  |  | 3 | J-68 |
|  |  | 4 | J-69 |
|  |  | 5 | J-70 |
| ⸺O⟋₅N₃ | 5 | 1 | J-71 |
|  |  | 2 | J-72 |
|  |  | 3 | J-73 |
|  |  | 4 | J-74 |
|  |  | 5 | J-75 |
| ⸺O⟋₄O−NH₂ | 1 | 1 | J-76 |
|  |  | 2 | J-77 |
|  |  | 3 | J-78 |
|  |  | 4 | J-79 |
|  |  | 5 | J-80 |
| ⸺O⟋₄O−NH₂ | 2 | 1 | J-81 |
|  |  | 2 | J-82 |
|  |  | 3 | J-83 |
|  |  | 4 | J-84 |
|  |  | 5 | J-85 |
| ⸺O⟋₄O−NH₂ | 3 | 1 | J-86 |
|  |  | 2 | J-87 |
|  |  | 3 | J-88 |
|  |  | 4 | J-89 |
|  |  | 5 | J-90 |
| ⸺O⟋₄O−NH₂ | 4 | 1 | J-91 |
|  |  | 2 | J-92 |
|  |  | 3 | J-93 |
|  |  | 4 | J-94 |
|  |  | 5 | J-95 |
| ⸺O⟋₄O−NH₂ | 5 | 1 | J-96 |
|  |  | 2 | J-97 |
|  |  | 3 | J-98 |
|  |  | 4 | J-99 |
|  |  | 5 | J-100 |

TABLE 9-continued
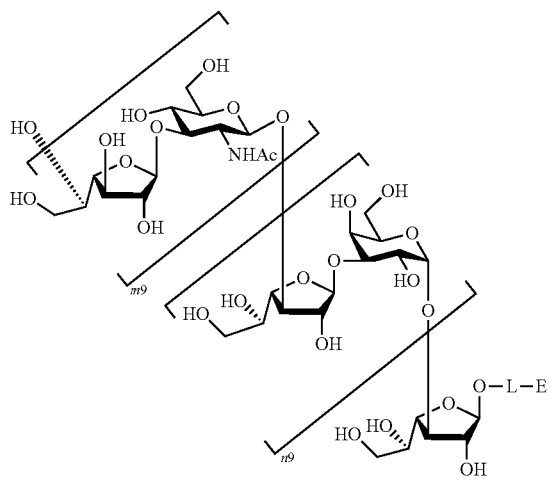
(II-I)
| —O—L—E | m9 | n9 | Compound No. |
|---|---|---|---|
| ⟶O—(⟶)₃—C(=O)OH | 1 | 1 | J-101 |
| | | 2 | J-102 |
| | | 3 | J-103 |
| | | 4 | J-104 |
| | | 5 | J-105 |
| ⟶O—(⟶)₃—C(=O)OH | 2 | 1 | J-106 |
| | | 2 | J-107 |
| | | 3 | J-108 |
| | | 4 | J-109 |
| | | 5 | J-110 |
| ⟶O—(⟶)₃—C(=O)OH | 3 | 1 | J-111 |
| | | 2 | J-112 |
| | | 3 | J-113 |
| | | 4 | J-114 |
| | | 5 | J-115 |
| ⟶O—(⟶)₃—C(=O)OH | 4 | 1 | J-116 |
| | | 2 | J-117 |
| | | 3 | J-118 |
| | | 4 | J-119 |
| | | 5 | J-120 |
| ⟶O—(⟶)₃—C(=O)OH | 5 | 1 | J-121 |
| | | 2 | J-122 |
| | | 3 | J-123 |
| | | 4 | J-124 |
| | | 5 | J-125 |
| ⟶O—(⟶)₁₀—C(=O)OH | 1 | 1 | J-126 |
| | | 2 | J-127 |
| | | 3 | J-128 |
| | | 4 | J-129 |
| | | 5 | J-130 |
| ⟶O—(⟶)₁₀—C(=O)OH | 2 | 1 | J-131 |
| | | 2 | J-132 |
| | | 3 | J-133 |
| | | 4 | J-134 |
| | | 5 | J-135 |
| ⟶O—(⟶)₁₀—C(=O)OH | 3 | 1 | J-136 |
| | | 2 | J-137 |
| | | 3 | J-138 |
| | | 4 | J-139 |
| | | 5 | J-140 |
| ⟶O—(⟶)₁₀—C(=O)OH | 4 | 1 | J-141 |
| | | 2 | J-142 |
| | | 3 | J-143 |
| | | 4 | J-144 |
| | | 5 | J-145 |

TABLE 9-continued
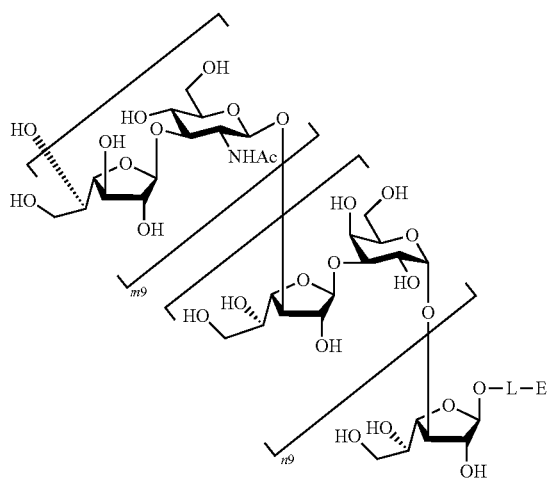
(II-I)
| —O—L—E | m9 | n9 | Compound No. |
|---|---|---|---|
| ⋯O−(⸺)₁₀−C(O)OH | 5 | 1 | J-146 |
|  |  | 2 | J-147 |
|  |  | 3 | J-148 |
|  |  | 4 | J-149 |
|  |  | 5 | J-150 |
| ⋯O−(⸺)₅−C(O)NHNH₂ | 1 | 1 | J-151 |
|  |  | 2 | J-152 |
|  |  | 3 | J-153 |
|  |  | 4 | J-154 |
|  |  | 5 | J-155 |
| ⋯O−(⸺)₅−C(O)NHNH₂ | 2 | 1 | J-156 |
|  |  | 2 | J-157 |
|  |  | 3 | J-158 |
|  |  | 4 | J-159 |
|  |  | 5 | J-160 |
| ⋯O−(⸺)₅−C(O)NHNH₂ | 3 | 1 | J-161 |
|  |  | 2 | J-162 |
|  |  | 3 | J-163 |
|  |  | 4 | J-164 |
|  |  | 5 | J-165 |
| ⋯O−(⸺)₅−C(O)NHNH₂ | 4 | 1 | J-166 |
|  |  | 2 | J-167 |
|  |  | 3 | J-168 |
|  |  | 4 | J-169 |
|  |  | 5 | J-170 |
| ⋯O−(⸺)₅−C(O)NHNH₂ | 5 | 1 | J-171 |
|  |  | 2 | J-172 |
|  |  | 3 | J-173 |
|  |  | 4 | J-174 |
|  |  | 5 | J-175 |
| ⋯O−(⸺)₃−SH | 1 | 1 | J-176 |
|  |  | 2 | J-177 |
|  |  | 3 | J-178 |
|  |  | 4 | J-179 |
|  |  | 5 | J-180 |
| ⋯O−(⸺)₃−SH | 2 | 1 | J-181 |
|  |  | 2 | J-182 |
|  |  | 3 | J-183 |
|  |  | 4 | J-184 |
|  |  | 5 | J-185 |
| ⋯O−(⸺)₃−SH | 3 | 1 | J-186 |
|  |  | 2 | J-187 |
|  |  | 3 | J-188 |
|  |  | 4 | J-189 |
|  |  | 5 | J-190 |

TABLE 9-continued
(II-I)
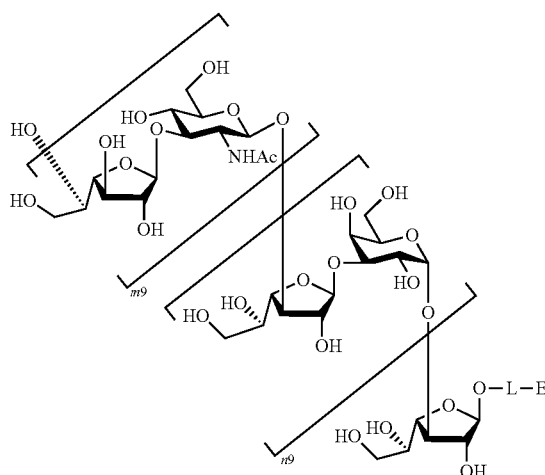
| —O—L—E | m9 | n9 | Compound No. |
|---|---|---|---|
| ⋯O⟶(⟶)₃⟶SH | 4 | 1 | J-191 |
|  |  | 2 | J-192 |
|  |  | 3 | J-193 |
|  |  | 4 | J-194 |
|  |  | 5 | J-195 |
| ⋯O⟶(⟶)₃⟶SH | 5 | 1 | J-196 |
|  |  | 2 | J-197 |
|  |  | 3 | J-198 |
|  |  | 4 | J-199 |
|  |  | 5 | J-200 |
| ⋯O⟶(⟶)₃⟶CH=CH₂ | 1 | 1 | J-201 |
|  |  | 2 | J-202 |
|  |  | 3 | J-203 |
|  |  | 4 | J-204 |
|  |  | 5 | J-205 |
| ⋯O⟶(⟶)₃⟶CH=CH₂ | 2 | 1 | J-206 |
|  |  | 2 | J-207 |
|  |  | 3 | J-208 |
|  |  | 4 | J-209 |
|  |  | 5 | J-210 |
| ⋯O⟶(⟶)₃⟶CH=CH₂ | 3 | 1 | J-211 |
|  |  | 2 | J-212 |
|  |  | 3 | J-213 |
|  |  | 4 | J-214 |
|  |  | 5 | J-215 |
| ⋯O⟶(⟶)₃⟶CH=CH₂ | 4 | 1 | J-216 |
|  |  | 2 | J-217 |
|  |  | 3 | J-218 |
|  |  | 4 | J-219 |
|  |  | 5 | J-220 |
| ⋯O⟶(⟶)₃⟶CH=CH₂ | 5 | 1 | J-221 |
|  |  | 2 | J-222 |
|  |  | 3 | J-223 |
|  |  | 4 | J-224 |
|  |  | 5 | J-225 |
| ⋯O⟶CH₂⟶C≡CH | 1 | 1 | J-226 |
|  |  | 2 | J-227 |
|  |  | 3 | J-228 |
|  |  | 4 | J-229 |
|  |  | 5 | J-230 |
| ⋯O⟶CH₂⟶C≡CH | 2 | 1 | J-231 |
|  |  | 2 | J-232 |
|  |  | 3 | J-233 |
|  |  | 4 | J-234 |
|  |  | 5 | J-235 |

TABLE 9-continued
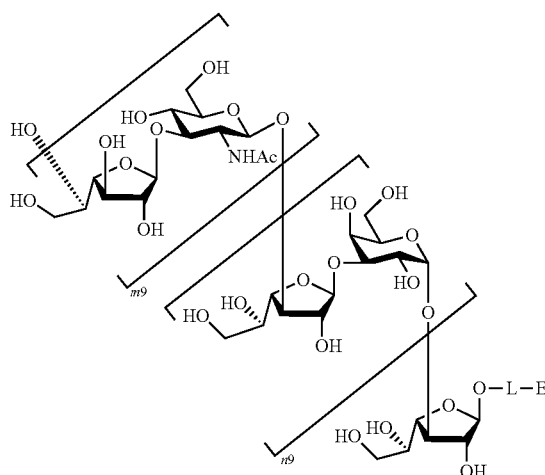
(II-I)
| —O—L—E | m9 | n9 | Compound No. |
|---|---|---|---|
| ...O⟶≡ | 3 | 1 | J-236 |
| | | 2 | J-237 |
| | | 3 | J-238 |
| | | 4 | J-239 |
| | | 5 | J-240 |
| ...O⟶≡ | 4 | 1 | J-241 |
| | | 2 | J-242 |
| | | 3 | J-243 |
| | | 4 | J-244 |
| | | 5 | J-245 |
| ...O⟶≡ | 5 | 1 | J-246 |
| | | 2 | J-247 |
| | | 3 | J-248 |
| | | 4 | J-249 |
| | | 5 | J-250 |
| ...O(CH₂)₅Br | 1 | 1 | J-251 |
| | | 2 | J-252 |
| | | 3 | J-253 |
| | | 4 | J-254 |
| | | 5 | J-255 |
| ...O(CH₂)₅Br | 2 | 1 | J-256 |
| | | 2 | J-257 |
| | | 3 | J-258 |
| | | 4 | J-259 |
| | | 5 | J-260 |
| ...O(CH₂)₅Br | 3 | 1 | J-261 |
| | | 2 | J-262 |
| | | 3 | J-263 |
| | | 4 | J-264 |
| | | 5 | J-265 |
| ...O(CH₂)₅Br | 4 | 1 | J-266 |
| | | 2 | J-267 |
| | | 3 | J-268 |
| | | 4 | J-269 |
| | | 5 | J-270 |
| ...O(CH₂)₅Br | 5 | 1 | J-271 |
| | | 2 | J-272 |
| | | 3 | J-273 |
| | | 4 | J-274 |
| | | 5 | J-275 |
| ...OCH₂CH₂OCH₂CH₂NH₂ | 1 | 1 | J-276 |
| | | 2 | J-277 |
| | | 3 | J-278 |
| | | 4 | J-279 |
| | | 5 | J-280 |

TABLE 9-continued
(II-I)
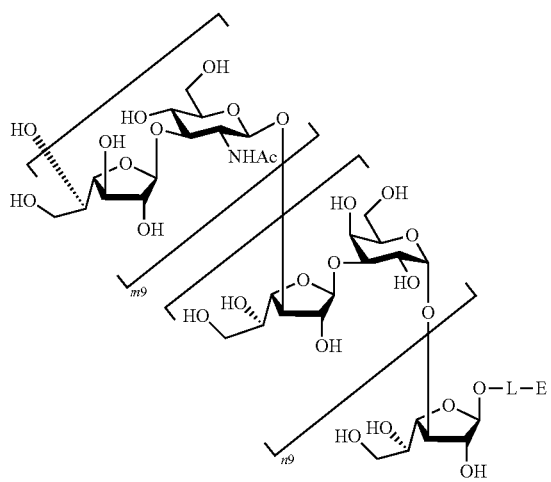
| —O—L—E | m9 | n9 | Compound No. |
|---|---|---|---|
| ⋯O⌒O⌒NH₂ | 2 | 1 | J-281 |
| | | 2 | J-282 |
| | | 3 | J-283 |
| | | 4 | J-284 |
| | | 5 | J-285 |
| ⋯O⌒O⌒NH₂ | 3 | 1 | J-286 |
| | | 2 | J-287 |
| | | 3 | J-288 |
| | | 4 | J-289 |
| | | 5 | J-290 |
| ⋯O⌒O⌒NH₂ | 4 | 1 | J-291 |
| | | 2 | J-292 |
| | | 3 | J-293 |
| | | 4 | J-294 |
| | | 5 | J-295 |
| ⋯O⌒O⌒NH₂ | 5 | 1 | J-296 |
| | | 2 | J-297 |
| | | 3 | J-298 |
| | | 4 | J-299 |
| | | 5 | J-300 |
| ⋯O⌒(O⌒)₃NH₂ | 1 | 1 | J-301 |
| | | 2 | J-302 |
| | | 3 | J-303 |
| | | 4 | J-304 |
| | | 5 | J-305 |
| ⋯O⌒(O⌒)₃NH₂ | 2 | 1 | J-306 |
| | | 2 | J-307 |
| | | 3 | J-308 |
| | | 4 | J-309 |
| | | 5 | J-310 |
| ⋯O⌒(O⌒)₃NH₂ | 3 | 1 | J-311 |
| | | 2 | J-312 |
| | | 3 | J-313 |
| | | 4 | J-314 |
| | | 5 | J-315 |
| ⋯O⌒(O⌒)₃NH₂ | 4 | 1 | J-316 |
| | | 2 | J-317 |
| | | 3 | J-318 |
| | | 4 | J-319 |
| | | 5 | J-320 |

TABLE 9-continued
(II-I)
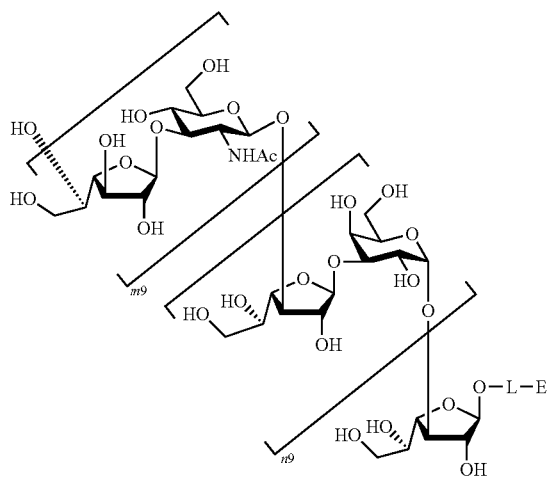
| —O—L—E | m9 | n9 | Compound No. |
|---|---|---|---|
| 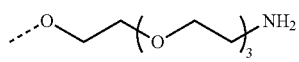 | 5 | 1 | J-321 |
|  |  | 2 | J-322 |
|  |  | 3 | J-323 |
|  |  | 4 | J-324 |
|  |  | 5 | J-325 |
| 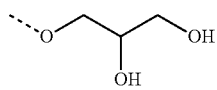 | 1 | 1 | J-326 |
|  |  | 2 | J-327 |
|  |  | 3 | J-328 |
|  |  | 4 | J-329 |
|  |  | 5 | J-330 |
| 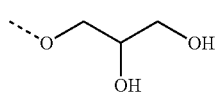 | 2 | 1 | J-331 |
|  |  | 2 | J-332 |
|  |  | 3 | J-333 |
|  |  | 4 | J-334 |
|  |  | 5 | J-335 |
| 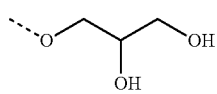 | 3 | 1 | J-336 |
|  |  | 2 | J-337 |
|  |  | 3 | J-338 |
|  |  | 4 | J-339 |
|  |  | 5 | J-340 |
| 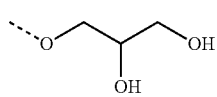 | 4 | 1 | J-341 |
|  |  | 2 | J-342 |
|  |  | 3 | J-343 |
|  |  | 4 | J-344 |
|  |  | 5 | J-345 |
| 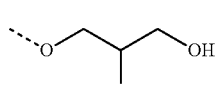 | 5 | 1 | J-346 |
|  |  | 2 | J-347 |
|  |  | 3 | J-348 |
|  |  | 4 | J-349 |
|  |  | 5 | J-350 |

TABLE 10
(II-K)
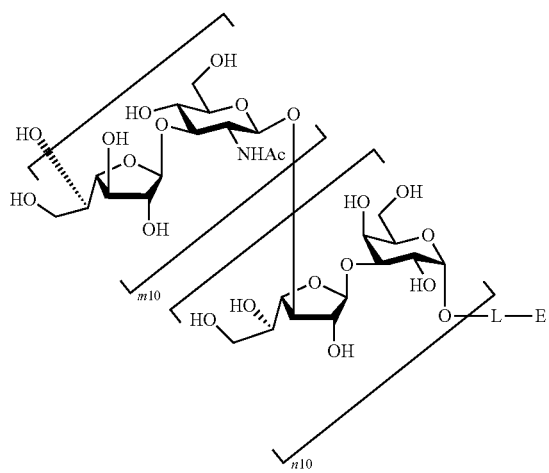
| —O—L—E | m10 | n10 | Compound No. |
|---|---|---|---|
| 5NH2) | 1 | 1 | K-01 |
| | | 2 | K-02 |
| | | 3 | K-03 |
| | | 4 | K-04 |
| | | 5 | K-05 |
| 5NH2) | 2 | 1 | K-06 |
| | | 2 | K-07 |
| | | 3 | K-08 |
| | | 4 | K-09 |
| | | 5 | K-10 |
| 5NH2) | 3 | 1 | K-11 |
| | | 2 | K-12 |
| | | 3 | K-13 |
| | | 4 | K-14 |
| | | 5 | K-15 |
| 5NH2) | 4 | 1 | K-16 |
| | | 2 | K-17 |
| | | 3 | K-18 |
| | | 4 | K-19 |
| | | 5 | K-20 |
| 5NH2) | 5 | 1 | K-21 |
| | | 2 | K-22 |
| | | 3 | K-23 |
| | | 4 | K-24 |
| | | 5 | K-25 |
| 10NH2) | 1 | 1 | K-26 |
| | | 2 | K-27 |
| | | 3 | K-28 |
| | | 4 | K-29 |
| | | 5 | K-30 |
| 10NH2) | 2 | 1 | K-31 |
| | | 2 | K-32 |
| | | 3 | K-33 |
| | | 4 | K-34 |
| | | 5 | K-35 |
| 10NH2) | 3 | 1 | K-36 |
| | | 2 | K-37 |
| | | 3 | K-38 |
| | | 4 | K-39 |
| | | 5 | K-40 |
| 10NH2) | 4 | 1 | K-41 |
| | | 2 | K-42 |
| | | 3 | K-43 |
| | | 4 | K-44 |
| | | 5 | K-45 |

TABLE 10-continued
(II-K)
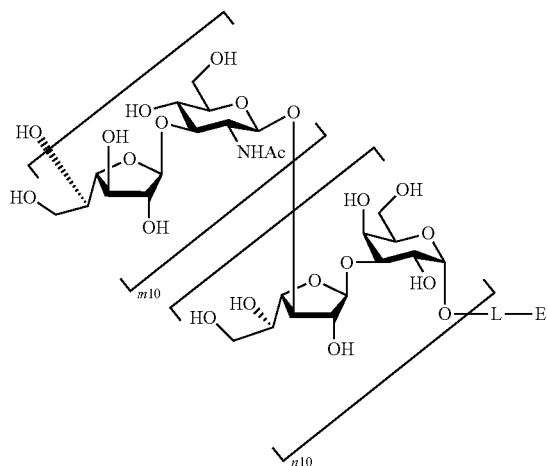
| —O—L—E | m10 | n10 | Compound No. |
|---|---|---|---|
| ![O(CH2)10NH2] | 5 | 1 | K-46 |
| | | 2 | K-47 |
| | | 3 | K-48 |
| | | 4 | K-49 |
| | | 5 | K-50 |
| ![O(CH2)5N3] | 1 | 1 | K-51 |
| | | 2 | K-52 |
| | | 3 | K-53 |
| | | 4 | K-54 |
| | | 5 | K-55 |
| ![O(CH2)5N3] | 2 | 1 | K-56 |
| | | 2 | K-57 |
| | | 3 | K-58 |
| | | 4 | K-59 |
| | | 5 | K-60 |
| ![O(CH2)5N3] | 3 | 1 | K-61 |
| | | 2 | K-62 |
| | | 3 | K-63 |
| | | 4 | K-64 |
| | | 5 | K-65 |
| ![O(CH2)5N3] | 4 | 1 | K-66 |
| | | 2 | K-67 |
| | | 3 | K-68 |
| | | 4 | K-69 |
| | | 5 | K-70 |
| ![O(CH2)5N3] | 5 | 1 | K-71 |
| | | 2 | K-72 |
| | | 3 | K-73 |
| | | 4 | K-74 |
| | | 5 | K-75 |
| ![O(CH2)4ONH2] | 1 | 1 | K-76 |
| | | 2 | K-77 |
| | | 3 | K-78 |
| | | 4 | K-79 |
| | | 5 | K-80 |
| ![O(CH2)4ONH2] | 2 | 1 | K-81 |
| | | 2 | K-82 |
| | | 3 | K-83 |
| | | 4 | K-84 |
| | | 5 | K-85 |
| ![O(CH2)4ONH2] | 3 | 1 | K-86 |
| | | 2 | K-87 |
| | | 3 | K-88 |
| | | 4 | K-89 |
| | | 5 | K-90 |

TABLE 10-continued
(II-K)
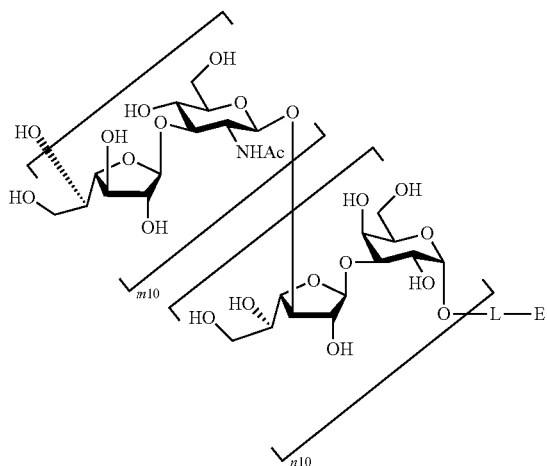
| —O—L—E | m10 | n10 | Compound No. |
|---|---|---|---|
| ˙˙˙O(̶ )̶₄O^NH₂ | 4 | 1 | K-91 |
|  |  | 2 | K-92 |
|  |  | 3 | K-93 |
|  |  | 4 | K-94 |
|  |  | 5 | K-95 |
| ˙˙˙O(̶ )̶₄O^NH₂ | 5 | 1 | K-96 |
|  |  | 2 | K-97 |
|  |  | 3 | K-98 |
|  |  | 4 | K-99 |
|  |  | 5 | K-100 |
| ˙˙˙O(̶ )̶₃COOH | 1 | 1 | K-101 |
|  |  | 2 | K-102 |
|  |  | 3 | K-103 |
|  |  | 4 | K-104 |
|  |  | 5 | K-105 |
| ˙˙˙O(̶ )̶₃COOH | 2 | 1 | K-106 |
|  |  | 2 | K-107 |
|  |  | 3 | K-108 |
|  |  | 4 | K-109 |
|  |  | 5 | K-110 |
| ˙˙˙O(̶ )̶₃COOH | 3 | 1 | K-111 |
|  |  | 2 | K-112 |
|  |  | 3 | K-113 |
|  |  | 4 | K-114 |
|  |  | 5 | K-115 |
| ˙˙˙O(̶ )̶₃COOH | 4 | 1 | K-116 |
|  |  | 2 | K-117 |
|  |  | 3 | K-118 |
|  |  | 4 | K-119 |
|  |  | 5 | K-120 |
| ˙˙˙O(̶ )̶₃COOH | 5 | 1 | K-121 |
|  |  | 2 | K-122 |
|  |  | 3 | K-123 |
|  |  | 4 | K-124 |
|  |  | 5 | K-125 |
| ˙˙˙O(̶ )̶₁₀COOH | 1 | 1 | K-126 |
|  |  | 2 | K-127 |
|  |  | 3 | K-128 |
|  |  | 4 | K-129 |
|  |  | 5 | K-130 |
| ˙˙˙O(̶ )̶₁₀COOH | 2 | 1 | K-131 |
|  |  | 2 | K-132 |
|  |  | 3 | K-133 |
|  |  | 4 | K-134 |
|  |  | 5 | K-135 |

TABLE 10-continued
(II-K)
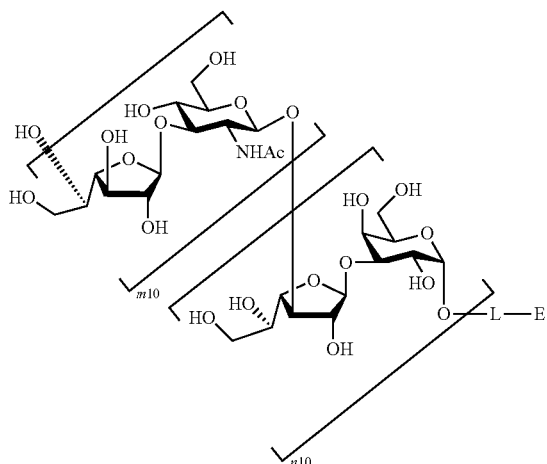
| —O—L—E | m10 | n10 | Compound No. |
|---|---|---|---|
| ![structure]·O–(CH₂)₁₀–C(O)OH | 3 | 1 | K-136 |
|  |  | 2 | K-137 |
|  |  | 3 | K-138 |
|  |  | 4 | K-139 |
|  |  | 5 | K-140 |
| ![structure]·O–(CH₂)₁₀–C(O)OH | 4 | 1 | K-141 |
|  |  | 2 | K-142 |
|  |  | 3 | K-143 |
|  |  | 4 | K-144 |
|  |  | 5 | K-145 |
| ![structure]·O–(CH₂)₁₀–C(O)OH | 5 | 1 | K-146 |
|  |  | 2 | K-147 |
|  |  | 3 | K-148 |
|  |  | 4 | K-149 |
|  |  | 5 | K-150 |
| ![structure]·O–(CH₂)₅–C(O)NHNH₂ | 1 | 1 | K-151 |
|  |  | 2 | K-152 |
|  |  | 3 | K-153 |
|  |  | 4 | K-154 |
|  |  | 5 | K-155 |
| ![structure]·O–(CH₂)₅–C(O)NHNH₂ | 2 | 1 | K-156 |
|  |  | 2 | K-157 |
|  |  | 3 | K-158 |
|  |  | 4 | K-159 |
|  |  | 5 | K-160 |
| ![structure]·O–(CH₂)₅–C(O)NHNH₂ | 3 | 1 | K-161 |
|  |  | 2 | K-162 |
|  |  | 3 | K-163 |
|  |  | 4 | K-164 |
|  |  | 5 | K-165 |
| ![structure]·O–(CH₂)₅–C(O)NHNH₂ | 4 | 1 | K-166 |
|  |  | 2 | K-167 |
|  |  | 3 | K-168 |
|  |  | 4 | K-169 |
|  |  | 5 | K-170 |
| ![structure]·O–(CH₂)₅–C(O)NHNH₂ | 5 | 1 | K-171 |
|  |  | 2 | K-172 |
|  |  | 3 | K-173 |
|  |  | 4 | K-174 |
|  |  | 5 | K-175 |
| ![structure]·O–(CH₂)₃–SH | 1 | 1 | K-176 |
|  |  | 2 | K-177 |
|  |  | 3 | K-178 |
|  |  | 4 | K-179 |
|  |  | 5 | K-180 |

TABLE 10-continued
(II-K)
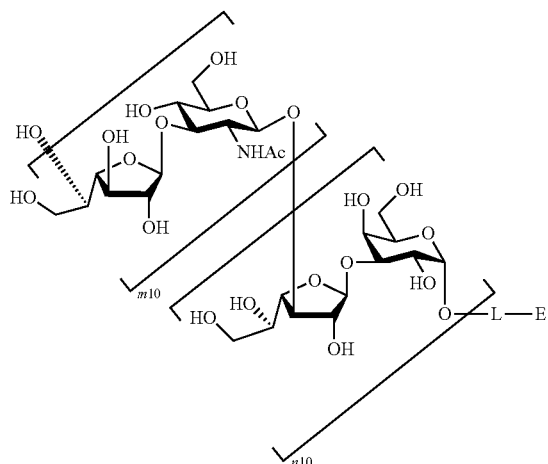
| —O—L—E | m10 | n10 | Compound No. |
|---|---|---|---|
| ⋯O⧸₃SH | 2 | 1 | K-181 |
|  |  | 2 | K-182 |
|  |  | 3 | K-183 |
|  |  | 4 | K-184 |
|  |  | 5 | K-185 |
| ⋯O⧸₃SH | 3 | 1 | K-186 |
|  |  | 2 | K-187 |
|  |  | 3 | K-188 |
|  |  | 4 | K-189 |
|  |  | 5 | K-190 |
| ⋯O⧸₃SH | 4 | 1 | K-191 |
|  |  | 2 | K-192 |
|  |  | 3 | K-193 |
|  |  | 4 | K-194 |
|  |  | 5 | K-195 |
| ⋯O⧸₃SH | 5 | 1 | K-196 |
|  |  | 2 | K-197 |
|  |  | 3 | K-198 |
|  |  | 4 | K-199 |
|  |  | 5 | K-200 |
| ⋯O⧸₃ | 1 | 1 | K-201 |
|  |  | 2 | K-202 |
|  |  | 3 | K-203 |
|  |  | 4 | K-204 |
|  |  | 5 | K-205 |
| ⋯O⧸₃ | 2 | 1 | K-206 |
|  |  | 2 | K-207 |
|  |  | 3 | K-208 |
|  |  | 4 | K-209 |
|  |  | 5 | K-210 |
| ⋯O⧸₃ | 3 | 1 | K-211 |
|  |  | 2 | K-212 |
|  |  | 3 | K-213 |
|  |  | 4 | K-214 |
|  |  | 5 | K-215 |
| ⋯O⧸₃ | 4 | 1 | K-216 |
|  |  | 2 | K-217 |
|  |  | 3 | K-218 |
|  |  | 4 | K-219 |
|  |  | 5 | K-220 |
| ⋯O⧸₃ | 5 | 1 | K-221 |
|  |  | 2 | K-222 |
|  |  | 3 | K-223 |
|  |  | 4 | K-224 |
|  |  | 5 | K-225 |

TABLE 10-continued
(II-K)
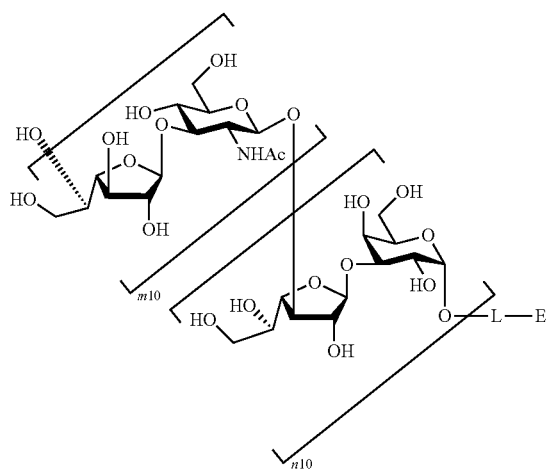
| —O—L—E | m10 | n10 | Compound No. |
|---|---|---|---|
| ⋯O⟶≡ | 1 | 1 | K-226 |
| | | 2 | K-227 |
| | | 3 | K-228 |
| | | 4 | K-229 |
| | | 5 | K-230 |
| ⋯O⟶≡ | 2 | 1 | K-231 |
| | | 2 | K-232 |
| | | 3 | K-233 |
| | | 4 | K-234 |
| | | 5 | K-235 |
| ⋯O⟶≡ | 3 | 1 | K-236 |
| | | 2 | K-237 |
| | | 3 | K-238 |
| | | 4 | K-239 |
| | | 5 | K-240 |
| ⋯O⟶≡ | 4 | 1 | K-241 |
| | | 2 | K-242 |
| | | 3 | K-243 |
| | | 4 | K-244 |
| | | 5 | K-245 |
| ⋯O⟶≡ | 5 | 1 | K-246 |
| | | 2 | K-247 |
| | | 3 | K-248 |
| | | 4 | K-249 |
| | | 5 | K-250 |
| ⋯O⟶(⟶)$_5$Br | 1 | 1 | K-251 |
| | | 2 | K-252 |
| | | 3 | K-253 |
| | | 4 | K-254 |
| | | 5 | K-255 |
| ⋯O⟶(⟶)$_5$Br | 2 | 1 | K-256 |
| | | 2 | K-257 |
| | | 3 | K-258 |
| | | 4 | K-259 |
| | | 5 | K-260 |
| ⋯O⟶(⟶)$_5$Br | 3 | 1 | K-261 |
| | | 2 | K-262 |
| | | 3 | K-263 |
| | | 4 | K-264 |
| | | 5 | K-265 |
| ⋯O⟶(⟶)$_5$Br | 4 | 1 | K-266 |
| | | 2 | K-267 |
| | | 3 | K-268 |
| | | 4 | K-269 |
| | | 5 | K-270 |

TABLE 10-continued
(II-K)
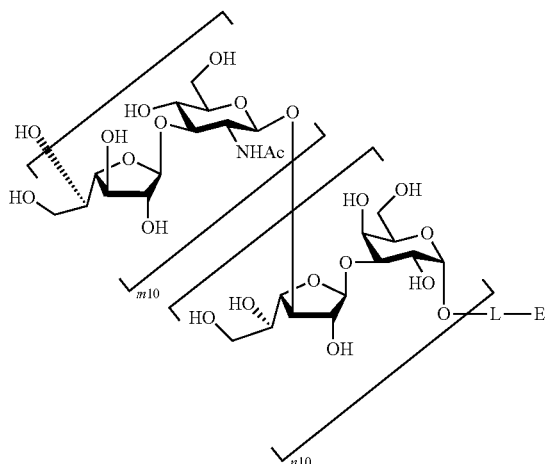
| —O—L—E | m10 | n10 | Compound No. |
|---|---|---|---|
| ...O—(CH₂)₅—Br | 5 | 1 | K-271 |
|  |  | 2 | K-272 |
|  |  | 3 | K-273 |
|  |  | 4 | K-274 |
|  |  | 5 | K-275 |
| ...O—CH₂CH₂—O—CH₂CH₂—NH₂ | 1 | 1 | K-276 |
|  |  | 2 | K-277 |
|  |  | 3 | K-278 |
|  |  | 4 | K-279 |
|  |  | 5 | K-280 |
| ...O—CH₂CH₂—O—CH₂CH₂—NH₂ | 2 | 1 | K-281 |
|  |  | 2 | K-282 |
|  |  | 3 | K-283 |
|  |  | 4 | K-284 |
|  |  | 5 | K-285 |
| ...O—CH₂CH₂—O—CH₂CH₂—NH₂ | 3 | 1 | K-286 |
|  |  | 2 | K-287 |
|  |  | 3 | K-288 |
|  |  | 4 | K-289 |
|  |  | 5 | K-290 |
| ...O—CH₂CH₂—O—CH₂CH₂—NH₂ | 4 | 1 | K-291 |
|  |  | 2 | K-292 |
|  |  | 3 | K-293 |
|  |  | 4 | K-294 |
|  |  | 5 | K-295 |
| ...O—CH₂CH₂—O—CH₂CH₂—NH₂ | 5 | 1 | K-296 |
|  |  | 2 | K-297 |
|  |  | 3 | K-298 |
|  |  | 4 | K-299 |
|  |  | 5 | K-300 |
| ...O—CH₂CH₂—(O—CH₂CH₂)₃—NH₂ | 1 | 1 | K-301 |
|  |  | 2 | K-302 |
|  |  | 3 | K-303 |
|  |  | 4 | K-304 |
|  |  | 5 | K-305 |
| ...O—CH₂CH₂—(O—CH₂CH₂)₃—NH₂ | 2 | 1 | K-306 |
|  |  | 2 | K-307 |
|  |  | 3 | K-308 |
|  |  | 4 | K-309 |
|  |  | 5 | K-310 |
| ...O—CH₂CH₂—(O—CH₂CH₂)₃—NH₂ | 3 | 1 | K-311 |
|  |  | 2 | K-312 |
|  |  | 3 | K-313 |
|  |  | 4 | K-314 |
|  |  | 5 | K-315 |

TABLE 10-continued
(II-K)
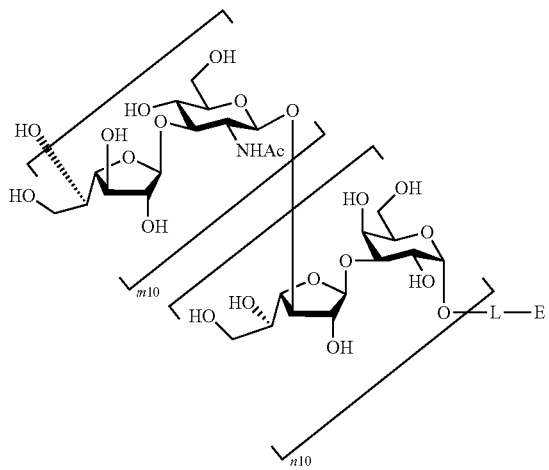
| —O—L—E | m10 | n10 | Compound No. |
|---|---|---|---|
| ⌇O∼O(∼O)₃NH₂ | 4 | 1 | K-316 |
| | | 2 | K-317 |
| | | 3 | K-318 |
| | | 4 | K-319 |
| | | 5 | K-320 |
| ⌇O∼O(∼O)₃NH₂ | 5 | 1 | K-321 |
| | | 2 | K-322 |
| | | 3 | K-323 |
| | | 4 | K-324 |
| | | 5 | K-325 |
| ⌇O∼OH, OH | 1 | 1 | K-326 |
| | | 2 | K-327 |
| | | 3 | K-328 |
| | | 4 | K-329 |
| | | 5 | K-330 |
| ⌇O∼OH, OH | 2 | 1 | K-331 |
| | | 2 | K-332 |
| | | 3 | K-333 |
| | | 4 | K-334 |
| | | 5 | K-335 |
| ⌇O∼OH, OH | 3 | 1 | K-336 |
| | | 2 | K-337 |
| | | 3 | K-338 |
| | | 4 | K-339 |
| | | 5 | K-340 |
| ⌇O∼OH, OH | 4 | 1 | K-341 |
| | | 2 | K-342 |
| | | 3 | K-343 |
| | | 4 | K-344 |
| | | 5 | K-345 |
| ⌇O∼OH, OH | 5 | 1 | K-346 |
| | | 2 | K-347 |
| | | 3 | K-348 |
| | | 4 | K-349 |
| | | 5 | K-350 |

TABLE 11

(II-M)

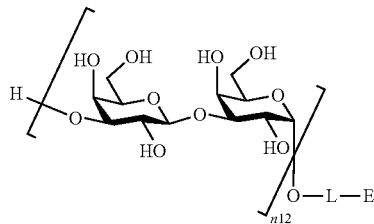

| —O—L—E | n12 | Compound No. |
|---|---|---|
| ⋯O(CH₂)₅NH₂ | 2 | M-01 |
|  | 3 | M-02 |
|  | 4 | M-03 |
|  | 5 | M-04 |
|  | 6 | M-05 |
| ⋯O(CH₂)₁₀NH₂ | 2 | M-06 |
|  | 3 | M-07 |
|  | 4 | M-08 |
|  | 5 | M-09 |
|  | 6 | M-10 |
| ⋯O(CH₂)₅N₃ | 2 | M-11 |
|  | 3 | M-12 |
|  | 4 | M-13 |
|  | 5 | M-14 |
|  | 6 | M-15 |
| ⋯O(CH₂)₄ONH₂ | 2 | M-16 |
|  | 3 | M-17 |
|  | 4 | M-18 |
|  | 5 | M-19 |
|  | 6 | M-20 |
| ⋯O(CH₂)₃COOH | 2 | M-21 |
|  | 3 | M-22 |
|  | 4 | M-23 |
|  | 5 | M-24 |
|  | 6 | M-25 |
| ⋯O(CH₂)₁₀COOH | 2 | M-26 |
|  | 3 | M-27 |
|  | 4 | M-28 |
|  | 5 | M-29 |
|  | 6 | M-30 |
| ⋯O(CH₂)₅C(O)NHNH₂ | 2 | M-31 |
|  | 3 | M-32 |
|  | 4 | M-33 |
|  | 5 | M-34 |
|  | 6 | M-35 |
| ⋯O(CH₂)₃SH | 2 | M-36 |
|  | 3 | M-37 |
|  | 4 | M-38 |
|  | 5 | M-39 |
|  | 6 | M-40 |
| ⋯O(CH₂)₃CH=CH₂ | 2 | M-41 |
|  | 3 | M-42 |
|  | 4 | M-43 |
|  | 5 | M-44 |
|  | 6 | M-45 |
| ⋯OCH₂C≡CH | 2 | M-46 |
|  | 3 | M-47 |
|  | 4 | M-48 |
|  | 5 | M-49 |
|  | 6 | M-50 |
| ⋯O(CH₂)₅Br | 2 | M-51 |
|  | 3 | M-52 |
|  | 4 | M-53 |
|  | 5 | M-54 |
|  | 6 | M-55 |

TABLE 11-continued (II-M)

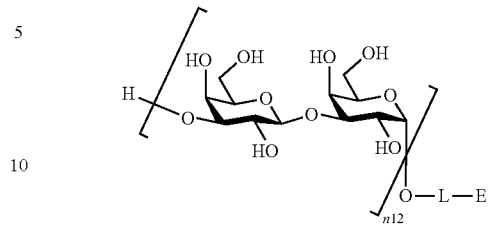

| —O—L—E | n12 | Compound No. |
|---|---|---|
| ⋯OCH₂CH₂OCH₂CH₂NH₂ | 2 | M-56 |
|  | 3 | M-57 |
|  | 4 | M-58 |
|  | 5 | M-59 |
|  | 6 | M-60 |
| ⋯OCH₂CH₂(OCH₂CH₂)₃NH₂ | 2 | M-61 |
|  | 3 | M-62 |
|  | 4 | M-63 |
|  | 5 | M-64 |
|  | 6 | M-65 |
| ⋯OCH₂CH(OH)CH₂OH | 2 | M-66 |
|  | 3 | M-67 |
|  | 4 | M-68 |
|  | 5 | M-69 |
|  | 6 | M-70 |

TABLE 12

(II-N)

| —O—L—E | n13 | Compound No. |
|---|---|---|
| ⋯O(CH₂)₅NH₂ | 1 | N-01 |
|  | 2 | N-02 |
|  | 3 | N-03 |
|  | 4 | N-04 |
|  | 5 | N-05 |
| ⋯O(CH₂)₁₀NH₂ | 1 | N-06 |
|  | 2 | N-07 |
|  | 3 | N-08 |
|  | 4 | N-09 |
|  | 5 | N-10 |
| ⋯O(CH₂)₅N₃ | 1 | N-11 |
|  | 2 | N-12 |
|  | 3 | N-13 |
|  | 4 | N-14 |
|  | 5 | N-15 |
| ⋯O(CH₂)₄ONH₂ | 1 | N-16 |
|  | 2 | N-17 |
|  | 3 | N-18 |
|  | 4 | N-19 |
|  | 5 | N-20 |

TABLE 12-continued (II-N)

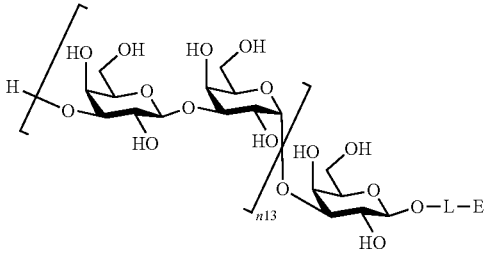

| —O—L—E | n13 | Compound No. |
|---|---|---|
| 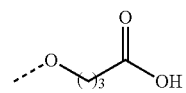 | 1<br>2<br>3<br>4<br>5 | N-21<br>N-22<br>N-23<br>N-24<br>N-25 |
| 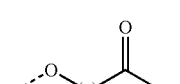 | 1<br>2<br>3<br>4<br>5 | N-26<br>N-27<br>N-28<br>N-29<br>N-30 |
| 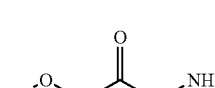 | 1<br>2<br>3<br>4<br>5 | N-31<br>N-32<br>N-33<br>N-34<br>N-35 |
| 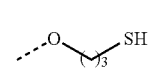 | 1<br>2<br>3<br>4<br>5 | N-36<br>N-37<br>N-38<br>N-39<br>N-40 |
| 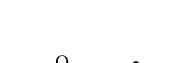 | 1<br>2<br>3<br>4<br>5 | N-41<br>N-42<br>N-43<br>N-44<br>N-45 |
|  | 1<br>2<br>3<br>4<br>5 | N-46<br>N-47<br>N-48<br>N-49<br>N-50 |
|  | 1<br>2<br>3<br>4<br>5 | N-51<br>N-52<br>N-53<br>N-54<br>N-55 |
|  | 1<br>2<br>3<br>4<br>5 | N-56<br>N-57<br>N-58<br>N-59<br>N-60 |
| 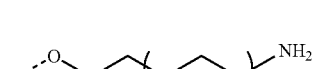 | 1<br>2<br>3<br>4<br>5 | N-61<br>N-62<br>N-63<br>N-64<br>N-65 |
| 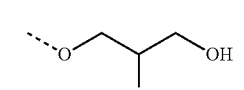 | 1<br>2<br>3<br>4<br>5 | N-66<br>N-67<br>N-68<br>N-69<br>N-70 |

TABLE 13

(II-O)

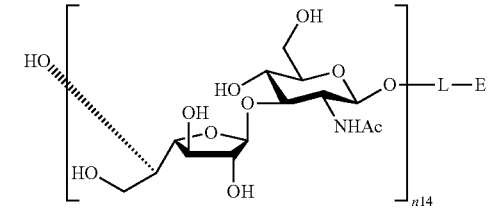

| —O—L—E | n14 | Compound No. |
|---|---|---|
| 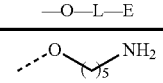 | 2<br>3<br>4<br>5<br>6 | O-01<br>O-02<br>O-03<br>O-04<br>O-05 |
| 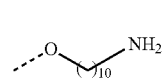 | 2<br>3<br>4<br>5<br>6 | O-06<br>O-07<br>O-08<br>O-09<br>O-10 |
| 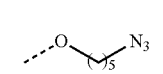 | 2<br>3<br>4<br>5<br>6 | O-11<br>O-12<br>O-13<br>O-14<br>O-15 |
| 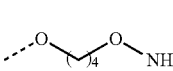 | 2<br>3<br>4<br>5<br>6 | O-16<br>O-17<br>O-18<br>O-19<br>O-20 |
|  | 2<br>3<br>4<br>5<br>6 | O-21<br>O-22<br>O-23<br>O-24<br>O-25 |
| 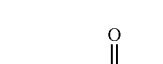 | 2<br>3<br>4<br>5<br>6 | O-26<br>O-27<br>O-28<br>O-29<br>O-30 |
|  | 2<br>3<br>4<br>5<br>6 | O-31<br>O-32<br>O-33<br>O-34<br>O-35 |
| 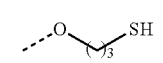 | 2<br>3<br>4<br>5<br>6 | O 36<br>O 37<br>O 38<br>O 39<br>O 40 |
| 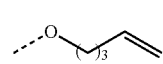 | 2<br>3<br>4<br>5<br>6 | O-41<br>O-42<br>O-43<br>O-44<br>O-45 |
| 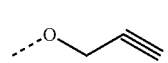 | 2<br>3<br>4<br>5<br>6 | O-46<br>O-47<br>O-48<br>O-49<br>O-50 |
| 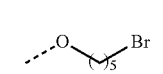 | 2<br>3<br>4<br>5<br>6 | O-51<br>O-52<br>O-53<br>O-54<br>O-55 |

TABLE 13-continued (II-O)

| —O—L—E | n14 | Compound No. |
|---|---|---|
| ...O~~O~~NH₂ | 2 | O-56 |
|  | 3 | O-57 |
|  | 4 | O-58 |
|  | 5 | O-59 |
|  | 6 | O-60 |
| ...O~(~O~)₃~NH₂ | 2 | O-61 |
|  | 3 | O-62 |
|  | 4 | O-63 |
|  | 5 | O-64 |
|  | 6 | O-65 |
| ...O-CH₂-CH(OH)-CH₂-OH | 2 | O-66 |
|  | 3 | O-67 |
|  | 4 | O-68 |
|  | 5 | O-69 |
|  | 6 | O-70 |

TABLE 14

(II-P)

| —O—L—E | n15 | Compound No. |
|---|---|---|
| ...O(CH₂)₅NH₂ | 1 | P-01 |
|  | 2 | P-02 |
|  | 3 | P-03 |
|  | 4 | P-04 |
|  | 5 | P-05 |
| ...O(CH₂)₁₀NH₂ | 1 | P-06 |
|  | 2 | P-07 |
|  | 3 | P-08 |
|  | 4 | P-09 |
|  | 5 | P-10 |
| ...O(CH₂)₅N₃ | 1 | P-11 |
|  | 2 | P-12 |
|  | 3 | P-13 |
|  | 4 | P-14 |
|  | 5 | P-15 |

TABLE 14-continued (II-P)

| —O—L—E | n15 | Compound No. |
|---|---|---|
| ...O(CH₂)₄ONH₂ | 1 | P-16 |
|  | 2 | P-17 |
|  | 3 | P-18 |
|  | 4 | P-19 |
|  | 5 | P-20 |
| ...O(CH₂)₃COOH | 1 | P-21 |
|  | 2 | P-22 |
|  | 3 | P-23 |
|  | 4 | P-24 |
|  | 5 | P-25 |
| ...O(CH₂)₁₀COOH | 1 | P-26 |
|  | 2 | P-27 |
|  | 3 | P-28 |
|  | 4 | P-29 |
|  | 5 | P-30 |
| ...O(CH₂)₅C(O)NHNH₂ | 1 | P-31 |
|  | 2 | P-32 |
|  | 3 | P-33 |
|  | 4 | P-34 |
|  | 5 | P-35 |
| ...O(CH₂)₃SH | 1 | P-36 |
|  | 2 | P-37 |
|  | 3 | P-38 |
|  | 4 | P-39 |
|  | 5 | P-40 |
| ...O(CH₂)₃CH=CH₂ | 1 | P-41 |
|  | 2 | P-42 |
|  | 3 | P-43 |
|  | 4 | P-44 |
|  | 5 | P-45 |
| ...O-CH₂-C≡CH | 1 | P-46 |
|  | 2 | P-47 |
|  | 3 | P-48 |
|  | 4 | P-49 |
|  | 5 | P-50 |
| ...O(CH₂)₅Br | 1 | P-51 |
|  | 2 | P-52 |
|  | 3 | P-53 |
|  | 4 | P-54 |
|  | 5 | P-55 |
| ...O~~O~~NH₂ | 1 | P-56 |
|  | 2 | P-57 |
|  | 3 | P-58 |
|  | 4 | P-59 |
|  | 5 | P-60 |

TABLE 14-continued (II-P)

| —O—L—E | n15 | Compound No. |
|---|---|---|
| (—O—(CH₂CH₂O)₃—CH₂CH₂NH₂) | 1 | P-61 |
| | 2 | P-62 |
| | 3 | P-63 |
| | 4 | P-64 |
| | 5 | P-65 |

TABLE 14-continued (II-P)

| —O—L—E | n15 | Compound No. |
|---|---|---|
| (—O—CH₂CH(OH)CH₂OH) | 1 | P-66 |
| | 2 | P-67 |
| | 3 | P-68 |
| | 4 | P-69 |
| | 5 | P-70 |

TABLE 15

(II-Q)

| —O—L—E | m11 | k1 | n16 | Compd. No. |
|---|---|---|---|---|
| (—O—(CH₂)₅—NH₂) | 10 | 1 | 1 | Q-1 |
| | | | 2 | Q-2 |
| | | | 3 | Q-3 |
| | | | 4 | Q-4 |
| | | | 5 | Q-5 |

TABLE 15-continued
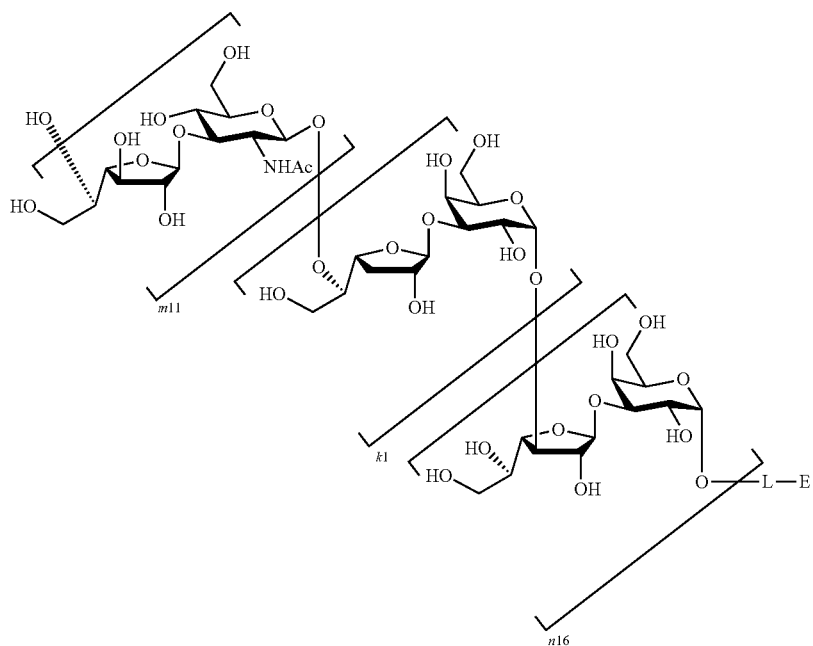
(II-Q)
| —O—L—E | m11 | k1 | n16 | Compd. No. |
|---|---|---|---|---|
| ⋯O(CH₂)₅NH₂ | 11 | 1 | 1 | Q-6 |
| | | | 2 | Q-7 |
| | | | 3 | Q-8 |
| | | | 4 | Q-9 |
| | | | 5 | Q-10 |
| ⋯O(CH₂)₅NH₂ | 12 | 1 | 1 | Q-11 |
| | | | 2 | Q-12 |
| | | | 3 | Q-13 |
| | | | 4 | Q-14 |
| | | | 5 | Q-15 |
| ⋯O(CH₂)₅NH₂ | 13 | 1 | 1 | Q-16 |
| | | | 2 | Q-17 |
| | | | 3 | Q-18 |
| | | | 4 | Q-19 |
| | | | 5 | Q-20 |
| ⋯O(CH₂)₅NH₂ | 14 | 1 | 1 | Q-21 |
| | | | 2 | Q-22 |
| | | | 3 | Q-23 |
| | | | 4 | Q-24 |
| | | | 5 | Q-25 |
| ⋯O(CH₂)₁₀NH₂ | 10 | 1 | 1 | Q-26 |
| | | | 2 | Q-27 |
| | | | 3 | Q-28 |
| | | | 4 | Q-29 |
| | | | 5 | Q-30 |
| ⋯O(CH₂)₁₀NH₂ | 11 | 1 | 1 | Q-31 |
| | | | 2 | Q-32 |
| | | | 3 | Q-33 |
| | | | 4 | Q-34 |
| | | | 5 | Q-35 |
| ⋯O(CH₂)₁₀NH₂ | 12 | 1 | 1 | Q-36 |
| | | | 2 | Q-37 |
| | | | 3 | Q-38 |
| | | | 4 | Q-39 |
| | | | 5 | Q-40 |

TABLE 15-continued
(II-Q)
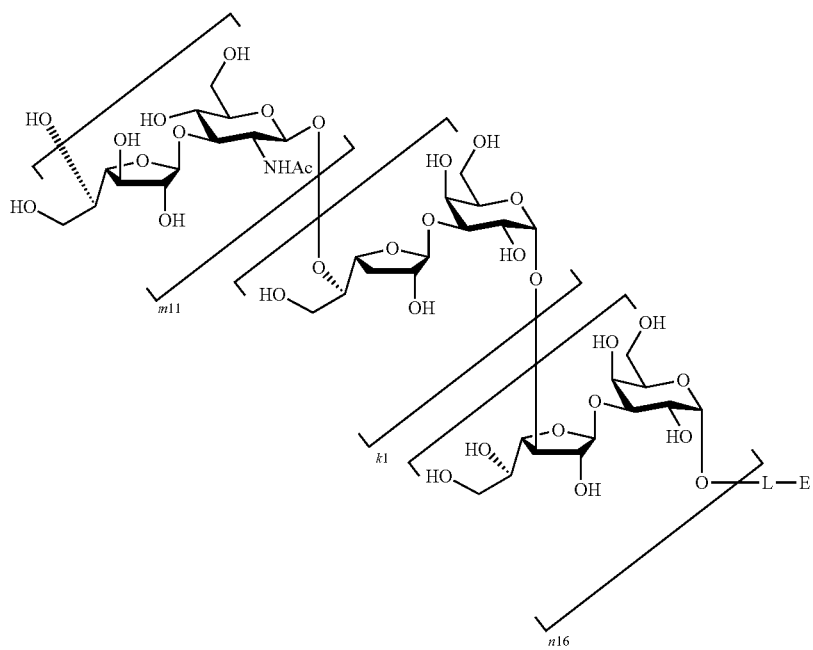
| —O—L—E | m11 | k1 | n16 | Compd. No. |
|---|---|---|---|---|
| ⸺O⸺(CH₂)₁₀⸺NH₂ | 13 | 1 | 1 | Q-41 |
| | | | 2 | Q-42 |
| | | | 3 | Q-43 |
| | | | 4 | Q-44 |
| | | | 5 | Q-45 |
| ⸺O⸺(CH₂)₁₀⸺NH₂ | 14 | 1 | 1 | Q-46 |
| | | | 2 | Q-47 |
| | | | 3 | Q-48 |
| | | | 4 | Q-49 |
| | | | 5 | Q-50 |
| ⸺O⸺(CH₂)₅⸺NH₂ | 10 | 2 | 1 | Q-51 |
| | | | 2 | Q-52 |
| | | | 3 | Q-53 |
| | | | 4 | Q-54 |
| | | | 5 | Q-55 |
| ⸺O⸺(CH₂)₅⸺NH₂ | 11 | 2 | 1 | Q-56 |
| | | | 2 | Q-57 |
| | | | 3 | Q-58 |
| | | | 4 | Q-59 |
| | | | 5 | Q-60 |
| ⸺O⸺(CH₂)₅⸺NH₂ | 12 | 2 | 1 | Q-61 |
| | | | 2 | Q-62 |
| | | | 3 | Q-63 |
| | | | 4 | Q-64 |
| | | | 5 | Q-65 |
| ⸺O⸺(CH₂)₅⸺NH₂ | 13 | 2 | 1 | Q-66 |
| | | | 2 | Q-67 |
| | | | 3 | Q-68 |
| | | | 4 | Q-69 |
| | | | 5 | Q-70 |
| ⸺O⸺(CH₂)₅⸺NH₂ | 14 | 2 | 1 | Q-71 |
| | | | 2 | Q-72 |
| | | | 3 | Q-73 |
| | | | 4 | Q-74 |
| | | | 5 | Q-75 |

TABLE 15-continued
(II-Q)
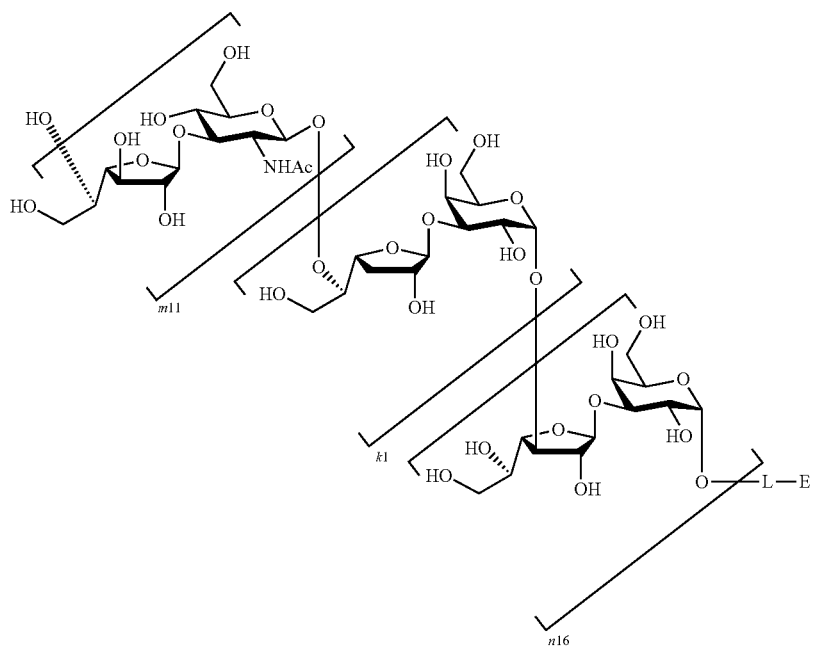
| —O—L—E | m11 | k1 | n16 | Compd. No. |
|---|---|---|---|---|
| ⟨O(CH₂)₁₀NH₂⟩ | 10 | 2 | 1 | Q-76 |
|  |  |  | 2 | Q-77 |
|  |  |  | 3 | Q-78 |
|  |  |  | 4 | Q-79 |
|  |  |  | 5 | Q-80 |
| ⟨O(CH₂)₁₀NH₂⟩ | 11 | 2 | 1 | Q-81 |
|  |  |  | 2 | Q-82 |
|  |  |  | 3 | Q-83 |
|  |  |  | 4 | Q-84 |
|  |  |  | 5 | Q-85 |
| ⟨O(CH₂)₁₀NH₂⟩ | 12 | 2 | 1 | Q-86 |
|  |  |  | 2 | Q-87 |
|  |  |  | 3 | Q-88 |
|  |  |  | 4 | Q-89 |
|  |  |  | 5 | Q-90 |
| ⟨O(CH₂)₁₀NH₂⟩ | 13 | 2 | 1 | Q-91 |
|  |  |  | 2 | Q-92 |
|  |  |  | 3 | Q-93 |
|  |  |  | 4 | Q-94 |
|  |  |  | 5 | Q-95 |
| ⟨O(CH₂)₁₀NH₂⟩ | 14 | 2 | 1 | Q-96 |
|  |  |  | 2 | Q-97 |
|  |  |  | 3 | Q-98 |
|  |  |  | 4 | Q-99 |
|  |  |  | 5 | Q-100 |
| ⟨O(CH₂)₅N₃⟩ | 10 | 1 | 1 | Q-101 |
|  |  |  | 2 | Q-102 |
|  |  |  | 3 | Q-103 |
|  |  |  | 4 | Q-104 |
|  |  |  | 5 | Q-105 |
| ⟨O(CH₂)₅N₃⟩ | 11 | 1 | 1 | Q-106 |
|  |  |  | 2 | Q-107 |
|  |  |  | 3 | Q-108 |
|  |  |  | 4 | Q-109 |
|  |  |  | 5 | Q-110 |
| ⟨O(CH₂)₅N₃⟩ | 12 | 1 | 1 | Q-111 |
|  |  |  | 2 | Q-112 |

TABLE 15-continued
(II-Q)
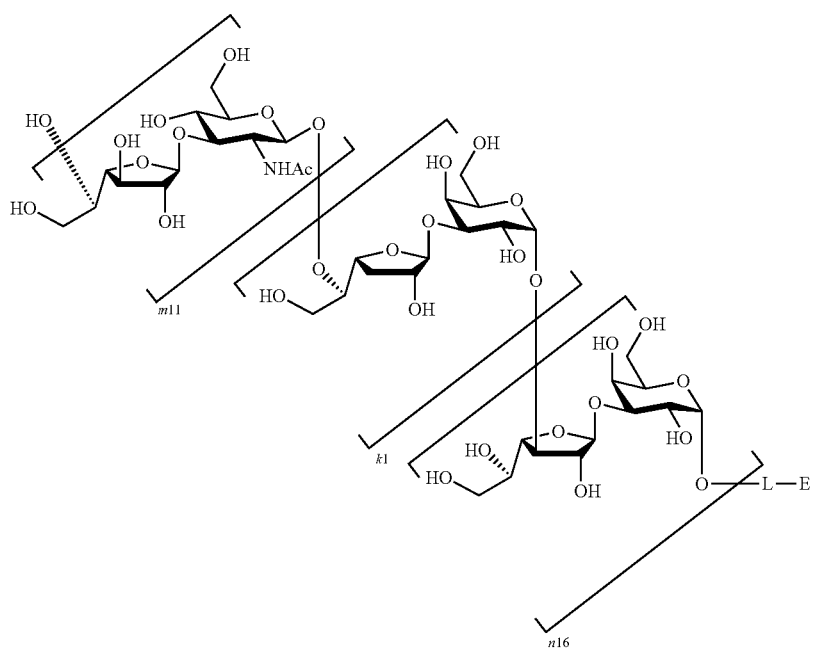
| —O—L—E | m11 | k1 | n16 | Compd. No. |
|---|---|---|---|---|
| | | | 3 | Q-113 |
| | | | 4 | Q-114 |
| | | | 5 | Q-115 |
| ⋯O∼(∼)₅N₃ | 13 | 1 | 1 | Q-116 |
| | | | 2 | Q-117 |
| | | | 3 | Q-118 |
| | | | 4 | Q-119 |
| | | | 5 | Q-120 |
| ⋯O∼(∼)₅N₃ | 14 | 1 | 1 | Q-121 |
| | | | 2 | Q-122 |
| | | | 3 | Q-123 |
| | | | 4 | Q-124 |
| | | | 5 | Q-125 |
| ⋯O∼(∼)₅N₃ | 10 | 2 | 1 | Q-126 |
| | | | 2 | Q-127 |
| | | | 3 | Q-128 |
| | | | 4 | Q-129 |
| | | | 5 | Q-130 |
| ⋯O∼(∼)₅N₃ | 11 | 2 | 1 | Q-131 |
| | | | 2 | Q-132 |
| | | | 3 | Q-133 |
| | | | 4 | Q-134 |
| | | | 5 | Q-135 |
| ⋯O∼(∼)₅N₃ | 12 | 2 | 1 | Q-136 |
| | | | 2 | Q-137 |
| | | | 3 | Q-138 |
| | | | 4 | Q-139 |
| | | | 5 | Q-140 |
| ⋯O∼(∼)₅N₃ | 13 | 2 | 1 | Q-141 |
| | | | 2 | Q-142 |
| | | | 3 | Q-143 |
| | | | 4 | Q-144 |
| | | | 5 | Q-145 |
| ⋯O∼(∼)₅N₃ | 14 | 2 | 1 | Q-146 |
| | | | 2 | Q-147 |
| | | | 3 | Q-148 |

TABLE 15-continued
(II-Q)
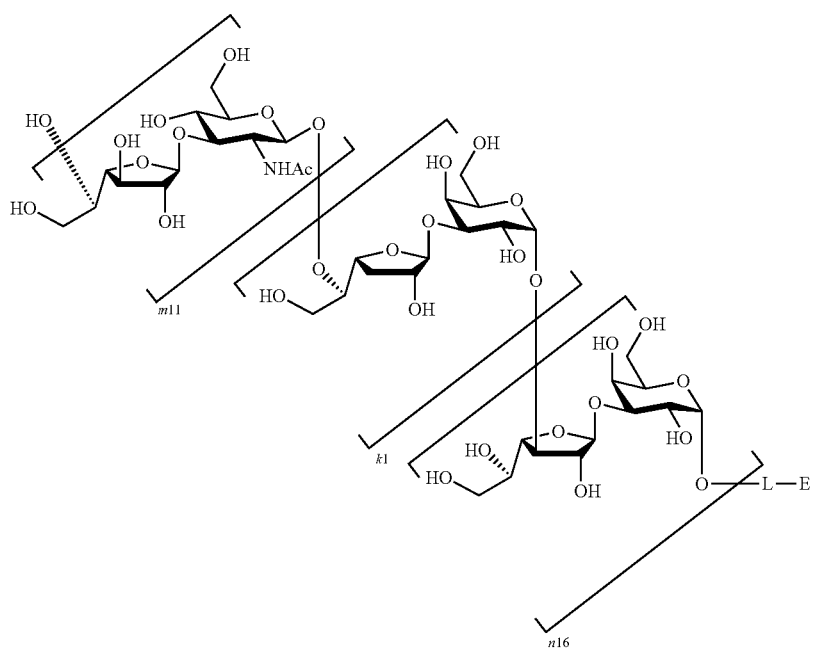
| —O—L—E | m11 | k1 | n16 | Compd. No. |
|---|---|---|---|---|
| | | | 4 | Q-149 |
| | | | 5 | Q-150 |
| ⋯O〜〜〜〜O〜NH₂ (₄) | 10 | 1 | 1 | Q-151 |
| | | | 2 | Q-152 |
| | | | 3 | Q-153 |
| | | | 4 | Q-154 |
| | | | 5 | Q-155 |
| ⋯O〜〜〜〜O〜NH₂ (₄) | 11 | 1 | 1 | Q-156 |
| | | | 2 | Q-157 |
| | | | 3 | Q-158 |
| | | | 4 | Q-159 |
| | | | 5 | Q-160 |
| ⋯O〜〜〜〜O〜NH₂ (₄) | 12 | 1 | 1 | Q-161 |
| | | | 2 | Q-162 |
| | | | 3 | Q-163 |
| | | | 4 | Q-164 |
| | | | 5 | Q-165 |
| ⋯O〜〜〜〜O〜NH₂ (₄) | 13 | 1 | 1 | Q-166 |
| | | | 2 | Q-167 |
| | | | 3 | Q-168 |
| | | | 4 | Q-169 |
| | | | 5 | Q-170 |
| ⋯O〜〜〜〜O〜NH₂ (₄) | 14 | 1 | 1 | Q-171 |
| | | | 2 | Q-172 |
| | | | 3 | Q-173 |
| | | | 4 | Q-174 |
| | | | 5 | Q-175 |
| ⋯O〜〜〜〜O〜NH₂ (₄) | 10 | 2 | 1 | Q-176 |
| | | | 2 | Q-177 |
| | | | 3 | Q-178 |
| | | | 4 | Q-179 |
| | | | 5 | Q-180 |
| ⋯O〜〜〜〜O〜NH₂ (₄) | 11 | 2 | 1 | Q-181 |
| | | | 2 | Q-182 |
| | | | 3 | Q-183 |

TABLE 15-continued
(II-Q)
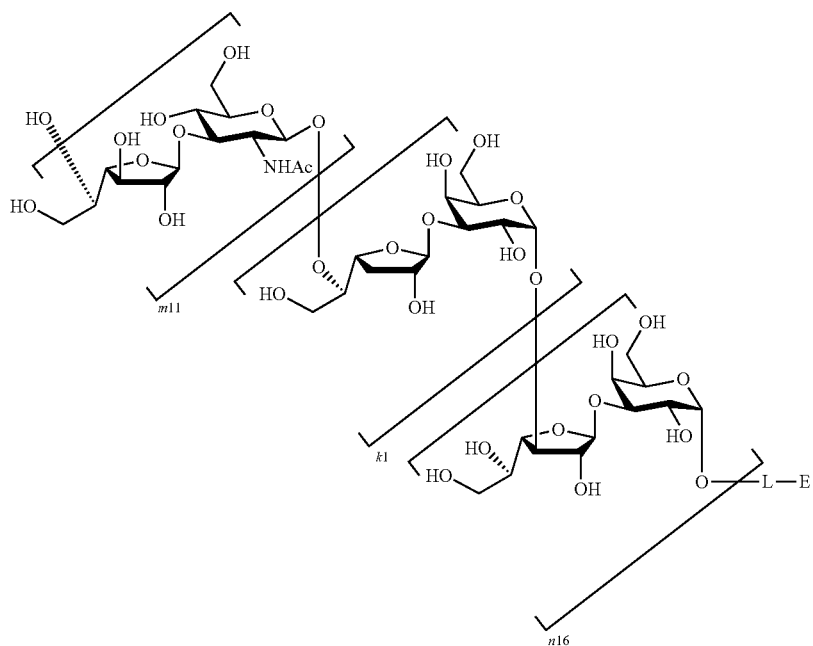
| —O—L—E | m11 | k1 | n16 | Compd. No. |
|---|---|---|---|---|
| | | | 4 | Q-184 |
| | | | 5 | Q-185 |
| ⋯O‒(⤳)₄‒O‒NH₂ | 12 | 2 | 1 | Q-186 |
| | | | 2 | Q-187 |
| | | | 3 | Q-188 |
| | | | 4 | Q-189 |
| | | | 5 | Q-190 |
| ⋯O‒(⤳)₄‒O‒NH₂ | 13 | 2 | 1 | Q-191 |
| | | | 2 | Q-192 |
| | | | 3 | Q-193 |
| | | | 4 | Q-194 |
| | | | 5 | Q-195 |
| ⋯O‒(⤳)₄‒O‒NH₂ | 14 | 2 | 1 | Q-196 |
| | | | 2 | Q-197 |
| | | | 3 | Q-198 |
| | | | 4 | Q-199 |
| | | | 5 | Q-200 |
| ⋯O‒(⤳)₃‒C(O)OH | 10 | 1 | 1 | Q-201 |
| | | | 2 | Q-202 |
| | | | 3 | Q-203 |
| | | | 4 | Q-204 |
| | | | 5 | Q-205 |
| ⋯O‒(⤳)₃‒C(O)OH | 11 | 1 | 1 | Q-206 |
| | | | 2 | Q-207 |
| | | | 3 | Q-208 |
| | | | 4 | Q-209 |
| | | | 5 | Q-210 |
| ⋯O‒(⤳)₃‒C(O)OH | 12 | 1 | 1 | Q-211 |
| | | | 2 | Q-212 |
| | | | 3 | Q-213 |
| | | | 4 | Q-214 |
| | | | 5 | Q-215 |
| ⋯O‒(⤳)₃‒C(O)OH | 13 | 1 | 1 | Q-216 |
| | | | 2 | Q-217 |
| | | | 3 | Q-218 |
| | | | 4 | Q-219 |
| | | | 5 | Q-220 |

TABLE 15-continued
(II-Q)
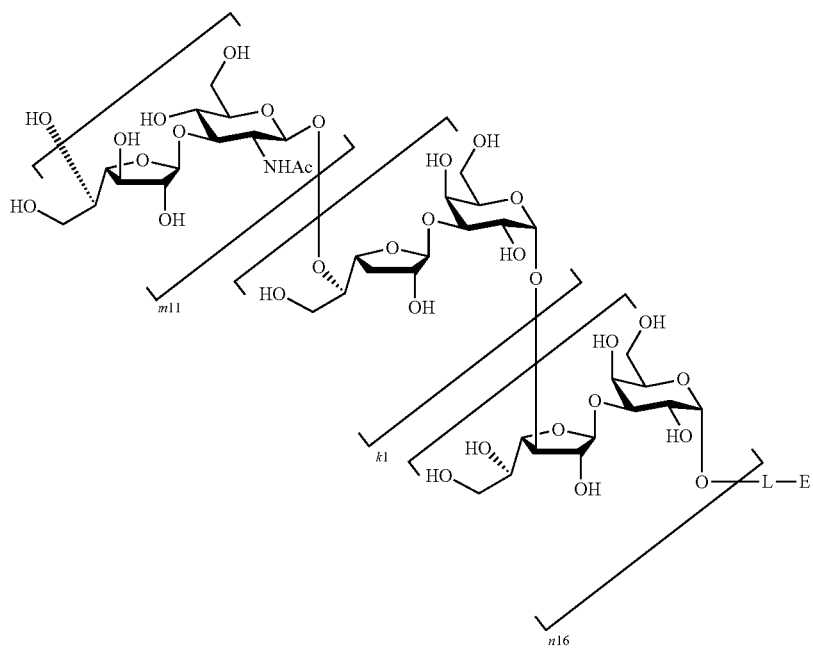
| —O—L—E | m11 | k1 | n16 | Compd. No. |
|---|---|---|---|---|
| ![structure with (CH2)3, COOH] | 14 | 1 | 1 | Q-221 |
|  |  |  | 2 | Q-222 |
|  |  |  | 3 | Q-223 |
|  |  |  | 4 | Q-224 |
|  |  |  | 5 | Q-225 |
| ![structure with (CH2)3, COOH] | 10 | 2 | 1 | Q-226 |
|  |  |  | 2 | Q-227 |
|  |  |  | 3 | Q-228 |
|  |  |  | 4 | Q-228 |
|  |  |  | 5 | Q-230 |
| ![structure with (CH2)3, COOH] | 11 | 2 | 1 | Q-231 |
|  |  |  | 2 | Q-232 |
|  |  |  | 3 | Q-233 |
|  |  |  | 4 | Q-234 |
|  |  |  | 5 | Q-235 |
| ![structure with (CH2)3, COOH] | 12 | 2 | 1 | Q-236 |
|  |  |  | 2 | Q-237 |
|  |  |  | 3 | Q-238 |
|  |  |  | 4 | Q-239 |
|  |  |  | 5 | Q-240 |
| ![structure with (CH2)3, COOH] | 13 | 2 | 1 | Q-241 |
|  |  |  | 2 | Q-242 |
|  |  |  | 3 | Q-243 |
|  |  |  | 4 | Q-244 |
|  |  |  | 5 | Q-245 |
| ![structure with (CH2)3, COOH] | 14 | 2 | 1 | Q-246 |
|  |  |  | 2 | Q-247 |
|  |  |  | 3 | Q-248 |
|  |  |  | 4 | Q-249 |
|  |  |  | 5 | Q-250 |
| ![structure with (CH2)10, COOH] | 10 | 1 | 1 | Q-251 |
|  |  |  | 2 | Q-252 |
|  |  |  | 3 | Q-253 |
|  |  |  | 4 | Q-254 |
|  |  |  | 5 | Q-255 |

TABLE 15-continued
(II-Q)
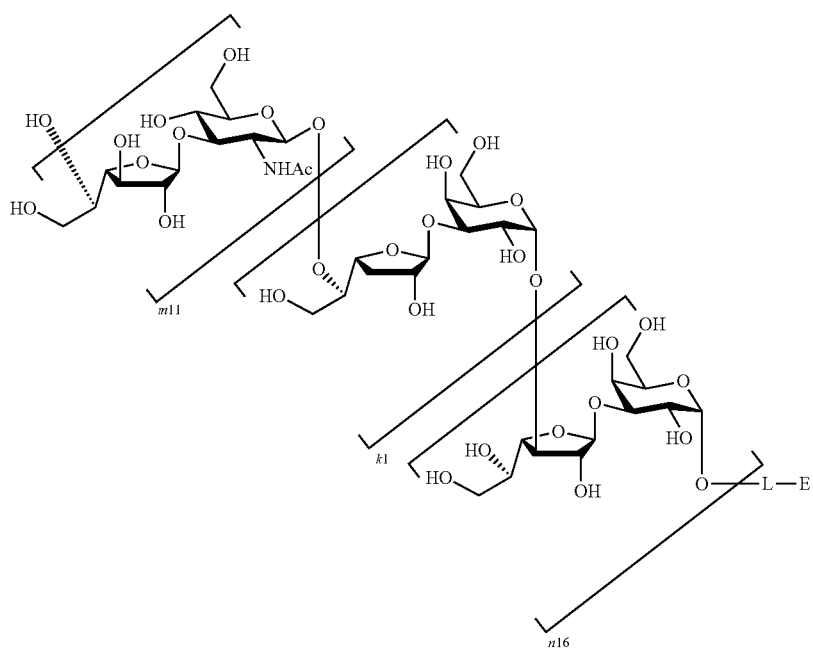
| —O—L—E | m11 | k1 | n16 | Compd. No. |
|---|---|---|---|---|
| 10-COOH) | 11 | 1 | 1 | Q-256 |
|  |  |  | 2 | Q-257 |
|  |  |  | 3 | Q-258 |
|  |  |  | 4 | Q-259 |
|  |  |  | 5 | Q-260 |
| 10-COOH) | 12 | 1 | 1 | Q-261 |
|  |  |  | 2 | Q-262 |
|  |  |  | 3 | Q-263 |
|  |  |  | 4 | Q-264 |
|  |  |  | 5 | Q-265 |
| 10-COOH) | 13 | 1 | 1 | Q-266 |
|  |  |  | 2 | Q-267 |
|  |  |  | 3 | Q-268 |
|  |  |  | 4 | Q-269 |
|  |  |  | 5 | Q-270 |
| 10-COOH) | 14 | 1 | 1 | Q-271 |
|  |  |  | 2 | Q-272 |
|  |  |  | 3 | Q-273 |
|  |  |  | 4 | Q-274 |
|  |  |  | 5 | Q-275 |
| 10-COOH) | 10 | 2 | 1 | Q-276 |
|  |  |  | 2 | Q-277 |
|  |  |  | 3 | Q-278 |
|  |  |  | 4 | Q-279 |
|  |  |  | 5 | Q-280 |
| 10-COOH) | 11 | 2 | 1 | Q-281 |
|  |  |  | 2 | Q-282 |
|  |  |  | 3 | Q-283 |
|  |  |  | 4 | Q-284 |
|  |  |  | 5 | Q-285 |
| 10-COOH) | 12 | 2 | 1 | Q-286 |
|  |  |  | 2 | Q-287 |
|  |  |  | 3 | Q-288 |
|  |  |  | 4 | Q-289 |
|  |  |  | 5 | Q-290 |

TABLE 15-continued
(II-Q)
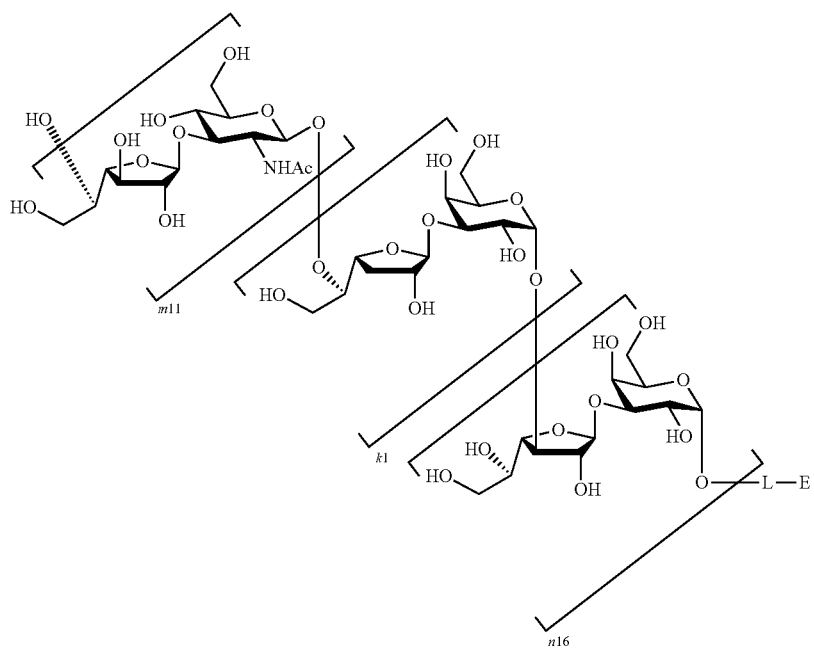
| —O—L—E | m11 | k1 | n16 | Compd. No. |
|---|---|---|---|---|
| ⋯O—(CH₂)₁₀—C(=O)OH | 13 | 2 | 1 | Q-291 |
| | | | 2 | Q-292 |
| | | | 3 | Q-293 |
| | | | 4 | Q-294 |
| | | | 5 | Q-295 |
| ⋯O—(CH₂)₁₀—C(=O)OH | 14 | 2 | 1 | Q-296 |
| | | | 2 | Q-297 |
| | | | 3 | Q-298 |
| | | | 4 | Q-299 |
| | | | 5 | Q-300 |
| ⋯O—(CH₂)₅—C(=O)NHNH₂ | 10 | 1 | 1 | Q-301 |
| | | | 2 | Q-302 |
| | | | 3 | Q-303 |
| | | | 4 | Q-304 |
| | | | 5 | Q-305 |
| ⋯O—(CH₂)₅—C(=O)NHNH₂ | 11 | 1 | 1 | Q-306 |
| | | | 2 | Q-307 |
| | | | 3 | Q-308 |
| | | | 4 | Q-309 |
| | | | 5 | Q-310 |
| ⋯O—(CH₂)₅—C(=O)NHNH₂ | 12 | 1 | 1 | Q-311 |
| | | | 2 | Q-312 |
| | | | 3 | Q-313 |
| | | | 4 | Q-314 |
| | | | 5 | Q-315 |
| ⋯O—(CH₂)₅—C(=O)NHNH₂ | 13 | 1 | 1 | Q-316 |
| | | | 2 | Q-317 |
| | | | 3 | Q-318 |
| | | | 4 | Q-319 |
| | | | 5 | Q-320 |
| ⋯O—(CH₂)₅—C(=O)NHNH₂ | 14 | 1 | 1 | Q-321 |
| | | | 2 | Q-322 |
| | | | 3 | Q-323 |
| | | | 4 | Q-324 |
| | | | 5 | Q-325 |

(II-Q)
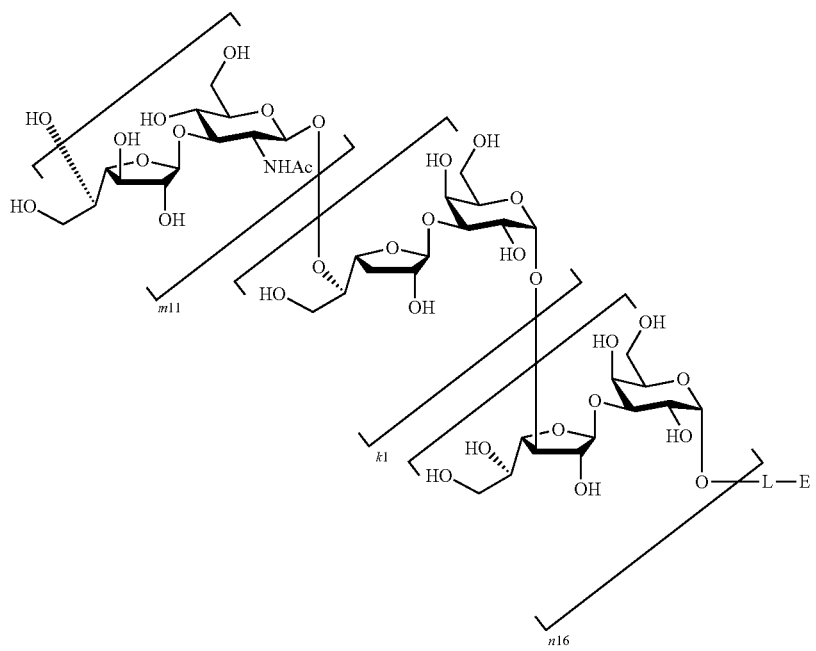
| —O—L—E | m11 | k1 | n16 | Compd. No. |
|---|---|---|---|---|
| ⋯O\~\~\~(CH₂)₅C(O)NHNH₂ | 10 | 2 | 1 | Q-326 |
|  |  |  | 2 | Q-327 |
|  |  |  | 3 | Q-328 |
|  |  |  | 4 | Q-329 |
|  |  |  | 5 | Q-330 |
| ⋯O\~\~\~(CH₂)₅C(O)NHNH₂ | 11 | 2 | 1 | Q-331 |
|  |  |  | 2 | Q-332 |
|  |  |  | 3 | Q-333 |
|  |  |  | 4 | Q-334 |
|  |  |  | 5 | Q-335 |
| ⋯O\~\~\~(CH₂)₅C(O)NHNH₂ | 12 | 2 | 1 | Q-336 |
|  |  |  | 2 | Q-337 |
|  |  |  | 3 | Q-338 |
|  |  |  | 4 | Q-339 |
|  |  |  | 5 | Q-340 |
| ⋯O\~\~\~(CH₂)₅C(O)NHNH₂ | 13 | 2 | 1 | Q-341 |
|  |  |  | 2 | Q-342 |
|  |  |  | 3 | Q-343 |
|  |  |  | 4 | Q-344 |
|  |  |  | 5 | Q-345 |
| ⋯O\~\~\~(CH₂)₅C(O)NHNH₂ | 14 | 2 | 1 | Q-346 |
|  |  |  | 2 | Q-347 |
|  |  |  | 3 | Q-348 |
|  |  |  | 4 | Q-349 |
|  |  |  | 5 | Q-350 |
| ⋯O\~\~(CH₂)₃SH | 10 | 1 | 1 | Q-351 |
|  |  |  | 2 | Q-352 |
|  |  |  | 3 | Q-353 |
|  |  |  | 4 | Q-354 |
|  |  |  | 5 | Q-355 |
| ⋯O\~\~(CH₂)₃SH | 11 | 1 | 1 | Q-356 |
|  |  |  | 2 | Q-357 |
|  |  |  | 3 | Q-358 |
|  |  |  | 4 | Q-359 |
|  |  |  | 5 | Q-360 |
| ⋯O\~\~(CH₂)₃SH | 12 | 1 | 1 | Q-361 |
|  |  |  | 2 | Q-362 |

TABLE 15-continued
(II-Q)
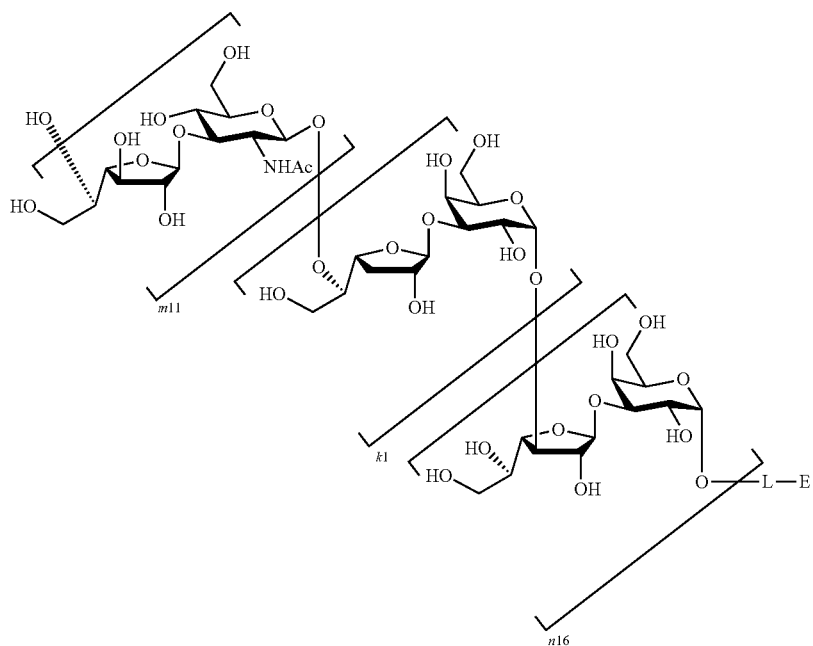
| —O—L—E | m11 | k1 | n16 | Compd. No. |
|---|---|---|---|---|
| | | | 3 | Q-363 |
| | | | 4 | Q-364 |
| | | | 5 | Q-365 |
| ⸺O⸺SH | 13 | 1 | 1 | Q-366 |
| | | | 2 | Q-367 |
| | | | 3 | Q-368 |
| | | | 4 | Q-369 |
| | | | 5 | Q-370 |
| ⸺O⸺SH | 14 | 1 | 1 | Q-371 |
| | | | 2 | Q-372 |
| | | | 3 | Q-373 |
| | | | 4 | Q-374 |
| | | | 5 | Q-375 |
| ⸺O⸺ | 10 | 1 | 1 | Q-376 |
| | | | 2 | Q-377 |
| | | | 3 | Q-378 |
| | | | 4 | Q-379 |
| | | | 5 | Q-380 |
| ⸺O⸺ | 11 | 1 | 1 | Q-381 |
| | | | 2 | Q-382 |
| | | | 3 | Q-383 |
| | | | 4 | Q-384 |
| | | | 5 | Q-385 |
| ⸺O⸺ | 12 | 1 | 1 | Q-386 |
| | | | 2 | Q-387 |
| | | | 3 | Q-388 |
| | | | 4 | Q-389 |
| | | | 5 | Q-390 |
| ⸺O⸺ | 13 | 1 | 1 | Q-391 |
| | | | 2 | Q-392 |
| | | | 3 | Q-393 |
| | | | 4 | Q-394 |
| | | | 5 | Q-395 |
| ⸺O⸺ | 14 | 1 | 1 | Q-396 |
| | | | 2 | Q-397 |
| | | | 3 | Q-398 |

TABLE 15-continued
(II-Q)
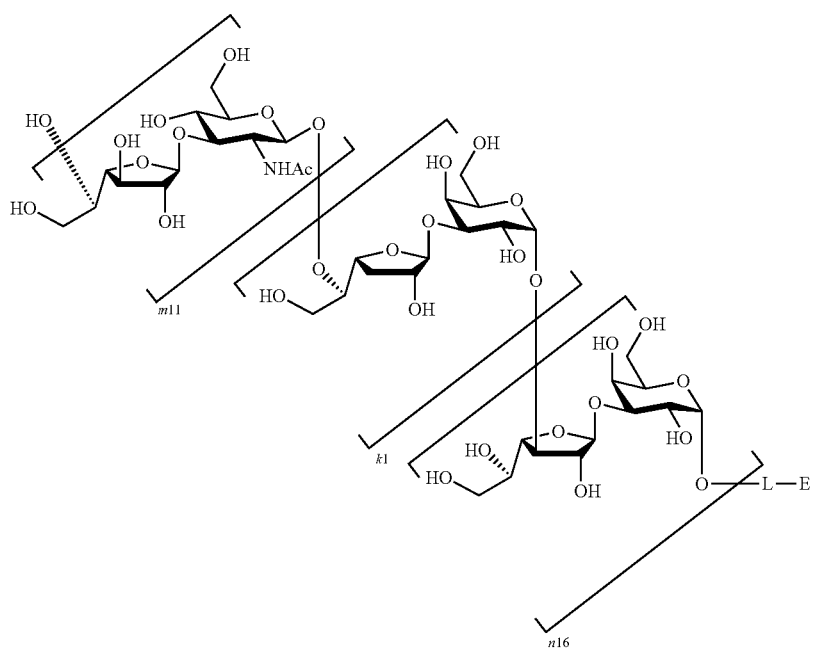
| —O—L—E | m11 | k1 | n16 | Compd. No. |
|---|---|---|---|---|
| | | | 4 | Q-399 |
| | | | 5 | Q-400 |
| ⋯O⟨⟩₃SH | 10 | 2 | 1 | Q-401 |
| | | | 2 | Q-402 |
| | | | 3 | Q-403 |
| | | | 4 | Q-404 |
| | | | 5 | Q-405 |
| ⋯O⟨⟩₃SH | 11 | 2 | 1 | Q-406 |
| | | | 2 | Q-407 |
| | | | 3 | Q-408 |
| | | | 4 | Q-409 |
| | | | 5 | Q-410 |
| ⋯O⟨⟩₃SH | 12 | 2 | 1 | Q-411 |
| | | | 2 | Q-412 |
| | | | 3 | Q-413 |
| | | | 4 | Q-414 |
| | | | 5 | Q-415 |
| ⋯O⟨⟩₃SH | 13 | 2 | 1 | Q-416 |
| | | | 2 | Q-417 |
| | | | 3 | Q-418 |
| | | | 4 | Q-419 |
| | | | 5 | Q-420 |
| ⋯O⟨⟩₃SH | 14 | 2 | 1 | Q-421 |
| | | | 2 | Q-422 |
| | | | 3 | Q-423 |
| | | | 4 | Q-424 |
| | | | 5 | Q-425 |
| ⋯O⟨⟩₃═ | 10 | 2 | 1 | Q-426 |
| | | | 2 | Q-427 |
| | | | 3 | Q-428 |
| | | | 4 | Q-429 |
| | | | 5 | Q-430 |
| ⋯O⟨⟩₃═ | 11 | 2 | 1 | Q-431 |
| | | | 2 | Q-432 |
| | | | 3 | Q-433 |
| | | | 4 | Q-434 |

TABLE 15-continued
(II-Q)
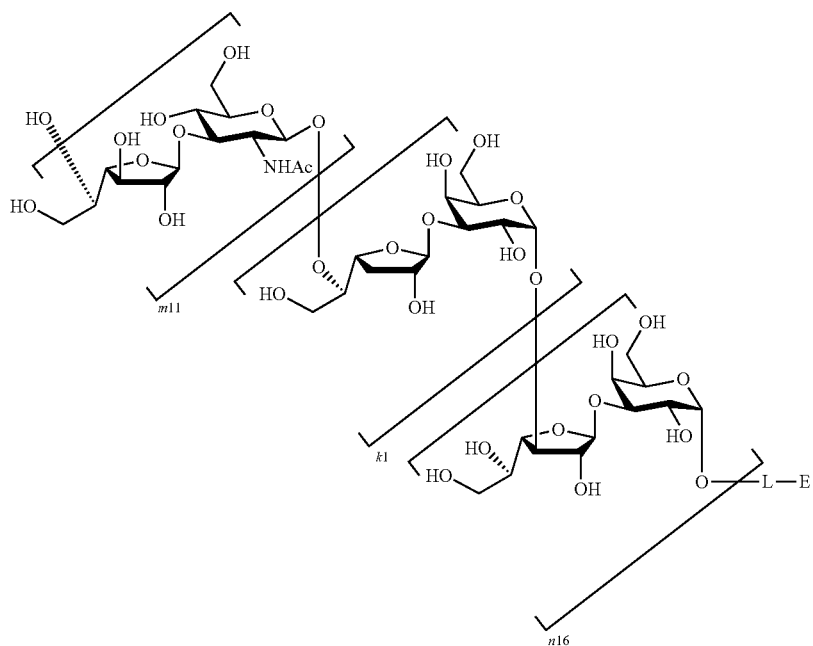
| —O—L—E | m11 | k1 | n16 | Compd. No. |
|---|---|---|---|---|
| | | | 5 | Q-435 |
| ⸺O⸺(⸺)₃⸺CH=CH₂ | 12 | 2 | 1 | Q-436 |
| | | | 2 | Q-437 |
| | | | 3 | Q-438 |
| | | | 4 | Q-439 |
| | | | 5 | Q-440 |
| ⸺O⸺(⸺)₃⸺CH=CH₂ | 13 | 2 | 1 | Q-441 |
| | | | 2 | Q-442 |
| | | | 3 | Q-443 |
| | | | 4 | Q-444 |
| | | | 5 | Q-445 |
| ⸺O⸺(⸺)₃⸺CH=CH₂ | 14 | 2 | 1 | Q-446 |
| | | | 2 | Q-447 |
| | | | 3 | Q-448 |
| | | | 4 | Q-449 |
| | | | 5 | Q-450 |
| ⸺O⸺CH₂⸺C≡CH | 10 | 1 | 1 | Q-451 |
| | | | 2 | Q-452 |
| | | | 3 | Q-453 |
| | | | 4 | Q-454 |
| | | | 5 | Q-455 |
| ⸺O⸺CH₂⸺C≡CH | 11 | 1 | 1 | Q-456 |
| | | | 2 | Q-457 |
| | | | 3 | Q-458 |
| | | | 4 | Q-459 |
| | | | 5 | Q-460 |
| ⸺O⸺CH₂⸺C≡CH | 12 | 1 | 1 | Q-461 |
| | | | 2 | Q-462 |
| | | | 3 | Q-463 |
| | | | 4 | Q-464 |
| | | | 5 | Q-465 |
| ⸺O⸺CH₂⸺C≡CH | 13 | 1 | 1 | Q-466 |
| | | | 2 | Q-467 |
| | | | 3 | Q-468 |
| | | | 4 | Q-469 |
| | | | 5 | Q-470 |

TABLE 15-continued
(II-Q)
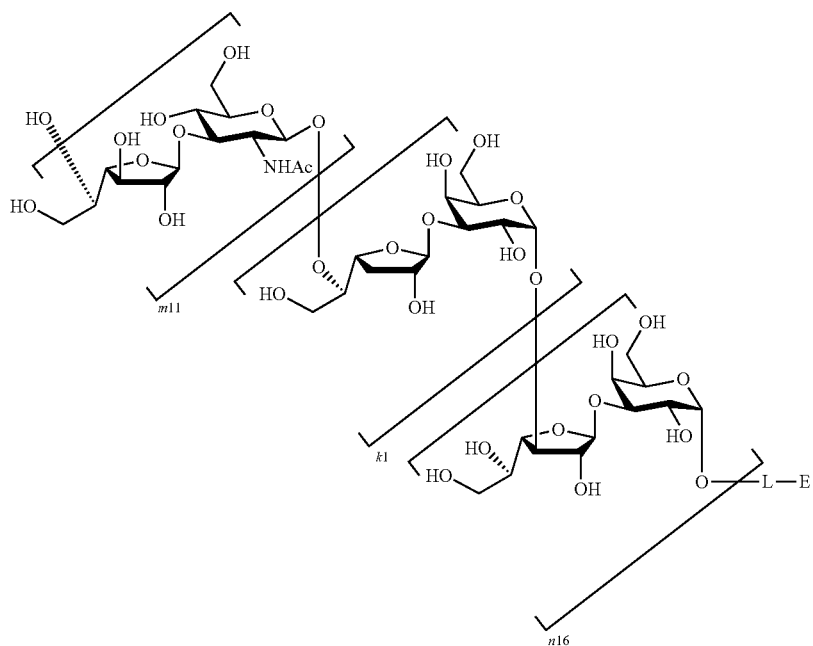
| —O—L—E | m11 | k1 | n16 | Compd. No. |
|---|---|---|---|---|
| ⋯O⟍⟍≡ | 14 | 1 | 1 | Q-471 |
|  |  |  | 2 | Q-472 |
|  |  |  | 3 | Q-473 |
|  |  |  | 4 | Q-474 |
|  |  |  | 5 | Q-475 |
| ⋯O⟍⟍≡ | 10 | 2 | 1 | Q-476 |
|  |  |  | 2 | Q-477 |
|  |  |  | 3 | Q-478 |
|  |  |  | 4 | Q-479 |
|  |  |  | 5 | Q-480 |
| ⋯O⟍⟍≡ | 11 | 2 | 1 | Q-481 |
|  |  |  | 2 | Q-482 |
|  |  |  | 3 | Q-483 |
|  |  |  | 4 | Q-484 |
|  |  |  | 5 | Q-485 |
| ⋯O⟍⟍≡ | 12 | 2 | 1 | Q-486 |
|  |  |  | 2 | Q-487 |
|  |  |  | 3 | Q-488 |
|  |  |  | 4 | Q-489 |
|  |  |  | 5 | Q-490 |
| ⋯O⟍⟍≡ | 13 | 2 | 1 | Q-491 |
|  |  |  | 2 | Q-492 |
|  |  |  | 3 | Q-493 |
|  |  |  | 4 | Q-494 |
|  |  |  | 5 | Q-495 |
| ⋯O⟍⟍≡ | 14 | 2 | 1 | Q-496 |
|  |  |  | 2 | Q-497 |
|  |  |  | 3 | Q-498 |
|  |  |  | 4 | Q-499 |
|  |  |  | 5 | Q-500 |
| ⋯O$(\ )_5$Br | 10 | 1 | 1 | Q-501 |
|  |  |  | 2 | Q-502 |
|  |  |  | 3 | Q-503 |
|  |  |  | 4 | Q-504 |
|  |  |  | 5 | Q-505 |

TABLE 15-continued
(II-Q)
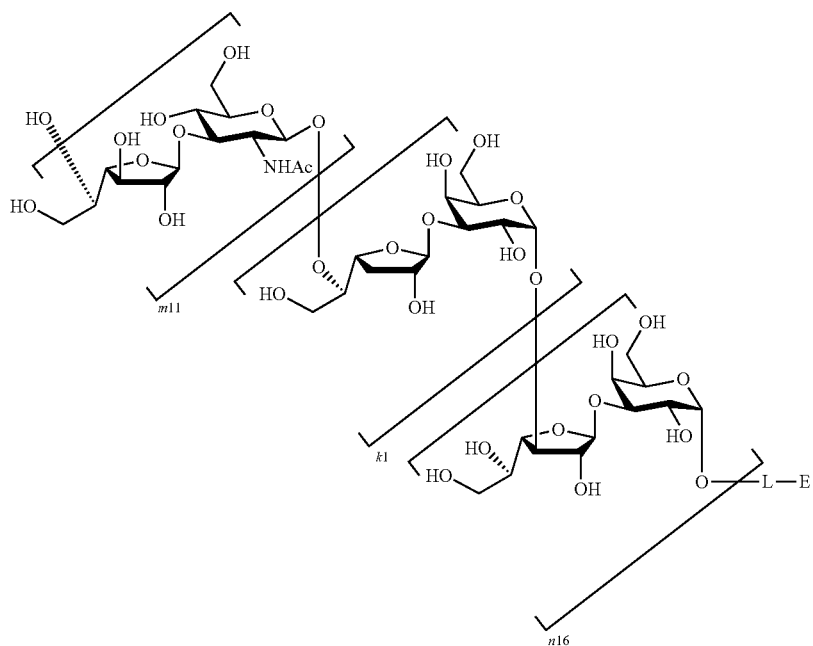
| —O—L—E | m11 | k1 | n16 | Compd. No. |
|---|---|---|---|---|
| ⸺O⤳₅Br | 11 | 1 | 1 | Q-506 |
|  |  |  | 2 | Q-507 |
|  |  |  | 3 | Q-508 |
|  |  |  | 4 | Q-509 |
|  |  |  | 5 | Q-510 |
| ⸺O⤳₅Br | 12 | 1 | 1 | Q-511 |
|  |  |  | 2 | Q-512 |
|  |  |  | 3 | Q-513 |
|  |  |  | 4 | Q-514 |
|  |  |  | 5 | Q-515 |
| ⸺O⤳₅Br | 13 | 1 | 1 | Q-516 |
|  |  |  | 2 | Q-517 |
|  |  |  | 3 | Q-518 |
|  |  |  | 4 | Q-519 |
|  |  |  | 5 | Q-520 |
| ⸺O⤳₅Br | 14 | 1 | 1 | Q-521 |
|  |  |  | 2 | Q-522 |
|  |  |  | 3 | Q-523 |
|  |  |  | 4 | Q-524 |
|  |  |  | 5 | Q-525 |
| ⸺O⤳₅Br | 10 | 2 | 1 | Q-526 |
|  |  |  | 2 | Q-527 |
|  |  |  | 3 | Q-528 |
|  |  |  | 4 | Q-529 |
|  |  |  | 5 | Q-530 |
| ⸺O⤳₅Br | 11 | 2 | 1 | Q-531 |
|  |  |  | 2 | Q-532 |
|  |  |  | 3 | Q-533 |
|  |  |  | 4 | Q-534 |
|  |  |  | 5 | Q-535 |
| ⸺O⤳₅Br | 12 | 2 | 1 | Q-536 |
|  |  |  | 2 | Q-537 |
|  |  |  | 3 | Q-538 |
|  |  |  | 4 | Q-539 |
|  |  |  | 5 | Q-540 |

TABLE 15-continued
(II-Q)
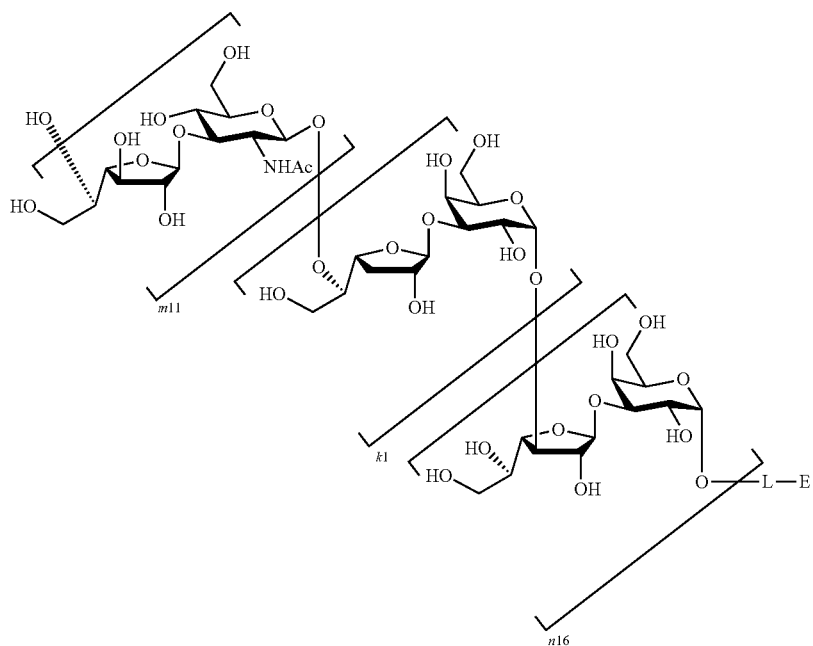
| —O—L—E | m11 | k1 | n16 | Compd. No. |
|---|---|---|---|---|
| ⋯O⌒(⌒)₅Br | 13 | 2 | 1 | Q-541 |
|  |  |  | 2 | Q-542 |
|  |  |  | 3 | Q-543 |
|  |  |  | 4 | Q-544 |
|  |  |  | 5 | Q-545 |
| ⋯O⌒(⌒)₅Br | 14 | 2 | 1 | Q-546 |
|  |  |  | 2 | Q-547 |
|  |  |  | 3 | Q-548 |
|  |  |  | 4 | Q-549 |
|  |  |  | 5 | Q-550 |
| ⋯O⌒O⌒NH₂ | 10 | 1 | 1 | Q-551 |
|  |  |  | 2 | Q-552 |
|  |  |  | 3 | Q-553 |
|  |  |  | 4 | Q-554 |
|  |  |  | 5 | Q-555 |
| ⋯O⌒O⌒NH₂ | 11 | 1 | 1 | Q-556 |
|  |  |  | 2 | Q-557 |
|  |  |  | 3 | Q-558 |
|  |  |  | 4 | Q-559 |
|  |  |  | 5 | Q-560 |
| ⋯O⌒O⌒NH₂ | 12 | 1 | 1 | Q-561 |
|  |  |  | 2 | Q-562 |
|  |  |  | 3 | Q-563 |
|  |  |  | 4 | Q-564 |
|  |  |  | 5 | Q-565 |
| ⋯O⌒O⌒NH₂ | 13 | 1 | 1 | Q-566 |
|  |  |  | 2 | Q-567 |
|  |  |  | 3 | Q-568 |
|  |  |  | 4 | Q-569 |
|  |  |  | 5 | Q-570 |
| ⋯O⌒O⌒NH₂ | 14 | 1 | 1 | Q-571 |
|  |  |  | 2 | Q-572 |
|  |  |  | 3 | Q-573 |
|  |  |  | 4 | Q-574 |
|  |  |  | 5 | Q-575 |
| ⋯O⌒O⌒NH₂ | 10 | 2 | 1 | Q-576 |
|  |  |  | 2 | Q-577 |

TABLE 15-continued
(II-Q)
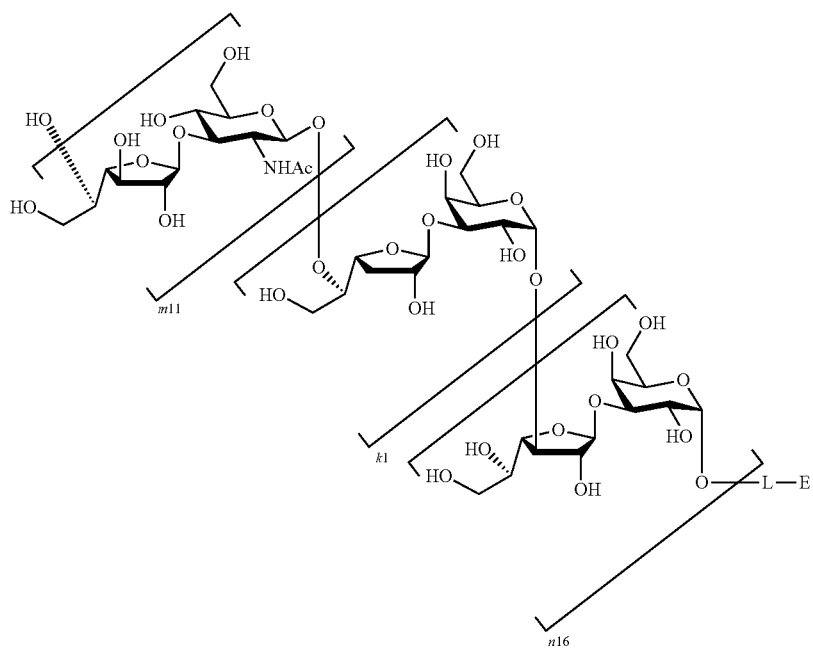
| —O—L—E | m11 | k1 | n16 | Compd. No. |
|---|---|---|---|---|
| | | | 3 | Q-578 |
| | | | 4 | Q-579 |
| | | | 5 | Q-580 |
| ⋯O⁀⁀O⁀⁀NH₂ | 11 | 2 | 1 | Q-581 |
| | | | 2 | Q-582 |
| | | | 3 | Q-583 |
| | | | 4 | Q-584 |
| | | | 5 | Q-585 |
| ⋯O⁀⁀O⁀⁀NH₂ | 12 | 2 | 1 | Q-586 |
| | | | 2 | Q-587 |
| | | | 3 | Q-588 |
| | | | 4 | Q-589 |
| | | | 5 | Q-590 |
| ⋯O⁀⁀O⁀⁀NH₂ | 13 | 2 | 1 | Q-591 |
| | | | 2 | Q-592 |
| | | | 3 | Q-593 |
| | | | 4 | Q-594 |
| | | | 5 | Q-595 |
| ⋯O⁀⁀O⁀⁀NH₂ | 14 | 2 | 1 | Q-596 |
| | | | 2 | Q-597 |
| | | | 3 | Q-598 |
| | | | 4 | Q-599 |
| | | | 5 | Q-600 |
| ⋯O(⁀⁀O)₃⁀⁀NH₂ | 10 | 1 | 1 | Q-601 |
| | | | 2 | Q-602 |
| | | | 3 | Q-603 |
| | | | 4 | Q-604 |
| | | | 5 | Q-605 |
| ⋯O(⁀⁀O)₃⁀⁀NH₂ | 11 | 1 | 1 | Q-606 |
| | | | 2 | Q-607 |
| | | | 3 | Q-608 |
| | | | 4 | Q-609 |
| | | | 5 | Q-610 |

TABLE 15-continued
(II-Q)
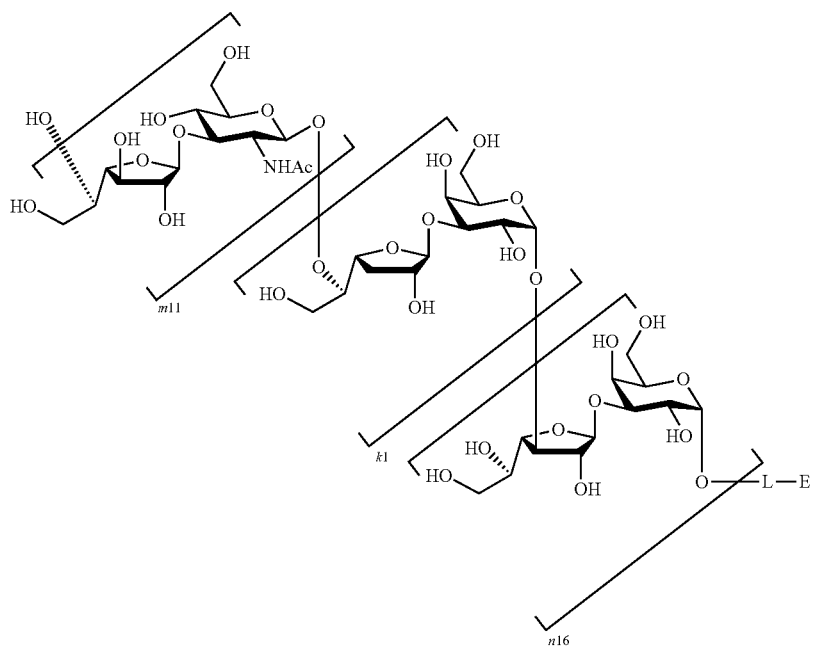
| —O—L—E | m11 | k1 | n16 | Compd. No. |
|---|---|---|---|---|
| ⋯O(O)₃NH₂ | 12 | 1 | 1 | Q-611 |
|  |  |  | 2 | Q-612 |
|  |  |  | 3 | Q-613 |
|  |  |  | 4 | Q-614 |
|  |  |  | 5 | Q-615 |
| ⋯O(O)₃NH₂ | 13 | 1 | 1 | Q-616 |
|  |  |  | 2 | Q-617 |
|  |  |  | 3 | Q-618 |
|  |  |  | 4 | Q-619 |
|  |  |  | 5 | Q-620 |
| ⋯O(O)₃NH₂ | 14 | 1 | 1 | Q-621 |
|  |  |  | 2 | Q-622 |
|  |  |  | 3 | Q-623 |
|  |  |  | 4 | Q-624 |
|  |  |  | 5 | Q-625 |
| ⋯O(O)₃NH₂ | 10 | 2 | 1 | Q-626 |
|  |  |  | 2 | Q-627 |
|  |  |  | 3 | Q-628 |
|  |  |  | 4 | Q-629 |
|  |  |  | 5 | Q-630 |
| ⋯O(O)₃NH₂ | 11 | 2 | 1 | Q-631 |
|  |  |  | 2 | Q-632 |
|  |  |  | 3 | Q-633 |
|  |  |  | 4 | Q-634 |
|  |  |  | 5 | Q-635 |
| ⋯O(O)₃NH₂ | 12 | 2 | 1 | Q-636 |
|  |  |  | 2 | Q-637 |
|  |  |  | 3 | Q-638 |
|  |  |  | 4 | Q-639 |
|  |  |  | 5 | Q-640 |
| ⋯O(O)₃NH₂ | 13 | 2 | 1 | Q-641 |
|  |  |  | 2 | Q-642 |
|  |  |  | 3 | Q-643 |
|  |  |  | 4 | Q-644 |
|  |  |  | 5 | Q-645 |

TABLE 15-continued (II-Q)

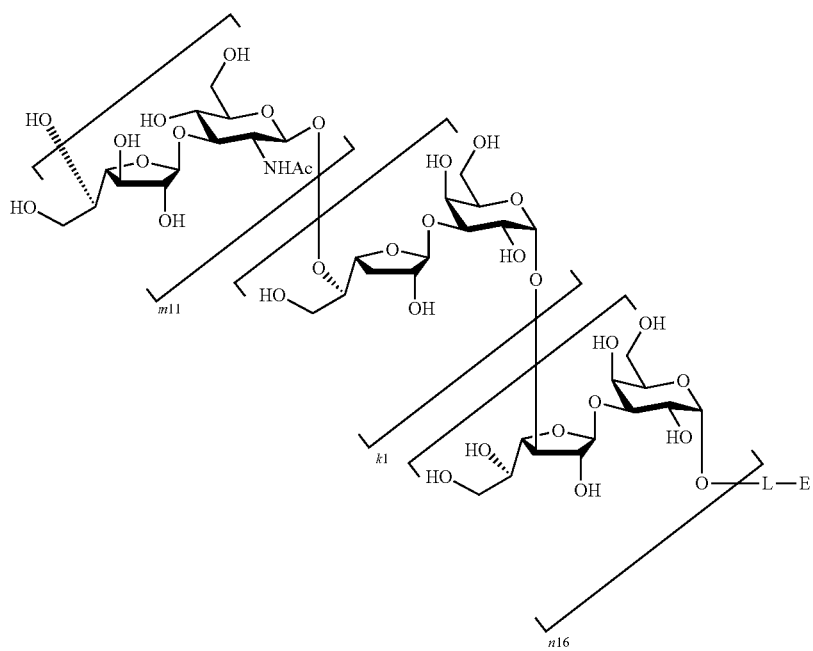

| —O—L—E | m11 | k1 | n16 | Compd. No. |
|---|---|---|---|---|
| ⋯O\~\~O(\~\~O)₃\~\~NH₂ | 14 | 2 | 1<br>2<br>3<br>4<br>5 | Q-646<br>Q-647<br>Q-648<br>Q-649<br>Q-650 |
| ⋯O\~\~OH, OH | 10 | 1 | 1<br>2<br>3<br>4<br>5 | Q-651<br>Q-652<br>Q-653<br>Q-654<br>Q-655 |
| ⋯O\~\~OH, OH | 11 | 1 | 1<br>2<br>3<br>4<br>5 | Q-656<br>Q-657<br>Q-658<br>Q-659<br>Q-660 |
| ⋯O\~\~OH, OH | 12 | 1 | 1<br>2<br>3<br>4<br>5 | Q-661<br>Q-662<br>Q-663<br>Q-664<br>Q-665 |
| ⋯O\~\~OH, OH | 13 | 1 | 1<br>2<br>3<br>4<br>5 | Q-666<br>Q-667<br>Q-668<br>Q-669<br>Q-670 |
| ⋯O\~\~OH, OH | 14 | 1 | 1<br>2<br>3<br>4<br>5 | Q-671<br>Q-672<br>Q-673<br>Q-674<br>Q-675 |
| ⋯O\~\~OH, OH | 10 | 2 | 1<br>2<br>3<br>4<br>5 | Q-676<br>Q-677<br>Q-678<br>Q-679<br>Q-680 |

TABLE 15-continued
(II-Q)
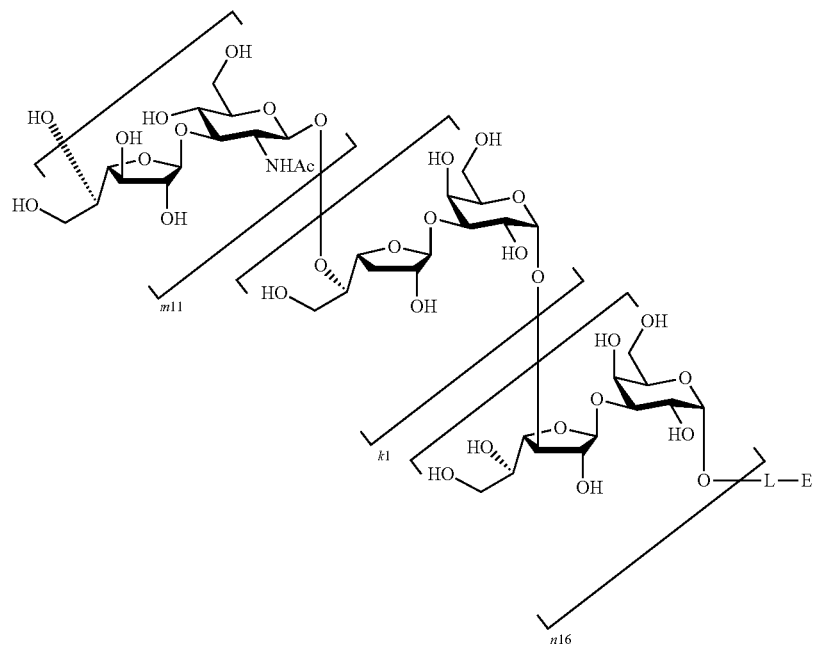
| —O—L—E | m11 | k1 | n16 | Compd. No. |
|---|---|---|---|---|
| -ch2oh) | 11 | 2 | 1 | Q-681 |
| | | | 2 | Q-682 |
| | | | 3 | Q-683 |
| | | | 4 | Q-684 |
| | | | 5 | Q-685 |
| -ch2oh) | 12 | 2 | 1 | Q-686 |
| | | | 2 | Q-687 |
| | | | 3 | Q-688 |
| | | | 4 | Q-689 |
| | | | 5 | Q-690 |
| -ch2oh) | 13 | 2 | 1 | Q-691 |
| | | | 2 | Q-692 |
| | | | 3 | Q-693 |
| | | | 4 | Q-694 |
| | | | 5 | Q-695 |
| -ch2oh) | 14 | 2 | 1 | Q-696 |
| | | | 2 | Q-697 |
| | | | 3 | Q-698 |
| | | | 4 | Q-699 |
| | | | 5 | Q-700 |

Chemical Synthesis

Another aspect of the present invention is directed to a synthetic method of the general formula (I) comprising:

A1) providing a disaccharide D1

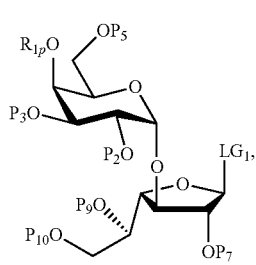
(D1)

wherein $LG_1$ is a leaving group, $R_{1P}$ is $P_4$ or $U_{5p}$; $U_{5p}$ is

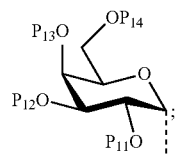

B1) reacting D1 with a disaccharide D2

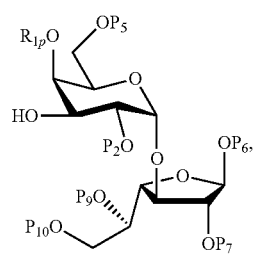
(D2)

to obtain a saccharide O1a

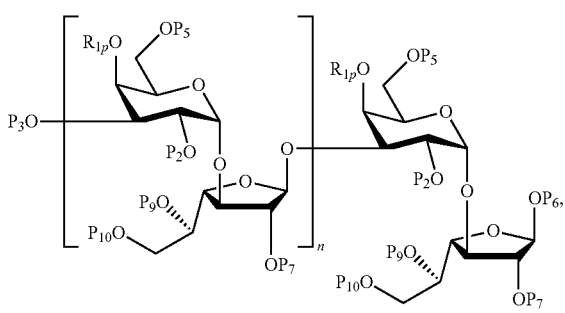
(O1a)

wherein n is 1,
when n is an integer from 2 to 20,
then repeating following steps B2) and B3) for n-1 times B2) removing the protecting group $P_3$ of a saccharide obtained by reacting with the saccharide D1;

B3) reacting the saccharide D1 with the saccharide obtained after the step B2) to obtain a saccharide O1a

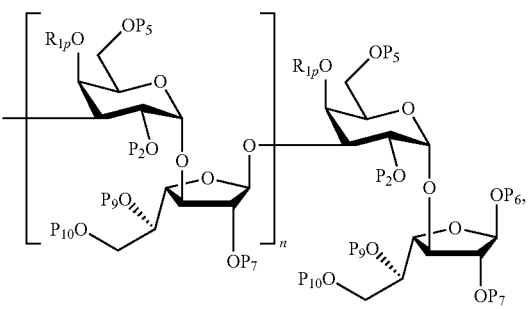
(O1a)

wherein n is an integer from to 20;

C) removing a protecting group $P_6$ of the saccharide O1a and introducing an leaving group $LG_2$ to obtain a saccharide O1b

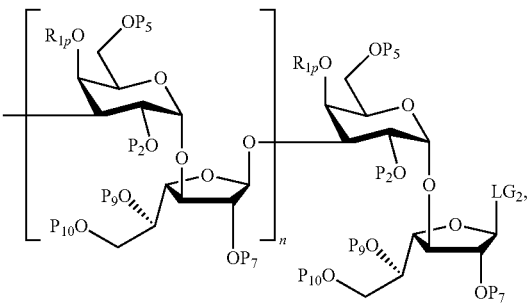
(O1b)

D1) coupling the saccharide O1b with a reactant HO-L-$E_p$ to obtain a saccharide O1c

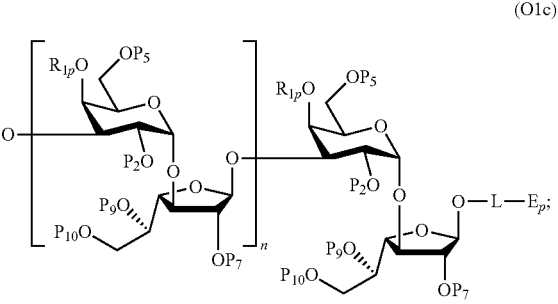
(O1c)

or
D2) reacting the saccharide O1b with a saccharide M1
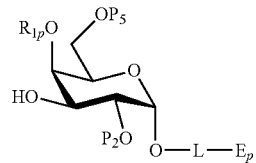
(M1)
to obtain a saccharide O2a
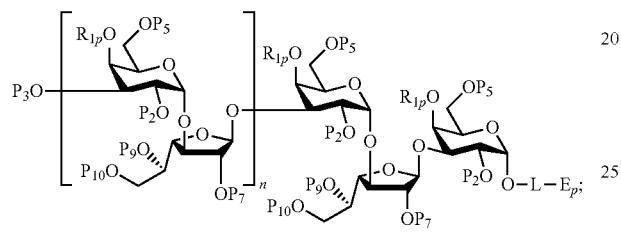
(O2a)
optionally,
E1) removing the protecting group $P_3$ of the saccharide (O1c) to obtain a saccharide O1d,
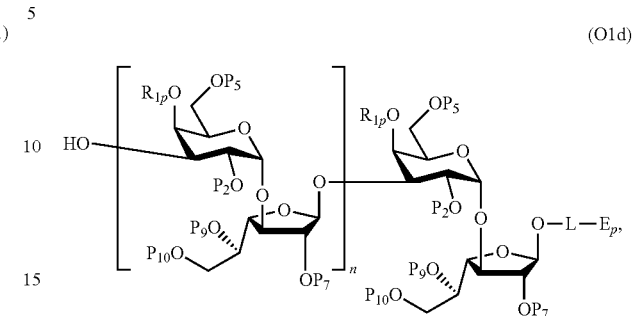
(O1d)
reacting the saccharide O1d with a saccharide M2
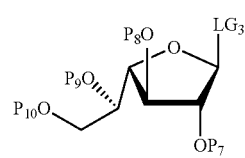
(M2)
to obtain a saccharide O3a
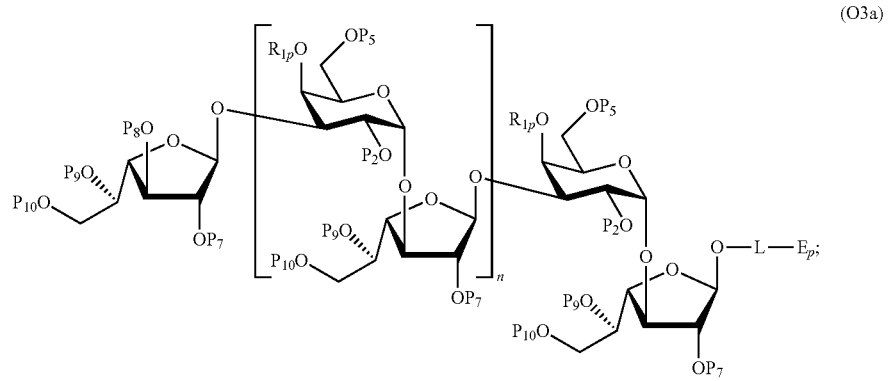
(O3a)

or
E2) removing the protecting group $P_3$ of the saccharide (O2a) to obtain a saccharide O2b,
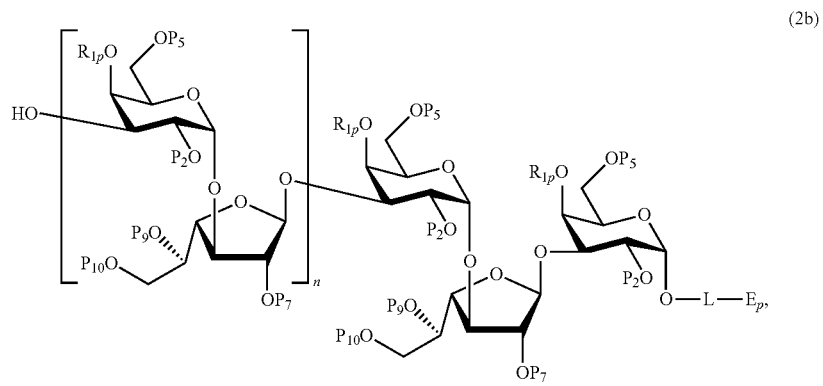
(2b)
reacting the saccharide O2b with a saccharide M2
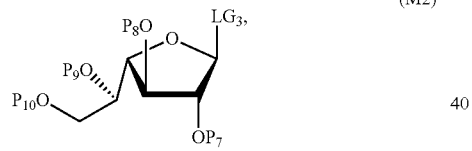
(M2)
to obtain a saccharide O4a
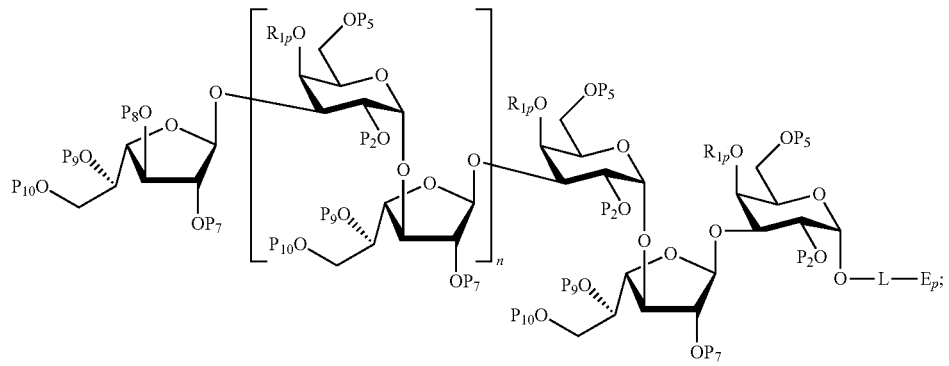
(O4a)

and
F1) removing all protecting groups of the saccharide O1c, O2a, O3a or O4a to obtain a corresponding saccharide of formula (I-1), (I-2), (I-3), or (I-4),
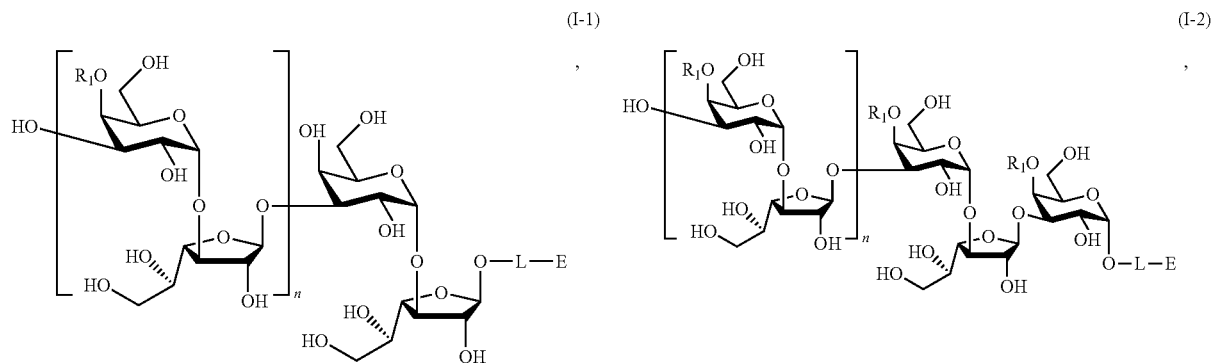
(I-1), (I-2)
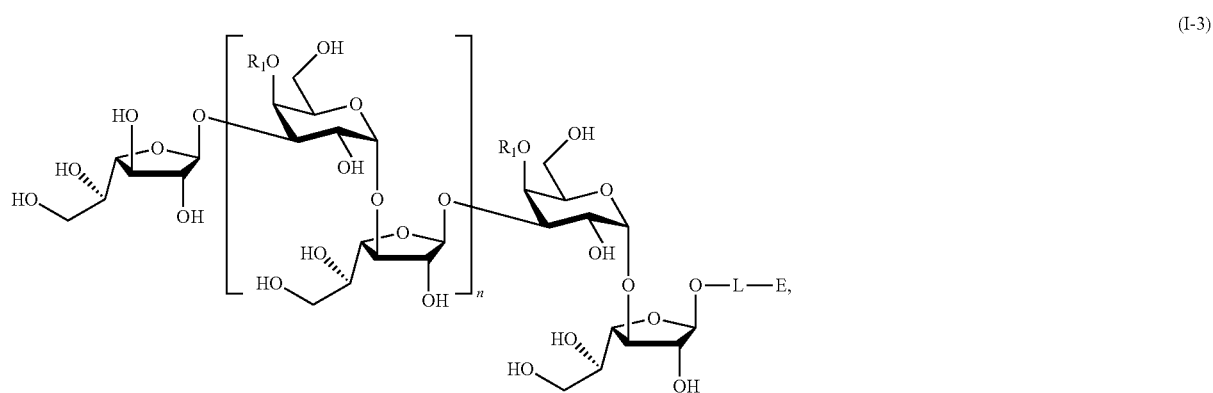
(I-3)
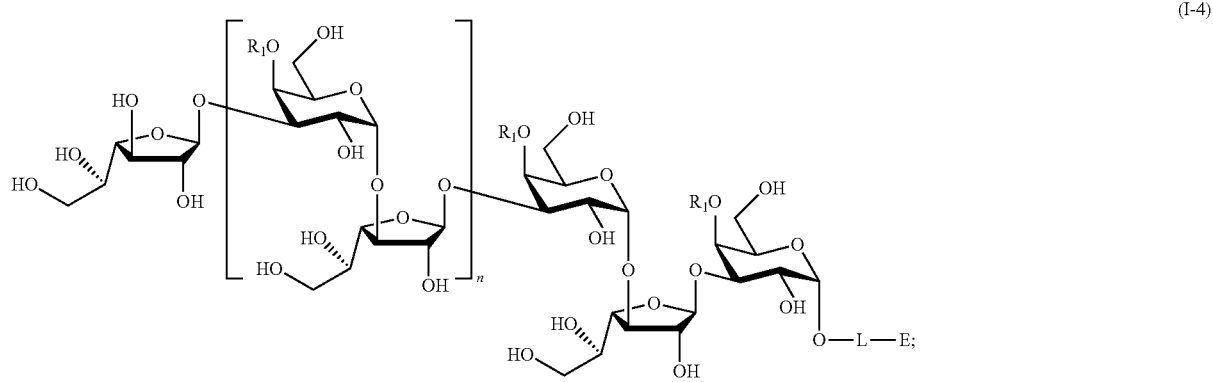
(I-4)

wherein $E_p$ is a protected end group, $LG_1$-$LG_3$ are leaving groups, $P_1$, $P_2$, $P_3$, $P_5$, $P_6$, $P_7$, $P_8$, $P_9$, $P_{10}$, $P_{11}$, $P_{12}$, $P_{13}$, and $P_{14}$ represent protecting groups, and L, E, $R_1$, $R_{1p}$ have the same meanings as defined herein.

Preferably $R_{1p}$ is $P_4$.

Therefore, according to the above described synthetic method, following combinations of the steps may be carried out to obtain the inventive synthetic saccharides:

Steps: A1)→B1)→C)→D1)→F1), A1)→B1)→C)→D2) →F1), A1)→B1)→C)→D1)→E1)→F1), or A1)→B1)→C) →D2)→E2)→F1).

Alternatively, a method for synthesis of a saccharide of general formula (I) comprising:

A2) providing a disaccharide D6

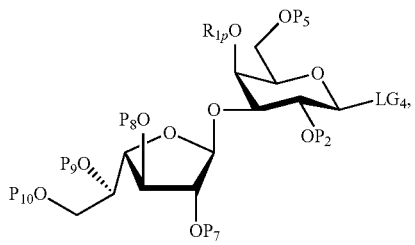

(D6)

wherein $R_{1p}$ is $P_4$ or $U_{5p}$;

$U_{5p}$ is

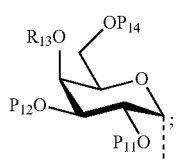

B1') reacting the saccharide D6 with a saccharide D8

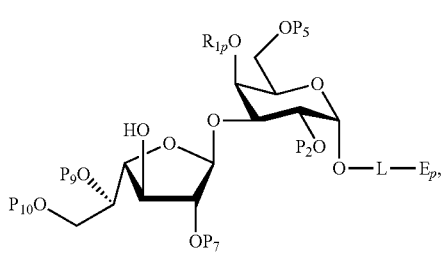

(D8)

to obtain a saccharide O2b

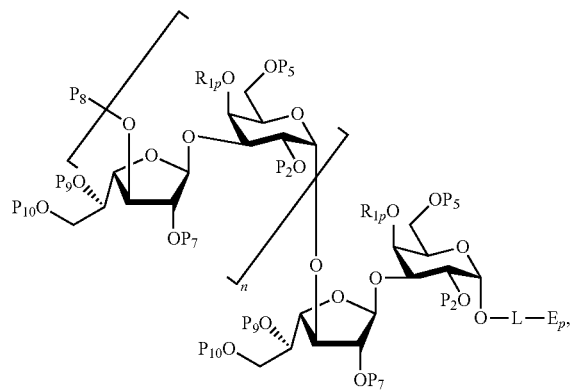

O3b wherein n is 1;

when n is an integer from 2 to 20, then repeating the following steps B2') and B3') for n−1 times B2') removing the protecting group $P_8$ of a saccharide obtained by reacting with the saccharide D6;

B3') reacting the saccharide D6 with the saccharide obtained after the step B2') to obtain a saccharide O3b

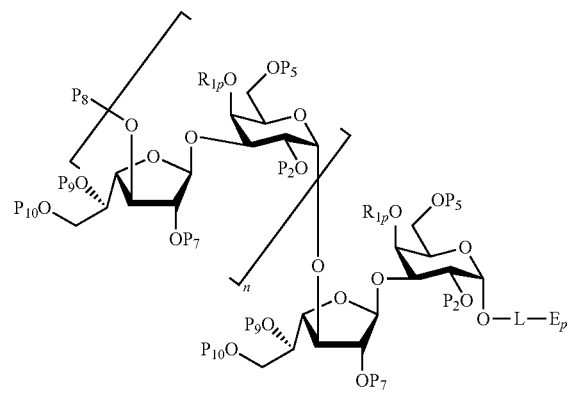

O3b wherein n is an integer from 2 to 20, optionally,

E3) removing the protecting group $P_8$ of the saccharide O3b to obtain a saccharide O3c,

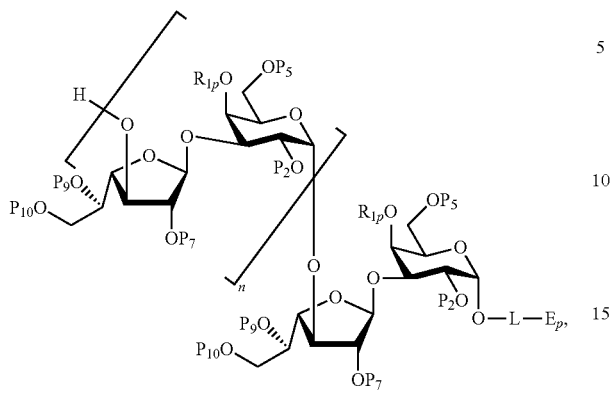

(O3c)

E4) reacting the saccharide O3c with a saccharide M3

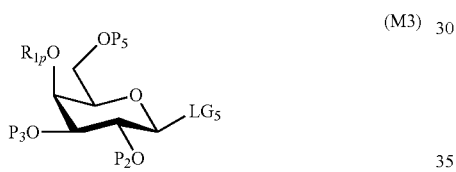

(M3)

to obtain a saccharide O4b

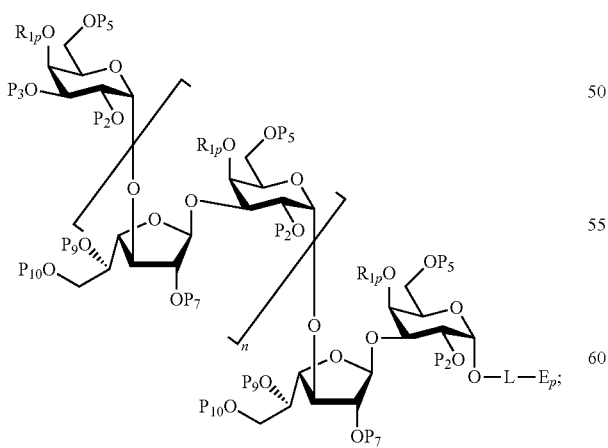

(O4b)

or

E5) reacting the saccharide O3c with a disaccharide D4

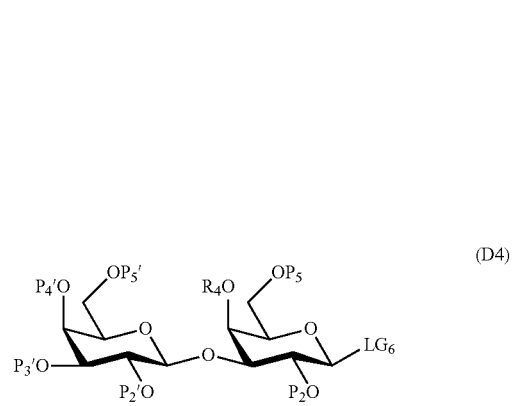

(D4)

to obtain a saccharide O5a

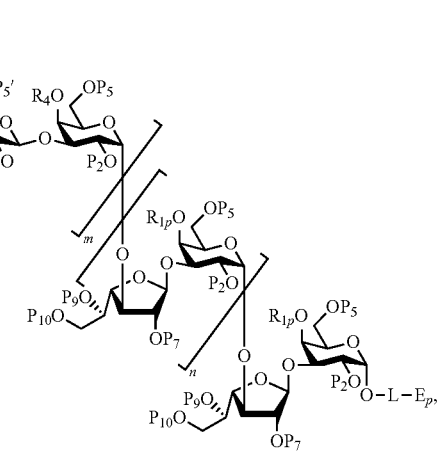

O5a wherein m is 1, when m is an integer from 2 to 20, then repeating the following steps e5) and e6) for m−1 times e5) removing the protecting group $P_3'$ of a saccharide obtained by reacting with the monosaccharide D4;

e6) reacting the saccharide D4 with the saccharide obtained after the step e5) to obtain a saccharide O5a (O5a)
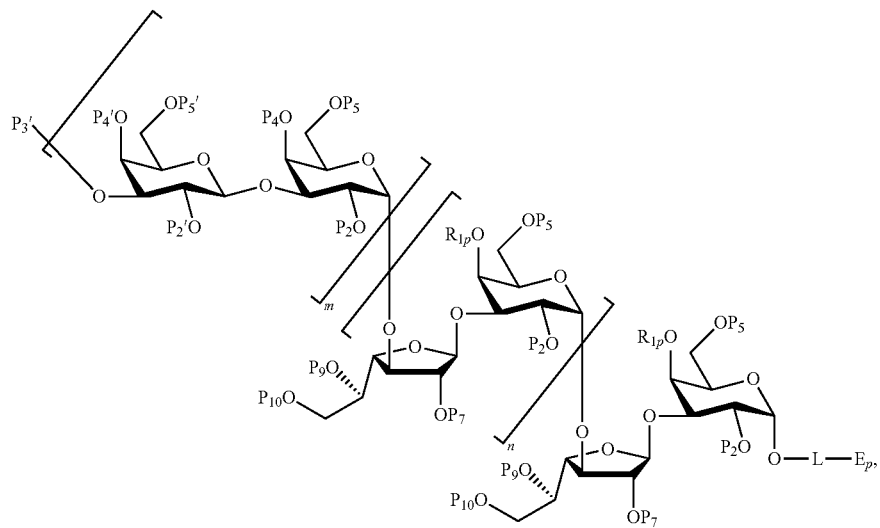
wherein m is an integer from 2 to 20;
or
E6) reacting the saccharide O3c with a disaccharide D5
(D5)
wherein LG$_7$ represents a leaving group
to obtain a saccharide O5b
O5b wherein m is 1,
when m is an integer from 1 to 20,
then repeating following steps e7) and e8) for m−1 times e7) removing the protecting group P$_9$' of a saccharide obtained by reacting with the monosaccharide D5;
e8) reacting the saccharide D5 with the saccharide obtained after the step e7) to obtain a saccharide O5b

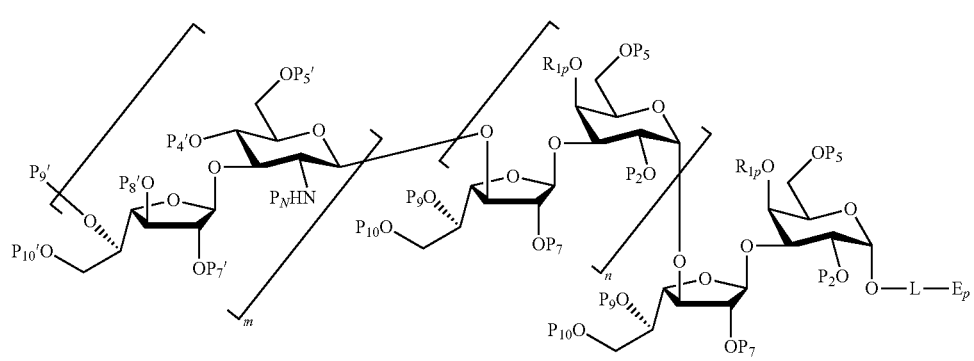

O5b wherein m is an integer from 2 to 20;
e9) removing a protecting groups P$_N$ and converting resulting —NH$_2$ groups to —NHAc groups to obtain a saccharide O5c

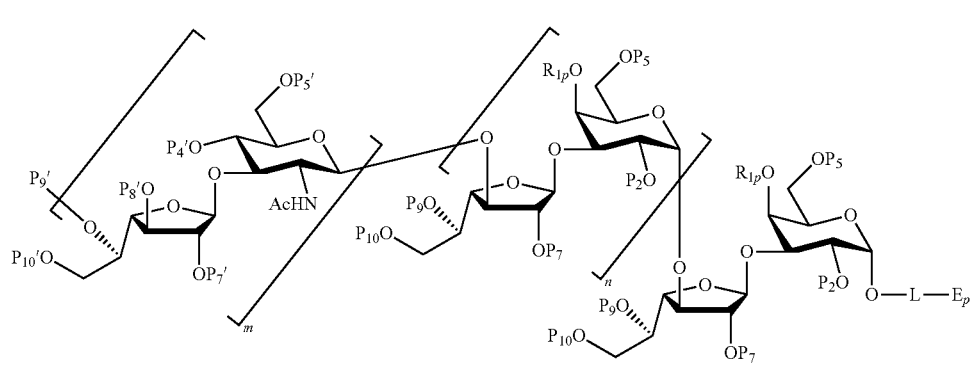

O5c

F2) removing all protecting groups of the saccharide O3b, O4b, O5a, or O5c, to obtain a corresponding saccharide of the formula (I-5), (I-6), (I-7), or (I-8),

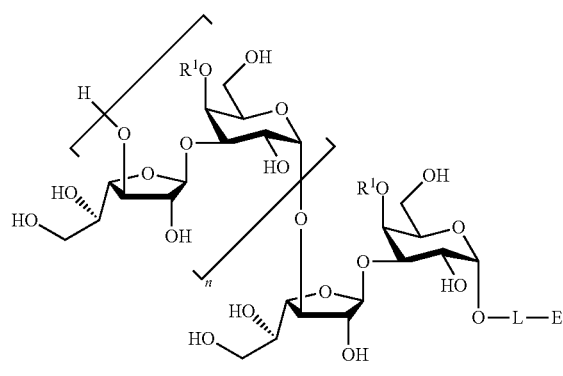

(I-5)

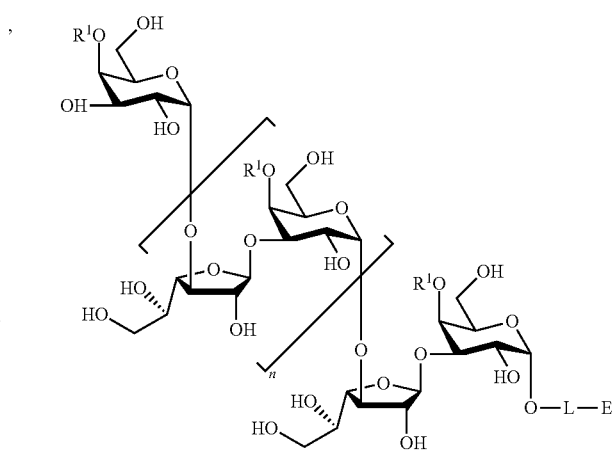

(I-6)

(I-7)

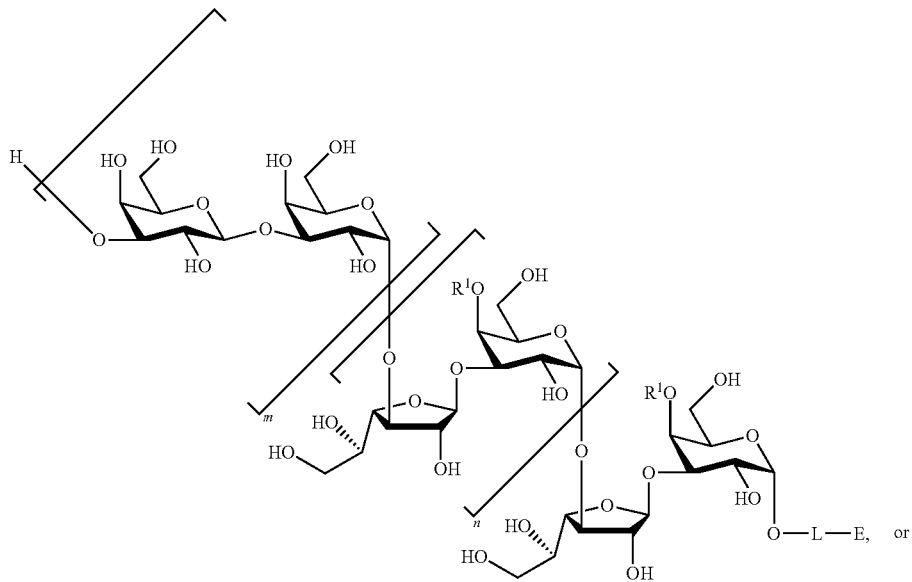

or (I-8)

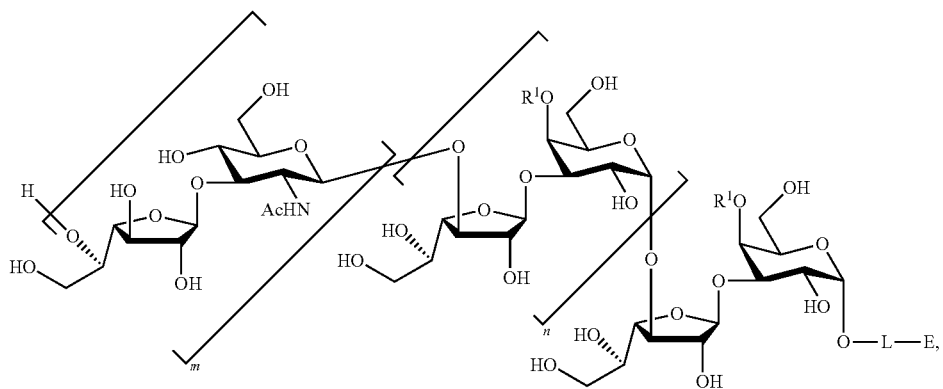

wherein $E_p$ is a protected end group; $LG_4$-$LG_7$ are leaving groups; $P_N$, $P_1$, $P_2$, $P_2'$, $P_3$, $P_3'$, $P_4$, $P_4'$, $P_5$, $P_5'$, $P_6$, $P_7$, $P_7'$, $P_8$, $P_8'$, $P_9$ % $P_9$, $P_{10}$, $P_{10}'$, $P_{11}$, $P_{12}$, $P_{13}$ and $P_{14}$ represent protecting groups, and L, E, $R_1$, $R_{1p}$, m, and n have the same meanings as defined herein.

Preferably $R_{1p}$ is $P_4$, and $R_1$ is H.

Therefore, according to the above described synthetic method, following combinations of the steps may be carried out to obtain the inventive synthetic saccharides:

Steps: A2)→B1')→E3)→F2), A2)→B1')→B2')→B3') →E3)→F2), A2)→B1')→B2')→B3')→E3)→E4) →F2), A2)→B1')→B2')→B3')→E3)→E5)→F2), A2)→B1')→B2')→B3')→E3)→E5)→F2).

$P_1$, $P_2$, $P_2'$, $P_3$, $P_3'$, $P_4$, $P_4'$, $P_5$, $P_5'$, $P_6$, $P_7$, $P_7'$, $P_8$, $P_8'$, $P_9$, $P_9'$, $P_{10}$, $P_{10}'$, $P_{11}$, $P_{12}$, $P_{13}$ and $P_{14}$ represent protecting groups. The term "protecting group" as used herein refers to commonly used groups in organic synthesis, preferably used for protection hydroxyl groups, and thiols. $P_N$ represents protecting group used for protection amine group.

More preferably, $P_1$, $P_2'$, $P_3$, $P_3'$, $P_4$, $P_4'$, $P_5$, $P_5'$, $P_6$, $P_7$, $P_7'$, $P_8$, $P_8'$, $P_9$, $P_9'$, $P_{10}$, $P_{10}'$, $P_{11}$, $P_{12}$, $P_{13}$ and $P_{14}$ are suitable protecting groups for hydroxyl groups, more preferably different suitable protecting groups for hydroxyl groups capable of being removed subsequently one after another by a suitable sequence of deprotection reactions. Preferred protecting groups for hydroxyl groups are acetyl, phenyl, benzyl, isopropylidene, benzylidene, naphthylidene, benzoyl, p-methoxybenzyl, p-bromobenzyl, p-methoxybenzylidene, p-methoxyphenyl, p-bromobenzylidene, p-nitrophenyl, allyl, trichloroacetyl, (2-nitrophenyl)acetyl, isopropyl, p-bromobenzyl, dimethoxytrityl, trityl, 2-naphthylmethyl, pivaloyl, chloroacetyl, triisopropylsilyl, tert-butyldimethylsilyl, tert-butyldiphenylsilyl, tert-butylmethoxy phenylsilyl, triethylsilyl, trimethylsilyl, 2-trimethylsilylethoxymethyl, 9-fluorenyl methoxycarbonyl, benzyloxymethyl, methyloxymethyl, tert-butyloxymethyl, methoxyethyloxymethyl, levulinoyl and $P_N$ represents 2,2,2-trichloroethyl carbonyl (Troc) or 9-fluorenylmethyloxycarbonyl (Fmoc).

Specifically, protecting groups $P_1$ and $P_6$ represent phenyl, protecting groups $P_3$ and $P_3'$ represent 2-naphthylmethyl, protecting groups $P_2$, $P_4$, $P_4'$, $P_5'$, $P_{11}$, $P_{12}$, and $P_{14}$ represent benzyl, p-methoxybenzyl, protecting groups $P_2'$, $P_5$, $P_7$, $P_7'$, $P_8$, $P_8'$, $P_9$, $P_{10}$, $P_{10}'$, and $P_{13}$ are benzoyl, and protecting group $P_6$ represents butyldimethylsilyl. Optionally, $OP_4$ and $OP_5$, $OP_4'$ and $OP_5'$ form a phenyl hemiacetal. $P_9'$ is benzoyl or levulinoyl. $P_N$ is 2,2,2-Trichloroethyl carbonyl (Troc).

Examples of leaving groups suitable for the present synthesis are well known to the person skilled in carbohydrate chemistry and include halides, thioethers, imidates, acetate, and phosphate.

Preferably, leaving groups $LG_1$, $LG_2$, $LG_3$, $LG_4$, $LG_5$, $LG_6$ and $LG_7$ are selected from halogen (Cl, Br, F, I), —O—C(=NH)—CCl$_3$, —O—C(=NPh)-CF$_3$, —OAc, —SR$^L$, —SO-Ph, —O—(CH$_2$)$_3$—CH=CH$_2$, —O—P(OR$^L$)$_2$, —O—PO(OR$^L$)$_2$, —O—CO—OR$^L$, —O—CO—SR$^L$, —O—CS—SR$^L$, —O—CS—OR$^L$,

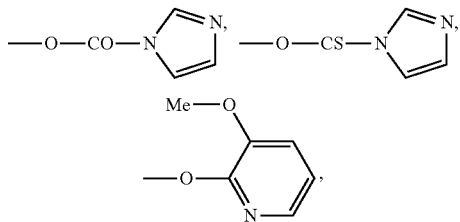

wherein R$^L$ may be any alkyl or aryl group, preferably, methyl, ethyl, propyl, isopropyl, phenyl or toluyl.

Preferably, leaving groups $LG_1$, $LG_2$, $LG_3$, $LG_4$, $LG_5$, $LG_6$ and $LG_7$ are selected from the group of leaving groups consisting of:

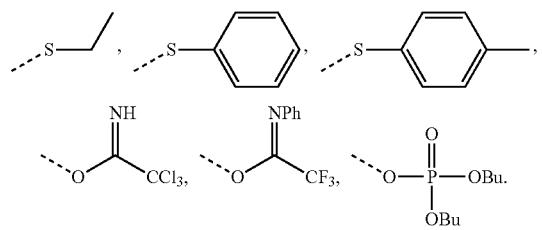

As mentioned, the provision of an oxocarbenium intermediate relies on the activation of the leaving group installed at the anomeric position of the glycosylating agent with an appropriate or suitable activating agent. It is common knowledge for the skilled person that suitable activating agents for phosphate (i.e. phosphate activating agents) and imidate (i.e. imidate activating agents) are Lewis acids, such as silyl triflate or silver triflate, while suitable activating agents for thioether i.e. thioether activating agents include, but are not restricted to: NIS/TfOH, NIS/TMSOTf, NIS/BF$_3$·Et$_2$O, NIS/AgOTf, DMTST/Tf$_2$O, IDPC, BSP/Tf$_2$O, Ph$_2$SO/Tf$_2$O. Examples of silyl triflate include, but are not restricted to trimethylsilyl trifluoromethanesulfonate, tert-butyl dimethyl trifluoromethanesulfonate, triiospropyl trifluoromethanesulfonate.

Preferably, $LG_1$, $LG_2$, $LG_3$, $LG_4$, $LG_5$, $LG_6$ and $LG_7$ are thioethers (see Carbohydr. Res. 2015, 13-22) and even more preferred is when $LG_1$, $LG_2$, $LG_3$, $LG_4$, $LG_5$, $LG_6$ and $LG_7$ are selected from the group consisting of:

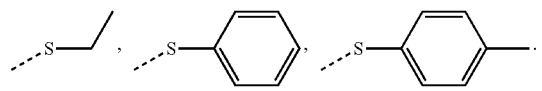

$E_p$ represents a protected end group. E represents —NH$_2$, —N$_3$, —CN, —O—NH$_2$, —CH=CH$_2$, —C≡CH, —Br, —Cl, —I, —CO$_2$R', —CONHNH$_2$, —SH, or —SAc; and The corresponding protected end group $E_p$ represents —N(P$_{N1}$)(P$_{N2}$), —N$_3$, —CN, —O—N(P$_{N1}$)(P$_{N2}$), —CH=CH$_2$, —C≡CH, —Br, —Cl, —I, —CO$_2$R', —CONHN(P$_{N1}$)(P$_{N2}$), —SP$_s$, or —SAc;

$P_{N1}$, and $P_{N2}$ are suitable protecting groups for amines and form together with the amine to be protected carbamates or amides. Examples of protecting groups forming carbamates include tert-butyloxy carbonyl, 9-fluorenylmethyl carbonyl, allyl carbonyl, trichloroethyl carbonyl and benzyloxy carbonyl. Examples of protecting groups forming amides include acetyl or trichloro acetyl. Preferably, protecting group P$^{12}$ represents benzyl and protecting group P$^{13}$ represents benzyloxy carbonyl.

$P_s$ is suitable protecting group for thiol and selected from phenyl, benzyl, p-methoxybenzyl, p-methoxyphenyl, p-nitrophenyl, and allyl.

The coupling reaction between the saccharides can be performed in the presence of a glycosylation reagent. Suitable reagents include, but are not restricted to: AgOTf, BF$_3$·OEt$_2$, trimethylsilyl trifluoromethanesulfonate (TMSOTf), trifluoromethanesulfonic acid (TfOH), trifluoromethanesulfonic anhydride (Tf$_2$O, triflic anhydride), lanthanoid(III) triflates, NIS/AgOTf, NIS/TfOH or dimethyl (methylthio)sulfonium trifluoromethanesulfonate (DMTST).

It is preferred that the coupling reaction between saccharides in the steps B1), B1'), B1"), B1'"), B3), B3'), B3"), B3'"), B5"), B5'"), D1), D2), E1), E2), E4), E5), E6), a4), e6), e8) is performed by activation with NIS/TfOH or TBSOTf, in a mixture of apolar solvent and polar aprotic solvent at a temperature of between −80° C. and −60° C. Even more preferred is that said reaction is performed by activation with TBSOTf, in a mixture of toluene and diethyl ether at −70° C.

Preferably, the coupling reaction between the monosaccharide M5 and the saccharide M3 in step a4) is performed by activation with TBSOTf in an apolar solvent at a temperature of between −10° C. to +10° C.

The removal of protecting groups P$^1$, P$^3$, P$^5$-P$^{13}$ performed at steps F1)-F3) involves:

first cleavage of the base-labile protecting groups by treatment with a base in presence of hydrogen peroxide in a mixture of solvents. Preferably, the base is NaOMe or LiOH; and second cleavage of the protecting groups sensitive to hydrogenation by subjecting the compound to hydrogen in presence of a palladium catalyst in a mixture of solvents.

A further aspect according to the present invention refers to an intermediate compound for preparing a saccharide of the general formula (I), wherein the intermediate compound has any one of general formulae (O1b), (O1c), (O1d), (O2a), (O2b), (O3a), (O3b), (O3c), (O4a), (O4b), (O5a), (O5b) and (O5c):

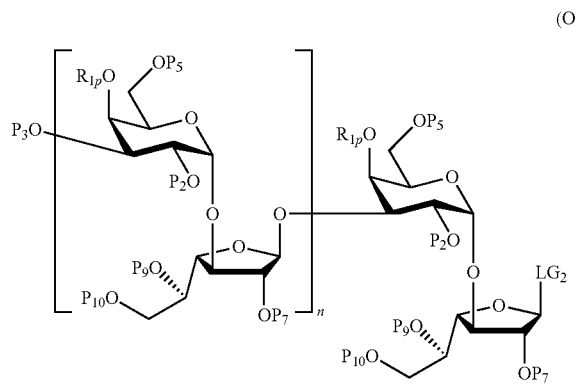
(O1b)
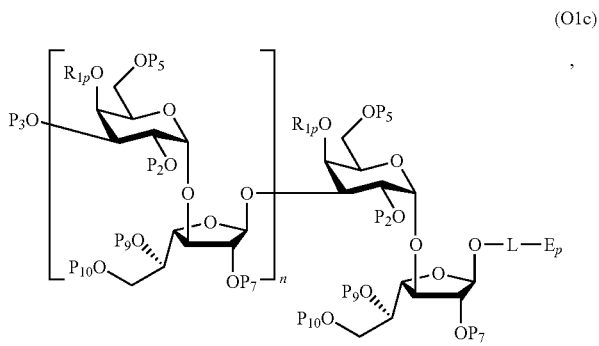
(O1c)
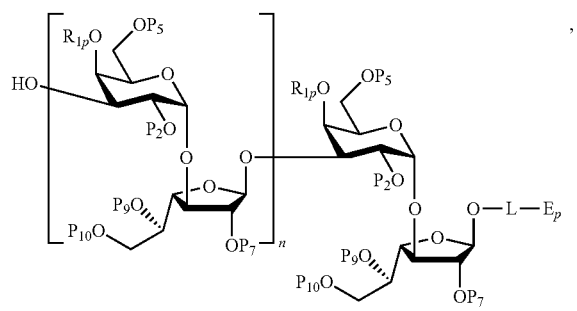
(O1d)
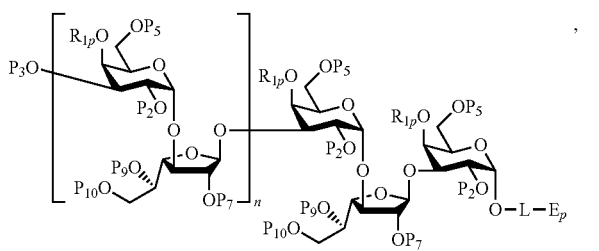
(O2a)
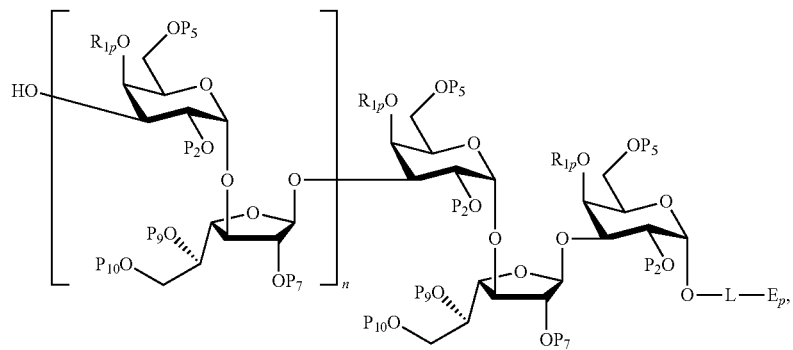
(2b)
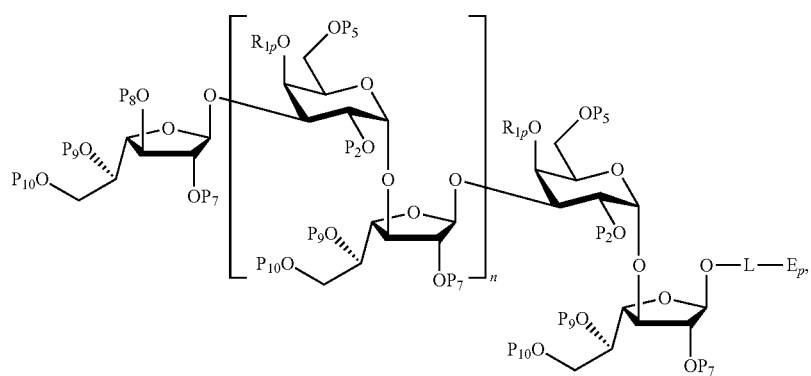
(O3a)

-continued
(O3b)
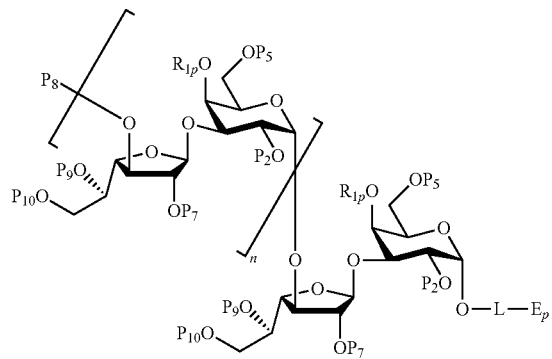
(O3c)
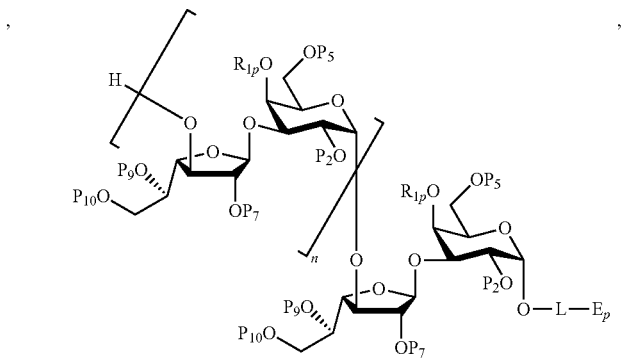
(O4a)
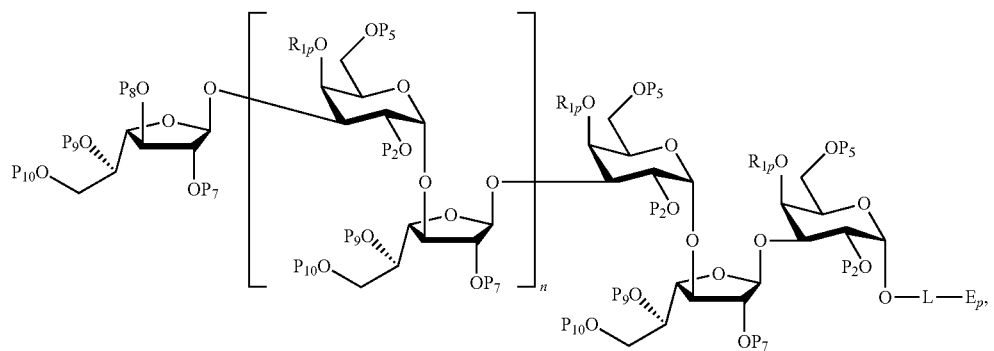
(O4b)
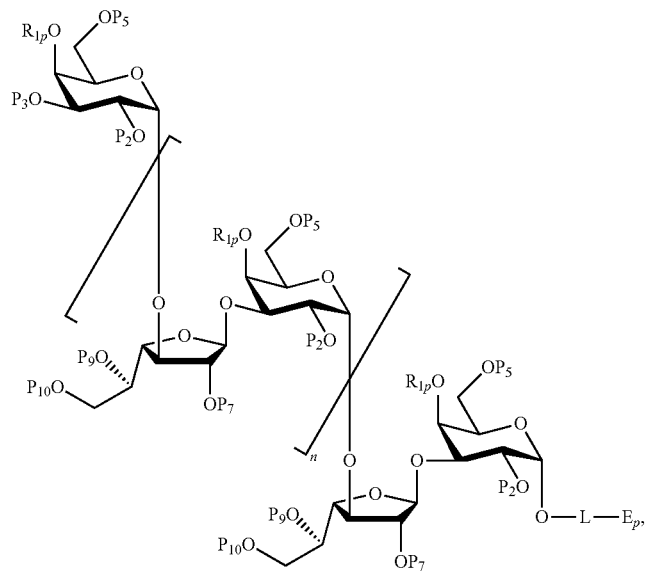

(O5a)
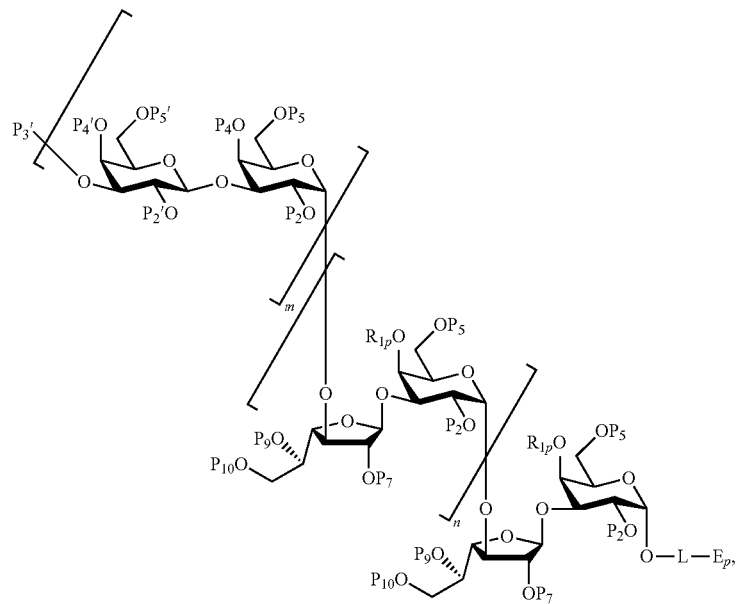
(O5b)
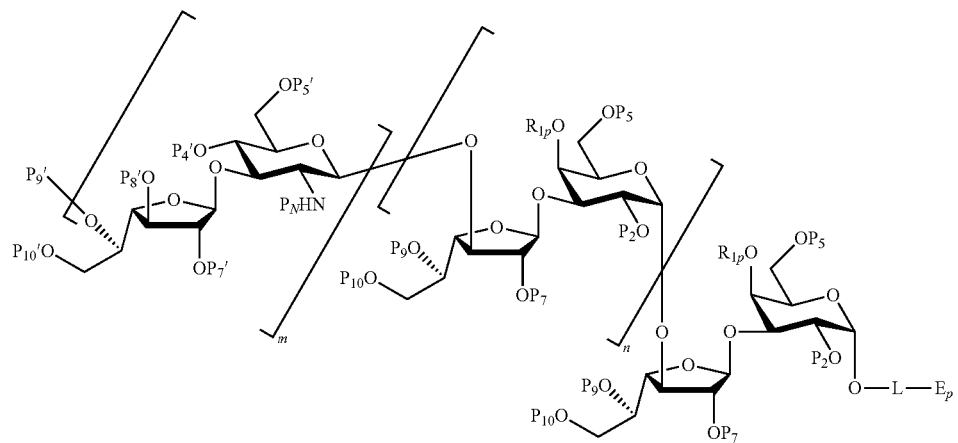
O5c
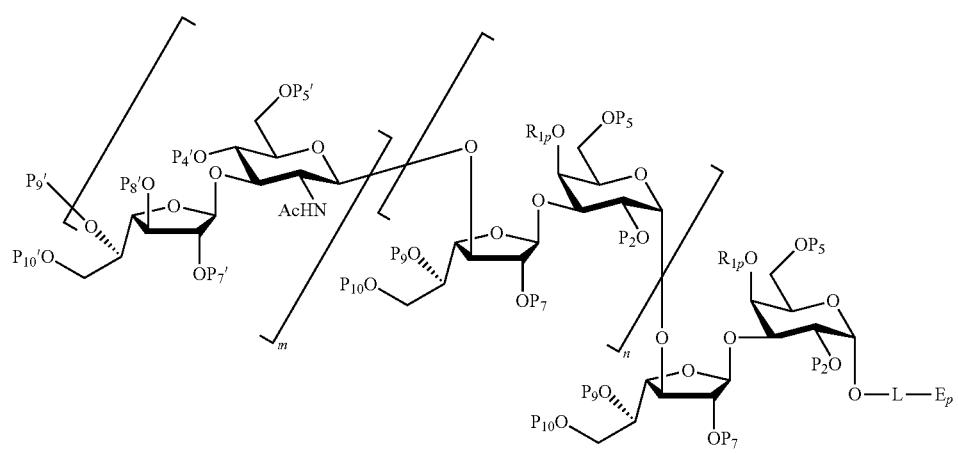

wherein, $LG_2$ represents a leaving group; $E_P$ is protected end group, $P_N$, $P_2$, $P_2'$, $P_3'$, $P_4$, $P_4'$, $P_5$, $P_5'$, $P_7$, $P_7'$, $P_8$, $P_8'$, $P_9$, $P_9'$, $P_{10}$, $P_{10}'$, $P_{11}$, $P_{12}$, $P_{13}$ and $P_{14}$ represent protecting groups, and L, $R_{1P}$, m, and n have the same meanings as defined above.

In formulae (O1b), (O1c), (O1d), (O2a), (O2b), (O3a), (O3b), (O3c), (O4a), (O4b), (O5a), (O5b) and (O5c), preferably the linker -L- represents $-L^a-$, $-L^a-L^e-$, $-L^a-L^b-L^e-$, or $-L^a-L^d-L^e-$;

- $-L^a-$ represents $-(CH_2)_o-$, $-(CH_2-CH_2-O)_o-C_2H_4-$, or $-(CH_2-CH_2-O)_o-CH_2$;
- $-L^b-$ represents $-O-$, $-NH-CO-NH-$, $-NH-CO-CH_2-NH-$, $-NH-CO-$; $-L^d-$ represents $-(CH_2)_q-$, $-(CH(OH))_q-$, $-(CF_2)_q-$, $-(CH_2-CH_2-O)_q$g$-C_2H_4-$, or $-(CH_2-CH_2-O)_q$g$-CH_2-$;
- $-L^e-$ represents $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ or $-(CH_2)_{p1}-O-(CH_2)_{p2}-$; and
- o, q, p1 and p2 are independently of each other an integer selected from 1, 2, 3, 4, 5, and 6, with the proviso that L is not $-C_3H_6-$ if -E is $-NH_2$.

An especially preferred intermediate is an intermediate of formula (O1b), (O1c), (O1d), (O2a), (O2b), (O3a), (O3b), (O3c), (O4a), (O4b), (O5a), (O5b), and (O5c), wherein -L- represents $-(CH_2)_o-$ and o is an integer selected from 4, 5 and 6.

$P_2$, $P_2'$, $P_3'$, $P_4$, $P_4'$, $P_5$, $P_5'$, $P_7$, $P_8$, $P_9$, $P_{10}$, $P_{11}$, $P_{12}$, $P_{13}$, and $P_{14}$ are suitable protecting groups for hydroxyl groups, more preferably different suitable protecting groups for hydroxyl groups capable of being removed subsequently one after another by a suitable sequence of deprotection reactions. Preferred protecting groups for hydroxyl groups are acetyl, phenyl, benzyl, isopropylidene, benzylidene, naphthylidene, benzoyl, p-methoxybenzyl, p-bromobenzyl, p-methoxybenzylidene, p-methoxyphenyl, p-bromobenzylidene, p-nitrophenyl, allyl, trichloroacetyl, (2-nitrophenyl)acetyl, isopropyl, p-bromobenzyl, dimethoxytrityl, trityl, 2-naphthylmethyl, pivaloyl, chloroacetyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, 9-fluorenylmethoxycarbonyl, benzyloxymethyl, methyloxymethyl, tert-butyloxymethyl, methoxyethyloxymethyl and levulinoyl.

$P_N$ represents protecting group used for protection amine group, more preferably 2,2,2-Trichloroethyl carbonyl (Troc) or Fluorenylmethyloxycarbonyl (Fmoc).

Thus, intermediates (O1b), (O1c), (O1d), (O2a), (O2b), (O3a), (O3b), (O3c), (O4a), (O4b), (O5a), (O5b) and (O5c), are especially preferred: protecting groups $P_1$ and $P_6$ represent phenyl, protecting groups $P_3$ and $P_3'$ represent 2-naphthylmethyl, protecting groups $P_2$, $P_4$, $P_4'$, $P_5'$, $P_{11}$, $P_{12}$ and $P_{14}$ represent benzyl, p-methoxybenzyl, protecting groups $P_2'$, $P_5$, $P_7$, $P_7'$, $P_8$, $P_8'$, $P_9$, $P_{10}$, $P_{10}'$ and $P_{13}$ are benzoyl, $P_9'$ is benzoyl or levulinoyl and protecting group $P_6$ represents butyldimethylsilyl. $P_N$ is 2,2,2-Trichloroethyl carbonyl (Troc). Optionally, $OP_4$ and $OP_5$, $OP_4'$ and $OP_5'$ form a phenyl hemiacetal.

A further aspect of the present invention refers to a compound of formula (I-1)-(I-5):

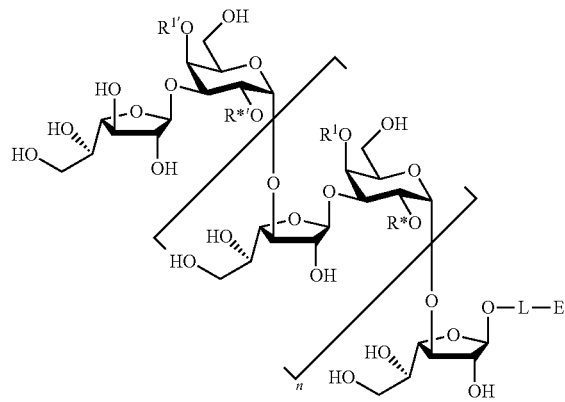

(I-1)

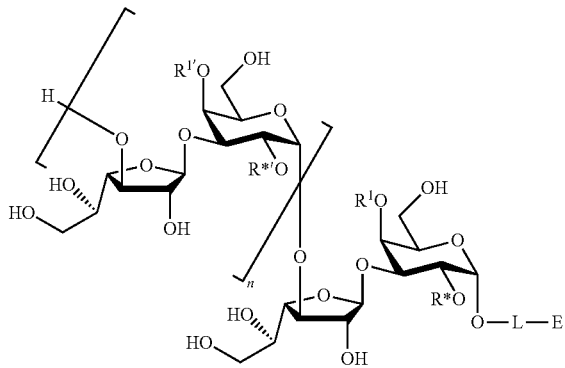

(I-2)

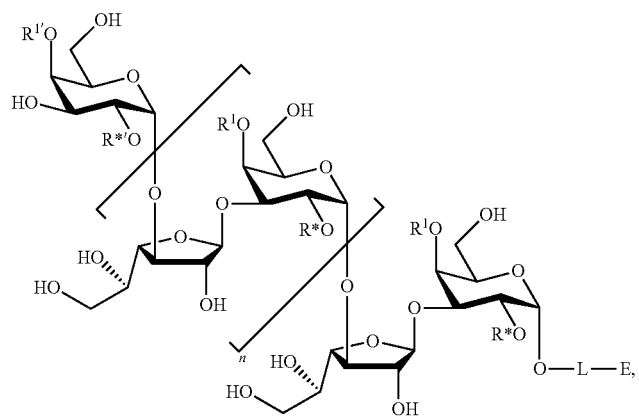

(I-3)

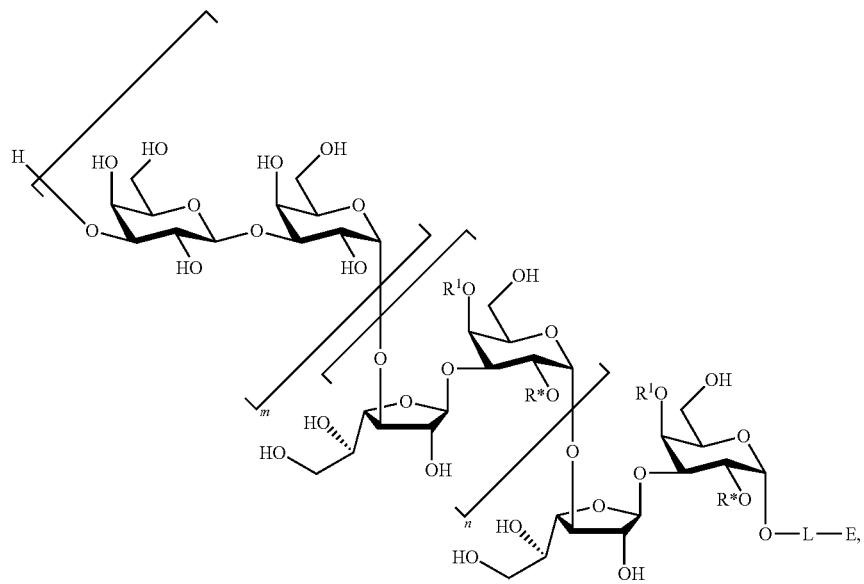

(I-4)

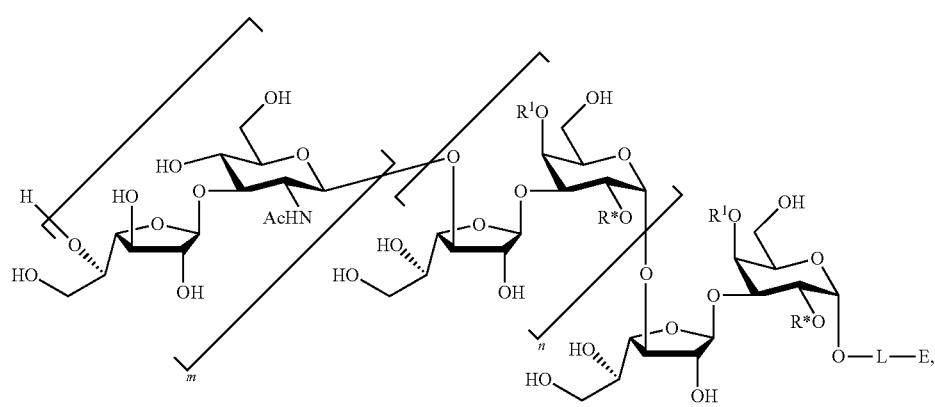

(I-5)

wherein m, n, L, E, R¹, R*, R¹' and R*' have the meanings as defined herein.

Glycoconjugates

Another aspect of the present invention refers to a conjugate comprising a saccharide according to the present invention. Surprisingly, said conjugate proved to be efficient as a vaccine for immunization against diseases associated with *Klebsiella pneumoniae* bacteria.

Preferred, the *Klebsiella pneumoniae* bacteria is selected from O-serotypes comprising or consisting of O1, O2, O2ac, O3, O4, O5, O7, O8, O12 and subtypes thereof and carbapenem resistant *Klebsiella pneumoniae* (CRKP). Preferred, O-serotypes O1, O2a, O2ac, O2ae, O2aeh, O2afg, O8, and CRKP strain ST 258, more preferred O1, O2a, O2ab, O2ac, O2afg (Galactan-III), O8, CRKP strain ST 258. Still more preferred, *Klebsiella pneumoniae* strains serotypes are O1:K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70, O2a, O2ac, and CRKP strain ST 258.

Saccharides are known by the person skilled in the art as generally TI-2 (T cell independent-2) antigens and poor immunogens, if they are not immunogenic. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, saccharides are known poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, the saccharides of general formulae (I), (I-1)-(I-5), and (II-1)-(II-17), preferred saccharides A-01-A-140, B-01-B-140, C-01-C-70, D-01-D-70, E-01-E-70, F-01-F-530, G-01-G-350, H-01-H-350, J-01-J-350, K-01-K-350, M-01-M-70, N-01-N-70, O-01-O-70, P-01-P-70 and Q-1-Q-700 are conjugated to an immunogenic carrier to provide conjugates, which present increased immunogenicity in comparison with the saccharide. Hence, under the scope of the present application is covered also a conjugate of general formula (III)

(III)

$$[H{\text{+}}U_5{-}U_4\overline{)_m}{\text{+}}U_3\overline{)_k}{\text{+}}U_2{-}U_1\overline{)_n}{\text{+}}U_2\overline{)_x}{\text{+}}U_1\overline{)_y}{-}O{-}L{-}E_1{-}T]_i{-}(CP)$$

wherein
i is an integer selected from 2 to 25; preferably 2 to 18
-$E_1$- represents a covalent bond, —NH—, —O—NH—, —O—, —S—, —CO—, —CH=CH—, —CONH—, —CO—NHNH—,

[triazole/pyrazole ring structures], or

[triazole ring structure];

-T- represents

[diketone/diester structures], or

[PEG-linked diester structure];

a represents an integer from 1 to 10;
b represents an integer from 1 to 4;
CP is a carrier protein; and
$U_1$, $U_2$, $U_3$, $U_4$, $U_5$ L, m, n, k, x, and y have the same meanings as defined herein.

Preferably $E_1$ is a covalent bond, —NH—, —CH=CH—, —CONH—,

[triazole structures], or [pyrazole structure].

Said conjugate consists of at least one synthetic saccharide of the general formula (I) and an immunogenic carrier, preferred carrier proteins, to which the at least one saccharide (I) is covalently bound.

Surprisingly, it was found that immunization with a conjugate comprising a saccharide of general formula (I) covalently linked to an immunogenic carrier, preferred carrier proteins, results in the production of high titers of antibodies specific to the carbohydrate part of the saccharide of general formula (I) Said antibodies are cross-reacting with the *Klebsiella pneumoniae* serotype O1, O2, O2ac, O8 O-polysaccharide as well as carbapenem-resistant *Klebsiella pneumoniae* ST258 O-polysaccharide and present opsonophagocytosis and bactericidal activity, thus conferring protection against *Klebsiella pneumoniae*.

Preferred, the *Klebsiella pneumoniae* bacteria is selected from O-serotypes comprising or consisting of O1, O2, O2ac, O3, O4, O5, O7, O8, O12 and subtypes thereof and carbapenem resistant *Klebsiella pneumoniae* (CRKP). Preferred, O-serotypes O1, O2a, O2ac, O2ae, O2aeh, O2afg (Galactan-III), O8, and CRKP strain ST 258, more preferred O1, O2a, O2ab, O2ac, O2afg, O8, CRKP strain ST 258. Still more preferred, *Klebsiella pneumoniae* strains serotypes are O1:K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70, O2a, O2ac, and CRKP strain ST 258.

Vaccines containing at least one conjugate of the present invention cause fewer side effects and/or non-protective immune responses in comparison to vaccines containing isolated (and not synthesized) mixtures of saccharides obtained by non-selective cleavage of the capsular polysaccharide of *Klebsiella pneumoniae* or conjugates thereof. Moreover, the inventive vaccines can be easier manufactured in accordance with the GMP regulations than the vaccines containing isolated mixtures of non-selectively cleaved capsular polysaccharides and are easier characterized, which makes stability and purity control easier as well as detection of kind and amount of impurities.

In this context the term "immunogenic carrier" is defined as a structure, which is conjugated to the saccharide to form a conjugate that presents an increased immunity in comparison with the saccharide per se. Thus, the conjugate (III) is obtained by conjugation of the saccharides of the general formulae (I), (I-1)-(I-5), (II-1)-(II-17), preferred the saccharides A-01-A-140, B-01-B-140, C-01-C-70, D-01-D-70, E-01-E-70, F-01-F-530, G-01-G-350, H-01-H-350, J-01-J-350, K-01-K-350, M-01-M-70, N-01-N-70 and O-01-O-70, P-01-P-70 and Q-1-Q-700 to the immunogenic carrier has as effect the stimulation of the immune response against the saccharide of general formula (I) without inducing an immune response against said immunogenic carrier.

Most preferred, the conjugate (III) is obtained by conjugation of the saccharides selected from the group consisting of: compounds A-01-A-O7, A-11-A17, A-21-A-27, A-31-A-37, A-41-A-47, A-51-A-57, A-61-A-67, A-71-A-77, A-81-A-87, A-91-A-97, A-101-A-107, A-111-A-117, A-121-A-127, A-131-A-137, F-01, F-19, F-27, F-31, F-36, F-54, F-62, F-66, F-71, F-89, F-97, F-101, F-106, F-124, F-132, F-136, F-141, F-159, F-167, F-171, F-176, F-194, F-202, F-206, F-211, F-229, F-237, F-241, F-246, F-264, F-299, F-281, F-272, F-276, F-307, F-311, F-316, F-334, F-342, F-346, F-351, F-414, F-417, F-421, F-426, F-444, F-452, F-456, F-461, F-479, F-487, F-491, F-496, F-514, F-522, F-526, K-O1, K-O6, K-11, K-26, K-31, K-36, K-51, K-56, K-61, K-76, K-81, K-86, K-101, K-106, K-111, K-126, K-131, K-136, K-151, K-156, K-161, K-176, K-181, K-186, K-201, K-206, K-211, K-226, K-231, K-236, K-251, K-256, K-261, K-276, K-281, K-286, K-301, K-306, K-311, K-326, K-331, K-336, O-01, O-02, O-03, O-06, O-07, O-08, O-11, O-12, O-13, O-16, O-17, 0-18, O-21, O-22, O-23, O-26, O-27, O-28, O-31, O-32, O-33, O-36, O-37, O-38, O-41, 0-42, O-43, O-46, O-47, O-48, O-51, O-52, O-53, O-56, O-57, O-58, O-61, O-62, O-63, 0-66, O-67, O-88, P-01-P-03, P-06-P-08, P-11-P-13, P-16-P-18, P-21-P-23, P-26-P-28, P-31-P-33, P-36-P-38, P-41-P-43, P-46-P-48, P-51-P-53, P-56-P-58, P-61-P-63, P-66-P-68, Q-1, Q-26, Q-101, Q-151, Q-251, Q-301, Q-351, Q-376, Q-451, Q-501, Q-551, Q-601 and Q-651. Include from 53

Preferred immunogenic carriers are carrier proteins (CP) or glycosphingolipids with immunomodulatory properties. For the person skilled in the art, a carrier protein (CP) is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, outer membrane protein (OMP), bovine serum albumin (BSA), keyhole limpet hemocyanine (KLH), recombinant non-toxic form of *Pseudomonas aeruginosa* (rEPA) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue.

Activated esters include N-(γ-maleimidobutyryloxy)sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarate (DSG), disuccinimidyl adipate (DSA), 2-pyridyldithiol-tetraoxatetradecane-N-hydroxysuccinimide (PEG-4-SPDP), bis-(4-nitrophenyl) adipate and bis-(4-nitrophenyl) succinate (see FIG. 3). Preferred activated esters are disuccinimidyl adipate (DSA), disuccinimidyl glutarate (DSG), bis-(4-nitrophenyl) adipate and bis-(4-nitrophenyl) succinate.

The cysteine residue on the carrier protein can be converted to the corresponding dehydroalanine that can be further reacted with a suitable interconnecting molecule to provide modified carrier protein having on their surface the functional group X of the interconnecting molecule.

It is especially preferred that the saccharides of general formula (I) are conjugated to the non-toxic mutated diphtheria toxin $CRM_{197}$ as carrier protein (CP) presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is used as a carrier protein in a number of approved conjugate vaccines for diseases, such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal amino group of the linker of the compounds of general formula (I).

Said functional group X of the interconnecting molecules is selected of the group comprising or consisting of maleimide, α-iodoacetyl, α-bromoacetyl, N-hydroxysuccinimide ester (NHS), aldehyde, imidoester, carboxylic acid, alkyl sulfonate, sulfonyl chloride, epoxide, anhydride, carbonate.

Preferred is a conjugate of general formula (IV)

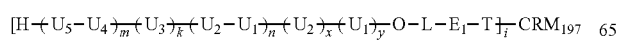

(IV)

wherein i is an integer selected from 2 to 25, preferably 2-18

-$E_1$- represents a covalent bond, —NH—, —O—NH—, —S—, —CO—, —CH═CH—, —CONH—, —CO—NHNH—,

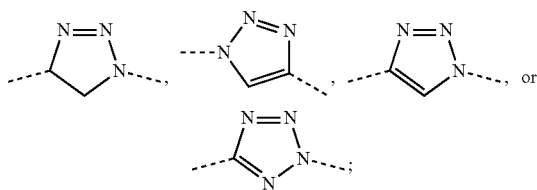

T- represents

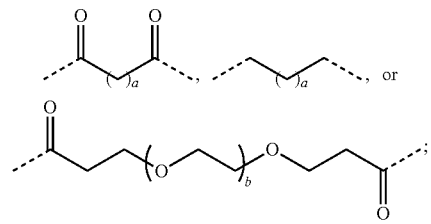

a represents an integer from 1 to 10;

b represents an integer from 1 to 4; and $U_1$, $U_2$, $U_3$, $U_4$, $U_5$, L, m, n, k, x, and y have the same meanings as defined herein such as in general formula (I).

Preferred is a conjugate of general formula (IV)

(IV)

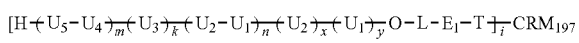

wherein i is an integer selected from 2 to 25, preferably 2-18;

-$E_1$- represents a covalent bond, —NH—, —O—NH—, —S—, —CO—, —CH═CH—, —CONH—, —CO—NHNH—,

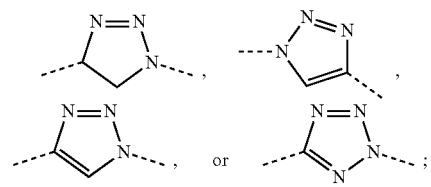

T- represents

-continued

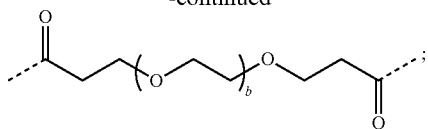

a represents an integer from 1 to 10;
b represents an integer from 1 to 4; and
when $U_2$—$U_1$ represents

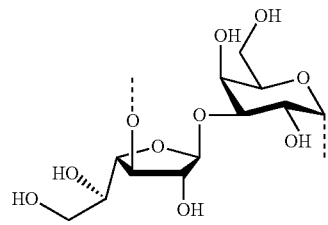

m cannot be 0 and
$U_5$—$U_4$ cannot be $U_2$—$U_1$;
$U_1$, $U_2$, $U_3$, $U_4$, $U_5$, L, m, n, k, x, and y have the same meanings as defined herein such as in general formula (I).
Check 115-129
Preferably $E_1$ is a covalent bond, —NH—, —CH═CH—, —CONH—

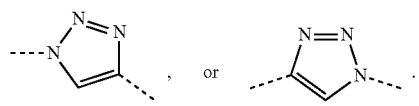

Preferred is the conjugate of the formula (IV) wherein
$U_1$ represents

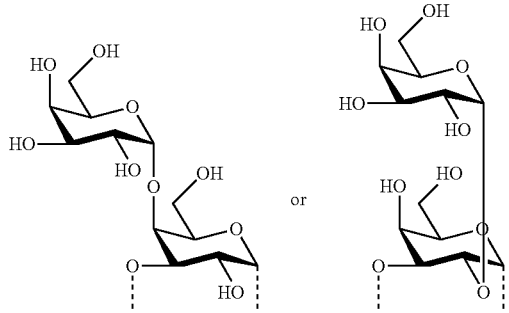

$U_2$ represents

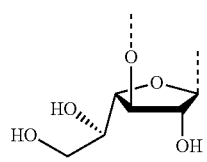

$U_5$ represents a covalent bond or

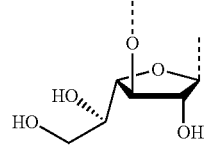

k is 0, L, $E_1$, i, m, n, x, and y have the same meanings as defined herein,
or anomers, hydrates, or pharmaceutically acceptable salt thereof.
Preferred is also the conjugate of the formula (IV) wherein
$U_1$ represents

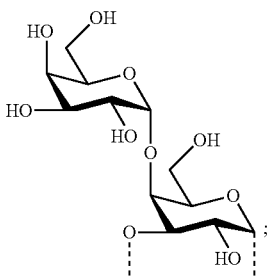

$U_2$ represents

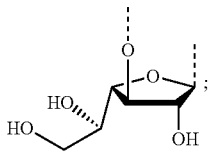

m is 0;
L, $E_1$, i, n, k, x, and y have the same meanings as defined herein.
Preferred, are synthetic saccharides of general formula (IV), wherein
$U_1$ represents

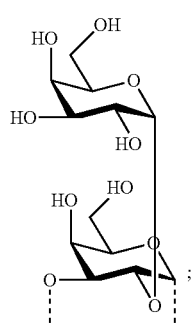

U₂ represents

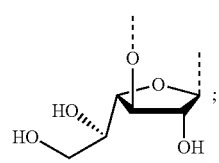

u₄ represents

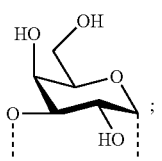

U5 represents a covalent bond, or

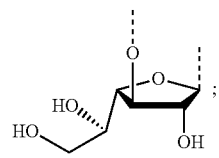

m is an integer selected from 0 and 1;
L, E₁, i, n, k, x, and y have the meanings as defined herein.
Preferred is the conjugate of the formula (IV) wherein U₁ represents G

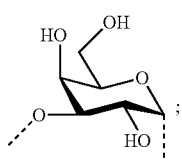

U₂ represents

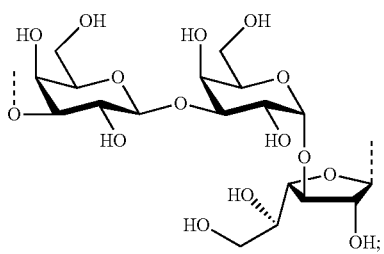

U₄ represents

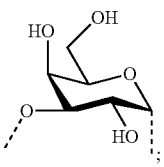

U₅ represents a covalent bond,

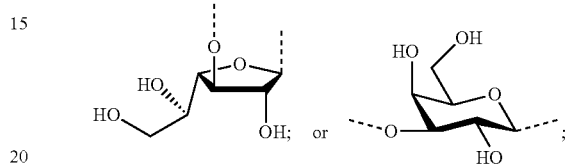

m is an integer from 0 or 1,
L, E₁, i, n, k, x, and y have the same meanings as defined herein.
Preferred is the conjugate of the formula (IV), wherein U₁ represents

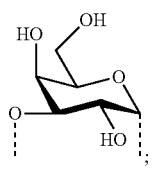

U₂ represents

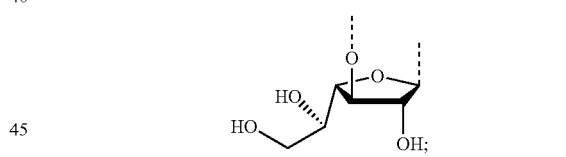

U₄ represents

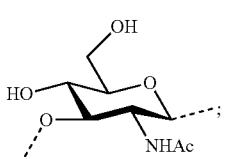

U₅ represents a covalent bond, or

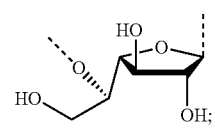

m is an integer from 1 to 10,

L, $E_1$, i, n, k, x, and y have the same meanings as defined herein.

Preferred is also the conjugate of the formula (V)

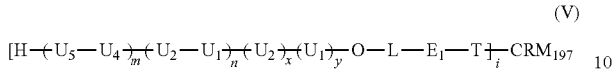

wherein $U_1$ represents

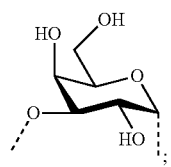

$U_2$ represents

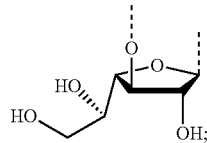

$U_4$ represents

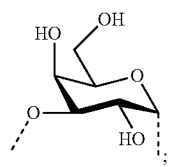

$U_5$ represents a covalent bond or

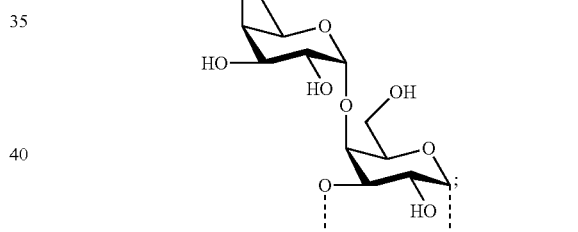

L, $E_1$, i, m, n, k, x, and y have the same meanings as defined herein.

Preferred is also the conjugate of the formula (V), wherein $U_1$ represents

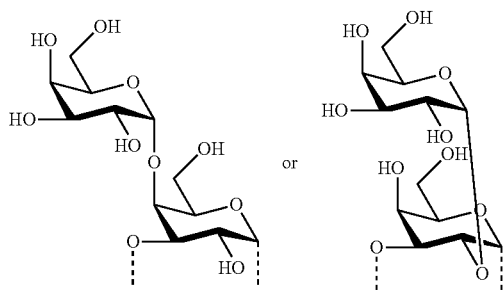

$U_2$ represents

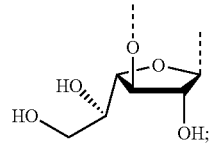

m is 0, L, $E_1$, i, n, k, x, and y have the same meanings as defined herein.

Preferred is also the conjugate of the formula (V), wherein $U_1$ represents

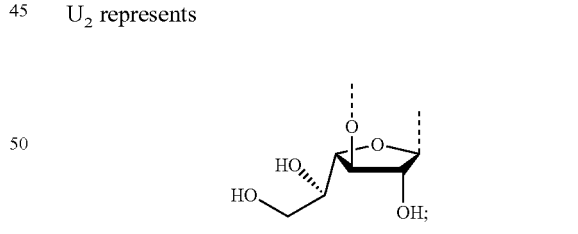

$U_2$ represents

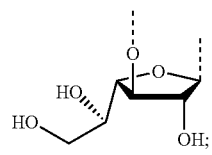

$U_4$ represents

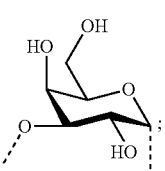

m is 0, L, $E_1$, i, n, k, x, and y have the same meanings as defined herein.

Preferred is also the conjugate of the formula (V), wherein U₁ represents

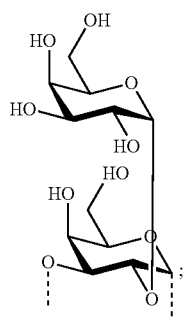

U₂ represents

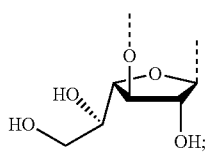

m is 0, L, E₁, i, n, k, x, and y have the same meanings as defined herein.

Preferred is also the conjugate of the formula (V). wherein U₁ represents

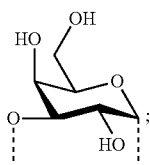

U₂ represents

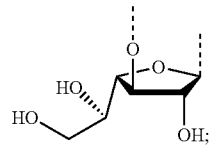

U₄ represents

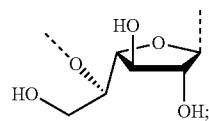

U₅ represents a covalent bond, or HO,

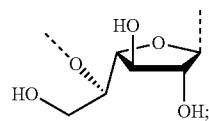

m is an integer from 1 to 10;

L, E₁, i, n, k, x, and y have the same meanings as defined herein.

More preferred is a conjugate of any one of the formulae (V-1)-(V-14):

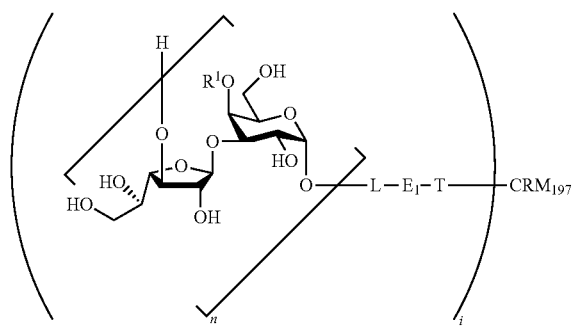

(V-1)

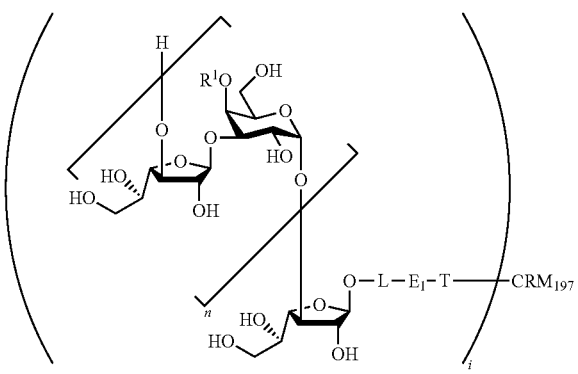

(V-2)

-continued
(V-3)
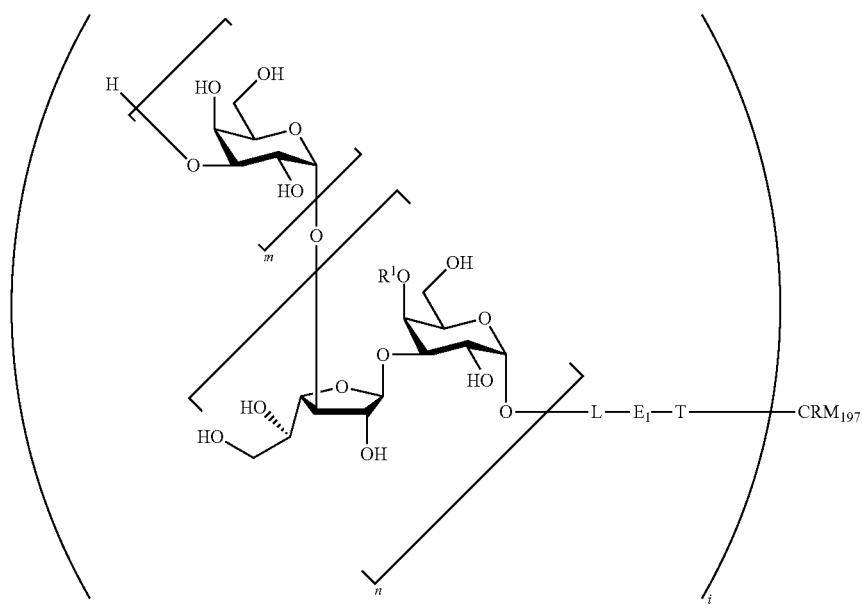
(V-4)
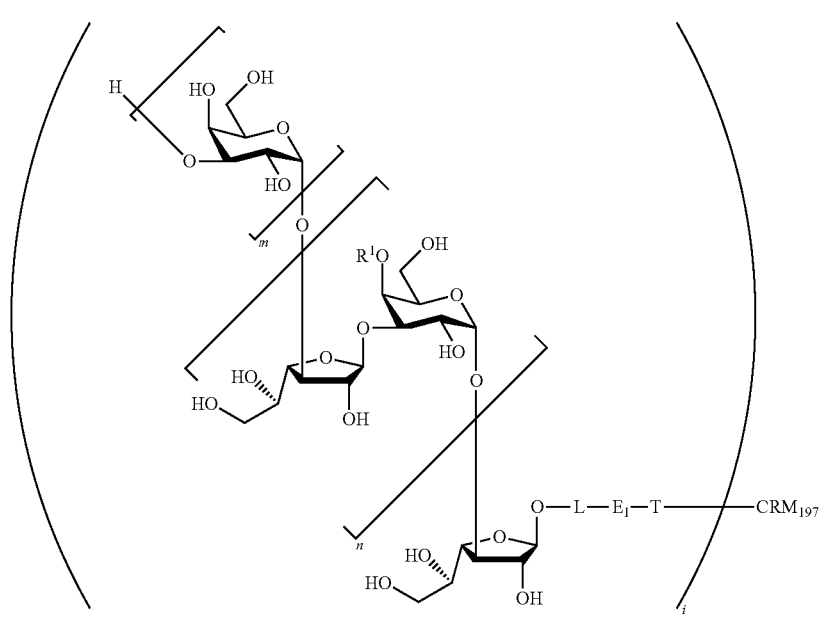

-continued
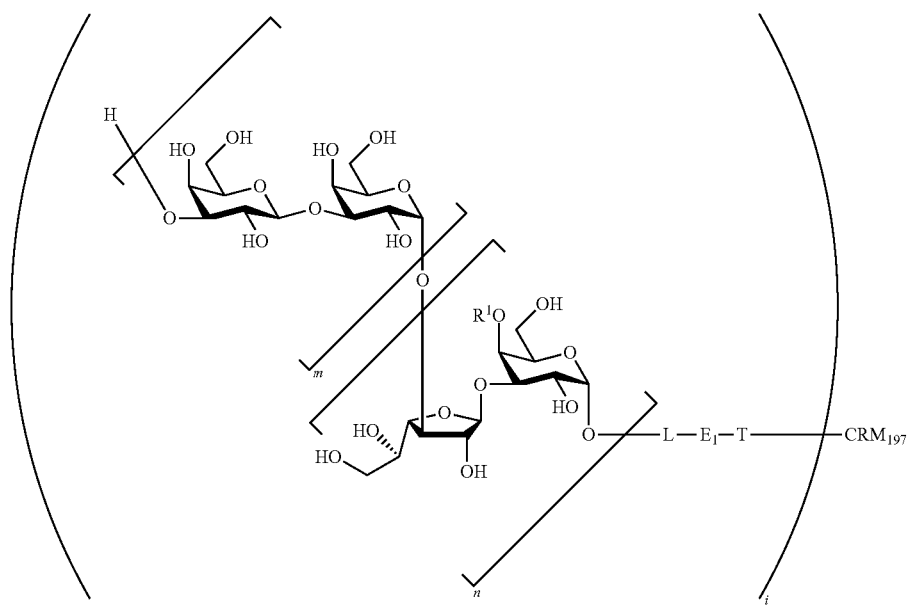
(V-5)
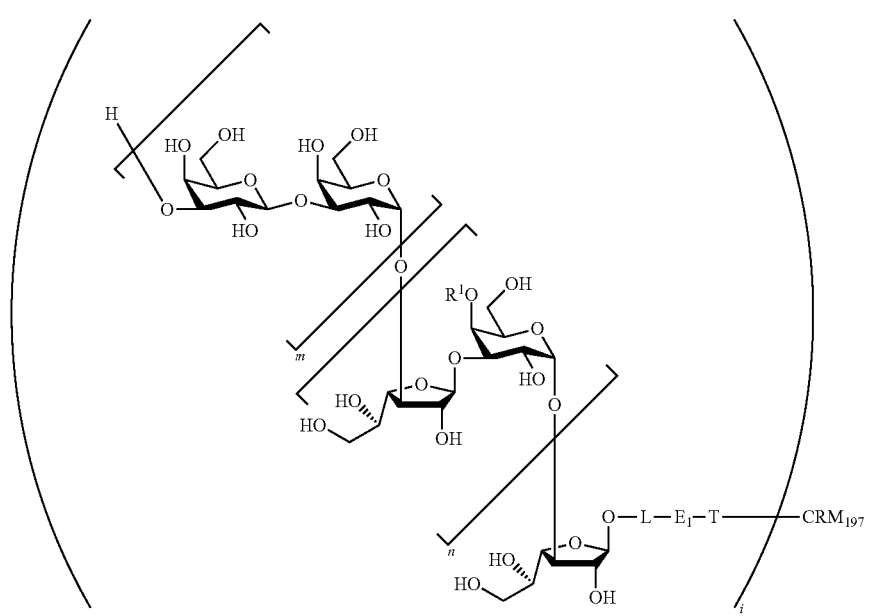
(V-6)

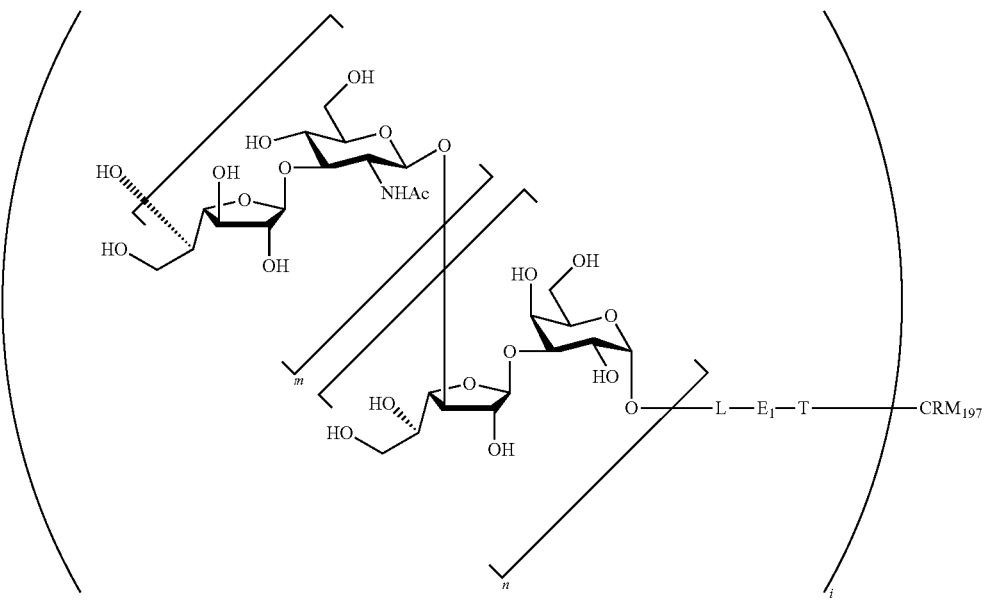
(V-7)
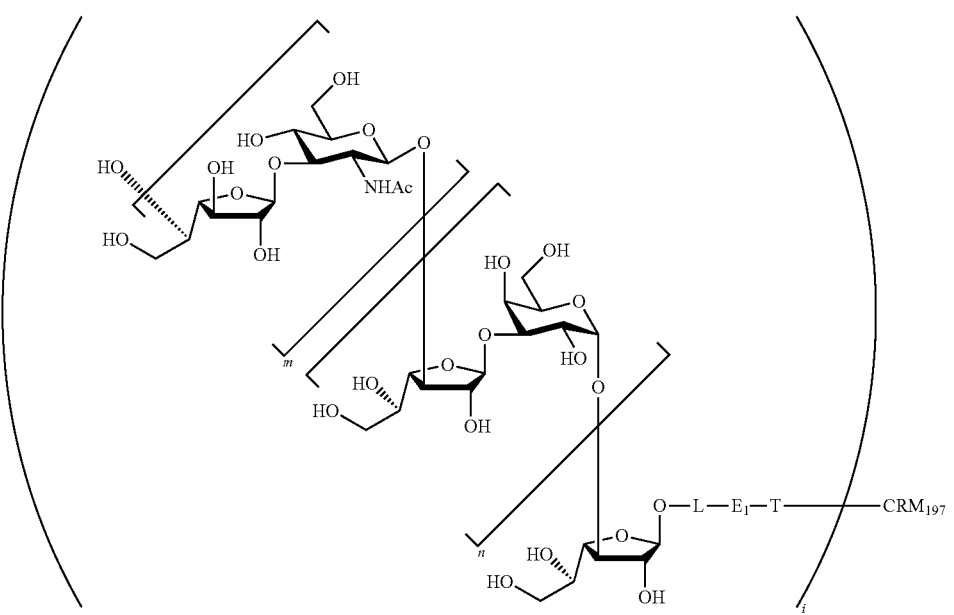
(V-8)
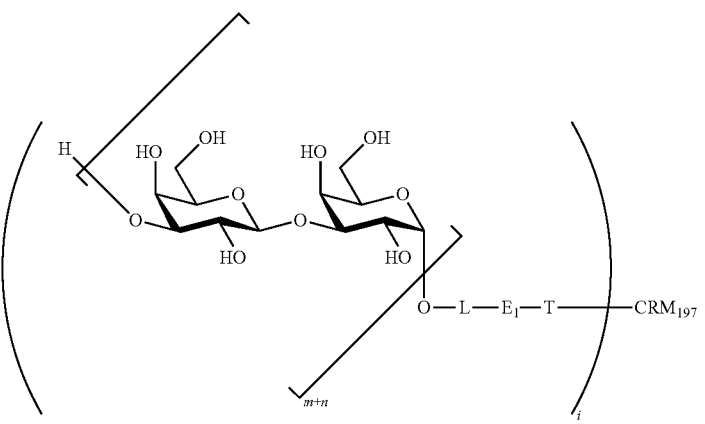
(V-9)

-continued
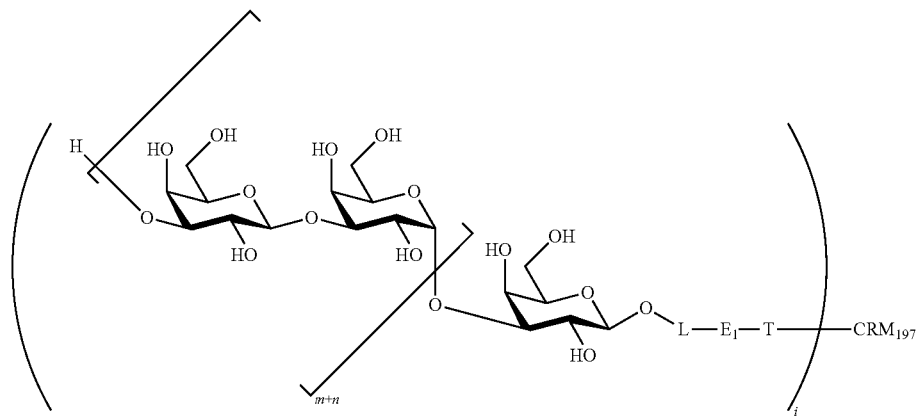
(V-10)
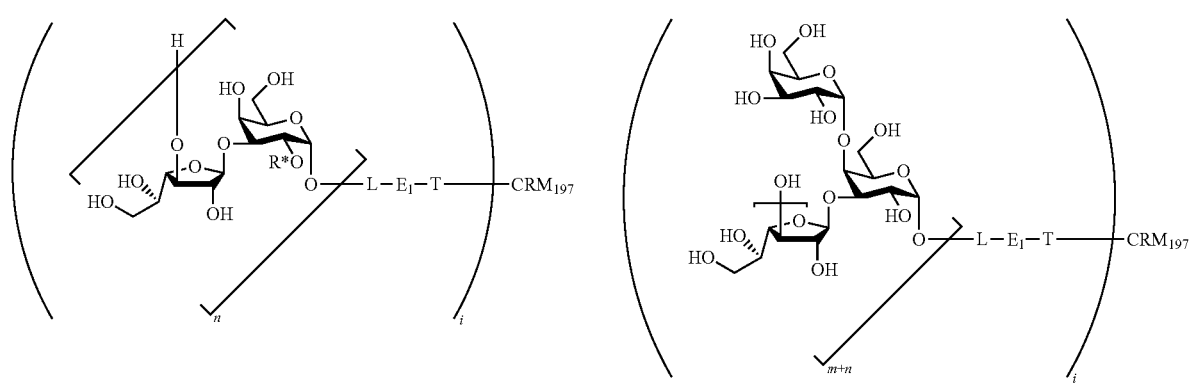
(V-11) (V-12)
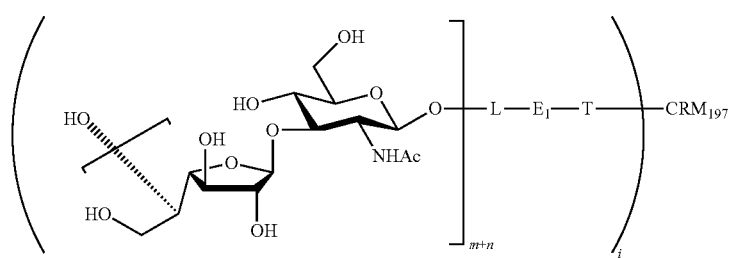
(V-13)

(V-14)

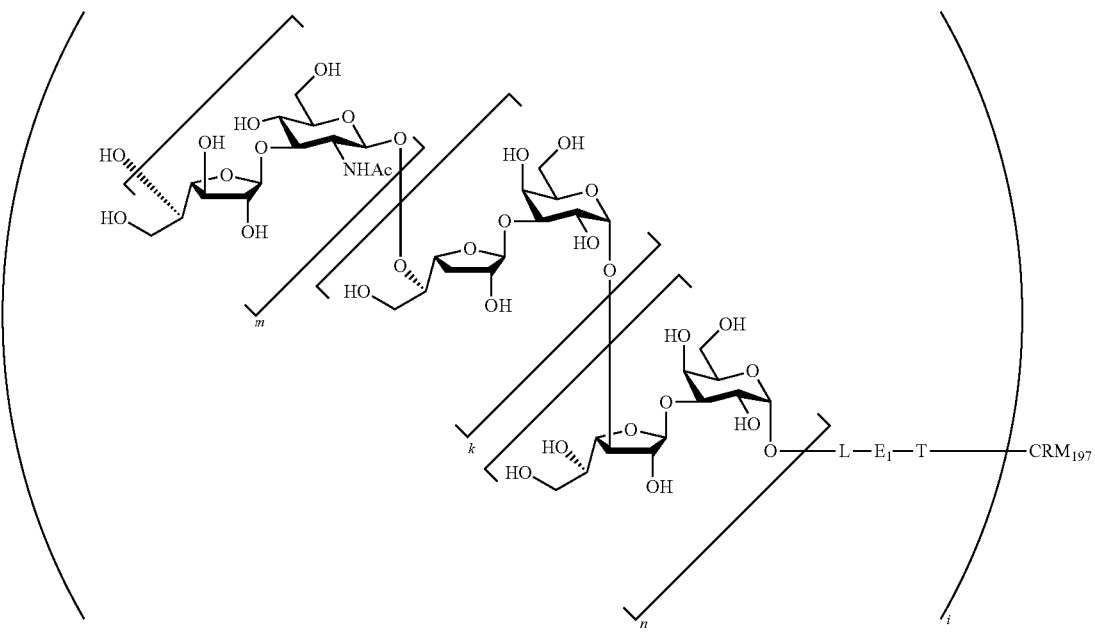

wherein
R¹ and R* represent independently —H, or

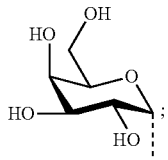

wherein R¹ and R* cannot be simultaneously

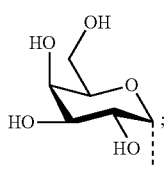

and
L, $E_1$, T, i, m, k, and n have the same meanings as defined above, preferably, n and m is an integer from 1 to 10.
More preferred the conjugate of any one of the formulae (III), (IV), (V) and (V-1)-(V-14), wherein n is an integer from 1 to 10.
More preferred the conjugate of any one of the formulae (III), (IV), (V) and (V-1)-(V-14), wherein i is selected from 4 to 10.
Preferably -T- represents

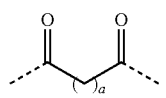

and a is an integer selected from 2, 3, 4, 5 and 6.

Thus, a conjugate of any one of general formulae (IV), (V) and (V-1)-(V-17), wherein -T- represents

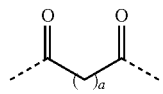

and a is an integer selected from 2, 3, 4, 5 and 6 is especially preferred.

Preferably, the linker -L- represents -$L^a$-, -$L^a$-$L^e$-, -$L^a$-$L^b$-$L^e$-, or -$L^a$-$L^d$-$L^e$-;
- -$L^a$- represents —(CH$_2$)$_o$—, —(CH$_2$—CH$_2$—O)$_o$—C$_2$H$_4$—, or —(CH$_2$—CH$_2$—O)$_o$—CH$_2$;
- -$L^b$- represents —O—, —NH—CO—NH—, —NH—CO—CH$_2$—NH—, —NH—CO—; -$L^d$- represents —(CH$_2$)$_q$—, —(CH(OH))$_q$, —(CF$_2$)$_q$—, —(CH$_2$—CH$_2$—O)$_q$G-C$_2$H$_4$—, or —(CH$_2$—CH$_2$—O)$_q$G-CH$_2$—;
- -$L^e$- represents —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and o, q, p1 and p2 are independently of each other an integer selected from 1, 2, 3, 4, 5, and 6

In the most preferred embodiment, $E_1$ is a covalent bond, —NH—, —CH═CH—, —CONH—,

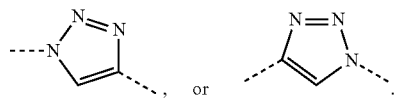

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glycosphingolipid with immunomodulatory properties, as used herein, refers to a suitable glycosphingolipid capable of stimulating the immune system's response to a target antigen, but which does not in itself confer immunity as defined above.

Glycosphingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or polysubstituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci. USA,* 1998, 95, 5690).

The conjugates of the saccharides of general formula I with a glycosphingolipid with immunomodulatory properties have the advantage of being heat stable. Additionally, they are able to produce in mice high titers of IgG1, IgG2a and IgG3 antibodies against the saccharide of general formula (I) and the O-polysaccharide of CRKP. To be suitable for conjugation, a functionality is introduced on the glycosphingolipid with immuno-modulatory properties. Said functionality is prone to react directly with the terminal amino group of the linker of the saccharides of general formula (I) to provide conjugates of the saccharides of general formula (I), or with the functional group Y of the interconnecting molecule to provide the modified glycosphingolipid with immunomodulatory properties.

Preferably, said functionality is introduced at the carbon 6 of the galactose moiety of the glycosphingolipid with immunomodulatory properties. Thus, the glycosphingolipid with immunomodulatory properties is functionalized with a functionality, which is prone of reacting with the terminal amino group of the saccharides or with the functional group Y of the interconnecting molecule. A functionality prone to react with an amino group includes, but it is not restricted to activated ester, isocyanate group, aldehyde, epoxide, imidoester, carboxylic acid, alkyl sulfonate and sulfonyl chloride. A functionality prone to react with the functional group Y of the interconnecting molecule so that to provide the modified glycosphingolipid with immunomodulatory properties presenting the functional group X of the interconnecting molecule includes, but it is not restricted to amine, alcohol, thiol, activated ester, isocyanate group, aldehyde, epoxide, vinyl, imidoester, carboxylic acid, alkyl sulfonate, sulfonyl chloride, vinyl group, alkynyl group and azido group.

Preferably, the functionality introduced at the $C_6$ of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS) and 2-pyridyldithiols.

Said functional group X of the interconnecting molecules is selected of the group comprising or consisting of: maleimide, α-iodoacetyl, α-bromoacetyl, N-hydroxysuccinimide ester (NHS), aldehyde, carboxylic acid, epoxyde, alkyl sulfonate, sulfonyl chloride, anhydride and carbonate.

As used herein, the term "interconnecting molecule" refers to a bifunctional molecule containing functional group X and functional group Y, wherein functional group X is capable of reacting with the terminal amino group on the linker -L- and the functional group Y is capable of reacting with a functionality present on the immunogenic carrier or on the solid support.

It was found that a conjugate comprising at least one saccharide of any one of general formulae (I), (I-A), (I-B), (I-1)-(I-5), (II-1)-(II-17), preferred any one of the saccharides A-01-A-140, B-01-B-140, C-01-C-70, D-01-D-70, E-01-E-70, F-01-F-530, G-01-G-350, H-01-H-350, J-01-J-350, K-01-K-350, M-01-M-70, N-01-N-70, O-01-O-70, P-01-P-70 and Q-1-Q-700. and particularly a conjugate of any one of general formulae (III), (IV), (V) and (V-1)-(V-14), elicits a protective immune response in a human and/or animal host, and therefore is useful for prevention and/or treatment of diseases associated with *Klebsiella pneumoniae* bacteria. Thus, the conjugates comprising the saccharides of general formula (I) conjugated to an immunogenic carrier are useful for prevention and/or treatment of diseases associated with *Klebsiella pneumoniae* bacteria. The diseases associated with *Klebsiella pneumoniae* bacteria include pneumonia, bronchitis, meningitis, urinary tract infection, nosocomial pneumonia, intra-abdominal infections, wound infection, infection of blood, osteomyelitis, bacteremia, septicemia and ankylosing spondylitis.

Preferred, the *Klebsiella pneumoniae* bacteria is selected from O-serotypes comprising or consisting of O1, O2, O2ac, O3, O4, O5, O7, O8, O12 and subtypes thereof and carbapenem resistant *Klebsiella pneumoniae* (CRKP). Preferred, O-serotypes O1, O2a, O2ac, O2ae, O2aeh, O2afg (Galactan-III), O8, and CRKP strain ST 258, more preferred O1, O2a, O2ab, O2ac, O2afg, O8, CRKP strain ST 258. Still more preferred, *Klebsiella pneumoniae* strains serotypes are O1:K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70, O2a, O2ac, and CRKP strain ST 258.

Pharmaceutical Compositions

Another aspect of the present invention is directed to a pharmaceutical composition or a vaccine comprising at least one conjugate that comprises at least one saccharide of general formula (I) conjugated to an immunogenic carrier and/or at least one saccharide of general formula (I) as an active ingredient together with at least one pharmaceutically acceptable adjuvant and/or excipient. Said pharmaceutical composition can be used for raising a protective immune response in a human and/or animal host. Ideally, the pharmaceutical composition is suitable for use in humans.

Particularly said pharmaceutical composition or said vaccine elicits a protective immune response in a human and/or animal host, and therefore is useful for prevention and/or treatment of diseases associated with *Klebsiella pneumoniae* bacteria. Thus, said pharmaceutical composition or said vaccine is useful for prevention and/or treatment of diseases associated with *Klebsiella pneumoniae* bacteria. The diseases associated with *Klebsiella pneumoniae* bacteria include pneumonia, bronchitis, meningitis, urinary tract infection, nosocomial pneumonia, intra-abdominal infections, wound infection, infection of blood, osteomyelitis, bacteremia, septicemia and ankylosing spondylitis.

Preferred, said pharmaceutical composition or said vaccine is useful for prevention and/or treatment of diseases associated with *Klebsiella pneumoniae* bacteria. wherein the Klebsiella pneumoniae bacteria is selected from O-serotypes comprising or consisting of O1, O2, O2ac, O3, O4, O5, O7, O8, O12 and subtypes thereof and carbapenem resistant Klebsiella pneumoniae (CRKP). Preferred, O-serotypes O1, O2a, O2ab, O2ac, O2ae, O2aeh, O2afg (Galactan-III), O8, and CRKP strain ST 258, more preferred O1, O2a, O2ab, O2ac, O2afg, O8, CRKP strain ST 258. Still more preferred, Klebsiella pneumoniae strains serotypes are O1:K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70, O2a, O2ac, and CRKP strain ST 258.

Preferred, the pharmaceutical composition or a vaccine comprises at least one saccharide of any one of general formulae (I-1)-(I-5), (II-1)-(II-17) and/or at least one of the conjugates comprising at least one saccharide of any one of general formulae (I-1)-(I-5), (II-1)-(II-17) as an active ingredient.

Particularly, the pharmaceutical composition or a vaccine comprises at least one conjugate of any one of general formulae (III), (IV), (V) and (V-1)-(V-14), More preferred, the pharmaceutical composition or a vaccine comprises at least one of the saccharides A-01-A-140, B-01-B-140, C-01-C-70, D-01-D-70, E-01-E-70, F-01-F-530, G-01-G-350, H-01-H-350, J-01-J-350, K-01-K-350, M-01-M-70, N-01-N-70, O-01-O-70, and P-01-P-70 and/or at least one of the conjugates comprising at least one of the saccharides A-01-A-140, B-01-B-140, C-01-C-70, D-01-D-70, E-01-E-70, F-01-F-530, G-01-G-350, H-01-H-350, J-01-J-350, K-01-K-350, M-01-M-70, N-01-N-70, O-01-O-70, P-01-P$_{70}$ and Q-1-Q-700.

More preferred, the pharmaceutical composition or a vaccine comprises at least one of the saccharides A-01-A-O7, A-11-A17, A-21-A-27, A-31-A-37, A-41-A-47, A-51-A-57, A-61-A-67, A-71-A-77, A-81-A-87, A-91-A-97, A-101-A-107, A-111-A-117, A-121-A-127, A-131-A-137, F-01, F-19, F-27, F-31, F-36, F-54, F-62, F-66, F-71, F-89, F-97, F-101, F-106, F-124, F-132, F-136, F-141, F-159, F-167, F-171, F-176, F-194, F-202, F-206, F-211, F-229, F-237, F-241, F-246, F-264, F-299, F-281, F-272, F-276, F-307, F-311, F-316, F-334, F-342, F-346, F-351, F-414, F-417, F-421, F-426, F-444, F-452, F-456, F-461, F-479, F-487, F-491, F-496, F-514, F-522, F-526, K-O1, K-O6, K-11, K-26, K-31, K-36, K-51, K-56, K-61, K-76, K-81, K-86, K-101, K-106, K-111, K-126, K-131, K-136, K-151, K-156, K-161, K-176, K-181, K-186, K-201, K-206, K-211, K-226, K-231, K-236, K-251, K-256, K-261, K-276, K-281, K-286, K-301, K-306, K-311, K-326, K-331, K-336, O-01, O-02, O-03, O-06, O-07, O-08, O-11, O-12, O-13, O-16, O-17, O-18, 0-21, O-22, O-23, O-26, O-27, O-28, O-31, O-32, O-33, O-36, O-37, O-38, O-41, O-42, 0-43, O-46, O-47, O-48, O-51, O-52, O-53, O-56, O-57, O-58, O-61, O-62, O-63, O-66, 0-67, O-88, P-01-P-03, P-06-P-08, P-11-P-13, P-16-P-18, P-21-P-23, P-26-P-28, P-31-P-33, P-36-P-38, P-41-P-43, P-46-P-48, P-51-P-53, P-56-P-58, P-61-P-63, P-66-P-68, Q-1, Q-26, Q-101, Q-151, Q-251, Q-301, Q-351, Q-376, Q-451, Q-501, Q-551, Q-601 and Q-651. and/or at least one of the conjugates comprising at least one of the saccharides A-01-A-O7, A-11-A17, A-21-A-27, A-31-A-37, A-41-A-47, A-51-A-57, A-61-A-67, A-71-A-77, A-81-A-87, A-91-A-97, A-101-A-107, A-111-A-117, A-121-A-127, A-131-A-137, F-01, F-19, F-27, F-31, F-36, F-54, F-62, F-66, F-71, F-89, F-97, F-101, F-106, F-124, F-132, F-136, F-141, F-159, F-167, F-171, F-176, F-194, F-202, F-206, F-211, F-229, F-237, F-241, F-246, F-264, F-299, F-281, F-272, F-276, F-307, F-311, F-316, F-334, F-342, F-346, F-351, F-414, F-417, F-421, F-426, F-444, F-452, F-456, F-461, F-479, F-487, F-491, F-496, F-514, F-522, F-526, K-O1, K-O6, K-11, K-26, K-31, K-36, K-51, K-56, K-61, K-76, K-81, K-86, K-101, K-106, K-111, K-126, K-131, K-136, K-151, K-156, K-161, K-176, K-181, K-186, K-201, K-206, K-211, K-226, K-231, K-236, K-251, K-256, K-261, K-276, K-281, K-286, K-301, K-306, K-311, K-326, K-331, K-336, O-01, O-02, O-03, O-06, O-07, O-08, O-11, O-12, O-13, O-16, O-17, O-18, 0-21, O-22, O-23, O-26, O-27, O-28, O-31, O-32, O-33, O-36, O-37, O-38, O-41, O-42, 0-43, O-46, O-47, O-48, O-51, O-52, O-53, O-56, O-57, O-58, O-61, O-62, O-63, O-66, 0-67, O-88, P-01-P-03, P-06-P-08, P-11-P-13, P-16-P-18, P-21-P-23, P-26-P-28, P-31-P-33, P-36-P-38, P-41-P-43, P-46-P-48, P-51-P-53, P-56-P-58, P-61-P-63, P-66-P-68, Q-1, Q-26, Q-101, Q-151, Q-251, Q-301, Q-351, Q-376, Q-451, Q-501, Q-551, Q-601 and Q-651.

Concentration of Oligosaccharide

In another aspect of the present invention, said pharmaceutical composition or vaccine further comprises at least one of capsular polysaccharides, O-polysaccharides and/or capsular polysaccharide fragments, O-polysaccharide fragments and/or protein conjugates thereof of Klebsiella pneumoniae bacteria selected from the group comprising or consisting of Klebsiella pneumoniae serotypes O1, O2, O2a, O2ac, O3, O4, O5, O7, O8, O12 and carbapenem-resistant Klebsiella pneumoniae ST258.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples of immunological adjuvants include, but are not restricted to oil emulsions (e.g. Freund's adjuvant), saponins, aluminum or calcium salts (e.g. alum), non-ionic block polymer surfactants, and many others.

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions may include a physiological salt, such as a sodium salt e.g. to control tonicity. Sodium chloride (NaCl) is typical and may be present at between 1 and 20 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg.

Pharmaceutical compositions may include compounds (with or without an insoluble metal salt) in plain water (e.g. w.f.i.), but will usually include one or more buffers. Typical buffers include: a phosphate buffer; a Tris buffer; a borate buffer; a succinate buffer; a histidine buffer (particularly with an aluminium hydroxide adjuvant); or a citrate buffer. Buffer salts will typically be included in the 5-20 mM range.

Pharmaceutical compositions typically have a pH between 5.0 and 9.5 e.g. between 6.0 and 8.0.

Pharmaceutical compositions are preferably sterile and gluten free.

Pharmaceutical compositions are suitable for administration to animal (and, in particular, human) patients, and thus include both human and veterinary uses. They may be used in a method of raising an immune response in a patient, comprising the step of administering the composition to the patient.

The pharmaceutical compositions of the present invention may be administered before a subject is exposed to a *Klebsiella pneumoniae* and/or after a subject is exposed to a *Klebsiella pneumoniae*.

Preferred, the *Klebsiella pneumoniae* bacteria is selected from O-serotypes comprising or consisting of O1, O2, O2ac, O3, O4, O5, O7, O8, O12 and subtypes thereof and carbapenem resistant *Klebsiella pneumoniae* (CRKP). Preferred, O-serotypes O1, O2a, O2ab, O2ac, O2ae, O2aeh, O2afg, O8, and CRKP strain ST 258, more preferred O1, O2a, O2ab, O2ac, O2afg, O8, CRKP strain ST 258. Still more preferred, *Klebsiella pneumoniae* strains serotypes are O1: K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70, O2a, O2ac, and CRKP strain ST 258.

In another aspect of the present invention, the present invention is directed to use of at least one conjugate that comprises at least one saccharide of general formula (I) conjugated to an immunogenic carrier and/or at least one saccharide of general formula (I) for the manufacture of said pharmaceutical composition or said vaccine for prevention and/or treatment of diseases associated with *Klebsiella pneumoniae* bacteria, particularly, diseases associated with *Klebsiella pneumoniae* bacteria is selected from the group comprising or consisting of pneumonia, bronchitis, meningitis, urinary tract infection, nosocomial pneumonia, intra-abdominal infections, wound infection, infection of blood, osteomyelitis, bacteremia, septicemia and ankylosing spondylitis.

Preferred, the *Klebsiella pneumoniae* bacteria is selected from O-serotypes comprising or consisting of O1, O2, O2ac, O3, O4, O5, O7, O8, O12 and subtypes thereof and carbapenem resistant *Klebsiella pneumoniae* (CRKP). Preferred, O-serotypes O1, O2a, O2ab, O2ac, O2ae, O2aeh, O2afg, O8, and CRKP strain ST 258, more preferred O1, O2a, O2ab, O2ac, O2afg, O8, CRKP strain ST 258. Still more preferred, *Klebsiella pneumoniae* strains serotypes are O1:K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70, O2a, O2ac, and CRKP strain ST 258.

Preferred, the present invention refers to the use of at least one saccharide of any one of general formulae (I-1)-(I-7), (II-1)-(II-17) and/or at least one of the conjugates comprising at least one saccharide of any one of general formulae (I-1) -(I-7), (II-1)-(II-17) for the manufacture of said pharmaceutical composition or said vaccine.

More preferred, the present invention refers to the use of at least one of the saccharides A-01-A-140, B-01-B-140, C-01-C-70, D-01-D-70, E-01-E-70, F-O1-F-530, G-01-G-350, H-01-H-350, J-01-J-350, K-01-K-350, M-01-M-70, N-01-N-70, O-01-O-70, P-01-P-70 and Q-1-Q-700 and/or at least one of the conjugates comprising at least one of the saccharides A-01-A-140, B-01-B-140, C-01-C-70, D-01-D-70, E-01-E-70, F-01-F-530, G-01-G-350, H-01-H-350, J-01-J-350, K-01-K-350, M-01-M-70, N-01-N-70, O-01-O-70 and P-01-P-70 and Q-1-Q-700 for the manufacture of said pharmaceutical composition or said vaccine.

Particularly, the present invention refers to the use of at least one conjugate of any one of general formulae (III), (IV), (V) and (V-1)-(V-14) for the manufacture of said pharmaceutical composition or said vaccine, Pharmaceutical compositions may be prepared in unit dose form. Preferably, the dose of the inventive conjugate is between 0.1 and 10 µg, preferably 1 and 10 µg, preferably 0.2 and 9 µg, more preferably 0.5 and 9 µg, preferably 1 and 6 µg, and most preferably 1 and 5 µg. In some embodiments a unit dose may have a volume of between 0.1-1.0 mL e.g. about 0.5 mL.

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. by an inhaler, using a fine powder or a spray. The composition may be prepared as a suppository. The composition may be prepared for nasal, aural or ocular administration e.g. as a spray or drops. Injectables for intramuscular administration are typical.

The pharmaceutical compositions may comprise an effective amount of an adjuvant i.e. an amount which, when administered to an individual, either in a single dose or as part of a series, is effective for enhancing the immune response to a co-administered *Klebsiella* pneumoniae antigen.

Preferred, the *Klebsiella pneumoniae* is selected from O-serotypes comprising or consisting of O1, O2, O2ac, O3, O4, O5, O7, O8, O12 and subtypes thereof and carbapenem resistant *Klebsiella pneumoniae* (CRKP). Preferred, O-serotypes O1, O2a, O2ab, O2ac, O2ae, O2aeh, O2afg, O8, and CRKP strain ST 258, more preferred O1, O2a, O2ab, O2ac, O2afg, O8, CRKP strain ST 258. Still more preferred, *Klebsiella pneumoniae* strains serotypes are O1:K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70, O2a, O2ac, and CRKP strain ST 258.

This amount can vary depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range that can be determined through routine trials.

Techniques for the formulation and administration of the vaccine of the present invention may be found in "Remington's Pharmaceutical Sciences" Mack Publishing Co., Easton PA A therapeutically effective dosage of one conjugate according to the present invention or of one saccharide of general formula (I) refers to that amount of the compound that results in an at least a partial immunization against a disease. Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgement of the prescribing physician.

Another aspect of the present invention is directed to a method of inducing immune response against Klebsiella pneumoniae in a human and/or animal host, said method comprising administering of the saccharide of general formula (I) and/or salt thereof and/or a conjugate thereof or pharmaceutical composition thereof to said human and/or animal host. A method of treating or preventing diseases caused by Klebsiella pneumoniae, in a human and/or animal host according to the present invention comprises administering of at least one saccharide of general formula (I) and/or salt thereof and/or a conjugate thereof or pharmaceutical composition thereof to said human and/or animal host. Preferred, the Klebsiella pneumoniae bacteria is selected from O-serotypes comprising or consisting of O1, O2, O2ac, O3, O4, O5, O7, O8, O12 and subtypes thereof and carbapenem resistant Klebsiella pneumoniae (CRKP). Preferred, O-serotypes O1, O2a, O2ab, O2ac, O2ae, O2aeh, O2afg, O8, and CRKP strain ST 258, more preferred O1, O2a, O2ab, O2ac, O2afg, O8, CRKP strain ST 258. Still more preferred, Klebsiella pneumoniae strains serotypes are O1:K1, O1:K2, O1:K7, O1:K8, O1:K10, O1:K12, O1:K16, O1:K19, O1:K21, O1:K22, 01:K27, O1:K34, O1:K42, O1:K45, O1:K55, O1:K57, O1:K62, O1:K65, O1:K66, O1:K69 and O1:K70, O2a, O2ac, and CRKP strain ST 258.

Immunological Assays

Yet another aspect of the present invention refers to saccharide of general formula (I) for use as marker in immunological assays for detection of antibodies against bacteria containing in their 0-polysaccharide or capsular polysaccharide one of the following saccharide fragments:

→3)-β-D-Galf-(1→3)-α-D-Galp-(1-

→3)-α-D-Galp-(1→3)-α-D-Galp-(1→

[→3)-β-D-Galp-(1→3)-α-D-Galp-(1→]$^m$-[→3)-β-D-Galf-(1→3)-α-D-Galp-(1→]$_n$

[→5)-β-D-Galf-(1→3)-β-D-GlcNAc-(1→]$_m$-[→3)-β-D-Galf-(1→3)-α-D-Galp-(1→]$_n$.

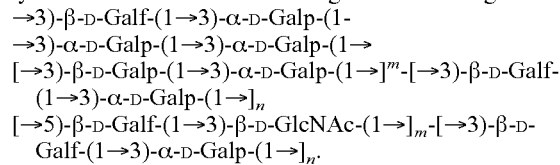

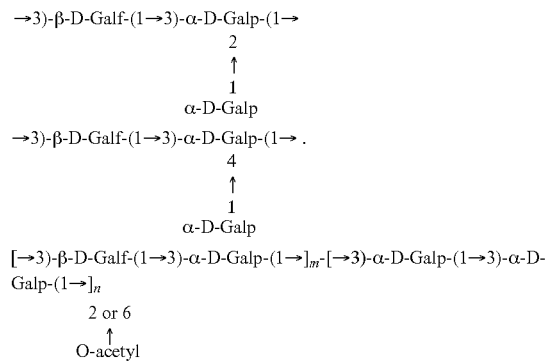

Preferred, the saccharide of general formula (I) is useful as marker in immunological assays for detection of antibodies against Klebsiella pneumoniae.

Such assays comprise, for instance, microarray and ELISA useful for detection of antibodies against Klebsiella pneumoniae.

The saccharides of the present invention can be easily conjugated to solid supports for providing immunological assays useful for detection of antibodies against Klebsiella pneumoniae.

Preferred, the Klebsiella pneumoniae bacteria is selected from O-serotypes comprising or consisting of O1, O2, O2ac, O3, O4, O5, O7, O8, O12 and subtypes thereof and carbapenem resistant Klebsiella pneumoniae (CRKP). Preferred, O-serotypes O1, O2a, O2ab, O2ac, O2ae, O2aeh, O2afg, O8, and CRKP strain ST 258, more preferred O1, O2a, O2ab, O2ac, O2afg, O8, CRKP strain ST 258. Still more preferred, Klebsiella pneumoniae strains serotypes are O1:K1, O1:K2, O1:K7, O1:K8, O1:K10, O1:K12, O1:K16, O1:K19, O1:K21, O1:K22, O1:K27, O1:K34, O1:K42, O1:K45, O1:K55, O1:K57, O1:K62, O1:K65, O1:K66, O1:K69 and O1:K70, O2a, O2ac, and CRKP strain ST 258.

Said solid supports present on their surface a functionality that is prone to react with the amino group of saccharides of general formula (I) or with the functional group Y of the interconnecting molecule to provide modified solid supports, presenting on their surface the functional group X of the interconnecting molecule that can further react with the amino group of saccharides of general formula (I). In an embodiment according to the present invention the solid supports are microarray slides, which present on their surface a functionality that is prone to react with the functional group Y of the interconnecting molecule to provide modified microarray slides, presenting of their surface the functional group X of the interconnecting molecule. Examples of such microarray slides include, but are not restricted to Corning® epoxide coated slides or Corning® GAPS™ II coated slides.

In a preferred embodiment the solid supports are microarray slides presenting on their surface a functionality that is prone to react with the amino group of saccharides of general formula (I), and more preferably an N-hydroxysuccinimide (NHS) activated ester. Such microarray slides are for example CodeLink® NHS slides.

DESCRIPTION OF THE FIGURES

FIG. 1 shows the chemical structure of the repeating unit of Klebsiella pneumoniae O-polysaccharide.

FIG. 2 shows the chemical structure of the repeating unit of Klebsiella pneumoniae O-polysaccharide FIG. 3 provides examples of functional group X of the interconnecting molecule according to the present invention.

FIG. 4B lists some examples of inventive saccharides conjugated to CRM$_{197}$ carrier protein.

FIG. 4C lists some examples of inventive saccharides conjugated to CRM$_{197}$ carrier protein.

FIG. 11 shows further linkers L' and the starting material used within the oligosaccharides of the present invention.

EXAMPLES

Figure 4A:
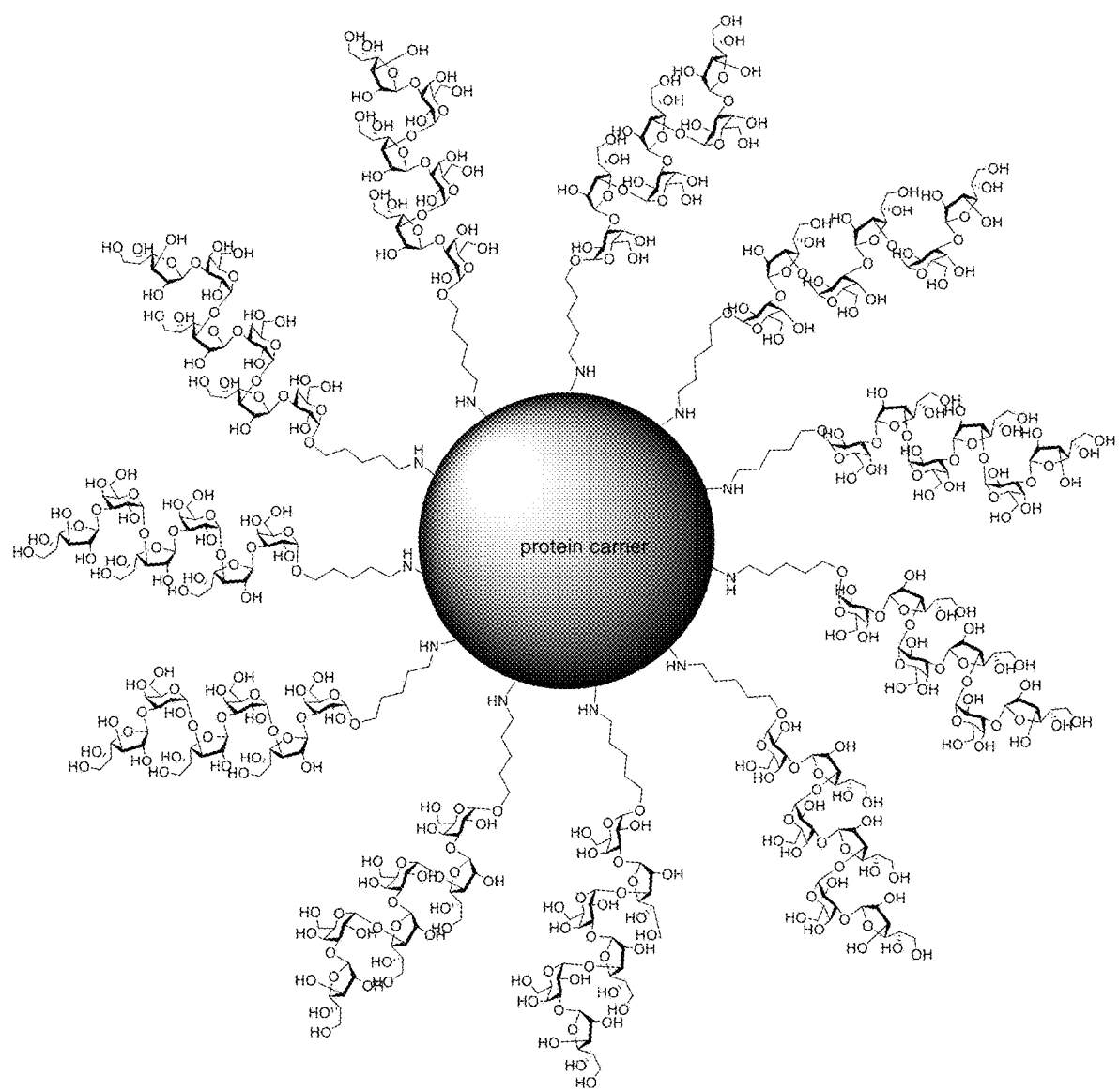
FIG. 4A presents schematically a conjugate of inventive oligosaccharides.
Figure 4D:
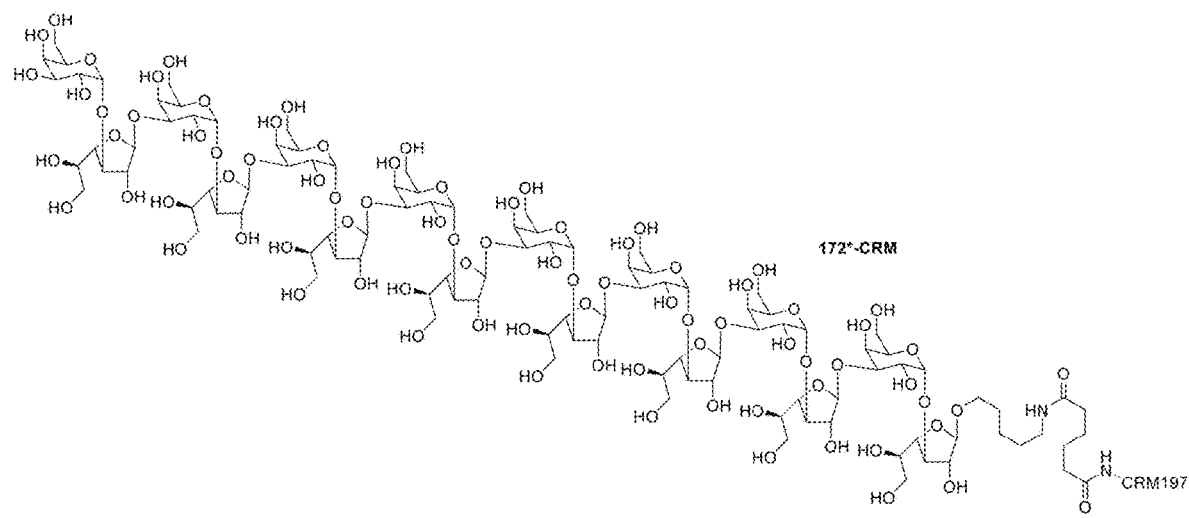
FIG. 4D lists an example of an inventive saccharide conjugated to CRM$_{197}$ carrier protein.

A. Chemical Synthesis
General Information:

Commercial grade solvents were used unless stated otherwise. Dry solvents were obtained from a Waters Dry Solvent System. Solvents for chromatography were distilled prior to use. Sensitive reactions were carried out in heat-dried glassware and under an argon atmosphere. Analytical thin layer chromatography (TLC) was performed on Kieselgel 60 F254 glass plates precoated with a 0.25 mm thickness of silica gel. Spots were visualized by staining with vanillin solution (6% (w/v) vanillin and 10% (v/v) sulfuric acid in 95% EtOH) or Hanessian's stain (5% (w/v) ammonium molybdate, 1% (w/v) cerium(II) sulfate and 10% (v/v) sulfuric acid in water). Silica column chromatography was performed on Fluka Kieselgel 60 (230-400 mesh).

$^1$H, $^{13}$C and two-dimensional NMR spectra were measured with a Varian 400-MR spectrometer at 296 K. Chemical shifts (d) are reported in parts per million (ppm) relative to the respective residual solvent peaks (CDCl$_3$: d 7.26 in $^1$H and 77.16 in $^{13}$C NMR; CD$_3$OD: d 3.31 in $^1$H and 49.15 in $^{13}$C NMR). The following abbreviations are used to indicate peak multiplicities: s singlet; d doublet; dd doublet of doublets; t triplet; dt doublet of triplets; q quartet; m multiplet. Coupling constants (J) are reported in Hertz (Hz).

Optical rotation (OR) measurements were carried out with a Schmidt & Haensch UniPol L1000 polarimeter at λ=589 nm and a concentration (c) expressed in g/100 mL in the solvent noted in parentheses. High resolution mass spectrometry (HRMS) was performed at the Free University Berlin, Mass Spectrometry Core Facility, with an Agilent 6210 ESI-TOF mass spectrometer. Infrared (IR) spectra were measured with a Perkin Elmer 100 FTIR spectrometer at applicant's facility.

Abbreviations

AcOH Acetic acid
Alloc Allyloxycarbonyl
aq. aqueous
BH$_3$ borane
BBr$_3$ boron tribromide
BnBr benzyl bromide
Boc tert-Butoxycarbonyl
br. broad
CAS CAS Registry Number (CAS=Chemical Abstracts Service)
CHCl$_3$ chloroform
cHex cyclohexane
d doublet
dd doublet of doublets
DCM dichloromethane
DEAD diethyl azodicarboxylate
DIPEA N,N-diisopropyl-ethylamine
DME dimethoxyethane
DMF dimethylformamide
DMSO dimethylsulfoxide
DPPA diphenylphosphoryl azide
EA Ethyl acetate
EDC.HCl N1-((ethylimino)methylene)-N3,N3-dimethyl-propane-1,3-diamine hydrochloride
ES electrospray
Et$_2$O diethyl ether
EtOAc ethyl acetate
h hour
HCl hydrochloric acid
H$_2$O water
HOBt.H$_2$O 1H-benzo[d][1,2,3]triazol-1-ol hydrate
K$_2$CO$_3$ potassium carbonate
LiAlH$_4$ lithium aluminium hydride
m multiplet
ACN acetonitrile
MeOH methanol
MeI methyl iodide
MgSO$_4$ magnesium sulphate
min minutes
MS mass spectrometry
Na$_2$CO$_3$ sodium carbonate
NaCNBH$_3$ sodium cyanoborohydride
NaHCO$_3$ sodium hydrogencarbonate
NaH sodium hydride
NaOH sodium hydroxide
Na$_2$SO$_4$ sodium sulphate
NCS N-chlorosuccinimide
NMR nuclear magnetic resonance
PBS phosphate-buffered saline
Pd/C palladium on carbon
q quartet
RM reaction mixture
RBF round bottom flask
rt room temperature
s singlet sat. saturated
sep septet
SM starting material
t triplet
TFA trifluoroacetic acid
THF tetrahydrofuran
TsOH tosic acid
Wt weight.

General Methods

Imidate Synthesis—General Protocol A: Substrate (1 eq) was dried azeotropically using toluene in the rotary evaporator and overnight under high vacuum. The solid was taken in DCM under nitrogen atmosphere, added $Cs_2CO_3$ (4 eq) to it and stirred for 10 min. Added (E)-2,2,2-trifluoro-N-phenylacetimidoyl chloride (3 eq) to the RM neat and stirred the RM at rt for 3 h. RM was filtered through the celite, washed with DCM. Combined filtrate was evaporated in vacuum to get the crude product. Purification was done on silica column treated with triethylamine and ethyl acetate/cyclohexane as eluents. Solvent removal and drying under vacuum yielded the compound as pale yellowish solid.

Imidate Synthesis—General Protocol B: Substrate (1 eq) was dried azeotropically using toluene in the rotary evaporator and overnight under high vacuum. The solid was taken in DCM under nitrogen atmosphere, added $Cs_2CO_3$ (4 eq) to it and stirred for 10 min. Added (E)-2,2,2-trifluoro-N-phenylacetimidoyl chloride (3 eq) to the RM neat and stirred the RM at rt for 3 h. RM was filtered through the celite, washed with DCM. Combined filtrate was evaporated and dried under vacuum yielding pale yellow product.

Glycosylation Method—General Protocol A: Both the Acceptor (1 eq) and the donor (1 eq-1.5 eq) were taken in RBF and dried azeotropically using dry toluene in the vacuum. Mixture was taken in Toluene-Dioxane (3:1) at rt, added 4 A molecular sieves to it and stirred at room temperature (rt) for 30 min under $N_2$ atmosphere. Cooled the RM to −2° C. using Ice water bath and added TMSOTf (0.2 eq) to the RM and stirred the RM at 5° C. for 20 mins. RM was then allowed to warm slowly to room temp over one hr. TLC analysis was carried out to monitor the completion of the reaction. RM was quenched with sat. $NaHCO_3$, stirred for 10 mins and extracted with EA. Combined organics were washed with water, brine, dried ($Na_2SO_4$), evaporated in vacuum to get crude product. Column purification on silica was done using EA/cyclohexane on Biotage using silica column. Fractions containing product were evaporated and dried under vacuum to get desired product.

Glycosylation Method—General Protocol B: Both the Acceptor (1 eq) and the donor (1 eq-1.5 eq) were taken in RBF and dried azeotropically using dry toluene in the vacuum. Mixture was taken in DCM at rt, added 4 A molecular sieves to it and stirred at rt for 30 min under $N_2$ atmosphere. Cooled the RM to −2° C. using Ice water bath and added TMSOTf (0.2 eq) to the RM and stirred the RM at 5° C. for 20 mins. RM was then allowed to warm slowly to room temp over one hr. TLC analysis was carried out to monitor the completion of the reaction. RM was quenched with sat. $NaHCO_3$ (or with TEA), stirred for 10 mins and extracted with DCM. Combined organics were washed with water, brine, dried ($Na_2SO_4$), evaporated in vacuum to get crude product. Column purification on silica was done using EA/cyclohexane on Biotage using silica column. Fractions containing product were evaporated and dried in vacuum to get desired product.

Lev Group Deprotection—General Protocol A: Lev-containing substrate (1 eq) was taken in Pyridine at rt, added hydrazine acetate (3 eq) to it and stirred at rt for 18 h. Reaction was monitored by TLC analysis. RM was then quenched with acetone (100 eq) and stirred for 45 mins at rt. The RM was then evaporated to dryness in vacuum. The residue was purified using Biotage on silica column with EA-Cyclohexane as eluents to get the sugar active spot, on evaporation and drying in the high vacuum the desired compound was obtained as colorless gummy liquid.

Nap Group Deprotection—General Protocol A: NAP-containing substrate (1 eq) was taken in DCM-buffer solution (1-2) at rt, added DDQ (3-4 eq) in portions over 20 mins-1 h, RM became black then it turned to reddish brown color. RM stirred for 2-5 h. Reaction was monitored by TLC analysis for reaction completion. RM was quenched with $NaHCO_3$ solution, and extracted with DCM. Combined organics were washed with brine solution, dried ($Na_2SO_4$), filtered, concentrated in vacuum to get crude product. Crude product was purified using Biotage on silica column-EA/Chx as eluents obtain the product.

TDS Group Deprotection—General Protocol A: Substrate (1 eq) was taken in pyridine in a 50 mL falcon tube, at rt and stirred for 5 mins. Then added HF-Py (15 eq) to it (careful: bubbles and exothermic). RM was stirred at rt for 18 h. TLC analysis showed that SM was present and a polar spot formed as well. So, added 10 equivalent of HF-Py one more time to RM and RM was stirred at rt for 30 h more and TLC analysis showed that still some SM was present and a major polar spot as well. RM was quenched with water, and diluted with DCM, mixed the layers well with stirring at rt, separated the layers. The aqueous layer was extracted with DCM. The combined organic layer was washed with $NaHCO_3$ wash (careful some effervescence), brine, dried ($Na_2SO_4$), filtered, evaporated in vacuum to get white gummy liquid. Crude product was purified using Biotage with silica column-EA/CHx as eluents to obtain the product.

TDS Group Deprotection—General Protocol B: Substrate (1 eq) was taken in pyridine in a 50 mL falcon tube, at rt and stirred for 5 mins. Then added HF-Py (50-150 eq) to it (careful: bubbles and exothermic). RM was stirred at rt for 18 h. Reaction was monitored by TLC analysis. RM was quenched with water, and diluted with DCM, mixed the layers well with stirring at rt, separated the layers. The aqueous layer was extracted with DCM. The combined organic layer was washed with $NaHCO_3$ wash (careful some effervescence), brine, dried ($Na_2SO_4$), filtered, evaporated in vacuum to get white gummy liquid. Crude product was purified using Biotage with silica column-EA/CHx as eluents to get the product out.

Methanolysis—General Protocol A: Substrate (1 eq) was taken in THF-MeOH (1:1 mL) at rt, added excess 0.5 M NaOMe solution in methanol to it and continued stirring at 55° C. for 18 h. RM was evaporated in vacuum. Diluted with EA and water. Acidified with AcOH till neutral pH. Extracted with EA. Combined organics were washed with brine solution, dried ($Na_2SO_4$), filtered, and evaporated in vacuum to get crude product as pale yellowish layer.

Methanolysis—General Protocol B: Substrate (1 eq) was taken in THF-MeOH (1:1 mL) at rt, added excess 0.5 M NaOMe solution in methanol to it and continued stirring at 55° C. for 3 days. RM was evaporated in vacuum. Diluted with EA and water. Acidified with AcOH till neutral pH. Extracted with EA. Combined organics were washed with brine solution, dried ($Na_2SO_4$), filtered, and evaporated in vacuum to get crude product as pale yellowish layer.

Hydrogenation—General Protocol A: Substrate (1 eq) was taken in mixture of $DCM:tBuOH:H_2O$, added suspension of Pd/C (1 eq, w/w) in butanol (0.2 mL) to it and hydrogenated under ~10 bar $H_2$ atmosphere for 18-24 h. RM was filtered through the PTFE filter, washed with methanol, 50% methanol in water. The filtrate was concentrated under vacuum to get crude product. The product was purified using C18 sepak column using water-acetonitrile as the eluents. Fractions containing product were lyophilized for 24 h to get white fluffy solid as the desired product.

Hydrogenation—General Protocol B: Substrate (1 eq) was taken in mixture of DCM:tBuOH:H$_2$O, added suspension of Pd(OH)$_2$ (1 eq, w/w) in butanol (0.2 mL) to it and hydrogenated under ~10 bar H$_2$ atmosphere for 18-24 h. RM was filtered through the PTFE filter, washed with methanol, 50% Methanol in water. The filtrate was concentrated under vacuum to get crude product. The product was purified using C$_{18}$ sepak column using water-acetonitrile as the eluents. Fractions containing product were lyophilized for 24 h to get white fluffy solid as the desired product.

Hydrogenation—General Protocol C: Substrate (1 eq) was taken in mixture of DCM:IPA:H$_2$O, added suspension of Pd/C (1 eq, w/w) in IPA to it and hydrogenated under ~10 bar H$_2$ atmosphere for 18-24 h. RM was filtered through the PTFE filter, washed with methanol, 50% Methanol in water. The filtrate was concentrated under vacuum to get crude product. The product was purified using C18 sepak column using water-acetonitrile as the eluents. Fractions containing product were lyophilized for 24 h to get white fluffy solid as the desired product.

A-1 Preparation of Monosaccharide Building Blocks

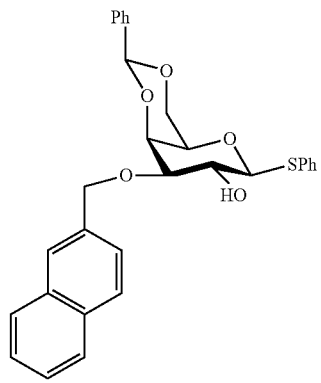

Compound 1*

Compound 1* was prepared according to a procedure described in J. Org. Chem., 2007, 72 (17), pp 6513-6520.

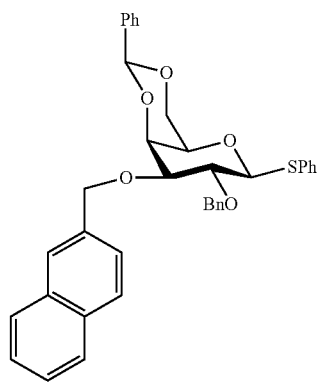

Compound 2*

Compound 1* (40 g, 80 mmol) was dissolved in anhydrous THF/DMF 9:1 (390 mL) and cooled to 0° C. with an ice/water bath. BnBr (20.9 g, 120 mmol) was added and the mixture was stirred for 5 minutes at 0° C. Then, NaH (6.39 g, 160 mmol) was added in 5 portions at 0° C. After complete addition of NaH the mixture was stirred at 0° C. for another five minutes, then the ice bath was removed and the mixture was allowed to warm to room temperature. It was stirred at room temperature overnight. The reaction was quenched by slow addition of methanol under cooling with an ice/water bath and then poured on EtOAc/brine. The layers were separated and the aqueous layer was extracted with EtOAc twice. The organic layer was dried over Na$_2$SO$_4$, filtered, evaporated and dried under high vacuum to give an orange solid. The solid was washed with methanol and filtrated. The solvent was evaporated to give the product as a white solid (47.1 g, 100%). HRMS (ESI+) Calcd for C$_{37}$H$_{34}$O$_5$SNa$^+$ [M+Na]$^+$ 613.2025, found 613.2024.

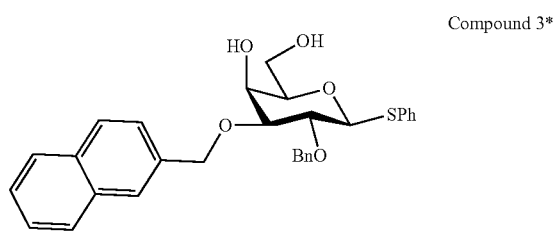

Compound 3*

Compound 2* (47.1 g, 80 mmol) was dissolved in anhydrous DCM (500 mL) and ethanethiol (35.4 mL, 478 mmol) and pTSOH (9.1 g, 47.8 mmol) were added sequentially. The mixture was stirred at room temperature for 0.5 h. The reaction was quenched with triethylamine (50 mL) and the solvent was evaporated to give crude product as a pale yellow oil. The crude was purified by column chromatography using ethyl acetate/cyclohexane to give the product after evaporation of the solvent (38.18 g, 95%). HRMS (ESI+) Calcd for C$_{30}$H$_{30}$O$_5$SNa$^+$ [M+Na]$^+$ 525.1712, found 525.1708.

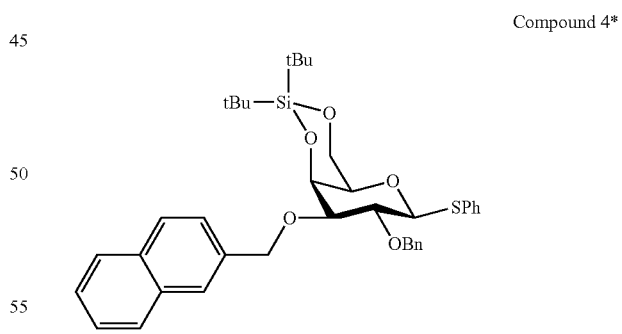

Compound 4*

Diol 3* (15 g, 29.8 mmol) was dissolved in anhydrous DMF (300 mL) and cooled to 0° C. with an ice/water bath. $^t$Bu$_2$Si(OTf)$_2$ (19.72 g, 44.8 mmol) was added and the reaction mixture was stirred at 0° C. for 30 minutes. The mixture was neutralized with Et$_3$N (9 mL) and stirred for 5 additional minutes. The mixture was then diluted with water and extracted three times with ethyl acetate. The combined organic fractions were washed with brine, dried over Na$_2$SO$_4$, filtered and concentrated in vacuum. The crude compound was charged on Isolute® and purified using the automated purification system with ethyl acetate/cyclohexane to give the product (18.18 g, 95%). HRMS (ESI+) Calcd for $C_{38}H_{46}O_5SSiNa^+$ [M+Na]$^+$ 665.2733, found 665.2682.

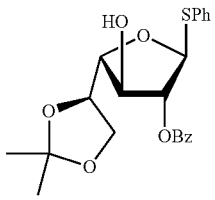

Compound 5*

Compound 5* was prepared according to a procedure described in J. Org. Chem. 2006, 71, 9658.

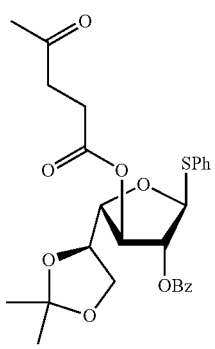

Compound 6*

Compound 5* (8.6 g, 20.65 mmol) was dissolved in anhydrous DCM (86 mL) and levulinic acid (3.6 g, 31 mmol), EDC (5.94 mmol, 31 mmol) and DMAP (2.5 g, 20.65 mmol) were added sequentially. The reaction mixture was stirred at room temperature for 2 h. The mixture was partitioned between DCM and brine. The aqueous layer was extracted with DCM twice. The organic layers were dried over $Na_2SO_4$, filtered and evaporated to give crude product. The crude was charged on isolute and purified using the automated purification system (ethyl acetate/cyclohexane) and the solvent evaporated to give the product as a colorless oil (12.26 g, 99%). HRMS (ESI+) Calcd for $C_{27}H_{30}O_8SNa^+$ [M+Na]$^+$ 537.1559, found 537.1544.

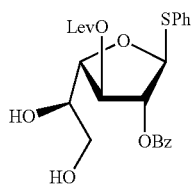

Compound 7*

Compound 6* (6.59 g, 12.81 mmol) was dissolved in THF/water 1:1 (250 mL) and pTsOH (2.92 g, 15.37 mmol) was added. The mixture was stirred under reflux (~80° C.) and monitored by TLC. After 1.5 h the mixture was cooled to room temperature and neutralised with sat. aq. NaHCO$_3$. The aqueous layer was extracted with EtOAc three times, the organic layer dried over Na$_2$SO$_4$, filtered and evaporated to give a colorless oil (5.76 g, 95%). HRMS (ESI+) Calcd for $C_{24}H_{26}O_8SNa^+$ [M+Na]$^+$ 497.1246, found 497.1230.

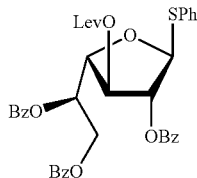

Compound 8*

Diol 7* (4.5 g, 9.48 mmol) was dissolved in anhydrous DCM (45 mL) and cooled to 0° C. with an ice/water bath. Pyridine (4.5 g, 56.9 mmol) and DMAP (0.116 g, 0.948 mmol) were added and then BzCl (8 g, 56.9 mmol) was added dropwise. The solution was stirred while it slowly was allowed to warm to room temperature. After stirring overnight, the reaction was quenched with sat. aq. NaHCO$_3$ solution and extracted with DCM twice. The organic layer was dried over Na$_2$SO$_4$, filtered and concentrated under reduced pressure to give crude product. The crude was charged on isolute and purified using the automated purification system using silica (ethyl acetate/cyclohexane) and the solvent evaporated to give the product as a white foam (5.78 g, 89%). HRMS (ESI+) Calcd for $C_{38}H_{34}O_{10}SNa^+$ [M+Na]$^+$ 705.1770, found 705.1744.

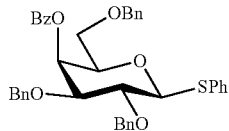

Compound 9*

Compound 9* was prepared according to a procedure described in Tetrahedron 2015, 71, 33, 5315-5320.

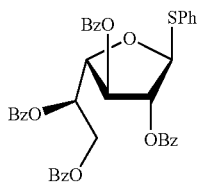

Compound 10*

Compound 10* was prepared according to a procedure described in J. Carb. Chem. 2001, 20, 9, 855-865.

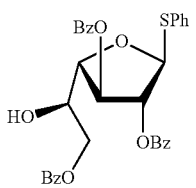

Compound 11*

Compound 11* was prepared according to a procedure described in J. Org. Chem. 2014, 79, 10203-10217.

Compound 12*

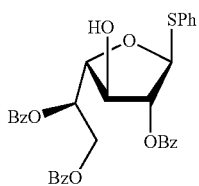

Compound 12* was prepared according to a procedure described in J. Org. Chem. 2014, 79, 10203-10217.

Compound 13*

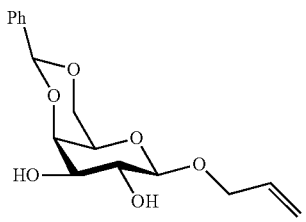

A solution of 1-O-allylgalactose (10 g, 45.4 mmol), benzaldehyde dimethyl acetal (10.37 g, 68.1 mmol) and camphor sulfonic acid (29.5 g, 127 mmol) in acetonitrile (100 mL) was stirred for 30 min at rt. After 30 min the TLC showed the completion conversion that starting materials to the product. The Reaction was quenched with triethylamine and was then concentrated to a thick syrup. Automated purification (Combiflash) using silica gel and dichloromethane/methanol as the eluent gave the product as a white solid (12 g, 86%). HRMS (ESI+) Calcd for $C_{16}H_{20}O_6Na^+$ [M+Na]$^+$ 331.1158, found 331.1098.

Compound 14*

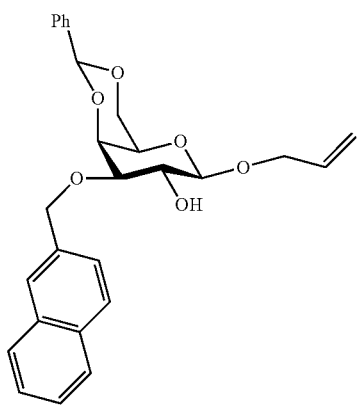

Bu$_2$SnO (14.53 g, 58.4 mmol) was added to a clear solution of diol 13* (12 g, 38.9 mmol) in toluene 423 mL at rt in a 250 mL RBF Then reaction mixture was kept for reflux at 130° C. for 6 h. After 6 h, solvents were removed under vacuum and the reaction was azeotroped with toluene (3×10 mL). After complete removal of solvents acetal was dried under vacuum for 0.5 h. Acetal was removed from vacuum in presence of argon and dissolved in DMF (423 mL). To this solution 2-(bromomethyl)naphthalene (12.91 g, 58.4 mmol) and TBAI (28.5 g, 78 mmol) were added and the reaction mixture was kept for stirring at 110° C. for 20 h. Reaction was monitored by TLC (40% EtOAc in n-hexane). After 20 h, reaction mixture was diluted with ethyl acetate and water. The aqueous layer was separated and washed with EtOAc (2×30 mL). The combined organic layers were dried over Na$_2$SO$_4$, filtered, and the filtrate was concentrated under vacuum at 35° C. bath temperature of rotary evaporator for 30 min to obtain the crude product. The crude product was purified on automated flash column chromatography using ethyl acetate in cyclohexane (gradient, 0 to 100%) as the eluent. Concentration of solvent from test tubes containing impure product in vacuum at 30-35° C. bath temperature in a 100 mL RBF resulted in the colourless oil. Additionally washing with ice cold ethyl acetate gave the pure product (14.49 g, 83%).

Compound 15*

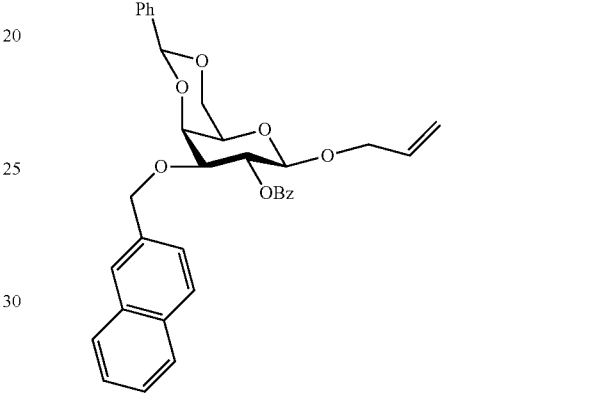

Compound 14* (14.30 g, 31.9 mmol) was dissolved in DCM (130 mL) and cooled to 0° C. with an ice/water bath. Pyridine (7.74 mL, 96 mmol) and DMAP (0.390 g, 3.19 mmol) were added and then BzCl (10.15 mL, 96 mmol) was added dropwise. The solution was stirred while it slowly was allowed to warm to room temperature. After stirring overnight, the reaction was quenched with sat. aq. NaHCO$_3$ solution and extracted with DCM twice. The organic layer was dried over Na$_2$SO$_4$, filtered and concentrated under reduced pressure to give crude product. The crude was charged on isolute and purified using the automated purification system using ethyl acetate/cyclohexane and the solvent evaporated to give the product as a white foam (10.1 g, 57%).

Compound 16*

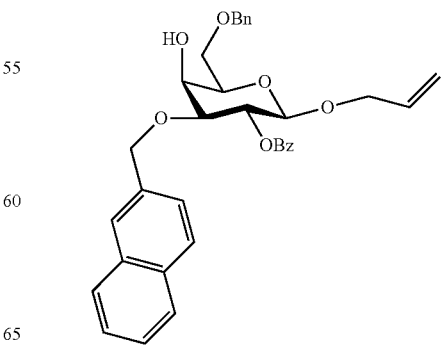

Compound 15* (8.7 g, 15.74 mmol) was dissolved in dichloromethane (102 mL). The solution was cooled to 0° C. and triethylsilane (17.78 mL, 110 mmol) and 2,2,2-trifluoroacetic acid (8.44 mL, 110 mmol) were added. The mixture was stirred at 0° C. for 10 minutes, and then at room temperature for overnight.. The reaction was quenched wit sat. aq. NaHCO$_3$ solution. The mixture was extracted with DCM and the organic layer washed with brine, dried over Na$_2$SO$_4$, filtered, concentrated to give the crude product. The crude was charged on isolute and purified using the automated purification system using ethyl acetate/cyclohexane and the solvent evaporated to give the product as a white foam (5.8 g, 66.4%). HRMS (ESI+) Calcd for C$_{34}$H$_{34}$O$_7$Na$^+$ [M+Na]$^+$ 577.2202, found 577.2078.

Compound 17*

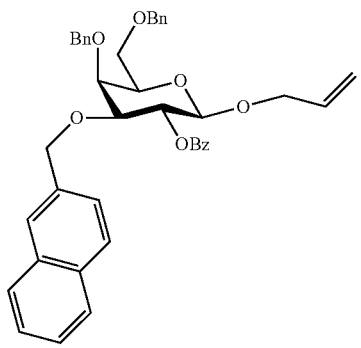

Compound 16* (5.8 g, 10.46 mmol) was dissolved in THF/DMF 9:1 (47 mL/5 mL) and cooled to 0° C. Benzyl bromide (2.54 mL, 20.91 mmol) was added and the mixture was stirred for 5 minutes at 0° C. Then sodium hydride (0.837 g, 20.91 mmol) was added in portions at 0° C. After complete addition of sodium hydride the mixture was stirred at 0° C. for another five minutes, and was allowed to warm to room temperature over 2 h. The reaction was quenched by slow addition of saturated ammonium chloride solution under cooling and then poured into ethyl acetate/water. The layers were separated and the aqueous layer was extracted with ethylacetate and the combined organic layer washed with NaHCO$_3$ and brine. The filtrate was dried over Na$_2$SO$_4$, filtered, evaporated and dried under high vacuum to obtain an orange solid. The solid was washed with methanol filtered and dried to obtain the product as a white solid (5.8 g, 86%). HRMS (ESI+) Calcd for C$_{41}$H$_{40}$O$_7$Na$^+$ [M+Na]$^+$ 667.2672, found 667.2567.

Compound 18*

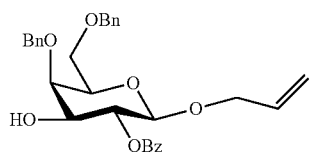

Monosaccharide compound 17* (0.995 g, 1.543 mmol) was transferred to a solution of DCM (34 mL) and phosphate buffer pH 7.4 (17 mL) in a 50 mL RBF DDQ (1.576 g, 6.94 mmol) was added slowly over a period of 2.5 h, and stirred for 6 h. The reaction was quenched by the addition of sat. aq. NaHCO$_3$ (40 mL) and extracted with DCM. The combined organic layer was washed with sat. NaHCO$_3$ (50 mL), brine (100 mL), dried over Na$_2$SO$_4$ filtered and concentrated under to obtain the crude as a pale yellow oil. Purification was done on silica gel column chromatography using ethyl acetate in cyclohexanes. The compound obtained was then dissolved in dichloromethane and continued evaporation under vacuum resulted in a colorless transparent gummy liquid which was dried under high vacuum to form a fluffy white solid (0.55 g, 71%). HRMS (ESI+) Calcd for C$_{30}$H$_{32}$O$_7$Na$^+$ [M+Na]$^+$ 527.2046, found 527.1978.

Compound 19*

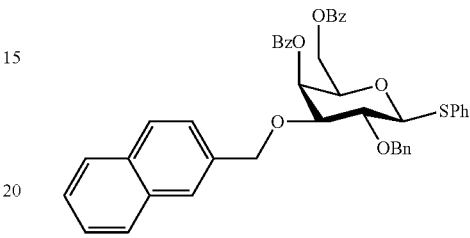

Compound 3* (10.90 g, 21.7 mmol) was dissolved in DCM (89 mL) and cooled to 0° C. Pyridine (5.26 mL, 65 mmol) and DMAP (0.265 g, 2.2 mmol) were added followed by BzCl (6.90 mL, 65 mmol) dropwise. The solution was allowed to warm to room temperature. After stirring overnight, the reaction was quenched with sat. aq. NaHCO$_3$ and extracted with DCM. The organic layer was dried over Na$_2$SO$_4$, filtered and concentrated to obtain the crude product. The crude was charged on isolute and purified using the automated purification system using ethyl acetate/cyclohexane and the solvent evaporated to obtain the product as white foam (13.85 g, 90%). HRMS (ESI+) Calcd for C$_{44}$H$_{38}$O$_7$SNa$^+$ [M+Na]$^+$ 733.2236, found 733.2134.

Compound 20*

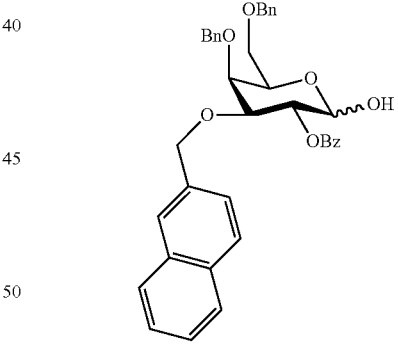

[1,5-Cyclooctadiene)(pyridine)(tricyclohexylphosphine)-Ir(I)]PF$_6$ (0.79 g, 0.155 mmol) was dissolved in tetrahydrofuran (30 mL) and nitrogen was bubbled through the solution for two minutes at room temperature while the red colored catalyst dissolved. The solution was then purged with hydrogen for two minutes, by which time the red solution changed to colorless and the solution was stirred for 15 min under hydrogen. The solution of the active catalyst was then added to a solution of compound 15* (1 g, 1.55 mmol) in tetrahydrofuran (15 mL) under nitrogen via a syringe and stirred for 2 h at room temperature. The reaction mixture was quenched with saturated aq. NaHCO$_3$ (10 mL) and extracted with dichloromethane (3×10 mL). Combined organic layers were washed with brine (10 mL), dried over Na₂SO₄, filtered and evaporated to get the allyl isomerized compound. The vinyl substrate was then taken up in a mixture of tetrahydrofuran:water (2:1.45 mL) and iodine (0.787 g, 3.10 mmol) was added at room temperature. The brown colored solution was stirred for 2 h before quenching with 10% Na₂S₂O₃ (10 mL). The aqueous phase was extracted with ethyl acetate (3×15 mL) and the combined organic layers were dried over Na₂SO₄, filtered and evaporated. Flash column chromatography (ethyl acetate in hexane 30%) afforded the product as yellow solid (0.55 g, 59%). HRMS (ESI+) Calcd for $C_{38}H_{36}O_7Na^+$ $[M+Na]^+$ 627.2359, found 627.2267.

Compound 21*

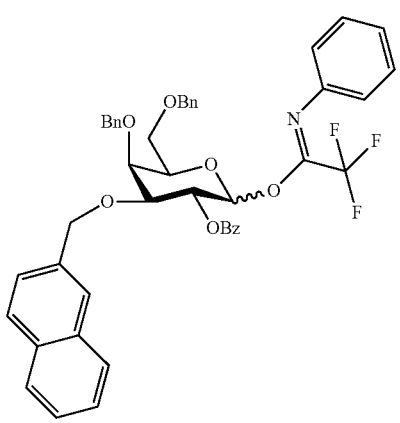

Compound 20* (0.55 g, 0910 mmol) was dissolved in dichloromethane (11 mL). Cs₂CO₃ (0.593 g, 1.82 mmol) and 2,2,2-trifluoro-N-phenylacetimidoyl chloride (0.566 g, 2.73 mmol) were the added and the reaction mixture was stirred at room temperature overnight. The reaction mixture was filtrated through a Celite pad (2 cm), washed with DCM (50 mL) and the filtrate concentrated to give a pale yellow oil. Purification was done by flash silica gel column chromatography (cyclohexane/ethylacetate+0.1% Et₃N) afforded the imidate as yellow foam (0.608 g, 86%). HRMS (ESI+) Calcd for $C_{46}H_{40}F_3NO_7Na^+$ $[M+Na]^+$ 798.2655, found 798.2555.

Compound 22*

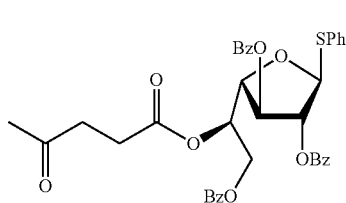

Compound 11* (3.65 g, 6.24 mmol) was dissolved in DCM (40 mL) and Levulinic acid (1.087 g, 9.36 mmol), EDC (1.795 g, 9.36 mmol) and DMAP (0.763 g, 9.36 mmol) were added sequentially. The reaction mixture was stirred at room temperature for 17 h. The mixture was partitioned between DCM and sat. NaHCO₃ solution. The aqueous layer was extracted with DCM. The organic layers were dried over Na₂SO₄, filtered and evaporated to give crude product. The crude was charged on isolute and purified using the automated purification system (ethyl acetate/cyclohexane) and the solvent evaporated to give the product as a colorless oil (3.82 g, 90%). HRMS (ESI+) Calcd for $C_{38}H_{34}O_{10}SNa^+$ 705.1765 [M+Na]⁺, found 705.1763.

Compound 23*

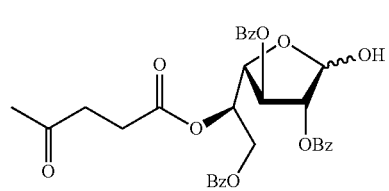

Compound 22* (2.8 g, 4.10 mmol) was dissolved in DCM/water 3:1 (40 mL) and N-bromosuccinimide (2.19 g, 12.30 mmol) was added. The mixture was stirred at room temperature for 45 minutes. The mixture was partitioned between DCM and sat. NaHCO₃ solution. The aqueous layer was extracted with DCM. The organic layers were washed with 0.1 M Na₂S₂O₃, dried over Na₂SO₄, filtered and evaporated to give crude product. The crude was charged on Isolute® and purified using the automated purification system (ethyl acetate/cyclohexane) and the solvent was evaporated to give the product as colorless oil (2.30 g, 95%). HRMS (ESI+) Calcd for $C_{32}H_{30}O_{11}Na^+$ 613.1680 [M+Na]⁺, found 613.1678.

Compound 24*

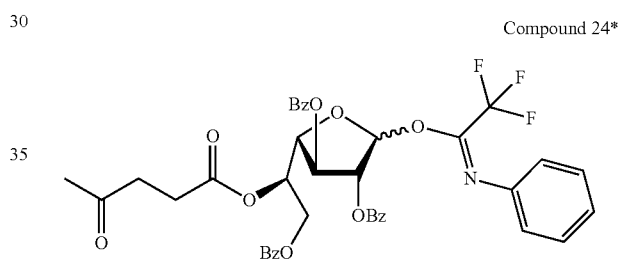

Compound 23* (2 g, 3.39 mmol) was dissolved in DCM (20 mL) and cesium carbonate (2.207 g, 6.77 mmol) and (E)-2,2,2-trifluoro-N-phenylacetimidoyl chloride (2.109 g, 10.16 mmol) were added sequentially. The reaction mixture was stirred at room temperature for 2 h. The mixture was filtered over celite, washed with DCM and the filtrate evaporated to give product as colorless oil (2.5 g, 97%).

Compound 25*

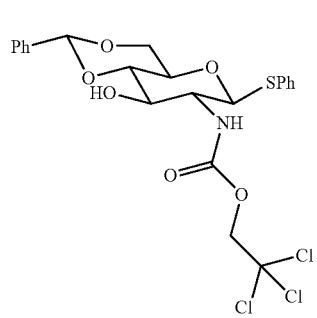

Compound 25* was prepared according to a procedure described in Nakashima, S.; Ando, H.; Imamura, A.; Yuki, N.; Ishida, H.; Kiso, M. Chem.—Eur. J. 2011, 17, 588-597.

Compound 26*

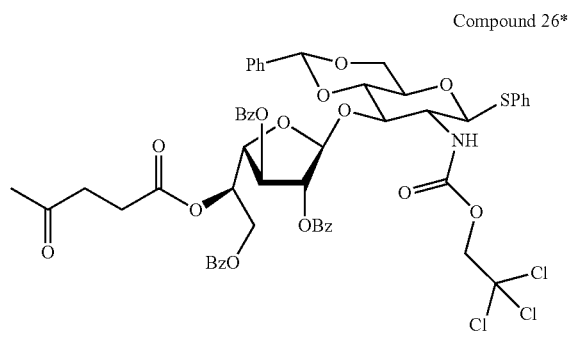

Compound 28*

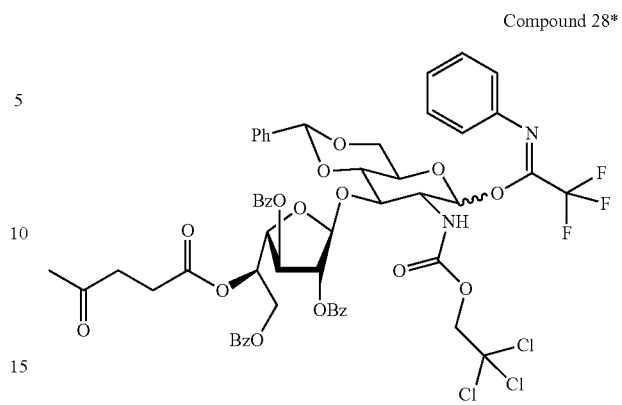

Compound 24* (2.5 g, 3.28 mmol) and compound 25* (1.46 g, 2.74 mmol) were taken in 100 mL RBF, toluene (40 mL) was added and the compound azeotroped under vacuum (twice). The material dried under high vacuum was dissolved in dichloromethane (25 mL) and dried 4 A molecular sieves (MS) were added and stirred at room temperature for 10 min before cooling to −10° C. TMS-OTf (50 μL, 0.274 mmol) was added to the reaction mixture and stirred while it was slowly warmed to 0° C. over 1.5 h. The reaction was quenched by the addition of sat. aq. NaHCO$_3$. The layers were separated and the aqueous layer was extracted with DCM. The organic layers were dried over Na$_2$SO$_4$, filtered and evaporated. The crude was charged on isolute and purified using the automated purification system (ethyl acetate/cyclohexane) and the solvent was evaporated to obtain the product as colorless oil (2.51 g, 83%). HRMS (ESI+) Calcd for C$_{54}$H$_{50}$Cl$_3$NO$_{16}$SNa$^+$ 1128.1808 [M+Na]$^+$, found 1128.1904.

Compound 27* (1.05 g, 1.034 mmol) was dissolved in anhydrous DCM (10 mL) and cesium carbonate (0.674 g, 2.068 mmol) and (E)-2,2,2-trifluoro-N-phenylacetimidoyl chloride (0.644 g, 3.10 mmol) were added sequentially. The reaction mixture was stirred at room temperature for 3 h. The mixture was filtered over celite, washed with DCM and the filtrate evaporated to give product as colorless oil (1.2 g, 98%). HRMS (ESI+) Calcd for C$_{56}$H$_{50}$Cl$_3$F$_3$N$_2$O$_{17}$Na$^+$ 1207.2019 [M+Na], found 1207.2043.

Compound 27*

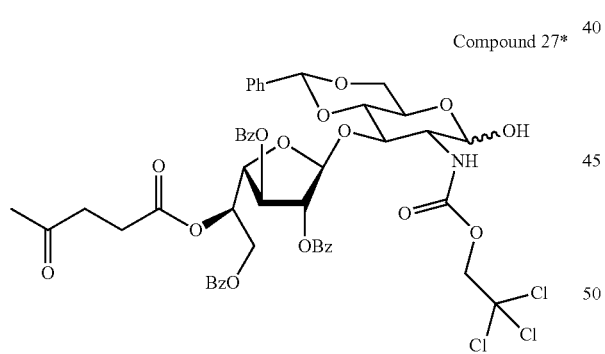

Compound 29*

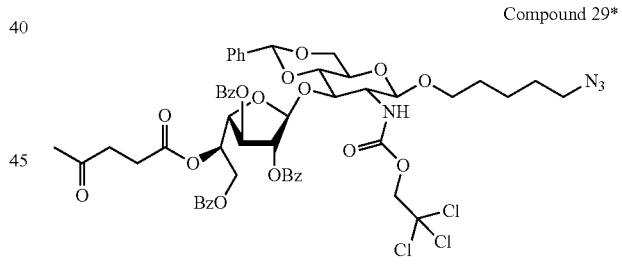

Compound 26* (2.5 g, 2.26 mmol) was dissolved in DCM/water 10:1 (27.5 mL) and N-iodosuccinimide (0.508 g, 2.26 mmol) and trifluoroacetic acid (0.173 mL, 2.26 mmol) were added at 0° C. The mixture was stirred at 0° C. for 2 h and then partitioned between DCM and sat. aq. NaHCO$_3$. The aqueous layer was extracted with DCM and the organic layers were washed with 0.1 M Na$_2$S$_2$O$_3$, dried over Na$_2$SO$_4$, filtered and evaporated. The crude was charged on isolute and purified using the automated purification system (ethyl acetate/cyclohexane) and the solvent was evaporated to give the product as colorless oil (1.09 g, 47.4%). HRMS (ESI+) Calcd for C$_{48}$H$_{46}$Cl$_3$NO$_{17}$Na$^+$ 1036.1724 [M+Na]$^+$, found 1036.1828.

Compound 28* (200 mg, 0.169 mmol) and 5-azidopentanol (43.5 mg, 0.337 mmol) were taken in 10 mL RBF. Toluene (3 mL) was added and the compound evaporated under vacuum (twice). After drying overnight dichloromethane (4 mL) and dried 4 A molecular sieves (MS) were added and stirred at room temperature for 10 min before cooling to −10° C. TMS-OTf (3 μL, 0.017 mmol) was added to the reaction mixture and stirred while it was slowly warmed to 0° C. over 1.5 h. The reaction was quenched by the addition of sat. ag. NaHCO$_3$ solution. The layers were separated and the aqueous layer was extracted with DCM. The organic layer was dried over Na$_2$SO$_4$, filtered and evaporated. The crude was charged on isolute and purified using the automated purification system (ethyl acetate/cyclohexane) and the solvent was evaporated to give the product as colorless oil (64.4 mg, 74%). HRMS (ESI+) Calcd for C$_{53}$H$_{55}$Cl$_3$N$_4$O$_{17}$Na$^+$ 1147.252 [M+Na]$^+$, found 1147.2558.

Compound 30*

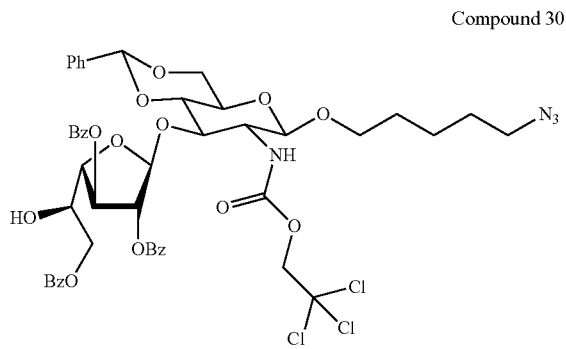

Compound 29* (80 mg, 0.071 mmol) was dissolved in pyridine (1 mL) and hydrazine acetate (19.6 mg, 0.213 mmol) was added. The reaction mixture was stirred at room temperature for 17 h. The reaction was quenched by the addition of acetone and stirred for 45 minutes before evaporating. The crude was charged on isolute and purified using the automated purification system (ethyl acetate/cyclohexane) and the solvent was evaporated to give the product as colorless oil (72.8 mg, 100%). HRMS (ESI+) Calcd for $C_{48}H_{49}Cl_3N_4O_{15}Na^+$ 1049.2152 [M+Na], found 1049.2176.

A-2 Preparation of *Klebsiella pneumoniae* Galactan-I ($O_1$) Saccharide

A-2-1 Preparation of *Klebsiella pneumoniae* O1 Tetrasaccharide

Compound 33*

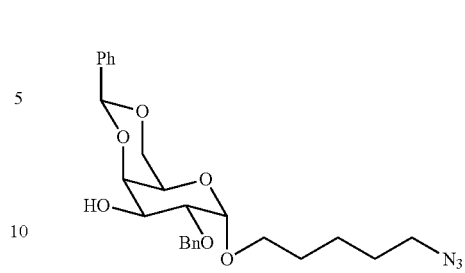

Compound 32* (300 mg, 0.492 mmol) was taken in DCM (5 mL) and buffer solution (10 mL) at rt, and added DDQ (335 mg, 1.476 mmol) in portions over 20 mins And stirred for 1.5 h. RM was quenched with sat. $NaHCO_3$ (10 mL) and extracted with DCM (10 mL×3). Combined organics were washed with sat. $NaHCO_3$ (5 mL), brine (10 mL), dried ($Na_2SO_4$), filtered, concentrated in vacuum to obtain crude product. Purification using Biotage (silica column-EA/CHx as eluents) led to the product as the colorless gummy liquid (210 mg, 91%).

Compound 34*

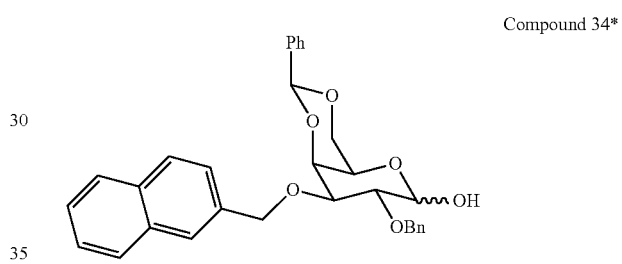

Compound 34* was prepared from compound 2* according to the procedure described for the synthesis of compound 23* from 22*

Compound 32*

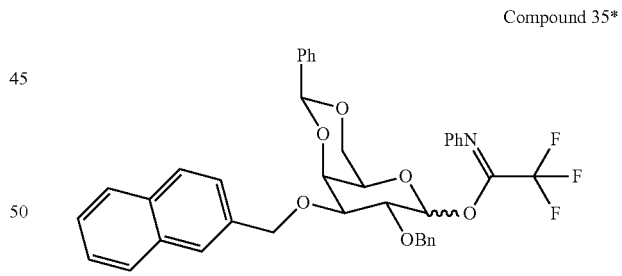

Both 5-azidopentanol (0.226 g, 1.747 mmol) and compound 35* (0.9 g, 1.344 mmol) were dried azeotropically using toluene in vacuum. Redissolved the compound in toluene (6 mL) and 1.4 dioxane (2 mL) mixture at rt, added 4 A molecular sieves and stirred for 20 min. Cooled the RM to −5° C. added TMSOTf and stirred the RM at −5° C. for 5 mins and slowly warmed to 2° C. over one hour. RM was quenched with sat. aq. $NaHCO_3$ (2 mL) at 10° C., separated the layers, dried the organic layer ($Na_2SO_4$), filtered, and evaporated in vacuum. Purification using automated purification system Biotage (silica column chromatography using EA/CHx) led to the product as a mixture of anomers (fr1, 314 mg, alpha product) and (fr2, 300 mg, beta product) (75%).

Compound 35*

Compound 34* (15.5 g, 31.1 mmol) was dried azeotropically using toluene in the rotary evaporator and overnight under high vacuum. The solid was taken in DCM (300 mL) under nitrogen atmosphere, added $Cs_2CO_3$ (30.4 g, 93 mmol) to it and stirred for 10 min. Added (E)-2,2,2-trifluoro-N-phenylacetimidoyl chloride (16.13 g, 78 mmol) to the RM neat and stirred the RM at rt for 3 h. RM was filtered through the celite, washed with DCM (50 mL×4). Combined filtrate was evaporated in vacuum to get the crude product. Purification was done on silica column treated with triethylamine and ethyl acetate/cyclohexane as eluents to get product out, on evaporation and drying under vacuum it yielded pale yellowish fluffy solid (18.5 g, 89%).

Compound 36*

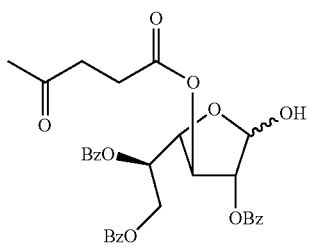

To a solution of thioglycoside 8*(1.58 g, 2.31 mmol) dissolved in DCM:H$_2$O (1:0.3, 26 mL) was added NBS (1.23 g, 6.94 mmol) at room temperature. The reaction was stirred at the same temperature for 1 h. TLC (50% ethyl acetate/cyclohexane) showed complete consumption of the starting material. The reaction was diluted with DCM (20 mL), and washed with 10% Na$_2$S$_2$O$_3$ (10 mL) and sat. NaHCO$_3$ (10 mL) and the organic layer separated, dried over Na$_2$SO$_4$ and the solvent evaporated to give the crude material. Automated purification (Combiflash) using silica gel and ethyl acetate/cyclohexane as the eluent gave the product as a colorless oil (1.12 g, 1.89 mmol). HRMS (ESI+) Calcd for C$_{32}$H$_{30}$O$_{11}$Na$^+$ [M+Na]$^+$ 613.1686, found 613.1628.

Compound 37*

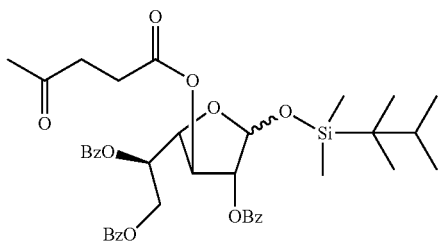

Lactol 36* (18.5 g, 31.3 mmol) was taken in DCM (300 mL) at rt, added imidazole (6.40 g, 94 mmol) and the TDSCl (11.20 g, 62.7 mmol) to it and stirred at rt for 5 min. White precipitation formation was observed and stirring continued for 18 hours more. TLC analysis showed the presence of intense non polar spots (major beta and minor alpha) and very less SM. RM was then quenched with water, extracted with DCM(100 mL×3). Combined organics were washed with brine solution (100 mL), dried (Na$_2$SO$_4$), filtered and evaporated in vacuum to get colourless gummy residue. On Biotage silica column(220 g) purification using EA-Cyclohexane, the non-polar spots were collected as fr1 (only beta anomer), and fr2 (mixture of two anomers, major alpha) and polar spots as fr3, evaporated in vacuum to get desired product as colourless gummy liquid as fr1 (16 g, pure beta) and fr2 (4.6 g, major alpha). So, total yield of the reaction was 90% (20.6 g).

Compound 38*

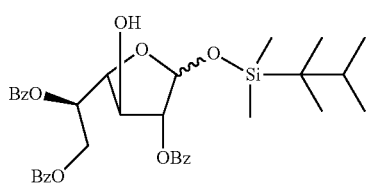

Compound 37* (15.9 g, 21.69 mmol) was taken in Pyridine (100 mL) at rt, added hydrazine acetate (5.99 g, 65.1 mmol) to it and stirred at rt for 18 h. TLC showed the presence of a sugar active spot slightly non-polar to the Rf value of the SM in 40% EA/Hexanes. RM was then quenched with acetone and stirred for 45 mins at rt. The RM was then evaporated to dryness in vacuum. The residue was purified using Biotage with EA-Cyclohexane as eluents to get the sugar active spot, on evaporation and drying in the high vacuum the desired compound was obtained as colourless gummy liquid (12.8 g, 93%).

Compound 39*

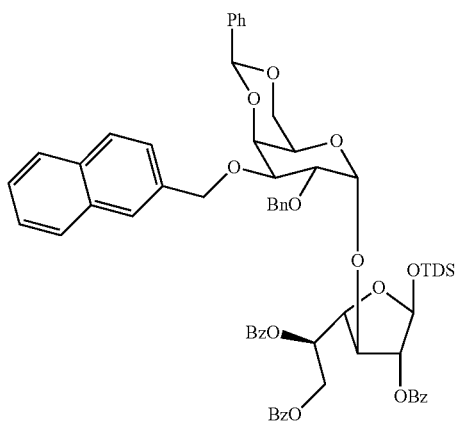

Both compound 38* (5.40 g, 8.51 mmol) and compound 35* (7.41 g, 11.06 mmol) were taken in RBF and dried azeotropically using dry toluene in the vacuum. The mixture was taken in Toluene (60 ml) and Dioxane (20 mL) at rt, added 4 A molecular sieves to it and stirred at rt for 30 min under N$_2$ atmosphere. Cooled the RM to −2 deg using Ice water bath and added TMSOTf (0.189 g, 0.851 mmol) to the RM and stirred the RM at 5° C. for 20 mins. TLC showed almost completion of the reaction. RM was then allowed to warm slowly to room temp over one hr. TLC analysis showed the completion of the reaction. RM was quenched with sat. NaHCO$_3$ (100 mL), stirred for 10 mins. Extracted with EA(50 mL×3). Combined organics were washed with water (100 mL), brine (50 mL), dried (Na$_2$SO$_4$), evaporated in vacuum to get crude product. Column purification on silica was done using EA/cyclohexane on Biotage. So, yield of the reaction was 8.35 g, 88%. HRMS (ESI+) Calcd for C$_{66}$H$_{70}$O$_{14}$SiNa$^+$ [M+Na]$^+$ 1137.4433, found 1137.4339.

Compound 40*

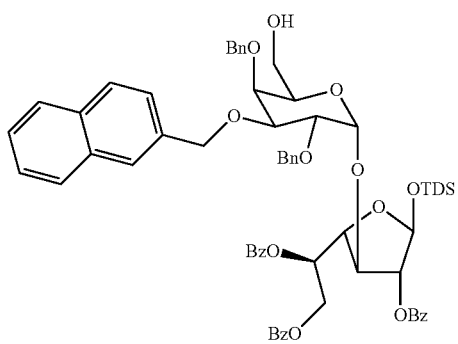

Compound 39* (1.15 g, 1.031 mmol) was taken in THF (6 mL), added dried 4 A molecular sieves to it and stirred at rt for 15 mins. Added BH$_3$-THF (8.25 mL, 8.25 mmol) solution to the RM and stirred for 5 mins before the addition of the TMSOTf and stirred at rt for 16 hrs. RM was quenched with methanol (10 mL) slowly (careful, effervescence) at rt and stirred for 45 mins. and then diluted with sat. NaHCO$_3$ solution (25 mL) and EA (10 mL). Stirred the RM well for 2 hrs. Separated the layers. The aqueous layer was extracted with EA (25 mL×3). Combined organics were washed with brine solution(10 mL), dried (Na2SO4), filtered, and evaporated in vacuum to get colourless gummy liquid. Crude product was column purified using EA/Cyclohexane and product eluted with 20-30% EA/Cyclohexane, evaporation of fractions containing product spots in rotary evaporator yielded the colourless gummy liquid (0.73 g, 63.4%).

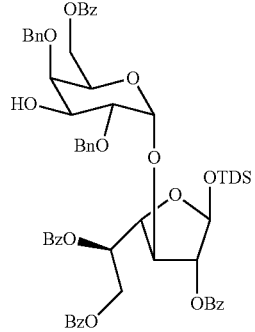

Compound 42*

Compound 41* (125 mg, 0.120 mmol) was taken in DCM (3 mL) and buffer solution (3 mL) at rt, added DDQ (69.7 mg, 0.307 mmol) in portions over 20 mins, RM became black then it turned to reddish brown colour. RM stirred for 2 h. TLC analysis (20% EA/CHx) showed the presence of polar spot and little SM. So continued stirring for 0.5 h more. RM was quenched with NaHCO$_3$ solution (10 mL) and extracted with DCM (10 mL×3). Combined organics were washed with brine solution (10 mL), dried (Na$_2$SO$_4$), filtered, concentrated in vacuum to get crude product. Crude product was purified using Biotage with silica column-EA/Chx as eluents to get product out (86 mg, 78%).

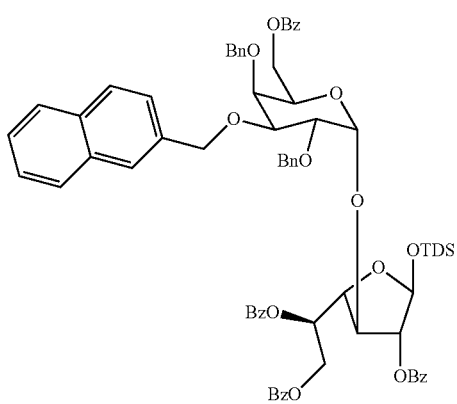

Compound 41*

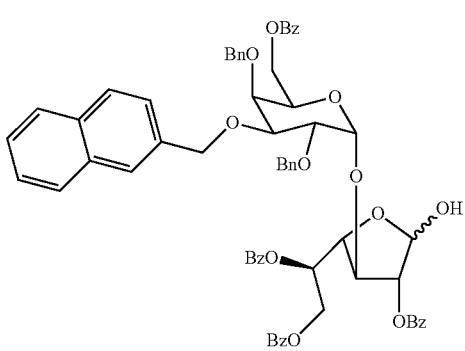

Compound 43*

Compound 40* (1.0 g, 0.895 mmol) was taken in DCM (20 mL) at rt, added pyridine (1.086 mL, 13.42 mmol) and DMAP (0.022 g, 0.179 mmol) to it and stirred for 5 mins. Then added BzCl (0.503 g, 3.58 mmol) to it and stirred for 48 h. TLC analysis (20% EA/CHx) showed completion of the reaction. RM was diluted with DCM (25 mL) and NaHCO$_3$ (20 mL), separated the layers. The Organic layer was washed with brine solution (10 mL), dried(Na$_2$SO$_4$), filtered and evaporated in vacuum to get pale brown residue. Purification using Biotage-Silica column with EA and CHx as solvents gave pure product out, which on evaporation of fractions containing product in vacuum to get colourless gummy solid. Added dry toluene to it and azeotropically dried the material in rotavapour twice and then dried under high vacuum to get colourless gummy solid (900 mg, 82%).

Compound 41* (940 mg, 0.770 mmol) was taken in pyridine (10 mL) in a 50 mL falcon tube, at rt and stirred for 5 mins. Then added HF-Py (1144 mg, 11.54 mmol) to it (careful: bubbles and exothermic). RM was stirred at rt for 18 h. TLC analysis (20% EA/Chx) showed that SM was present and a polar spot formed as well. So, added 10 equivalent of HF-Py one more time to RM and RM was stirred at rt for 30 h more and TLC analysis (20% EA/Chx) showed that still some SM was present and a major polar spot as well. RM was quenched with water (50 mL), and diluted with DCM(50 mL), mixed the layers well with stirring at rt, separated the layers. The aqueous layer was extracted with DCM (25 mL×2). The combined organic layer was washed with NaHCO$_3$ wash(50 mL×2, careful some effervescence), brine (3 mL), dried (Na$_2$SO$_4$), filtered, evaporated in vacuum to get white gummy liquid. Crude product was purified using Biotage with silica column-EA/CHx as eluents to get the product out (661 mg, 80%).

Compound 44*

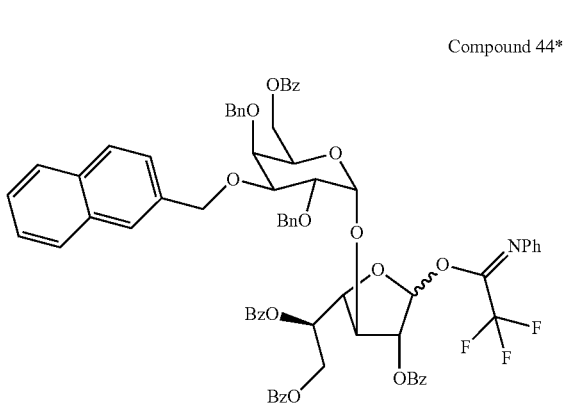

Lactol 43* (600 mg, 0.556 mmol) was taken in DCM (20 mL) at rt under $N_2$ atmosphere, added $Cs_2CO_3$ (725 mg, 2.224 mmol) to it and stirred for 5 mins. Then added the Imidoyl chloride reagent (346 mg, 1.668 mmol) to it and stirred for 2 h. TLC analysis showed that the reaction was complete and intense non polar spot was present and no SM was present. So, RM was filtered to remove the solid, washed the residue with DCM. The Filtrate was concentrated in vacuum. Crude product was purified using Silica column (treated with TEA in cyclohexanes before loading the column) using EA/CHx+1% TEA as eluents to get product fractions out. On evaporation and drying under vacuum off-white coloured fluffy solid was obtained (682 mg, 98%).

Compound 45*

Both compound 33* (80 mg, 0.170 mmol) and compound 44* (256 mg, 0.204 mmol) were dried azeotropically using dry toluene in the vacuum together. They were taken in DCM (5 mL) at rt, added 4 A molecular sieves to it and stirred for 20 min under $N_2$ atmosphere. Cooled the RM to −5° C. using Ice-Acetone bath and added TMSOTf (6.16 µL, 0.034 mmol) to the RM and stirred the RM at −5° C. for 5 mins slowly warmed to 2° C. over 1 h. TLC analysis (30% EA/CHx then in 20% EA/CHx) showed that the reaction was complete. RM was quenched with $NaHCO_3$ solution (5 mL) at 10° C., separated the layers. Aqueous layer was extracted with DCM (3 mL×2). Combined organics were washed with brine solution (5 mL), dried ($Na_2SO_4$), filtered, and evaporated in vacuum. Purified by Biotage on silica column chromatography using EA/CHx to get fractions containing product spot on evaporation under vacuum yielded desired product as colorless gummy solid (231 mg, 89%).

Compound 46*

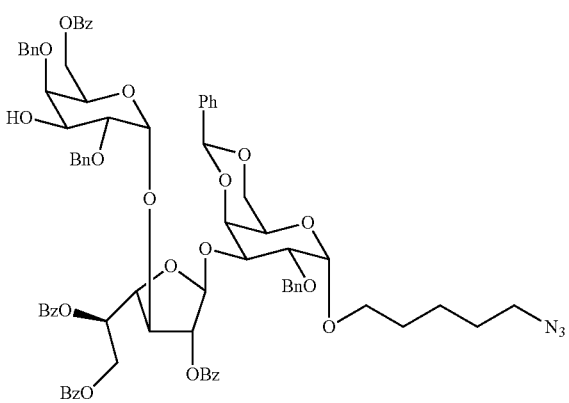

Compound 45* (220 mg, 0.144 mmol) was taken in DCM (6 mL) and buffer solution (12 mL) at rt, added DDQ (98 mg, 0.431 mmol) in portions over 20 mins, RM became black then it turned to reddish brown color. RM stirred for 1.5 h. TLC analysis (20% EA/CHx) showed the presence of polar spot and little SM. So continued stirring for 0.5 h more. RM was quenched with sat. $NaHCO_3$ solution (15 mL) and extracted with DCM (10 mL×3). Combined organics were washed with sat. $NaHCO_3$ solution (5 mL), brine solution (10 mL), dried ($Na_2SO_4$), filtered, concentrated in vacuum to get crude product. Crude product was purified using Biotage with silica column-EA/CHx as eluents to get product out as colorless gummy solid (160 mg, 80%). HRMS (ESI+) Calcd for $C_{79}H_{79}O_{20}N_3Na$ [M+Na]$^+$ 1412.5155, found 1412.5040.

Compound 47*

Both compound 46* (25 mg, 0.018 mmol) and compound 21* (27.9 mg, 0.036 mmol) were dried azeotropically using dry toluene in the vacuum together. They were taken in DCM (2 mL) at rt, added 4 Å molecular sieves to it and stirred for 20 min under $N_2$ atmosphere. Cooled the RM to −10° C. using Ice-Acetone bath and added TMSOTf (0.650 µL, 3.60 µmol) to the RM and stirred the RM at −10° C. for 5 mins slowly warmed to 2° C. over one hour. TLC analysis (30% EA/CHx then in 20% EA/CHx) showed that the reaction was complete and presence of intense spot. RM was quenched with $NaHCO_3$ solution (5 mL) at 10° C., separated the layers. Aqueous layer was extracted with DCM (3 mL×2). Combined organics were washed with brine solution (5 mL), dried ($Na_2SO_4$), filtered, and evaporated in vacuum. Purified by Biotage on silica column chromatography using EA/CHx to get fractions containing product spot on evaporation under vacuum yielded desired product as colorless layer (6 mg, 17%).

Compound 47* (6 mg, 3.03 µmol) was taken in THF-MeOH (1:1, 2 mL) at rt, added NaOMe solution in methanol (0.121 mL, 0.061 mmol) to it and continued stirring for 18 h. TLC analysis (30% EA/CHx) showed the absence of the SM and presence of a polar spot. So, RM was evaporated in vacuum. Diluted with EA (3 mL) and water (2 mL). Acidified with AcOH (~0.2 mL). Extracted with EA (2 mL×3). Combined organics were washed with brine solution (2 mL), dried ($Na_2SO_4$), filtered, and evaporated in vacuum to get crude product. $^1H$ NMR and HRMS shows that the crude product has desired product as well the intermediate products where one Bz and may be two Bz groups still present in the molecule. So, RM was resubjected to the reaction conditions again at rt. RM was diluted with EA (3 mL) and water (2 mL). Acidified with AcOH (~0.1 mL). Extracted with EA (2 mL×3). Combined organics were washed with water (2 mL), brine solution (2 mL), dried ($Na_2SO_4$), filtered, and evaporated in vacuum to get crude product. $^1H$ NMR and HRMS shows that the crude product has desired product as well a little mono Bz containing intermediate. So, RM was resubjected to the reaction conditions again at 50° C. for 18 h. RM was cooled to rt and then diluted with EA (3 mL) and water (2 mL). Acidified with AcOH (~0.1 mL). Extracted with EA (2 mL×3). Combined organics were washed with water (2 mL), brine solution (2 mL), dried ($Na_2SO_4$), filtered, and evaporated in vacuum to get crude product (3 mg, 68%).

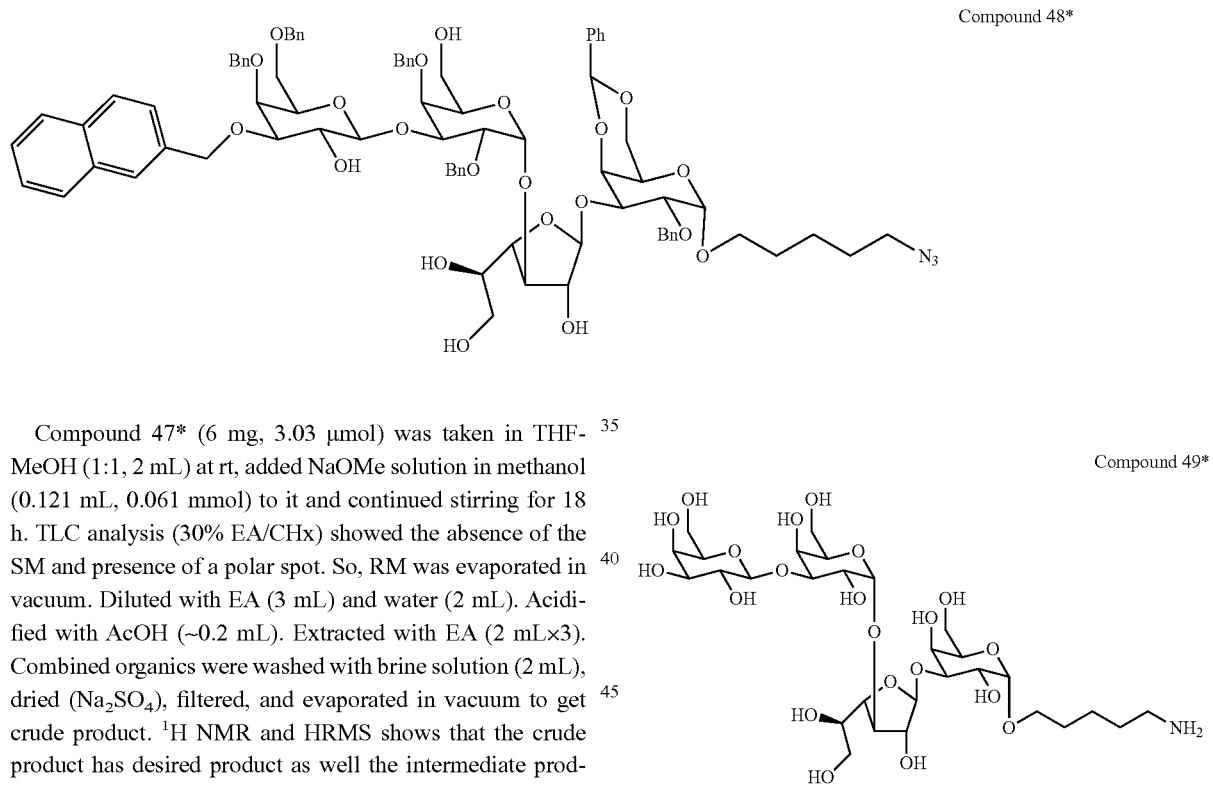

Compound 48*

Compound 49*

Compound 48* (3 mg, 2.060 mmol) was taken in solvent mixture (DCM-tBuOH-two drops of water), added Pd/C in tBuOH (0.5 mL) to it and hydrogenated for 24 h at 5 bar pressure of $H_2$ at rt. RM was filtered through PTFE filter, washed the residue with Methanol (6 mL), (50% Methanol-water(6 mL). The filtrate was evaporated in vacuum to get the crude product. 1H nmr analysis showed the completion of the reaction and the presence of product. So, crude product was purified through the C18 Sepak column using water (3 mL×2, fr1), 20% ACN-water (3 mL×2, fr2) and ACN (3 mL, fr3). All the fractions were frozen and lyophilized for 24 h to get fr1 as the desired product (colorless layer, 0.71 mg, 46%). LRMS (ESI+) Calcd for $C_{29}H_{54}NO_{21}H^+$ $[M+H]^+$ 753.3222, found 753.4608.

A-2-2 Preparation of *Klebsiella pneumoniae* O1Hexasaccharide

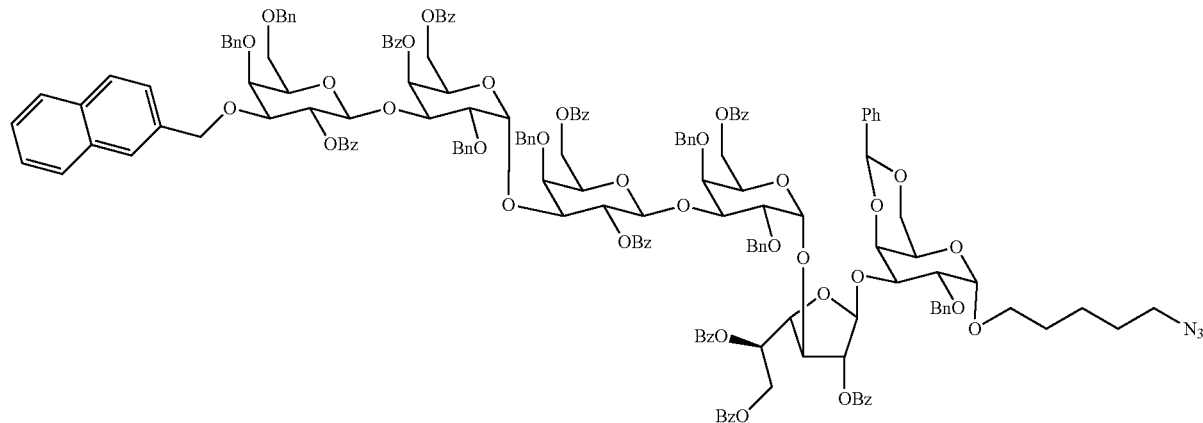

Compound 50*

Both compound 46* (125 mg, 0.090 mmol) and compound 107* (227 mg, 0.135 mmol) were dried azeotropically using dry toluene in the vacuum together. They were taken in DCM (5 mL) at rt, added 4 A molecular sieves to it and stirred for 20 min under $N_2$ atmosphere. Cooled the RM to −10° C. using Ice-Acetone bath and added TMSOTf (3.25 μL, 0.018 mmol) to the RM and stirred the RM at −10° C. for 5 mins slowly warmed to 2° C. over 1 h. TLC analysis (30% EA/CHx then in 20% EA/CHx) showed that the reaction was complete and presence of intense spot. RM was quenched with $NaHCO_3$ solution (5 mL) at 10° C., separated the layers. Aqueous layer was extracted with DCM (3 mL×2). Combined organics were washed with brine solution (5 mL), dried ($Na_2SO_4$), filtered, and evaporated in vacuum. Purified by Biotage on silica column chromatography using EA/CHx to get the desired product as a colorless layer (160 mg, 62%). LRMS (ESI+) Calcd for $C_{171}H_{163}N_3O_{39}Na^+$ [M+Na]$^+$ 2906.0795, found 2906.0327.

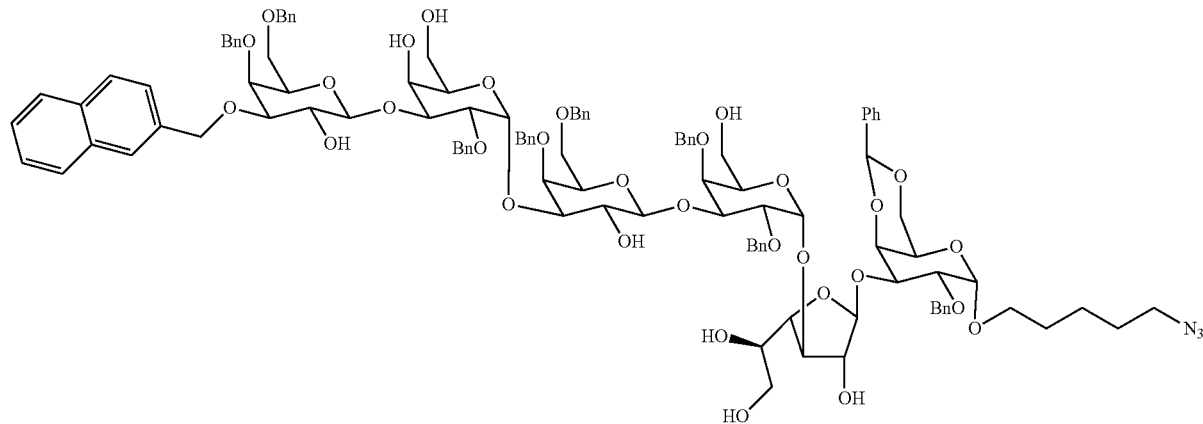

Compound 51*

Compound 50* was subjected to methanolysis according to general protocol A:

Product obtained as white gummy solid (65 mg, 91%).

MALDI-TOF Calcd for $C_{115}H_{131}N_3NaO_{31}{}^+$ [M+Na]$^+$ 2072.8664, found 2073.540.

Compound 52*

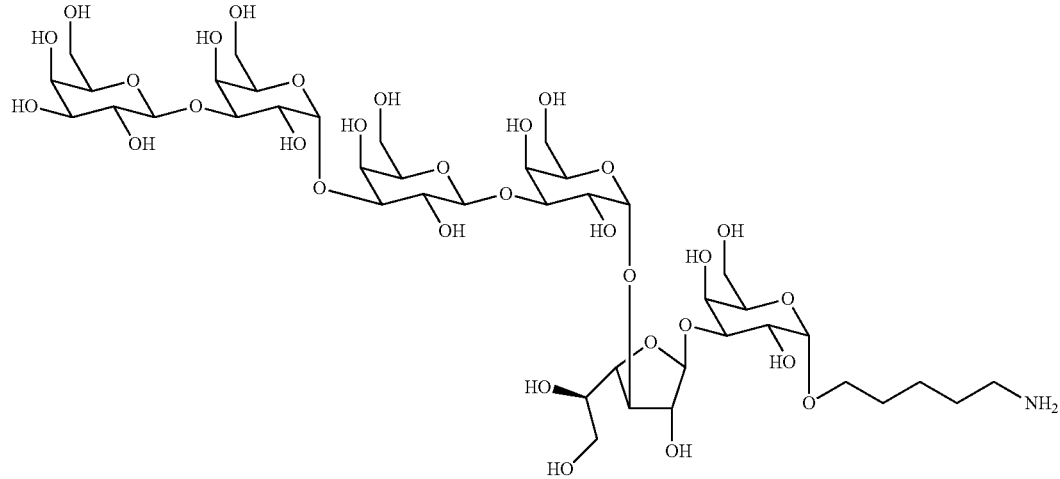

Compound 51* was subjected to hydrogenation reaction according to general protocol A:

Product obtained as white fluffy solid (9 mg, 69%).

HRMS (ESI+) Calcd for $C_{41}H_{74}NO_{31}$ [M+H]$^+$ 1076.4245, found 1076.4282.

$^1$H NMR (400 MHz, Deuterium Oxide) δ 5.26 (s, 1H), 5.22 (d, J=3.9 Hz, 1H), 5.14 (d, J=2.8 Hz, 1H), 5.00 (d, J=3.3 Hz, 1H), 4.71 (d, J=7.4 Hz, 1H), 4.66 (d, J=7.6 Hz, 1H), 4.46 (dd, J=3.0, 1.5 Hz, 1H), 4.37-4.05 (m, 12H), 4.02-3.89 (m, 5H), 3.87-3.63 (m, 19H), 3.62-3.53 (m, 1H), 3.11-2.99 (m, 2H), 1.84-1.64 (m, 4H), 1.58-1.44 (m, 2H).

Compound 52a-I*

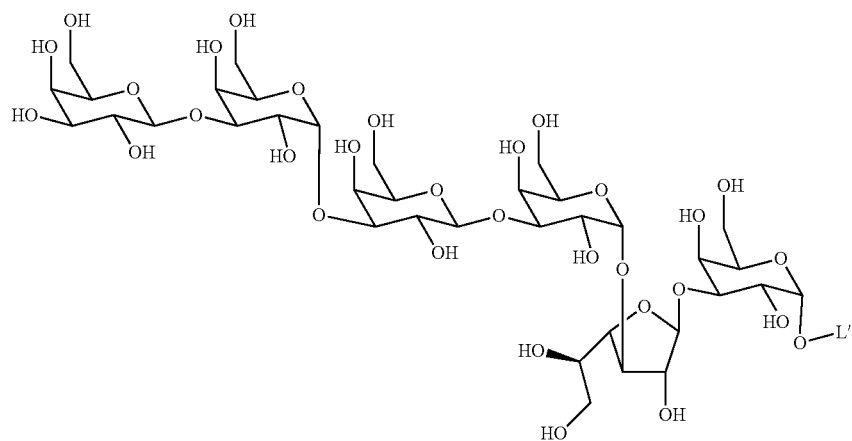

Figure 11:
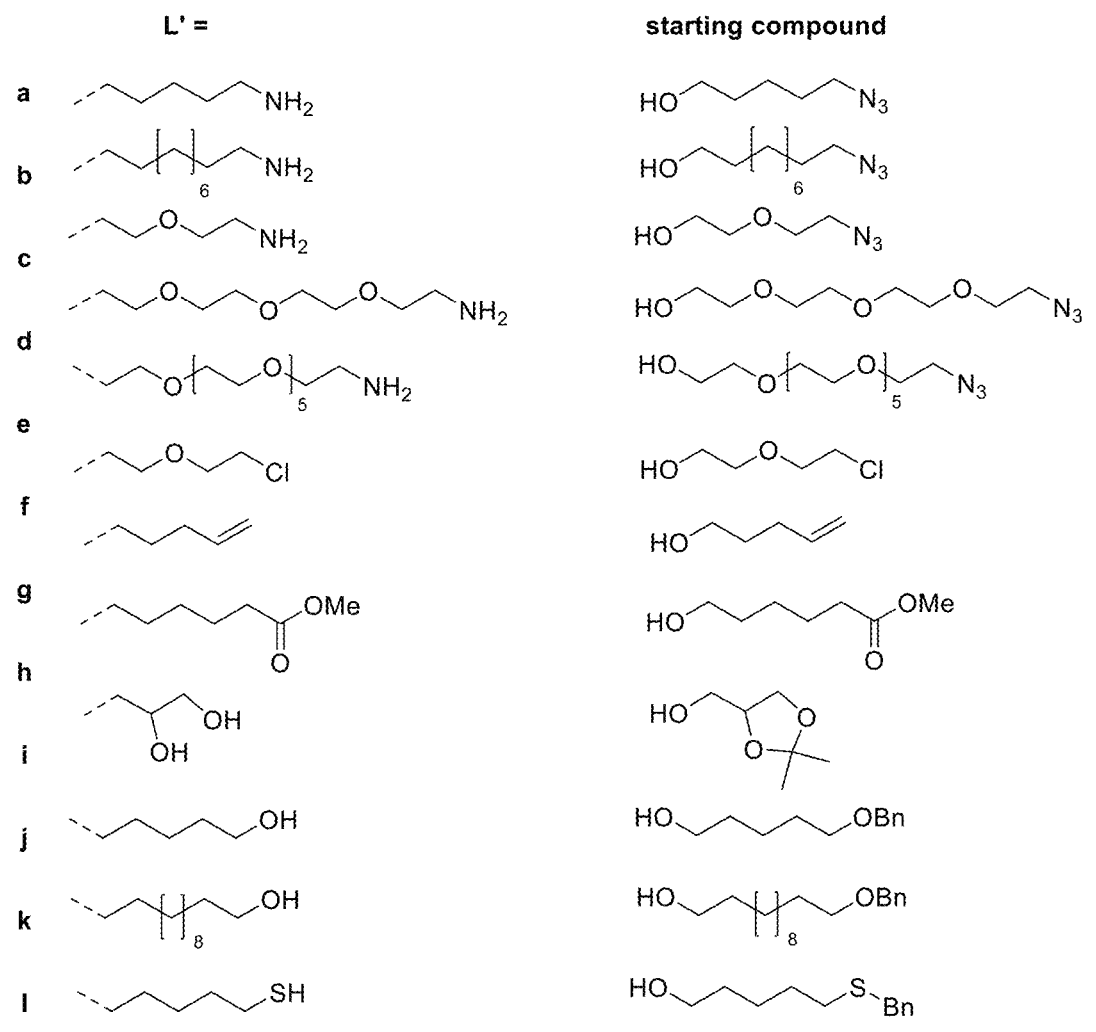

Compounds 52a-l* are prepared similarly to compound 52* from compound 35* and the corresponding alcohol as shown in FIG. 11.

A-2-3 Preparation of *Klebsiella pneumoniae* O1 Octasaccharide

Compound 53*

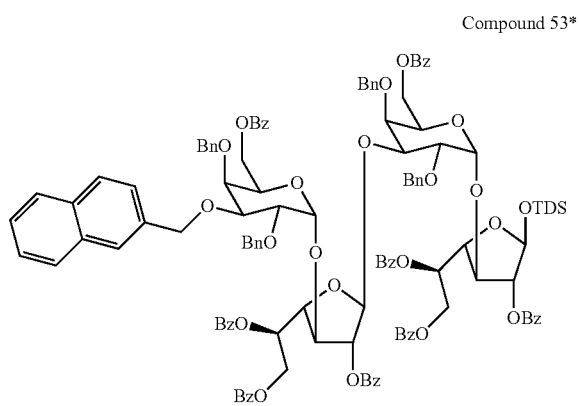

Both compound 42* (40 mg, 0.037 mmol) and compound 44* (445 mg, 0.356 mmol) were dried azeotropically using dry toluene in the vacuum separately. They were taken in DCM (10 mL) at rt, added 4 A molecular sieves to it and stirred for 10 min. To this Imidate donor in DCM (1 mL) was added and stirred at rt for 30 min under $N_2$ atmosphere. Cooled the RM to -20 deg using dry Ice-ACN bath and added TMSOTf (7.40 μL, 1.34 μmol) to the RM and stirred the RM at -20 deg for 5 mins slowly warmed to 2 deg over one h. TLC analysis (30% EA/CHx then in 20% EA/CHx) showed that the reaction was complete and absence of the SM 42* and presence of a slightly polar spot. RM was quenched with NaHCO₃ solution (2 mL) at 10 deg, separated the layers, dried the organice layer (Na₂SO₄), filtered, and evaporated in vacuum. Purified by silica column chromatography using EA/CHx to get fractions containing product, on evaporation under vacuum yielded desired product colourless layer (630 mg, 91%). HRMS (ESI+) Calcd for $C_{127}H_{124}O_{29}SiNa^+$ [M+Na]⁺ 2164.7929, found 2164.7727.

Compound 54*

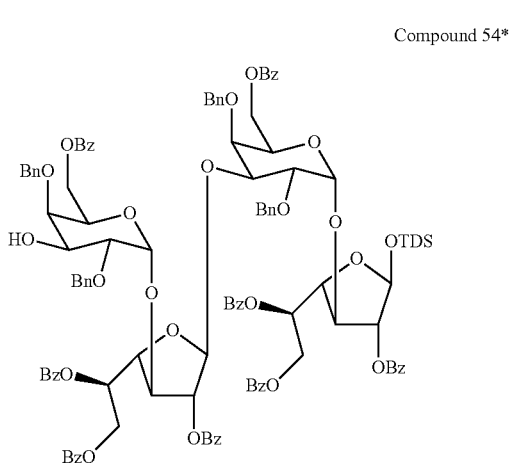

Compound 53* (300 mg, 0.140 mmol) was taken in DCM (5 mL) and buffer solution (pH 7.4, 7 mL) at rt, added DDQ (95 mg, 0.420 mmol) in portions over 20 mins, RM became black then it turned to reddish brown color. RM stirred for 2 h. TLC analysis (30% EA/CHx) showed the presence of polar spot and little SM. So continued stirring for 0.5 h more. RM was quenched with NaHCO₃ solution (10 mL) and extracted with DCM (10 mL×3). Combined organics were washed with brine solution (10 mL), dried (Na₂SO₄), filtered, concentrated in vacuum to get crude product. Crude product was purified using Biotage with silica column-EA/Chx as eluents to get product out (215 mg, 76%).

Compound 55*

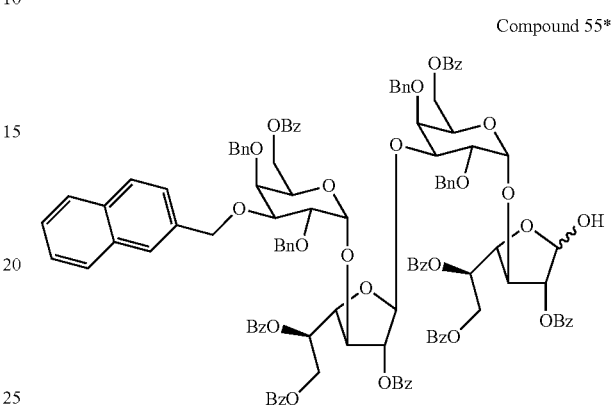

Compound 53* (1.0 g, 0.467 mmol) was taken in pyridine (10 mL) in a 50 mL Falcon tube, at rt and stirred for 5 mins. Then added HF-Py (1.5 ml, 16.34 mmol) to it (careful: bubbles and exothermic). RM was stirred at rt for 18 h. TLC analysis (30% EA/Chx) showed that a polar spot formed. RM was quenched with water (50 mL), and diluted with DCM (50 mL), mixed the layers well with stirring at rt, separated the layers. The aqueous layer was extracted with DCM (25 mL×2). The combined organic layer was washed with NaHCO₃ wash (50 mL×2, careful some effervescence), brine (3 mL), dried (Na₂SO₄), filtered, evaporated in vacuum to get white gummy liquid. Crude product was purified using biotage with silica column-EA/CHx as eluents to get the product out (930 mg, quantitative).

Compound 56*

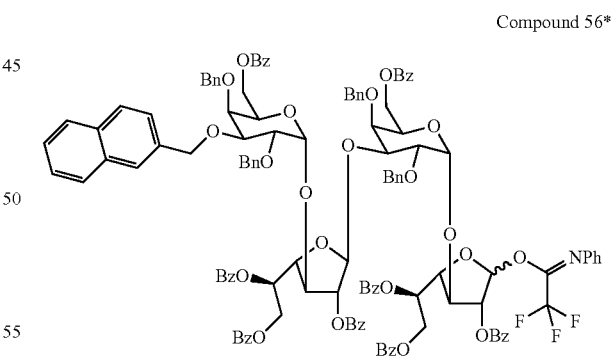

Lactol 55* (1.1 g, 0.550 mmol) was taken in DCM (20 mL) at rt under $N_2$ atmosphere, added Cs₂CO₃ (717 mg, 2.200 mmol) to it and stirred for 5 mins. Then added the Imidoyl chloride reagent (0.261 mL, 1.65 mmol) to it and stirred for 2 h. TLC analysis showed that the reaction was complete and intense non polar spot was present and no SM was present. So, RM was filtered to remove the solid, washed the residue with DCM. The Filtrate was concentrated in vacuum. On evaporation and drying under vacuum off-white coloured fluffy solid was obtained (1.2 g, 100%).

Compound 57*

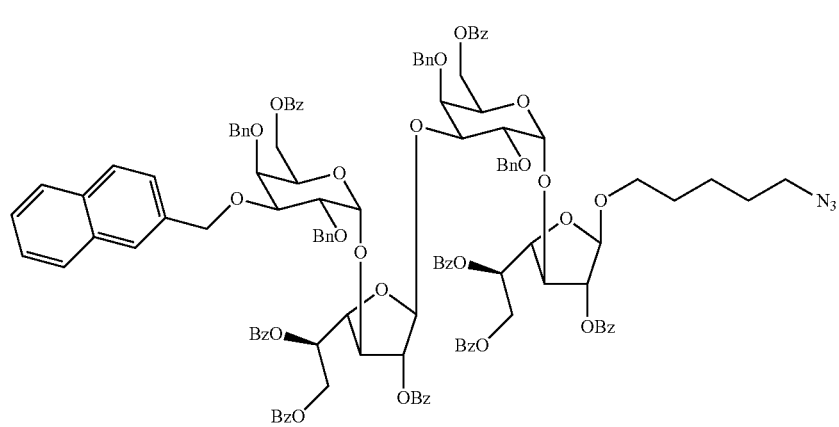

Compound 57* was obtained from compound 56* by glycosylation reaction with 5-azidopentanol according to general procedure B:

Product obtained as white fluffy solid (218 mg, 90%).

MALDI-TOF Calcd for $C_{124}H_{116}N_3O_{29}^+$ [M+H]$^+$ 2110.7694, found 2110.169.

Compound 58*

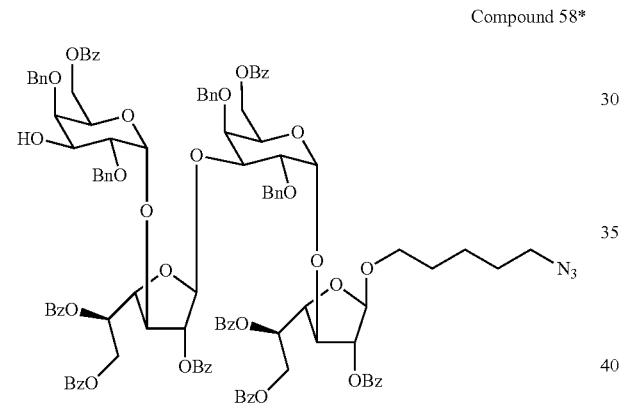

Compound 58* was obtained from compound 57* by performing removal of the Nap protecting group according to general procedure A:

Product obtained as white fluffy solid (102 mg, 51%).

MALDI-TOF Calcd for $C_{113}H_{108}N_3O_{29}^+$ [M+H]$^+$ 1970.7068, found 1969.901.

Compound 59*

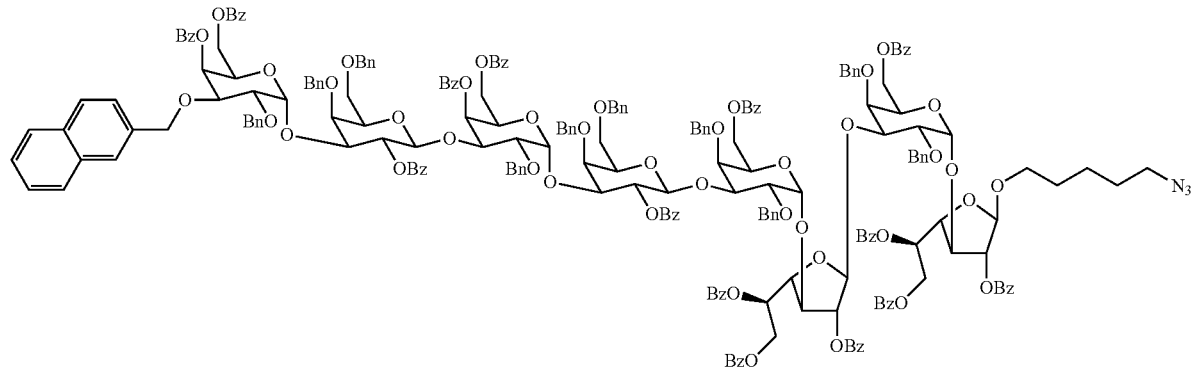

Compound 59* was obtained from compound 58* and compound 110* by glycosylation reaction according to general procedure B:

Product obtained as white fluffy solid (128 mg, 63%).

MALDI-TOF Calcd for $C_{232}H_{216}N_3O_{55}^+$ [M+H]$^+$ 3923.4197, found 3923.293.

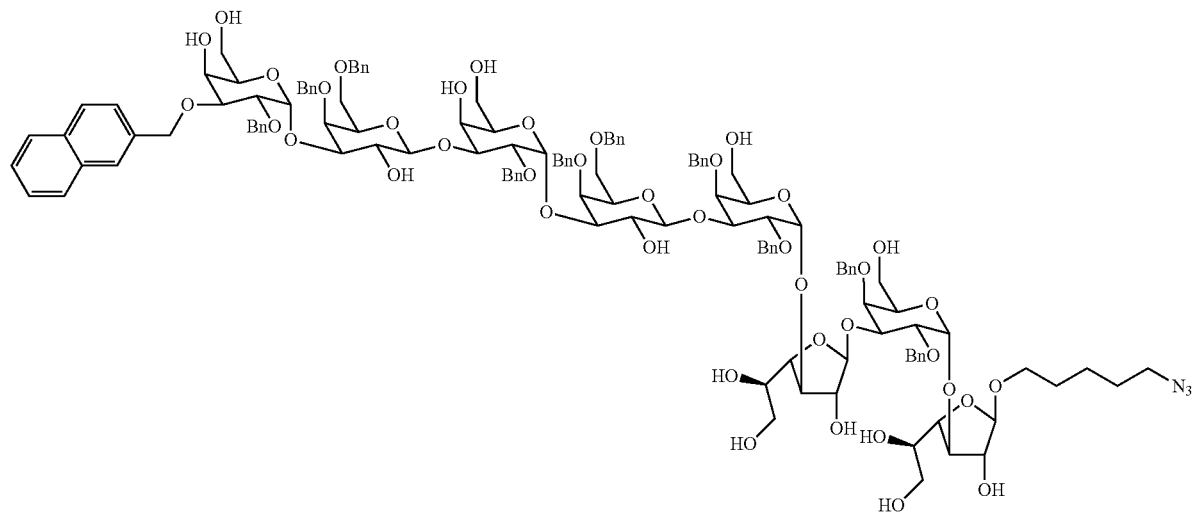

Compound 60*

Compound 59* was subjected to methanolysis according to general protocol B:

Product obtained as white solid layer (44 mg, quantitative).

MALDI-TOF Calcd for $C_{134}H_{160}N_3O_{41}$ [M+H]$^+$ 2467.0527, found 2466.377.

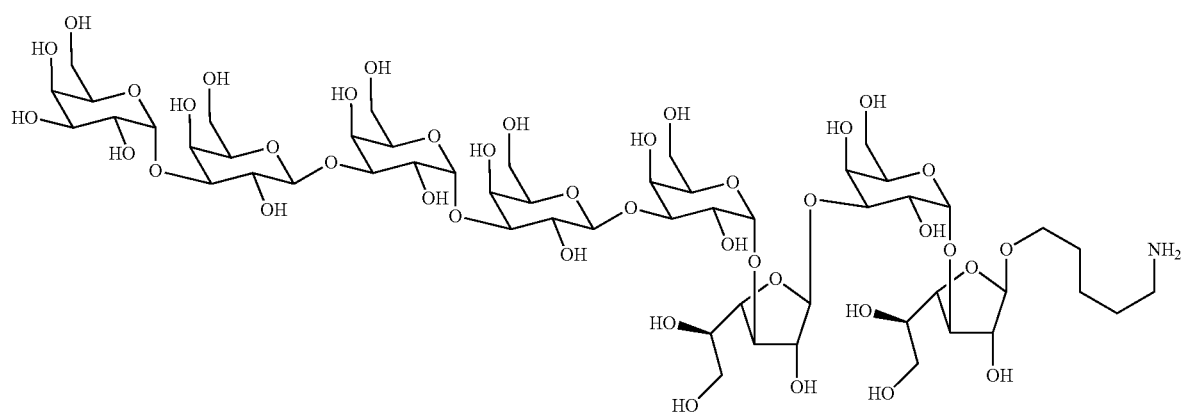

Compound 61*

Compound 60* is subjected to hydrogenation reaction according to general protocol C.

Product obtained as white fluffy solid (21 mg, 95%).

HRMS (ESI+) Calcd for $C_{53}H_{94}NO_{41}$ $[M+H]^+$ 1400.5301, found 1400.5375.

$^1$H NMR (400 MHz, Deuterium Oxide) δ 5.19 (s, 1H), 5.17 (d, J=3.9 Hz, 1H), 5.13 (d, J=3.9 Hz, 1H), 5.06 (dd, J=4.9, 3.1 Hz, 2H), 5.02 (d, J=1.6 Hz, 1H), 4.67 (d, J=7.4 Hz, 1H), 4.64 (d, J=7.6 Hz, 1H), 4.40 (dd, J=2.8, 1.3 Hz, 1H), 4.31-4.10 (m, 11H), 4.08-3.53 (m, 38H), 3.02-2.93 (m, 2H), 1.66 (dp, J=14.2, 7.1, 6.5 Hz, 4H), 1.52-1.34 (m, 2H).

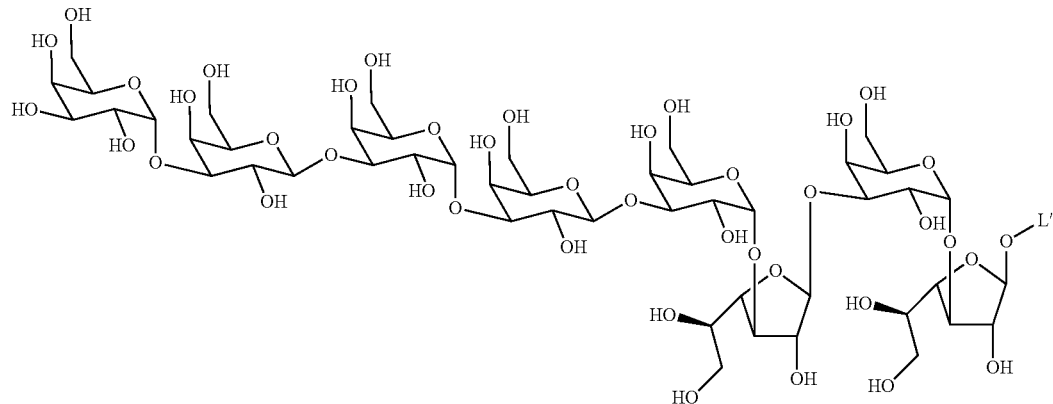

Compound 61a-l*

Compounds 61a-l* are prepared similarly to compound 61* from compound 56* and the corresponding alcohol as shown in FIG. 11.

A-2-4 Preparation of *Klebsiella pneumoniae* O1 Pentadecasaccharide

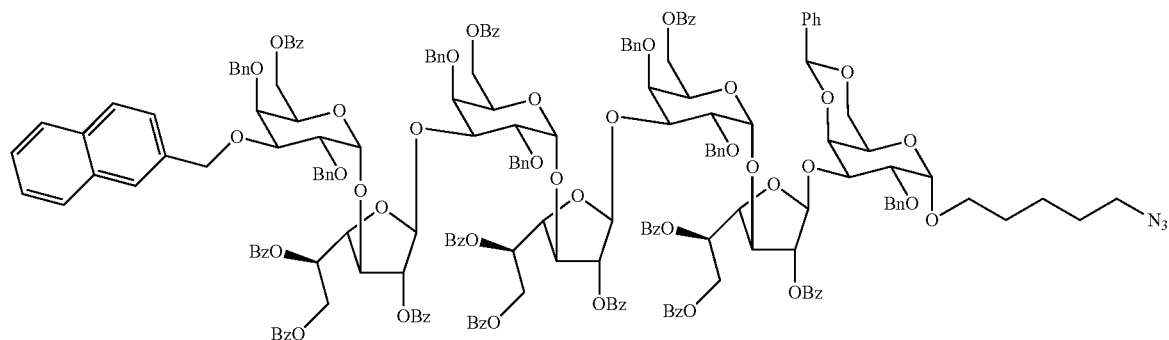

Compound 62*

Compound 62* was obtained by glycosylation reaction of compound 56* and compound 46* according to general protocol B:

Product obtained as white fluffy solid (293 mg, 81%).

MALDI-TOF Calcd for $C_{198}H_{184}N_3O_{48}{}^+$ [M+H]$^+$, 3371.2049 found 3372.109.

Compound 63*

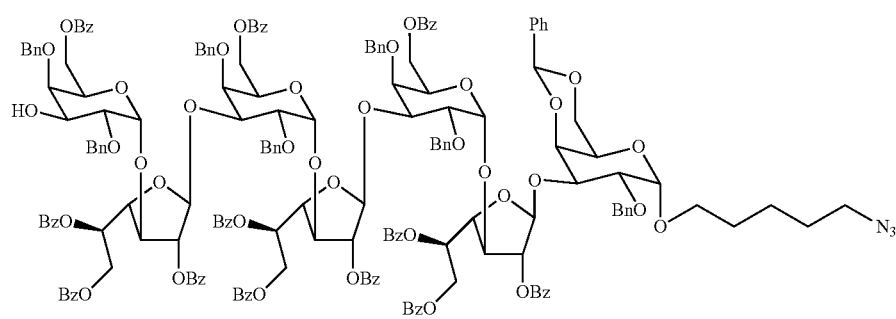

Compound 63* was obtained from compound 62* by performing removal of the Nap protecting group according to general procedure A:

Product obtained as white fluffy solid (152 mg, 63%).

MALDI-TOF Calcd for $C_{187}H_{176}N_3O_{48}{}^+$ [M+H]$^+$ 3231.1423, found 3232.291.

Compound 64*

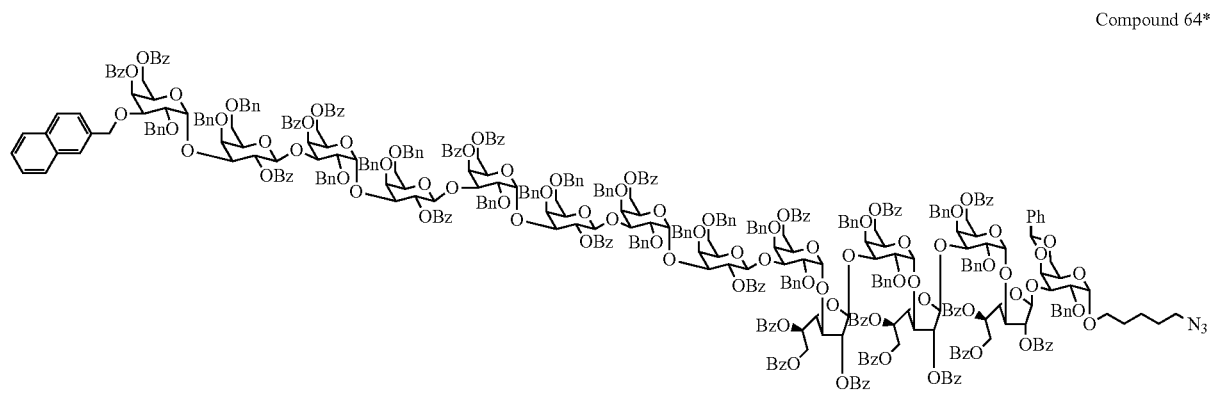

Compound 64* was obtained from compound 63* and compound 115* by glycosylation reaction according to general procedure B:

Product obtained as white fluffy solid (52 mg, 32%).

MALDI-TOF Calcd for $C_{414}H_{384}N_3O_{100}{}^+$ [M+H]$^+$ 6996.5055, found 7001.685.

Compound 65*

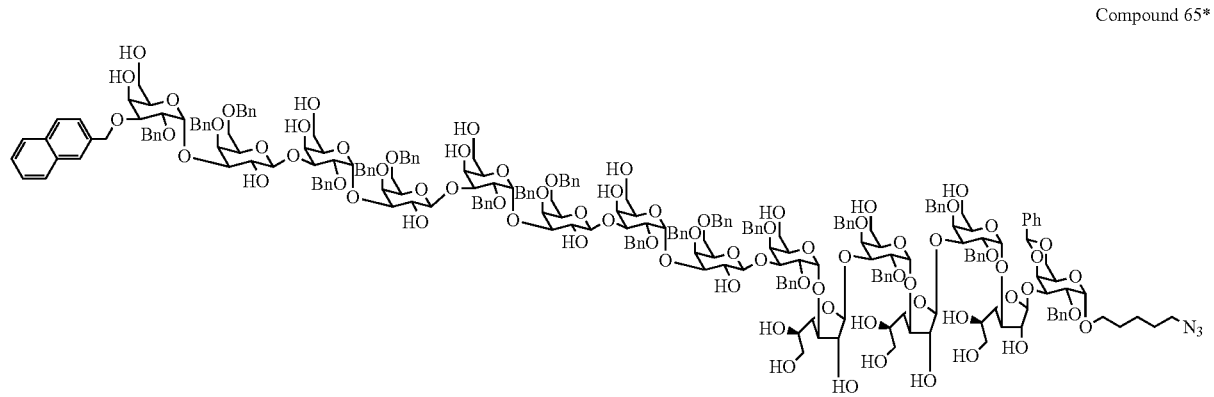

Compound 64* was subjected to methanolysis according to general protocol B:
Product obtained as white solid (25 mg, 97%).
MALDI-TOF Calcd for $C_{246}H_{288}N_3O_{76}$ [M+H]$^+$ 4499.8763, found 4500.132.

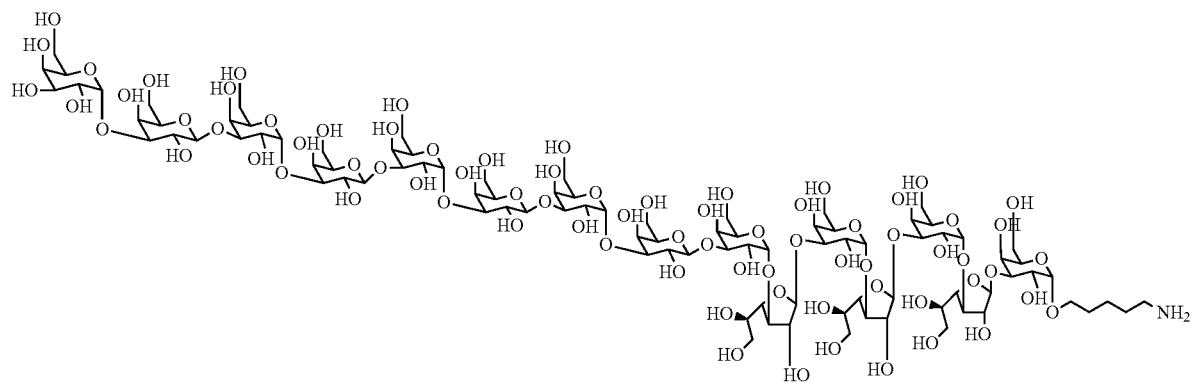

Compound 66*

Compound 65* is subjected to hydrogenation reaction according to general protocol B C.

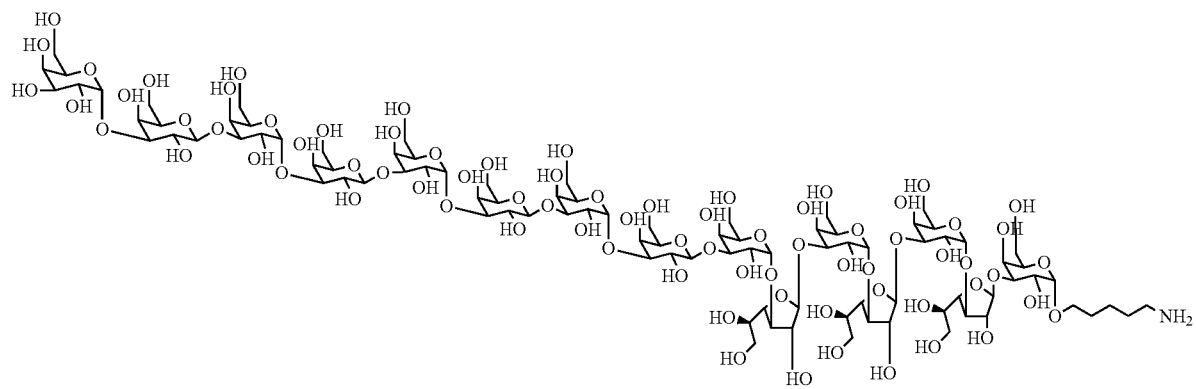

Compound 66a-l*

Compounds 66a-l* are prepared similarly to compound 66* from compound 35* and the corresponding alcohol as shown in FIG. 11.

A-3 Preparation of *Klebsiella pneumoniae* O2 (2c) Saccharides

A-3-1 Preparation of *Klebsiella pneumoniae* O2 Disaccharide

Compound 29* (15 mg, 0.013 mmol) was dissolved in anhydrous THF (1 mL) and 1M TBAF solution in THF (133 µL, 0.133 mmol) was added. The reaction mixture was stirred at room temperature for 18 h. The mixture was evaporated and the residue was partitioned between ethyl acetate and water. The aqueous layer was extracted with ethyl acetate twice, the organic layers were dried over Na$_2$SO$_4$ and evaporated to give the product as a pale yellow oil (13.2 mg). HRMS (ESI+) Calcd for $C_{50}H_{54}N_4O_{15}H^+$ 951.3658 [M+H]$^+$, 951.3650 found.

Compound 67*

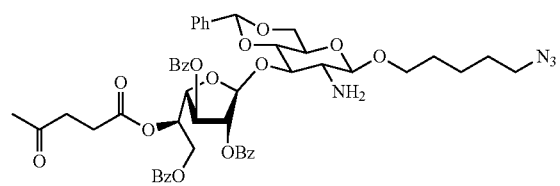

Compound 68*

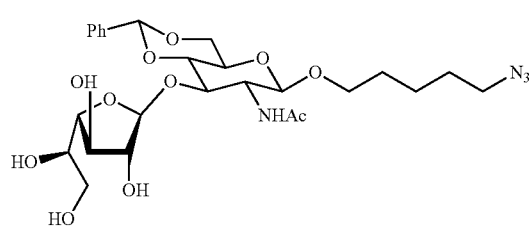

Compound 67* (13 mg, 0.014 mmol) was taken in 5 mL RBF, anhydrous toluene (2 mL) was added and evaporated under vacuum for 30 min to dryness and repeated this azeotropic drying process one times more. The material was dried under high vacuum for 30 min. It was dissolved in anhydrous DCM (1 mL) and acetic anhydride (3.88 µL, 0.041 mmol) and triethylamine (9.53 µL, 0.068 mmol) were added at 0° C. The reaction mixture was stirred at room temperature for 1.5 h. The mixture was evaporated and the residue was partitioned between ethyl acetate and sat. aqu. NaHCO$_3$ solution. The aqueous layer was extracted with ethyl acetate twice, the organic layers were dried over Na$_2$SO$_4$ and evaporated. The residue was taken in 5 mL RBF, anhydrous toluene (2 mL) was added and evaporated under vacuum for 30 min to dryness and repeated this azeotropic drying process one times more. The material was dried under high vacuum for 30 min. It was dissolved in anhydrous THF/methanol 1:1 (1 mL) and 0.5M sodium methoxide solution in methanol (1.108 mL, 0.70 mmol) was added. The reaction mixture was stirred at room temperature for 16 h. The mixture was evaporated and the residue was partitioned between ethyl acetate and water. The aqueous layer was extracted with ethyl acetate twice, the organic layers were dried over Na$_2$SO$_4$ and evaporated to give the product as a pale yellow oil (5.4 mg).

HRMS (ESI+) Calcd for $C_{26}H_{38}N_4O_{11}Na^+$ 605.2435 [M+Na]$^+$, 605.2548 found.

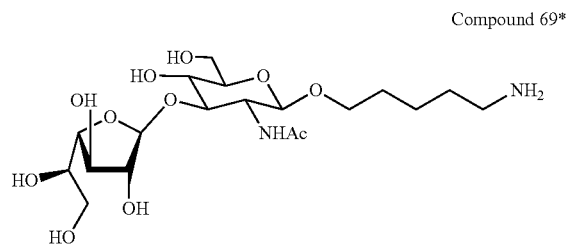

Compound 69*

Compound 68* (5 mg, 8.58 µmol) was subjected to hydrogenation reaction according to general protocol C. The mixture was purified first by SEC chromatography (G-25, water) and then by C18 Sepak column (water/acetonitrile) to give product (0.81 mg, 13.3% over 5 steps).

HRMS (ESI+) Calcd for $C_{19}H_{36}N_2O_{11}H^+$ 469.2392 [M+H]$^+$, 469.2419 found.

A-3-2 Preparation of *Klebsiella pneumoniae* O2(2c) Hexasaccharide

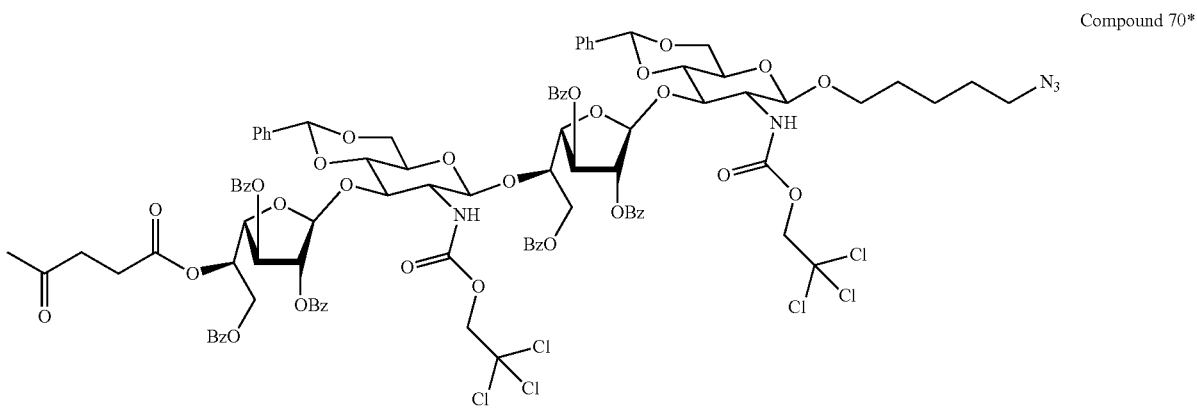

Compound 70*

Compound 28* (38 mg, 0.032 mmol) and compound 30* (30 mg, 0.029 mmol) were taken in 10 mL RBF, anhydrous toluene (4 mL) was added and evaporated under vacuum for 30 min to dryness and repeated this azeotropic drying process two times more. The material was dried under high vacuum for 12 h. Anhydrous dichloromethane (1 mL) and dried 4 A molecular sieves (MS) were added to it under nitrogen atmosphere and stirred at room temperature for 10 min and then cooled to -10° C. TMSOTf (0.53 µL, 2.92 µmol) was added to the reaction mixture and stirred while it was slowly warmed to 0° C. over a time period of 2h. TLC analysis showed the disappearance of the donor spot and the presence of a new spot. The reaction was quenched by the addition of sat. NaHCO$_3$ solution. The layers were separated and the aqueous layer was extracted with DCM. The organic layers were dried over Na$_2$SO$_4$, filtered and evaporated to give crude product. The crude was purified by column chromatography (ethyl acetate/cyclohexane) and the solvent was evaporated to give the product as a colorless oil (40.5 mg, 68.5%). HRMS (ESI+) Calcd for $C_{96}H_{93}Cl_6N_5O_{31}K^+$ 2064.6023 [M+K]$^+$, 2064.3657 found.

Compound 71*

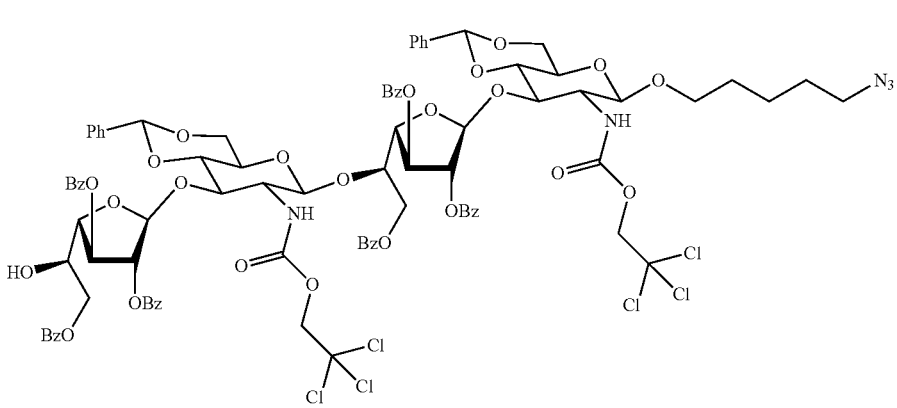

Compound 70* (40 mg, 0.020 mmol) was dissolved in anhydrous pyridine (1 mL) and hydrazine acetate (5.46 mg, 0.059 mmol) was added. The reaction mixture was stirred at room temperature for 17 h. The reaction was quenched by the addition of acetone. It was stirred for 45 minutes and then evaporated to give crude product. The crude was purified by column chromatography (ethyl acetate/cyclohexane) and the solvent was evaporated to give the product as a colorless oil (32.9 mg, 86%). HRMS (ESI+) Calcd for $C_{91}H_{87}Cl_6N_5O_{29}Na^+$ 1950.3928 [M+Na]$^+$, 1950.3255 found.

Compound 72*

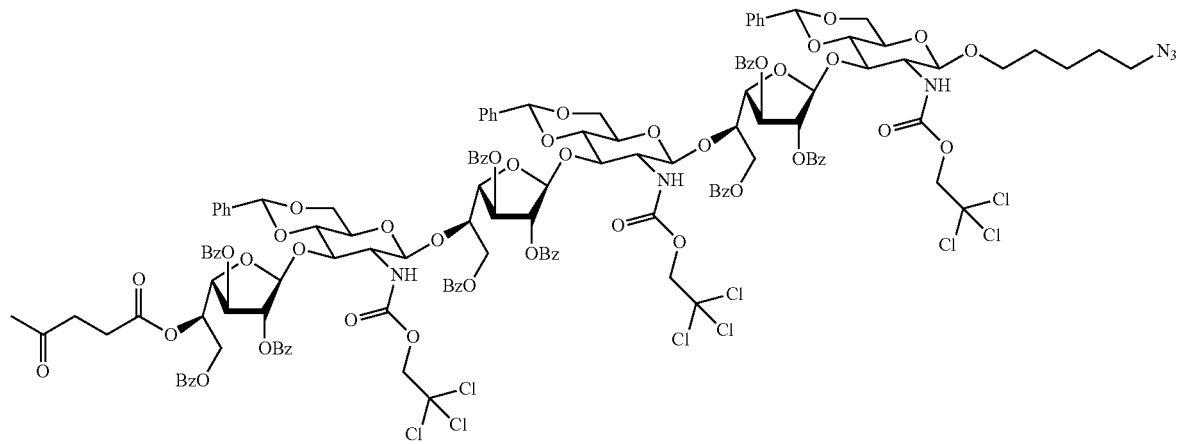

Compound 28* (20.3 mg, 0.017 mmol) and compound 71* (30 mg, 0.016 mmol) were taken in 10 mL RBF, anhydrous toluene (4 mL) was added and evaporated under vacuum for 30 min to dryness and repeated this azeotropic drying process two times more. The material was dried under high vacuum for 12 h. Anhydrous dichloromethane (1 mL) and dried 4 A molecular sieves (MS) were added to it under nitrogen atmosphere and stirred at room temperature for 10 min and then cooled to -10° C. TMS-OTf (0.28 µL, 1.56 µmol) was added to the reaction mixture and stirred while it was slowly warmed to 0° C. over a time period of 1.5h. TLC analysis showed the disappearance of the donor spot and the presence of a new spot. The reaction was quenched by the addition of sat. NaHCO$_3$ solution. The layers were separated and the aqueous layer was extracted with DCM. The organic layers were dried over Na$_2$SO$_4$, filtered and evaporated to give crude product. The crude was purified by column chromatography (ethyl acetate/cyclohexane) and the solvent was evaporated to give the product as a white solid (18.9 mg, 41.5%). HRMS (ESI+) Calcd for C$_{139}$H$_{131}$Cl$_9$N$_6$O$_{45}$Na$^+$ 2947.6132 [M+Na]$^+$, 2947.5147 found.

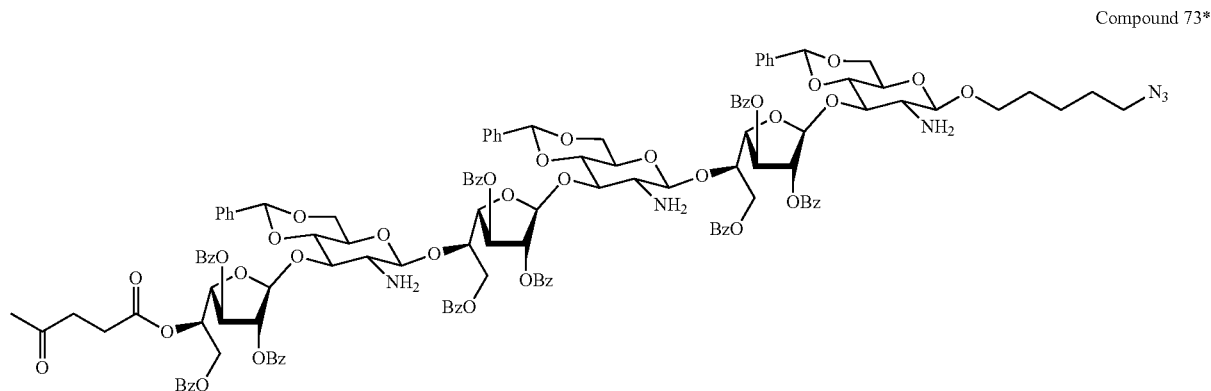

Compound 73*

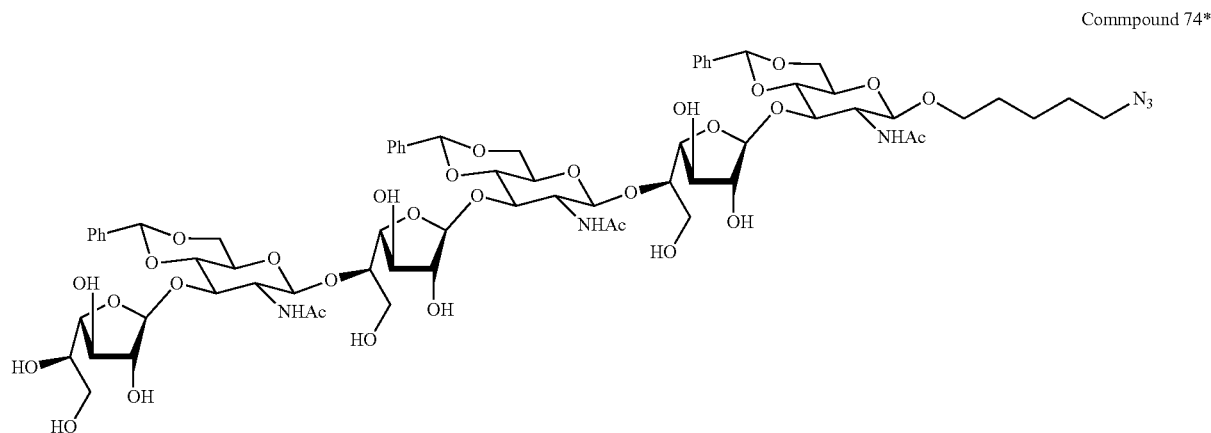

Commpound 74*

Compound 73* is prepared from compound 72* according to the procedure described for the synthesis of compound 67*.

Compound 74* is prepared from compound 73* according to the procedure described for the synthesis of compound 68*.

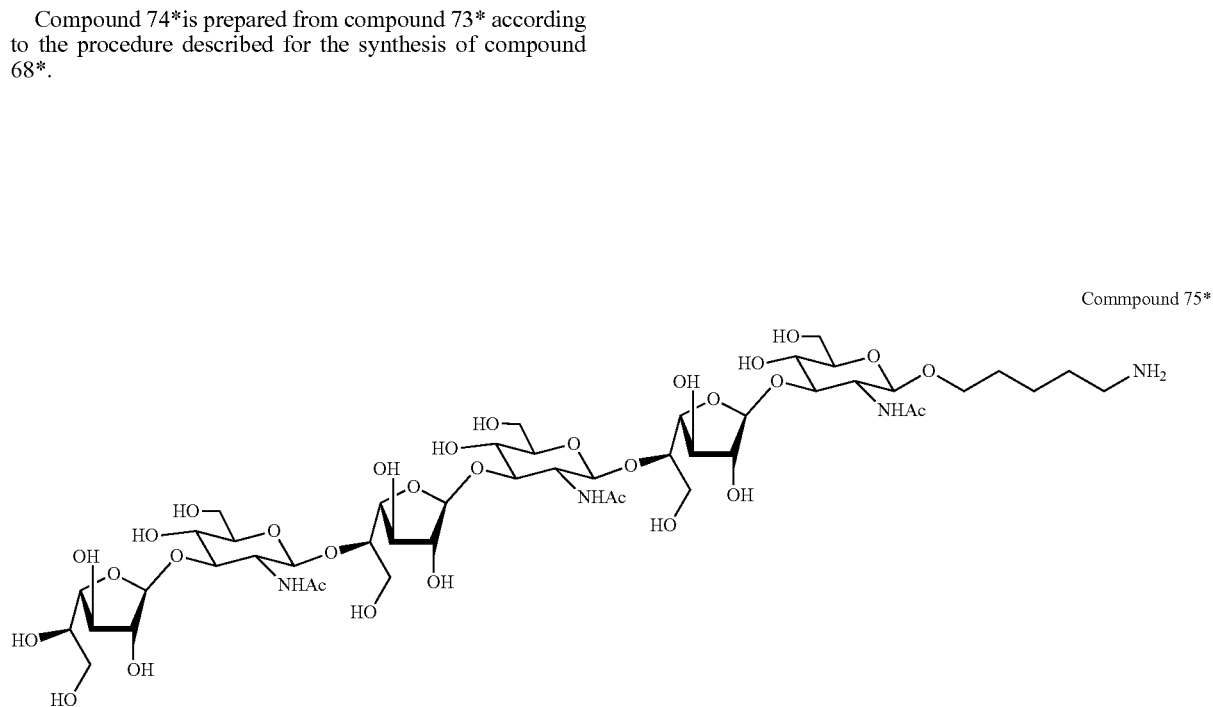

Commpound 75*

Compound 75* is prepared from compound 74* according to the procedure described for the synthesis of compound 69*.

A-4 Preparation of *Klebsiella pneumoniae* O2ac Saccharide

A-4-1 Preparation of *Klebsiella pneumoniae* O2ac Tetrasaccharide

Compound 76*

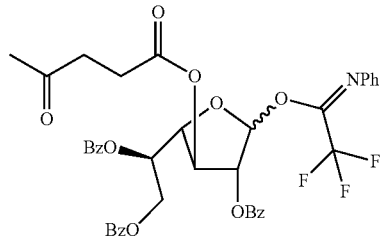

Cs$_2$CO$_3$ (2.2 g, 6.77 mmol) and 2,2,2-trifluro-N-phenyl-acetimidoyl chloride (2.1 g, 3.39 mmol) were added to a solution of lactol 36* (2.0 g, 3.39 mmol) in DCM (20 mL). The reaction mixture was stirred at room temperature and monitored by TLC. After 2 hours all the starting material was consumed and the reaction was filtered through celite and washed with DCM (20 mL). The solvent was evaporated and the product purified by column chromatography using silica-gel and ethyl acetate/cyclohexane+1% Et$_3$N as the eluent. The tubes containing the product by TLC were combined and the solvent evaporated to give the product as a colorless oil (2.58 g, 100%).

Compound 77*

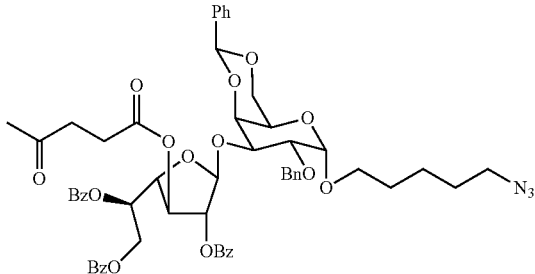

Compound 77* was prepared by glycosylation reaction between compound 76* and compound 33* according to general protocol B:

Product obtained as white fluffy solid (249 mg, 75%).

HRMS (ESI+) Calcd for C$_{57}$H$_{59}$N$_3$NaO$_{16}$ [M+Na]$^+$ 1064.3793, found 1064.3801.

Compound 78*

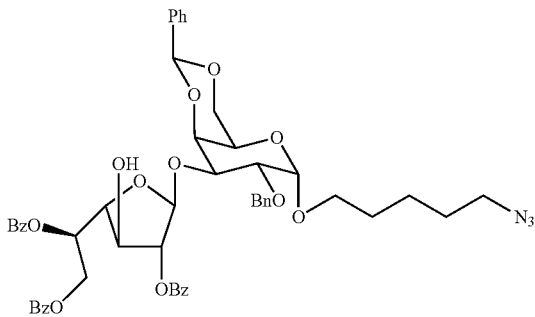

Compound 78* was prepared from compound 77* according to general protocol A for the removal of the Lev protecting group:

Product obtained as white fluffy solid (171 mg, 79%).

HRMS (ESI+) Calcd for $C_{52}H_{53}N_3NaO_{14}$ [M+Na]$^+$ 966.3425, found 966.3422.

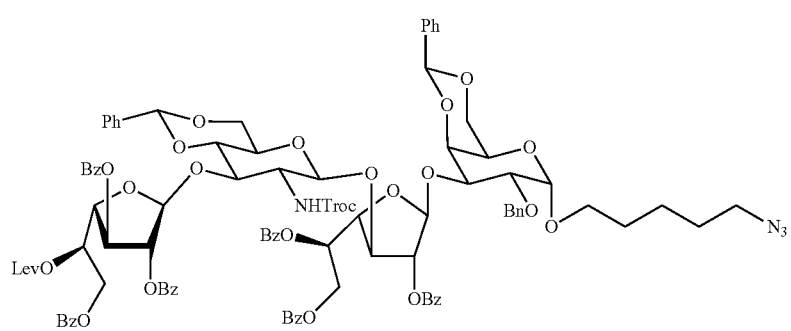

Compound 79*

Compound 79* was prepared by glycosylation reaction between compound 78* and compound 28* according to general protocol B:

Product obtained as white fluffy solid (44 mg, 46%).

MALDI-TOF Calcd for $C_{100}H_{97}Cl_3N_4NaO_{30}{}^+$ [M+Na]$^+$ 1961.5151, found 1963.686.

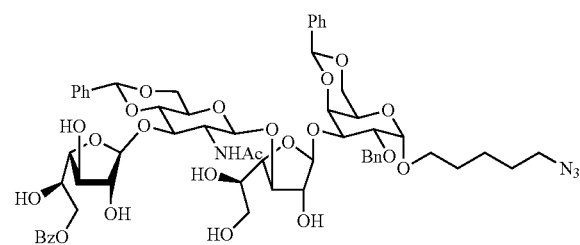

Compound 80*

Compound 79* (10 mg, 5.48 μmol) was taken in THF (2 mL), at rt, added 1M TBAF solution (0.11 mL, 0.11 mol) in THF to the reaction mixture and stirred at rt for 18 h. RM was quenched with water (5 mL) and diluted with EA (5 mL). Separated the layers, aqueous layer was extracted with EA (5 mL×3). Combined organic layer was washed with brine solution (5 mL), dried (Na$_2$SO$_4$), filtered, and evaporated in vacuum to get the crude amine product. This crude product was taken in DCM, added TEA (50 eq) and Ac2O (40 eq) to it and stirred overnight. The reaction mixture was quenched with water (5 mL) and diluted with DCM (5 mL). Separated the layers, aqueous layer was extracted with DCM (5 mL×3). Combined organic layer was washed with brine solution (5 mL), dried (Na$_2$SO$_4$), filtered, and evaporated in vacuum to get the crude NHAc product. This crude mixture was then taken in THF-MeOH (1:1 mL) at rt, added excess 0.5 M NaOMe solution in methanol to it and continued stirring at 55° C. for 18 h. RM was evaporated in vacuum. Diluted with EA and water. Acidified with AcOH till neutral pH. Extracted with EA. Combined organics were washed with brine solution, dried (Na$_2$SO$_4$), filtered, and evaporated in vacuum to get crude product as pale yellowish layer (5 mg, 84%, over three steps).

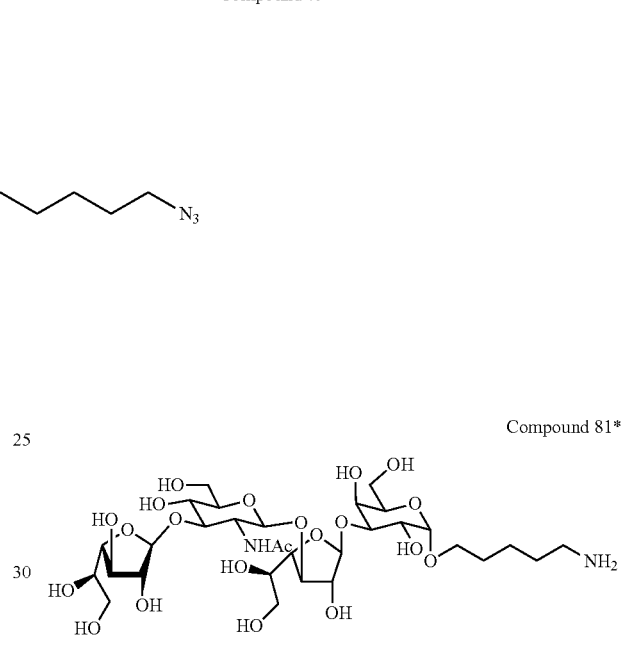

Compound 81*

Compound 80* was subjected to hydrogenation reaction according to general protocol C:

Product obtained as white fluffy solid.

HRMS (ESI+) Calcd for $C_{31}H_{57}N_2O_{21}$ [M+H]$^+$ 793.3454, found 793.3455.

A-4-2 Preparation of *Klebsiella pneumoniae* O2ac Octasaccharide

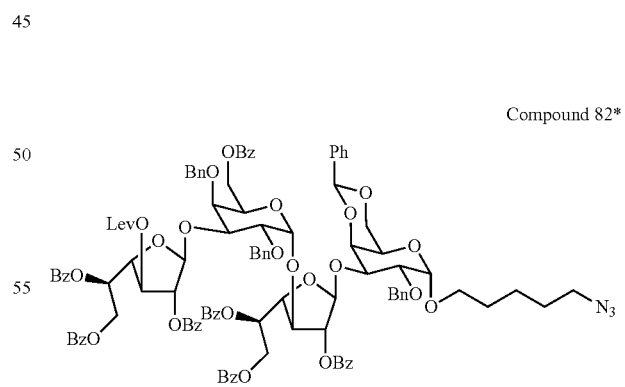

Compound 82*

Compound 82* was prepared by glycosylation reaction between compound 76* and compound 46* according to general protocol B:

Product obtained as colorless glassy layer (155 mg, 73%).

MALDI-TOF Calcd for $C_{111}H_{108}N_3O_{30}{}^+$ [M+H]$^+$ 1962.7018, found 1963.426.

Compound 83*

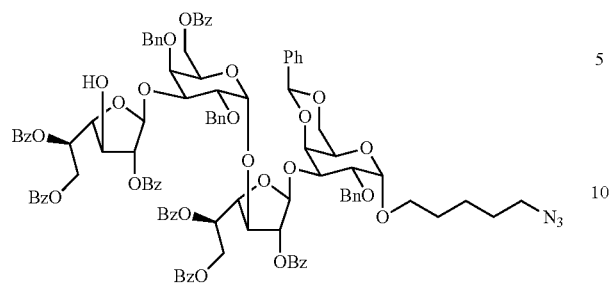

Compound 83* was prepared from compound 82* according to general protocol A for the removal of the Lev protecting group:
Product obtained as white fluffy solid (140 mg, 98%).
MALDI-TOF Calcd for $C_{106}H_{102}N_3O_{28}^+$ [M+H]$^+$ 1864.6650, found 1864.973.

Compound 84*

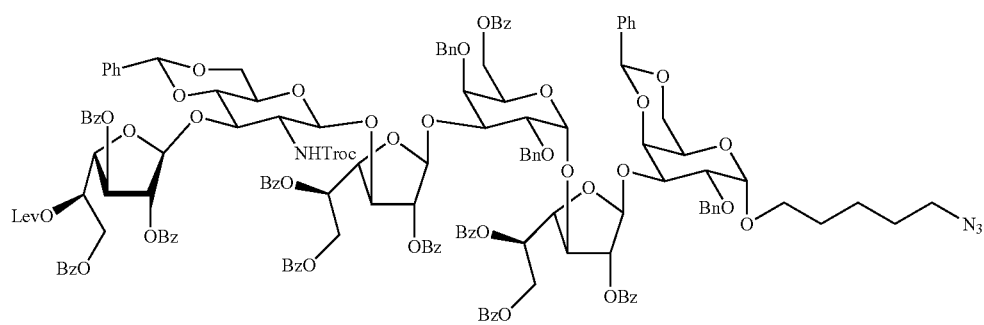

Compound 84* was prepared by glycosylation reaction between compound 83* and compound 28* according to general protocol B:
Product obtained as colorless glassy layer (85 mg, 55%).
MALDI-TOF Calcd for $C_{154}H_{146}Cl_3N_4O_{44}^+$ [M+H]$^+$ 2859.8376, found 2859.868.

Compound 85*

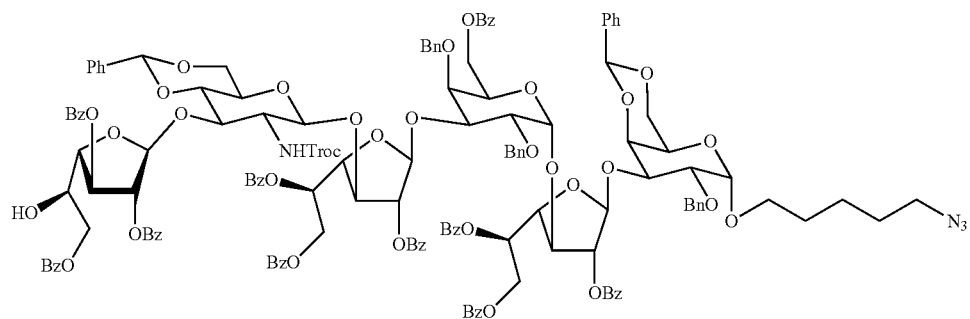

Compound 85* was prepared from compound 84* according to general protocol A for the removal of the Lev protecting group:

Product obtained as white fluffy solid (70 mg, 91%).

MALDI-TOF Calcd for $C_{149}H_{140}Cl_3N_4O_{42}^+$ $[M+H]^+$ 2761.8008, found 2763.646.

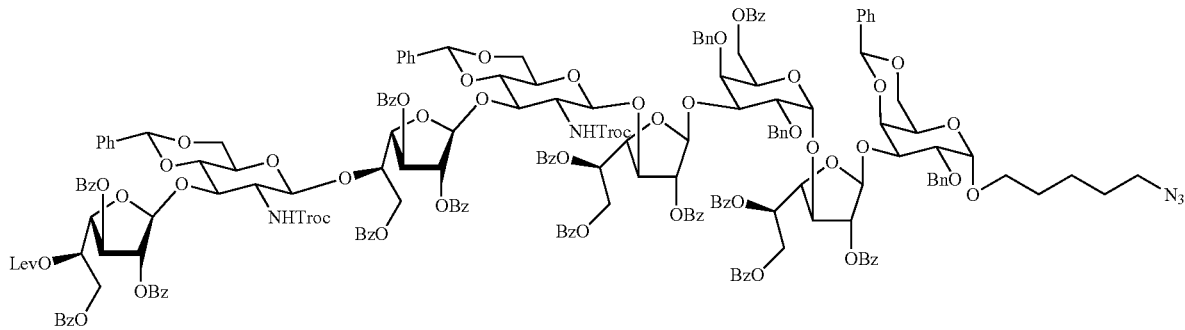

Compound 86*

Compound 86* was prepared by glycosylation reaction between compound 85* and compound 28* according to general protocol B:

Product obtained as colorless glassy layer (31 mg, 46%).

MALDI-TOF Calcd for $C_{197}H_{184}Cl_6N_5O_{58}^+$ $[M+Na]^+$ 3756.9733, found 3759.266.

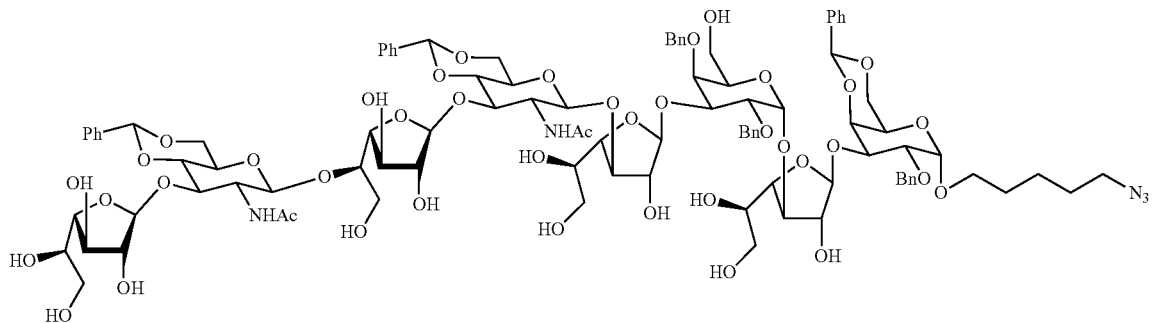

Compound 87*

Compound 87* is prepared from compound 86* according to the procedure described for the synthesis of compound 80*.

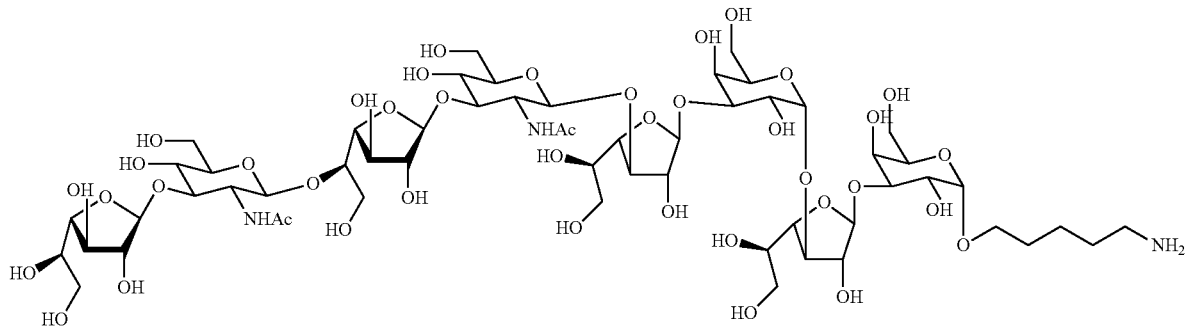

Compound 88*

Compound 87* is subjected to hydrogenation reaction according to general protocol C.

A-4-3 Preparation of *Klebsiella pneumoniae* O2ac Hexasaccharide

Compound 88*

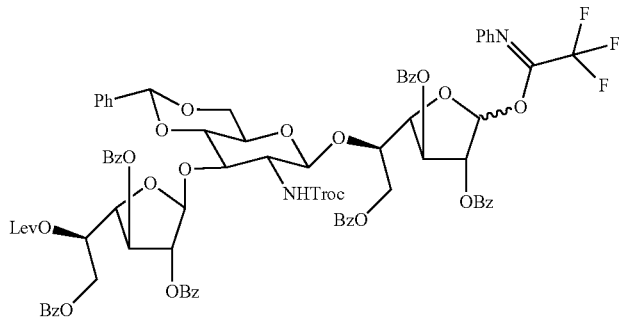

Compound 89*

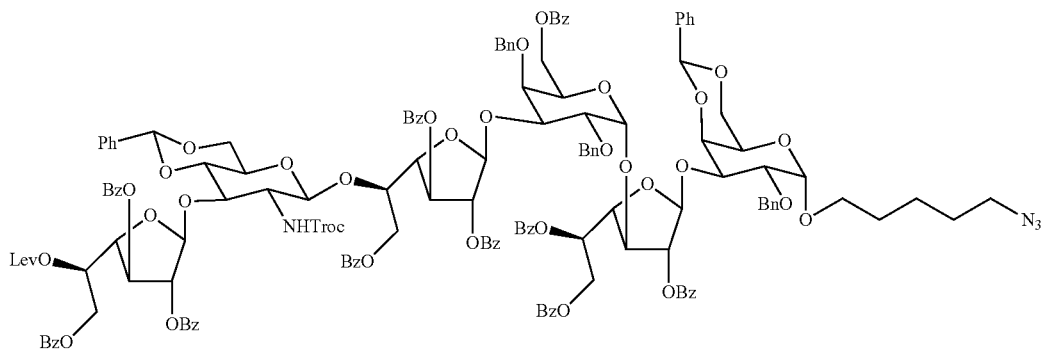

Compound 89* was obtained from compound 88* by glycosylation reaction with compound 46* according to general procedure B:

Product obtained as colorless glassy layer (9 mg, 17%).

MALDI-TOF Calcd for $C_{154}H_{145}Cl_3KN_4O_{44}^+$ [M+K]$^+$ 2897.7934, found 2898.015.

Compound 90*

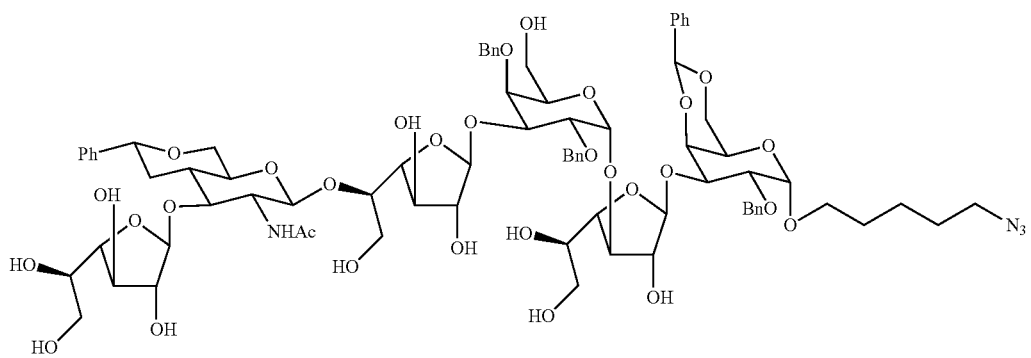

Compound 90* is prepared from compound 89* according to the procedure described for the synthesis of compound 80*.

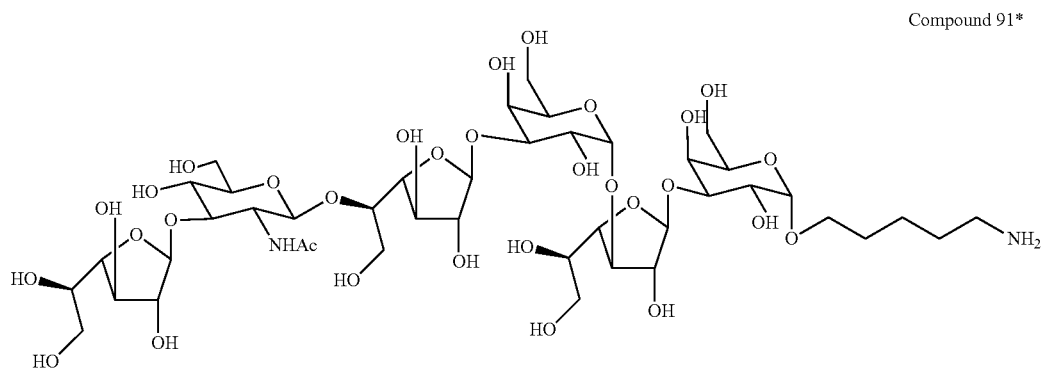 [SMILES: CC(=O)NC1C(O[C@H](CO)C2OC(OC3C(O)C(CO)OC(OC4C(O)C(OC5C(O)C(CO)OC(OCCCCCN)C5O)OC4[C@H](O)CO)C3O)C(O)C2O)OC(CO)C(O)C1OC1OC([C@H](O)CO)C(O)C1O]

Compound 91*

Compound 90* is subjected to hydrogenation reaction according to general protocol C.

A-5 Preparation of *Klebsiella pneumoniae* O2aeh Saccharide

Compound 92*

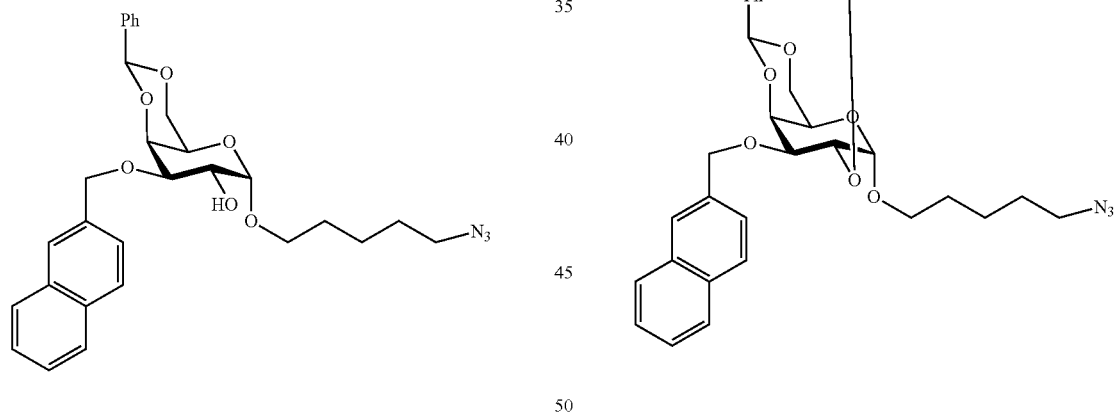

Compound 93*

To a solution of the thioglycoside 1* (1 g, 1.998 mmol) in DCM (26 mL) was added 4 A MS. Dimethylformamide (0.928 mL, 11.99 mmol) was added and the solution stirred for 30 min. Then, NIS (0.674 g, 3.00 mmol) was added, the reaction was cooled to 0° C. and TMSOTf (0.397 mL, 2.197 mmol) was added. The reaction was warmed to room temperature over 2.5 h. TLC (50% ethyl acetate/cyclohexane) showed complete consumption of the starting material. The reaction was diluted with DCM (20 mL), and washed with 10% $Na_2S_2O_3$ (10 mL) and sat. $NaHCO_3$ (10 mL) and the organic layer separated, dried over $Na_2SO_4$ and the solvent evaporated to give the crude material. Automated purification using silica gel and ethyl acetate/cyclohexane as the eluent gave the product as a colorless oil (360 mg, 35%). HRMS (ESI+) Calcd for $C_{29}H_{33}N_3O_6Na^+$ [M+Na]$^+$ 542.2267, found 542.2293.

To a solution of compound 9* (687 mg, 1.039 mmol) and compound 92* (360 mg, 0.693 mmol) in toluene:dioxane (3:1, 13.5 mL) was added 4 A MS and the mixture let stir at room temperature for 2 h. Then, NIS (312 mg, 1.386 mmol) was added and the reaction mixture cooled to 0° C. TMSOTf (0.013 mL, 0.069 mmol) was added and the reaction mixture stirred for 1 h at 0° C. The reaction was diluted with ethyl acetate (10 mL), filtered and extracted with $Na_2SO_3$ and $NaHCO_3$ sat. aq. sol. The organic layer was dried over $Na_2SO_4$ and the solvent concentrated in rotavapor. Purification by automated purification system (Ethyl acetate in cyclohexane, 0-50%) afforded the product along with some impurities (685 mg, 92%). HRMS (ESI+) Calcd for $C_{63}H_{63}N_3O_{13}Na^+$ [M+Na]$^+$ 1092.4259, found 1092.4306.

Compound 94*

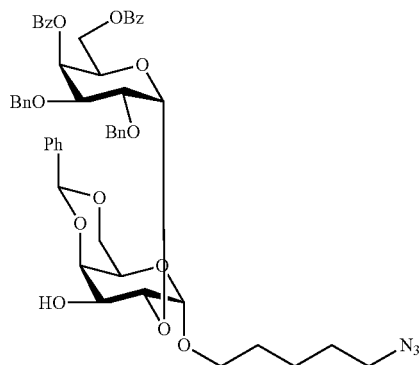

To a solution of compound 93* (250 mg, 0.234 mmol) in DCM:Phosphate Buffer 7.4 (2:1, 9 mL) in a 25 mL RBF was added 2,3-dichloro-5,6-dicyano-1,4-benzoquinone (80 mg, 0.350 mmol) at 0° C. The reaction mixture was stirred for 1.5 h at room temperature. Reaction was diluted with DCM (10 mL) and quenched with sat. NaHCO$_3$ (5 mL). The organic layer was washed with sat. NaHCO$_3$ (5 mL) and brine (5 mL). The organic layer was dried over Na$_2$SO$_4$ (0.2 g), filtered, and the filtrate was concentrated under vacuum for 15 min to obtain the crude product. The crude product was purified by automated flash chromatography using silica (ethyl acetate/cyclohexane). Concentration of solvent from test tubes containing the product (based on TLC) in vacuum resulted in a colorless oil (178 mg, 82%). HRMS (ESI+) Calcd for $C_{52}H_{55}N_3O_{13}Na^+$ [M+Na]$^+$ 952.3633, found 952.3665.

Compound 95*

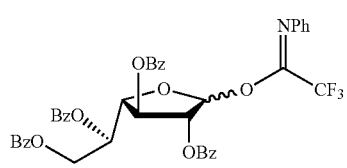

Compound 95* was prepared as follows:

To a solution of thioglycoside 10*(1 g, 1.45 mmol) dissolved in DCM:H$_2$O (1:0.3, 14 mL) was added NBS (0.775 g, 4.36 mmol) at room temperature. The reaction was stirred at the same temperature for 1 h. TLC (50% ethyl acetate/cyclohexane) showed complete consumption of the starting material. The reaction was diluted with DCM (20 mL), and washed with 10% Na$_2$S$_2$O$_3$ (10 mL) and sat. NaHCO$_3$ (10 mL) and the organic layer separated, dried over Na$_2$SO$_4$ and the solvent evaporated to give the crude material. Automated purification (Combiflash) using silica gel and ethyl acetate/cyclohexane as the eluent gave the lactol product as a colorless oil (0.85 g, 98%). Cs$_2$CO$_3$ (1.3 mg, 4.02 mmol) and 2,2,2-trifluro-N-phenyl-acetimidoyl chloride (0.557 mg, 2.68 mmol) were added to a solution of lactol (0.8 g, 1.34 mmol) in DCM (5 mL). The reaction mixture was stirred at room temperature and monitored by TLC. After 2 hours all the starting material was consumed and the reaction was filtered through celite and washed with DCM (20 mL). The solvent was evaporated and the product purified by column chromatography using silica-gel (ethyl acetate/cyclohexane+1% Et$_3$N). The tubes containing the product by TLC were combined and the solvent evaporated to give the product as a colorless oil (850 mg, 83%).

Compound 96*

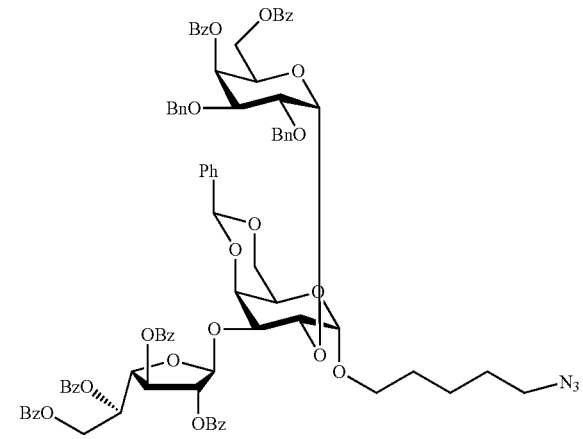

To a solution of compound 95* (198 mg, 0.258 mmol) and compound 94* (120 mg, 0.129 mmol) in DCM (3 mL) was added 4 A MS and the mixture let stir at room temperature for 20 min. Then, the reaction mixture was cooled to -50° C., TMSOTf (0.005 mL, 0.028 mmol) was added and the reaction mixture warmed to -5° C. over 2 h. The reaction was filtered and the solvent evaporated. Purification by automated purification system (Ethyl acetate in cyclohexane) afforded the product (120 mg, 62%). HRMS (ESI+) Calcd for $C_{86}H_{81}N_3O_{22}Na^+$ [M+Na]$^+$ 1531.5234, found 1531.5304.

Compound 97*

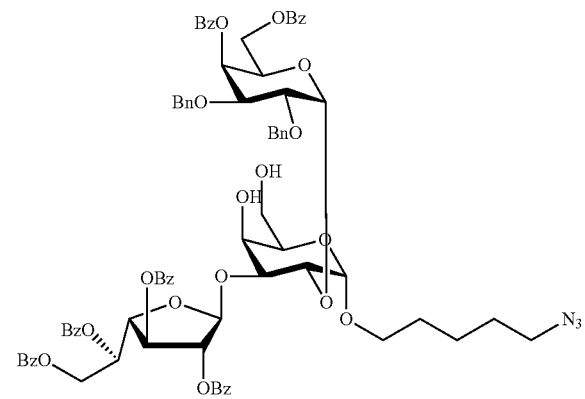

Compound 96* (120 mg, 0.080 mmol) was dissolved in anhydrous DCM (2 mL) and ethanethiol (0.071 mL, 0.955 mmol) and pTSOH (18 mg, 0.095 mmol) were added sequently. The mixture was stirred at room temperature for 30 min. TLC analysis showed the conversion of the starting material and a new more polar spot. The reaction was quenched with triethylamine (0.2 mL) and the solvent evaporated to give crude product as a pale yellow oil. The crude was purified by automated column chromatography using cyclohexane/ethyl acetate to give the product as an oil (110 mg, 97%). HRMS (ESI+) Calcd for $C_{79}H_{77}N_3O_{22}Na^+$ [M+Na]$^+$ 1442.4896, found 1441.4948.

Compound 98*

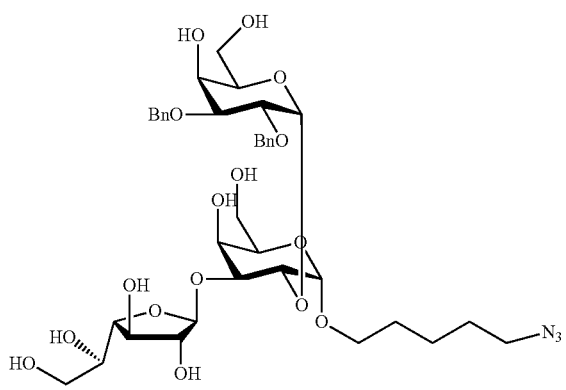

Sodium methoxide solution in MeOH 25% w/w (0.319 mL, 1.478 mmol) was added to a solution of compound 97* (105 mg, 0.074 mmol) in a mixture of MeOH:THF (2:1, 1.5 mL). The reaction was stirred at the same temperature for 20h. The reaction was quenched by the addition of AcOH (1 mL) and the solvent evaporated. The crude material was loaded in isolute. Purification by silica gel chromatography using the eluent sequence: 1) cyclohexane, 2) Ethyl acetate and 3) MeOH in DCM 5%, afforded the product after evaporation of the solvent as a white solid (29 mg, 49%).

Compound 99*

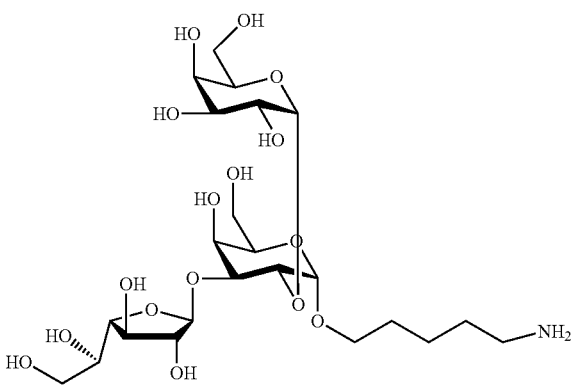

Compound 98* (29 mg, 0.036 mmol) was dissolved in a mixture of DCM:tBuOH:H2O (0.4:1.6:0.4, 2.4 mL). PdC (25 mg, 0.023 mmol) was added and the reaction mixture was purged with hydrogen (5 times) and the reaction let stir under hydrogen pressure (5 bar) for 22 h. Then, the reaction mixture was filtered through PTFE filter using H$_2$O:ACN (1:1), the organic solvents evaporated in rotavapor and the crude material was lyophilized. The crude was purified by SepPack using miliQ H$_2$O to give the product as a white solid (17.7 mg, 82%). Calcd for $C_{23}H_{44}NO_{16}$ [M+H]$^+$ 590.2660, found 590.2656. $^1$H NMR (400 MHz, D$_2$O) δ 5.21 (d, J=3.5 Hz, 1H), 5.18 (d, J=1.9 Hz, 1H), 5.11 (d, J=3.7 Hz, 1H), 4.16-4.05 (m, 4H), 4.06-3.90 (m, 5H), 3.89-3.49 (m, 11H), 2.99 (t, J=1.9 Hz, 2H), 1.73-1.62 (m, 4H), 1.51-1.41 (m, 2H), $^{13}$C NMR (101 MHz, D$_2$O) δ 108.9, 95.2, 95.1, 82.5, 81.8, 77.3, 75.1, 71.0, 70.7, 70.6, 70.0, 69.6, 69.4, 69.3, 68.2, 67.8, 62.7, 61.2, 39.4, 28.0, 26.5, 22.4.

A-6 Preparation of *Klebsiella pneumoniae* Galactan-II Saccharide

A-6-1 Preparation of *Klebsiella pneumoniae* Galactan-II Hexasaccharide

Compound 100*

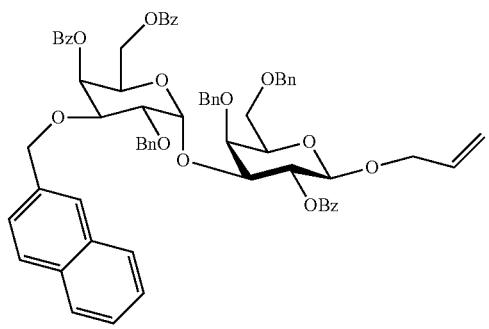

Compound 19* (85 mg, 0.119 mmol) and compound 18* (50 mg, 0.099 mmol) were taken in 10 mL RBF added anhydrous Toluene (5 mL) and evaporated under vacuum for 30 min to dryness and repeated this azeotropic drying process two times more. The material was dried under high vacuum for 12h. Then anhyd. Anhydrous didchloromethane (1 mL) and dried 4 A molecular sieves (MS) were added to it under nitrogen atmosphere and stirred at room temperature for 45 min and then cooled to 0° C. (ice-water mixture in isotherm). NIS (31 mg, 0.139 mmol) and triflic acid (0.8 μL, 9.91 μmol) were added to the reaction mixture and stirred for 15 min. Then it was slowly warmed to 10° C. for 0.5 h and then stirred at RT for 1h. TLC analysis showed the disappearance of the donor spot and the presence of a new spot. The reaction was quenched at 5° C. by the addition Triethylamine. The crude compound was extracted into DCM and washed with sat. Na$_2$S$_2$O$_3$ solution, sat. NaHCO$_3$ solution, and brine. After separation, organic layer was dried over anhydrous Na$_2$SO$_4$, filtered and concentrated. The crude organic product was purified by a flash chromatography system using cyclohexane/ethyl acetate gradient system and gave pale yellow solid (70 mg, 63%). HRMS (ESI+) Calcd for $C_{68}H_{64}O_{14}Na^+$ [M+Na]$^+$ 1127.4194, found 1127.4009.

Compound 101*

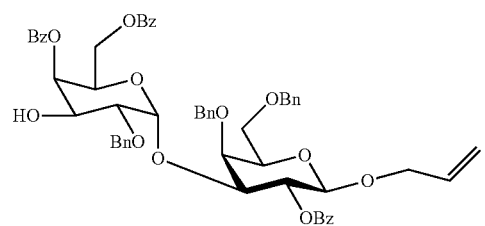

Disaccharide 100* (0.14 g, 0.127 mmol) was transferred to a stirring solution of DCM (2.8 mL) and Phosphate buffer ph 7.4 (1.4 mL) in a 10 mL RBF under nitrogen atmosphere. DDQ (0.129 g, 0.570 mmol) was added slowly over a period of 2.5 h, TLC analysis (40% ethyl acetate/cyclohexanes)

showed the presence of a new spot slightly polar to the major amount of starting material even after 2 h, so stirred the reaction mixture for additional 4 h at RT. TLC showed the absence of the starting material, but presence of product as well as a faint polar spot. The reaction was quenched by the addition of sat. aq. NaHCO$_3$ (10 mL) and extracted into DCM. The combined organic layer was washed with sat. NaHCO$_3$ solution (10 mL), brine (10 mL), dried over anhyd. sodium sulfate, filtered and concentrated under vacuum at 30-35° C. bath temperature of rotary evaporator in a 100 mL RBF for 1 h to obtain the crude as a pale yellow oil. Purification was done on silica gel column chromatography using ethyl acetate in cyclohexane. Dichloromethane was then added to this and continued evaporation under vacuum for 30 min resulted in a colorless transparent gummy liquid which was dried under high vacuum for 16-18 h to form a fluffy white solid (81 mg, 66%). HRMS (ESI+) Calcd for C$_{57}$H$_{56}$O$_{14}$Na$^+$ [M+Na]$^+$ 987.3569, found 987.3387.

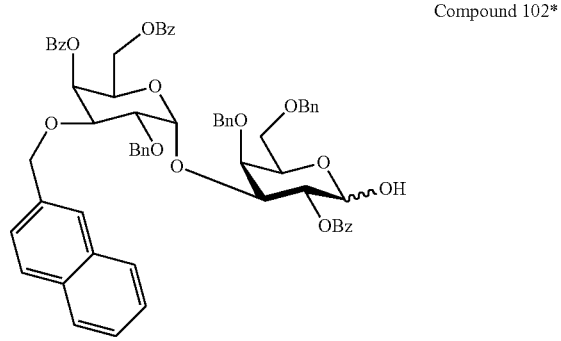

Compound 102*

(1,5-Cyclooctadiene)(pyridine)(tricyclohexylphosphine)-Ir(I)]PF$_6$ (7.65 mg, 9.05 μmol) was dissolved in tetrahydrofuran (2 mL) and nitrogen was bubbled through the solution for two minutes at room temperature while the red colored catalyst dissolved. The solution was then purged with hydrogen for two minutes, by which time the red solution changed to colorless and the solution was stirred for 15 min under hydrogen. The solution of the active catalyst was then added to a solution of compound 100* (0.1 g, 0.09 mmol) in tetrahydrofuran (1 mL) under nitrogen via a syringe and stirred for 2 h at room temperature. The reaction mixture was quenched with saturated aqueous NaHCO$_3$ solution (5 mL) and extracted with dichloromethane (3×5 mL). Combined organic layers were washed with brine (5 mL), dried over Na$_2$SO$_4$, filtered and evaporated to get the allyl isomerized compound (isomerization confirmed by $^1$H NMR). The vinyl substrate was then taken up in a mixture of tetrahydrofuran:water (2:1, 3 mL) and iodine (46 mg, 0.18 mmol) was added at room temperature. The brown colored solution was stirred for 2 h before quenching with 10% solution of Na$_2$S$_2$O$_3$ solution (5 mL). The aqueous phase was extracted with ethyl acetate (3×5 mL) and the combined organic layers were dried over Na$_2$SO$_4$, filtered and the solvent evaporated. Purification by flash column chromatography (ethyl acetate in cyclohexane 30%) afforded the product as a yellow solid (60 mg, 63%). HRMS (ESI+) Calcd for C$_{65}$H$_{60}$O$_{14}$Na$^+$ [M+Na]$^+$ 1087.3881, found 1087.3766.

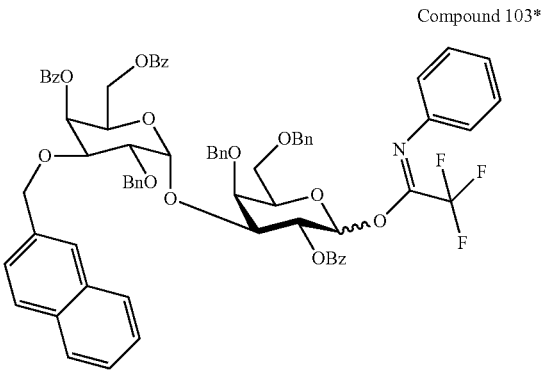

Compound 103*

Compound 102* (60 mg, 0.06 mmol) was dissolved in anhydrous dichloromethane (0.7 mL) Cs$_2$CO$_3$ (37 mg, 0.113 mmol) and 2,2,2-trifluoro-N-phenylacetimidoyl chloride (0.03 mL, 0.17 mmol) were added to the solution. The reaction mixture was stirred at room temperature overnight. TLC analysis showed a complete conversion of the starting material and new spots. The reaction mixture was filtrated through a Celite pad (1 cm). The pad was washed with DCM (20 mL), the filtrate concentrated under reduced pressure and dried under high vacuum to give a pale yellow oil. Purification was done by flash silica gel column chromatography (Cyclohexane/Ethyl acetate+0.1% Et$_3$N) and afforded a yellow foam (60 mg, 86%). HRMS (ESI+) Calcd for C$_{73}$H$_{64}$F$_3$NO$_{14}$Na$^+$ [M+Na]$^+$ 1258.4177, found 1258.3969.

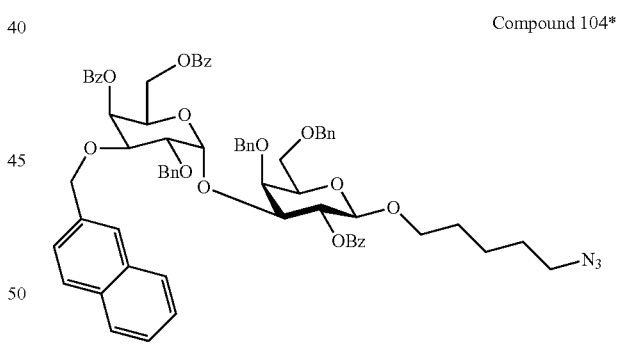

Compound 104*

Compound 103* (13 mg, 0.097 mmol) and 5-azidopentanol (60 mg, 0.049 mmol) were taken in 10 mL RBF added anhydrous toluene (20 mL) and evaporated under vacuum for 30 min to dryness and repeated this azeotropic drying process two times more. The material was dried under high vacuum for 12 h. Then anhyd. dichloromethane and dried 4 A molecular sieves (MS) were added to it under nitrogen atmosphere and stirred at room temperature for 45 min and then cooled to 0° C. TMS-OTf (1.8 μL, 9.7 μL) were added to the reaction mixture and stirred for 30 min. Then it was slowly warmed to 10° C. for 0.5 h and then stirred at RT for 1h. TLC analysis showed the disappearance of the donor spot and the presence of a new spot. The reaction was quenched at 5° C. by the addition of triethylamine. The crude organic product was purified by flash chromatography system using cyclohexane/ethyl acetate gradient system. The collected fraction were concentrated in vacuo and then was dried under high vacuum for 16 h to afford the product as a white foam (35 mg, 61%). HRMS (ESI+) Calcd for $C_{70}H_{69}O_{14}Na^+$ [M+Na]$^+$ 1198.4677, found 1198.4798.

Compound 105*

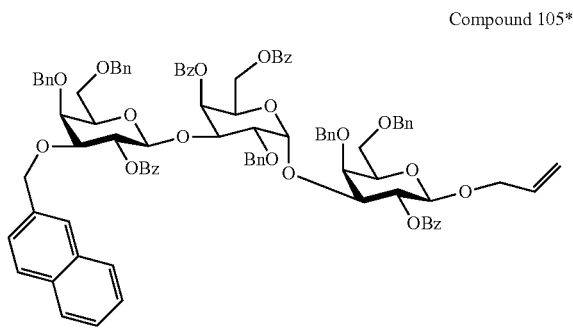

Compound 21* (355 mg, 0.458 mmol) and compound 101* (0.340 mg, 0.352 mmol) were taken in 25 mL RBF added anhydrous toluene (10 mL) and evaporated under vacuum for 30 min to dryness and repeated this azeotropic drying process two times more. The starting material (0.355 g, 0.458 mmol) material was dried under high vacuum for 12 h. Then anhyd. dichloromethane (7 mL) and dried 4 A molecular sieves (MS) were added to it under nitrogen atmosphere and stirred at room temperature for 45 min and then cooled to 0° C. TMS-OTf (13 µL, 0.07 mmol) was added to the reaction mixture and stirred for 30 min. Then it was slowly warmed to 10° C. for 0.5 h and then stirred at RT for 1h. TLC analysis showed the disappearance of the donor spot and the presence of a new spot. The reaction was quenched at 5° C. by the addition of triethylamine. The crude organic product was purified by flash chromatography system using cyclohexane/ethyl acetate gradient system. The collected fraction were concentrated in vacuo and then was dried under high vacuum for 16 h to afford the product as a white foam (0.380 g, 70%). HRMS (ESI+) Calcd for $C_{95}H_{90}O_{20}Na^+$ [M+Na]$^+$ 1573.5923, found 1573.5657.

Compound 106*

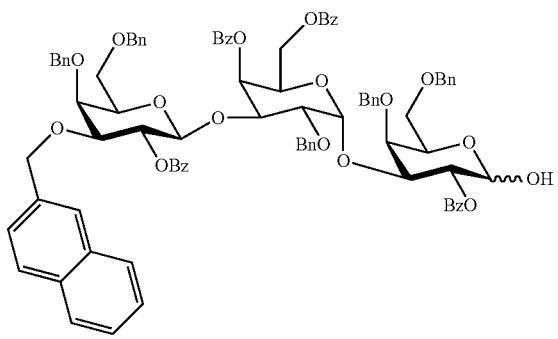

1,5-Cyclooctadiene)(pyridine)(tricyclohexylphosphine)-Ir(I)]PF$_6$ (18 mg, 0.02 mmol) was dissolved in tetrahydrofuran (4 mL) and nitrogen was bubbled through the solution for two minutes at room temperature while the red colored catalyst dissolved. The solution was then purged with hydrogen for two minutes, by which time the red solution changed to colorless and the solution was stirred for 15 min under hydrogen. The solution of the active catalyst was then added to a solution of compound 105* (0.33 g, 0.21 mmol) in tetrahydrofuran (2 mL) under nitrogen via a syringe and stirred for 2 h at room temperature. The reaction mixture was quenched with saturated aqueous NaHCO$_3$ solution (5 mL) and extracted with dichloromethane (3×5 mL). Combined organic layers were washed with brine (5 mL), dried over Na$_2$SO$_4$, filtered and evaporated to get the allyl isomerized compound (isomerization confirmed by $^1$H NMR). The vinyl substrate was then taken up in a mixture of tetrahydrofuran:water (2:1, 3 mL) and iodine (0.11 g, 0.43 mmol) was added at room temperature. The brown colored solution was stirred for 2 h before quenching with 10% solution of Na$_2$S$_2$O$_3$ solution (5 mL). The aqueous phase was extracted with ethyl acetate (3×5 mL) and the combined organic layers were dried over Na$_2$SO$_4$, filtered and the solvent evaporated. Purification by flash column chromatography (ethyl acetate in cyclohexane 30%) afforded the product as a yellow solid (240 mg, 75%). HRMS (ESI+) Calcd for $C_{92}H_{86}O_{20}Na^+$ [M+Na]$^+$ 1533.5610, found 1533.5387.

Compound 107*

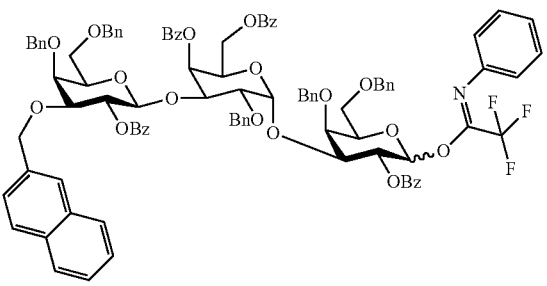

Compound 106* (0.242 g, 0.160 mmol) was dissolved in anhydrous dichloromethane (2.0 mL) Cs$_2$CO$_3$ (0.104 g, 0.320 mmol) and 2,2,2-trifluoro-N-phenylacetimidoyl chloride (0.08 mL, 0.480 mmol) were added to the solution. The reaction mixture was stirred at room temperature overnight. TLC analysis showed a complete conversion of the starting material and new spots. The reaction mixture was filtrated through a celite pad (1 cm). The pad was washed with DCM (20 mL), the filtrate concentrated under reduced pressure and dried under high vacuum to give a pale yellow oil. Purification was done by flash silica gel column chromatography (Cyclohexane/Ethyl acetate+0.1% Et$_3$N) and afforded a yellow foam (240 mg, 89%). HRMS (ESI+) Calcd for $C_{100}H_{90}F_3NO_{20}Na^+$ [M+Na]$^+$ 1704.5906, found 1704.5603.

Compound 108*

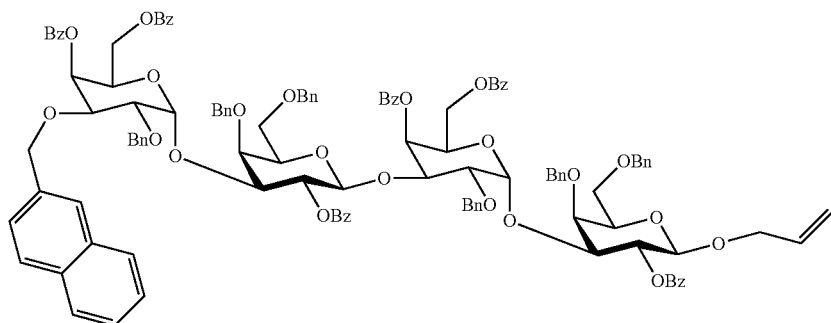

Compound 107* (0.666 g, 0.539 mmol) and compound 101* (0.4 g, 0.414 mmol) were taken in 25 mL RBF added anhydrous toluene (10 mL) and evaporated under vacuum for 30 min to dryness and repeated this azeotropic drying process two times more. The starting material was dried under high vacuum for 12 h. Then anhyd. dichloromethane (8 mL) and dried 4 A molecular sieves (MS) were added to it under nitrogen atmosphere and stirred at room temperature for 45 min and then cooled to 0° C. TMS-OTf (15 µL, 0.018 mmol) was added to the reaction mixture and stirred for 30 min. Then it was slowly warmed to 10° C. for 0.5 h and then stirred at RT for 1 h. TLC analysis showed the disappearance of the donor spot and the presence of a new spot. The reaction was quenched at 5° C. by the addition of triethylamine.

The crude organic product was purified by flash chromatography system using cyclohexane/ethyl acetate gradient system. The collected fraction were concentrated in vacuo and then was dried under high vacuum for 16 h to afford the product as a white solid (0.650 g, 78%). HRMS (ESI+) Calcd for $C_{122}H_{114}O_{27}Na^+$ [M+Na]$^+$ 2033.7445, found 2033.7077.

Compound 109*

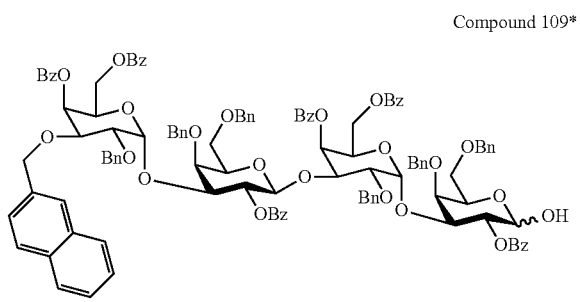

(1,5-Cyclooctadiene)(pyridine)(tricyclohexylphosphine)-Ir(I)]PF$_6$ (6.3 mg, 7.45 µmol) was dissolved in tetrahydrofuran (1.5 mL) and nitrogen was bubbled through the solution for two minutes at room temperature while the red colored catalyst dissolved. The solution was then purged with hydrogen for two minutes, by which time the red solution changed to colorless and the solution was stirred for 15 min under hydrogen. The solution of the active catalyst was then added to a solution of compound 108* (0.15 g, 0.075 mmol) in tetrahydrofuran (0.8 mL) under nitrogen via a syringe and stirred for 2 h at room temperature. The reaction mixture was quenched with saturated aqueous NaHCO$_3$ solution (5 mL) and extracted with dichloromethane (3×5 mL). Combined organic layers were washed with brine (5 mL), dried over Na$_2$SO$_4$, filtered and evaporated to get the allyl isomerized compound (isomerization confirmed by $^1$H NMR). The vinyl substrate was then taken up in a mixture of tetrahydrofuran:water (2:1, 2.5 mL) and iodine (37.8 mg, 0.149 mmol) was added at room temperature. The brown colored solution was stirred for 2 h before quenching with 10% solution of Na$_2$S$_2$O$_3$ solution (5 mL). The aqueous phase was extracted with ethyl acetate (3×5 mL) and the combined organic layers were dried over Na$_2$SO$_4$, filtered and the solvent evaporated. Purification by flash column chromatography (ethyl acetate in cyclohexane 30%) afforded the product as a yellow solid (94 mg, 64%). HRMS (ESI+) Calcd for $C_{119}H_{110}O_{27}Na^+$ [M+Na]$^+$ 1993.7132, found 1993.6822.

Compound 110*

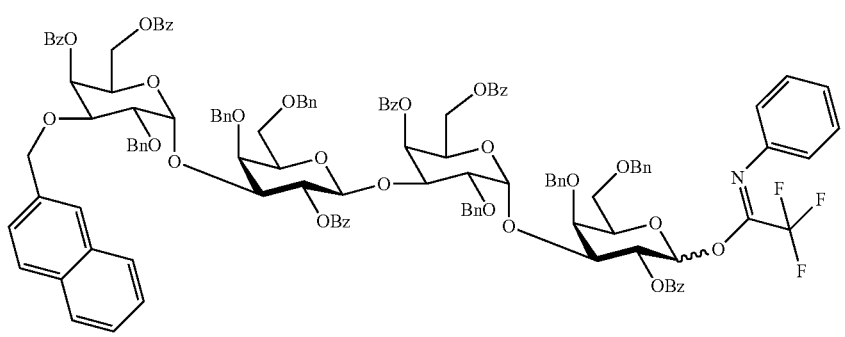

Compound 109* (0.094 g, 0.048 mmol) was dissolved in anhydrous dichloromethane (0.6 mL) $Cs_2CO_3$ (31 mg, 0.095 mmol) and 2,2,2-trifluoro-N-phenylacetimidoyl chloride (23 μL, 0.143 mmol) were added to the solution. The reaction mixture was stirred at room temperature overnight. TLC analysis showed a complete conversion of the starting material and new spots.

The reaction mixture was filtrated through a celite pad (1 cm). The pad was washed with DCM (20 mL), the filtrate concentrated under reduced pressure and dried under high vacuum to give a pale yellowish solid.

Purification was done by flash silica gel column chromatography (Cyclohexane/Ethyl acetate+0.1% $Et_3N$) and afforded a yellow foam (85 mg, 83%). HRMS (ESI+) Calcd for $C_{127}H_{114}F_3NO_{27}Na^+$ $[M+Na]^+$ 2164.7428, found 2164.7056.

Compound 111*

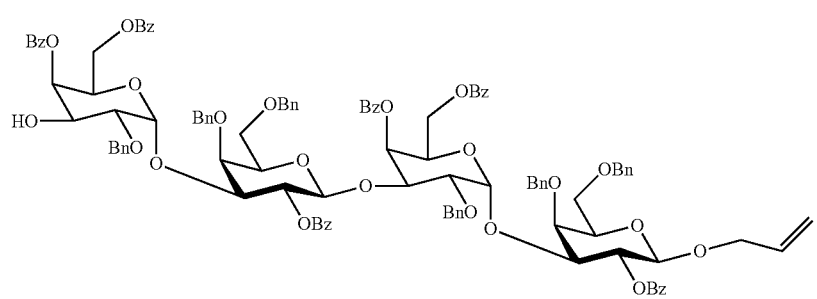

Compound 108* (0.100 g, 0.050 mmol) was transferred to a stirring solution of DCM (1.3 mL) and Methanol (0.3 mL) in a 10 mL RBF under nitrogen atmosphere equipped with a stir bar and stirring of 400 rpm. DDQ (0.056 g, 0.248 mmol) was added, TLC analysis (40% ethyl acetate/cyclohexanes) showed the presence of a new spot slightly polar to the major amount of starting material even after 2 h, so stirred the reaction mixture for additional 4 h at RT. TLC showed the absence of the starting material, but presence of product as well as a faint polar spot. The reaction was quenched by the addition of sat. aq. $NaHCO_3$ (10 mL) and extracted into DCM. The combined organic layer was washed with sat. $NaHCO_3$ solution (10 mL), brine (10 mL), dried over anhyd. Sodium sulfate, filtered and concentrated under vacuum at 30-35° C. bath temperature of rotary evaporator in a 100 mL RBF for 1 h to obtain the crude as a pale yellow oil. Purification was done on silica gel column chromatography using ethyl acetate in cyclohexane. Dichloromethane was then added to this and continued evaporation under vacuum for 30 min resulted in a colorless transparent gummy liquid which was dried under high vacuum for 16-18 h to form a fluffy white solid (43 mg, 46%). HRMS (ESI+) Calcd for $C_{111}H_{106}O_{27}Na^+$ $[M+Na]^+$ 1893.6819, found 1893.6498.

Compound 112*

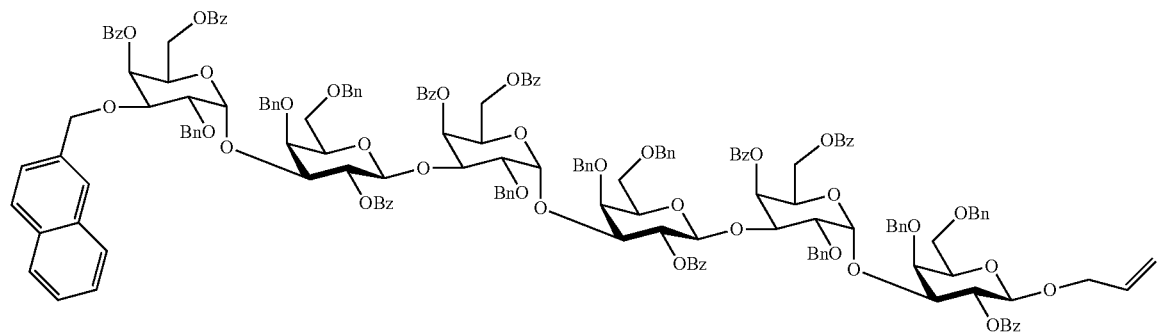

Compound 103* (29 mg, 0.024 mmol) and compound 111* (34 mg, 0.018 mmol) were taken in 10 mL RBF added anhydrous toluene (3 mL) and evaporated under vacuum for 30 min to dryness and repeated this azeotropic drying process two times more. The starting material material was dried under high vacuum for 12 h. Then anhyd. dichloromethane (0.3 mL) and dried 4 A molecular sieves (MS) were added to it under nitrogen atmosphere and stirred at room temperature for 45 min and then cooled to 0° C. TMS-OTf (0.6 µL, 3.63 µmol) was added to the reaction mixture and stirred for 30 min. Then it was slowly warmed to 10° C. for 0.5 h and then stirred at RT for 1 h. TLC analysis showed the disappearance of the donor spot and the presence of a new spot. The reaction was quenched at 5° C. by the addition of triethylamine. The crude organic product was purified by a flash chromatography system using cyclohexane/ethyl acetate gradient system. The collected fraction were concentrated in vacuo and then was dried under high vacuum for 16 h to afford the product as a white solid (35 mg, 66%). Maldi Calcd for $C_{176}H_{164}O_{40}Na^+$ $[M+Na]^+$ 2942.2, found 2942.3.

Compound 113*

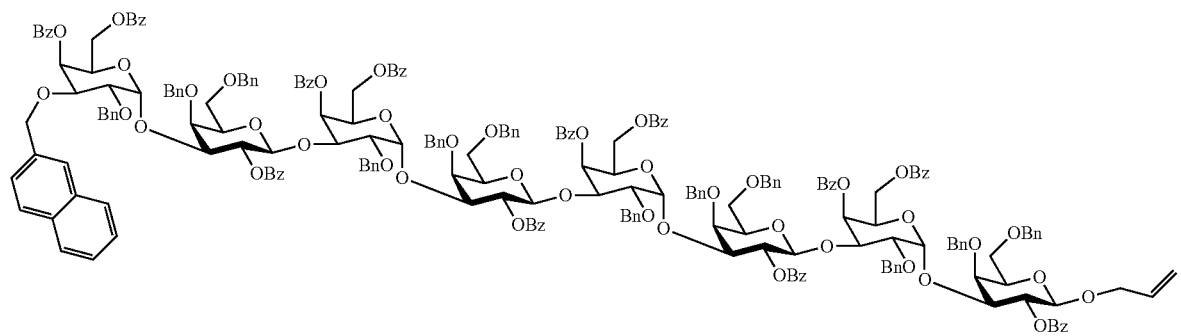

Compound 110* (64 mg, 0.030 mmol) and compound 111* (43 mg, 0.023 mmol) were taken in 10 mL RBF added anhydrous toluene (3 mL) and evaporated under vacuum for 30 min to dryness and repeated this azeotropic drying process two times more. The starting material was dried under high vacuum for 12 h. Then anhyd. dichloromethane (0.5 mL) and dried 4 A molecular sieves (MS) were added to it under nitrogen atmosphere and stirred at room temperature for 45 min and then cooled to 0° C. TMS-OTf (0.8 µL, 4.59 µmol) was added to the reaction mixture and stirred for 30 min. Then it was slowly warmed to 10° C. for 0.5 h and then stirred at RT for 1 h. TLC analysis showed the disappearance of the donor spot and the presence of a new spot. The reaction was quenched at 5° C. by the addition of triethylamine. The crude organic product was purified by a flash chromatography system using cyclohexane/ethyl acetate gradient system. The collected fraction were concentrated in vacuo and then was dried under high vacuum for 16 h to afford the product as a white fluffy solid (66 mg, 75%). Maldi Calcd for $C_{230}H_{214}O_{53}Na^+$ $[M+Na]^+$ 3849.2, found 3849.4.

Compound 114*

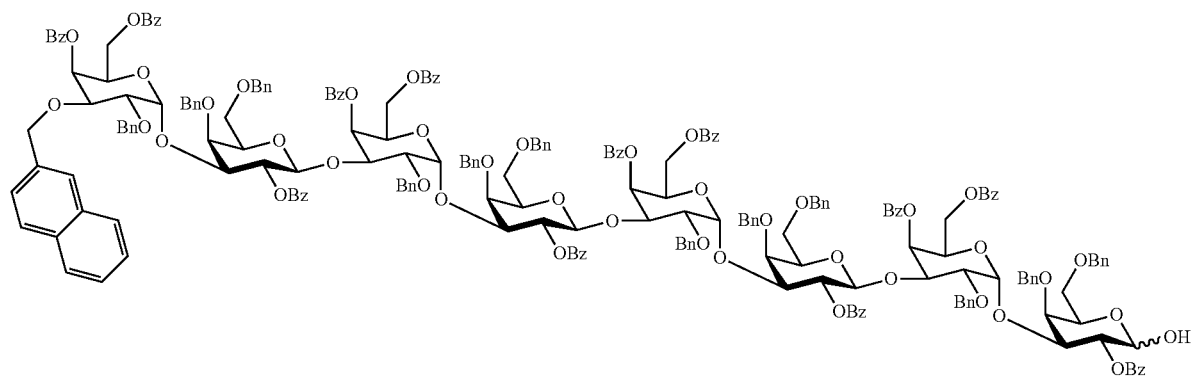

(1,5-Cyclooctadiene)(pyridine)(tricyclohexylphosphine)-Ir(I)]PF$_6$ (8.18 mg, 9.7 µmol) was dissolved in tetrahydrofuran (1.9 mL) and nitrogen was bubbled through the solution for two minutes at room temperature while the red colored catalyst dissolved. The solution was then purged with hydrogen for two minutes, by which time the red solution changed to colorless and the solution was stirred for 15 min under hydrogen. The solution of the active catalyst was then added to a solution of compound 113* (0.370 g, 0.097 mmol) in tetrahydrofuran (0.9 mL) under nitrogen via a syringe and stirred for 2 h at room temperature. The reaction mixture was quenched with saturated aqueous NaHCO$_3$ solution (5 mL) and extracted with dichloromethane (3×5 mL). Combined organic layers were washed with brine (5 mL), dried over Na$_2$SO$_4$, filtered and evaporated to get the allyl isomerized compound (isomerization confirmed by $^1$H NMR). The vinyl substrate was then taken up in a mixture of tetrahydrofuran:water (2:1, 2.5 mL) and iodine (49 mg, 0.193 mmol) was added at room temperature. The brown colored solution was stirred for 2 h before quenching with 10% solution of Na$_2$S$_2$O$_3$ solution (5 mL). The aqueous phase was extracted with ethyl acetate (3×5 mL) and the combined organic layers were dried over Na$_2$SO$_4$, filtered and the solvent evaporated. Purification by flash column chromatography (ethyl acetate in cyclohexane 30%) afforded the product as a yellow solid (270 mg, 57%). Maldi Calcd for C$_{227}$H$_{210}$O$_{53}$Na$^+$ [M+Na]$^+$ 3809.1, found 3809.0.

Compound 115*

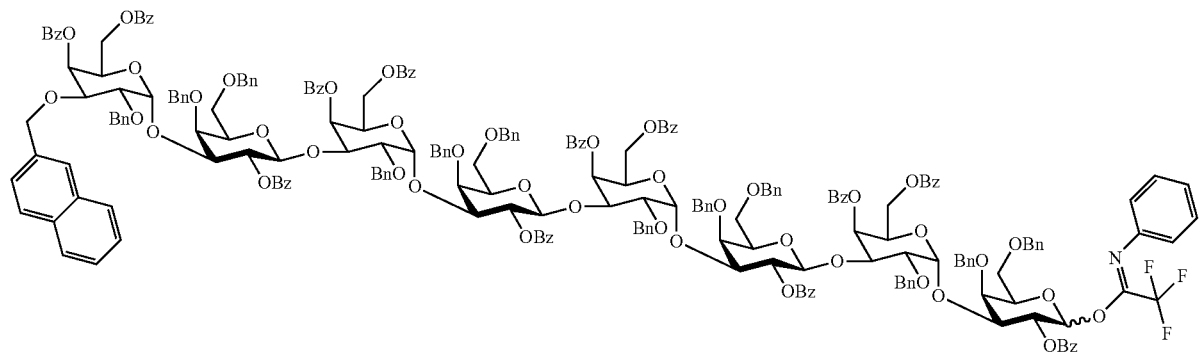

Compound 114* (0.210 g, 0.055 mmol) was dissolved in anhydrous dichloromethane (0.7 mL) Cs$_2$CO$_3$ (36 mg, 0.111 mmol) and 2,2,2-trifluoro-N-phenylacetimidoyl chloride (26 µL, 0.166 mmol) were added to the solution. The reaction mixture was stirred at room temperature overnight. TLC analysis showed a complete conversion of the starting material and new spots. The reaction mixture was filtrated through a celite pad (1 cm). The pad was washed with DCM (20 mL), the filtrate concentrated under reduced pressure and dried under high vacuum to give a pale yellowish solid. Purification was done by flash silica gel column chromatography (Cyclohexane/Ethyl acetate+0.1% Et$_3$N) and afforded a yellow foam (180 mg, 82%). Maldi Calcd for C$_{235}$H$_{214}$O$_{53}$Na$^+$ [M+Na]$^+$ 3980.2, found 3981.3.

Compound 116*

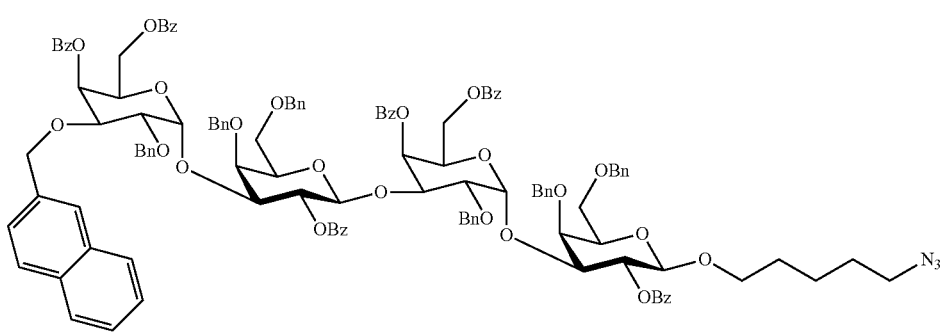

Compound 110* (0.013 mg, 0.103 mmol) and 5-azidopentanol (0.110 g, 0.05 mmol) were taken in 10 mL RBF added anhydrous Toluene (20 mL) and evaporated under vacuum for 30 min to dryness and repeated this azeotropic drying process two times more. The material was dried under high vacuum for 12h. Then anhyd. Dichloromethane (1 mL) was added to it under Nitrogen atmosphere equipped with a stir bar and stirring of 300 rpm. −100 mg dried 4 A molecular sieves (MS) were added and stirred at room temperature for 45 min and then cooled to 0° C. TMS-OTf (1.9 µL, 10.26 µmol) were added to the reaction mixture and stirred for 30 min. Then it was slowly warmed to 10° C. for 0.5 h and then stirred at RT for 1 h. TLC analysis showed the disappearance of the donor spot and the presence of a new spot. The reaction was quenched at 5° C. by the addition of triethylamine. The crude organic product was purified by a flash chromatography system using Cyclohexane/Ethyl acetate gradient system. The collected fraction were concentrated in vacuo and then was dried under high vacuum for 16 h to afford the product as a white fluffy solid (0.091 g, 85%). HRMS (ESI+) Calcd for $C_{124}H_{119}N_3O_{27}Na^+$ $[M+Na]^+$ 2104.7929, found 2104.7905.

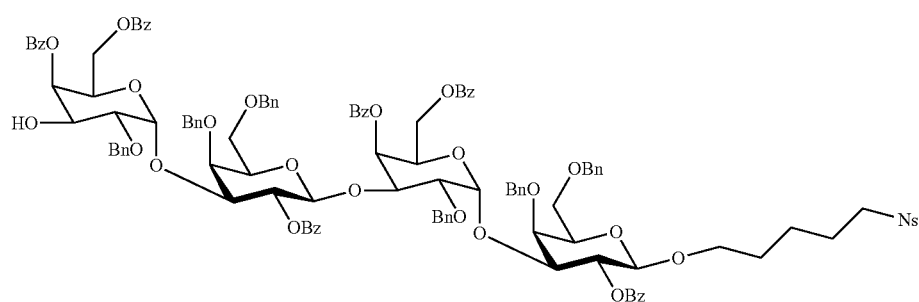

Compound 117*

Compound 116* (0.091 g, 0.044 mmol) was transferred to a stirring solution of DCM (0.8 mL) and Phosphate buffer pH 7.4 (0.8 mL) in a 10 mL RBF under nitrogen atmosphere equipped with a stir bar and stirring of 400 rpm. DDQ (0.02 g, 0.087 mmol) was added, TLC analysis (40% ethyl acetate/cyclohexane) showed the presence of a new spot slightly polar to the major amount of starting material even after 2 h, so stirred the reaction mixture for additional 4 h at RT. TLC showed the absence of the starting material, but presence of product as well as a faint polar spot. The reaction was quenched by the addition of sat. aq. NaHCO$_3$ and extracted into DCM. The combined organic layer was washed with sat. NaHCO$_3$ solution (50 mL), brine (100 mL), dried over anhyd. sodium sulfate, filtered and concentrated under vacuum at 30-35° C. bath temperature of rotary evaporator in a 50 mL RBF for 1 h to obtain the crude as a pale yellow oil. The crude organic product was purified by a flash chromatography system using Cyclohexane/Ethyl acetate gradient system. The collected fraction were concentrated in vacuo and then was dried under high vacuum for 16 h to afford the product as a white fluffy solid (0.041 g, 47%). HRMS (ESI+) Calcd for $C_{113}H_{111}N_3O_{27}Na^+$ $[M+Na]^+$ 1964.7303, found 1964.7309.

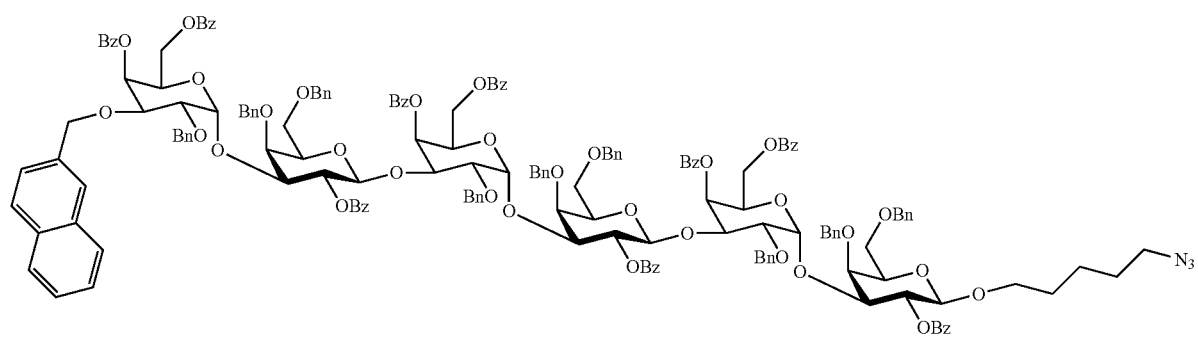

Compound 118*

Compound 103* (33 mg, 0.027 mmol) and compound 117* (40 mg, 0.021 mmol) were taken in 10 mL RBF added anhydrous toluene (3 mL) and evaporated under vacuum for 30 min to dryness and repeated this azeotropic drying process two times more. The starting material was dried under high vacuum for 12 h. Then anhyd. dichloromethane (0.4 mL) and dried 4 A molecular sieves (MS) were added to it under nitrogen atmosphere and stirred at room temperature for 45 min and then cooled to 0° C. TMS-OTf (0.7 µL, 4.12 µmol) was added to the reaction mixture and stirred for 30 min. Then it was slowly warmed to 10° C. for 0.5 h and then stirred at RT for 1 h. TLC analysis showed the disappearance of the donor spot and the presence of a new spot. The reaction was quenched at 5° C. by the addition of triethylamine.

The crude organic product was purified by a flash chromatography system using cyclohexane/ethyl acetate gradient system. The collected fraction were concentrated in vacuo and then was dried under high vacuum for 16 h to afford the product as a white solid (37 mg, 60%). Maldi Calcd for $C_{178}H_{169}N_3O_{40}Na^+$ [M+Na]$^+$ 3013.3, found 3014.2.

Compound 119*

Compound 118* (27 mg, 0.009 mmol) was taken in THF (0.6 mL) under nitrogen atmosphere equipped with a stir bar. 0.5 M methanolic solution of sodium methoxide (18 µL, 9.03 µmol) was added. The resulting solution was stirred at 50° C. for 25 h. Reaction was monitored by HRMS and the TLC [(50% Ethyl acetate in Cyclohexane). The reaction mixture was evaporated in vacuum for 15 min to minimum volume and then diluted with ethyl acetate and water. The reaction mixture was acidified using 50% aq. AcOH solution (5 mL) and separated the layers. The aqueous layer was then extracted with ethyl acetate (5 mL×3). Combined organic layer was washed with water, brine, dried (Na$_2$SO4), filtered, and concentrated in vacuum at 30-35° C. bath temperature of rotary evaporator in a 10 mL RBF for 1h under vacuum to get yellow solid. Then -2% Ethylacetate/hexanes (~5 mL) was added to the solid in the RBF, warmed the RBF to 45° C. in the water bath and triturated, cooled to rt and filtered. The solid was washed with warm ~2% Ethylacetate/hexanes two more times and dried in high vacuum to afford pale yellow solid as the desired product. All the filtrates were concentrated in vacuo and then was dried under high vacuum for 16 h to afford the product as a yellow solid (14 mg, 76%). HRMS (ESI+) Calcd for $C_{115}H_{113}N_3O_{31}Na^+$ [M+Na]$^+$ 2074.8821, found 2074.8574.

Compound 120*

Compound 119* was taken in a solvent mixture of ⁱPrOH, DCM, and H₂O, in a 20 mL Wheaton Vial (10 min oven dried) under nitrogen atmosphere equipped with a stir bar and stirring of 250 rpm (Heidolph stirrer) at RT. Added a suspension of 10% Pd/C to it. The reaction mixture was purged under hydrogen gas and subsequently stirred under a pressure of 10 bar for 24 h at RT using the in house Hydrogenator. The reaction mixture was then filtered through a PTFE hydrophobic filter (0.45 μm) and the filter was washed thoroughly with methanol (3 mL×5), water-methanol (6:4, 3 mL×5). The filtrate was evaporated to dryness under vacuum at 30-35° C. bath temperature of rotary evaporator for 1 h to obtain the off-white solid as crude product. 1H NMR of the crude product showed the completion of the reaction but a presence of intermediates.

The crude product was then purified using C18 Sepak column using Water and Acetonitril as eluents to get desired pure product in water fraction (fr1). The side products eluted in 50% Water-Acetonitril fraction (fr2) and impurity eluted in Acetonitrile washes (fr3). The impure water fraction (fr1) was additional purified through a SEC column with water as eluent. Lyophilization of the water fraction yielded the desired pure product as the white foamy solid (2 mg, 28%). HRMS (ESI+) Calcd for $C_{115}H_{113}N_3O_{31}H^+$ $[M+H]^+$ 1076.4245, found 1076.4256.

$^1$H NMR (400 MHz, D₂O) δ 5.20-5.11 (m, 3H), 4.70-4.66 (m, 2H), 4.45 (d, J=7.9 Hz, 1H), 4.30-4.11 (m, 9H), 4.07-3.91 (m, 6H), 3.87-3.62 (m, 23H), 2.91 (t, J=7.3 Hz, 2H), 1.81-1.57 (m, 4H), 1.50-1.41 (m, 2H).

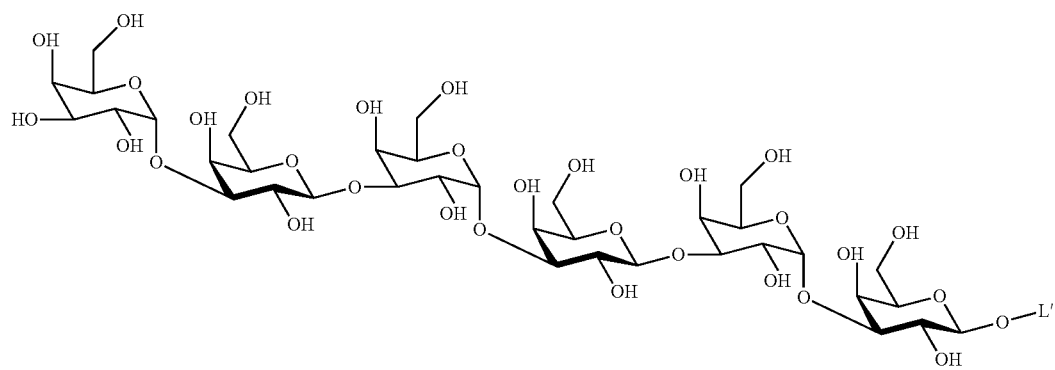

Compound 120a-l*

Compounds 120-l* are prepared similarly to compound 120* from compound 110* and the corresponding alcohol as shown in FIG. 11.

A-6-2 Preparation of *Klebsiella pneumoniae* Galactan-II Octasaccharide

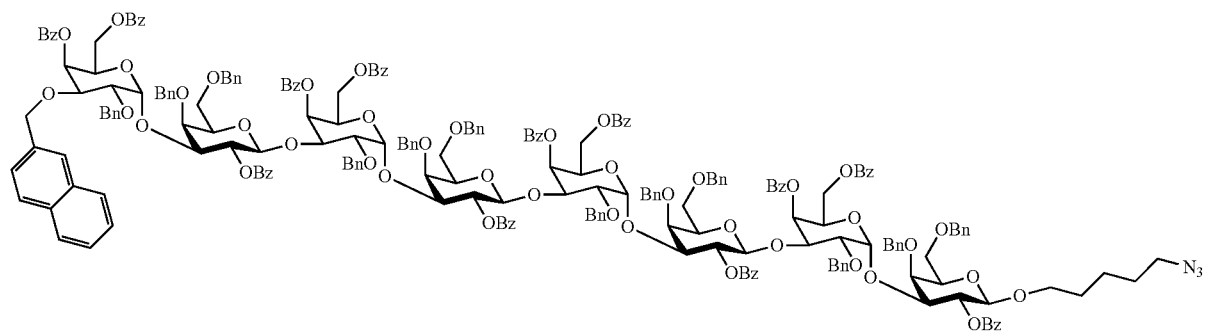

Compound 121*

Compound 110* (0.172 mg, 0.080 mmol) and compound 117* (120 mg, 0.062 mmol) were taken in 10 mL RBF added anhydrous toluene (3 mL) and evaporated under vacuum for 30 min to dryness and repeated this azeotropic drying process two times more. The starting material was dried under high vacuum for 12 h. Then anhyd. dichloromethane (1.2 mL) and dried 4 A molecular sieves (MS) were added to it under nitrogen atmosphere and stirred at room temperature for 45 min and then cooled to 0° C. TMS-OTf (2.2 µL, 12 µmol) was added to the reaction mixture and stirred for 30 min. Then it was slowly warmed to 10° C. for 0.5 h and then stirred at RT for 1 h. TLC analysis showed the disappearance of the donor spot and the presence of a new spot. The reaction was quenched at 5° C. by the addition of triethylamine. The crude organic product was purified by a flash chromatography system using cyclohexane/ethyl acetate gradient system. The collected fraction were concentrated in vacuo and then was dried under high vacuum for 16 h to afford the product as a white fluffy solid (125 mg, 52%). Maldi Calcd for $C_{230}H_{214}O_{53}Na^+$ $[M+Na]^+$ 3920.3, found 3921.1.

Compound 122*

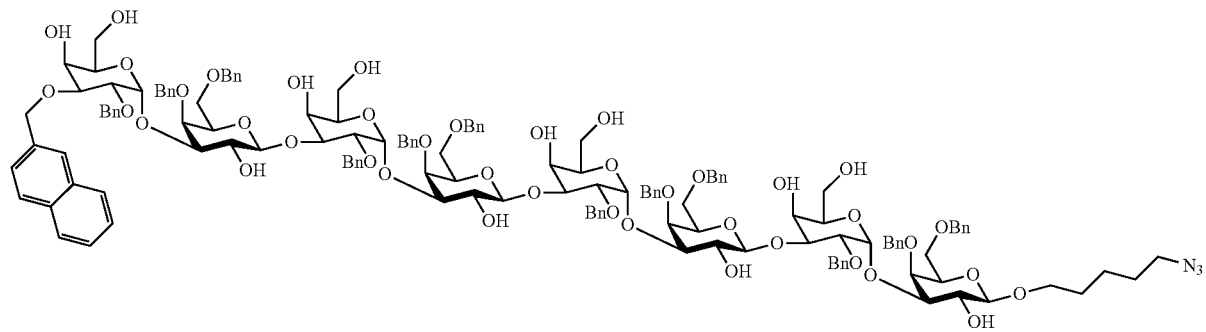

Compound 121* (24 mg, 6.2 µmol) was taken in THF (0.6 mL) under nitrogen atmosphere equipped with a stir bar. 0.5 M methanolic solution of sodium methoxide (12 µL, 6.2 µmol) was added. The resulting solution was stirred at 50° C. for 25 h. Reaction was monitored by HRMS and the TLC (50% Ethyl acetate in Cyclohexane). The reaction mixture was evaporated in vacuum for 15 min to minimum volume and then diluted with ethyl acetate and water. The reaction mixture was acidified using 50% aq. AcOH solution (10 mL) and separated the layers. The aqueous layer was then extracted with ethyl acetate (5 mL×3). Combined organic layer was washed with water, brine, dried ($Na_2SO_4$), filtered, and concentrated in vacuum at 30-35° C. bath temperature of rotary evaporator in a 50 mL RBF for 1h under vacuum to get yellow solid. Then ~2% Ethylacetate/hexanes (~5 mL) was added to the solid in the RBF, warmed the RBF to 45° C. in the water bath and triturated, cooled to rt and filtered. The solid was washed with warm ~2% Ethylacetate/hexanes two more times and dried in high vacuum to afford pale yellow solid as the desired product. All the filtrates were concentrated in vacuo and then was dried under high vacuum for 16 h to afford the product as a yellow solid (11 mg, 66%). HRMS (ESI+) Calcd $C_{148}H_{171}N_3O_{41}Na^+$ $[M+Na]^+$ 2669.1286, found 2669.1233.

Compound 123*

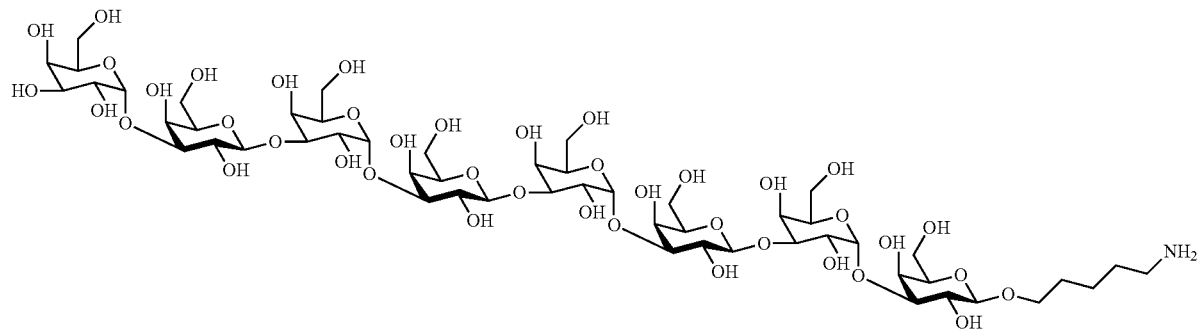

Compound 122* (11 mg, 4.2 μmol) was taken in a solvent mixture of $^i$PrOH, DCM, and H$_2$O, in a 20 mL Wheaton Vial (10 min oven dried) under nitrogen atmosphere equipped with a stir bar and stirring of 250 rpm (Heidolph stirrer) at r.t. Hydrogenation reaction was carried out according to general protocol C. $^1$H NMR of the crude product showed the completion of the reaction but a presence of intermediates. The crude product was then purified using C18 Sepak column using Water and Acetonitrile as eluents to get desired pure product in water fraction (fr1). The side products eluted in 50% Water-Acetonitrile fraction (fr2) and impurity eluted in Acetonitrile washes (fr3). The impure water fraction (fr1) was additional purified through a SEC column with water as eluent. Lyophilization of the water fraction yielded the desired pure product as the white foamy solid (2 mg, 34%). HRMS (ESI+) Calcd for C$_{115}$H$_{113}$N$_3$O$_{31}$H$^+$ [M+H]$^+$ 1400.5301, found 1400.5376. $^1$H NMR (400 MHz, D$_2$O) δ 5.20-5.16 (m, 3H), 5.15 (d, J=3.4 Hz, 1H), 4.70-4.66 (m, 3H), 4.46 (d, J=7.9 Hz, 1H), 4.33-4.09 (m, 12H), 4.07-3.88 (m, 5H), 3.88-3.58 (m, 33H), 3.00 (t, J=7.6 Hz, 2H), 1.50-1.40 (m, 4H), 1.42-1.29 (m, 2H).

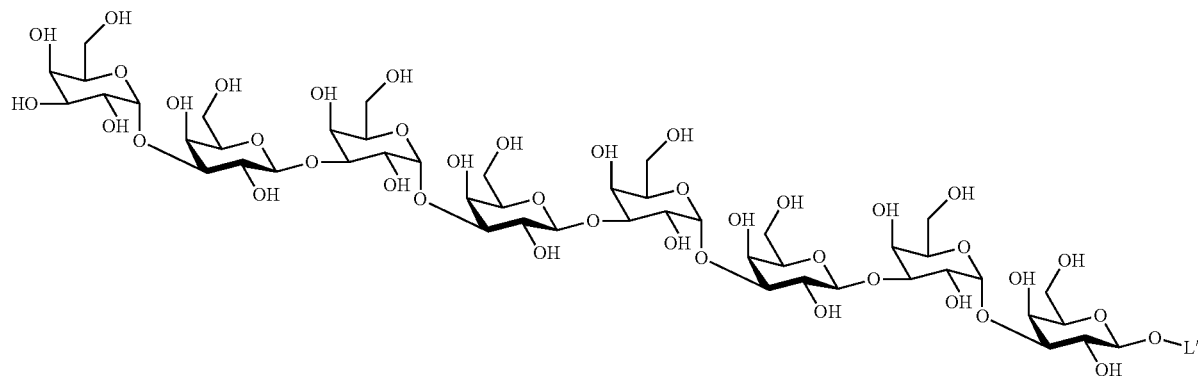

Compound 123a-l*

Compounds 123-l* are prepared similarly to compound 123* from compound 110* and the corresponding alcohol as shown in FIG. 11.

A-6-3 Preparation of *Klebsiella pneumoniae* Galactan-II Dodecasaccharide

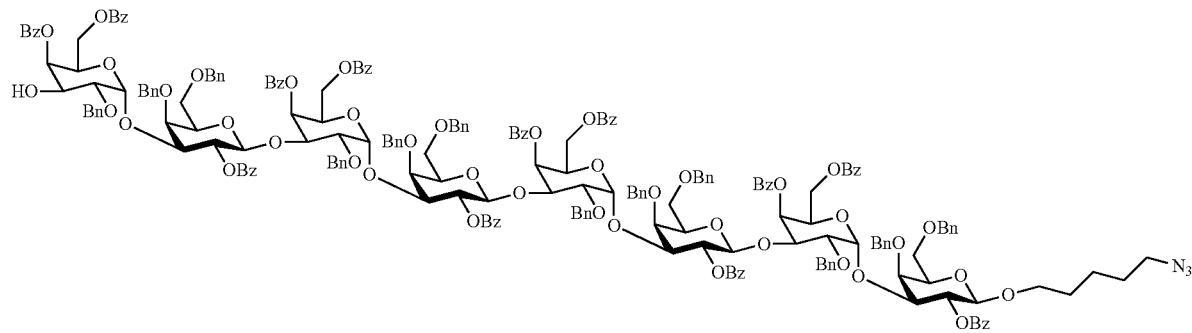

Compound 124*

Compound 121* (0.105 g, 0.027 mmol) was transferred to a stirring solution of DCM (0.5 mL) and phosphate buffer ph 7.4 (0.5 mL) in a 10 mL RBF under nitrogen atmosphere equipped with a stir bar and stirring of 400 rpm. DDQ (0.028 g, 0.121 mmol) was added, TLC analysis (40% Ethyl acetate/Cyclohexane) showed the presence of a new spot slightly polar to the major amount of starting material even after 2 h, so stirred the reaction mixture for additional 4 h at RT. TLC showed the absence of the starting material, but presence of product as well as a faint polar spot. The reaction was quenched by the addition of sat. aq. NaHCO$_3$ and extracted into DCM. The combined organic layer was washed with sat. NaHCO$_3$ solution (10 mL), brine (20 mL), dried over anhyd. Sodium sulfate, filtered and concentrated under vacuum at 30-35° C. bath temperature of rotary evaporator in a 50 mL RBF for 1 h to obtain the crude as a pale yellow oil. The crude organic product was purified by a flash chromatography system using Cyclohexane/Ethyl acetate gradient system. The collected fraction were concentrated in vacuo and then was dried under high vacuum for 16 h to afford the product as a white fluffy solid (0.044 g, 44%). MALDI Calcd for $C_{221}H_{211}O_{53}H^+$ [M+H]$^+$ 3758.1, found 3758.4.

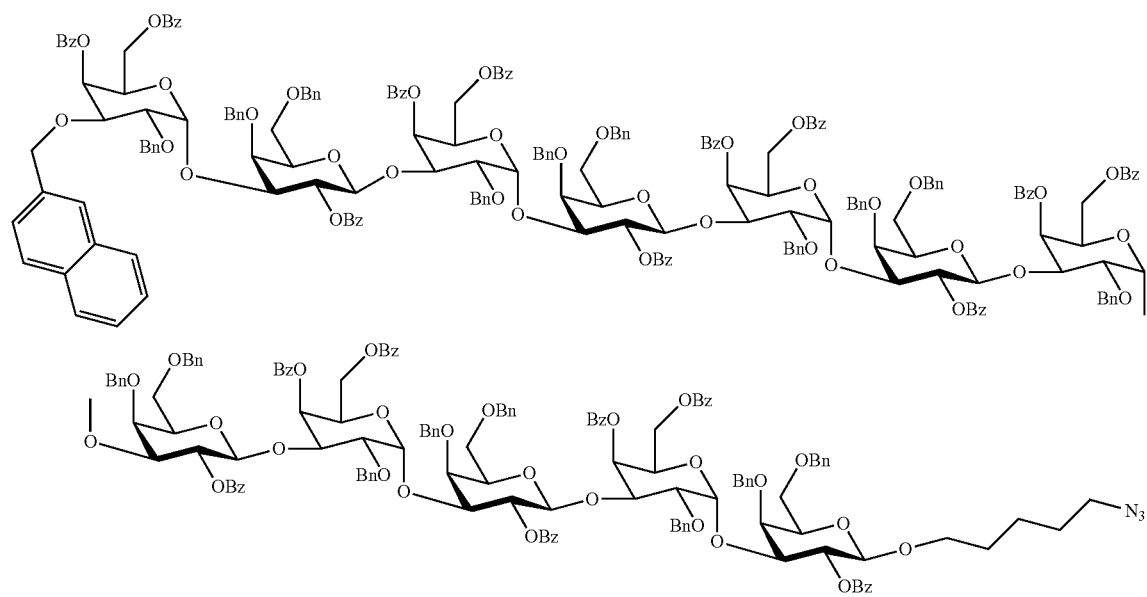

Compound 125*

Compound 110* (26 mg, 0.012 mmol) and compound 124* (45 mg, 0.012 mmol) were taken in 10 mL RBF added anhydrous toluene (3 mL) and evaporated under vacuum for 30 min to dryness and repeated this azeotropic drying process two times more. The starting material was dried under high vacuum for 12 h. Then anhyd. dichloromethane (0.2 mL) and dried 4 A molecular sieves (MS) were added to it under nitrogen atmosphere and stirred at room temperature for 45 min and then cooled to 0° C. TMS-OTf (0.2 µL, 2.4 µmol) was added to the reaction mixture and stirred for 30 min. Then it was slowly warmed to 10° C. for 0.5 h and then stirred at RT for 1 h. TLC analysis showed the disappearance of the donor spot and the presence of a new spot. The reaction was quenched at 5° C. by the addition of triethylamine.

The crude organic product was purified by a flash chromatography system using cyclohexane/ethyl acetate gradient system. The collected fraction were concentrated in vacuo and then was dried under high vacuum for 16 h to afford the product as a white fluffy solid (22 mg, 32%). Maldi Calcd for $C_{340}H_{319}N_3O_{53}H^+$ [M+H]$^+$ 5711.2, found 5715.6.

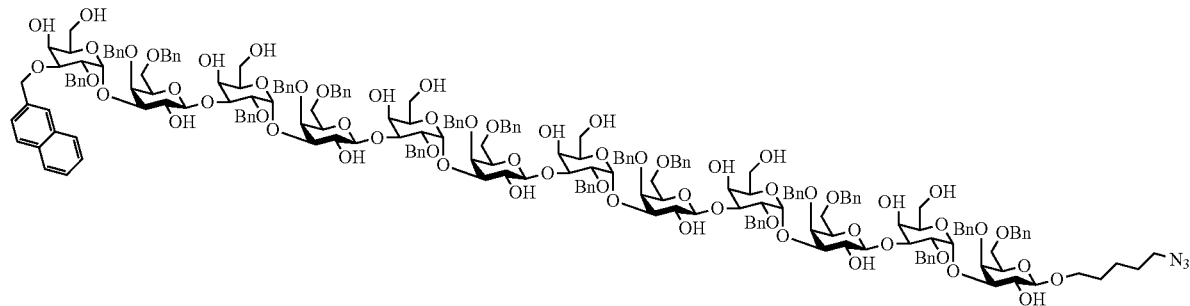
Compound 126*
Compound 126* is prepared from compound 125* according to the procedure described for the synthesis of compound 119*.
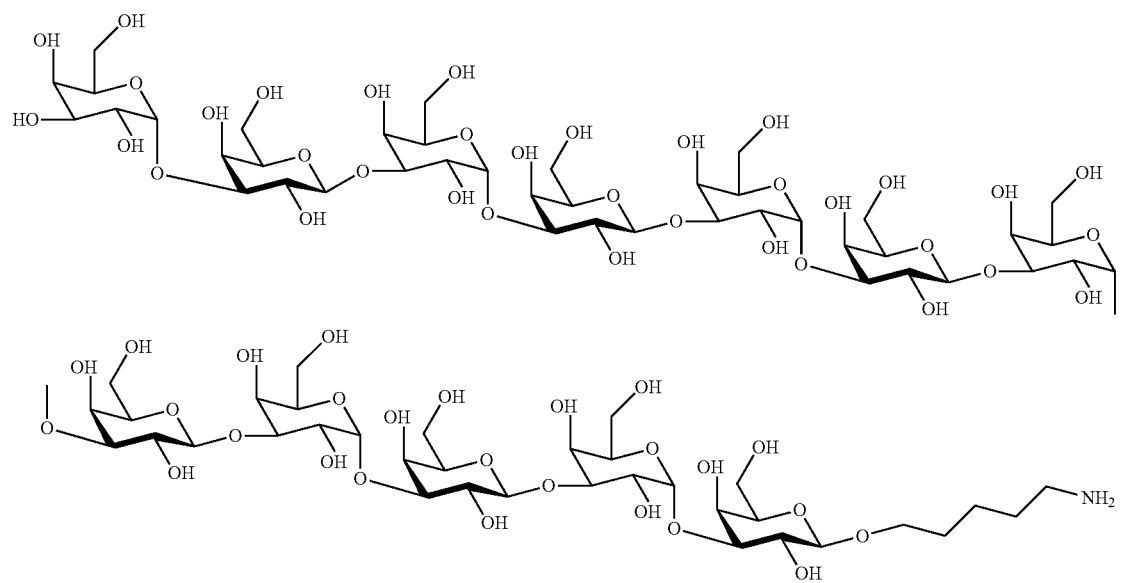
Compound 127*

Compound 127* is prepared from compound 126* according to the procedure described for the synthesis of compound 120*.

A-7 Preparation of *Klebsiella pneumoniae* Galactan-III Saccharide

A-7-1 Preparation of *Klebsiella pneumoniae* Galactan-III Trisaccharide

Compound 128*

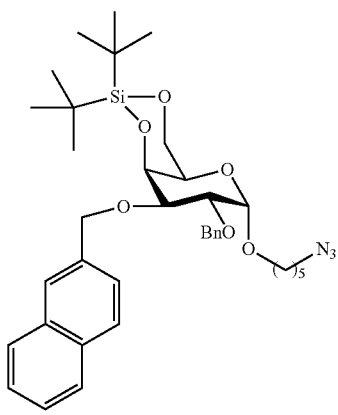

To a solution of compound 4* (420 mg, 0.653 mmol) in DCM (13 mL) were added 4 A MS, Ph$_2$SO (172 mg, 0.849 mmol) and 2,4,6-tri-tert-butylpyrimidine (404 mg, 1.633 mmol) and mixture stirred for 20 min. The reaction mixture was cooled to −78° C. Tf$_2$O (240 mg, 0.849 mmol) was added and the reaction mixture stirred for 20 min at the same temperature. Then, 5-azidopentanol (169 mg, 1.307 mmol) was added dropwise dissolved in 2 mL DCM. The reaction mixture was warmed to −40° C. over 3 h and was then quenched with triethylamine (3 mL). The reaction mixture was diluted with DCM (20 mL), washed with brine (30 mL) and the organic layer dried over Na$_2$SO$_4$. The crude mixture was purified using automated purification using silica gel (ethyl acetate/cyclohexane). Concentration of solvent from test tubes containing the products (based on TLC) in vacuum gave the product as a colorless oil (350 mg, 81%). Calcd for C$_{37}$H$_{51}$N$_3$O$_6$Na [M+Na]$^+$ 684.3445, found 684.3371.

Compound 129*

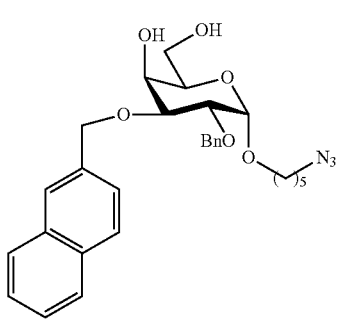

To a solution of compound 128* (350 mg, 0.529 mmol) in THF (5 mL) was added HF.py (0.11 mL, 4.23 mmol) and the reaction let stir at room temperature for 2 h. After complete consumption of the starting material (TLC), the reaction was quenched with triethylamine (0.5 mL) and washed with sat. NaHCO$_3$ and brine. The organic layer was dried over Na$_2$SO$_4$ and the solvent removed under vacuum. The crude reaction mixture was purified by automated purification system using silica (ethyl acetate/cyclohexane) to give the product as a colorless oil (199 mg, 72%).

Compound 130*

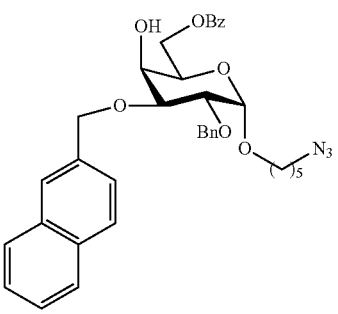

Benzoic anhydride (99 mg, 0.437 mmol) and triethylamine (295 mg, 2.91 mmol) were added to a solution of diol 129* (190 mg, 0.364 mmol) in DCM (2 mL) and the reaction let stir overnight at room temperature. The reaction was diluted with DCM (10 mL) and washed with sat. NaHCO$_3$ (5 mL). The organic layer was dried over Na$_2$SO$_4$ and the solvent concentrated in rotavapor. The residue was purified using automated purification system (combiflash) using silica gel (ethyl acetate/cyclohexane). The tubes containing the product were combined and the solvent evaporated to give the product as a colorless oil (225 mg, 99%). Calcd for C$_{36}$H$_{39}$N$_3$O$_7$Na [M+Na]$^+$ 648.2686, found 648.2625.

Compound 131*

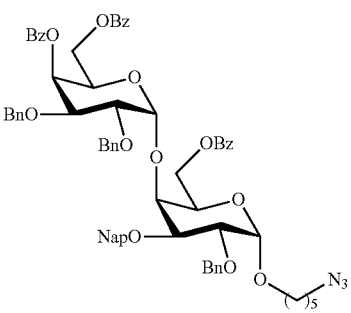

To a solution of compound 9* (65 mg, 0.100 mmol) and compound 130* (55 mg, 0.088 mmol) in toluene:dioxane (3:1, 1.2 mL) was added 4 A MS and the mixture let stir at room temperature for 1 h. Then, NIS (28 mg, 0.123 mmol) was added and the reaction mixture cooled to 0° C. TMSOTf (1.6 µL, 8.8 µmol) was added and the reaction mixture stirred for 1.5 h at 0° C. The reaction was quenched with triethylamine (0.1 mL), diluted with DCM (10 mL) and extracted with 10% Na$_2$SO$_3$ and sat. NaHCO$_3$. The organic layer was dried over Na$_2$SO$_4$ and the solvent concentrated in rotavapor. Purification by automated purification system using silica (ethyl acetate/cyclohexane) afforded the product after evaporation of the solvent as a colorless oil (60 mg, 59%). Calcd for C$_{70}$H$_{71}$N$_3$O$_{13}$Na [M+Na]$^+$ 1184.4885, found 1184.4783.

Compound 132*

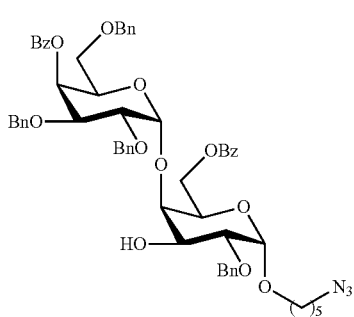

To a solution of compound 131* (60 mg, 0.052 mmol) in DCM:MeOH (4:1, 2 mL) in a 10 mL RBF under argon atmosphere was added 2,3-dichloro-5,6-dicyano-1,4-benzoquinone at 0° C. The reaction mixture was stirred for 2h 40 min at room temperature. Reaction was monitored by TLC (EtOAc in Cyclohexane, 2:1). Reaction was diluted with DCM (10 mL) and quenched with sat. NaHCO$_3$ (5 mL). The organic layer was washed with sat. NaHCO$_3$ (5 mL) and brine (5 mL). The organic layer was dried over Na$_2$SO$_4$ (0.2 g), filtered, and the filtrate was concentrated under vacuum for 15 min to obtain the crude product. The crude product was purified by automated flash chromatography using silica (ethyl acetate/cyclohexane). Concentration of solvent from test tubes containing the product (based on TLC) in vacuum resulted in a colorless oil (35 mg, 66%). Calcd for C$_{59}$H$_{63}$N$_3$O$_{13}$Na [M+Na]$^+$ 1044.4259, found 1044.4156.

Compound 133*

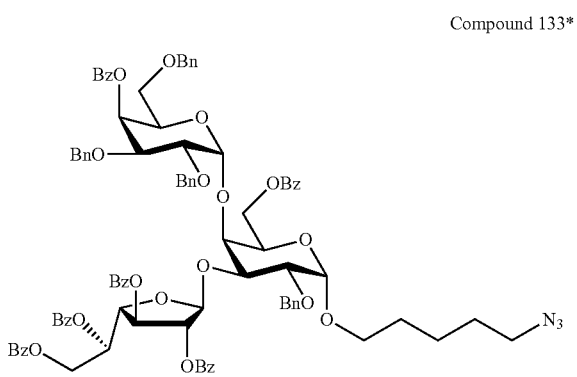

Compound 10* (33 mg, 0.032 mmol) and compound 132* (30 mg, 0.044 mmol) were coevaporated with toluene and dried in high vacuum for 20 min. To a solution of the donor and acceptor in DCM (6 mL) was added 4 A MS and the mixture let stir at room temperature for 30 min. Then, the reaction mixture was cooled to −40° C. NIS (11 mg, 0.048 mmol) and AgOTf (2 mg, 8.07 mmol) were added and the reaction mixture warmed to −20° C. over 1 h. The reaction was stirred at the same temperature for 1 h. The reaction was quenched with triethylamine (0.2 mL), diluted with DCM (10 mL) and extracted with Na$_2$SO$_3$ and sat. NaHCO$_3$. The organic layer was dried over Na$_2$SO$_4$ and the solvent concentrated in rotavapor. Purification by automated purification system (ethyl acetate/cyclohexane) afforded the product after evaporation of the solvent as a colorless oil (34 mg, 66%). Calcd for C$_{93}$H$_{89}$N$_3$O$_{22}$Na [M+Na]$^+$ 1623.5869, found 1623.5714.

Compound 134*

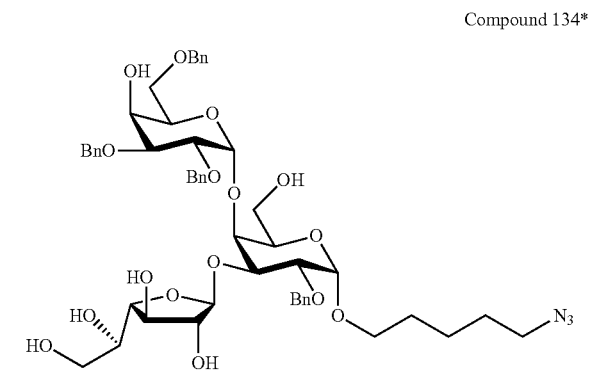

Sodium methoxide solution in MeOH 25% w/w (0.029 mL, 0.127 mmol) was added to a solution of compound 133* (17 mg, 0.010 mmol) in a mixture of MeOH:THF (2:1, 1.5 mL). The reaction was stirred at the same temperature for 20 h. The reaction was quenched by the addition of AcOH (0.2 mL) and the solvent evaporated. Purification by silica gel chromatography using 5% MeOH in DCM as the eluent afforded the product after evaporation of the solvent as a white oil (9 mg, 87%).

Compound 135*

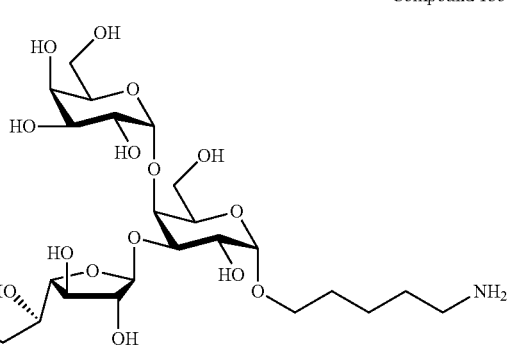

Compound 134* (9 mg, 0.009 mmol) was dissolved in a mixture of MeOH:DCM:EtOAc (2:0.5:0.5, 3 mL). Pd/C (10 mg, 0.009 mmol) was added and the reaction mixture was purged with hydrogen (5 times) and the reaction let stir under hydrogen pressure (10 bar) for 60 h. Then, the reaction mixture was filtered through PTFE filter using H$_2$O:MeOH (1:1), the organic solvents evaporated in rotavapor and the crude material was lyophilized. The crude was purified by SepPack using miliQ H$_2$O to give the product as a white solid (1 mg, 18%). Calcd for C$_{23}$H$_{44}$NO$_{16}$Na [M+H]$^+$ 590.2660, found 590.2593. $^1$H NMR (400 MHz, D$_2$O) δ 5.26 (d, J=2.7 Hz, 1H), 5.10 (d, J=3.6 Hz, 1H), 5.05 (d, J=3.7 Hz, 1H), 4.31-4.21 (m, 3H), 4.17-4.04 (m, 5H), 4.03-3.94 (m, 2H), 3.94-3.67 (m, 9H), 3.66-3.57 (m, 1H), 3.07 (t, J=7.4 Hz, 2H), 1.82-1.65 (m, 4H), 1.59-1.45 (m, 2H). $^{13}$C NMR (101 MHz, D$_2$O) δ 109.0, 100.1, 98.3, 82.2, 80.9, 78.3, 76.8, 76.1, 71.6, 70.8, 70.5, 69.1, 68.9, 68.0, 67.9, 62.7, 60.7, 60.4, 39.4, 28.1, 26.5, 22.4.

A-7-2 Preparation of *Klebsiella pneumoniae* Galactan-III Hexasaccharide

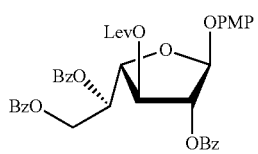

Compound 137*

To a solution of imidate donor 76* (2.6 g, 3.41 mmol) and 4-methoxyphenol (1.06, 8.53 mmol) in DCM (40 mL) was added 4 Å MS and the mixture let stir at room temperature for 30 min. TMSOTf (0.076 g, 0.341 mmol) was added and the reaction mixture stirred at rt for 2h. The reaction was quenched with triethylamine (0.2 mL), filtered and the solvent evaporated in rotavapor. Purification by automated purification system using silica gel (ethyl acetate/cyclohexane) afforded the product after evaporation of the solvent as a foam (2.14 g, 90%). HRMS (ESI+) Calcd for $C_{39}H_{36}O_{12}Na^+$ [M+Na]$^+$ 719.2104, found 719.2036.

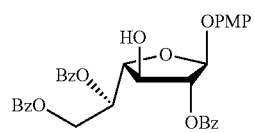

Compound 138*

To a solution of compound 137* (2.14 g, 3.07 mmol) in DCM (30 mL), a solution of hydrazine hydrate (0.394 g, 12.29 mmol) dissolved in acetic acid (2.4 mL, 41.9 mmol) and pyridine (3.6 mL, 44.5 mmol) was added. The resulting reaction mixture was stirred at room temperature for 2 h. The reaction was quenched by the addition of acetone (3 mL) and the solvent removed under vacuum to obtain the crude product (some pyridine remained). The crude product was purified by automated flash chromatography using silica gel (ethyl acetate/cyclohexane). Concentration of solvent from test tubes containing the products (based on TLC) in vacuum gave the product as a white foam (1.79 g, 97%). HRMS (ESI+) Calcd for $C_{34}H_{30}O_{10}Na^+$ [M+Na]$^+$ 621.1737, found 621.1672.

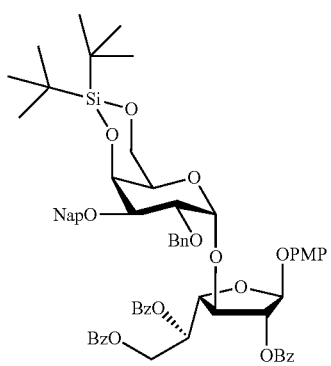

Compound 139*

To a solution of compound 4* (2.5 g, 3.89 mmol) in DCM (60 mL) were added 4 Å MS, Ph$_2$SO (1.15 g, 5.68 mmol) and 2,4,6-tri-tert-butylpyrimidine (2.6 g, 10.47 mmol) and mixture stirred for 20 min. The reaction mixture was cooled to −78° C. Tf$_2$O (1.8 g, 6.37 mmol) was added and the reaction mixture stirred for 20 min at the same temperature. Then, compound 138* was added dropwise dissolved in 10 mL DCM. The reaction mixture was warmed to −50° C. over 3 h and was then quenched with triethylamine (3 mL). The reaction mixture was diluted with DCM (50 mL), washed with brine (30 mL) and the organic layer dried over Na$_2$SO$_4$. The crude mixture was purified using automated purification using silica gel (ethyl acetate/cyclohexane). Concentration of solvent from test tubes containing the products (based on TLC) in vacuum gave the product as a colorless oil (3.05 g, 90%). HRMS (ESI+) Calcd for $C_{66}H_{70}O_{15}Na^+$ [M+Na]$^+$ 1153.4392, found 1153.4268.

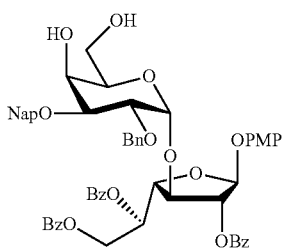

Compound 140*

To a solution of compound 139* (3 g, 2.65 mmol) in THF (40 mL) in 2×50 mL falcon tubes (solution divided in 2 tubes due to the large volume) was added HF.py (21 mL, 21 mmol) and the reaction let stir at room temperature for 2 h. After complete consumption of the starting material (TLC), the reaction was quenched with triethylamine (5 mL), diluted with DCM (30 mL) and washed with sat. NaHCO$_3$ (20 mL) and brine (20 mL). The organic layer was dried over Na$_2$SO$_4$ and the solvent removed under vacuum. The oil residue was purified using automated purification system (Combiflash) using silica gel (ethyl acetate/cyclohexane). Concentration of solvent from test tubes containing the product (based on TLC) in vacuum gave the product as a colorless oil (2.4 g, 91%).

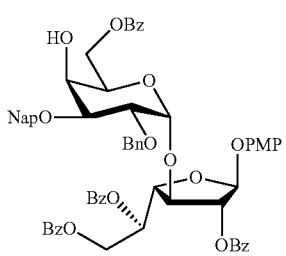

Compound 141*

Benzoic anhydride (0.66 g, 2.91 mmol) and triethylamine (1.96 g, 19.37 mmol) were added to a solution of diol 140* (2.4 g, 2.42 mmol) in DCM (48 mL) and the reaction let stir overnight at room temperature. The reaction was diluted with DCM (30 mL) and washed with sat. NaHCO$_3$ (20 mL). The layers were separated and the aqueous layer extracted with DCM (2×30 mL). The combined organic layers were dried over Na$_2$SO$_4$ and the solvent concentrated in rotavapor. The residue was purified using automated purification system (combiflash) using silica gel (ethyl acetate/cyclohexane). The tubes containing the product were combined and the solvent evaporated to give the product as a colorless oil (2.4 g, 90%). HRMS (ESI+) Calcd for $C_{65}H_{58}O_{16}Na^+$ [M+Na]$^+$ 1117.3623, found 1117.3515.

Compound 142*

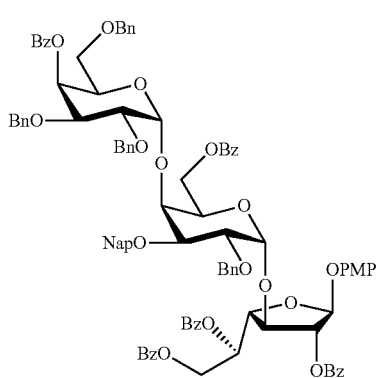

To a solution of compound 9* (2.216 g, 3.29 mmol) and compound 141* (2.4 g, 2.191 mmol) in toluene:dioxane (3:1, 40 mL) was added 4 Å MS and the mixture let stir at room temperature for 1h. Then, NIS (0.986 g, 4.38 mmol) was added and the reaction mixture cooled to 0° C. TMSOTf (0.049 g, 0.219 mmol) was added and the reaction mixture stirred for 1.5 h at 0° C. The reaction was quenched with triethylamine (3 mL), diluted with DCM (70 mL) and extracted with Na$_2$SO$_3$ and sat. NaHCO$_3$. The organic layer was dried over Na$_2$SO$_4$ and the solvent concentrated in rotavapor. Purification by automated purification system using silica (ethyl acetate/cyclohexane) afforded the product after evaporation of the solvent as a yellowish solid (3.27 g, 91%). HRMS (ESI+) Calcd for $C_{99}H_{90}O_{22}Na^+$ [M+Na]$^+$ 1654.5855, found 1654.5658.

Compound 143*

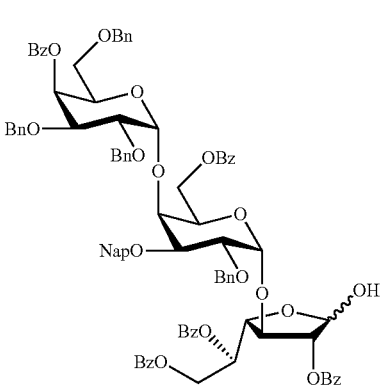

Ceric ammonium nitrate (249 mg, 0.453 mmol) was added to a solution of compound 142* (370 mg, 0.227 mmol) in ACN/H$_2$O (8:1, 4.5 mL) at 0° C. The reaction mixture was stirred for 20 min at the same temperature and warmed to room temperature. After 4 h, another aliquote of CAN (100 mg, 0.182 mmol) were added at 0° C. and the reaction mixture was stirred for 30 min at the same temperature. After 30 min, the reaction was diluted with DCM (20 mL) and washed with brine (10 mL). The organic layer was dried over Na$_2$SO$_4$ and the solvent concentrated in rotavapor (water bath ~35° C.). The residue was purified using automated purification system using silica (ethyl acetate/cyclohexane). The tubes containing the product were combined and the solvent evaporated to give the product as a yellow oil (275 mg, 79%). HRMS (ESI+) Calcd for $C_{92}H_{84}O_{21}Na^+$ [M+Na]$^+$ 1548.5436, found 1548.5278.

Compound 144*

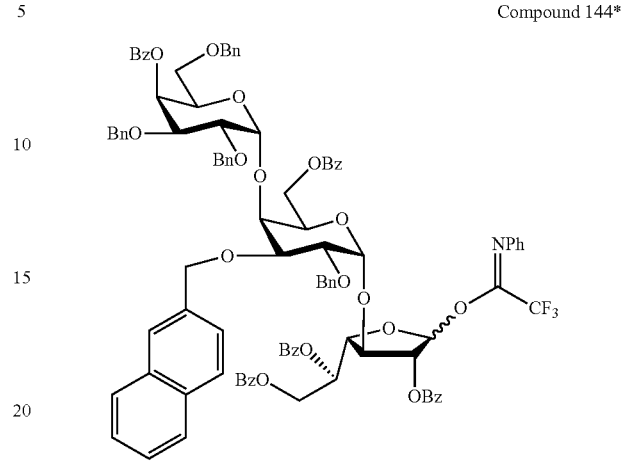

Cs$_2$CO$_3$ (141 mg, 0.433 mmol) and 2,2,2-trifluro-N-phenyl-acetimidoyl chloride (135 mg, 0.649 mmol) were added to a solution of lactol 143* (330 mg, mmol) in DCM (10 mL). The reaction mixture was stirred at room temperature and monitored by TLC. After 2 hours all the starting material was consumed and the reaction was filtered through celite and washed with DCM (20 mL). The solvent was evaporated and the product purified by column chromatography using silica-gel (ethyl acetate/cyclohexane+1% Et$_3$N). The tubes containing the product by TLC were combined and the solvent evaporated to give the product as a colorless oil (310 mg, 84%).

Compound 145*

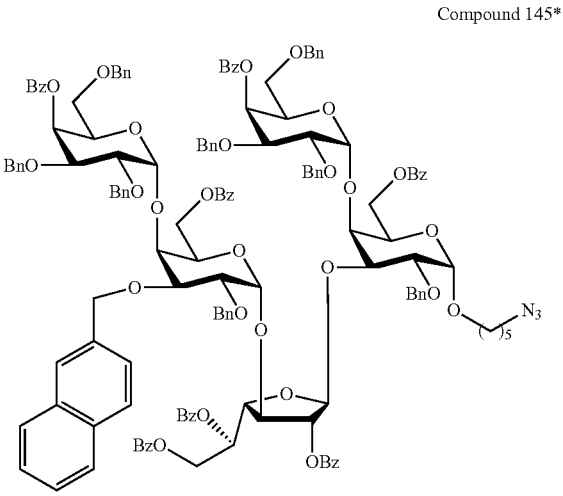

Compound 144* (250 mg, 0.147 mmol) and compound 132* (137 mg, 0.134 mmol) were dissolved in DCM (5 mL), 4 Å MS was added and stirred for 30 min. The reaction mixture was cooled to −30° C., TMSOTf (6 mg, 0.028 mmol) added and the reaction warmed to −5° C. over 3 h. Reaction was quenched by addition of triethylamine (0.5 mL). The reaction mixture was filtered, diluted with DCM (20 mL) and washed with sat. NaHCO$_3$. The organic phase was dried over Na$_2$SO$_4$ and the solvent evaporated to give an oil residue. The crude reaction mixture was purified by automated purification system using silica (ethyl acetate/cyclohexane). The tubes containing the product by TLC were combined and the solvent evaporated to give the product as a colorless oil (259 mg, 76%).

Compound 146*

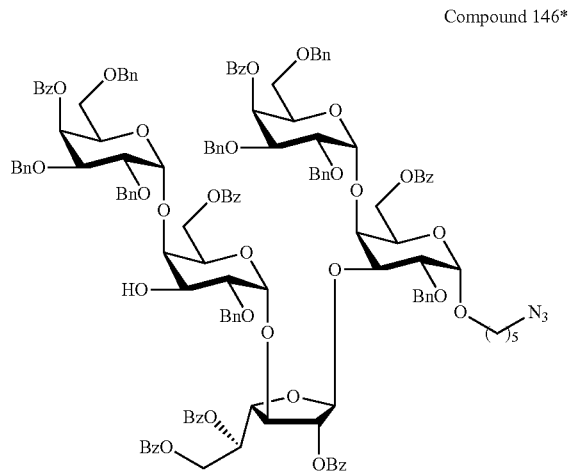

To a solution of compound 145* (255 mg, 0.101 mmol) in DCM:MeOH (4:1, 2 mL) in a 10 mL RBF under argon atmosphere was added 2,3-dichloro-5,6-dicyano-1,4-benzoquinone at 0° C. The reaction mixture was stirred for 2h 40 min at room temperature. Reaction was monitored by TLC (EtOAc in Cyclohexane, 2:1). Reaction was diluted with DCM (10 mL) and quenched with sat. NaHCO$_3$ (5 mL). The organic layer was washed with sat. NaHCO$_3$ (5 mL) and brine (5 mL). The organic layer was dried over Na$_2$SO$_4$ (0.2 g), filtered, and the filtrate was concentrated under vacuum for 15 min to obtain the crude product. The crude product was purified by automated flash chromatography using silica (ethyl acetate/cyclohexane). Concentration of solvent from test tubes containing the product (based on TLC) in vacuum resulted in a colorless oil (120 mg, 50%). HRMS (ESI+) Calcd for $C_{140}H_{137}N_3O_{33}Na^+$ [M+Na]$^+$ 2411.9066, found 2411.8844.

Compound 147*

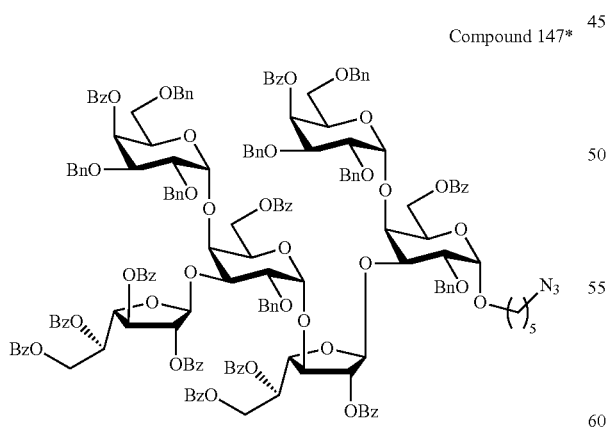

Compound 95* (54 mg, 0.070 mmol) and compound 146* (84 mg, 0.035 mmol) were coevaporated with toluene and left under vacuum overnight. Then, the mixture was dissolved in DCM (5 mL), 4 Å MS was added and stirred for 30 min. The reaction mixture was cooled to −50° C., TMSOTf (6 mg, 0.028 mmol) added and the reaction warmed to −5° C. over 4 h. Reaction was quenched by addition of triethylamine (0.03 mL). The reaction mixture was filtered and the solvent evaporated to give an oil residue. The crude reaction mixture was purified by automated purification system using silica (ethyl acetate/cyclohexane) to give the product as a colorless oil (80 mg, 77%). HRMS (ESI+) Calcd for $C_{174}H_{163}N_3O_{42}Na^+$ [M+Na]$^+$ 2411.9066, found 2411.8844.

Compound 148*

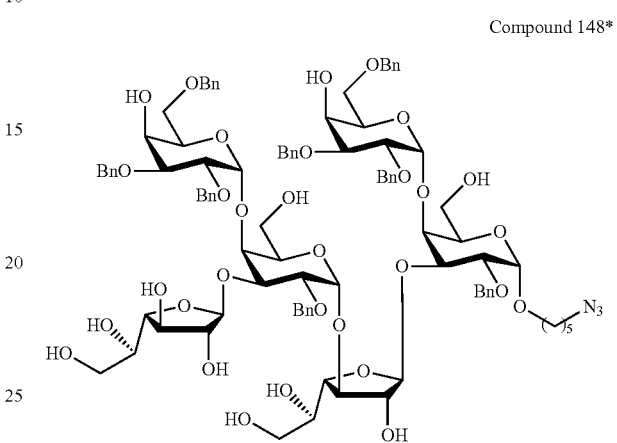

Sodium methoxide solution in MeOH 25% w/w (0.12 mL, 0.539 mmol) was added to a solution of hexasaccharide 147* (80 mg, 0.027 mmol) in a mixture of MeOH:THF (2:1, 3 mL). The reaction was stirred at the same temperature for 20h. The reaction was quenched by the addition of AcOH (0.2 mL) and the solvent evaporated. The crude material was loaded in isolute. Purification by silica gel chromatography using the eluent sequence: 1) cyclohexane, 2) Ethyl acetate and 3) MeOH in DCM 5%, afforded the product after evaporation of the solvent as a white oil (44 mg, 90%). Calcd for $C_{97}H_{119}N_3O_{31}Na^+$ [M+Na]$^+$ 1845.7759, found 1845.7556.

Compound 149*

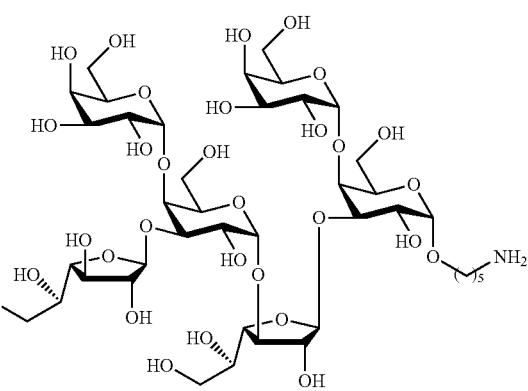

The hexasaccharide 148* (40 mg, 0.022 mmol) was dissolved in a mixture of DCM:tBuOH:H$_2$O (1:0.8:0.2, 2 mL). PdC (40 mg, 0.038 mmol) was added and the reaction mixture was purged with hydrogen (5 times) and the reaction let stir under hydrogen pressure (5 bar) for 22 h. Then, the reaction mixture was filtered through PTFE filter using H$_2$O:ACN (1:1), the organic solvents evaporated in rotavapor and the crude material was lyophilized. The crude was purified by SepPack using miliQ H₂O to give the product as a white solid (17 mg, 72%). Calcd for $C_{41}H_{74}NO_{31}$ [M+H]⁺ 1076.4245, found 1076.4123. ¹H NMR (400 MHz, D₂O) δ 5.08-5.04 (m, 2H), 4.94 (d, J=3.9 Hz, 1H), 4.90 (d, J=3.7 Hz, 1H), 4.88-4.81 (m, 2H), 4.18 (dd, J=5.4, 2.9 Hz, 1H), 4.14 (dd, J=8.5, 3.0 Hz, 1H), 4.11-3.84 (m, 13H), 3.83-3.37 (m, 22H), 2.85 (t, J=7.54 Hz 1H), 1.62-1.43 (m, 2H), 1.38-1.23 (m, 1H). ¹³C NMR (101 MHz, D₂O) δ 109.5, 109.1, 100.3, 100.2, 98.4, 84.7, 82.3, 81.0, 80.5, 79.8, 78.3, 78.2, 76.9, 76.6, 76.1, 72.1, 71.9, 70.9, 70.7, 70.6, 70.1, 69.2, 69.2, 69.0, 68.7, 68.1, 67.9, 67.9, 62.9, 62.8, 60.6, 60.4, 60.0, 39.5, 28.2, 26.6, 22.5.

Compound 149a-l*

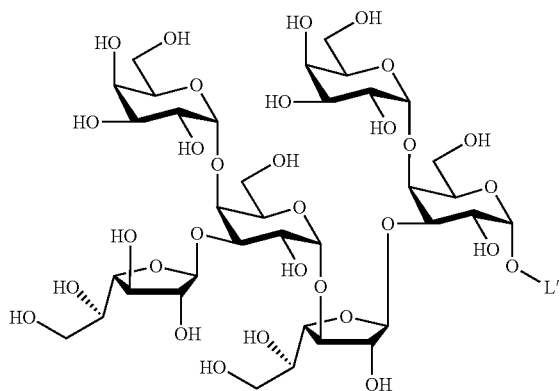

Compounds 149a-l* are prepared similarly to compound 149* from compound 4* and the corresponding alcohol as shown in FIG. 11.

A-7-3 Preparation of *Klebsiella pneumoniae* Galactan-III Nonasaccharide

Compound 150*

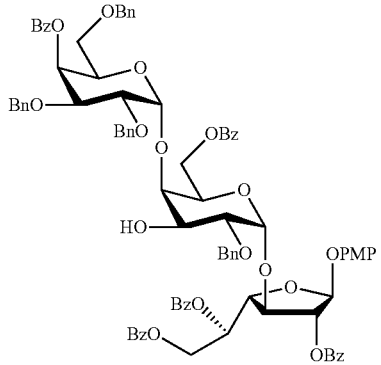

To a solution of compound 142* (500 mg, 0.306 mmol) in DCM:MeOH (4:1, 3.75 mL) in a 25 mL RBF under argon atmosphere was added 2,3-dichloro-5,6-dicyano-1,4-benzoquinone (348 mg, 1.532 mmol) at 0° C. The reaction mixture was stirred for 2h at room temperature. Reaction was monitored by TLC (EtOAc in Cyclohexane, 2:1). Reaction was diluted with DCM (10 mL) and quenched with sat. NaHCO₃ (5 mL). The organic layer was washed with sat. NaHCO₃ (5 mL) and brine (5 mL). The organic layer was dried over Na₂SO₄ (0.2 g), filtered, and the filtrate was concentrated under vacuum to obtain the crude product. The crude product was purified by automated flash chromatography using silica (ethyl acetate/cyclohexane). Concentration of solvent from test tubes containing the product (based on TLC) in vacuum resulted in a colorless oil (350 mg, 77%). Calcd for $C_{88}H_{82}O_{22}Na$ [M+Na]⁺ 1514.5229, found 1514.5256.

Compound 151*

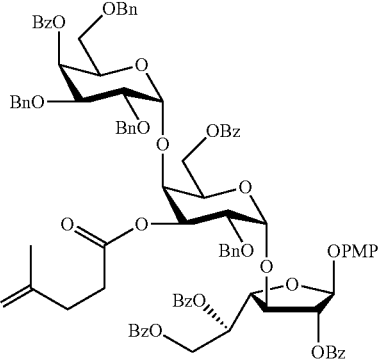

To a solution of trisaccharide 150* (340 mg, 0.228 mmol) in DCM (3 mL) in a 25 mL RBF under argon atmosphere was added levulinic acid (119 mg, 1.026 mmol), N-(3-dimethylaminopropyl)-N'-ethylcarbodiimide hydrochloride (197 mg, 1.026 mmol) and DMAP (84 mg, 0.684 mmol). The resulting reaction mixture was stirred at room temperature. The reaction was monitored by TLC. After 5 h, the reaction did not go to completion. The reaction mixture was diluted with DCM (10 mL) and washed with brine (5 mL). The aqueous layer was extracted with DCM (1×5 mL). The organic layer was dried over Na₂SO₄ (0.2 g), filtered, and the filtrate was concentrated under vacuum to obtain the crude product. The crude product was purified by automated flash chromatography using EtOAc in cyclohexane as the eluent. Concentration of solvent from test tubes containing the products (based on TLC) in vacuum resulted in a white oil (260 mg, 72%).

Compound 152*

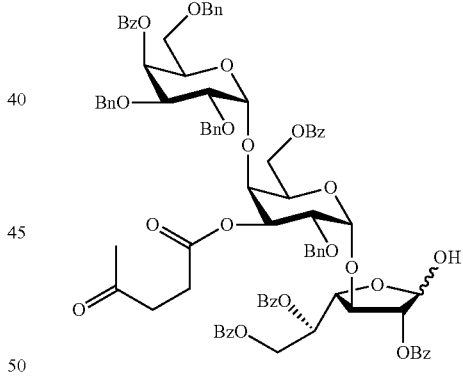

Ceric ammonium nitrate (179 mg, 0.327 mmol) was added to a solution of compound 151* (260 mg, 0.164 mmol) in ACN/H₂O (8:1, 3.3 mL) at 0° C. The reaction mixture was stirred for 20 min at the same temperature and warmed to room temperature. After 4 h, another aliquot of CAN (100 mg, 0.182 mmol) were added at 0° C. and the reaction mixture was stirred for 30 min at the same temperature. After 30 min, the reaction was diluted with DCM (20 mL) and washed with brine (10 mL). The organic layer was dried over Na₂SO₄ and the solvent concentrated in rotavapor (water bath 35° C.). The residue was purified using automated purification system using silica (ethyl acetate/cyclohexane). The tubes containing the product were combined and the solvent evaporated to give the product as a yellow oil (209 mg, 86%). HRMS (ESI+) Calcd for $C_{86}H_{82}O_{23}Na^+$ [M+Na]⁺ 1505.5145, found 1505.5186.

Compound 153*

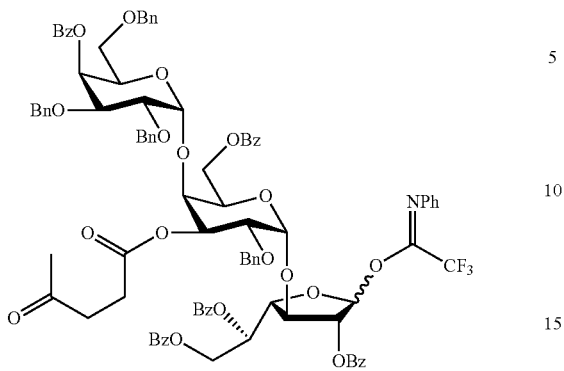

Cs$_2$CO$_3$ (115 mg, 0.354 mmol) and 2,2,2-trifluro-N-phenyl-acetimidoyl chloride (49 mg, 0.236 mmol) were added to a solution of lactol 152* (175 mg, 0.118 mmol) in DCM (20 mL). The reaction mixture was stirred at room temperature and monitored by TLC. After 2 hours all the starting material was consumed and the reaction was filtered through celite and washed with DCM (2 mL). The solvent was evaporated and the product purified by column chromatography using silica-gel and ethyl acetate/cyclohexane+1% Et$_3$N as the eluent. The tubes containing the product by TLC were combined and the solvent evaporated to give the product as a colorless oil (188 mg, 96%).

Compound 154*

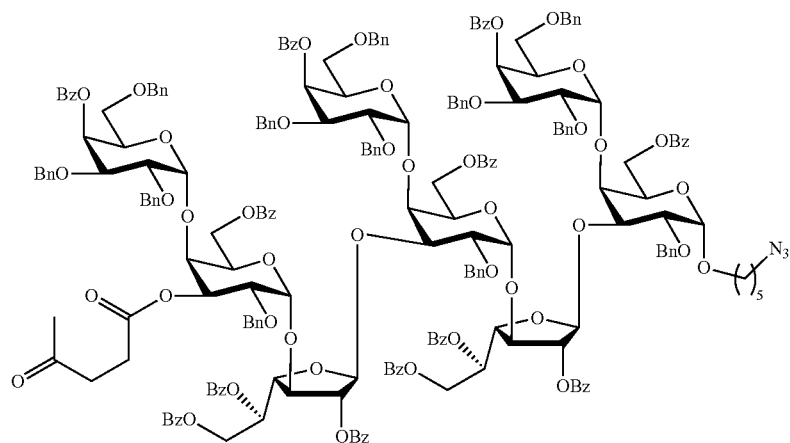

Trisaccharide 153* (69 mg, 0.042 mmol) and compound 146* (50 mg, 0.021 mmol) were coevaporated with toluene and left under vacuum for 1 h. Then, the mixture was dissolved in DCM (1.5 mL), 4 Å MS was added and stirred for 30 min. The reaction mixture was cooled to −50° C., TMSOTf (5 μL, 0.028 mmol) added and the reaction warmed to −10° C. over 4 h. Reaction was quenched by addition of triethylamine (0.03 mL). The reaction mixture was filtered and the solvent evaporated to give an oil residue. The crude reaction mixture was purified by automated purification system using silica (ethyl acetate/cyclohexane) to give the product as a colorless oil (50 mg, 62%). HRMS (ESI+) Calcd for C$_{226}$H$_{217}$N$_3$O$_{55}$Na$^+$ [M+Na]$^+$ 3877.4240, found 3877.3947.

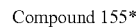
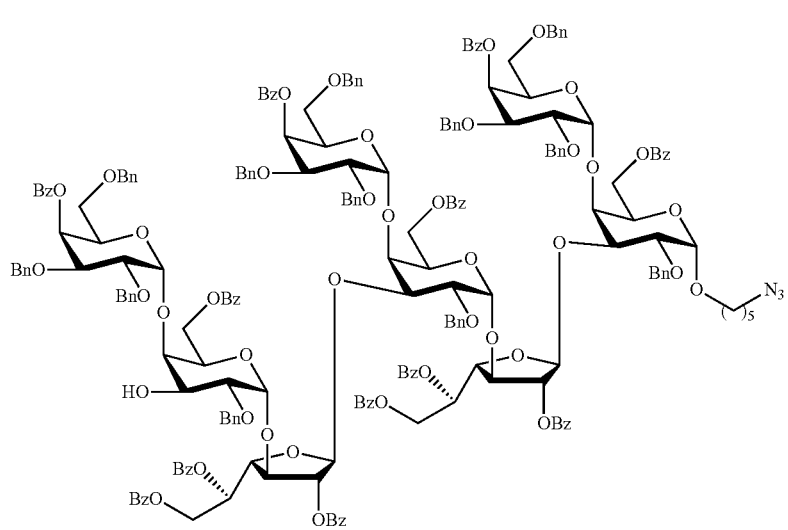

To a solution of compound 154* (100 mg, 0.026 mmol) in DCM (3 mL), a solution of hydrazine hydrate (8.14 µL) dissolved in acetic acid (0.04 mL) and pyridine (0.06 mL) was added. The resulting reaction mixture was stirred at room temperature for 2 h. The reaction was quenched by the addition of acetone (0.3 mL) and the solvent removed under vacuum to obtain the crude product. The crude product was purified by automated flash chromatography using EtOAc in n-hexane (0-80%) as the eluent. Concentration of solvent from test tubes containing the product (based on TLC) in vacuum resulted in a white oil (97 mg, 100%). HRMS (ESI+) Calcd for $C_{221}H_{211}N_3O_{53}Na^+$ [M+Na]$^+$ 3779.3873, found 3779.3708.

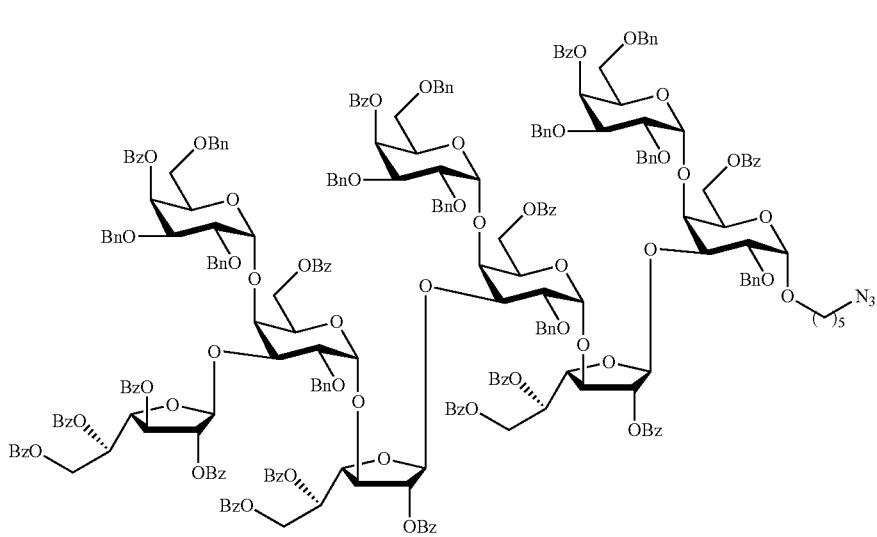

Compound 95* (25 mg, 0.033 mmol) and compound 155* (50 mg, 0.013 mmol) were coevaporated with toluene and left under vacuum for 30 min. Then, the mixture was dissolved in DCM (2 mL), 4 Å MS was added and stirred for 30 min. The reaction mixture was cooled to −50° C., TMSOTf (5 µL, 0.028 mmol) added and the reaction warmed to −5° C. over 2 h. Reaction was quenched by addition of triethylamine (0.03 mL). The reaction mixture was filtered and the solvent evaporated to give an oil residue. The crude reaction mixture was purified by automated purification system using silica (ethyl acetate/cyclohexane) to give the product as a colorless oil (27 mg, 47%). LRMS (ESI+) Calcd for $C_{255}H_{237}N_3O_{62}Na^+$ [M+Na]$^+$ 4358.5483, found 4358.5.

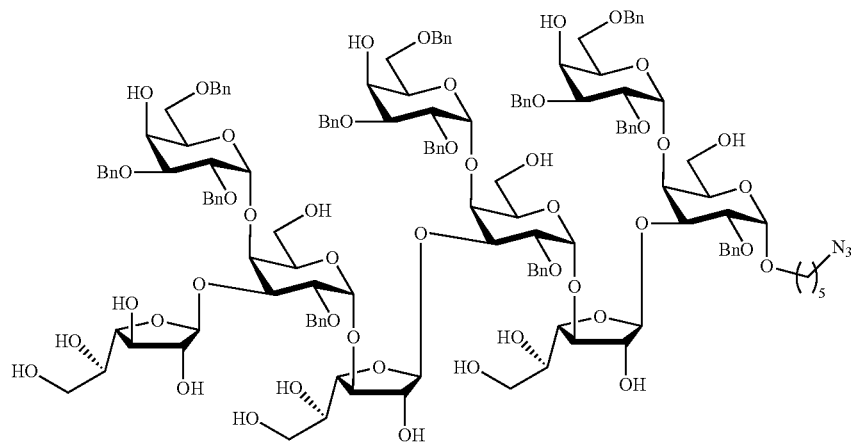

Compound 157*

Sodium methoxide solution in MeOH 25% w/w (0.025 mL, 0.115 mmol) was added to a solution of compound 156* (25 mg, 5.77 µmol) in a mixture of MeOH:THF (2:1, 1.5 mL). The reaction was stirred at the same temperature for 60 h. The reaction was quenched by the addition of AcOH (0.1 mL) and the solvent evaporated. The crude material was loaded in isolute. Purification by silica gel chromatography using the eluent sequence: 1) cyclohexane, 2) Ethyl acetate and 3) MeOH in DCM 5%, afforded the product after evaporation of the solvent as a white oil (13 mg, 84%).

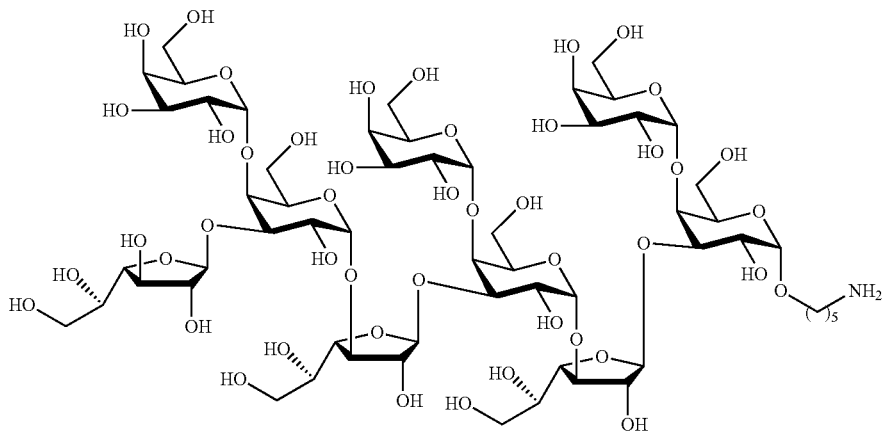

Compound 158*

The nonasaccharide 157* (13 mg, 4.87 µmol) was dissolved in a mixture of DCM:tBuOH:H2O (1:0.8:0.2, 1.4 mL). PdC (12 mg, 0.011 mmol) was added and the reaction mixture was purged with hydrogen (5 times) and the reaction let stir under hydrogen pressure (5 bar) for 22 h. Then, the reaction mixture was filtered through PTFE filter using $H_2O$:ACN (1:1), the organic solvents evaporated in rotavapor and the crude material was lyophilized. The crude was purified by SepPack using miliQ $H_2O$ to give the product as a white solid (5.6 mg, 74%). Calcd for $C_{59}H_{103}NO_{46}$ [M+H]$^+$ 1561.5751, found 1562.5728. $^1$H NMR (400 MHz, $D_2O$) δ 5.23-5.17 (m, 3H), 5.10-5.06 (m, 2H), 5.04 (d, J=3.7 Hz, 1H), 5.02-4.94 (m, 3H), 4.37-4.27 (m, 4H), 4.26-4.13 (m, 8H), 4.12-3.98 (m, 11H), 3.98-3.62 (m, 32H), 3.59-3.52 (d, J=9.8 Hz, 1H), 2.99 (t, J=7.5 Hz, 2H), 1.75-1.61 (m, 4H), 1.53-1.38 (m, 2H).

Compound 158a-l*

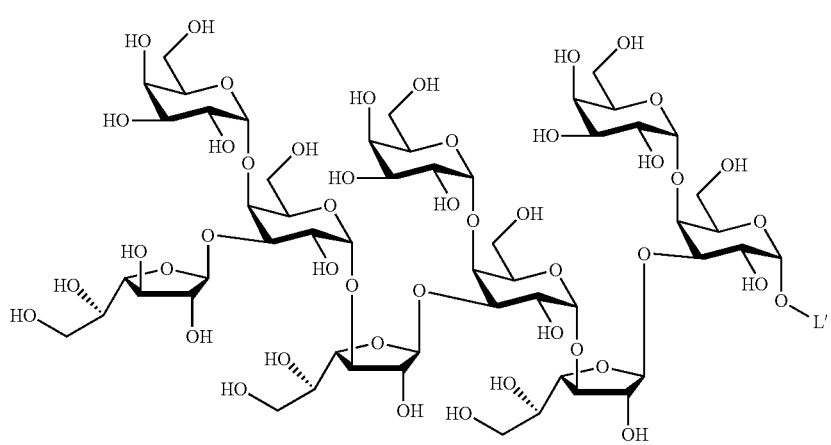

Compounds 158a-l* are prepared similarly to compound 158* from compound 4* and the corresponding alcohol as shown in FIG. 11.

A-8 Preparation of *Klebsiella pneumoniae* O2a (Galactan-I) Saccharide

Compound 159*

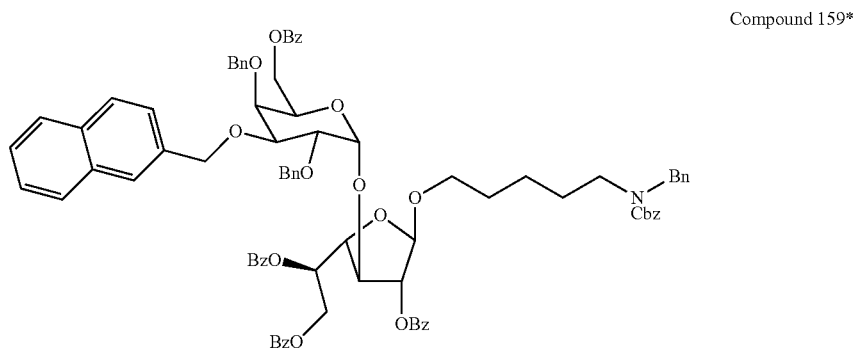

Compound 44* (35 mg, 0.028 mmol) was dried azeotropically using dry toluene in the vacuum separately. It was taken in DCM (2 mL) at rt, added 4 Å molecular sieves to it and stirred for 10 min. To this 5-N-Carboxybenzyl-N-benzylaminopentanol (18.33 mg, 0.056 mmol) was added (neat) and stirred at for 10 min under N2 atmosphere at rt. Cooled the RM to -20 deg using dry Ice-ACN bath and added TMSOTf (1.2 mg, 5.60 µmol) to the RM and stirred the RM at -20 deg for 5 mins slowly warmed to 2 deg over one h. TLC analysis showed the presence of new intense spot and absence of the donor material. So RM was quenched with NaHCO₃ solution (5 mL) and separated the layers. Aqueous layer was Organic layer was washed with brine solution (5 mL) and dried (Na₂SO₄), filtered, evaporated in vacuum to get crude which was purified using Biotage on silica column with EtOAc and Cyclohexane as eluents to get product as colourless layer (21.4 mg, 55%).

Compound 160*

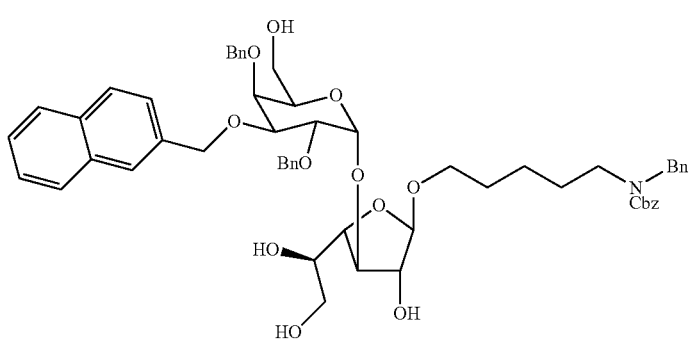

Compound 159* (21 mg, 0.015 mmol) was taken in THF-MeOH (2 mL) at rt, added NaOMe solution in methanol (0.605 mL, 0.0302 mmol) to it and continued stirring for 18 h. TLC analysis (30% EA/CHx) showed the absence of the SM and presence of a polar spot. So, RM was evaporated in vacuum. Diluted with EA (5 mL) and water (5 mL). Acidified with AcOH till neutral pH (~0.3 mL). Extracted with EA (5 mL×3). Combined organics were washed with brine solution (5 mL), dried (Na$_2$SO$_4$), filtered, and evaporated in vacuum to get crude product as pale yellowish layer (11.7 mg, 80%).

Compound 161*

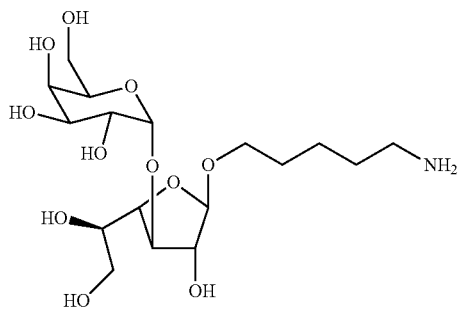

Compound 160* (11 mg, 0.011 mmol) was taken in mixture of DCM:tBuOH:H$_2$O (1:1:0.2, 2.2 mL), added suspension of Pd/C (1 mg, 0.011 mmol) in butanol (0.2 mL) to it and hydrogenated under ~10 bar H$_2$ atmosphere for 23 h. RM was filtered through the PTFE filter, washed with methanol (2 mL×3), 50% Methanol in water (2 mL×3). The filtrate was concentrated under vacuum to get colourless layer. 1H nmr looked like there was still one benzyl group left in the molecule, so resubjected the material to the hydrogenation using water and butanol as solvents and ~10 mg of Pd/C for 14 h. RM was filtered through the PTFE filter, washed with methanol (2 mL×3), 50% Methanol in water (2 mL×3). The filtrate was concentrated under vacuum to get colourless layer (2.7 mg, 56%). LRMS (ESI+) Calcd for C$_{17}$H$_{33}$NO$_{11}$H$^+$ [M+H]$^+$ 428.2132, found 428.2037.

Compound 162*

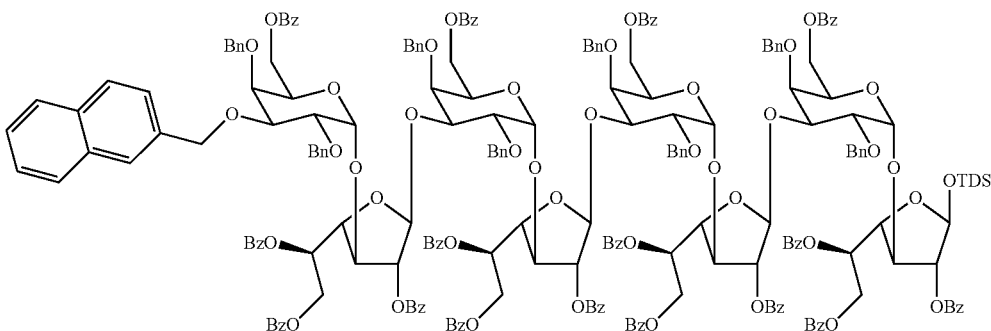

Both compound 54* (500 mg, 0.250 mmol) and compound 56* (651 mg, 0.30 mmol) were taken together in a RBF and dried azeotropically using dry toluene in the vacuum. The mixture was taken in DCM (20 mL) at rt, added 4 Å molecular sieves to it and stirred for 30 min. Cooled the RM to -10 deg using Ice-acetone bath and added TMSOTf (9.20 μL, 0.05 μmol) to the RM and stirred the RM at -10 deg for 5 mins slowly warmed to 5 deg over one h. TLC analysis (30% EA/CHx) showed that the reaction was complete and absence of the acceptor SM and presence of a slightly polar spot. RM was quenched with NaHCO$_3$ solution (2 mL) at 10 deg, separated the layers, dried the organic layer (Na$_2$SO$_4$), filtered, and evaporated in vacuum. Purified by silica column chromatography using EA/CHx to get fractions containing product, on evaporation under vacuum yielded desired product (890 mg, 89%). MALDI-TOF Calcd for C$_{235}$H$_{220}$NaO$_{57}$Si [M+Na]$^+$ 4004.3983, found 4007.795.

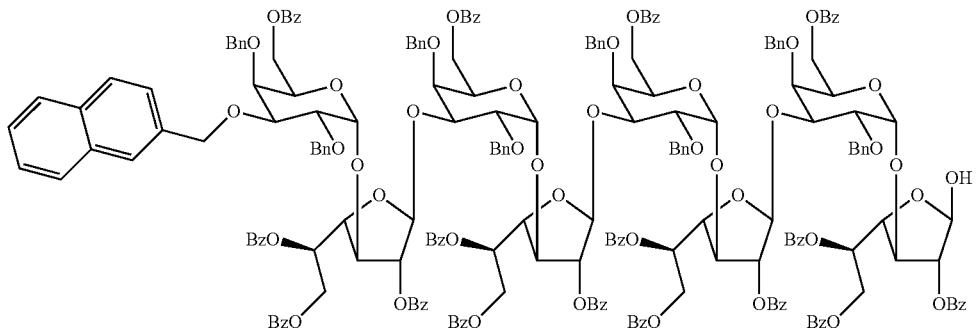

Compound 163*

Compound 162* was subjected to TDS removal reaction according to general protocol B:
Product 163* as white fluffy solid obtained (617 mg, 97%).
MALDI-TOF Calcd for $C_{227}H_{202}NaO_{57}{}^{+}$ [M+Na]$^{+}$ 3862.2806, found 3864.889.

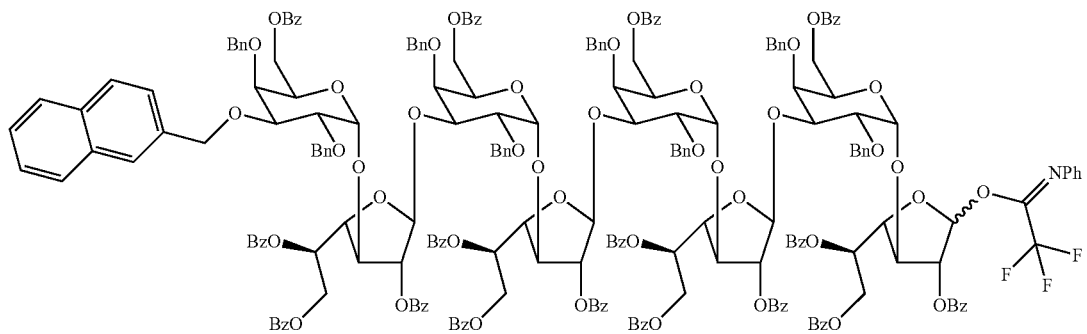

Compound 164*

Compound 163* was converted to imidate 164* in the presence of 2,2,2-trifluro-N-phenyl-acetimidoyl according to general protocol B.
Product as white fluffy solid obtained (625 mg, quantitative).
MALDI-TOF Calcd for $C_{235}H_{206}F_3NNaO_{57}{}^{+}$ [M+Na] 4033.3101, found 4037.043.

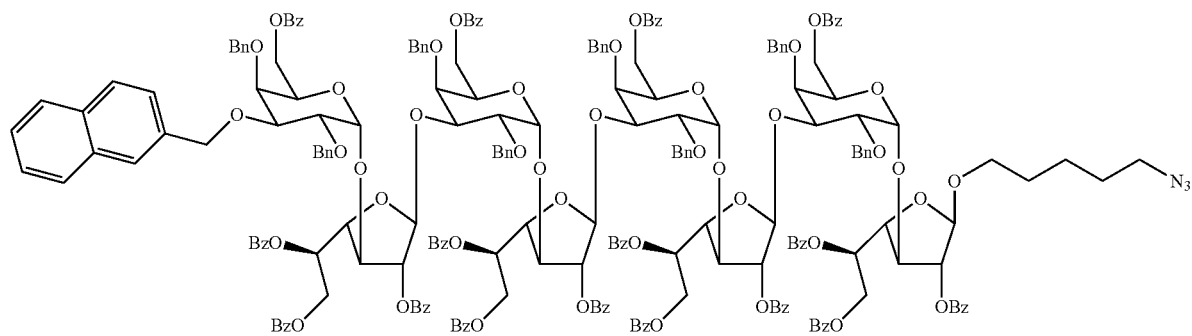

Compound 165*

Compound 165* was obtained from 5-azidopentanol and compound 164* by glycosylation reaction according to general protocol B:

product as white gummy solid obtained (310 mg, 79%).

MALDI-TOF Calcd for $C_{232}H_{212}N_3O_{57}{}^+$ [M+H]$^+$ 3951.3783, found 3954.175.

Compounds 165L1-L10*

Compounds 165L1-L10* were prepared from compound 164* and the corresponding alcohol by glycosylation reaction according to general protocol B:

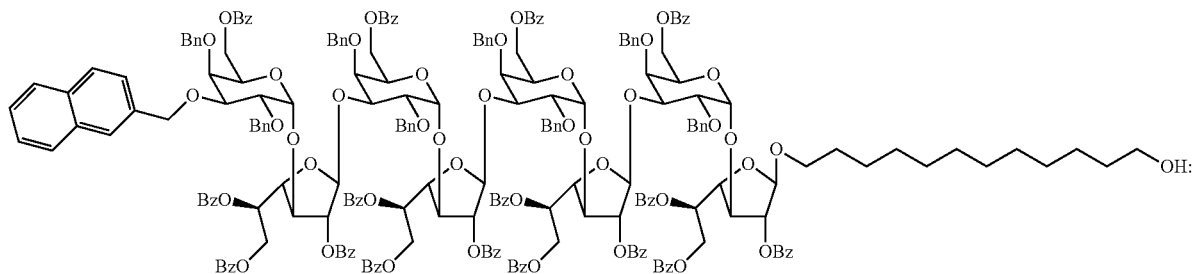

L1

White solid layer, 16 mg, 64%

MALDI-TOF Calcd for $C_{239}H_{226}NaO_{58}{}^+$ [M+Na]$^+$ 4046.4633, found 4046.458.

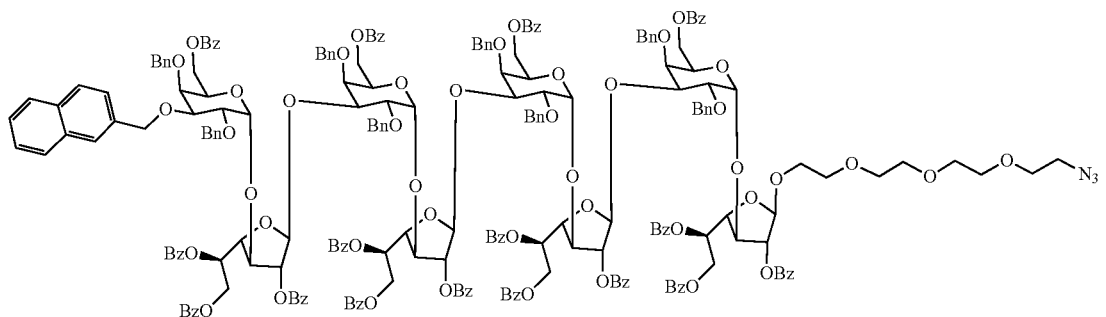

White solid layer, 23.4 mg, 95%

MALDI-TOF Calcd for $C_{235}H_{218}N_3O_{60}{}^+$ [M+H]$^+$ 4041.4100, found 4041.378.

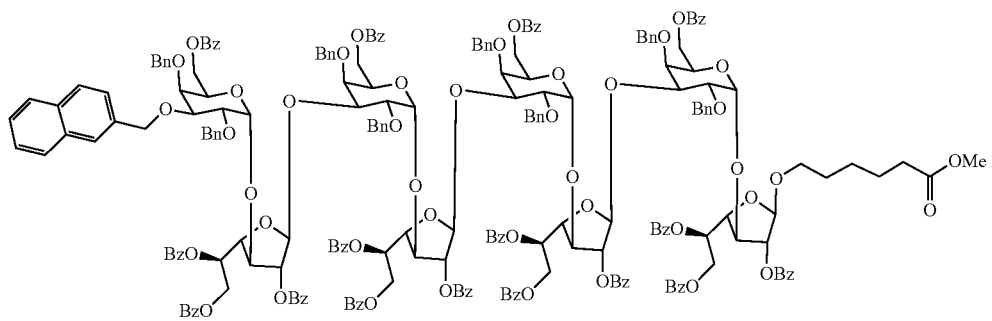

White solid layer, 23.7 mg, 96%
MALDI-TOF Calcd for C234H214NaO59+ [M+Na]+ 3990.3643, found 3990.379.
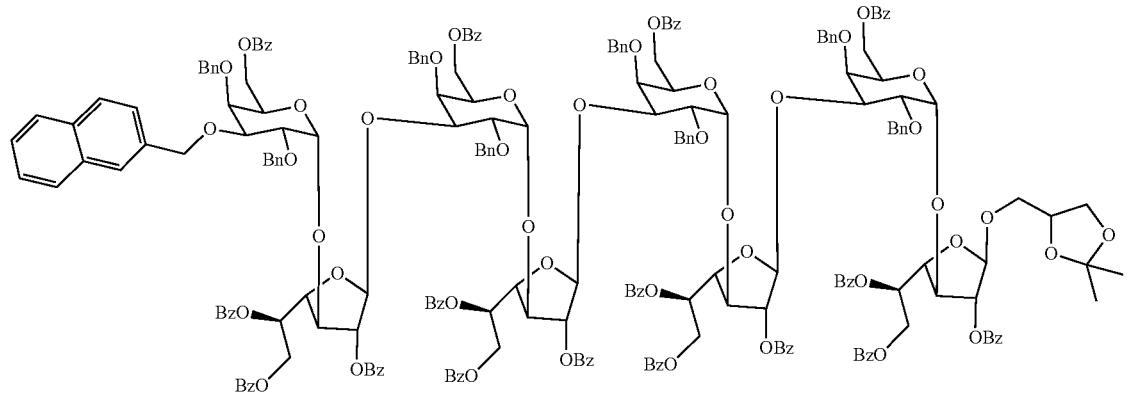
White solid layer, 23.9 mg, 98%
MALDI-TOF Calcd for C233H212NaO59+ [M+Na]+ 3976.3486, found 3979.155.
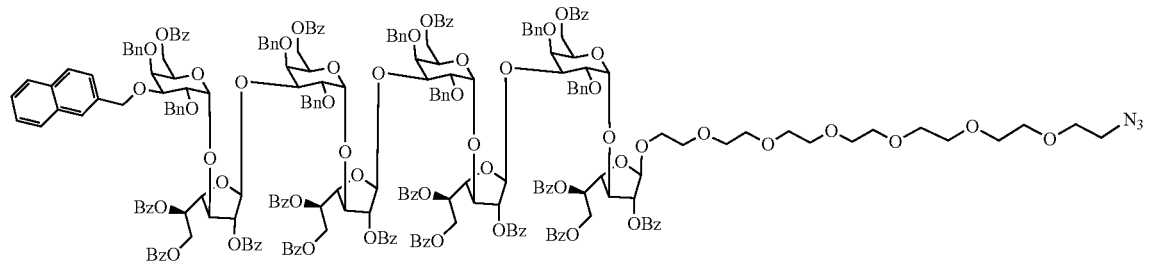
White solid layer, 22 mg, 85%
MALDI-TOF Calcd for C241H229N3NaO63 [M+Na]+ 4195.4705, found 4195.435.
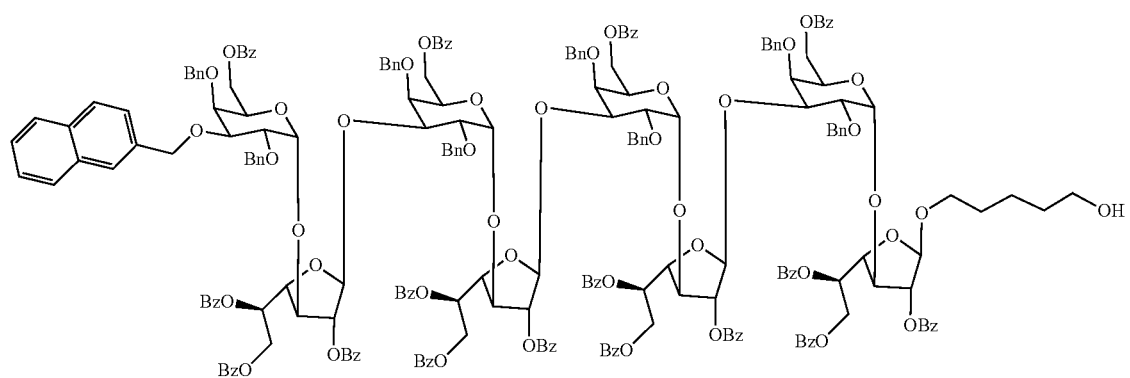

White solid layer, 24 mg, 99%.
MALDI-TOF Calcd for C232H212NaO58~ [M+Na]~ 3948.3537, found 3950.639.
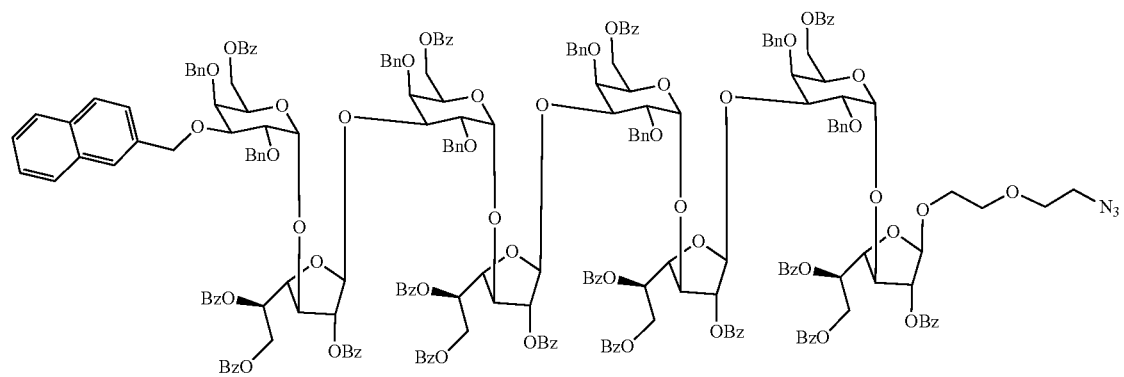
White solid layer, 21.4 mg, 86%
MALDI-TOF Calcd for C237H212N3NaO58+ [M+Na]+ 3947.3835, found 3970.916.
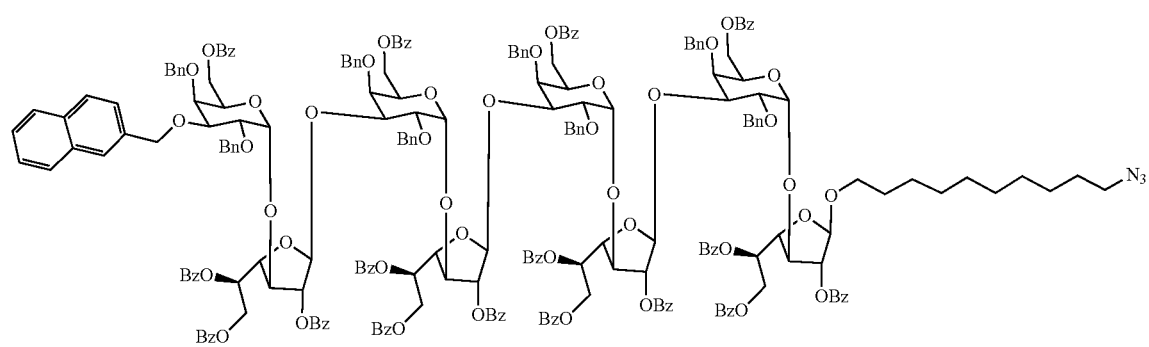
White solid layer, 216.4 mg, 86%
MALDI-TOF Calcd for C2317H229N3NaO58+ [M+Na]+ 4043.43895, found 40397.4316.
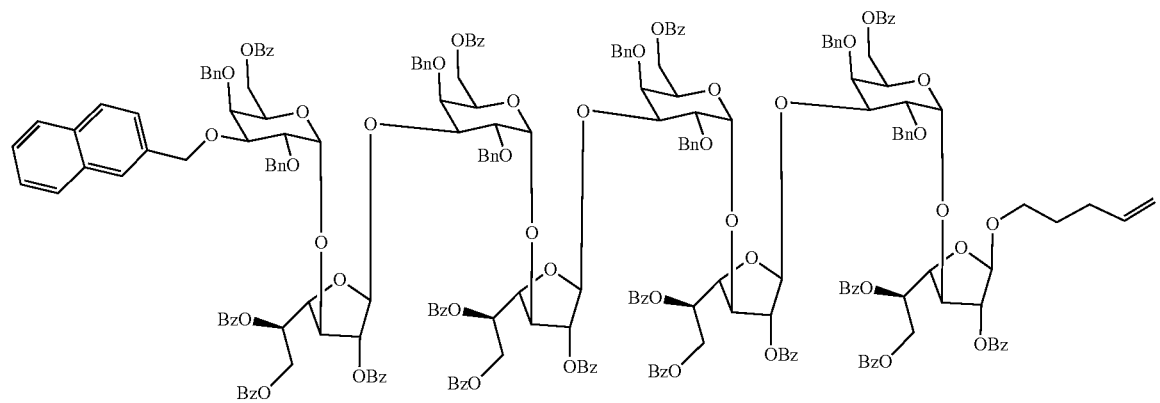

White solid layer, 20.3 mg, 83%
MALDI-TOF Calcd for C232H210NaO578 [M+Na]+ 3930.3432, found 3933.349.
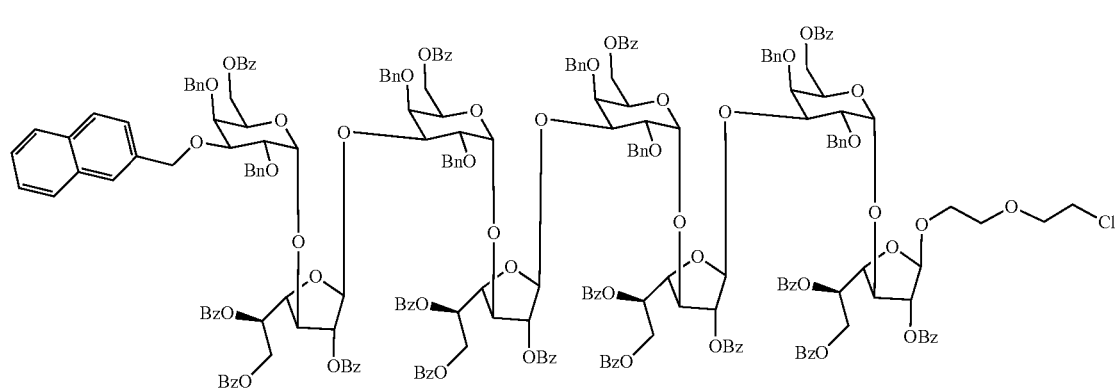
L10
White solid layer, 24 mg, 98%
MALDI-TOF Calcd for C231H2O9ClNaO58+ [M+Na]+ 3968.2991, found 3969.032.
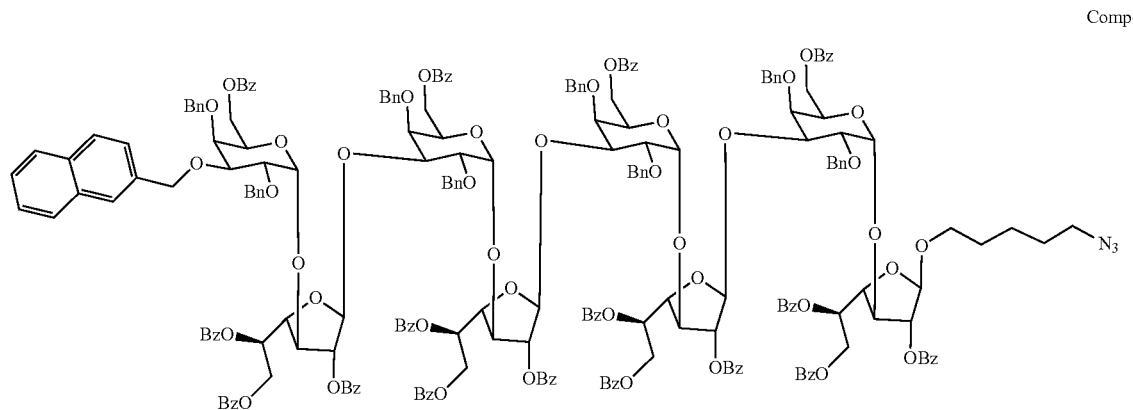
Compound 166*
Compound 165* was subjected to methanolysis according to general protocol A:
Product as white gummy solid obtained (43 mg, 99%).
MALDI-TOF Calcd for $C_{120}H_{147}KN_3O_{41}^+$ [M+K]+ 2324.9147, found 2327.888.
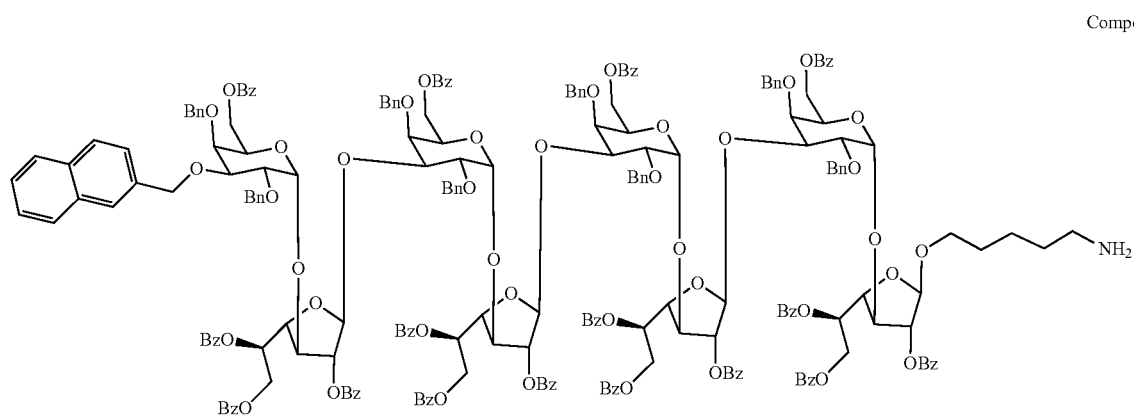
Compound 167*

Compound 166* was subjected to hydrogenation reaction according to general protocol A:

Product as white fluffy solid obtained (8 mg, 64%).

$^1$H NMR (400 MHz, Deuterium Oxide) δ 5.06 (s, 3H), 4.93 (s, 3H), 4.90 (d, J=3.5 Hz, 1H), 4.88 (d, J=1.8 Hz, 1H), 4.32-4.22 (m, 3H), 4.15-4.06 (m, 4H), 4.04-3.42 (m, 43H), 2.91-2.78 (m, 2H), 1.52 (dp, J=13.9, 7.2, 6.6 Hz, 4H), 1.29 (p, J=7.7, 7.1 Hz, 2H).

HRMS (ESI+) Calcd for $C_{53}H_{94}NO_{41}^+$ [M+H]$^+$ 1400.5301, found 1400.5381.

Compound 168*

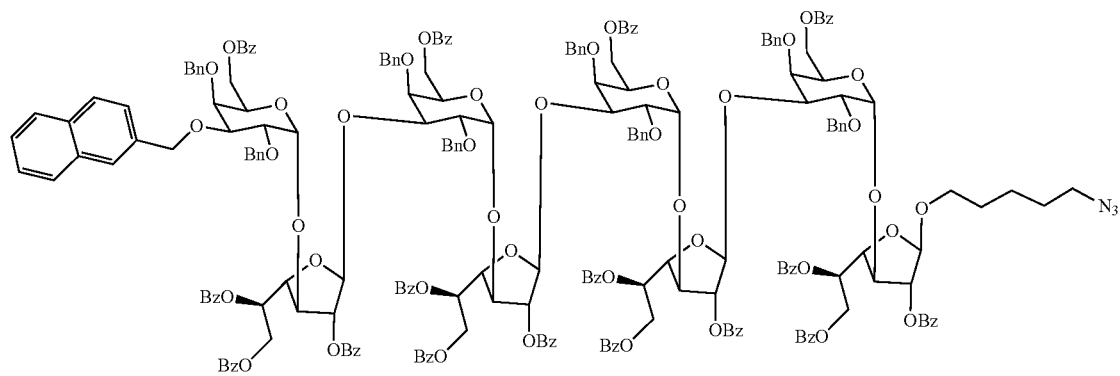

Compound 165* was subjected to Nap-deprotection reaction according to general protocol A:

Product as white fluffy solid obtained (153 mg, 88%).

MALDI-TOF Calcd for $C_{221}H_{204}N_3O_{57}^+$ [M+H]$^+$ 3811.3157, found 3812.015.

Compound 169*

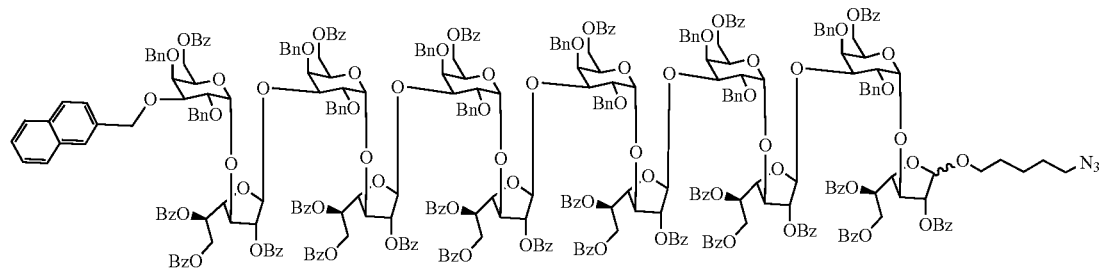

Compound 169* was obtained from compound 168* and compound 56* by glycosylation reaction according to general protocol B:

Product as white fluffy solid obtained (43 mg, 70%).

MALDI-TOF Calcd for $C_{340}H_{307}KN_3O_{85}$ [M+K]$^+$ 5829.9430, found 5834.474.

Compound 170*

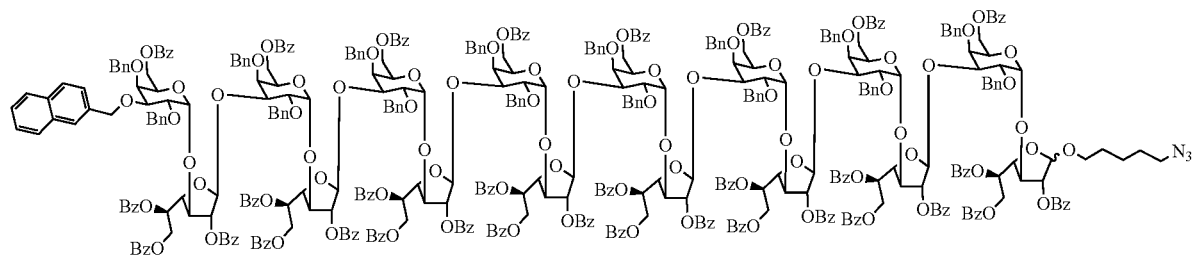

Compound 170* was obtained from compound 168* and compound 164* by glycosylation reaction according to general protocol B:

Product as white fluffy solid obtained (105 mg, 58%).

MALDI-TOF Calcd $C_{448}H_{403}KN_3O_{113}^+$ $[M+K]^+$ 7670.5518, found 7670.338.

Compound 171*

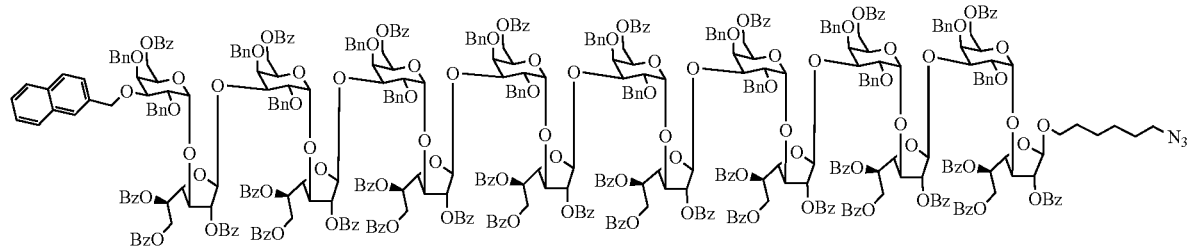

Compound 170* was subjected to methanolysis according to general protocol B:

product as white gummy solid obtained (29 mg, 79%).

MALDI-TOF Calcd for $C_{224}H_{276}N_3O_{81}^+$ $[M+H]^+$ 4303.7570, found 4305.070.

Compound 172*

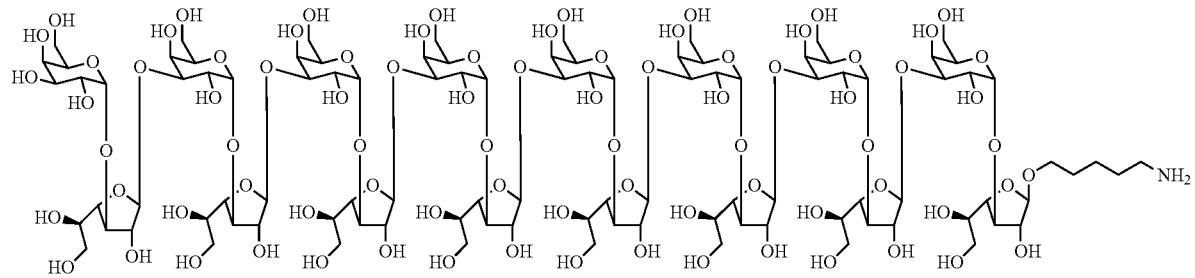

Compound 171* was subjected to hydrogenation reaction according to general protocol A:

Product as white fluffy solid obtained (4.8 mg, 77%).

$^1$H NMR (400 MHz, Deuterium Oxide) δ 5.27-5.17 (i, 7H), 5.04 (d, J=19.4 Hz, 9H), 4.43-4.38 (m, 7H), 4.30-4.00 (m, 31H), 4.00-3.55 (m, 60H), 2.98 (t, J=7.6 Hz, 2H), 1.66 (dp, J=13.4, 7.3, 6.6 Hz, 4H), 1.50-1.36 (in, 2H).

MALDI-TOF Calcd for $C_{101}H_{174}NNaO_{81}^{2+}$ $[M+Na+H]^{2+}$ 1359.4827, found 1359.4820.

Compound 173*

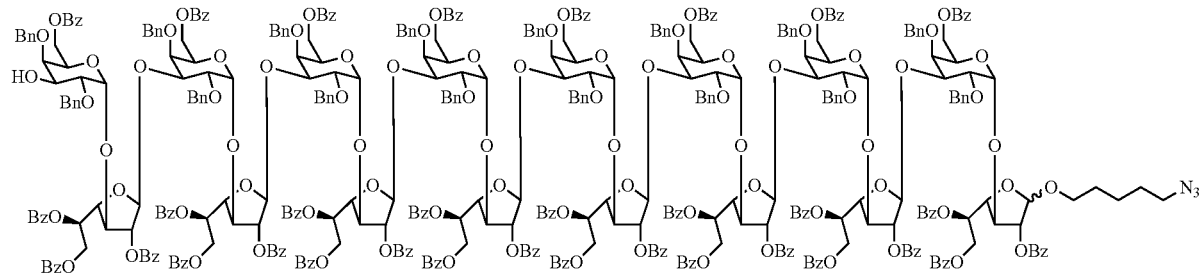

Compound 170* was subjected to Nap-deprotection reaction according to general protocol A:
Product as white fluffy solid obtained (77 mg, 78%).
MALDI-TOF Calcd for C437H395N3O113+ [M+H]+ 7492.5333, found 7496.204.

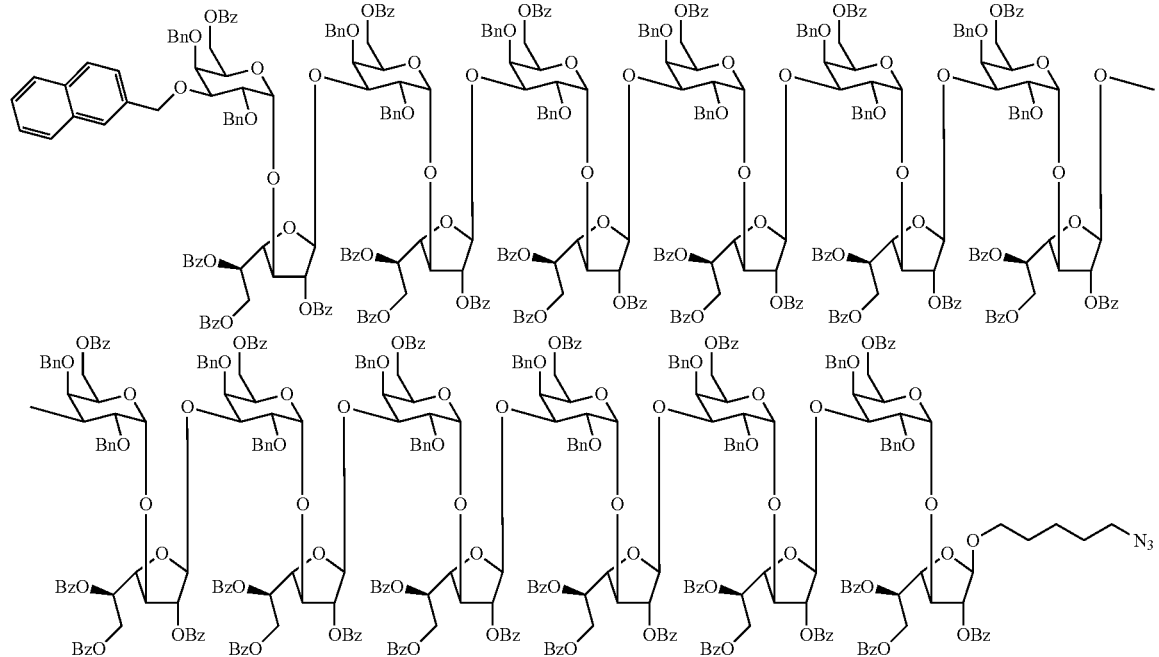

Compound 174*

Compound 174* was obtained from compound 173* and compound 164* by glycosylation reaction according to general protocol B: Product as white fluffy solid obtained (39 mg, 57%). MALDI Calcd for C664H595KN3O169+ [M+K]+ 11351.7694, found 11355.171.

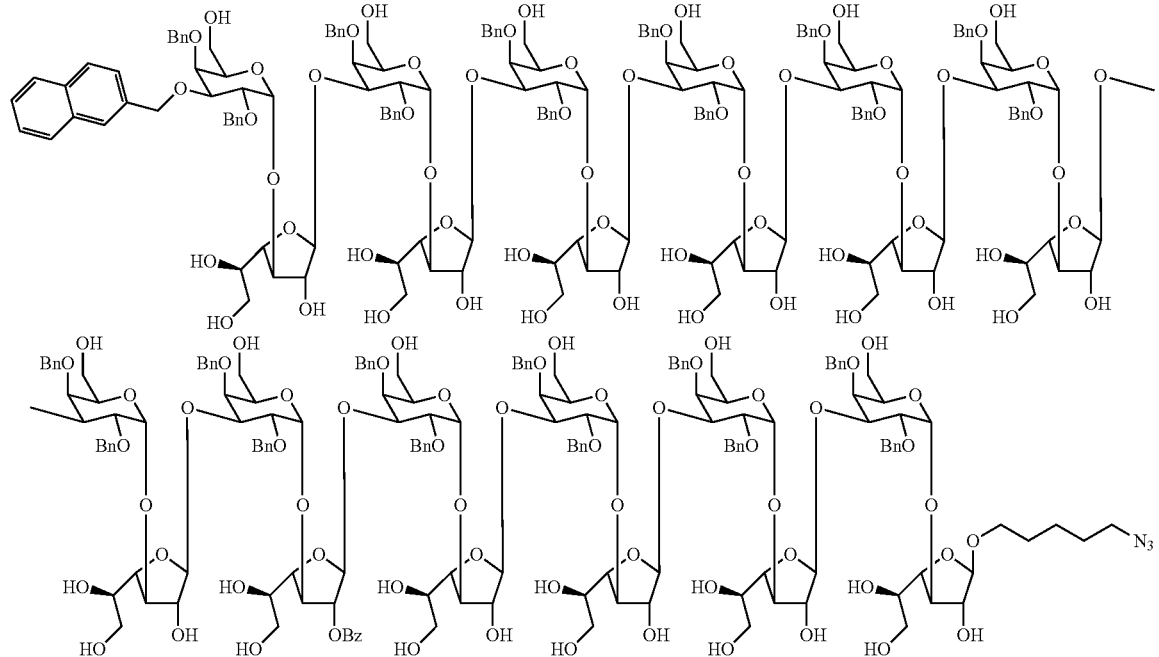

Compound 175*

Compound 174* is subjected to methanolysis according to general protocol B.

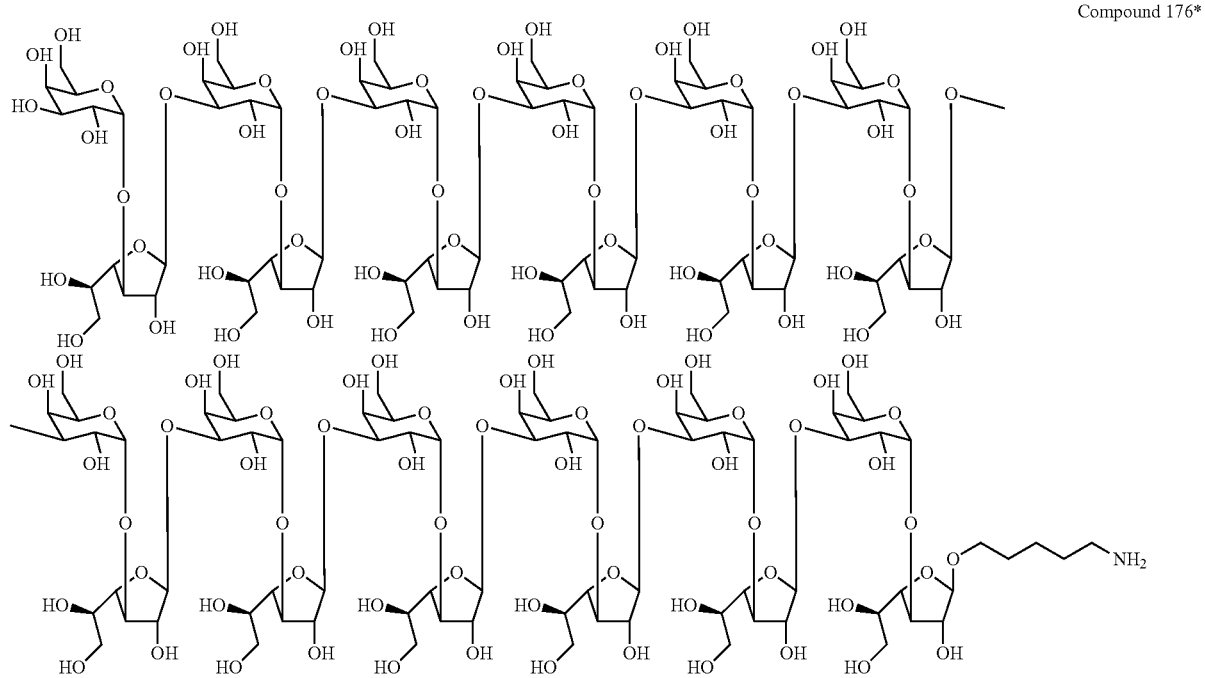

Compound 176*

Compound 175* is subjected to subjected to hydrogenation reaction according to general protocol A.

B Preparation and Characterization of Glycoconjugates

The KPC synthetic antigens 52*, 61*, 66*, 69*, 75* 81*, 88*, 91*, 99* 120*, 123*, 149* and 158* are conjugated to the carrier protein $CRM_{197}$ (XX-$CRM_{197}$) for immunization experiments and to Bovine Serum Albumin (BSA; (XX-BSA) as coating antigen for ELISA (see Example C) according to the procedure described below.

General Conjugation Protocol

Step 1: PNP-Ester Synthesis

Compound 52*, 61*, 120*, 123*, 149* or 158* (1 eq) was dissolved in DMSO or DMSO-pyridine or DMSO-$H_2O$ at room temperature in a 8 mL vial. Activated bis-(4-nitrophenyl) adipate (20 eq) was added to it and stirred for 5 minutes. Triethylamine (50 eq) was added and the reaction mixture was allowed to stir at room temperature for 3-5 h. The reaction mixture was frozen using liquid nitrogen and then lyophilized for 18 h to dryness to afford pale yellow colored crude product along with the excess of the reagent. The crude product was washed thoroughly with sufficient $CHCl_3$ followed by DCM to remove excess reagent. The solid para-nitrophenyl (PNP) ester was dried and taken for the next step.

Step 2: Conjugation to the Protein

Conjugation procedure: The PNP ester of 52*, 61*, 120*, 123*, 149* or 158* in 50 μL of 0.15 M NaCl in NaPi buffer was added dropwise to the reaction vial containing $CRM_{197}$ or BSA in buffer (~150 μL) (PNP ester of 120* was conjugated only to $CRM_{197}$). The vial was finally rinsed with 50 μL of buffer solution and transferred to the reaction vial completely. Thus making the volume of the reaction in the vial ~200 μL. The reaction mixture became yellow in colour and stirred the reaction mixture at r.t. for 24h. The conjugate solution was transferred to a Amicon® Ultra-0.5 mL centrifugal filter, centrifuged for 6 minutes at 2-8° C. 300 μL of buffer were added to the reaction vial, rinsed and transferred to the filter and centrifuged again. Additional washings were done using 1×PBS solution and centrifuging till the yellow colour was gone and the conjugate became clear solution. After the final wash the conjugate was stored in 1×PBS solution at 2-8° C.

The conjugates were analyzed by SDS-PAGE, SEC chromatography, and MALDI analysis. It was found to be 1-15 for different antigens. The loading of the sugar on the carrier was specifically calculated by subtracting the mass between the conjugated and unconjugated protein using MALDI analysis. The protein content was estimated using the micro BCA method following manufacture protocol.

SDS-PAGE Analysis.

The samples were mixed in a microfuge tube and heated for 5 min at 95° C. on a thermocycler. After cooling to room temperature for 5 min, the samples at approximately 2.5 μg were loaded onto the respective wells of a 10% polyacrylamide gel along with 10 μL of the marker. The samples were run at a constant voltage of 120V for 1 h. Staining was done using the GelCode™ Blue Safe Protein Stain as per manufacture instructions. The gels were washed with deionized water overnight and scanned using the gel documentation system (see FIG. 5).

Size Exclusion Chromatography (SEC) of Glycoconjugates.

The glycoconjugates used for immunization studies were analyzed by SEC to observe a mass difference between the conjugated and unconjugated CRM protein. The samples were diluted in 50 mM Tris, 20 mM NaCl, pH 7.2 and run on a Agilent 1100 HPLC system fitted with Tosoh TSK G2000 column (SWxl, 7.8 mm×30 cm, 5 μm) and a Tosoh TSKgel® Guard Column (SWxl 6.0 mm×4 cm, 7 μm). The flow rate was kept at 1 mL/min (see FIG. 6).

Characterization of Glycoconjugates 61*-$CRM_{19}$r and 158*-$CRM_{197}$.

The KPC antigen glycoconjugates 61*-$CRM_{197}$ and 158*-$CRM_{197}$ used for the immunization studies were analyzed for the conjugation efficiency and antigen content. MALDI analysis of the glycoconjugates revealed a very good conjugation efficiency. The mass differences between the conjugated and unconjugated $CRM_{197}$ protein yielded a loading from 3-10 antigens/$CRM_{197}$ molecule for the different glycoconjugates.

Figure 5:
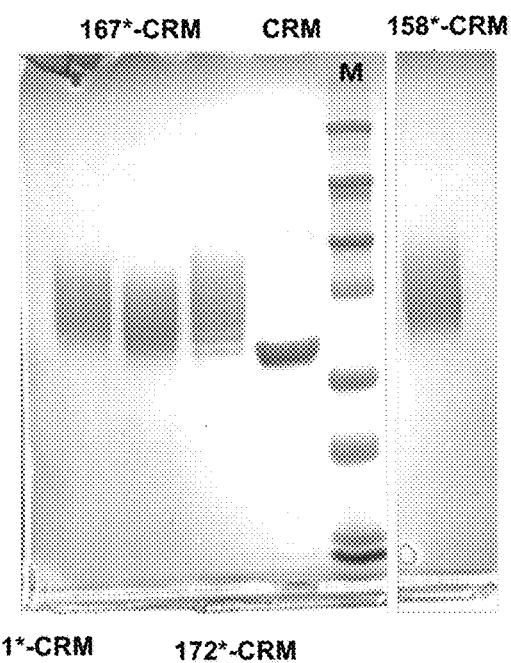
FIG. 5 shows SDS-PAGE of glycoconjugates (2.5 µg/well) 61*-CRM$_{197}$ and 158*-CRM$_{197}$ used in immunization experiments resolved using a 10% polyacrylamide gel.
Figure 6:
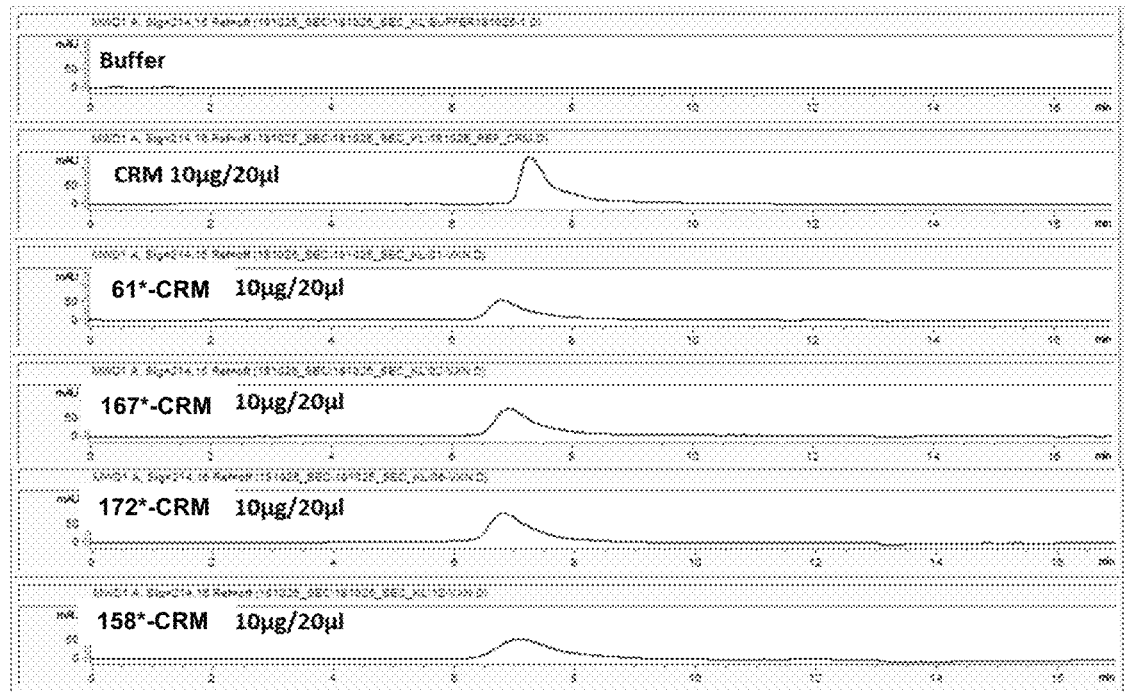
FIG. 6 presents SEC Chromatograms of KPC glycoconjugates 61*-CRM$_{197}$ and 158*-CRM$_{197}$.

The glycoconjugates were also analyzed by a 10% SDS-PAGE and SEC that revealed a clear mass shift as compared to the unconjugated $CRM_{197}$ protein (FIG. 5 and FIG. 6).

C Immunization Studies

Materials:
- ELISA plates (high-binding, EIA/RIA Plate, 96 well, flat bottom with low evaporation lid, company: Costar® 3361)
- Detection antibody: Goat anti rabbit IgG peroxidase conjugate (Sigma, #A4914) and Goat anti-Mouse IgG (H+L) peroxidase conjugate (Dianova Code: 115-035-068).
- Blocking solution: 1% FCS (v/v) in PBS.
- Antibody diluent: PBS+1% BSA (w/v).
- Wash Buffer: PBS+0.1% Tween 20 (PBS-T)
- Developing solution: 1 Step™ Ultra TMB-ELISA developer. (ThermoScientific, Cat #: 34028)
- Stop solution-2M sulphuric acid ($H_2SO4$).
- Plate reader: Anthos HT 2.
- Software: WinRead 2.36 for absorbance measurements and GraphPad Prism 7 for data plotting and analysis.
- Alum: Aluminium Hydroxide Gel Adjuvant (Alhydrogel® 2%), Brenntag, Batch #:5447 Exp Dt: February 2020.
- Incomplete Freund's Adjuvant (IFA). InvivoGen; Cat: vac-ifa-10, Batch #: IFA-39-03; Exp Dt: September 2019
- QuantiPro™ BCA Assay Kit (SIGMA) Product: QPBCA-1 KT; Lot #: SLBR7451V; Pcode: 1002296464
- Mini-PROTEAN® TGX™ Gels-10%, 10 well (30 µL/well) Control Nr:64175708,
- Precision Plus Dual Color, Cat: 1610374; Control Nr: 641798899
- GelCode™ Blue Safe Protein Stain; ThermoScientific; Ref: 1860957; Lot #: TA260266
- *Klebsiella pneumoniae* LPS. SIGMA- L4268; Lot #: 116 M 4057 V Methods:

1. Bacterial Strains and LPS.

*Klebsiella pneumoniae* (KPC) strains differing in their LPS (O-antigen) with/without the capsule were used to isolate and purify the corresponding LPS. The purified LPS were used as coating antigen in Enzyme Linked Immunosorbent Assay (ELISA). The O2a,c LPS was procured from Sigma-Aldrich.

TABLE 1

*Klebsiella pneumoniae* strains used for LPS isolation.

| # | LPS/O-antigen |
|---|---|
| 1 | O1 |
| 2 | O2a |
| 3 | O2a, c |
| 4 | Galactan-III |

2. Formulation of Vaccines for Immunization.

The glycoconjugates were formulated in aluminum hydroxide (alum) adjuvant for mice studies, and in Incomplete Freund's Adjuvant (IFA) for immunization in rabbits.

2.1 Formulation in Alum.

All the formulations were prepared under sterile conditions. The glycoconjugates (DS) and PBS were mixed in the appropriate pre-calculated ratio in a 50 mL Falcon™ tube corresponding to the final formulation volume leaving out the volume of alum (0.25 mg/mL) required. This formed the DS-PBS mixture. The antigen/DS dose per animal was kept at 5 µg/100 µL/animal. The DS-PBS mixture was gently mixed (5×) using a serological pipette. To the DS-PBS mixture, the corresponding volume of stock alum (10 mg/mL) was added to give a final alum ratio of 1:40 or 0.250 mg/mL. The mixture was immediately mixed by gentle pipetting (20×) using a 5 mL serological pipette. The Falcon™ tube was capped, wrapped with Parafilm® and allowed to mix on a shaker at 250 rpm for 2 h at room temperature (RT). After the incubation time of 2 h, the formulations were brought under the clean bench, aliquoted, and further stored at 4° C. till further use.

2.2 Formulation in IFA.

Incomplete Freund's Adjuvant (IFA) from InvivoGen was used for formulating the vaccines for rabbit immunization studies. Protocol was followed as per manufacture. Antigen: IFA concentration was kept at 1:1. The antigen dose per animal was kept at 5 µg/200 µL/animal (100 µL of antigen+ 100 µL IFA). IFA at the desired calculated volume (50% of the final immunization volume) was taken in a 15 mL sterile Falcon™ tube. The calculated amount of the diluted antigen solution (volume adjusted with PBS to 50% of the final immunization volume) was taken in a 3 mL sterile syringe, fitted with a 20 G needle. The DS solution was added into the Falcon™ tube containing the IFA and immediately vortexed for 15 sec (5×). The color of the formulation changes from pale-yellow to milky-white on vortexing which indicates the formation of stable emulsion. The resulting vaccine formulation was briefly vortexed and aliquoted into 2 mL sterile tubes with the desired dose volumes. Prior to immunizations, the tubes containing the vaccine formulations were vortexed and then injected into animals.

3.3 Characterization of Alum Formulations.

The glycoconjugates formulated in alum were characterized to determine the final alum concentration and the pH of the formulations.

3. Immunization Schedule:

Mice and rabbit immunizations were performed under specific pathogen-free conditions and were provided food and water ad libitum. Mice (n=6) and rabbits (n=4) were immunized sub cutaneous with the vaccine formulations (Table 2) at an injection volume of 100 µL/mice, and 200 µL/rabbit. The antigen dose for mice was kept at 5 µg/animal. The antigen dose for rabbit was kept at 5 µg/animal. Mice and rabbits were immunized on day 0, 14 and 28. Blood was drawn on day −1, 7, and 22 for mice and day 0, 7 and 21 for rabbits respectively, for the determination of antibody titers. On day 35, the animals were sacrificed, and blood collected.

TABLE 2

Immunization schedule and antigen dose information of mice (n = 6) and rabbits (n = 4).

| group | glycoconjugate | mice per group | rabbits per group |
|---|---|---|---|
| 1 | 61*-$CRM_{197}$ (O1) | 6 | 0 |
| 2 | 158*-$CRM_{197}$ (Gal-III) | 6 | 4 |

*All values for mice sera analysis were subtracted using the values from PBS/alum (negative control).

4. Enzyme Linked Immunosorbent Assay (ELISA) of Sera Using In-House antigen Coated plates:

Coating of Plates with Antigen:

Conjugates 61*-BSA and 158*-BSA, and LPS #1-#4 were used as the coating antigen. LPS was dissolved in isopropanol at a concentration of 10/20 µg/mL. 100 µL was used for coating each well resulting in a coating concentration of 1-2 µg/well. The LPS solutions were loaded into the well and subjected to overnight evaporation at r.t. inside the sterile bench. For conjugates 61*-BSA and 158*-BSA, the respective conjugates were dissolved at a concentration of 5 µg/mL in phosphate buffered saline (PBS) pH 7.4. 100 µL were coated per well and incubated overnight at 4° C. to get an antigen concentration of 0.5 µg/well.

Washing:
After overnight adsorption of the antigen, the plates were washed 1× with PBS-T (200 µL/well) and the excess fluid per well was removed by inverting the plate and tapping on a clean dry tissue towel.

Blocking:
The plates were blocked using 200 µL of the commercial blocking solution and incubated for 2h at RT.

Washing:
After blocking, the plates were washed 3× with PBS-T (200 µL/well) and the excess fluid per well was removed by inverting the plate and by tapping on a clean dry tissue towel.

Dilution of Sera and Incubations:
Pooled sera (n=4 rabbits or n=6 mice/group) from different time-points of the different experimental groups were diluted to their respective dilutions in the antibody diluent (PBS+1% BSA). 100 µL of the diluted sera samples of the different experimental groups were added in duplicates to the corresponding wells and incubated on a shaker set at 250 rpm for 2h at RT. 100 µL/well of the antibody diluent (PBS+1% BSA) formed the experimental blank. After incubation with sera, the plates were washed 4× with PBS-T (200 µL/well) and the excess fluid per well was removed by inverting the plate and by tapping on a clean dry tissue towel.

Incubation (Detection Antibody):
The corresponding detection antibody, anti-rabbit or anti-mouse IgG HRP conjugate was diluted 1:10,000 in the antibody diluent (PBS+1% BSA) and 100 µL/well was added and incubated on a shaker at 250 rpm for 1 h at RT. After the incubation with detection antibody, the plates were washed 5× with PBS-T (200 µL/well) and the excess fluid per well was removed by inverting the plate and by tapping on a clean dry tissue towel.

Substrate Addition:
To each well, 100 µL of the ready to use TMB (3,3,',5,5'-tetramethylbenzidine) substrate (normalized to r.t. from 4° C.) was added and incubated in dark for 15 min. The blue color of the enzymatic reaction was stopped by adding 50 µL/well of 2M $H_2SO_4$ solution resulting in a yellow colored solution. The absorption of the yellow colored solution was measured at 450 nm using a plate reader.

Results:
The absorption values were analyzed by plotting a graph using the GraphPad Prism software.

Figure 7:
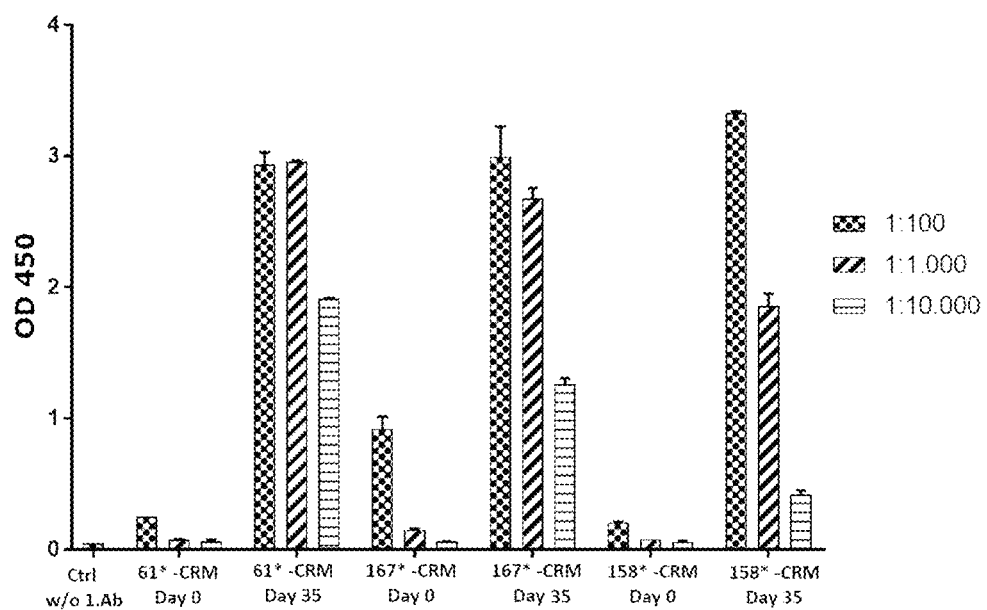
FIG. 7 shows ELISA titers of Day-0 and Day-35 pooled sera from mice (n=6) immunized with 61*-CRM$_{197}$ or 158*-CRM$_{197}$ formulation. Sera of said formulations were tested against corresponding O-antigen BSA conjugates 61*-BSA or 158*-BSA. Sera were diluted 1:100, 1000 and 10,000 with 1% BSA-PBS. Diluted sera (100 µL) was added per well of the microtiter plate which was coated with 0.5 µg of the corresponding O-antigen/BSA conjugates. Detection was done using a HRP conjugated goat anti-mouse secondary antibody diluted to 1:10000 and developed using the TMB substrate. Absorbance was measured at 450 nm and the data were plotted using the GraphPad prism software.
Figure 8:
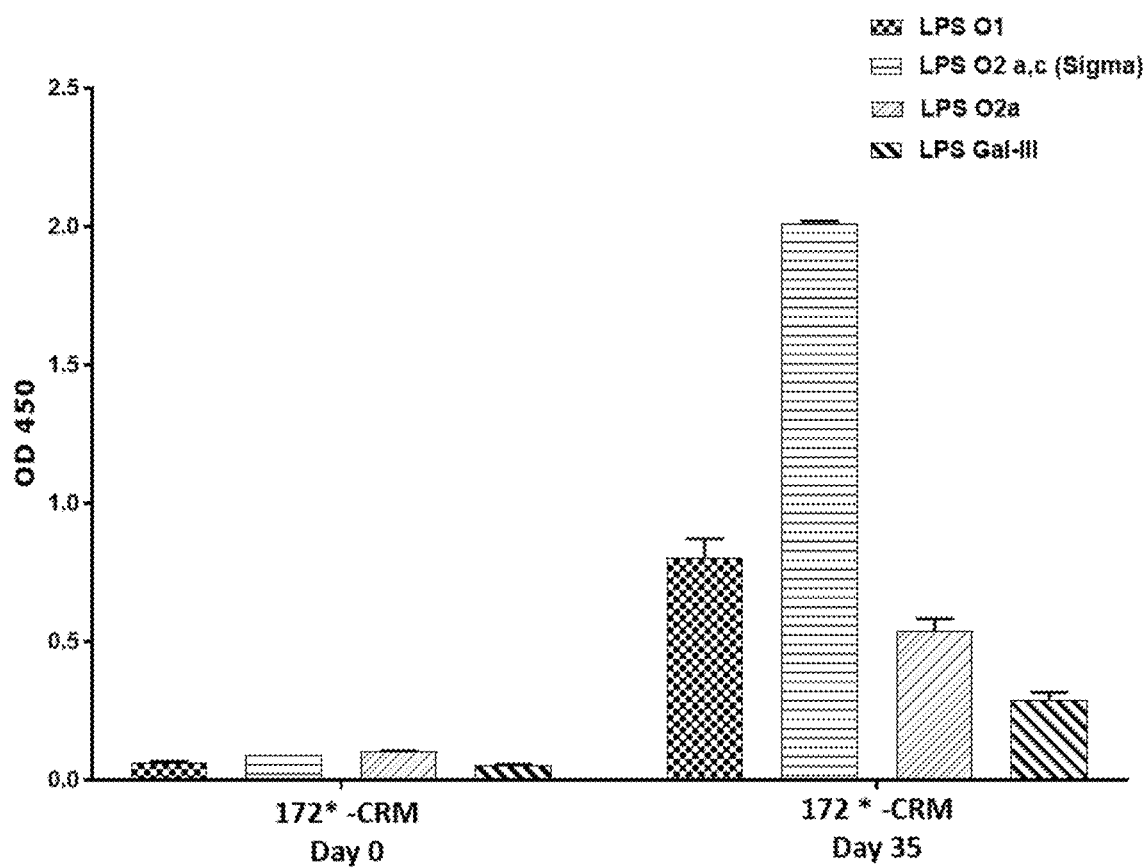
FIG. 8 shows cross-reactivity of Day-0 and Day-35 pooled sera from mice (n=6) immunized with 172*-CRM$_{197}$ formulation.
Figure 9:
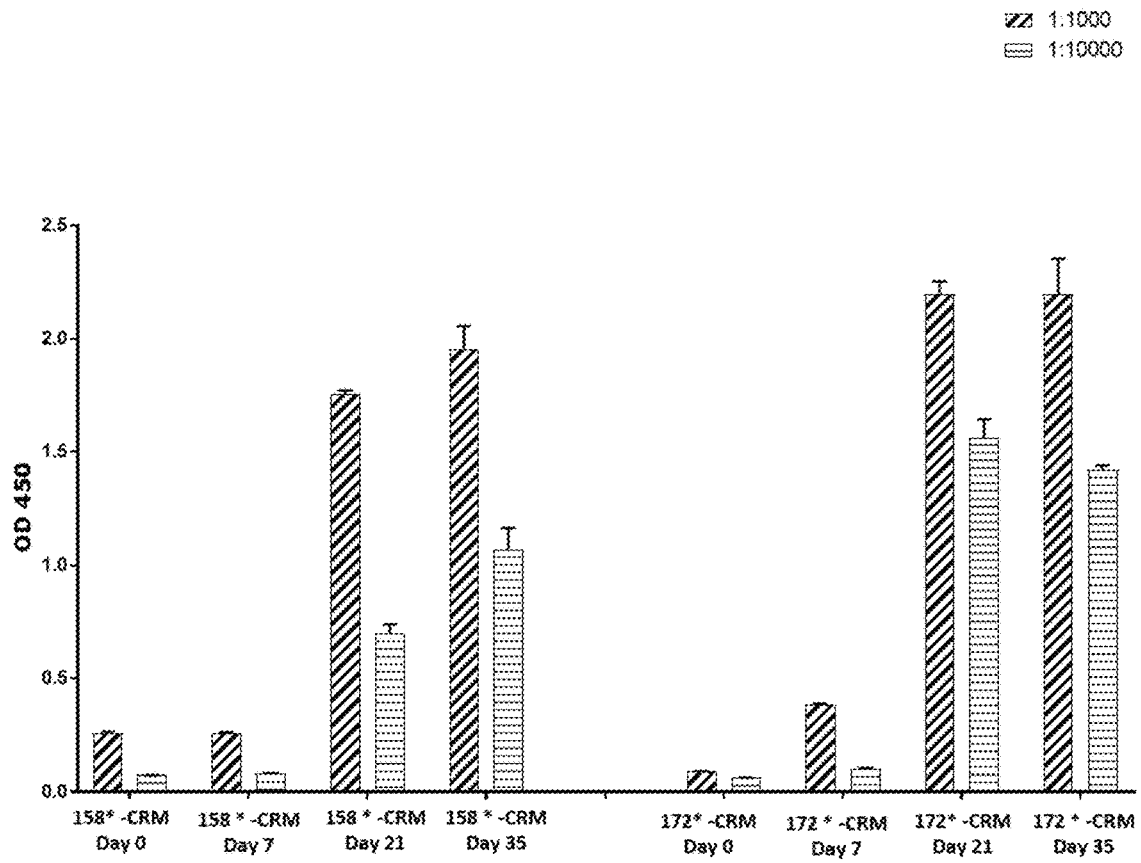
FIG. 9 shows ELISA titers of Day-0 Day-7, Day-21, and Day-35 pooled sera from rabbit (n=4) immunized with 158*-CRM$_{197}$ formulation. Sera 158*-CRM$_{197}$ formulation were tested against corresponding 0-antigen/BSA conjugate 158*-BSA. Sera were diluted 1:1000 and 10,000 with 1% BSA-PBS. Diluted sera (100 µL) was added per well of the microtiter plate which was coated with 0.5 µg of the corresponding O-antigen/BSA conjugates. Detection was done using a HRP conjugated goat anti-rabbit secondary antibody diluted to 1:10000 and developed using the TMB substrate. Absorbance was measured at 450 nm and the data were plotted using the GraphPad prism software.
Figure 10:
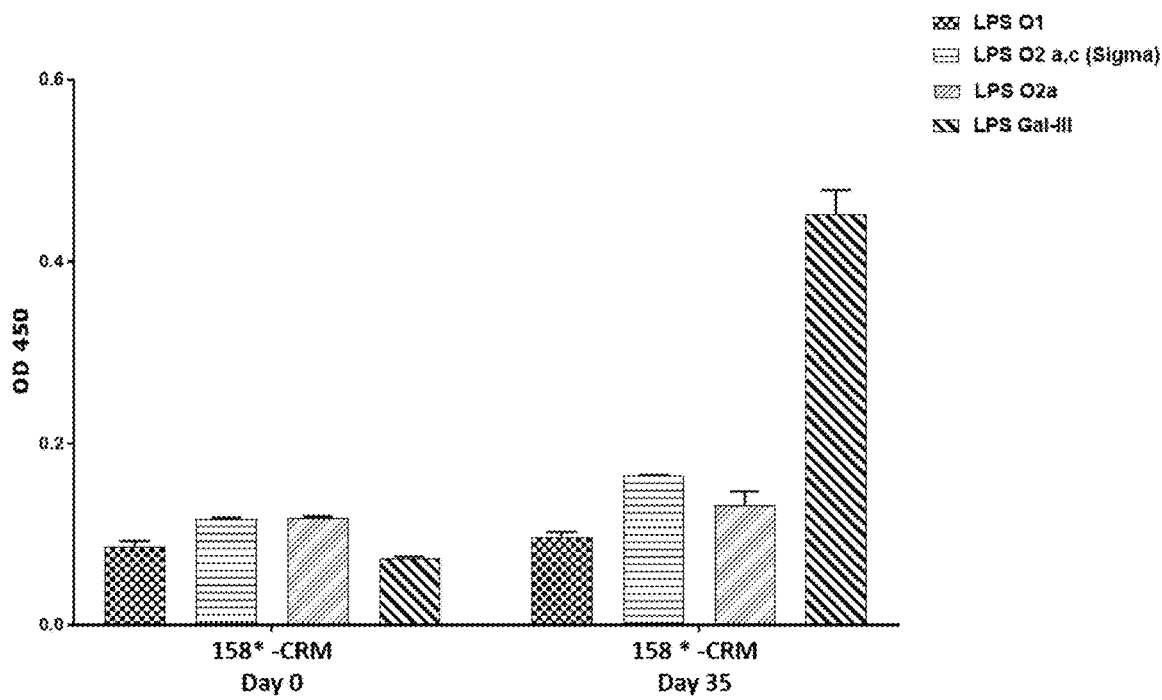
FIG. 10 shows cross-reactivity of Day-0 and Day-35 pooled sera from rabbit (n=4) immunized with 158*-CRM$_{97}$ formulation. Sera of 158*-CRM$_{97}$ formulation were tested against LPS isolated from different KPC strains. The sera was tested against the LPS (O1), Commercial-LPS (O2a,c), LPS (O2a), and LPS (Gal III). The sera were diluted 1:200 with 1% BSA-PBS and 100 µL of the diluted sera was added per well of the microtiter plate which was coated with 1.0 µg of the corresponding LPS. Detection was done using a HRP conjugated goat anti-rabbit secondary antibody diluted to 1:10000 and developed using the TMB substrate. Absorbance was measured at 450 nm and the data were plotted using the GraphPad prism software.
Figure 12:
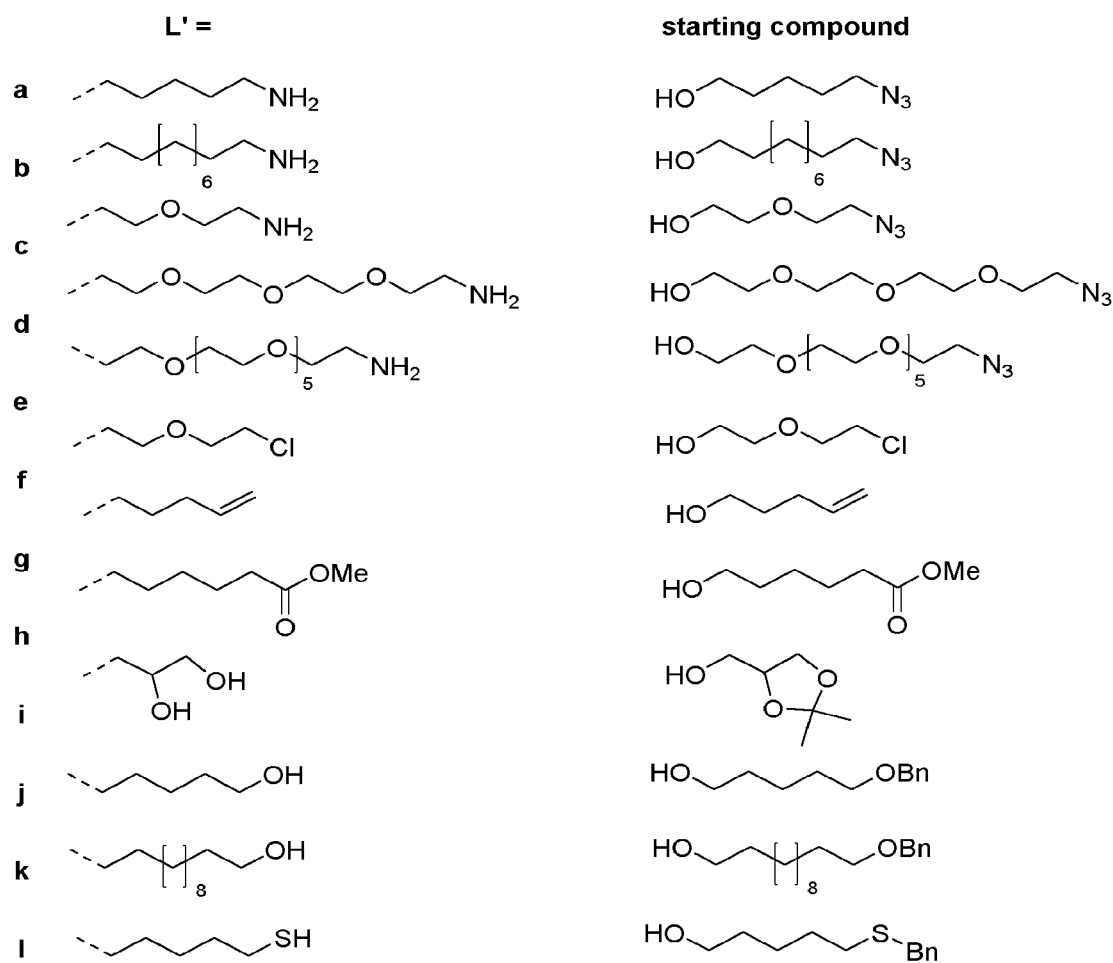

Results.
Sera from 61*-$CRM_{197}$, 158*-$CRM_{197}$, or 167*-$CRM_{197}$ immunized mice recognize the corresponding antigens (see FIG. 7). The sera of 172*-$CRM_{197}$ also cross-react with the corresponding *K. pneumoniae* LPS (see FIG. 8). Sera from 158*-$CRM_{197}$/172*-$CRM_{197}$ immunized rabbits recognize the corresponding O-antigens in the related BSA conjugates 158*-BSA and 172*-BSA, respectively (see FIG. 9). Sera from 158*-$CRM_{197}$ immunized rabbits recognize selectively the corresponding *K. pneumoniae* LPS (see FIG. 10).

The herein provided data demonstrate that after immunization with a conjugate of the present invention, functional antibodies against oligosaccharides of the present invention as well as against the natural 0-polysaccharides of *K. pneumoniae* serotypes O1, O2, O2ac and carbapanem-resistant ST258 were elicited in rabbits and mice. The Antibodies do cross-react with the natural 0-polysaccharides (LPS) of *K. pneumoniae* serotypes O1, O2, O2ac, and carbapanem-resistant ST258 indicating the potential of these antibodies to bind to *K. pneumoniae* bacteria and to confer protection against *K. pneumoniae* infection.

The ELISA data further proves that the conjugates of the present invention are immunogenic and induce high antibody titers. Hence, ELISA analysis shows that the saccharides of formula (I) of the present invention are immunogenic in rabbits and mice and generate cross-reactive antibodies.

The invention claimed is:
1. A conjugate of general formula (III-8), (III-11), (III-7), (III-2) or (III-3):

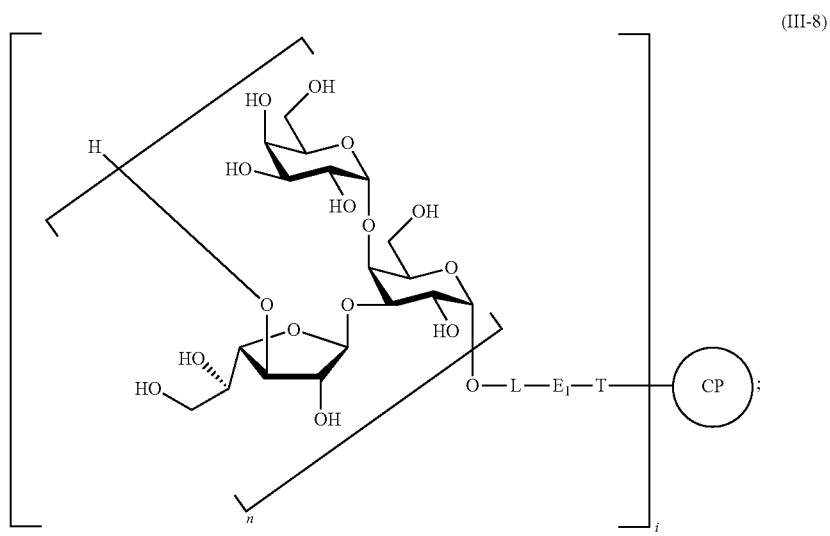

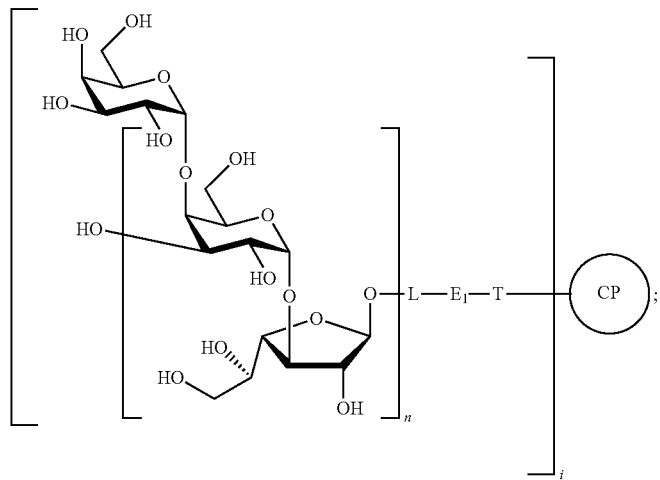
(III-11)
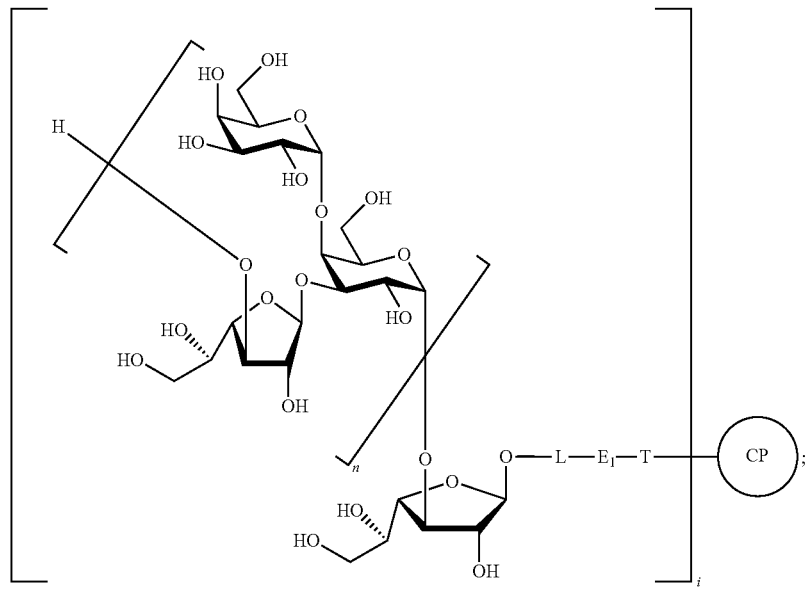
(III-7)
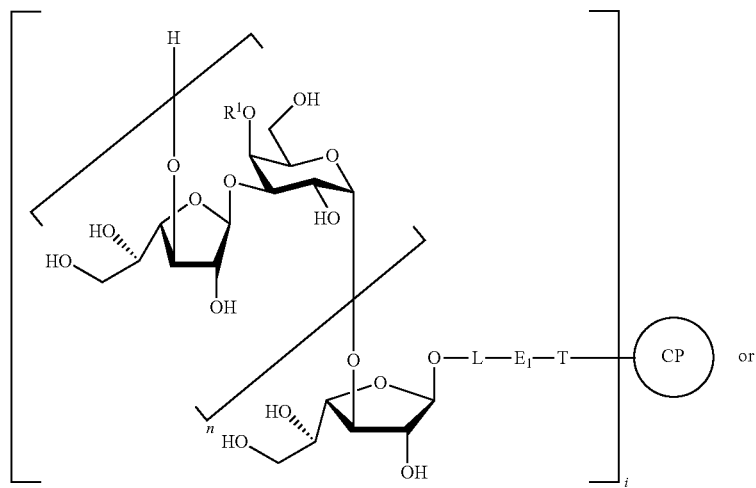
(III-2) or (III-3)

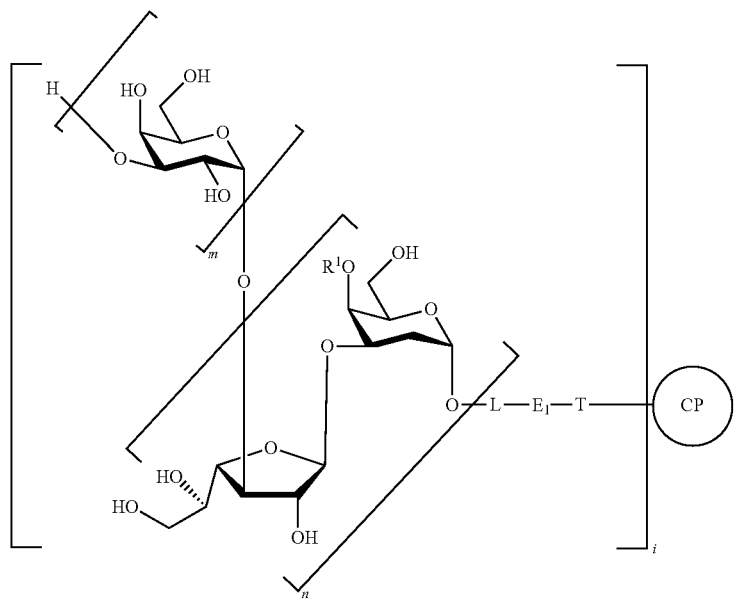

wherein
$R^1$ represents —H, or

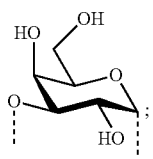

n is an integer from 1 to 20;
m is an integer from 0 to 20;
-L- represents —$L^a$-, -$L^a$-$L^e$-, -$L^a$-$L^b$-$L^e$-, or -$L^a$-$L^d$-$L^e$-;
-$L^a$- represents -(CH$_2$)$_o$-, -(CH$_2$-CH$_2$-O)$_o$-C$_2$H$_4$-, or -(CH$_2$-CH$_2$-O)$_o$—CH$_2$;
-$L^b$- represents —O—, —NH—CO—NH—, -NH—CO-CH$_2$-NH-, or -NH—CO—;
-$L^d$- represents -(CH$_2$)$_q$-, -(CH(OH)$_q$-, —(CF$_2$)$_q$-, -(CH$_2$-CH$_2$-O)$_q$—C$_2$H$_4$-, or —(CH$_2$-CH$_2$-O)$_q$-CH$_2$—;
-$L^e$- represents -(CH$_2$)$_{p1}$-, -(CF$_2$)$_{p1}$-, -C$_2$H$_4$-(O-CH$_2$-CH$_2$)$_{p1}$-, —CH$_2$-(O-CH$_2$-CH$_2$)$_{p1}$-, or -(CH$_2$)$_{p1}$-O-(CH$_2$)$_{p2}$-; and
o, q, p1 and p2 are independently of each other an integer selected from 1, 2, 3, 4, 5, and 6;
-$E_1$- represents a covalent bond, —NH—, —O—NH—, —O—, —S—, —CO—, —CH=CH—, —CONH—, —CO—NHNH—,

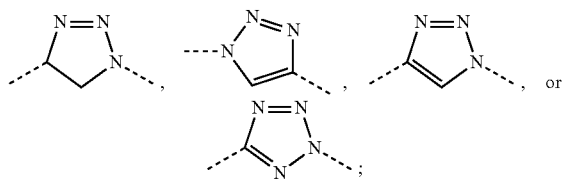

T- represents

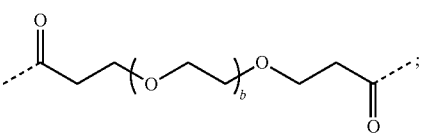

a represents an integer from 1 to 10;
b represents an integer from 1 to 4;
i is an integer selected from 2 to 25; and
CP is non-toxic mutated diphtheria toxin CRM$_{197}$.

2. The conjugate according to claim 1, wherein
n is an integer from 1 to 10; and
m is an integer from 1 to 10.

3. The conjugate according to claim 1, wherein
n is an integer from 1 to 10; and
m is 0 or 1.

4. The conjugate according to claim 1, wherein the conjugate is selected from general formula (III-8), (III-11), (III-7), or (III-2):

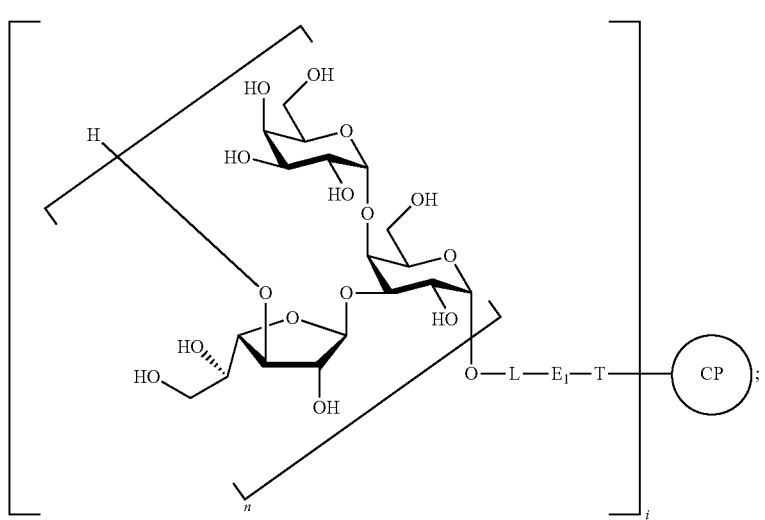
(III-8)
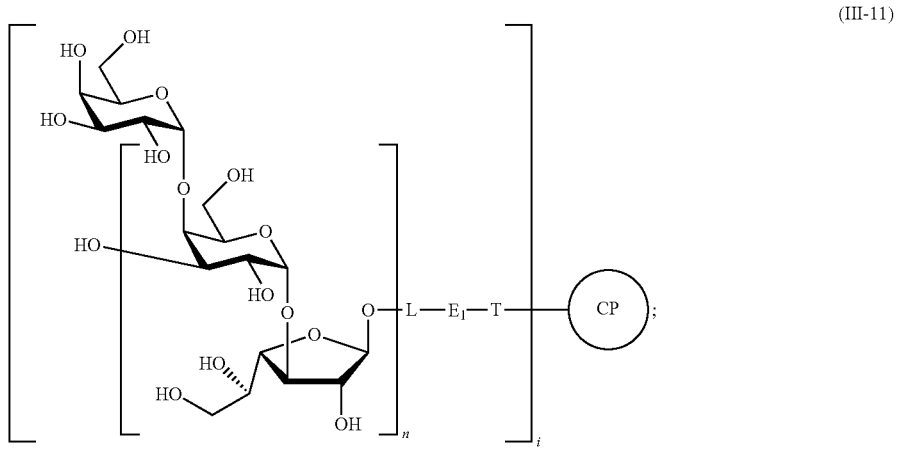
(III-11)
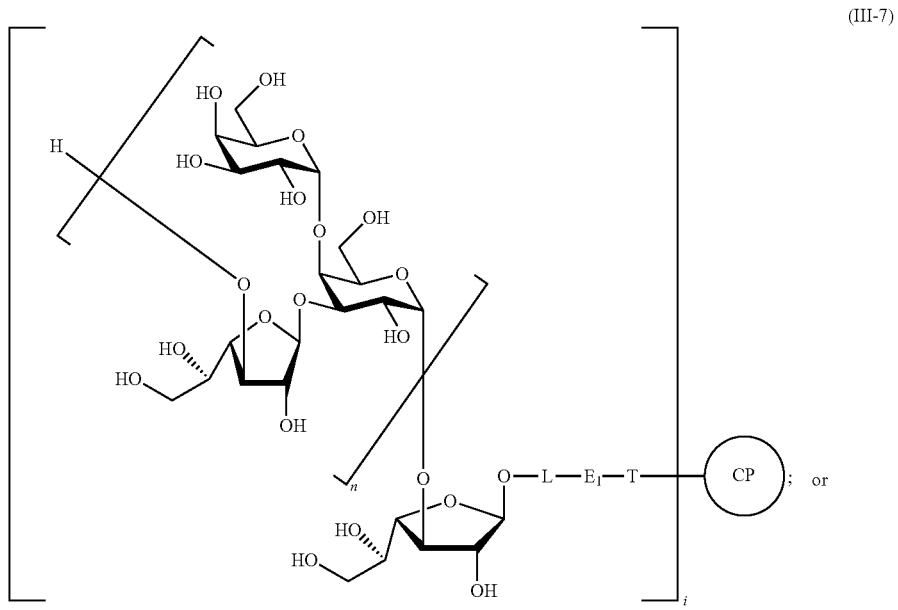
(III-7)
or (III-2)

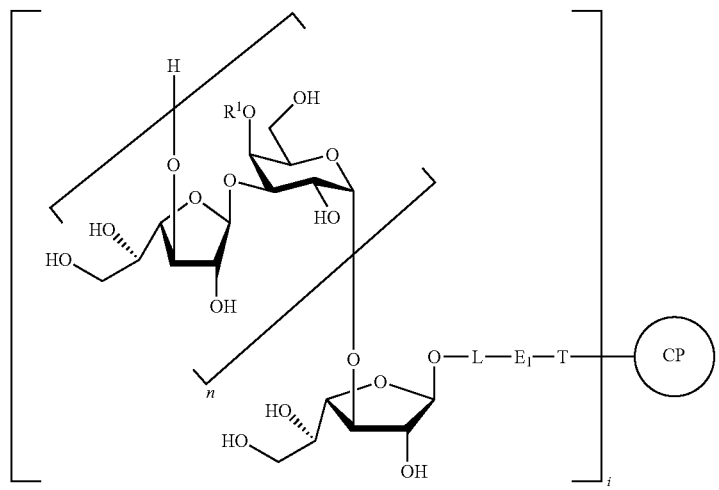

wherein $R^1$ is H, and n is an integer from 1 to 10.

5. The conjugate according to claim 4, wherein

-$E_1$- represents a covalent bond, —NH—, —CH=CH—, -CONH-,

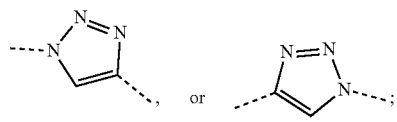

and

-T- represents

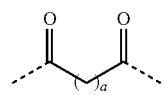

and a is an integer selected from 2, 3, 4, 5 and 6.

6. The conjugate according to claim 5, wherein -L- represents —$(CH_2)_o$— and o is an integer selected from 1, 2, 3, 4, 5 and 6.

7. The conjugate according to claim 6, wherein i is an integer selected from 2 to 18.

8. The conjugate according to claim 7, wherein i is an integer selected from 4 to 10.

9. A conjugate, wherein the conjugate comprises

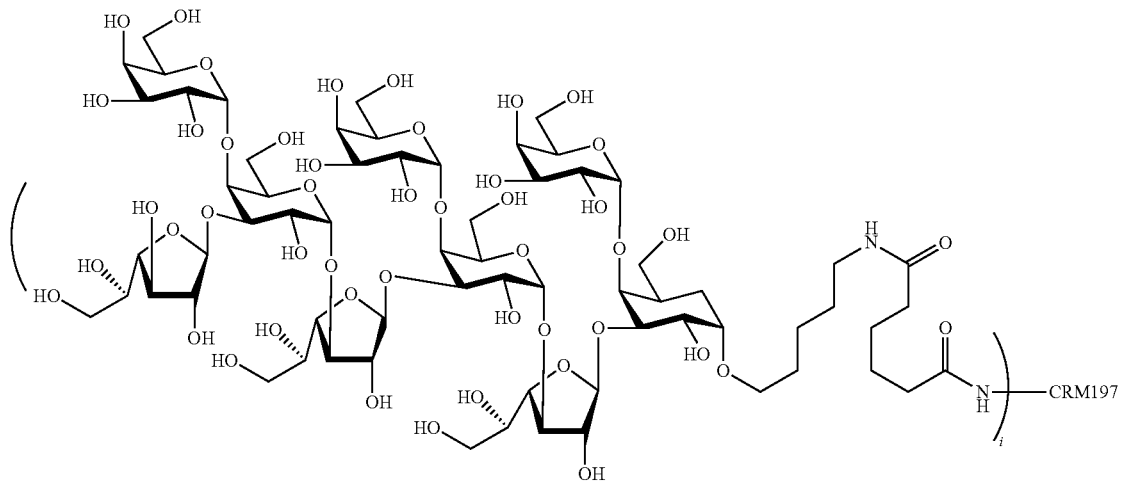

wherein i is an integer selected from 2 to 18.

10. The conjugate according to claim 9, wherein the conjugate comprises

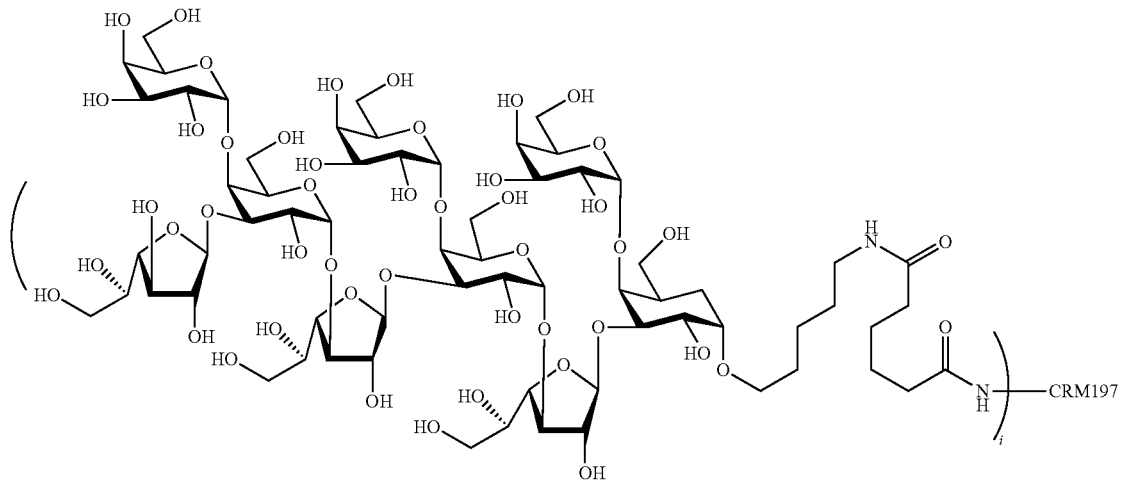

wherein i is an integer selected from 4 to 10.

11. A conjugate having the formula:

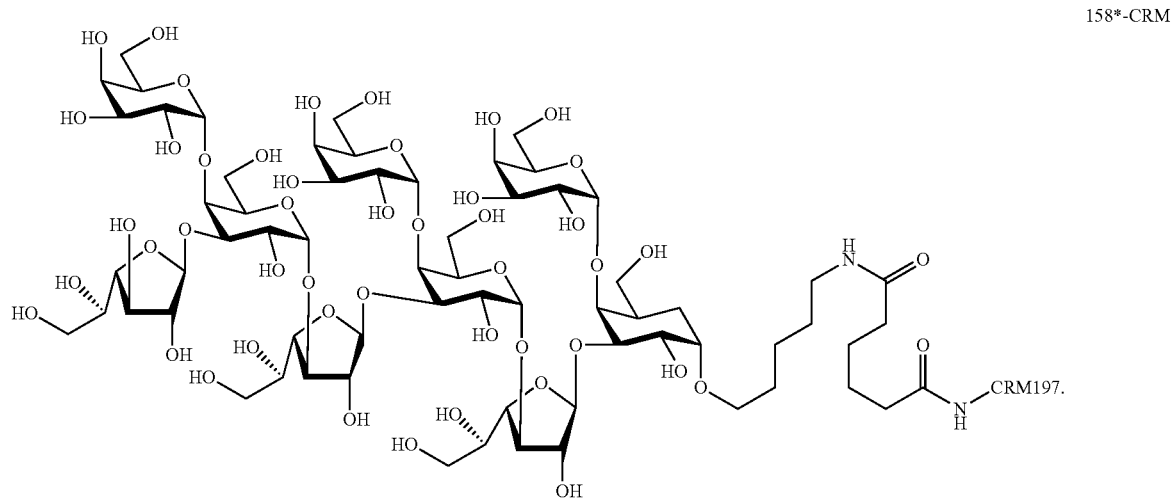

12. A pharmaceutical composition comprising at least one conjugate according to claim 1 as an active ingredient together with at least one pharmaceutically acceptable adjuvant and/or excipient.

13. A pharmaceutical composition comprising at least one conjugate according to claim 4 as an active ingredient together with at least one pharmaceutically acceptable adjuvant and/or excipient.

14. A pharmaceutical composition comprising at least one conjugate according to claim 9 as an active ingredient together with at least one pharmaceutically acceptable adjuvant and/or excipient.

15. A method of inducing immune response against *Klebsiella pneumoniae* in a human or animal host, said method comprising administering at least one conjugate according to claim 1 to said human or animal host.

16. A method of inducing immune response against *Klebsiella pneumoniae* in a human or animal host, said method comprising administering at least one conjugate according to claim 4 to said human or animal host.

17. A method of inducing immune response against *Klebsiella pneumoniae* in a human or animal host, said method comprising administering at least one conjugate according to claim 9 to said human or animal host.

18. The method according to claim 15, wherein the immune response is induced for the prevention and/or treatment of a disease associated with *Klebsiella pneumoniae*, wherein the disease is selected from meningitis, urinary tract infection, nosocomial pneumonia, intra-abdominal infections, wound infection, infection of blood, osteomyelitis, bacteremia, septicemia and ankylosing spondylitis.

19. The method according to claim 16, wherein the immune response is induced for the prevention and/or treatment of a disease associated with *Klebsiella pneumoniae*, wherein the disease is selected from meningitis, urinary tract infection, nosocomial pneumonia, intra-abdominal infections, wound infection, infection of blood, osteomyelitis, bacteremia, septicemia and ankylosing spondylitis.

20. The method according to claim 17, wherein the immune response is induced for the prevention and/or treatment of a disease associated with *Klebsiella pneumoniae*, wherein the disease is selected from meningitis, urinary tract infection, nosocomial pneumonia, intra-abdominal infections, wound infection, infection of blood, osteomyelitis, bacteremia, septicemia and ankylosing spondylitis.

21. The method according to claim 18, wherein the *Klebsiella pneumoniae* is selected from O-serotypes comprising or consisting of O1, O2a, O2ac, O2aeh, O2afg, O8, and carbapanem-resistant *Klebsiella pneumoniae* strain ST 258.

22. The method according to claim 19, wherein the *Klebsiella pneumoniae* is selected from O-serotypes comprising or consisting of O1, O2a, O2ac, O2aeh, O2afg, O8, and carbapanem-resistant *Klebsiella pneumoniae* strain ST 258.

23. The method according to claim 20, wherein the *Klebsiella pneumoniae* is selected from O-serotypes comprising or consisting of O1, O2a, O2ac, O2aeh, O2afg, O8, and carbapanem-resistant *Klebsiella pneumoniae* strain ST 258.

* * * * *